US012338279B2

(12) United States Patent
Chapron et al.

(10) Patent No.: US 12,338,279 B2
(45) Date of Patent: Jun. 24, 2025

(54) SELECTIVE AND POTENT INHIBITORY ANTIBODIES OF MYOSTATIN ACTIVATION

(71) Applicant: SCHOLAR ROCK, INC., Cambridge, MA (US)

(72) Inventors: Christopher Chapron, Cambridge, MA (US); Frederick C. Streich, Jr., Cambridge, MA (US); Kaleigh Canonico, Cambridge, MA (US); Shaun M. Cote, Cambridge, MA (US); Francis Danehy, Jr., Cambridge, MA (US); Melissa Fulham, Cambridge, MA (US); Yan Huang, Cambridge, MA (US); Justin William Jackson, Cambridge, MA (US); Mania Kavosi, Cambridge, MA (US); Sandeep Kumar, Cambridge, MA (US)

(73) Assignee: Scholar Rock, Inc., Cambridge, MA (US)

( * ) Notice: Subject to any disclaimer, the term of this patent is extended or adjusted under 35 U.S.C. 154(b) by 0 days.

(21) Appl. No.: 18/988,612

(22) Filed: Dec. 19, 2024

(65) Prior Publication Data

US 2025/0122274 A1 Apr. 17, 2025

Related U.S. Application Data

(63) Continuation of application No. PCT/US2023/085574, filed on Dec. 21, 2023.

(60) Provisional application No. 63/588,081, filed on Oct. 5, 2023, provisional application No. 63/515,267, filed on Jul. 24, 2023, provisional application No. 63/477,552, filed on Dec. 28, 2022, provisional application No. 63/476,908, filed on Dec. 22, 2022.

(51) Int. Cl.

| | |
|---|---|
| *C07K 16/22* | (2006.01) |
| *A61K 9/00* | (2006.01) |
| *A61K 31/155* | (2006.01) |
| *A61K 38/26* | (2006.01) |
| *A61K 39/00* | (2006.01) |
| *A61P 3/04* | (2006.01) |
| *A61P 3/10* | (2006.01) |

(52) U.S. Cl.

CPC ............ *C07K 16/22* (2013.01); *A61K 9/0019* (2013.01); *A61K 31/155* (2013.01); *A61K 38/26* (2013.01); *A61P 3/04* (2018.01); *A61P 3/10* (2018.01); *A61K 2039/505* (2013.01); *A61K 2039/54* (2013.01); *C07K 2317/21* (2013.01); *C07K 2317/565* (2013.01)

(58) Field of Classification Search

None

See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 4,816,397 | A | 3/1989 | Boss et al. |
| 4,816,567 | A | 3/1989 | Cabilly et al. |
| 5,013,556 | A | 5/1991 | Woodle et al. |
| 5,223,409 | A | 6/1993 | Ladner et al. |
| 5,981,568 | A | 11/1999 | Kunz et al. |
| 6,096,506 | A | 8/2000 | Lee et al. |
| 6,172,197 | B1 | 1/2001 | Mccafferty et al. |
| 6,291,158 | B1 | 9/2001 | Winter et al. |
| 6,582,915 | B1 | 6/2003 | Griffiths et al. |
| 6,593,081 | B1 | 7/2003 | Griffiths et al. |
| 6,656,475 | B1 | 12/2003 | Lee et al. |
| 6,696,245 | B2 | 2/2004 | Winter et al. |
| 6,858,208 | B2 | 2/2005 | Lee et al. |
| 7,083,784 | B2 | 8/2006 | Dall'acqua et al. |
| 7,138,501 | B2 | 11/2006 | Ruben et al. |
| 7,566,768 | B1 | 7/2009 | Lee et al. |
| 10,287,345 | B2 | 5/2019 | Donovan et al. |
| 10,307,480 | B2 | 6/2019 | Straub et al. |
| 10,751,413 | B2 | 8/2020 | Carven et al. |
| 10,882,904 | B2 | 1/2021 | Donovan et al. |
| 10,934,349 | B2 | 3/2021 | Pordy et al. |
| 10,946,036 | B2 | 3/2021 | Long et al. |
| 11,135,291 | B2 | 10/2021 | Straub et al. |
| 11,155,611 | B2 | 10/2021 | Donovan et al. |
| 11,439,704 | B2 | 9/2022 | Carven et al. |
| 11,925,683 | B2 | 3/2024 | Straub et al. |
| 12,006,359 | B2 | 6/2024 | Donovan et al. |
| 2002/0157126 | A1 | 10/2002 | Lee et al. |
| 2003/0167492 | A1 | 9/2003 | Lee et al. |
| 2005/0049402 | A1 | 3/2005 | Babcook et al. |
| 2005/0143306 | A1 | 6/2005 | Junker et al. |

(Continued)

FOREIGN PATENT DOCUMENTS

| | | | |
|---|---|---|---|
| AU | 2011244851 | A1 | 11/2011 |
| CN | 103097415 | A | 5/2013 |

(Continued)

OTHER PUBLICATIONS

Abdiche et al., "Antibodies Targeting Closely Adjacent or Minimally Overlapping Epitopes Can Displace One Another," PLoS One. Jan. 6, 2017;12(1):1-22.

(Continued)

*Primary Examiner* — Marianne P Allen

(74) *Attorney, Agent, or Firm* — FINNEGAN, HENDERSON, FARABOW, GARRETT & DUNNER, LLP

(57) ABSTRACT

The present disclosure relates to antibodies and antigen-binding fragments that specifically bind to pro/latent myostatin and uses thereof.

11 Claims, 65 Drawing Sheets

Specification includes a Sequence Listing.

(56) References Cited

U.S. PATENT DOCUMENTS

| | | |
|---|---|---|
| 2006/0025340 A1 | 2/2006 | Knopf et al. |
| 2006/0216279 A1 | 9/2006 | Glass et al. |
| 2006/0263354 A1 | 11/2006 | Chin et al. |
| 2007/0087000 A1 | 4/2007 | Walsh et al. |
| 2007/0178095 A1 | 8/2007 | Smith et al. |
| 2007/0218067 A1 | 9/2007 | Buttner et al. |
| 2008/0119426 A1 | 5/2008 | Dale |
| 2008/0213251 A1 | 9/2008 | Sexton et al. |
| 2008/0299126 A1 | 12/2008 | Han et al. |
| 2009/0031435 A1 | 1/2009 | Stockwell et al. |
| 2009/0131638 A1 | 5/2009 | Davies et al. |
| 2009/0148436 A1 | 6/2009 | Lavallie et al. |
| 2009/0324590 A1 | 12/2009 | Kambadur et al. |
| 2010/0080811 A1 | 4/2010 | Davies et al. |
| 2010/0087631 A1 | 4/2010 | Han et al. |
| 2010/0166764 A1 | 7/2010 | Sayers et al. |
| 2010/0183616 A1 | 7/2010 | Green et al. |
| 2010/0221777 A1 | 9/2010 | Choe et al. |
| 2010/0331252 A1 | 12/2010 | Hamrick et al. |
| 2011/0165175 A1 | 7/2011 | Linhard et al. |
| 2011/0239317 A1 | 9/2011 | Lee et al. |
| 2011/0256132 A1 | 10/2011 | Ashman et al. |
| 2011/0293630 A1 | 12/2011 | Stitt et al. |
| 2013/0065820 A1 | 3/2013 | Bower et al. |
| 2013/0209489 A1 | 8/2013 | Han et al. |
| 2013/0216548 A1 | 8/2013 | Neijssen et al. |
| 2013/0230515 A1 | 9/2013 | Han et al. |
| 2013/0336982 A1 | 12/2013 | Mader et al. |
| 2014/0017262 A1 | 1/2014 | Sanicola-Nadel et al. |
| 2014/0023638 A1 | 1/2014 | Lavallie et al. |
| 2016/0074474 A1 | 3/2016 | Passini et al. |
| 2016/0199458 A1 | 7/2016 | Knopf et al. |
| 2017/0198032 A1 | 7/2017 | Donovan et al. |
| 2017/0333558 A1 | 11/2017 | Straub et al. |
| 2021/0046180 A1 | 2/2021 | Carven et al. |
| 2021/0283166 A1 | 9/2021 | Long et al. |
| 2021/0332117 A1 | 10/2021 | Donovan et al. |
| 2024/0002490 A1 | 1/2024 | Nomikos et al. |
| 2024/0368262 A1 | 11/2024 | Long et al. |

FOREIGN PATENT DOCUMENTS

| | | |
|---|---|---|
| EP | 0171496 A2 | 2/1986 |
| EP | 0173494 A2 | 3/1986 |
| EP | 2853898 A1 | 4/2015 |
| EP | 3922645 A1 | 12/2021 |
| GB | 2177096 B | 5/1989 |
| JP | 2003520839 A | 7/2003 |
| JP | 2009545313 A | 12/2009 |
| JP | 2010502633 A | 1/2010 |
| KR | 20070105685 A | 10/2007 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 96/001845 A1 | 1/1996 |
| WO | WO 00/53211 A2 | 9/2000 |
| WO | WO 2002/009641 A2 | 2/2002 |
| WO | WO 2002/085306 A2 | 10/2002 |
| WO | WO 2003/027248 A2 | 4/2003 |
| WO | WO 2004/009776 A2 | 1/2004 |
| WO | WO 2004/024890 A2 | 3/2004 |
| WO | WO 2004/037861 A2 | 5/2004 |
| WO | WO 2005/066204 A2 | 7/2005 |
| WO | WO 2005/084699 A1 | 9/2005 |
| WO | WO 2005/103081 A2 | 11/2005 |
| WO | WO 2005/115439 A2 | 12/2005 |
| WO | WO 2006/116269 A2 | 11/2006 |
| WO | WO 2007/024535 A2 | 3/2007 |
| WO | WO 2007/044411 A2 | 4/2007 |
| WO | WO 2007/047112 A2 | 4/2007 |
| WO | WO 2007/061995 A2 | 5/2007 |
| WO | WO 2007/044411 A3 | 8/2007 |
| WO | WO 2008/030367 A2 | 3/2008 |
| WO | WO 2008/067480 A2 | 6/2008 |
| WO | WO 2008/119426 A1 | 10/2008 |
| WO | WO 2009/038760 A2 | 3/2009 |
| WO | WO 2010/070094 A1 | 6/2010 |
| WO | WO 2010/125003 A1 | 11/2010 |
| WO | WO 2010/144452 A1 | 12/2010 |
| WO | WO 2011/122011 A2 | 10/2011 |
| WO | WO 2011/150008 A1 | 12/2011 |
| WO | WO 2012/024242 A1 | 2/2012 |
| WO | WO 2013/071056 A2 | 5/2013 |
| WO | WO 2013/072902 A1 | 5/2013 |
| WO | WO 2013/074557 A1 | 5/2013 |
| WO | WO 2013/148284 A1 | 10/2013 |
| WO | WO 2013/165972 A2 | 11/2013 |
| WO | WO 2013/186719 A1 | 12/2013 |
| WO | WO 2014/074532 A2 | 5/2014 |
| WO | WO 2014/182676 A2 | 11/2014 |
| WO | WO 2015/070158 A1 | 5/2015 |
| WO | WO 2015/195094 A1 | 12/2015 |
| WO | WO 2016/073853 A1 | 5/2016 |
| WO | WO 2016/073879 A2 | 5/2016 |
| WO | WO 2016/073906 A2 | 5/2016 |
| WO | WO 2016/098357 A1 | 6/2016 |
| WO | WO 2016/168613 A1 | 10/2016 |
| WO | WO 2017/049011 A1 | 3/2017 |
| WO | WO 2017/120523 A2 | 7/2017 |
| WO | WO 2017/218592 A1 | 12/2017 |
| WO | WO 2018/116201 A1 | 6/2018 |
| WO | WO 2018/129395 A1 | 7/2018 |
| WO | WO 2019/193204 A1 | 10/2019 |
| WO | WO 2020/160291 A2 | 8/2020 |
| WO | WO 2022/093724 A1 | 5/2022 |
| WO | WO 2022/164351 A1 | 8/2022 |
| WO | WO 2022/271867 A1 | 12/2022 |
| WO | WO 2023/215384 A2 | 11/2023 |
| WO | WO 2024/064842 A1 | 3/2024 |

OTHER PUBLICATIONS

Abdiche et al., "High-throughput epitope binning assays on label-free array-based biosensors can yield exquisite epitope discrimination that facilitates the selection of monoclonal antibodies with functional activity," PLoS One. Mar. 20, 2014;9(3):1-16.

Ader, D., "Developing the patient-reported outcomes measurement information system (PROMIS)," Medical care 45.5 (2007): S1-S2.

Al-Zaidy et al., "Follistatin Gene Therapy Improves Ambulation in Becker Muscular Dystrophy," J Neuromuscul Dis. 2015; 2(3):185-192.

Alfano et al., "Validity and reliability of the neuromuscular gross motor outcome," Pediatric Neurology 122 (2021): 21-26.

Altschul et al., "Basic local alignment search tool," Journal of molecular biology 215.3 (1990): 403-410.

Altschul et al., "Gapped BLAST and PSI-BLAST: a new generation of protein database search programs," Nucleic acids research 25.17 (1997): 3389-3402.

Alves et al., "Serum creatinine is a biomarker of progressive denervation in spinal muscular atrophy," Neurology 94.9 (2020): e921-e931.

Amato et al., "Treatment of sporadic inclusion body myositis with bimagrumab," Neurology 83.24 (2014): 2239-2246.

Ambery et al., "MEDI0382, a GLP-1 and glucagon receptor dual agonist, in obese or overweight patients with type 2 diabetes: a randomised, controlled, double-blind, ascending dose and phase 2a study," The Lancet 391.10140 (2018): 2607-2618.

Amthor et al., "Lack of myostatin results in excessive muscle growth but impaired force generation, "Proc Natl Acad Sci U S A. Feb. 6, 2007;104(6):1835-1840.

Anderson et al., "Identification of a novel pool of extracellular pro myostatin in skeletal muscle," The Journal of Biological Chemistry, 2008, 283(11):7027-7035.

Angal et al., "A single amino acid substitution abolishes the heterogeneity of chimeric mouse/human (IgG4) antibody," Molecular immunology 30.1 (1993): 105-108.

(56) References Cited

OTHER PUBLICATIONS

Annoussamy et al., "Natural history of Type 2 and 3 spinal muscular atrophy: 2-year NatHis-SMA study," Annals of Clinical and Translational Neurology 8.2 (2021): 359-373.

Anterolateral Systems—Deficits, 2017, [online]. Retrieved from: http://www.neuroanatomy.wisc.edu/sc97/text/p2/deficits.htm; on Jul. 11, 2017 (1 page).

Applebaum et al., "Modified 30-second Sit to Stand test predicts falls in a cohort of institutionalized older veterans," Plos one 12.5 (2017): 1-13.

Aragon-Gawinska et al., "Nusinersen in patients older than 7 months with spinal muscular atrophy type 1: a cohort study," Neurology 91.14 (2018): e1312-e1318.

Aronne et al., "Continued treatment with tirzepatide for maintenance of weight reduction in adults with obesity: the SURMOUNT-4 randomized clinical trial," Jama, 331.1, (2024): 38-48.

ASIA (American Spinal Injury Association) Impairment Scale, Standard Neurological Classification of Spinal Cord Injury, (2000): 1-2.

Australian Application No. 202010134, filed Jul. 27, 2020, for Scholar Rock, Inc.: Examination Report No. 1, issued Oct. 15, 2020, 15 pages.

Awano et al., "Spinal muscular atrophy: journeying from bench to bedside," Neurotherapeutics 11.4 (2014): 786-795.

Axente et al., "Clinical features and genetics in non-5q spinal muscular atrophy caused by acid ceramidase deficiency," Journal of Medicine and Life 14.3 (2021): 1-5.

Bahne et al., "Metformin-induced glucagon-like peptide-1 secretion contributes to the actions of metformin in type 2 diabetes," JCI insight, 3.23, (2018): 1-16.

Bailey, C., "GIP analogues and the treatment of obesity-diabetes," Peptides. Mar. 2020;125:1-7.

Baranello et al., "Evaluation of body composition as a potential biomarker in spinal muscular atrophy," Muscle & Nerve, 2020, 61(4):530-534.

Baranello et al., "Risdiplam in type 1 spinal muscular atrophy," New England Journal of Medicine 384.10 (2021): 915-923.

Barrett et al., "A randomized phase 1 safety, pharmacokinetic and pharmacodynamic study of the novel myostatin inhibitor apitegromab (SRK-015): a potential treatment for spinal muscular atrophy," Advances in Therapy 38.6 (2021): 3203-3222.

Bartels et al., "Fatigability in spinal muscular atrophy: validity and reliability of endurance shuttle tests," Orphanet Journal of Rare Diseases 15 (2020): 1-9.

Becker et al., "Myostatin antibody (LY2495655) in older weak fallers: a proof-of-concept, randomised, phase 2 trial," The Lancet Diabetes & Endocrinology. 2015;3(12):948-957.

Belhayara et al., "The metabolic syndrome: emerging novel insights regarding the relationship between the homeostasis model assessment of insulin resistance and other key predictive markers in young adults of Western Algeria," Nutrients 12.3 (2020): 1-13.

Benatar, M., "Lost in translation: Treatment trials in the SOD1 mouse and in human ALS," Neurobiology of Disease, 2007, 26:1-13.

Benjamini et al., "Immunology: A Short Course," 1991, 2nd edition, p. 40 only.

Bergen et al., "Myostatin as a mediator of sarcopenia versus homeostatic regulator of muscle mass: insights using a new mass spectrometry-based assay," Skeletal muscle 5 (2015): 1-16.

Bernardo et al., "Postnatal PPARdelta activation and myostatin inhibition exert distinct yet complimentary effects on the metabolic profile of obese insulin-resistant mice," PLoS One, 2010, 25;5(6):1-11.

Bhattacharya et al., "Comparative analysis of silencing expression of myostatin (MSTN) and its two receptors (ACVR2A and ACVR2B) genes affecting growth traits in knock down chicken," Sci Rep . May 24, 2019;9(1):7789 (13 pgs.).

Biovendor, "Myostatin Propeptide Human, Chicken Polyclonal Antibody," Product Data Sheet, Apr. 11, 2013, 3 pages.

Bird et al. "Single-chain antigen-binding proteins," Science 242. 4877 (1988): 423-426.

Bolon et al., "STP position paper: recommended best practices for sampling, processing, and analysis of the peripheral nervous system (nerves and somatic and autonomic ganglia) during nonclinical toxicity studies," Toxicologic Pathology 46.4 (2018): 372-402.

Bolon et al., "STP position paper: recommended practices for sampling and processing the nervous system (brain, spinal cord, nerve, and eye) during nonclinical general toxicity studies," Toxicologic pathology 41.7 (2013): 1028-1048.

Bowerman et al., "Therapeutic strategies for spinal muscular atrophy: SMN and beyond," Dis Model Mech. 2017; 10(8):943-954.

Brakemeier et al., "Assessment of bulbar function in adult patients with 5q-SMA type 2 and 3 under treatment with nusinersen," Brain Sciences 11.9 (2021): 1-9.

Bräuninger et al., "Epstein-Barr virus (EBV)-positive lymphoproliferations in post-transplant patients show immunoglobulin V gene mutation patterns suggesting interference of EBV with normal B cell differentiation processes," 2003, Eur J Immunol., 33(6):1593-1602.

Breitbart et al., "Highly specific detection of myostatin prodomain by an immunoradiometric sandwich assay in serum of healthy individuals and patients," 2013, PLoS One, 8(11):1-10.

Brown et al., "Tolerance to single, but not multiple, amino acid replacements in antibody VH CDR 2: a means of minimizing B cell wastage from somatic hypermutation?" 1996, J Immunol., 156(9):3285-3291.

Burch et al., "Reduced serum myostatin concentrations associated with genetic muscle disease progression," Journal of Neurology, 2017, 264(3):541-553.

Butler et al., "Reversing type 1 diabetes with stem cell-derived islets: a step closer to the dream?" The Journal of Clinical Investigation 132.3 (2022): 1-2.

Cabri et al., "Therapeutic peptides targeting PPI in clinical development: Overview, mechanism of action and perspectives," Frontiers in Molecular Biosciences 8 (2021): 1-21.

Calder et al., "Small molecules in development for the treatment of spinal muscular atrophy: miniperspective," Journal of medicinal chemistry 59.22 (2016): 10067-10083.

Calucho et al., "Correlation between SMA type and SMN2 copy number revisited: an analysis of 625 unrelated Spanish patients and a compilation of 2834 reported cases," Neuromuscular Disorders 28.3 (2018): 208-215.

Campbell et al., "Myostatin inhibitor ACE-031 treatment of ambulatory boys with Duchenne muscular dystrophy: results of a randomized, placebo-controlled clinical trial," Muscle & nerve 55.4 (2017): 458-464.

Cances et al., "Natural history of type 1 spinal muscular atrophy: a retrospective, global, multicenter study," Orphanet Journal of Rare Diseases 17.1 (2022): 1-11.

Castellana et al., "Resurrection of a clinical antibody: template proteogenomic de novo proteomic sequencing and reverse engineering of an anti-lymphotoxin-α antibody," Proteomics. Feb. 2011;11(3):395-405.

Cava et al., "Preserving healthy muscle during weight loss," Advances in nutrition 8.3 (2017): 511-519.

Cavagnaro, J., "Preclinical safety evaluation of biotechnology-derived pharmaceuticals," Nature Reviews Drug Discovery 1.6 (2002): 469-475.

Cedarbaum et al., "The ALSFRS-R: a revised ALS functional rating scale that incorporates assessments of respiratory function. BDNF ALS Study Group (Phase III)," Journal of the neurological sciences 169.1-2 (1999): 13-21.

Chan et al., "Bone Geometry Is Altered by Follistatin-Induced Muscle Growth in Young Adult Male Mice," JBMR Plus, 2021, 5(4):1-12.

Chen et al., "Considerations for Developing Combination Therapies in SMA," Cure SMA Researcher Meeting, Jun. 16, 2016, 57 pages.

Chen et al., "The development and validation of a dysphagia-specific quality-of-life questionnaire for patients with head and neck cancer: the MD Anderson dysphagia inventory," Archives of Otolaryngology—Head & Neck Surgery 127.7 (2001): 870-876.

(56) References Cited

OTHER PUBLICATIONS

Chiriboga et al., "Longer-Term treatment with nusinersen: results in Later-onset spinal muscular atrophy from the shine study (1661)," Neurology 94.15 Supplement (2020): 1-3.

Chiriboga et al., "Results from a phase 1 study of nusinersen (ISIS-SMNRx) in children with spinal muscular atrophy," Neurology 86.10 (2016): 890-897.

Chitramuthu et al., "Progranulin modulates zebrafish motoneuron development in vivo and rescues truncation defects associated with knockdown of Survival motor neuron 1," Molecular neurodegeneration 5 (2010): 1-13.

Ciciliot et al., "Muscle type and fiber type specificity in muscle wasting," Int J Biochem Cell Biol., 2013, 45(10):2191-2199.

Clackson et al., "Making antibody fragments using phage display libraries," Nature 352.6336 (1991): 624-628.

Cohen et al., "Muscle wasting in disease: molecular mechanisms and promising therapies," Nat Rev Drug Discov., 2015, 14(1):58-74.

Coratti et al., "Age and baseline values predict 12 and 24-month functional changes in type 2 SMA," Neuromuscular Disorders 30.9 (2020): 756-764.

Coratti et al., "Clinical variability in spinal muscular atrophy type III," Annals of neurology 88.6 (2020): 1109-1117.

Corey, "Nusinersen, an antisense oligonucleotide drug for spinal muscular atrophy," Nature Neuroscience, vol. 20, Feb. 13, 2017, pp. 497-499.

Cornell, S., "A review of GLP-1 receptor agonists in type 2 diabetes: a focus on the mechanism of action of once-weekly agents," Journal of clinical pharmacy and therapeutics 45 (2020): 17-27.

Cote et al., "A sensitive and selective immunoassay for the quantitation of serum latent myostatin after in vivo administration of SRK-015, a selective inhibitor of myostatin activation," SLAS Discovery: Advancing Life Sciences R&D 25.1 (2020): 95-103.

Crawford et al., "Apitegromab in Spinal Muscular Atrophy (SMA): An Analysis of Multiple Efficacy Endpoints in the TOPAZ Trial (P15-5.005)," American Academy of Neurology, May 2022, vol. 98, No. 18 Supp, 8 pages.

Crawford et al., "Relationship of pharmacokinetics and pharmacodynamics to apitegromab efficacy in patients with later-onset spinal muscular atrophy (Types 2 and 3 SMA): Results from the TOPAZ study," Abstracts/Journal of Neurological Sciences Oct. 2021, vol. 429, 1 page.

Cully, "Beefing up the right splice variant to treat spinal muscular atrophy," Nat Rev Drug Discov, 2014, 13, (1 pg.).

Cure SMA Presentation filed in opposition of EP Patent No. 3368069 on Apr. 27, 2022 (86 pgs.).

D'Ydewalle et al., "Spinal muscular atrophy therapeutics: where do we stand?," Neurotherapeutics, (2015), 12(2):303-316.

Dagbay et al., "Structural basis of specific inhibition of extracellular activation of pro- or latent myostatin by the monoclonal antibody SRK-015," J. Biol. Chem., 2020, 295(16):5404-5418.

Dalbo et al., "Testosterone and trenbolone enanthate increase mature myostatin protein expression despite increasing skeletal muscle hypertrophy and satellite cell number in rodent muscle," Andrologia, 2017, 49(3):1-11.

Dankbar et al. "Myostatin—a new player in inflammatory bone loss," Annals of the Rheumatic Diseases 70.Suppl 2 (2011): A75-A76.

Darras et al., "Nusinersen in later-onset spinal muscular atrophy: long-term results from the phase 1/2 studies," Neurology 92.21 (2019): e2492-e2506.

Darras et al., "Risdiplam-treated infants with type 1 spinal muscular atrophy versus historical controls," New England Journal of Medicine 385.5 (2021): 427-435.

David et al., "Identification of BMP9 and BMP10 as functional activators of the orphan activin receptor-like kinase 1 (ALK1) in endothelial cells," Blood 109.5 (2007): 1953-1961.

Day et al., "Advances and limitations for the treatment of spinal muscular atrophy," BMC pediatrics 22.1 (2022): 1-15.

Day et al., "Onasemnogene abeparvovec gene therapy for symptomatic infantile-onset spinal muscular atrophy in patients with two copies of SMN2 (STR1VE): an open-label, single-arm, multicentre, phase 3 trial," Lancet Neurol, 2021, 20:284-293.

De Onis et al., "The WHO Multicentre Growth Reference Study: planning, study design, and methodology," Food and nutrition bulletin 25 (2004): S15-S26.

Deguise et al., "New insights into SMA pathogenesis: immune dysfunction and neuroinflammation," Ann Clin Transl Neurol., 2017, 4(7):522-530.

Dibernardo et al., "Translating preclinical insights into effective human trials in ALS," Biochimica et Biophysica Acta, 2006, 1762:1139-1149.

Ding et al., "BPI-3016, a novel long-acting hGLP-1 analogue for the treatment of Type 2 diabetes mellitus," Pharmacological Research 122 (2017): 130-139.

Dinicolantonio et al., "Postprandial insulin assay as the earliest biomarker for diagnosing pre-diabetes, type 2 diabetes and increased cardiovascular risk," Open Heart 4.2 (2017): 1-4.

Du et al., "Metformin in therapeutic applications in human diseases: Its mechanism of action and clinical study," Molecular Biomedicine 3.1 (2022): 1-32.

Ducata et al., "Solution equilibrium titration for high-throughput affinity estimation of unpurified antibodies and antibody fragments," Journal of Biomolecular Screening 20.10 (2015): 1256-1267.

Dunaway Young et al., "Scoliosis surgery significantly impacts motor abilities in higher-functioning individuals with spinal muscular atrophy," Journal of Neuromuscular Diseases 7.2 (2020): 183-192.

Dunaway Young et al., "Six-minute walk test is reliable and valid in spinal muscular atrophy," Muscle & nerve 54.5 (2016): 836-842.

Duong et al., "Use of the children's hospital of Philadelphia infant test of neuromuscular disorders (CHOP Intend) in X-linked myotubular myopathy: content validity and psychometric performance," Journal of Neuromuscular Diseases 8.1 (2021): 63-77.

Dwivedi et al., "Validation of the Sydney Swallow Questionnaire (SSQ) in a cohort of head and neck cancer patients," Oral oncology 46.4 (2010): e10-e14.

Egerman et al., "GDF11 Increases with Age and Inhibits Skeletal Muscle Regeneration," Cell Metabolism, 2015, 22(1):164-174.

Ellulu et al., "Obesity and inflammation: the linking mechanism and the complications," Archives of medical science 13.4 (2017): 851-863.

EMA (European Medicines Agency)., Zolgensma, European Public Assessment Report (EPAR). EMA/200482/2020. (2020): 1-150.

Eppstein et al., "Biological activity of liposome-encapsulated murine interferon gamma is mediated by a cell membrane receptor," Proceedings of the National Academy of Sciences 82.11 (1985): 3688-3692.

European Patent Application No. 16828657.3, by Scholar Rock, Inc.: Supplementary European Search Report and Opinion, dated Mar. 20, 2019, 14 pages.

European Patent Application No. 20179533.3, by Scholar Rock, Inc.: Partial European Search Report, dated Mar. 31, 2021, 12 pgs.

European Patent Application No. 20193425.4, by Scholar Rock, Inc.: European Search Report, dated Apr. 1, 2021, 9 pgs.

Extended European Search Report in EP Application No. 21170667.6 dated Nov. 11, 2021, 19 pages.

Extended European Search Report in EP23158609.0, dated Aug. 8, 2023, 27 pages.

Fallah et al., "Comparison of T1-weighted 2D TSE, 3D SPGR, and two-point 3D Dixon MRI for automated segmentation of visceral adipose tissue at 3 Tesla," Magnetic Resonance Materials in Physics, Biology and Medicine 30 (2017): 139-151.

Farrar et al., "Emerging therapies and challenges in spinal muscular atrophy" Ann Neural, 2017, 81(3): 355-368.

Feng et al., "Pharmacologically induced mouse model of adult spinal muscular atrophy to evaluate effectiveness of therapeutics after disease onset," Human Molecular Genetics, 2016, 25(5):964-975.

Ferrara et al., "Recombinant renewable polyclonal antibodies," MAbs, 2015, 7(1):32-41.

(56) References Cited

OTHER PUBLICATIONS

Fidler, "Scholar Rock Rolls Up $36M To Move Muscle Drug To Clinical Trials," 2016, https://xconomy.com/boston/2016/01/04/scholar-rock-rolls-up-36m-to-move-muscle-drug-to-clinical-trials/, 3 pages.
Finkel et al., "Nusinersen versus sham control in infantile-onset spinal muscular atrophy," New England Journal of Medicine 377.18 (2017): 1723-1732.
Finkel et al., "Treatment of infantile-onset spinal muscular atrophy with nusinersen: a phase 2, open-label, dose-escalation study," The Lancet 388.10063 (2016): 3017-3026.
Fock et al., "Diet and exercise in management of obesity and overweight," J Gastroenterol Hepatol. Dec. 2013; 28 Suppl 4:59-63.
Foster, "Malonyl-CoA: the regulator of fatty acid synthesis and oxidation", J Clin Invest. 2012;122(6):1958-1959.
Frohlich et al., "GDF11 inhibits adipogenesis and improves mature adipocytes metabolic function via WNT/β-catenin and ALK5/SMAD2/3 pathways," Cell Proliferation 55.10 (2022): 1-15.
Garito et al., "Bimagrumab improves body composition and insulin sensitivity in insulin-resistant individuals," Diabetes, obesity and metabolism 20.1 (2018): 94-102.
Gascon et al., "Non-viral delivery systems in gene therapy," Chapter 1 in: Gene therapy-tools and potential applications. IntechOpen, (2013) 1-43.
GDF-11/BMP-11 Mouse anti-Human, Clone: 743833, R&D Systems(TM), [online]. Retrieved from: http://www.fishersci.co.uk/shop/products/gdf-11bpm-11-mouse-anti-human-clone-743833-r-d-systems/15724724; on Feb. 28, 2019 (4 pgs.).
Ge et al., "GDF11 Forms a Bone Morphogenetic Protein 1-Activated Latent Complex That Can Modulate Nerve Growth Factor-Induced Differentiation of PC12 Cells," Molecular and Cellular Biology, 2005, 25(14):5846-5858.
Giangregorio et al., "Bone Loss and Muscle Atrophy in Spinal Cord Injury: Epidemiology, Fracture Prediction, and Rehabilitation Strategies," J Spinal Cord Med., 2006, 29(5):489-500.
Glanzman et al., "The Children's Hospital of Philadelphia infant test of neuromuscular disorders (CHOP Intend): test development and reliability," Neuromuscular Disorders 20.3 (2010): 155-161.
Glanzman et al., "Validation of the Expanded Hammersmith Functional Motor Scale in spinal muscular atrophy type II and III," Journal of child neurology 26.12 (2011): 1499-1507.
Godoy-Matos et al., "NAFLD as a continuum: from obesity to metabolic syndrome and diabetes," Diabetology & metabolic syndrome 12 (2020): 1-20.
Gogliotti et al., "Characterization of a commonly used mouse model of SMA reveals increased seizures susceptibility and heightened fear response in FVB/N mice," Neurobiol Dis., 2011, 43(1):142-151.
Golan et al., "LY2495655, an antimyostatin antibody, in pancreatic cancer: a randomized, phase 2 trial," Journal of Cachexia, Sarcopenia and Muscle. 2018;9(5):871-879.
Golay, A., "Metformin and body weight," International Journal of Obesity 32.1 (2008): 61-72.
Gonzalez et al., "BMP-1/Tolloid-like Metalloproteases Process Endorepellin, the Angiostatic C-terminal Fragment of Perlecan," The Journal of Biological Chemistry, 2005, 280(8):7080-7087.
Gonzalez Trotter et al., "34-OR: The Effect of Combined Activin A and Myostatin Blockade on Body Composition—A Phase 1 Trial. Diabetes," 2024;73(Supplement_1), 4 pages.
Gorgey et al., "Effects of spinal cord injury on body composition and metabolic profile—Part I" J Spinal Cord Med. 2014; 37(6):693-702.
Goyal et al., "Evaluation of TNF-α and IL-6 levels in obese and non-obese diabetics: pre-and postinsulin effects," North American journal of medical sciences 4.4 (2012): 180-184.
Graham et al., "A Soluble Myostatin Inhibitor Does Not Prevent Sublesional Muscle Atrophy 56 Days After Spinal Cord Injury in Mice," Medicine & Science in Sports & Exercise, 2015, Abstract No. 2219:587.
Guidance for Industry: S6 Preclinical Safety Evaluation of Biotechnology-Derived Pharmaceuticals. FDA, Jul. 1997, 1-14.
Guidance for Industry: S9 Nonclinical Evaluation for Anticancer Pharmaceuticals. FDA, Mar. 2010, 1-12.
"Guideline on development, production, characterization and specification for monoclonal antibodies and related products," European Medicines Agency, (2016): 1-13.
Guo et al., "Myostatin Inhibition in Muscle, but Not Adippose Tissue, Decreases Fat Mass and Improves Insulin Sensitivity," PLoS One, 2009, 4(3):1-11.
Gupta et al., "Myopathy associated with statins and SGLT2—a review of literature," Current problems in cardiology 46.4 (2021): 1-13.
Hagan, "When are mice considered old?" 2017, https://www.jax.org/news-and insights/jax-blog/2017/november/when-are-mice-considered-old, 2 pages.
Haley et al., "Assessing mobility in children using a computer adaptive testing version of the pediatric evaluation of disability inventory," Archives of Physical Medicine and Rehabilitation 86.5 (2005): 932-939.
Hamrick, M., "The skeletal muscle secretome: an emerging player in muscle-bone crosstalk," Bonekey Rep. Apr. 11, 2012;1:(2012): 1-5.
Hanna et al., "Safety and efficacy of intravenous bimagrumab in inclusion body myositis (RESILIENT): a randomised, double-blind, placebo-controlled phase 2b trial," The Lancet Neurology 18.9 (2019): 834-844.
Hansen et al., "Incretin mimetics: a novel therapeutic option for patients with type 2 diabetes—a review," Diabetes Metab Syndr Obes. May 17, 2010;3:155-63.
Harms et al., "Brown and beige fat: development, function and therapeutic potential," Nature medicine 19.10 (2013): 1252-1263.
Herweijer et al., "Progress and prospects: naked DNA gene transfer and therapy," Gene therapy 10.6 (2003): 453-458.
Heymsfield et al., "Effect of Bimagrumab vs Placebo on Body Fat Mass Among Adults With Type 2 Diabetes and Obesity: A Phase 2 Randomized Clinical Trial," JAMA Network. 4 (2021):1-13.
History of Change for Study NCT05115110: A Study to Investigate the Safety and Efficacy of RO7204239 in Combination With Risdiplam (RO7034067) in Ambulat Spinal Muscular Atrophy, Nov. 2021, URL:https://clinicaltrials.gov/ct2/history/NCT05115110?V_1=View#StudyPage Top, 8 pages.
History of Changes for Study NCT03921528: An Active Treatment Study of SRK-015 in Patients with Type 2 or Type 3 Spinal Muscular Atrophy, Jan. 2020. URL:https://clinicaltrials.gov/ct2/history/NCT03921528?V_13=View#StudyPage Top, 6 pages.
Holliger et al., "Diabodies": small bivalent and bispecific antibody fragments, Proceedings of the National Academy of Sciences 90.14 (1993): 6444-6448.
Holzbaur et al., "Myostatin inhibition slows muscle atrophy in rodent models of amyotrophic lateral sclerosis," Neurobiol Dis., 2006, 23(3):697-707.
Hori et al., "Elimination of plasma soluble antigen in cynomolgus monkeys by combining pH-dependent antigen binding and novel Fc engineering" MAbs., 2022, 14(1):1-12.
Hrebicek et al., "Detection of insulin resistance by simple quantitative insulin sensitivity check index QUICKI for epidemiological assessment and prevention," The Journal of Clinical Endocrinology & Metabolism 87.1 (2002): 144-147.
Hua et al., "Antisense correction of SMN2 splicing in the CNS rescues necrosis in a type III SMA mouse model," Genes & development 24.15 (2010): 1634-1644.
Hua et al., "Enhancement of SMN2 Exon 7 inclusion by Antisense Oligonucleotides Targeting the Exon," PLOS Biology 5.4 (2007): 0729-0742.
Hua et al., "Peripheral SMN restoration is essential for long-term rescue of a severe spinal muscular atrophy mouse model," Nature 478.7367 (2011): 123-126.
Human Myostatin ELISA—Prodomain specific, BioVendor Laboratory Medicine, Inc., 2005, XP055100354, Retrieved from the Internet: URL:http://deltaclon.es/pdf/RD193058100.pdf, 10 pages.
Huston et al., "Protein engineering of antibody binding sites: recovery of specific activity in an anti-digoxin single-chain Fv

(56) References Cited

OTHER PUBLICATIONS analogue produced in *Escherichia coli*," Proceedings of the National Academy of Sciences 85.16 (1988): 5879-5883.
Hwang et al., "Hepatic uptake and degradation of unilamellar sphingomyelin/cholesterol liposomes: a kinetic study," Proceedings of the National Academy of Sciences 77.7 (1980): 4030-4034.
Iannaccone et al., "The PedsQL™ in pediatric patients with spinal muscular atrophy: feasibility, reliability, and validity of the pediatric quality of life inventory™ generic core scales and neuromuscular module," Neuromuscular Disorders 19.12 (2009): 805-812.
Igawa et al., "Engineered Monoclonal Antibody with Novel Antigen-Sweeping Activity In Vivo". PLoS One, 2013, 8(5): 1-10.
Igawa et al., "pH-dependent antigen-binding antibodies as a novel therapeutic modality," Biochimica et Biophysica Acta 1844 (2014) 1943-1950.
Incretin mimetic drugs for type 2 diabetes—FDA, downloaded on Sep. 9, 2024, 1 page.
International Preliminary Report on Patentability for Application No. PCT/US2015/059468, dated May 9, 2017 (12 pgs.).
International Preliminary Report on Patentability for Application No. PCT/US2015/059515, dated May 9, 2017 (12 pgs.).
International Preliminary Report on Patentability for Application No. PCT/US2015/059557, dated May 9, 2017 (8 pgs.).
International Preliminary Report on Patentability for Application No. PCT/US2016/052014, dated Mar. 20, 2018 (11 pgs.).
International Search Report and Written Opinion for Application No. PCT/US2016/052014, dated Jan. 9, 2017 (17 pgs.).
International Search Report and Written Opinion in International Application No. PCT/US2016/043712, by Scholar Rock, Inc., mailed Jan. 13, 2017, 22 pages.
International Search Report and Written Opinion in International Application No. PCT/US2017/012606, by Scholar Rock, Inc., mailed Jul. 24, 2017, 35 pages.
International Search Report and Written Opinion in International Application No. PCT/US2017/037332, by Scholar Rock, Inc., mailed Nov. 14, 2017, 19 pages.
International Search Report and Written Opinion in International Application No. PCT/US2018/012686, by Scholar Rock, Inc., mailed Apr. 3, 2018, 13 pages.
International Search Report and Written Opinion of the International Searching Authority received in PCT/US2021/056517, mailed Mar. 2, 2022 (23 pgs.).
International Search Report and Written Opinion of the International Searching Authority received in PCT/US2022/034588, mailed on Oct. 6, 2022 (10 pages).
International Search Report and Written Opinion of the International Searching Authority received in PCT/US2023/020843, mailed Oct. 30, 2023 (19 pgs.).
International Search Report and Written Opinion of the International Searching Authority received in PCT/US2023/085574, mailed May 7, 2024 (16 pgs.).
International Search Report for Application No. PCT/US2015/059468, dated Apr. 4, 2016 (6 pgs.).
International Search Report for Application No. PCT/US2015/059515, dated Mar. 25, 2016 (8 pgs.).
International Search Report for Application No. PCT/US2015/059557, dated May 19, 2016 (5 pgs.).
Ito et al., "Skeletal muscle atrophy and short-term mortality in patients with acute exacerbation of idiopathic pulmonary fibrosis: an observational cohort study," Respiratory Investigation 61.4 (2023): 371-378.
Jablonka et al., "Therapy development for spinal muscular atrophy: perspectives for muscular dystrophies and neurodegenerative disorders," Neurol Res Pract., 2022, 4(7):522-530.
Japanese Patent Application No. 2019-517209, filed Jun. 13, 2017, by Scholar Rock, Inc., Decision to Grant a Patent, mailed Dec. 8, 2020 (7 pgs.).
Jarolim et al., "Determination of Cardiac Troponin with a Single-Molecule High-Sensitivity Assay and Outcomes in Patients with Stable Coronary Artery Disease: Analysis from Prove IT-TIMI 22,"
2013 AACC Annual Meeting Abstracts B-175, Retrieved from the Internet: URL:http://www.aacc.org/events/Annual_Meeting/abstracts/Documents/AACC_13_AM_B175-B239.pdf, p. S249.
Jedrzejowska, M., "Advances in newborn screening and presymptomatic diagnosis of spinal muscular atrophy," Degenerative Neurological and Neuromuscular Disease (2020): 39-47.
Jiang et al., "Genomic analysis of a spinal muscular atrophy (SMA) discordant family identifies a novel mutation in TLL2, an activator of growth differentiation factor 8 (myostatin): a case report," BMC Medical Genetics, 2019, 20(1):1-7.
Jobling et al., "Isoform-specific activation of latent transforming growth factor beta (LTGF-beta) by reactive oxygen species," Radiat Res., 2006, 166(6):839-848.
Jones et al., "A 30-s chair-stand test as a measure of lower body strength in community-residing older adults," Research quarterly for exercise and sport 70.2 (1999): 113-119.
Jones et al., "Validation of quantitative magnetic resonance for the determination of body composition of mice," International journal of body composition research 7.2 (2009): 67-72.
Kariya et al., "Requirement of enhanced Survival Motoneuron protein imposed during neuromuscular junction maturation," The Journal of Clinical Investigation, 2014, 124(2):785-800.
Karlin et al., "Applications and statistics for multiple high-scoring segments in molecular sequences," Proceedings of the National Academy of Sciences 90.12 (1993): 5873-5877.
Karlin et al., "Methods for assessing the statistical significance of molecular sequence features by using general scoring schemes," Proceedings of the National Academy of Sciences 87.6 (1990): 2264-2268.
Kaufmann et al., "Observational study of spinal muscular atrophy type 2 and 3: functional outcomes over 1 year," Arch Neurol. Jun. 2011;68(6):779-86.
Kaufmann et al., "Prospective cohort study of spinal muscular atrophy types 2 and 3," Neurology 79.18 (2012): 1889-1897.
Knappik et al., "Recombinant Antibody Expression and Purification," Chapter 203 of The Protein Protocols Handbook, 2009, (pp. 1929-1943).
Kohler et al., "Continuous cultures of fused cells secreting antibody of predefined specificity," Nature 256.5517 (1975): 495-497.
Kong et al., "Impaired prenatal motor axon development necessitates early therapeutic intervention in severe SMA," Science translational medicine 13.578 (2021): 1-30.
Kubo et al., "A new method for SMN1 and hybrid SMN gene analysis in spinal muscular atrophy using long-range PCR followed by Sequencing," Journal of Human Genetics, Published Feb. 26, 2015, pp. 233-238.
Lakshman et al., "Measurement of myostatin concentrations in human serum: circulating concentrations in young and older men and effects of testosterone administration," Molecular and cellular endocrinology 302.1 (2009): 26-32.
Lander et al., "Appion: an integrated, database-driven pipeline to facilitate EM image processing," Journal of structural biology 166.1 (2009): 95-102.
Landfeldt et al., "Quality of life of patients with spinal muscular atrophy: a systematic review," European journal of paediatric neurology 23.3 (2019): 347-356.
Latres et al., "Activin A more prominently regulates muscle mass in primates than does GDF8," Nature Communications, 2017, 8:1-13.
Latres et al., "Myostatin blockade with a fully human monoclonal antibody induces muscle hypertrophy and reverses muscle atrophy in young and aged mice," Skeletal Muscle, 2015, 5:1-13.
Le Berre et al., "The psychometric properties of a modified sit-to-stand test with use of the upper extremities in institutionalized older adults," Perceptual and motor skills 123.1 (2016): 138-152.
Lee et al., "Regulation of muscle growth by multiple ligands signaling through activin type II receptors," Proceedings of the National Academy of Sciences 102.50 (2005): 18117-18122.
Lee et al., "Regulation of myostatin activity and muscle growth," Proceedings of the National Academy of Sciences 98.16 (2001): 9306-9311.
Lee, "Myostatin: A Skeletal Muscle Chalone," Annu Rev Physiol., 2023, 10;85:269-291.

(56) References Cited

OTHER PUBLICATIONS

Le Verche et al., "Skeletal Muscle in Spinal Muscular Atrophy As an Opportunity for Therapeutic Intervention," Chapter 21 in Spinal Muscular Atrophy: Disease Mechanisms and Therapy, (2017): 341-356.

Lefebvre et al., "Identification and characterization of a spinal muscular atrophy-determining gene," Cell 80.1 (1995): 155-165.

Li et al., "Glutazumab, a novel long-lasting GLP-1/anti-GLP-1R antibody fusion protein, exerts anti-diabetic effects through targeting dual receptor binding sites," Biochemical Pharmacology 150 (2018): 46-53.

Ling et al., "Severe neuromuscular denervation of clinically relevant muscles in a mouse model of spinal muscular atrophy," Human Molecular Genetics, 2012, vol. 21, No. 1, pp. 185-195.

Liu et al., "Activin Receptor Type 11B Inhibition Improves Muscle Phenotype and Function in a Mouse Model of Spinal Muscular Atrophy," PLoS One, 2016, 11 (11): 1-17.

Liu et al., "New practice in semaglutide on type-2 diabetes and obesity: clinical evidence and expectation," Frontiers of Medicine, vol. 16, No. 1, Feb. 1, 2022, 17-24.

Liu et al., "The Smn-Independent Beneficial Effect of Trichostatin A on an Intermediate Mouse Model of Spinal Muscular Atrophy," PLOS ONE, 2014, 9(7):1-9.

Loffredo et al., "Growth differentiation factor 11 is a circulating factor that reverses age-related cardiac hypertrophy," Cell, 2013, 153(4):828-839.

Long et al., "Specific inhibition of myostatin activation is beneficial in mouse models of SMA therapy," Human Molecular Genetics, 2019, 28(7):1076-1089.

Lu et al., "Gdf11 gene transfer prevents high fat diet-induced obesity and improves metabolic homeostasis in obese and STZ-induced diabetic mice," Journal of Translational Medicine 17 (2019): 1-16.

Madeira et al., "The EMBL-EBI search and sequence analysis tools APIs in 2019," Nucleic acids research 47.W1 (2019): W636-W641.

Main et al., "The Hammersmith functional motor scale for children with spinal muscular atrophy: a scale to test ability and monitor progress in children with limited ambulation," European Journal of Paediatric Neurology 7.4 (2003): 155-159.

Malik et al., "Pediatric dose selection for therapeutic proteins," The Journal of Clinical Pharmacology 61 (2021): S193-S206.

Mariot et al., "Downregulation of myostatin pathway in neuromuscular diseases may explain challenges of anti-myostatin therapeutic approaches," Nature Communications, 2017, 8(1):1-8.

Markovits et al., "The diversity of the immune response to the A2 domain of human factor VIII," Blood. Apr. 4, 2013;121(14):2785-95.

Marks et al., "By-passing immunization: human antibodies from V-gene libraries displayed on phage," Journal of molecular biology 222.3 (1991): 581-597.

Mashhood et al., "Reproducibility of hepatic fat fraction measurement by magnetic resonance imaging," Journal of Magnetic Resonance Imaging 37.6 (2013): 1359-1370.

Matsuda et al., "Insulin sensitivity indices obtained from oral glucose tolerance testing: comparison with the euglycemic insulin clamp," Diabetes care 22.9 (1999): 1462-1470.

Mazzone et al., "Revised upper limb module for spinal muscular atrophy: development of a new module," Muscle & nerve 55.6 (2017): 869-874.

Mcallister et al., "Modified 30-second sit-to-stand test: reliability and validity in older adults unable to complete traditional sit-to-stand testing," Journal of geriatric physical therapy 43.3 (2020): 153-158.

Mchorney et al., "The SWAL-QOL and SWAL-CARE outcomes tool for oropharyngeal dysphagia in adults: III. Documentation of reliability and validity," Dysphagia 17 (2002): 97-114.

Mcpherron et al., "Metabolic Functions of Myostatin and GDF11," Immunol Endocr Metab Agents Med Chem., 2010, 10(4):217-231.

Mcpherron et al., "Regulation of skeletal muscle mass in mice by a new TGF-p superfamily member," Nature 387.6628 (1997): 83-90.

Meece, J., "The role of the pharmacist in managing type 2 diabetes with glucagon-like peptide-1 receptor agonists as add-on therapy," Advances in therapy 34 (2017): 638-657.

Mendell et al., "A phase 1/2a follistatin gene therapy trial for becker muscular dystrophy," Molecular Therapy 23.1 (2015): 192-201.

Mendell et al., "Five-year extension results of the phase 1 START trial of onasemnogene abeparvovec in spinal muscular atrophy," JAMA neurology 78.7 (2021): 834-841.

Mercuri et al., "Long-term progression in type II spinal muscular atrophy: a retrospective observational study," Neurology 93.13 (2019): e1241-e1247.

Mercuri et al., "Nusinersen versus sham control in later-onset spinal muscular atrophy," New England Journal of Medicine 378.7 (2018): 625-635.

Mercuri et al., "Patterns of disease progression in type 2 and 3 SMA: implications for clinical trials," Neuromuscular Disorders 26.2 (2016): 126-131.

Mercuri et al., "SUNFISH Part 2: Efficacy and Safety of Risdiplam (RG7916) in Patients with Type 2 or Non-Ambulant Type 3 Spinal Muscular Atrophy (SMA) (1260)," Neurology 94.15 Supplement (2020): 1-3.

Mercuri et al., Presented at World Muscle Society Congress 2020, p. 257.

Mercuri et al., "Spinal muscular atrophy—insights and challenges in the treatment era," Nature Reviews Neurology 16.12 (2020): 706-715.

Miller et al., "The danger of weight loss in the elderly," J Nutr Health Aging. Aug.-Sep. 2008;12(7):487-91.

Mix et al., "Quality of life in SMA patients under treatment with nusinersen," Frontiers in neurology 12 (2021): 1-8.

Mokdad et al., "Prevalence of obesity, diabetes, and obesity-related health risk factors, 2001," Jama 289.1 (2003): 76-79.

Monani et al., "A single nucleotide difference that alters splicing patterns distinguishes the SMA gene SMN1 from the copy gene SMN2," Human molecular genetics 8.7 (1999): 1177-1183.

Monani, U., "Spinal muscular atrophy: a deficiency in a ubiquitous protein; a motor neuron-specific disease," Neuron 48.6 (2005): 885-896.

Montes et al., "Nusinersen improves walking distance and reduces fatigue in later-onset spinal muscular atrophy," Muscle & nerve 60.4 (2019): 409-414.

Morrison et al., "A soluble activin type IIB receptor improves function in a mouse model of amyotrophic lateral sclerosis," Exp Neurol, 2009, 217(2):258-268.

Morrison et al., "Chimeric human antibody molecules: mouse antigen-binding domains with human constant region domains," Proceedings of the National Academy of Sciences 81.21 (1984): 6851-6855.

Mosler et al., "The anabolic steroid methandienone targets the hypothalamic-pituitary-testicular axis and myostatin signaling in a rat training model," Archives of Toxicology, 2012, 86(1):109-119.

Muramatsu et al., "Novel myostatin-specific antibody enhances muscle strength in muscle disease models," Scientifc Reports, vol. 11, No. 1, Jan. 25, 2021, 16 pages.

Nadkarni et al., "Regulation of glucose homeostasis by GLP-1," Progress in molecular biology and translational science 121 (2014): 23-65.

Nakano et al., "Remogliflozin etabonate improves fatty liver disease in diet-induced obese male mice," Journal of Clinical and Experimental Hepatology 5.3 (2015): 190-198.

Nardone et al., "Inflammatory bowel diseases and sarcopenia: the role of inflammation and gut microbiota in the development of muscle failure," Frontiers in Immunology 12 (2021): 1-11.

Naryshkin et al., "SMN2 splicing modifiers improve motor function and longevity in mice with spinal muscular atrophy," Science, 2014, vol. 345, Issue 6197, pp. 688-693.

National Cancer Institute, "Common Terminology Criteria for Adverse Events," Version 5.0, Published Nov. 2017, 1-147.

Nayerossadat et al., "Viral and nonviral delivery systems for gene delivery," Advanced biomedical research 1.2 (2012): 1-11.

Nguyen et al., "Oral-033: Bimagrumab + Semaglutide Causes> 30% Fat Loss and 5% Lean Mass Increase in Obese Mice After 2 Weeks," Obesity, vol. 30, No. SI, Nov. 1, 2022, 4-54.

(56) References Cited

OTHER PUBLICATIONS

O'Hagen et al., "An expanded version of the Hammersmith Functional Motor Scale for SMA II and III patients," Neuromuscular Disorders 17.9-10 (2007): 693-697.
Oestreich et al., "Myostatin deficiency partially rescues the bone phenotype of osteogenesis imperfecta model mice," Osteoporos Int. Jan. 2016;27(1):161-70.
Ojala et al., "In Search of a Cure: The Development of Therapeutics to Alter the Progression of Spinal Muscular Atrophy," Brain Sci., Feb. 5, 2021; 11(2):194, 39 pages.
Opposition filed in EP Patent No. 3368069 on Apr. 28, 2021 (37 pgs.).
Opposition filed in EP Patent No. 3368069 on May 4, 2021 (89 pgs.).
Opposition Pre-summons Response filed in EP Patent No. 3368069 on Apr. 27, 2022 (32 pgs.).
Opposition Proceedings in EP 3368069—Carpmaels submission, Feb. 9, 2024 (127 pgs.).
Opposition Proceedings in EP 3368069—Declaration of Ms. Ying Qian filed Feb. 9, 2024 (2pgs).
Opposition Proceedings in EP 3368069—DFMP submission pursuant to Rule 116 EPC, Feb. 9, 2024 (13 pgs.).
Opposition Proceedings in EP 3368069—Hoffmann Eitle comments under Rule 116 EPC, Feb. 9, 2024 (23 pgs.).
Opposition Proceedings in EP 3368069—Hoffmann Eitle Submission, Apr. 2, 2024 (23 pgs.).
Opposition Proceedings in EP 3368069—Second Declaration of Dr. Karen Chen filed on Feb. 3, 2024(3 pgs.).
Opposition Proceedings in EP 3368069—Jarecki Declaration filed on Apr. 27, 2022 (2 pgs.).
Opposition Proceedings in EP 3368069 Brief Communication from EPO Oct. 10, 2024(63 pgs.).
Opposition Proceedings in EP3368069—Dr. Karen Chen Declaration filed on Apr. 27, 2022 ( 2pgs.).
Oskoui et al., "SUNFISH Part 2: 24-month efficacy and safety of risdiplam in patients with type 2 or non-ambulant type 3 spinal muscular atrophy (SMA)," Presented at MDA Clinical and Scientific Conference; Poster 80, (2021): 1-16.
Oskoui et al., "Two-year efficacy and safety of risdiplam in patients with type 2 or non-ambulant type 3 spinal muscular atrophy (SMA)," Journal of Neurology 270.5 (2023): 2531-2546.
Ozempic (semaglutide) injection, for subcutaneous use; prescribing information, Novo Nordisk A/S, Revised Dec. 2017, 1-44.
Padwal et al., "Using the Edmonton obesity staging system to predict mortality in a population-representative cohort of people with overweight and obesity," Cmaj 183.14 (2011): E1059-E1066.
Palacino et al., "SMN2 splice modulators enhance U1—pre-mRNA association and rescue SMA mice," Nature chemical biology 11.7 (2015): 511-517.
Pan et al., "Everestmab, a novel long-acting GLP-1/anti GLP-1R nanobody fusion protein, exerts potent anti-diabetic effects," Artificial cells, nanomedicine, and Biotechnology 48.1 (2020): 854-866.
Pandya et al., "Therapeutic neuroprotective agents for amyotrophic lateral sclerosis," Cell Mol Life Sci., 2013, 70(24):4729-4745.
Pane et al., "Neurological assessment of newborns with spinal muscular atrophy identified through neonatal screening," European Journal of Pediatrics 181.7 (2022): 2821-2829.
Passey et al., "Emerging therapies for the treatment of skeletal muscle wasting in chronic obstructive pulmonary disease," Pharmacol Ther. 2016; 166:56-70.
Passini et al., "Antisense oligonucleotides delivered to the mouse CNS ameliorate symptoms of severe spinal muscular atrophy," Science translational medicine 3.72 (2011): 1-21.
Passini et al., "CNS-targeted gene therapy improves survival and motor function in a mouse model of spinal muscular atrophy," The Journal of clinical investigation 120.4 (2010): 1253-1264.
Pasternak et al., "Rasch analysis of the Pediatric Evaluation of Disability Inventory—computer adaptive test (PEDI-CAT) item bank for children and young adults with spinal muscular atrophy," Muscle & nerve 54.6 (2016): 1097-1107.

Patil et al., "DNA-based therapeutics and DNA delivery systems: a comprehensive review," The AAPS journal 7 (2005): E61-E77.
Pechmann et al., "Evaluation of children with SMA type 1 under treatment with nusinersen within the expanded access program in Germany," Journal of neuromuscular diseases 5.2 (2018): 135-143.
Peeters et al., "Clinical and genetic diversity of SMN1-negative proximal spinal muscular atrophies," Brain 137.11 (2014): 2879-2896.
Pierzchlewicz et al., "Spinal muscular atrophy: the use of functional motor scales in the era of disease-modifying treatment," Child neurology open 8 (2021): 1-9.
Pirruccello-Straub et al., "Blocking extracellular activation of myostatin as a strategy for treating muscle wasting," Scientific Reports, 2018, 8(1):1-15.
Pistilli et al., "Targeting Activin Type IIB Receptor to Improve Muscle Mass and Function in the mdx Mouse Model of Duchenne Muscular Dystrophy," Am J Pathol., 2011, 178(3):1287-1297.
Place et al., "A Phase 2 Study to Evaluate the Efficacy and Safety of SRK-015 in Patients with Later-Onset Spinal Muscular Atrophy (TOPAZ): An Introduction," May 26, 2020. URL:https://scholarrock.com/wp-content/uploads/2020/09/MDA-2020-TOPAZ-SMA-Introduction.pdf, 1 page.
Place et al., "Clinical Development of SRK-015, a Fully Human Anti-proMyostatin Monoclonal Antibody, for the Treatment of Later-Onset Spinal Muscular Atrophy," SMA—THERAPY p. 253, Abstracts/Neuromuscular Disorders, Elsevier Ltd., GB,vol. 30 (2020) (2 pgs.).
Place et al., "TOPAZ: Phase 2 study evaluating efficacy and safety of apitegromab in later-onset spinal muscular atrophy," Database accession No. EMB-635747941, abstract, 2 pages.
Points to Consider in the Manufacture and Testing of Monoclonal Antibody Products for Human Use, Feb. 1997, 1-50.
Poljak, R., "Production and structure of diabodies," Structure 2.12 (1994): 1121-1123.
Prasad-Reddy et al., "A clinical review of GLP-1 receptor agonists: efficacy and safety in diabetes and beyond," Drugs in context 4 (2015):1-19.
Pubchem Substance No. CID 310264710 (trevogrumab); Create Date Feb. 5, 2016 [online]. Retrieved from: http://pubchem.ncbi.nlm.nih.gov/substance/310264710; on Feb. 5, 2020 (6 pgs.).
Puckey, M., "Incretin Mimetics (GLP-1 Agonists), List of Incretin Mimetics—Drugs.com," Retrieved from: https://www.drugs.com/drug-class/incretin-mimetics.html, 2 pages.
Pyatt et al., "A feasibility study for the newborn screening of spinal muscular atrophy," Genetics in Medicine, Published Jul. 2006, vol. 8, pp. 428-435.
Ramsey et al., "Revised Hammersmith Scale for spinal muscular atrophy: A SMA specific clinical outcome assessment tool," PloS one 12.2 (2017): 1-19.
Ramsey et al., "Revised Hammersmith Scale for spinal muscular atrophy: Inter and intra-rater reliability and agreement," Plos one 17.12 (2022): 1-14.
Ratni et al., "Specific correction of alternative survival motor neuron 2 splicing by small molecules: discovery of a potential novel medicine to treat spinal muscular atrophy," Journal of medicinal chemistry 59.13 (2016): 6086-6100.
Ravenscroft et al., "Heterozygous loss-of-function variants significantly expand the phenotypes associated with loss of GDF11," Genetics in Medicine 23.10 (2021): 1889-1900.
Regolisti et al., "Management of congestion and diuretic resistance in heart failure," Nephrology@ Point of Care 2.1 (2016): e73-e87.
Rena et al., "The mechanisms of action of metformin," Diabetologia 60.9 (2017): 1577-1585.
Reply to Examination Report dated Feb. 13, 2019 in EP Application No. 17732001.7, on May 31, 2019, 3 pages.
Request for early entry and processing of EP Application No. 17732001.7, on Jun. 1, 2018, 5 pages.
Response to Communication dated Jul. 31, 2018 in EP Application No. 17732001.7, on Dec. 10, 2018, 5 Pages.
Rindt et al., "Transgenic inactivation of murine myostatin does not decrease the severity of disease in a model of Spinal Muscular Atrophy," Neuromuscul Disord. 2012, 22(3):277-85.

(56) References Cited

OTHER PUBLICATIONS

Robberecht et al., "Biomarkers of metabolic syndrome: biochemical background and clinical significance," Metabolic syndrome and related disorders 14.2 (2016): 47-93.

Robbie et al., "Population pharmacokinetics of palivizumab, a humanized anti-respiratory syncytial virus monoclonal antibody, in adults and children," Antimicrobial agents and chemotherapy 56.9 (2012): 4927-4936.

Roberts et al., "Classifications in brief: American spinal injury association (ASIA) impairment scale," (2017): 1499-1504.

Rodino-Klapac et al., "Inhibition of myostatin with emphasis on follistatin as a therapy for muscle disease" Muscle Nerve, 2009, 39(3):283-296.

Rohou et al., "CTFFIND4: Fast and accurate defocus estimation from electron micrographs," Journal of structural biology 192.2 (2015): 216-221.

Rooks et al., "Bimagrumab vs optimized standard of care for treatment of sarcopenia in community-dwelling older adults: a randomized clinical trial," JAMA network open 3.10 (2020): 1-13.

Rooks et al., "Treatment of sarcopenia with bimagrumab: results from a phase II, randomized, controlled, proof-of-concept study," Journal of the American Geriatrics Society 65.9 (2017): 1988-1995.

Rose et al., "Delivery of recombinant follistatin lessens disease severity in a mouse model of spinal muscular atrophy," Hum Mol Genet. Mar. 15, 2009; 18(6): 997-1005.

Rosenbaum et al., "Low-dose leptin reverses skeletal muscle, autonomic, and neuroendocrine adaptations to maintenance of reduced weight," The Journal of clinical investigation 115.12 (2005): 3579-3586.

Rosenstock et al., "Efficacy and safety of a novel dual GIP and GLP-1 receptor agonist tirzepatide in patients with type 2 diabetes (SURPASS-1): a double-blind, randomised, phase 3 trial," The Lancet 398.10295 (2021): 143-155.

Rossi et al., "Predictors of ectopic fat accumulation in liver and pancreas in obese men and women," Obesity 19.9 (2011): 1747-1754.

Roth et al., "Myostatin: a therapeutic target for skeletal muscle wasting," Curr Opin Clin Nutr Metab Care, 2004, 7(3):259-263.

Rouault et al., "Disease impact on general well-being and therapeutic expectations of European Type II and Type III spinal muscular atrophy patients," Neuromuscular Disorders 27.5 (2017): 428-438.

S11 Nonclinical Safety Testing in Support of Development of Paediatric Medicines, FDA, (2020):1-43.

Saitoh et al., "Myostatin inhibitors as pharmacological treatment for muscle wasting and muscular dystrophy," Journal of Cachexia, Sarcopenia and Muscle—Clinical Reports, vol. 2, Issue 1, 2017, e00037 (10 pgs.).

Salvi, J., "Columbia-suicide severity rating scale (C-SSRS)," Emergency medicine practice 21.5 (2019): CD3-CD4.

Saunders, K., "Conceptual approaches to modulating antibody effector functions and circulation half-life," Frontiers in immunology 10 (2019): 1-20.

Schiaffino et al., "Three myosin heavy chain isoforms in type 2 skeletal muscle fibres," Journal of Muscle Research & Cell Motility 10 (1989): 197-205.

Schoch et al., "Charge-mediated influence of the antibody variable domain on FcRn-dependent pharmacokinetics," Proceedings of the National Academy of Sciences, 2015, vol. 112, No. 19, pp. 5997-6002.

Scholar Rock Announces Positive 12-Month Top-Line Results From the TOPAZ Phase 2 Clinical Trial Evaluating Apitegromab in Patients With Type 2 and Type 3 Spinal Muscular Atrophy (SMA), Scholar Rock press release (2021), 4 pages.

Scholar Rock Announces Positive Interim Results from Phase 1 Trial of SRK-015 in Healthy Volunteers and Updates on Future Development Plans, Feb. 26, 2019. (3pgs.).

Scholar Rock Announces Positive Proof-of-Concept Data from TOPAZ Phase 2 Trial Interim Analysis of SRK-015 in Patients with Type 2 and Type 3 Spinal Muscular Atrophy, Business Wire, Oct. 27, 2020. (7pgs.).

Scholar Rock discovered SRK-015, a selective and local inhibitor or latent myostatin activation for the treatment of primary myopathies, ScholarRock.com (2016) (1 pg.).

Scholar Rock Presents First Data for Niche Modulator Inhibiting Myostatin Activation and Announces SRK-015 as Lead Drug Program, ScholarRock Announcement (2015), 1 page.

Scholar Rock stuns with positive results for SRK-015 in SMA patients (2020) (https://www.thepharmaletter.com/article/scholar-rock-stuns-with-positive-resultsfor-srk-015-in-smapatients#>:text= US%20clinical%2Dstage%20biotech%20Scholar,a%20public% 20offering%20of%20shares.), 2 pages.

Sengle et al., "Prodomains of transforming growth factor β (Tgfβ) superfamily members specify different functions: extracellular matrix interactions and growth factor bioavailability," Journal of Biological Chemistry 286.7 (2011): 5087-5099.

Sgoutas et al., "Effect of Lyophilization on Determinations of Lipoprotein(a) in Serum," Clin Chem., 1992, 38(7):1355-1360.

Shorrock et al., "Development and Translation of Therapies for Spinal Muscular Atrophy," EMJ Neurol. 2016, 4(1):64-73.

Sidis et al., "Biological activity of follistatin isoforms and follistatin-like-3 is dependent on differential cell surface binding and specificity for activin, myostatin, and bone morphogenetic proteins," Endocrinology. 2006; 147(7):3586-97.

Singapore Patent Application No. 11201805709R, filed Jan. 6, 2017, by Scholar Rock, Inc.: International Search Report and Written Opinion, mailed Oct. 11, 2019 (12 pgs.).

Singh et al.,"Translational pharmacokinetic/pharmacodynamic analysis of myo-029 antibody for muscular dystrophy," Clinical and Translational Science. 2016;9(6):302-310.

SMA Annual Conference "The 2016 Annual SMA Conference is here," https://www.curesma.org/the-2016-annual-sma-conference-is-here/ (3 pgs.).

SMA Researcher Meeting Summary, "2016 SMA Researcher Meeting Summary: The Changing Landscape of SMA ," 2016 (5 pgs.).

Smith et al., "GLP-1: Molecular mechanisms and outcomes of a complex signaling system," Neurochemistry international 128 (2019): 94-105.

Smith et al., "Myostatin inhibitors as therapies for muscle wasting associated with cancer and other disorders," Curr Opin Support Palliat Care, 2013, 7(4):352-360.

Smith et al., "Myostatin Neutralization Results in Preservation of Muscle Mass and Strength in Preclinical Models of Tumor-Induced Muscle Wasting," Mol Cancer Ther., 2015, 14(7):1661-1670.

Smith, G., "Filamentous fusion phage: novel expression vectors that display cloned antigens on the virion surface," Science 228.4705 (1985): 1315-1317.

Somiari et al., "Theory and in vivo application of electroporative gene delivery," Molecular Therapy 2.3 (2000): 178-187.

Sorzano et al., "XMIPP: a new generation of an open-source image processing package for electron microscopy," Journal of structural biology 148.2 (2004): 194-204.

Spinraza (Nusinersen) FDA label, Dec. 2016 (13 pgs.).

Staels et al., "Fibrates and future PPARalpha agonists in the treatment of cardiovascular disease," Nat Clin Pract Cardiovasc Med. 2008, 5(9):542-53.

Stam et al., "Protocol for a phase II, monocentre, double-blind, placebo-controlled, cross-over trial to assess efficacy of pyridostigmine in patients with spinal muscular atrophy types 2-4 (SPACE trial)," BMJ open 8.7 (2018): 1-9.

Stanford et al., "Brown adipose tissue regulates glucose homeostasis and insulin sensitivity," The Journal of clinical investigation 123.1 (2012): 215-223.

Staunton et al., "Development of a Clinical Global Impression of Change (CGI-C) and a Caregiver Global Impression of Change (CaGI-C) measure for ambulant individuals with Duchenne muscular dystrophy," Health and Quality of Life Outcomes 19 (2021): 1-16.

(56) References Cited

OTHER PUBLICATIONS

Suh et al., "GDF11 promotes osteogenesis as opposed to MSTN, and follistatin, a MSTN/GDF11 inhibitor, increases muscle mass but weakens bone," Proc Natl Acad Sci U S A. Mar. 3, 2020,;117(9):4910-4920.

Sumner et al., "Inhibition of myostatin does not ameliorate disease features of severe spinal muscular atrophy mice," Human Molecular Genetics, 2009, 18(17):3145-3152.

Sumner et al., "Spinal Muscular Atrophy: Disease Mechanisms and Therapy," Academic Press, 2016 pp. 6, 15-19 and 351-356. Publication details included (22 pgs).

Sumner et al., "Spinal Muscular Atrophy: Disease Mechanisms and Therapy," First edition, Academic Press, 2016, Chapters 15, 16, 21, and 23. Publication details included (91 pgs.).

Suragani et al., "Transforming growth factor-β superfamily ligand trap ACE-536 corrects anemia by promoting late-stage erythropoiesis," Nature Medicine, 2014, 20(4):408-414.

Szlama et al., "Latent myostatin has significant activity and this activity is controlled more efficiently by WFIKKN1 than by WFIKKN2," FEBS Journal, 2013, 280(16):3822-3839.

Takeda et al., "Construction of chimaeric processed immunoglobulin genes containing mouse variable and human constant region sequences," Nature 314.6010 (1985): 452-454.

Tan et al., "Albumin-binding domain extends half-life of glucagon-like peptide-1," European Journal of Pharmacology 890 (2021): 173650.

Tang et al., "Inhibiting myostatin signaling prevents femoral trabecular bone loss and microarchitecture deterioration in diet-induced obese rats," Exp Biol Med (Maywood). Feb. 2016;241(3):308-16.

Tanzeum® (albiglutide) for injection, for subcutaneous use prescribing information, GlaxoSmithKline LLC., Revised Aug. 2017, 1-60.

Tao et al., "Genetic Inactivation of Pyruvate Dehydrogenase Kinases Improves Hepatic Insulin Resistance Induced Diabetes," Plos One. 2013, 8(8):1-8.

Teoh et al., "Inherited paediatric motor neuron disorders: beyond spinal muscular atrophy," Neural plasticity 2017.1 (2017): 6509493.

Thimm et al., "Assessment of health-related quality of life in adult spinal muscular atrophy under nusinersen treatment—a pilot study," Frontiers in neurology 12 (2022): 1-9.

Trevogrumab: Statement on a Nonproprietary Name Adopted by the Usan Council (2015) (https://searchusan.amaassn.org/undefined/documentDownload?uri=%2Funstructured%2Fbinary%2Fusan%2Ftrevogrumab.pdf), 2 pages.

Tulsky et al., "Overview of the spinal cord injury—quality of life (SCI-QOL) measurement system," The journal of spinal cord medicine 38.3 (2015): 257-269.

UniProt: the universal protein knowledgebase in 2021. Nucleic acids research 49, No. D1 (2021): D480-D489.

U.S. Appl. No. 62/486,934, filed Apr. 18, 2017, 48 pages.

Vai et al., "Bone and Spinal Muscular Atrophy," Bone. 2015; 79:116-20.

Vuillerot et al., "Responsiveness of the motor function measure in patients with spinal muscular atrophy," Archives of physical medicine and rehabilitation 94.8 (2013): 1555-1561.

Wagner et al., "A phase I/II trial of MYO-029 in adult subjects with muscular dystrophy," Annals of Neurology. 2008;63(5):561-571.

Wagner et al., "Randomized phase 2 trial and open-label extension of domagrozumab in Duchenne muscular dystrophy," Neuromuscular Disorders. 2020;30(6):492-502.

Wagner, "The elusive promise of myostatin inhibition for muscular dystrophy," Current Opinion in Neurology, Oct. 2020; 33(5):621-628.

Walker et al., "Biochemistry and Biology of GDF11 and Myostatin: similarities, differences and questions for future investigation," Circ Res. Apr. 1, 2016;118(7):1125-41.

Walker et al., "Exogenous GDF11, but not GDF8, reduces body weight and improves glucose homeostasis in mice," Scientific Reports. vol. 10 (2020): 1-13.

Wallner et al., "Inhibition of GDF8 (Myostatin) accelerates bone regeneration in diabetes mellitus type 2," Sci Rep. Aug. 29, 2017;7(1):1-11.

Walter et al., "Improving Care and Empowering Adults Living with SMA: A Call to Action in the New Treatment Era," J Neuromuscul Dis. 2021;8(4):543-551.

Wan et al., "Health, wellbeing and lived experiences of adults with SMA: a scoping systematic review," Orphanet journal of rare diseases 15 (2020): 1-17.

Wang et al., "Reloading promotes recovery of disuse muscle loss by inhibiting TGFβ pathway activation in rats after hind limb suspension," American Journal of Physical Medicine & Rehabilitation 96.6 (2017): 430-437.

Wang, W., "Lyophilization and development of solid protein pharmaceuticals," International Journal of Pharmaceutics, 2000, 203(1-2):1-60.

Ward et al., "Binding activities of a repertoire of single immunoglobulin variable domains secreted from *Escherichia coli*," Nature 341.6242 (1989): 544-546.

Weiss et al., "Real-world weight change, adherence, and discontinuation among patients with type 2 diabetes initiating glucagon-like peptide-1 receptor agonists in the UK," BMJ Open Diabetes Research and Care 10.1 (2022): 1-9.

Weststrate et al., "Evolution of bulbar function in spinal muscular atrophy type 1 treated with nusinersen," Developmental Medicine & Child Neurology 64.7 (2022): 907-914.

Whittemore et al., "Inhibition of myostatin in adult mice increases skeletal muscle mass and strength," Biochem Biophys Res Commun, 2003, 300(4):965-971.

WHO Drug Information, vol. 34, No. 2, (2020): 272-273.

WHO Multicentre Growth Reference Study Group, "WHO Motor Development Study: windows of achievement for six gross motor development milestones," Acta paediatrica, Suppl. 450, (2006): 86-95.

Wijnhoven et al., "Assessment of gross motor development in the WHO Multicentre Growth Reference Study," Food and nutrition bulletin 25, Suppl 1 (2004): S37-S45.

Wilding et al., "Weight regain and cardiometabolic effects after withdrawal of semaglutide: the STEP 1 trial extension," Diabetes, Obesity and Metabolism 24.8 (2022): 1553-1564.

Williams et al., "Drug therapy in obesity: a review of current and emerging treatments," Diabetes Therapy 11.6 (2020): 1199-1216.

Williams et al., "Minimal clinically important differences of the expanded hammersmith functional motor scale in later-onset spinal muscular atrophy: results from the Phase 3 CHERISH trial," Presented at the 2019 AMCP Managed Care & Specialty Pharmacy Annual Meeting; San Diego, CA, J Manag Care Spec Pharm. (2019): S54.

Wintgens et al., "Plasma myostatin measured by a competitive ELISA using a highly specific antiserum," Clin Chim Acta., 2012, 413(15-16):1288-1294.

Wolfman et al., "Activation of latent myostatin by the BMP-1/tolloid family of metalloproteinases," Proc Natl Acad Sci U.S.A., 2003, 100(26):15842-15846.

Woodhouse et al., "A Phase 2 Randomized Study Investigating the Efficacy and Safety of Myostatin Antibody LY2495655 versus Placebo in Patients Undergoing Elective Total Hip Arthroplasty," The Journal of Frailty & Aging. 2016;5(1):62-70.

Written Opinion of the International Preliminary Examining Authority for PCT/US2017/012606 dated Jan. 3, 2018 (18 pgs.).

Yang et al., "Systematic literature review of clinical and economic evidence for spinal muscular atrophy," Advances in therapy 39.5 (2022): 1915-1958.

Yao et al., "Quality of life of children with spinal muscular atrophy and their caregivers from the perspective of caregivers: a Chinese cross-sectional study," Orphanet journal of rare diseases 16 (2021): 1-13.

Yokoyama et al., "Quantitative insulin sensitivity check index and the reciprocal index of homeostasis model assessment are useful indexes of insulin resistance in type 2 diabetic patients with wide range of fasting plasma glucose," The Journal of Clinical Endocrinology & Metabolism 89.3 (2004): 1481-1484.

(56) References Cited

OTHER PUBLICATIONS

Yumuk et al., "European Guidelines for Obesity Management in Adults," Obes Facts Dec. 1, 2015; 8 (6): 402-424.

Zhang et al., "Pharmacological inhibition of myostatin suppresses systemic inflammation and muscle atrophy in mice with chronic kidney disease," The FASEB journal 25.5 (2011): 1653-1663.

Zhao et al., "Pharmacokinetics, pharmacodynamics, and efficacy of a small molecule SMN2 splicing modifier in mouse models of spinal muscular atrophy," Human Molecular Genetics, 2016, 25(10):1885-1899.

Zhao et al., "Targeting fibrosis: Mechanisms and clinical trials," Signal transduction and targeted therapy, 2022, 7(1), 21 pages.

Zhou et al., "Myostatin inhibition in combination with antisense oligonucleotide therapy improves outcomes in spinal muscular atrophy," J Cachexia Sarcopenia Muscle. 2020, 11(3):768-782.

Zhou et al., "Reversal of cancer cachexia and muscle wasting by ActRIIB antagonism leads to prolonged survival," Cell 142.4 (2010): 531-543.

Adams et al., "Comparison of the effects of body-weight-supported treadmill training and tilt-table standing on spasticity in individuals with chronic spinal cord injury," J Spinal Cord Med. 2011;34(5):488-94.

Battaglino et al., "Spinal cord injury-induced osteoporosis: pathogenesis and emerging therapies," Curr Osteoporos Rep. Dec. 2012;10(4):278-85.

Bhattacharya et al. "Application of Quantitative Pharmacology Approaches in Bridging Pharmacokinetics and Pharmacodynamics of Domagrozumab From Adult Healthy Subjects to Pediatric Patients With Duchenne Muscular Disease," J Clin Pharmacol. Mar. 2018;58(3):314-326.

Bhattacharya et al., "Comparative analysis of silencing expression of myostatin (MSTN) and its two receptors (ACVR2A and ACVR2B) genes affecting growth traits in knock down chicken." Scientific reports 9.1 (2019): 1-13.

Crawford et al., "Apitegromab in SMA: An Analysis of Multiple Endpoints and PD Relationships to Efficacy in the TOPAZ Trial," Annual Congress of the World Muscle Society (Sep. 20, 2021), 1 pg.

Crawford et al., "TOPAZ extension: 24 month efficacy and safety of apitegromab in patients with later-onset Spinal Muscular Atrophy (type 2 and type 3 SMA)," presented at Cure SMA, Jun. 2022, 17 pages.

Deng et al., "Drug Development progress in duchenne muscular dystrophy." Frontiers in Pharmacology 13 (2022): 1-20.

Gorgey et al., "Skeletal muscle atrophy and increased intramuscular fat after incomplete spinal cord injury," Spinal Cord. Apr. 2007;45(4):304-9.

Graham et al., "A Soluble Activin Receptor IIB Fails to Prevent Muscle Atrophy in a Mouse Model of Spinal Cord Injury," J Neurotrauma. Jun. 15, 2016;33(12):1128-35.

Griffin et al., "Functional electrical stimulation cycling improves body composition, metabolic and neural factors in persons with spinal cord injury," J Electromyogr Kinesiol. Aug. 2009;19(4):614-22.

Kenward et al., "Small Sample Inference for Fixed Effects from Restricted Maximum Likelihood," 1997, Biometrics 53, pp. 983-997.

Macdonald et al., "Denervation atrophy is independent from Akt and mTOR activation and is not rescued by myostatin inhibition," Dis Model Mech. Apr. 2014;7(4):471-81.

Mastaitis et al., "Myostatin Inhibition Synergizes with GLP-1R Agonism to Accelerate Weight Loss in Male, Obese Nonhuman Primates" (Abstract). Diabetes Jun. 20, 2023; 72 (Supplement1): 207-OR.

Nomikos, "Clinical Development of SRK-015,a Fully Human Anti-proMyostatin Monoclonal Antibody, for the Treatment of Later-Onset Spinal Muscular Atrophy," Poster presented on Oct. 1, 2020, Annual Congress of the World Muscle Society.

Nusinersen, Office of Drug Evaluation Decisional Memorandum, FDA, (2016): 22 pages.

Place et al., "Insights into the Potential Pharmacological Effects of Apitegromab in Health and Disease: Data from Preclinical and Clinical Studies," Annual Congress of the World Muscle Society (Sep. 20, 2021), 2 pgs.

Shields et al., "Predictive Model of Muscle Fatigue after Spinal Cord Injury in Humans," Muscle Nerve. Jul. 2006; 34(1): 84-91.

Spungen et al., "Factors influencing body composition in persons with spinal cord injury: a cross-sectional study," J Appl Physiol 2003, 95: 2398-2407.

Wawersik et al., "A novel, highly specific TGFβ1 inhibiting antibody demonstrates antifibrotic activity without cardiotoxicity," Poster presented on Nov. 3, 2017, The American Society of Nephrology. 3 pgs.

Wu et al. "Spinal cord injury causes brain inflammation associated with cognitive and affective changes: role of cell cycle pathways," J Neurosci. Aug. 13, 2014;34(33):10989-1006.

Wu et al., "Cell Cycle Activation Contributes to Increased Neuronal Activity in the Posterior Thalamic Nucleus and Associated Chronic Hyperesthesia after Rat Spinal Cord Contusion," Neurotherapeutics (2013) 10:520-538.

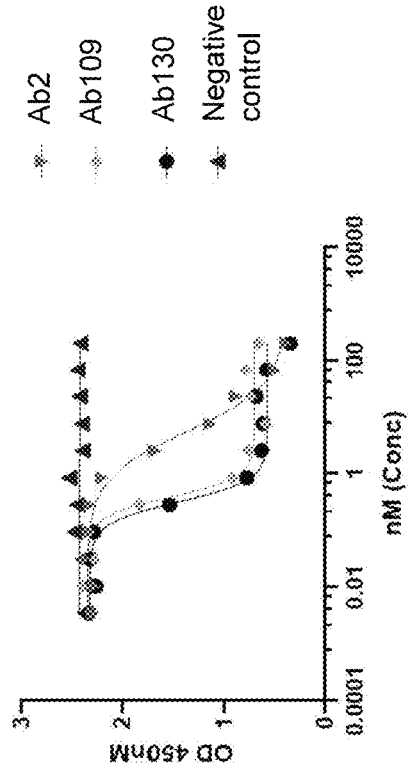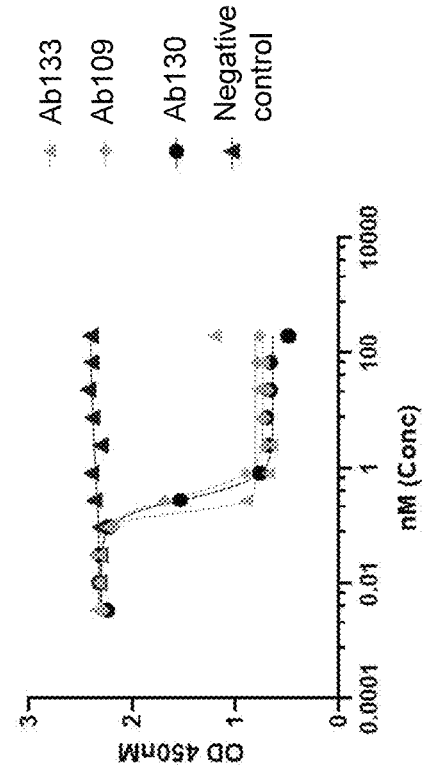
FIG. 1A
FIG. 1B

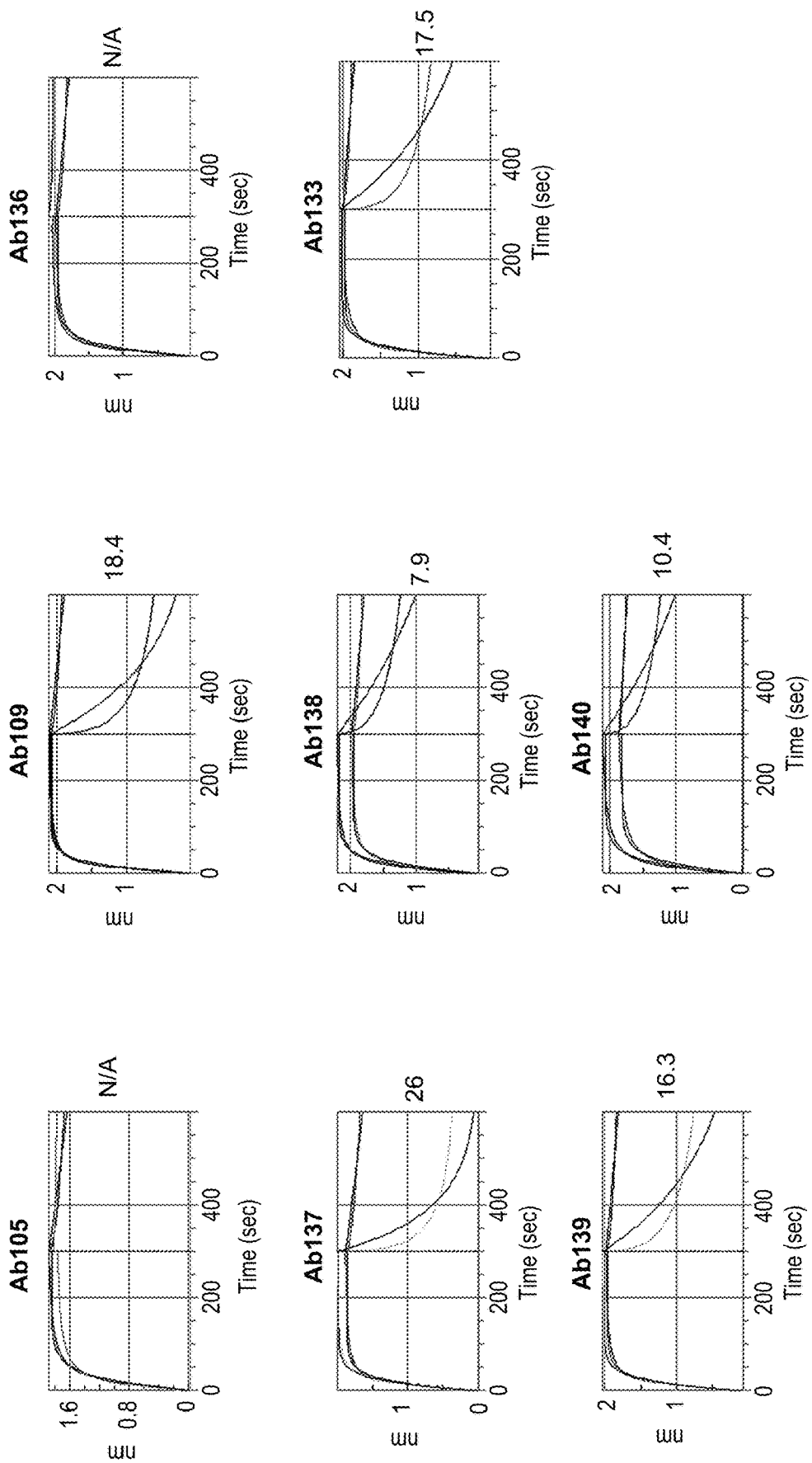
FIG. 4A pH-dependent dissociation of antibodies

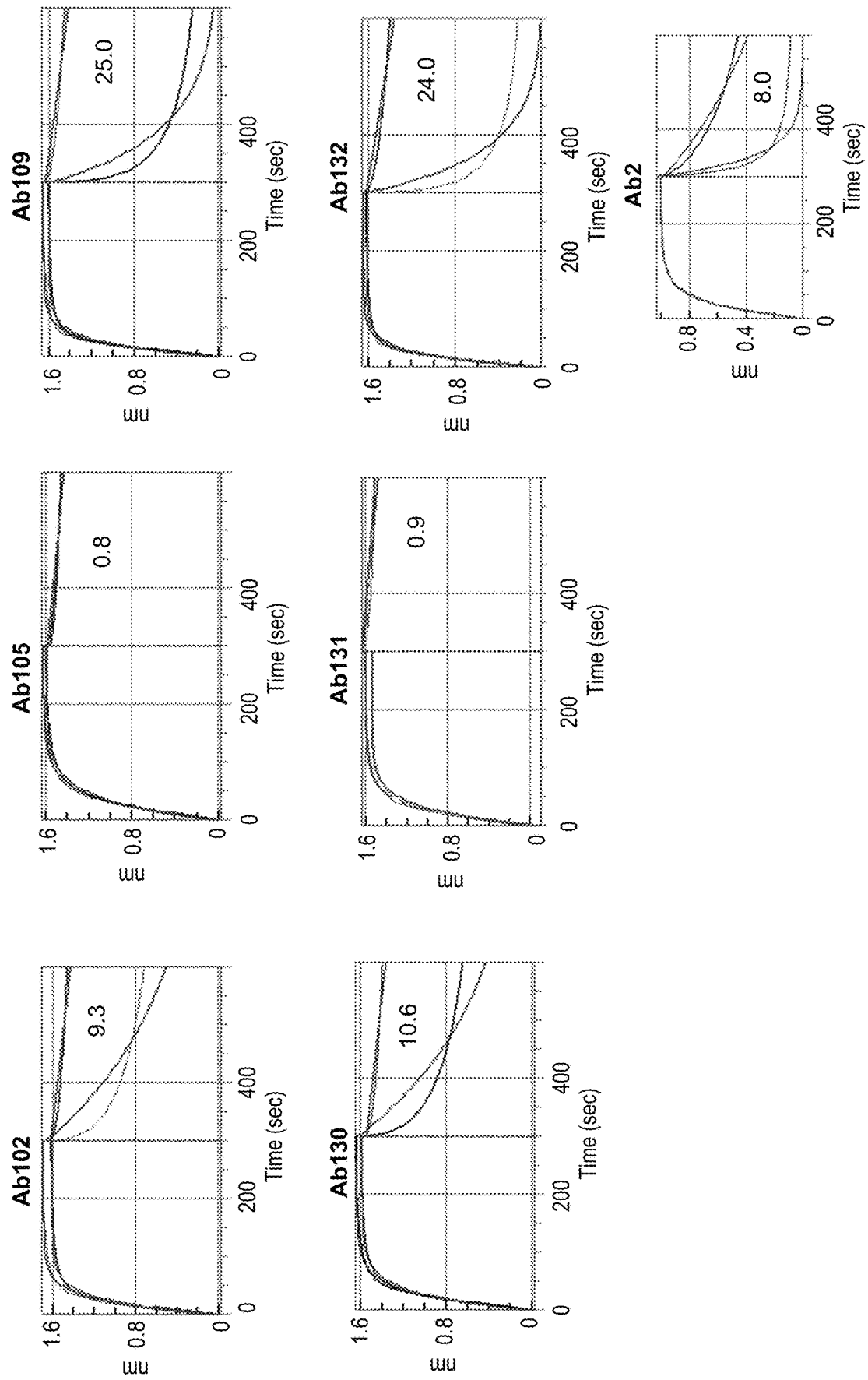
FIG. 4B  pH-dependent dissociation of antibodies

Stoichiometry of Ab109 binding to pro-/latent-myostatin

Stoichiometry of Ab130 binding to pro-/latent-myostatin

Stoichiometry of Ab105 binding to pro-/latent-myostatin

Stoichiometry of Ab133 binding to pro-/latent-myostatin

Stoichiometry of Ab112 binding to pro-/latent-myostatin: mAb is large poly daisy-chain; Fab is 2:1

Stoichiometry of Ab123 binding to pro-/latent-myostatin: mAb is 1:1; Fab is also 1:1

FIG. 14F

Absolute Inguinal Fat Pad (L+R Avg)

FIG. 14E

Absolute Gastroc Weight (L+R Avg)

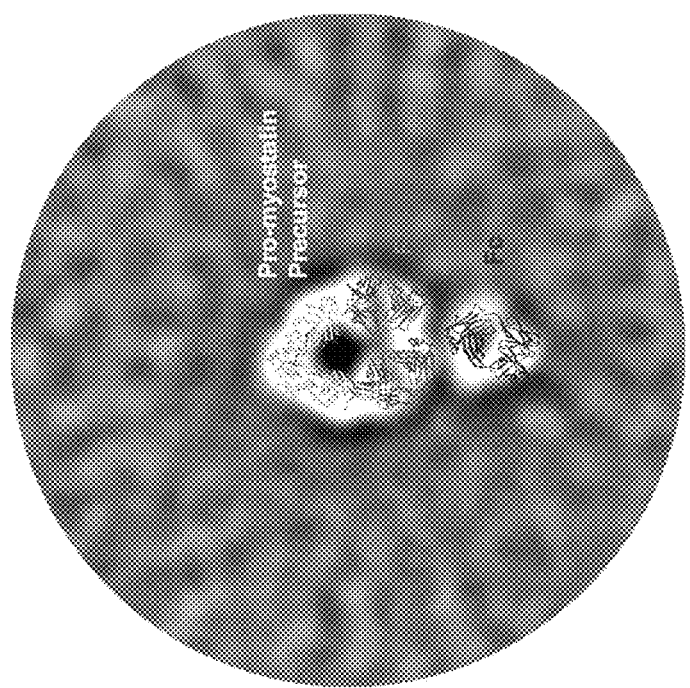
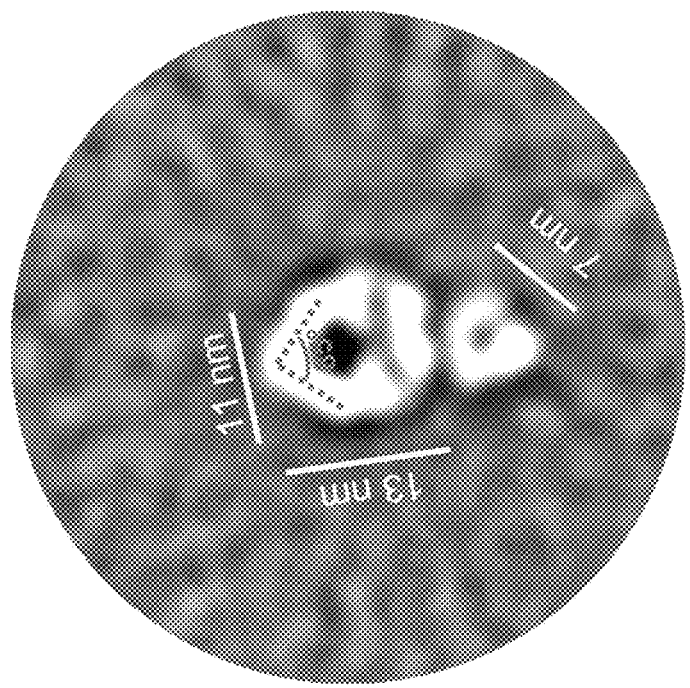
FIG. 23C

SELECTIVE AND POTENT INHIBITORY ANTIBODIES OF MYOSTATIN ACTIVATION

CROSS REFERENCE TO RELATED APPLICATIONS

This application is a continuation of International Patent Application No. PCT/US2023/085574, filed on Dec. 21, 2023, which claims the benefit of priority under 35 U.S.C. § 119(e) of U.S. Provisional Patent Application No. 63/476,908, filed on Dec. 22, 2022, U.S. Provisional Patent Application No. 63/477,552, filed on Dec. 28, 2022, U.S. Provisional Patent Application No. 63/515,267, filed on Jul. 24, 2023, and U.S. Provisional Patent Application No. 63/588,081, filed on Oct. 5, 2023. Each of these applications is incorporated herein by reference in its entirety for all purposes.

SEQUENCE LISTING

The instant application contains a Sequence Listing which has been submitted electronically in ST.26 XML format and is hereby incorporated by reference in its entirety. Said XML copy, created on Dec. 21, 2023, is named "15094_0054-00304_generic_SL.xml" and is 651,386 bytes in size.

FIELD

The instant application relates generally to novel myostatin-inhibiting antibodies and their use in treating disorders, including metabolic and neuromuscular disorders. The disclosure further relates to new adjunct and combination therapies for improving metabolic health.

BACKGROUND

Myostatin (also known as growth differentiation factor-8 or GDF8) is a member of the TGFβ superfamily of cytokines and in human is encoded by the MSTN gene. Like other members of the TGFβ superfamily, myostatin is a homodimer which is initially expressed as an inactive precursor polypeptide (referred to as pro-myostatin). In the overall structure of pro-myostatin, the mature growth factor is held locked in the prodomain, which is a cage-like structure comprised of two alpha helices connected by a loop termed the "latency lasso" (see, e.g., PCT/US2014/036933). The amino acid sequence of the human myostatin polypeptide corresponds to UniProt Accession No. O14793; murine counterpart corresponds to UniProt Accession No. O08689. Myostatin activation involves two separate protease cleavage steps. The first cleavage event in myostatin activation involves furin cleavage of pro-myostatin between the pro-domain and the growth factor domain, resulting in a "latent-myostatin," in which the mature myostatin remains non-covalently associated with the pro-domain and is shielded from binding to its receptors by the prodomain. The second cleavage event by BMP-1/Tolloid family of proteases (such as mammalian tolloid-like 2 (mTLL-2)) triggers activation, resulting in release of the mature, active myostatin growth factor from the latent complex. Following activation, mature myostatin signals by binding to a complex of Type I and II cell surface receptors (Alk4/5 and ActRIIB), whose downstream signaling induces muscle breakdown and atrophy.

Due to its central role as a negative regulator of muscle mass and its involvement in metabolic regulation, myostatin has been considered for muscle and metabolic disorders. Clinical programs that evaluated various myostatin inhibitors in a number of muscle indications have, however, failed and were discontinued, casting doubt as to its therapeutic potential. Myostatin inhibitors that either failed or were terminated in the clinic to date include neutralizing monoclonal antibodies to mature myostatin, such as stamulumab/MYO-029 (evaluated in Becker Muscular Dystrophy (BMD), Facioscapulohumeral muscular dystrophy (FSHD) and Limb-girdle muscular dystrophy (LGMD), domagrozumab/PF-06252616 (evaluated in Duchenne Muscular Dystrophy (DMD)), landogrozumab/LY2495655 (evaluated in cachexia associated with pancreatic cancer and osteoarthritis undergoing total hip replacement), trevogrumab/REGN1033 (evaluated in sporadic inclusion body myositis (sIBM)); soluble ActRIIB ligand traps such as ramatercept/ACE-031 (evaluated in sIMB); follistatin-Fc constructs such as ACE-083 (evaluated in FSHD and Charcot-Marie-Tooth); anti-myostatin adnectins such as BMS-986089/RG6202/RO-7239361 (evaluated in DMD); anti-ActRIIB antibodies such as bimagrumab/BYM338 (evaluated in sIBM and others); follistatin gene therapies such as AAAVI.CMV.F344 and rAAVI.CMV.huFollistatin334 (evaluated in BMD, sIBM and DMD); and anti-myostatin peptibodies such as AMG-745 (evaluated in age-associated muscle loss).

Bimagrumab, an anti-ActRIIB antibody, has been shown to reduce total body fat mass and increase lean mass in obese patients with type 2 diabetes (Heymsfield et al. 2021). However, antagonizing the ActRII receptor with bimagrumab inhibits not only myostatin but also other structurally similar ligands, including GDF11 and activins, the latter of which have a role in regulating follicle stimulating hormone secretion. As such, it is unclear whether the observed effects resulted from myostatin inhibition, other ligands, or a combination thereof. Notably, Muramatsu et al. (Sci Rep. 2021 Jan. 25; 11(1):2160) reported that GDF11 inhibition had a negative impact on muscle strength in a preclinical model, raising the possibility that blocking the common receptor may in fact be detrimental. While it has been shown that myostatin inhibition and follistatin overexpression can increase muscle mass, overexpression of follistatin in mice has been reported to result in altered bone structure and dysregulation of bone metabolism. See Suh et al. (Proc Natl Acad Sci USA. 2020 Mar. 3; 117(9):4910-4920) and Chang et al. (JBMR Plus. 5(4): e10477). This may be due to follistatin's broad-spectrum inhibition of myostatin, activins, and GDF11. Moreover, based on knockout studies, there are toxicity concerns associated with inhibiting GDF11 and Activin A. For example, inhibiting GDF11 signaling may have negative impacts on bone (Suh et al. Proc Natl Acad Sci (2020) 117:4910). Patients with nonsense, frameshift, or missense variants in GDF11 presented with craniofacial, vertebral, neurological, cardiac, auditory, and connective tissue abnormalities (Ravenscroft et al. Genet Med (2021) 23:1889). Furthermore, bimagrumab has been shown to significantly reduce follicle stimulating hormone (FSH) in women and clinical trials of bimagrumab require women of childbearing age to use multiple forms of contraception (Garito et al. Diabetes Obes Metab. 2018; 20(1):94-102). Hence, selectivity in targeting myostatin is beneficial to be able to drive efficacy in increasing or maintaining muscle mass while avoiding any potential toxicities that arise from inhibiting the signaling of closely related factors.

Currently, apitegromab remains the only selective myostatin inhibitor that has shown efficacy and safety in a Phase 2 human clinical trial that enrolled patients with SMA (TOPAZ; NCT03921528). Apitegromab is being investigated as an intravenous (i.v.) formulation in the ongoing phase 3 trial (SAPPHIRE; NCT05156320), which is suitable for conditions such as SMA. However, the subcutaneous route of administration might be a more attractive option for adult and/or ambulatory patients or patients suffering from certain other conditions. Accordingly, there remains an unmet need for potent and selective myostatin inhibitors to treat these conditions.

SUMMARY

The present disclosure provides, inter alia, novel antibodies and antigen-binding fragments thereof that are highly selective and highly potent inhibitors of myostatin activation, as well as therapeutic uses thereof. In some embodiments, the antibodies disclosed herein are suitable for subcutaneous administration, e.g., due at least in part to higher potency. Disclosed further herein are new adjunct and combination therapies comprising a myostatin-selective inhibitor (e.g., new medical use of myostatin-selective inhibitors) for the treatment of metabolic disorders such as obesity and type 2 diabetes, e.g., in combination with additional therapeutic agents and/or diet and exercise. Also disclosed are uses in treating cardiometabolic conditions (e.g., cardiovascular disease, metabolic disorders, e.g., obesity and type 2 diabetes, inflammatory diseases, chronic inflammation, chronic kidney disease, and fatty liver disease), as well as muscular disorders (e.g., spinal muscular atrophy, muscular dystrophies, and spinal cord injury), glycogen storage disorders, bone disorders (e.g., bone loss) and brain disorders (e.g. Alzheimer's disease, Parkinson's disease, and stroke).

Previously, Applicant disclosed antibodies that selectively bind latent myostatin, thereby preventing the activation step of myostatin. See, e.g., PCT/US2015/059468 and PCT/US2016/052014, the contents of which are hereby incorporated in their entireties. The crystal structure of one such antibody bound to the antigen revealed that both arms of the antibody interact with the homodimeric prodomain, forming a ring-like stable complex with a 1:1 binding stoichiometry. See Dagbay et al. J Biol Chem. 2020 Apr. 17; 295(16):5404-5418, the content of which is hereby incorporated in its entirety. This is consistent with the observation that the mAb (i.e., bivalent) affinity is markedly greater than the Fab (i.e., monovalent) affinity, indicating that the bivalent binding may provide substantial avidity to effectuate inhibitory activities. The epitope on the prodomain was found to be distal to the BMP-1/Tolloid proteolytic cleavage site of the prodomain required for myostatin activation, indicating that allosteric antibody binding inhibits protease-dependent activation of latent myostatin. Indeed, despite relatively weak monovalent affinity, the antibody exhibits robust efficacy in vivo in multiple preclinical models.

The identification of the inhibitory epitope discussed above provided a target region for developing additional antibodies, including those that compete for binding (e.g., cross-block) with the above-described antibody. Accordingly, Applicant sought to discover further novel inhibitory antibodies, including those that bind the same or a substantially overlapping region of the myostatin prodomain, i.e., cross-competing antibodies, particularly those that compete with Ab2 (disclosed in PCT/US2016/052014 and PCT/US2015/059468) for binding to pro-myostatin. Over 30 distinct antibodies were identified, which were subsequently confirmed to show greater inhibitory potency against protease-induced myostatin activation than Ab2. Modifications to some of these antibody sequences were also evaluated for various properties as described herein. Among them, a subclass of antibodies with unexpected characteristics has been identified. Surprisingly, these novel antibodies exhibit distinct properties, e.g., with respect to one or more of binding stoichiometry, pH sensitivity, and serum myostatin clearance behaviors in addition to having a higher affinity. In certain embodiments of the disclosure, the novel antibodies or antigen-binding fragments thereof bind to the same or an overlapping epitope as the prior art reference antibody as discussed above. In some embodiments, the novel antibody binds the same region of pro/latent myostatin as Ab2, but unexpectedly, does so with "one-arm" while retaining high affinity and inhibitory potency (e.g., IC50 of less than 1 nM as measured by functional ELISA detailed herein). These surprising features raise the possibility that the novel antibodies/antigen-binding fragments disclosed herein may be utilized to engineer multi-specific constructs, such as bispecific antibodies.

Accordingly, in some embodiments, the present disclosure encompasses an antibody or antigen-binding fragment thereof that binds to human pro/latent myostatin, but does not bind to mature myostatin or GDF11, wherein the binding is capable of inhibiting myostatin activation, wherein the antibody or antigen-binding fragment binds to the same epitope and/or competes for antigen binding with Ab2 as provided in PCT/US2015/059468, and/or wherein the antibody or antigen-binding fragment binds human pro/latent myostatin at/or near amino acid positions 147-170 and/or amino acid positions 205-210 as numbered according to the proGDF8 sequence provided herein (SEQ ID NO: 52). In some embodiments, any of the antibodies or the fragment discussed above may be characterized in that: i) a sum of the heavy chain variable domain and the light chain variable domain combined (i.e., cumulative VH+VL) shares less than 70% sequence identity with that of Ab2; ii) the heavy chain sequence shares less than 90%, 80%, or 70% sequence identity with that of Ab2; iii) the VL sequence of the antibody shares less than 50% sequence identity with the VL sequence of Ab2; iv) the L-CDR1 shares no more than 25% (e.g., no more than 20%) sequence identity to the L-CDR1 sequence of Ab2; v) the L-CDR2 shares less than 30% sequence identity with the L-CDR2 of Ab2; and/or, vi) the L-CDR3 shares no more than 20% (e.g., no more than 10%) sequence identity with the L-CDR3 of Ab2.

In some embodiments, an antibody or antigen-binding fragment disclosed herein binds human pro/latent myostatin with a KD of less than 1 nM (e.g. with a KD of less than 0.7 nM, of less than 0.5 nM or of less than 0.2 nM) as measured by a suitable in vitro binding assay, such as surface plasmon resonance (SPR) (e.g., Biacore™) Biolayer Interferometry (BLI) (e.g., Octet®), and/or solution equilibrium titration (e.g., MSD-SET). In some embodiments, KD is determined by an SPR-based assay (such as Biacore™).

In some embodiments, the antibody or antigen-binding fragment is capable of inhibiting mammalian tolloid-like 2 (mTLL-2)-induced activation of myostatin with an IC50 (mTLL2 $IC_{50}$) of less than 1 nM (e.g., under 0.5 nM) as measured by functional ELISA (e.g., to measure the ability of the antibody or antigen-binding fragment to inhibit protease-dependent activation of myostatin, as determined by detection of mature myostatin by ELISA).

In some embodiments, an antibody or antigen-binding fragment disclosed herein binds to human pro/latent myostatin in a pH-dependent manner, wherein, optionally, the pH dependency is greater than 10× as determined by comparing dissociation rates at pH 5.5/7.4, wherein the dissociation rates are measured by a BLI-based assay (e.g., Octet®).

In some embodiments, the present disclosure provides antibodies or antigen-binding fragments which are capable of monovalent binding to antigen (e.g., a latent myostatin complex) with a monovalent KD of 50 nM or less, as measured by, e.g., a BLI-based in vitro binding assay or an SPR-based in vitro binding assay. In some embodiments, the monoclonal antibody of the disclosure binds to human pro/latent myostatin in a 1:2 antibody to antigen stoichiometry. In some embodiments, the monoclonal antibody of the disclosure binds to human pro/latent myostatin in both a 1:2 antibody to antigen stoichiometry and in a daisy chain formation. In some embodiments, the monoclonal antibody of the disclosure binds to human pro/latent myostatin in a daisy chain formation. In some embodiments, an Fab fragment of a monoclonal antibody of the disclosure binds to human pro/latent myostatin in a 2:1 Fab to antigen stoichiometry. In some embodiments, an Fab fragment of the monoclonal antibody of the disclosure binds to human pro/latent myostatin in a 1:1 Fab to antigen stoichiometry. In some embodiments, the antibody binds to human pro/latent myostatin with a 1:2 mAb:Ag binding stoichiometry as measured by analytical SEC-MALS, wherein the mAb and Ag are present (i e.g., in a mAb:Ag mixture) in a 1:1, 2:1 or 3:1 ratio with a total protein concentrations ranging between about 3.5 mg/mL (e.g., about 15 µM each of mAb and Ag) and about 8 mg/mL (e.g., about 45 µM of mAb and about 15 µM of Ag) and are allowed to form immune complexes at a neutral pH at room temperature for a suitable duration of time, such as 1-48 hours, preferably about 24 hours. In some embodiments, the mAb:Ag mixture further comprises oligomeric complexes comprising a 2:1 mAb:Ag complex and/or a 2:2 mAb:Ag complex. In some embodiments, the mAb:Ag mixture does not comprise a detectable level of poly daisy-chains as measured by analytical SEC-MALS. In some embodiments, the antibody is capable of binding to the antigen with a 1:2 antibody to-antigen stoichiometry, when the antibody and the antigen are mixed at 15 µM each and are allowed to form immune complexes at a neutral pH, and wherein the binding stoichiometry is measured by analytical size exclusion chromatography (SEC) (e.g., SEC-MALS).

In some embodiments, an antibody or antigen-binding fragment disclosed herein (e.g., Ab109, Ab133, Ab141) does not cause accumulation of circulating myostatin (e.g., total myostatin or latent myostatin in serum). Whereas with certain prior art myostatin-selective activation inhibitors, such as apitegromab, which cause an accumulation of latent myostatin (e.g., latent myostatin-antibody immune complex) in serum (i.e., circulating myostatin), the antibody disclosed herein (e.g., Ab109), in some embodiments, is capable of reducing total serum myostatin levels in a subject as compared to a background level. In some embodiments, the antibody or antigen-binding fragment of the present disclosure causes a rapid reduction in circulating (i.e., serum) free latent myostatin. In some embodiments, when mice are administered with a single dose of 2-20 mg/kg of the antibody, free latent myostatin levels are reduced from background (e.g., approximately 50 ng/mL) to below detectable levels (e.g., within one day of dosing) and remains at undetectable or nearly undetectable levels (e.g., for at least 42 days).

In some embodiments, the antibody binds to human pro/latent myostatin with a 1:2 mAb:Ag binding stoichiometry as measured by analytical SEC-MALS. In some embodiments, serum myostatin levels may be determined in mouse (e.g., as described in Example 2). In some embodiments, serum myostatin levels may be determined in humans. In some embodiments, the antibody or antigen-binding fragment binds with a 1:2 antibody/fragment-to-antigen stoichiometry. In some embodiments, antibodies disclosed herein (e.g., Ab109) are capable of reducing serum concentrations of total myostatin or latent myostatin. Without wishing to be bound by theory, it is contemplated that faster serum clearance may correlate with larger immune complexes (e.g., poly daisy-chains) formed in vivo and that larger immune complex formation (e.g., oligomers) may facilitate clearance by, for example, increasing FcRn interactions. Advantageously, such enhanced clearance may be achieved or improved without engineering the antibody by introducing mutations to the Fc region (see, e.g., Muramatsu et al. Sci Rep. 2021; 11: 2160), thus minimizing the risk of unwanted immunogenicity.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence SYGMS (SEQ ID NO: 201), CDRH2 comprises the sequence SFTGSGGX$_1$YYPDSVKG (SEQ ID NO: 202) wherein X$_1$ is T or A, CDRH3 comprises the sequence DLLIRFLEWSHYYGMDV (SEQ ID NO: 203), CDRL1 comprises the sequence RSSQSLLHSSGHNFLH (SEQ ID NO: 204), CDRL2 comprises the sequence EVSNRVS (SEQ ID NO: 205), and CDRL3 comprises the sequence X$_1$QQTQYPX$_2$T (SEQ ID NO: 206), wherein X$_1$ is M or Q, X$_2$ is P or G, wherein the CDR sequences are numbered according to the Kabat numbering system.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence SYGMS (SEQ ID NO: 201), CDRH2 comprises the sequence SITGSGGETYYPDSVKG (SEQ ID NO: 207), CDRH3 comprises the sequence DLLVRFLEWSHYYGMDV (SEQ ID NO: 208), CDRL1 comprises the sequence RSSQSLLHSSGHNFLH (SEQ ID NO: 204), CDRL2 comprises the sequence EVSNRVS (SEQ ID NO: 205), and CDRL3 comprises the sequence X$_1$QATQFPRP (SEQ ID NO: 210), wherein X$_1$ is M or Q, wherein the CDR sequences are numbered according to Kabat.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence SYGMS (SEQ ID NO: 201), CDRH2 comprises the sequence SINPSGGTTYYAQKFKG (SEQ ID NO: 211), CDRH3 comprises the sequence DLLVRFLEWSHYYGMDV (SEQ ID NO: 208), CDRL1 comprises the sequence RX$_1$SQSX$_2$LHSX$_3$X$_4$HNFLH (SEQ ID NO: 212), wherein X$_1$ is S or A; X$_2$ is I or L; X$_3$ is S or L; and X$_4$ is G or A, CDRL2 comprises the sequence EX$_1$SNX$_2$X$_3$S (SEQ ID NO: 213), wherein X$_1$ is A or V; X$_2$ is R or L; X$_3$ is V or A, and CDRL3 comprises the sequence QQX$_1$TQYPPT (SEQ ID NO: 214), wherein X$_1$ is Q or Y, wherein the CDR sequences are numbered according to Kabat.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence SYGMS (SEQ ID NO: 201), CDRH2 comprises the sequence SX$_1$TGSGGX$_2$TYYPDSVKG (SEQ ID NO: 275) wherein X$_1$ is F or I, and X$_2$ is E or A, CDRH3 comprises the sequence DLLX$_1$RFLEWSHYYGMDV (SEQ ID NO: 272) wherein X$_1$ is I or V, CDRL1 comprises the sequence RSSQSLLHSSGHNFLH (SEQ ID NO: 204), CDRL2 comprises the sequence ETSNRX$_1$X$_2$ (SEQ ID NO: 276) wherein X$_1$ is V or A and X$_2$ is P or S, and CDRL3 comprises the sequence X$_1$QQX$_2$TQX$_3$PX$_4$X$_5$ (SEQ ID NO: 277) wherein X$_1$ is M or Q, X$_2$ is Q or A, X$_3$ is Y or F, X$_4$ is R, P, or G, and X$_5$ is T or P, wherein the CDR sequences are numbered according to the Kabat numbering system.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence GFTFX$_1$SY (SEQ ID NO: 278), wherein X is S or T, CDRH2 comprises the sequence TGSGG (SEQ ID NO: 279), CDRH3 comprises the sequence LLX$_1$RFLEWSHYYGMD (SEQ ID NO: 280) wherein X$_1$ is I or V, CDRL1 comprises the sequence SQSLLHSSGHNF (SEQ ID NO: 281), CDRL2 comprises the sequence EX$_1$S wherein X$_1$ is T or V, and CDRL3 comprises the sequence X$_1$X$_2$X$_3$X$_4$X$_5$X$_6$ wherein X$_1$ is Q, R, or A, X$_2$ is T or P, X$_3$ is Q or F, X$_4$ is Y, F, or G, X$_5$ is P or G, and X$_6$ is G, P, or R, wherein the CDR sequences are numbered according to the Chothia numbering system. In some embodiments, the CDRL3 comprises the sequence QTQYPX$_1$ (SEQ ID NO: 293), wherein X$_1$ is P or G.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence GFTFTSSYG (SEQ ID NO: 284), CDRH2 comprises the sequence X$_1$TGSGGX$_2$T (SEQ ID NO: 285) wherein X$_1$ is F or I and X$_2$ is E, T, or A, CDRH3 comprises the sequence ARDLLVRFLEWSHYYGMDV (SEQ ID NO: 286), CDRL1 comprises the sequence QSLLHSSGHNF (SEQ ID NO: 287), CDRL2 comprises the sequence EX$_1$S wherein X is T or V, or the sequence EVSNRVS (SEQ ID NO: 205) and CDRL3 comprises the sequence X$_1$QX$_2$TQX$_3$PX$_4$X$_5$ (SEQ ID NO: 288) wherein X$_1$ is Q or M, X$_2$ is Q or A, X$_3$ is Y or F, X$_4$ is Y, P, or G, and X$_5$ is P or T, wherein the CDR sequences are numbered according to the IMGT numbering system.

In some embodiments, the antibody or antigen-binding fragment comprises an HCDR1 of SEQ ID NO: 201; an HCDR2 of SEQ ID NO: 202, wherein X$_1$ is T or A; an HCDR3 of SEQ ID NO: 203; a LCDR1 of SEQ ID NO: 204; a LCDR2 of SEQ ID NO: 205; and a LCDR3 of SEQ ID NO: 206, wherein X$_1$ is M or Q and X$_2$ is P or G, as numbered according to the Kabat numbering system.

In some embodiments, the antibody or antigen-binding fragment comprises an HCDR1 of SEQ ID NO: 293; an HCDR2 of SEQ ID NO: 279; an HCDR3 of SEQ ID NO: 296; a LCDR1 of SEQ ID NO: 281; a LCDR2 of EVS; and a LCDR3 of SEQ ID NO: 297, wherein X$_1$ is P or G, as numbered according to the Chothia numbering system.

In some embodiments, the antibody or antigen-binding fragment comprises an HCDR1 of SEQ ID NO: 293; an HCDR2 of SEQ ID NO: 294, wherein X$_1$ is T or A; an HCDR3 of SEQ ID NO: 257; a LCDR1 of SEQ ID NO: 258; a LCDR2 of EVS; and a LCDR3 of SEQ ID NO: 292, wherein X$_1$ is M or Q and X$_2$ is P or G, as numbered according to the IMGT numbering system.

In some embodiments, an anti-pro/latent-myostatin antibody or an antigen-binding portion thereof suitable for carrying out various embodiments of the present disclosure comprises the following six CDRs: a CDRH1 comprising GFTFSSYG (SEQ ID NO: 3); a CDRH2 comprising FTGSGGX$_1$ (SEQ ID NO: 291) wherein X$_1$ is selected from T and A; a CDRH3 comprising ARDLLIRFLEWSHYYGMDV (SEQ ID NO: 257); a CDRL1 comprising QSLLHSSGHNF (SEQ ID NO: 258); a CDRL2 comprising EVSNRVS (SEQ ID NO: 289); and, a CDRL3 comprising X$_1$QQTQYPX$_2$T (SEQ ID NO: 292), wherein X$_1$ is selected from M and Q, and X$_2$ is selected from P and G. In preferred embodiments, the CDRH2 comprises FTGSGGT (SEQ ID NO: 256) or FTGSGGA (SEQ ID NO: 262) and/or the CDRL3 comprises QQQTQYPGT (SEQ ID NO: 261), MQQTQYPPT (SEQ ID NO: 260), or MQQTQYPGT (SEQ ID NO: 290).

In some embodiments, the antibody or antigen-binding fragment comprises six complementarity determining regions (CDRs): CDRH1, CDRH2, CDRH3, CDRL1, CDRL2, and CDRL3, wherein CDRH1 comprises SEQ ID NO: 201, CDRH2 comprises SEQ ID NO: 214, CDRH3 comprises SEQ ID NO: 215, CDRL1 comprises SEQ ID NO: 216, CDRL2 comprises SEQ ID NO: 217, and CDRL3 comprises any one of SEQ ID NOs: 218 or 224, as defined by the Kabat numbering system. In some embodiments, preferred antibodies, or antigen-binding fragments, for carrying out various embodiments of the present disclosure comprise an antibody or antigen-binding fragment comprising six complementarity determining regions (CDRs), CDRH1, CDRH2, CDRH3, CDRL1, CDRL2, or CDRL3, or combinations thereof, wherein CDRH1 comprises SEQ ID NO: 201, CDRH2 comprises any one of SEQ ID NOs: 219 or 226, CDRH3 comprises SEQ ID NO: 220, CDRL1 comprises SEQ ID NO: 216, CDRL2 comprises SEQ ID NO: 222, and CDRL3 comprises any one of SEQ ID NOs: 223, 225, or 227, as defined by the Kabat numbering system.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises SEQ ID NO: 201, CDRH2 comprises SEQ ID NO: 214, CDRH3 comprises SEQ ID NO: 215, CDRL1 comprises SEQ ID NO: 216, CDRL2 comprises SEQ ID No: 217, and CDRL3 comprises SEQ ID NO: 218, as defined by the Kabat numbering system. In some embodiments, the antibody or antigen-binding fragment comprises a CDRH1 comprising the sequence of SEQ ID NO: 201, a CDRH2 comprising the sequence of SEQ ID NO: 214, a CDRH3 comprising the sequence of SEQ ID NO: 215, a CDRL1 comprising the sequence of SEQ ID NO: 216, a CDRL2 comprising the sequence of SEQ ID NO: 217, and a CDRL3 comprising the sequence of SEQ ID No: 224, as defined by the Kabat numbering system. In some embodiments, the antibody or antigen-binding fragment comprises a CDRH1 comprising the sequence of SEQ ID NO: 201, a CDRH2 comprising any one of the sequences of SEQ ID NOs: 219 or 226, a CDRH3 comprising the sequence of SEQ ID NO: 220, a CDRL1 comprising the sequence of SEQ ID NO: 216, a CDRL2 comprising the sequence of SEQ ID NO: 222, and a CDRL3 comprising any one of the sequences of SEQ ID NOs: 223, 225, or 227, as defined by the Kabat numbering system. In some embodiments, the antibody or antigen-binding fragment comprises a CDRH1 comprising the sequence of SEQ ID NO: 201, a CDRH2 comprising the sequence of SEQ ID NO: 219, a CDRH3 comprising the sequence of SEQ ID NO: 220, a CDRL1 comprising the sequence of SEQ ID NO: 216, a CDRL2 comprising the sequence of SEQ ID NO: 222, and a CDRL3 comprising the sequence of SEQ ID NO: 223, as defined by the Kabat numbering system. In some embodiments, the antibody or antigen-binding fragment comprises a CDRH1 comprising the sequence of SEQ ID NO: 201, a CDRH2 comprising the sequence of SEQ ID NO: 219, a CDRH3 comprising the sequence of SEQ ID NO: 220, a CDRL1 comprising the sequence of SEQ ID NO: 216, a CDRL2 comprising the sequence of SEQ ID NO: 222, and a CDRL3 comprising the sequence of SEQ ID NO: 225, as defined by the Kabat numbering system. In some embodiments, the antibody or antigen-binding fragment comprises a CDRH1 comprising the sequence of SEQ ID NO: 201, a CDRH2 comprising the sequence of SEQ ID NO: 226, a CDRH3 comprising the sequence of SEQ ID NO: 220, a CDRL1 comprising the sequence of SEQ ID NO: 216, a CDRL2 comprising the sequence of SEQ ID NO: 222, and a CDRL3 comprising the sequence of SEQ ID NO: 227, as defined by the Kabat numbering system.

The novel antibodies and antigen-binding fragments thereof of the present disclosure are suitable for therapeutic use in human patients in the treatment of one or more myostatin-related conditions. Myostatin-related diseases and disorders include but are not limited to muscle disorders (e.g., atrophies and neuromuscular disorders such as SMA) and cardiometabolic disorders (e.g., obesity, diabetes, prediabetes, fatty liver, bone disorders and heart failure). Due in part to high potency and favorable developability, such antibodies are particularly suited for subcutaneous formulations. In some embodiments, a pharmaceutical composition comprising such antibody (or engineered construct comprising an antigen-binding fragment of such antibody) which is formulated for subcutaneous administration, is used in the treatment of metabolic disorder, wherein optionally the metabolic disorder is obesity, metabolic syndrome, diabetes, and/or prediabetes. In some embodiments, the antibody is selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141. In preferred embodiments, the antibody is Ab109, Ab133, or Ab141.

Currently available obesity treatments, such as GLP-1 receptor agonists, primarily focuses on weight loss. By contrast, the present disclosure takes into consideration the quality of weight management beyond mere weight loss (e.g., healthier weight loss) to achieve improved metabolic health. Accordingly, a myostatin inhibitor is incorporated into a weight management regimen, aimed to achieve preferential loss of fat mass over lean mass; maintenance of reduced fat mass; prevention of muscle loss; increased lean mass; increased endurance; reduced fatigue; prevention of bone loss; improved blood glucose levels; and/or improved liver health. Thus, myostatin inhibitors such as the novel antibodies and antigen-binding fragments disclosed herein, may contribute to safe and sustainable weight management, particularly when used in conjunction with another therapy aimed to address metabolic dysregulation.

Accordingly, the present disclosure provides a myostatin-selective inhibitor for use in the treatment of a metabolic disorder in a patient, wherein the treatment comprises administration of the myostatin-selective inhibitor to the patient alone or in conjunction with an additional agent, such as a GLP-1 pathway activator (e.g., a GLP-1 receptor agonist), in amounts effective to treat the metabolic disorder, wherein the myostatin-selective inhibitor is any one of the antibodies or antigen-binding fragment thereof described herein. In some embodiments, the metabolic disorder is obesity, prediabetes, diabetes (e.g., T2D), metabolic syndrome, and/or fatty liver disease. In some embodiments, the antibody is selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141. In preferred embodiments, the antibody is Ab109, Ab133 or Ab141, and optionally, the GLP-1 receptor agonist is semaglutide, tirzepatide, AMG-133 (a GLP-1 receptor agonist/GIP-1 receptor antagonist being developed by Amgen), or danuglipron (an oral GLP-1 receptor agonist being developed by Pfizer). In some embodiments, the amount and/or frequency of administration of the GLP-1 receptor agonist effective to treat the metabolic disorder may be reduced when used in conjunction with a myostatin-selective inhibitor disclosed herein.

In some embodiments, the present disclosure provides a method of treating a metabolic disorder in a subject comprising administering to the subject a myostatin-selective inhibitor (e.g., any one of the antibodies or antigen-binding fragments described herein), wherein, optionally, the subject is receiving or has received at least one dose of a GLP-1 receptor agonist and/or metformin. In some embodiments, the subject is administered metformin and not administered a GLP-1 receptor agonist. In some embodiments, the metabolic disorder is diabetes, obesity, or obesity with diabetes. In some embodiments, the GLP-1 receptor agonist comprises semaglutide. In some embodiments, the antibody is selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141. In some embodiments, the myostatin-selective inhibitor comprises Ab109, Ab133, or Ab141. In some embodiments, the myostatin-selective inhibitor is Ab109. In some embodiments, the amount and/or frequency of administration of the GLP-1 receptor agonist is reduced when used in conjunction with a myostatin-selective inhibitor disclosed herein.

In some embodiments, the present disclosure provides a method of treating obesity or improving body composition, comprising administering to the subject a myostatin-selective inhibitor (e.g., any one of the antibodies or antigen-binding fragments described herein), wherein, optionally, the subject is receiving or has received at least one dose of a GLP-1 receptor agonist and/or metformin. In some embodiments, the subject is receiving the GLP-1 receptor agonist. In some embodiments, the subject has discontinued the GLP-1 receptor agonist. In some embodiments, the GLP-1 receptor agonist comprises semaglutide. In some embodiments, the antibody is selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141. In some embodiments, the myostatin-selective inhibitor comprises Ab109, Ab133, or Ab141. In some embodiments, the myostatin-selective inhibitor is Ab109. In some embodiments, the myostatin-selective inhibitor is Ab109. In some embodiments, the amount and/or frequency of administration of the GLP-1 receptor agonist is reduced when used in conjunction with a myostatin-selective inhibitor disclosed herein.

In some embodiments, the present disclosure provides a method of treating obesity or improving body composition, comprising administering a myostatin-selective inhibitor to a subject who has discontinued treatment with a GLP-1 receptor agonist. In some embodiments, the myostatin-selective inhibitor is an antibody selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen-binding fragment thereof. In preferred embodiments, the antibody is Ab109, Ab133 or Ab141.

In some embodiments, the present disclosure provides a method of reducing fat mass regain in a subject after discontinuing treatment with a GLP-1 receptor agonist, wherein the method comprises administering to the subject a myostatin inhibitor in an amount effective to reduce fat mass gain as compared to a subject who has discontinued a GLP-1 receptor agonist therapy but is not treated with the myostatin inhibitor. In some embodiments, myostatin inhibitor treatment reduces the degree of fat mass regain following the discontinuation of GLP-1 receptor agonist therapy. In some embodiments, myostatin inhibitor treatment reduces the rate of fat mass regain following the discontinuation of GLP-1 receptor agonist therapy. In preferred embodiments, the myostatin inhibitor is a myostatin-selective inhibitor, e.g., any one of the antibodies or antigen-fragments disclosed herein (such as Ab109, Ab133, or Ab141), trevogrumab (REGN1033), and GYM329 (RO7204239) (which is an anti-latent myostatin Fc-engineered antibody, discovered by Chugai and being developed by Roche). In preferred embodiments, the myostatin selective inhibitor is an antibody or antigen binding fragment selective for pro/latent myostatin, e.g., any one of Ab101-141. In most preferred embodiments, the myostatin-selective inhibitor is Ab109, Ab133 or Ab141.

In some embodiments, the present disclosure provides a method of reducing liver fat in a subject, e.g., in an obese subject and/or a subject with fatty liver disease, comprising administering to the subject a myostatin-selective inhibitor in an amount effective to reduce liver fat. In preferred embodiments, the myostatin-selective inhibitor is used in conjunction with a GLP-1 receptor agonist for a duration sufficient to synergistically reduce relative liver weight (e.g., for a duration of longer than five weeks). In some embodiments, the myostatin-selective inhibitor is an antibody selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen-binding fragment thereof. In preferred embodiments, the antibody is Ab109, Ab133 or Ab141.

In some embodiments, the present disclosure provides a myostatin-selective inhibitor for use in the treatment of a metabolic disorder in a patient, wherein the treatment comprises administration of the myostatin-selective inhibitor to the patient alone or in conjunction with an additional agent suitable for treating the metabolic disorder. In some embodiments, the metabolic disorder is obesity, prediabetes, diabetes (e.g., T2D), metabolic syndrome, and/or fatty liver disease. In some embodiments, the myostatin-selective inhibitor is an antibody selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen-binding fragment thereof. In preferred embodiments, the antibody is Ab109, Ab133 or Ab141. In some embodiments, the amount and/or frequency of administration of the additional agent suitable for treating the metabolic disorder may be reduced when used in conjunction with a myostatin-selective inhibitor disclosed herein.

In some embodiments, the present disclosure provides a method of improving bone strength and/or preventing bone loss in a subject (e.g., an obese subject), comprising administering to the subject a myostatin-selective inhibitor in an amount effective to improve bone strength and/or prevent bone loss as compared to a subject (e.g., an obese subject) who has not been administered the myostatin-selective inhibitor. In some embodiments, bone strength is measured by bone mineral density and/or the frequency or severity of bone fracture. In some embodiments, the subject is or has been on a GLP-1 receptor agonist therapy. In some embodiments, the subject is on a weight loss regimen. In some embodiments, the subject is on or has received a therapy that causes GDF11 inhibition (e.g., selective or non-selective inhibitors of GDF11). In some embodiments, the GDF11 inhibitor therapy is replaced with a myostatin-selective inhibitor therapy (such as the novel antibodies disclosed herein). In some embodiments, the myostatin-selective inhibitor is an antibody selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen-binding fragment thereof. In preferred embodiments, the antibody is Ab109, Ab133 or Ab141.

In some embodiments, the present disclosure provides a method of improving blood glucose or hemoglobin A1C (A1C) levels in a pre-diabetic or diabetic subject who is receiving or has received a GLP-1 receptor agonist, comprising administering to the subject a myostatin-selective inhibitor in an amount effective to reduce blood glucose (e.g., fasting glucose) or A1C levels as compared to baseline (i.e., before the administration of the myostatin-selective inhibitor). In some embodiments, the myostatin-selective inhibitor is an antibody selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen-binding fragment thereof. In preferred embodiments, the antibody is Ab109, Ab133 or Ab141.

In any one of the embodiments disclosed herein, the GLP-1 receptor agonist may comprise semaglutide, tirzepatide, AMG-133 (a GLP-1 receptor agonist/GIP-1 receptor antagonist being developed by Amgen), or danuglipron (an oral GLP-1 receptor agonist being developed by Pfizer).

In any one of the embodiments disclosed herein, the myostatin-selective inhibitor for use according to the present disclosure may be an antibody or antigen-binding fragment described herein, e.g., Ab109, Ab133, or Ab141 or an antigen-binding fragment thereof, trevogrumab (REGN1033), or GYM329 (RO7204239) (which is an anti-latent myostatin, Fc-engineered antibody, discovered by Chugai and being developed in SMA by Roche). In some embodiments, the myostatin-selective inhibitor for use according to the present disclosure is an antibody selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen-binding fragment thereof. In preferred embodiments, the antibody is Ab109, Ab133 or Ab141. In some embodiments, the myostatin-selective inhibitor for use according to the present disclosure is Ab109.

The present disclosure further encompasses a combination or adjunct (add-on) therapy comprising a myostatin inhibitor and biguanide (e.g., metformin) without a GLP-1 receptor agonist. Such combination or adjunct (add-on) therapy may be used in the treatment of a metabolic disorder in a patient, wherein optionally the metabolic disorder is obesity, diabetes, prediabetes and/or metabolic syndrome. In some embodiments, the patient is poorly responsive to a GLP-1 receptor agonist therapy, has low tolerance to a GLP-1 receptor therapy, and/or is at risk of developing depression, suicidal ideation, or cancer. In some embodiments, the myostatin inhibitor is a non-selective inhibitor, such as an agent that inhibits both myostatin and GDF11 but not Activin A, or an agent that inhibits both myostatin and Activin A, but not GDF11. In some embodiments, the non-selective inhibitor is an ActRII receptor antagonist (such as bimagrumab), an anti-myostatin Adnectin® (such as taldefgrobep alfa) or a ligand trap that comprises a ligand-binding fragment/moiety of ActRII or follistatin. In preferred embodiments, the myostatin inhibitor is a myostatin-selective inhibitor that does not inhibit GDF11 or Activin A. In some embodiments, the myostatin-selective inhibitor to be used in conjunction with a biguanide (e.g., metformin) is selected from the novel antibodies or antigen-fragments disclosed herein (such as Ab109, Ab133 and Ab141), trevogrumab (REGN1033), and GYM329 (RO7204239) (which is an anti-latent myostatin Fc-engineered antibody, discovered by Chugai and being developed in SMA by Roche). In some embodiments, the myostatin-selective inhibitor for use according to the present disclosure is an antibody selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen-binding fragment thereof.

BRIEF DESCRIPTION OF THE FIGURES

FIGS. 1A and 1B show inhibition of myostatin activation by antibodies of the disclosure.

FIGS. 4A-B show pH-dependent dissociation of antibodies disclosed herein at pH 7.4 as compared to at pH 5.5. Numbers to the right of curves represent the calculated fold difference in off-rates at the different pH values tested.

FIG. 6A shows percent change in body weight from baseline. FIG. 6B shows percent change in lean mass from baseline. FIG. 6C shows percent change in gastrocnemius mass from baseline. The dashed line in each figure shows the average values for Ab2 treatment at 10 mg/kg. **$p<0.0001$; *$p<0.005$; **$p<0.01$; *$p<0.05$.

FIG. 7A shows change in body weight. FIG. 7B shows change in lean mass. FIG. 7C shows change in gastrocnemius mass. FIG. 7D shows change in quadricep mass. **$p<0.0001$; *$p<0.005$; **$p<0.01$; *$p<0.05$.

FIG. 9A shows change in body weight. FIG. 9B shows change in lean mass as measured by qNMR. FIG. 9C shows change in gastrocnemius mass. FIG. 9D shows change in quadricep mass. The dashed line in each figure corresponds to the average values for Ab2 treatment at 10 mg/kg. **$p<0.0001$; *$p<0.005$; **$p<0.01$; *$p<0.05$.

FIG. 10A shows percent change in body weight from baseline. FIG. 10B shows percent change of lean mass from baseline. FIG. 10C shows percent change in gastrocnemius weight from control. FIG. 10D shows percent change of quadricep weight from control. FIG. 10E shows gastrocnemius weight. FIG. 10F shows quadricep weight. The dashed line in each figure corresponds to the average value for Ab2 treatment at 3 mg/kg. **$p<0.0001$; *$p<0.005$; **$p<0.01$; *$p<0.05$.

FIGS. 11A-C shows body weight over the duration of the treatment. FIG. 11D shows percent change in body weight from baseline. FIG. 11E shows percent change in lean mass from baseline; **$p<0.0001$; *$p<0.005$; **$p<0.01$; *$p<0.05$. FIG. 11F shows percent change in gastrocnemius mass compared to liraglutide alone (left panel) or IgG control (right panel). FIG. 11G shows percent change in fat mass from baseline from day 15 to day 1 (left panel) or from day 29 to day 1 (right panel). FIG. 11H shows serum exposure of Ab2, Ab109, and Ab130.

FIG. 12A shows the effects of Ab109 and/or metformin on fat mass in mice that were fed with a 60% high fat diet and switched to a 45% high fat diet. FIG. 12B shows the effects of Ab109 and/or metformin on lean mass in mice that were fed with a 60% high fat diet and switched to a 45% high fat diet.

FIG. 13A shows the effect on subcutaneous adipose tissue weight. FIG. 13B shows the effect on epididymal adipose tissue weight.

FIG. 14A-K show in vivo effects of semaglutide treatment in combination with IgG control or Ab109 in DIO mice fed with a high fat diet. FIG. 14A shows the effect on body weight. FIGS. 14B and 14C show the effect on lean mass. FIG. 14D shows the effect on fat mass. FIG. 14E shows the effect on gastrocnemius weight. FIG. 14F shows the effect on inguinal fat pad weight. FIG. 14G shows the effect on epididymal fat pad weight. FIG. 14H shows the effect of Ab109 and semaglutide on lean mass (left panel) and fat mass (right panel) as measured by qNMR; statistical analysis was done using one-way ANOVA (Dunnett's multiple comparison test; **$p<0.0001$; *$p<0.005$; **$p<0.01$; *$p<0.05$. FIG. 14I shows fasting serum glucose throughout the study and at days 18 and 64 following treatment with Ab109 alone or in combination with semaglutide. FIG. 14J shows changes in relative liver weight (expressed as % liver weight to body weight) following semaglutide treatment in combination with 2 mg/kg or 20 mg/kg of Ab109. **$p<0.0001$; *$p<0.005$; **$p<0.01$; *$p<0.05$. FIG. 14K shows relative fat mass and circulating leptin in mice from this study, **$p<0.0001$; $p<0.01$; *$p<0.05$. Statistical analysis was done using one-way ANOVA (Tukey's multiple comparison test).

FIG. 19A shows the effect for 0.04 mg/kg semaglutide. FIG. 19B shows the effect for 0.01 mg/kg semaglutide. The upper panel for each figure shows absolute fat mass change; the lower panel for each figure shows percent fat mass change.

FIG. 20A shows the effect for 0.04 mg/kg semaglutide. FIG. 20B shows the effect for 0.01 mg/kg semaglutide.

FIG. 21A shows relative weight (left) and percent weight change (right) of quadricep muscle. FIG. 21B shows relative weight (left) and percent weight change (right) in gastrocnemius muscle.

FIG. 22A shows relative weight (left) and percent weight change (right) of perigonadal fat pad. FIG. 22B shows relative weight (left) and percent weight change (right) of inguinal fat pad.

FIGS. 23A-C show negative stain electron microscopy 2D class averages for: Ab2:Pro-myostatin in 1:1 complex from 1:1 input sample (FIG. 23A), Ab109:Pro-myostatin in 1:1 complex from 1:2 input sample (FIG. 23B), and Ab133:Pro-myostatin in 1:1 complex from 2:1 input sample (FIG. 23C).

DETAILED DESCRIPTION OF CERTAIN EMBODIMENTS

Figure 2A:
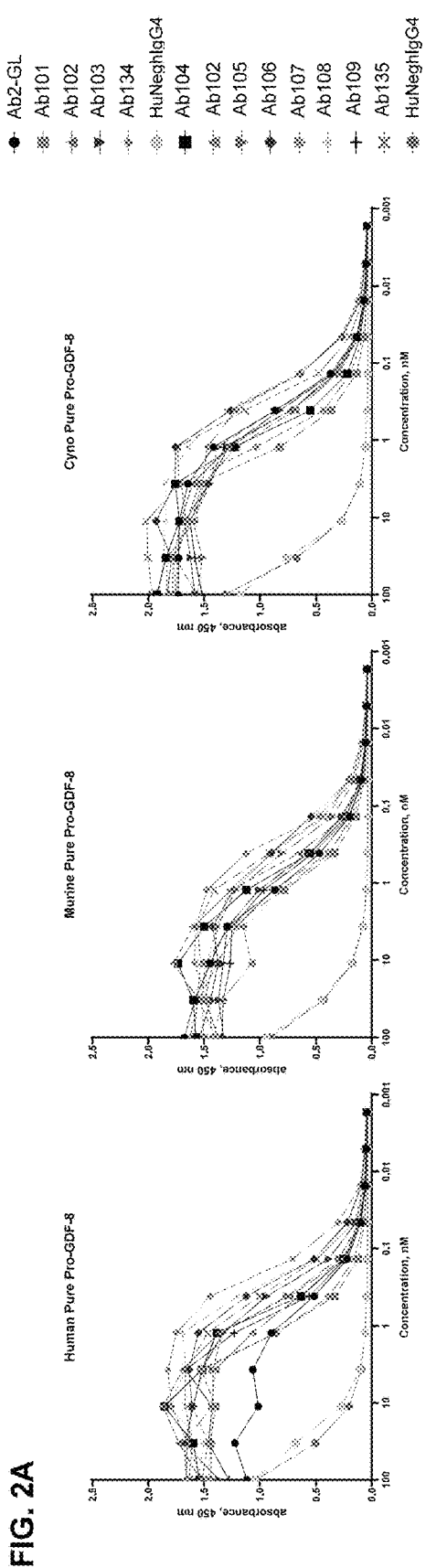
FIG. 2A shows binding of Abs 101-109, Ab135, Ab2, and controls to purified pro-myostatin from human, mouse, or *cynomolgus* monkeys.
Figure 2B:
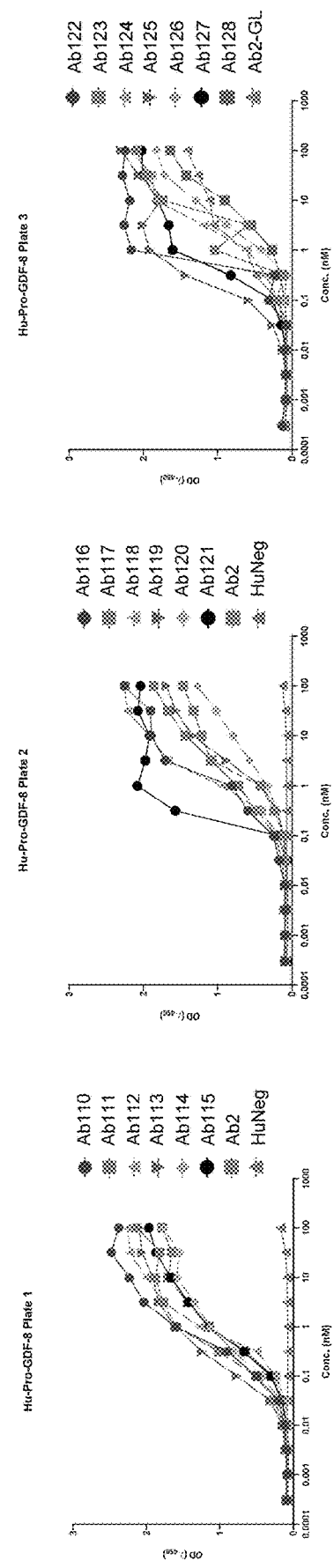
FIGS. 2B-D show binding of antibodies Ab122-128 and Ab2 to human pro-myostatin (FIG. 2B), mouse pro-myostatin (FIG. 2C), and *cynomolgus* monkey pro-myostatin (FIG. 2D).
Figure 2C:
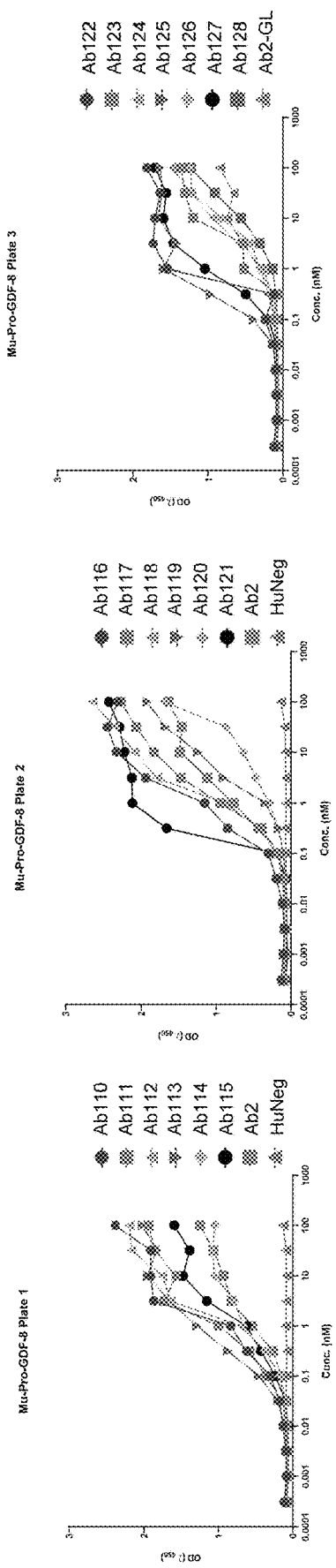
Figure 2D:
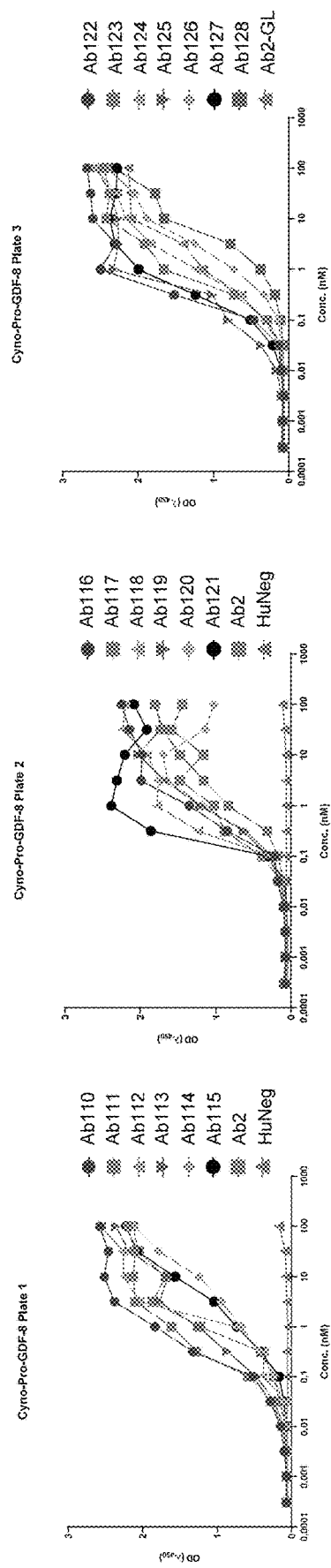

The present disclosure encompasses novel antibodies and antigen-binding fragments thereof that selectively bind to pro/latent myostatin with high affinity and are capable of inhibiting protease-dependent activation of myostatin with high potency (e.g., IC50 of less than 1 nM, e.g., IC50 of less than 0.5 nM, preferably as measured by functional ELISA). Such antibodies and antigen-binding fragments thereof specifically bind to pro/latent myostatin but do not bind to free mature myostatin or GDF11. In some embodiments, the antibodies and fragments bind a region (e.g., epitope) within the prodomain of the pro/latent myostatin complex that confers robust inhibitory potency, e.g., a similar or identical region to that bound by Ab2. Unlike the previously described inhibitors, however, in certain embodiments the antibodies/fragments disclosed herein are capable of binding to the antigen (i.e., pro/latent myostatin) with high monovalent affinities without compromising inhibitory potency. These features present an opportunity to engineer constructs such as bispecific antibodies comprising a first arm of the antibody that selectively binds pro/latent myostatin and inhibits its activation and a second arm of the antibody that binds a second target of interest. In some embodiments, the high binding affinity of the antibodies and fragments disclosed herein facilitates effective subcutaneous formulation and/or therapeutic use.

In some embodiments, the present disclosure also encompasses methods of treating or preventing conditions associated with myostatin dysregulation using a myostatin inhibitor disclosed herein, e.g., an antibody or antigen-binding fragment thereof that specifically binds to pro/latent myostatin and blocks activation of myostatin in an amount effective to treat or prevent such conditions. In some embodiments, the disclosure provides methods of treating or preventing a metabolic disorder, e.g., obesity and/or type 2 diabetes, comprising administering a therapeutically effective amount of an antibody or antigen-binding fragment disclosed herein that specifically binds to pro/latent myostatin and blocks activation of myostatin. In some embodiments, the disclosure encompasses use of such an antibody or antigen-binding fragment as a monotherapy or in conjunction with at least one other therapy for treating or preventing a metabolic disorder, e.g., obesity and/or type 2 diabetes. In some embodiments, the antibodies and fragments disclosed herein may also be used to treat other indications, e.g., muscle disorders such as various types of dystrophies, spinal cord injuries, or spinal muscular atrophy.

The present disclosure provides antibodies and antigen-binding fragments that are capable of selectively inhibiting myostatin by binding to pro/latent myostatin with high potency and specificity. Such highly potent antibodies and antigen-binding fragments thereof that specifically bind to pro/latent myostatin may not only be efficacious for treating conditions relating to myostatin signaling, but also may provide an improved therapeutic profile (including increased safety and improved tolerability) and/or facilitate ease of administration (e.g., at concentrations suitable for subcutaneous administration). The lack of specificity observed in myostatin antagonists described elsewhere may pose a greater risk to certain patient populations because of off-target effects. For instance, myostatin inhibitors that also bind to mature myostatin may block additional biological pathways in addition to the myostatin signaling pathway due to the high homology of the mature myostatin protein with other members of the TGFβ superfamily (e.g., Activin A or GDF11). Such off-target effects may therefore potentially limit the population of patients who can safely undergo therapy due to unacceptable adverse-effects such as abnormal bleeding, wound healing, or reproductive problems caused by off-target antibody binding (Campbell, et al. Muscle Nerve (2016); David, L., Blood 109, 1953-1961 (2007)). For example, Activin A is involved in both wound healing and reproductive biology, and inhibition of Activin A would therefore limit use in patients who have recently undergone surgery or injury, or in women of reproductive age. Such increased risk of adverse effects or toxicity may be particularly concerning where i) a patient population requires a long-term treatment (such as chronic conditions); and/or, ii) a patient population is or includes pediatric patients, who may be susceptible to such adverse effects and/or toxicity. Accordingly, the present disclosure provides improved myostatin inhibitors that target pro/latent myostatin specifically and with high potency, thereby providing potentially greater safety profiles.

In addition, antibodies or antigen-binding fragments thereof disclosed herein may provide additional surprising improvements as compared to antibodies known in the art. In some embodiments, the antibodies or antigen-binding fragments thereof disclosed herein can provide one or more (e.g., all) of the following effects: increased affinity to facilitate a lower administration concentration, increased myostatin binding stoichiometry, increased serum clearance of myostatin, reduced levels of circulating latent myostatin, and higher pH sensitivity of antigen binding (i.e., binding to pro/latent myostatin with greater affinity at physiological pH as compared to acidic pH), prevent muscle atrophy and preserve muscle during weight loss. In some embodiments, the antibodies and antigen binding fragments thereof disclosed herein provide improved subcutaneous bioavailability, e.g., at least 80%, 81%, 82%, 83%, 84%, or 85% bioavailability or greater, as compared to intravenous administration, e.g., as measured via serum exposure levels in an animal (e.g., monkey) receiving equal doses of antibody administered via intravenous and subcutaneous routes.

Definitions

The articles "a" and "an" are used herein to refer to one or to more than one (i.e., to at least one) of the grammatical objects of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages may mean±1%. Furthermore, the term "about" can mean within ±1% of a value.

Adjunct therapy: The terms "adjunct therapy" and "add-on" therapy are used interchangeably herein and are intended to refer to a therapeutic regimen in which a second agent (used as an adjunct therapy) is administered to a subject who is on, has received, or to be treated with, a first agent (e.g., background therapy). The terms "in conjunction with" and "complementary to" are used interchangeably herein and intended to refer to therapies used together, whether concurrent or partially overlapping in time.

Administer/administration: The terms "administer," "administering," or "administration" include any method or act of delivery of a pharmacological agent (e.g., a medicament) to an intended subject (e.g., a patient). The pharmacological agent may be any suitable therapeutic agent, such as a biologic agent, such as an antibody or an antigen-binding fragment thereof (e.g., a pharmaceutical composition comprising such an antibody or antigen-binding fragment), a peptide agent (e.g., a hormone or a modified analog thereof), or a low molecular weight agent (e.g., a structurally defined small molecule or chemical entity). The administration can be systemic or local administration. In some embodiments, administration may involve one or more agents that can be administered concurrently, simultaneously, or sequentially.

Affinity: Affinity (or "binding affinity") is the strength of binding of a molecule (such as an antibody) to its ligand (such as an antigen). It is typically measured and reported by the equilibrium dissociation constant (KD). In the context of antibody-antigen interactions, KD is the ratio of the antibody dissociation rate ("off rate" or Koff) to the antibody association rate ("on rate" or Kon) of the antibody. Koff is how quickly the antibody dissociates from its bound antigen, and Kon is how quickly the antibody binds to its antigen. For example, an antibody with an affinity of ≤5 nM has a KD value that is 5 nM or lower (i.e., 5 nM or higher affinity) determined by a suitable in vitro binding assay. Suitable in vitro binding assays can be employed to measure KD values of an antibody for its antigen. Suitable assays include, but are not limited to: Biolayer Interferometry (BLI)-based assays (such as Octet®), surface plasmon resonance (SPR)-based assays (such as Biacore™), MesoScale Discovery (MSD) immunoassays (such as MSD-solution equilibrium titration or MSD-SET). In some embodiments, KD is determined by BLI-based assay (such as Octet®). In preferred embodiments, KD is determined by an SPR-based assay (such as Biacore™).

Antibody: As used herein, the term "antibody" refers to full-length immunoglobulin molecules comprising four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. Antibodies provided in the present disclosure include human antibodies and humanized antibodies.

Antigen-binding fragment: The terms "antigen-binding fragment," "antigen binding fragment," "antigen-binding portion," "antibody fragment," or "antibody portion" are used interchangeably herein and refer to one or more fragments of an antibody that retain the ability to specifically bind to an antigen (e.g., pro/latent myostatin). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR); and (vii) an adnectin. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al. (1993) Proc. Natl. Acad. Sci. USA 90:6444-6448; Poljak, R. J. et al. (1994) Structure 2:1121-1123). Antigen-binding fragments may be incorporated into engineered constructs, such as multi-functional constructs comprising the antigen-binding fragment. Non-limiting examples of such engineered constructs include multi-specific antibodies, such as bispecific antibodies. In some embodiments, the bispecific antibody comprises a Fab fragment of any one of the novel antibodies disclosed herein, which allows single-arm binding to pro/latent myostatin.

Biolayer Interferometry (BLI): BLI is a label-free technology for optically measuring biomolecular interactions, e.g., between a ligand immobilized on the biosensor tip surface and an analyte in solution. BLI provides the ability to monitor binding specificity, rates of association and dissociation, and/or concentration. BLI platform instruments are commercially available, for example, from Pall/ForteBio and are commonly referred to as the Octet® System. Unless expressly specified otherwise, BLI-based assays are carried out according to the manufacturer's instructions (e.g., binding assayed at ambient/room temperature, for example, at ~20-25° C.).

Body composition: The term "body composition" refers to relative components that make up a body, including fat mass, muscle (lean) mass, bone, and water etc. In particular, in the context of weight management, body composition refers to the ratio of muscle mass to fat mass in the body. Unless explicitly stated otherwise, body composition refers to the body composition of the whole body. Body composition can be measured by various suitable methods known in the art, including but not limited to body density, dual energy X-ray absorptiometry (DEXA), air displacement plethysmography (ADP), bioelectrical impedance analysis (BIA), body volume indicator (BVI), skin folds (with measuring caliper), ultrasound, quantitative magnetic resonance (QMR), and measurement of circumferences (e.g., as measured at waistline).

Body mass index (BMI): The term "body mass index" or "BMI" is a numerical value derived from the mass and height of a person and is defined as weight in kilograms divided by height in meters squared (expressed in units of $kg/m^2$). BMI provides general body weight-height relationships which can be used to categorize a person as underweight, normal weight, overweight, obese, or extreme obese, based on tissue mass (muscle, fat and bone) relative to height.

Combination therapy: As used herein, "combination therapy" refers to a therapeutic regimen involving administration of two or more active agents (e.g., two or more pharmacological agents) intended to treat a predetermined indication and/or conditions associated therewith. The two or more agents may be formulated as separate compositions (e.g., formulations) or may be formulated as a single composition (formulation). "Combination therapy" encompasses therapies used in conjunction with each other and complementary to each other.

Compete: The term "compete" or "block," as used herein with regard to antigen binding by an antibody or an antigen-binding fragment, refers to when a first antibody or antigen-binding fragment binds to an epitope of a protein (e.g., latent myostatin) in a manner sufficiently similar to the binding of a second antibody or antigen-binding fragment, such that the result of binding of the first antibody or antigen-binding fragment with its epitope is detectably decreased in the presence of the second antibody or antigen-binding fragment compared to the binding of the first antibody or antigen-binding fragment in the absence of the second antibody or antigen-binding fragment. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. Competition between antibodies can be determined using any method known in the art, including Bio-Layer Interferometry (BLI)-based techniques (e.g., Octet®) or enzyme-linked immunosorbent assay (ELISA). In some embodiments, epitope binning experiments may be used to assess competitive binding between antibodies or antigen-binding fragments.

Cross-compete: The term "cross-compete" or "cross-block", as used herein with regard to antigen binding by an antibody or an antigen-binding fragment, refers to when a first antibody or antigen-binding fragment binds to an epitope of a protein (e.g., latent myostatin) in a manner sufficiently similar to the binding of a second antibody or antigen-binding fragment, such that each antibody detectably inhibits the binding of the other antibody with its epitope or ligand, whether to the same, greater, or lesser extent. For instance, a first antibody cross-competes with a second antibody if the first antibody measurably inhibits antigen binding by the second antibody, and vice versa. This differs from a first antibody that competes but does not cross-compete with second antibody, where the first antibody inhibits antigen binding by the second antibody but the second antibody does not necessarily inhibit antigen binding by the first antibody. Cross-competition between antibodies can be determined using any method known in the art, including Bio-Layer Interferometry (BLI)-based techniques (e.g., Octet®) or enzyme-linked immunosorbent assay (ELISA). In some embodiments, epitope binning experiments may be used to assess competitive binding between antibodies or antigen-binding fragments.

Both competing and cross-competing antibodies are within the scope of this disclosure. Regardless of the mechanism by which such competition or cross-competition occurs (e.g., steric hindrance, conformational change, or binding to a common epitope, or portion thereof), a skilled artisan would appreciate that such competing and/or cross-competing antibodies are encompassed and can be useful for the methods and/or compositions provided herein. In some embodiments, competition or cross-blocking (cross-competition) is determined using Bio-Layer Interferometry (BLI)-based assay. In some embodiments, a first antibody or antigen-binding fragment is immobilized onto a biosensor and binding between the first antibody or antigen-binding fragment and antigen is determined using a pre-mixed complex comprising a second antibody or antigen-binding fragment bound to the antigen. In some embodiments, a first antibody or antigen-binding fragment is immobilized onto a biosensor, after which a stepwise binding of the antigen and a second antibody or antigen-binding fragment is measured.

Decrease/reduce: The term "decrease" or "reduce," as used herein, in the context of a disease symptom refers to a statistically significant decrease in such level. The decrease can be, for example, at least 1%, 5%, 10%, 15%, 20%, 25%, 30%, 35%, 40%, 45%, 50%, 55%, 60%, 65%, 70%, 75%, 80%, 85%, 90%, or 95%. The decrease can also be, for example, about 1-10%, 10-20%, 1-30%, 20-50%, 30-60%, 40-70%, 50-80%, or 60-90%. In certain embodiments, an individual with a disorder may achieve a level of reduced effect that is comparable or within the normal range for that effect in an individual without such disorder.

Dieting/diet regimen: In the context of the present disclosure, certain dieting may be incorporated as part of weight management, e.g., obesity treatment which includes a pharmacological intervention. Dieting may include caloric/calorie restriction (i.e., reduced calorie intake or reduced absorption of calories) as well as alterations in choices about the type of food consumed (e.g., high protein, lower fat, and/or lower carbohydrate regimens), and/or regimented timing/schedules of food intake (e.g., intermittent fasting). Thus, a patient is on a "diet or reduced calorie regimen" when the patient incorporates or is instructed by a physician or equivalent to incorporate dieting into overall therapeutic regimen, e.g., as part of weight management.

Effective amount: As used herein, the terms "effective amount," "effective dose," and "therapeutically effective amount" are used interchangeably and refer to any amount or dose of a compound or composition that is sufficient to result in a desired biological or medicinal effect in a tissue or subject. For example, in certain embodiments of the present disclosure, the intended purpose may be to inhibit activation of myostatin in vivo or to achieve a clinically meaningful outcome associated with the myostatin inhibition. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex, and diet of the patient; the time of administration, route of administration, and/or rate of excretion or metabolism of the specific pharmaceutical agent employed; the duration of the treatment; and like factors as is well known in the medical arts. In some embodiments, an effective amount may refer to an amount that, when administered according to a particular regimen, produces a positive physiological or clinical outcome with a reasonably acceptable level of adverse effects (e.g., toxicity), such that the adverse effects, if present, are tolerable enough to continue the experiment or tolerable enough for a patient to continue the therapeutic regimen, and the benefit of the therapy outweighs the toxicity. Those of ordinary skill in the art will appreciate that in some embodiments of the disclosure, the administered amount may be considered an effective amount if it contains an amount appropriate for administration that is correlated with a positive outcome.

Epitope: The term "epitope" as used herein refers to a region of an antigen that is bound by an antibody or fragment thereof. It includes any polypeptide determinant capable of specific binding to the antibody or fragment. In certain embodiments, epitope determinants include chemically active surface groupings of molecules such as amino acids, sugar side chains, phosphonyls, or sulfonyls, and, in certain embodiments, may have specific three-dimensional structural characteristics, and/or specific charge characteristics. In certain embodiments, an antibody or fragment is said to specifically bind an antigen when it preferentially recognizes its target antigen in a complex mixture of proteins and/or macromolecules. The epitope can be a linear epitope or a conformational epitope. The epitope can be determined by, e.g., crystallography of the antigen in complex with the antibody. Antibodies are said to "bind to the same or similar epitope" if the antibodies cross-compete with one another.

Epitope binning: The term "epitope binning" (sometimes referred to as antibody binning or epitope mapping) refers to a process of sorting a set (e.g., "a library") of monoclonal antibodies made against a target protein or protein complex (i.e., antigen) based on competition for binding to the target. The antibodies in the library are tested in a pairwise fashion to evaluate if they block/cross-block one another's binding to the antigen. Closely related binning profiles indicate that the antibodies have the same or closely related (e.g., overlapping) epitope and are "binned" together. Binning may provide useful structure-function profiles of antibodies that share similar binding regions within the same antigen because biological activities (e.g., intervention; potency) effectuated by binding of an antibody to its target is likely to be carried over to another antibody in the same bin. Thus, among antibodies within the same epitope bin, those with higher affinities (lower KD) typically have greater potency.

Exercise/exercise regimen: As used herein, the term "exercise" includes any physical activities. The term "exercise regimen" refers to a treatment regimen that incorporates physical activity as a component.

Fc variant: As used herein, an "Fc variant" of a reference antibody refers to an antibody comprising one or more mutations within the Fc region as compared to the reference antibody. In some embodiments, the Fc variant antibody retains the same CDR sequences as the reference antibody. Fc variants can be generated to have altered (e.g., increased) affinities to the Fc receptor (FcR), such as the neonatal Fc receptor (FcRn). In some embodiments, an antibody that binds to FcRn with increased affinity can result in longer serum half-life of the Fc variant, as compared to the reference antibody without the Fc mutation(s).

GLP-1 analog: As used herein, the term "GLP-1 analog" or "incretin mimetic," refers to a peptide or modified peptide bearing structural similarities to the naturally occurring GLP-1 and is capable of binding to and activating the GLP-1 receptor. A GLP-1 analog may be an extendin-based therapy, a DPP-IV-resistant analog. Non-limiting examples of GLP-1 analogs include, albiglutide, beinaglutide, cotadutide, danuglipron, dulaglutide, exenatide, exenatide ER, liraglutide, lixisenatide, PEG-loxenatide, mazdutide, MEDI0382, noiiglutide, orforglipron, pemvidutide, PF-07081532, retatrutide, semaglutide, taspoglutide, tirzepatide, and XW003. GLP-1 analogs shall include analogues of human GLP-1 conjugated to substances that slow renal excretion, e.g., fatty acids, albumin, alpha-aminoisobutyric acid, etc.; they may be acylated. GLP-1 analogs shall include peptides or modified peptides comprising an amino acid sequence EGTFTSD (SEQ ID NO: 116). GLP-1 analogs may also include peptides or modified peptides comprising an amino acid sequence HXXGXFTXD (SEQ ID NO: 117), wherein X is any amino acid residue.

GLP-1 receptor agonist: The term "GLP-1 receptor agonist" or "GLP-1R agonist" or "GLP-1 RA" as used herein refers to an agent capable of binding to and activating the GLP-1 receptor. GLP-1 is a naturally occurring agonist of the GLP-1 receptor. GLP-1 receptor agonists encompass GLP-1 analogs. A GLP-1 receptor agonist may be a small molecule GLP-1 receptor agonist. In some embodiments, the GLP-1 receptor agonist is a long-acting small molecule GLP-1 receptor agonist. In some embodiments, the GLP-1 receptor agonist is a GLP-1 analog.

GLP-1 pathway activator The terms "GLP-1 pathway activator" and "activator of the GLP-1 signaling pathway" are used interchangeably herein and encompass any agent that increases or enhances the activity of the GLP-1 signaling pathway, irrespective of the mechanism of action. Increased or enhanced activity of the GLP-1 signaling pathway may be a result of, for example, a greater degree of activity, longer duration of activity, increased availability of one or more components of the signaling pathway, etc. In some embodiments, GLP-1 pathway activators include agents that modulate upstream regulators of GLP-1 (e.g., dipeptidyl peptidase (DPP-IV) inhibitors). The term GLP-1 pathway activator as used herein encompasses GLP-1 receptor agonists and GLP-1 analogs. In some embodiments, GLP-1 pathway activators include agents that regulate the amount or activity of GLP-1 (e.g., agents that increase production of or secretion of GLP-1; GLP-1 stabilizers). In some embodiments, GLP-1 pathway activators include agents that increase activation of the GLP-1 receptor (GLP-1R). In some embodiments, agents that increase activation of the GLP-1R include GLP-1 agonists, which include GLP-1 analogs. In some embodiments, GLP-1 pathway activators include agents that activate signaling downstream of the GLP-1R (e.g., activators of PI3K, PKC, cAMP, etc.). In some embodiments, GLP-1 pathway activators may include agents that modulate receptor GLP-1R expression and/or trafficking (e.g., inhibitors of GLP-1R internalization; see, e.g., Jones et al., Nat. Comm. (2018)9:1602). GLP-1 pathway activators encompass activators of the GLP-1R. In preferred embodiments, the GLP-1 pathway activator is a GLP-1 receptor agonist. GLP-1 pathway activators include, but are not limited to, antibodies and antigen-binding fragments thereof, engineered protein constructs (such as Fc conjugates and multi-functional molecules comprising a GLP-1 analog), peptides, GLP-1 gene therapy, and small molecules.

Human antibody: The term "human antibody", as used herein, refers to antibodies having variable and constant regions that are derived from human germline immunoglobulin sequences and fragments thereof.

Humanized antibody: The term "humanized antibody", as used herein, refers to antibodies derived from non-human species whose protein sequences have been modified to increase their similarity to human antibodies. "Humanized antibodies" may also refer to antibodies in which CDR sequences derived from the germline of another mammalian species, such as a mouse, have been grafted onto human framework sequences.

Inhibit or inhibition of: The term "inhibit" or "inhibition of," as used herein, means to reduce by a measurable amount, and can include, but does not require, complete prevention or inhibition.

Insulin sensitivity; insulin resistance: The term "insulin sensitivity" refers to the metabolic actions of insulin to promote glucose disposal in a subject's body. A subject is said to have increased insulin sensitivity if the subject requires smaller amounts of insulin to lower blood glucose levels as compared to the average in a human population. In contrast, a subject is said to have decreased insulin sensitivity if the subject requires higher amounts of insulin to lower blood glucose levels. A subject is said to have "insulin resistance" if the quantity of exogenous or endogenous insulin required to increase glucose uptake and utilization in a subject is significantly higher than that in a healthy subject. For instance, a subject is said to have "insulin resistance" if the quantity of exogenous or endogenous insulin required to increase glucose uptake and utilization in a subject is 10%, 20%, 30%, 40% 50%, 60%, 70%, 80%, 90%, 100%, or higher as compared to that in a healthy subject.

Latent myostatin in the circulation: As used herein, the phrase "latent myostatin in the circulation" or "circulating latent myostatin" refers to latent myostatin in the blood, plasma, or serum.

Lean/lean mass: As used herein, "lean" mass or tissue refers to muscle mass or muscle tissue, as opposed to fat mass or fat tissue (e.g., adipose).

Mature myostatin: The term "mature myostatin" refers to the dimeric growth factor, which is also known as GDF8, and is released from the latent myostatin complex. Mature myostatin is the soluble and biologically active ligand capable of binding to and activating its receptors. Unless explicitly stated otherwise, the term "mature myostatin" refers to a fully processed, biologically active form of myostatin, or fragments of the full-length mature myostatin which retain biological activity. A wildtype sequence of mature myostatin polypeptide sequence (i.e., single chain) is provided below (SEQ ID NO: 134). In some cases, mature myostatin may contain one or more mutations, which may exhibit altered structure/function or stability.

(SEQ ID NO: 134)
DFGLDCDEHSTESRCCRYPLTVDFEAFGWDWIIAPKRYKANYCSGECEF

VFLQKYPHTHLVHQANPRGSAGPCCTPTKMSPINMLYFNGKEQIIYGKI

PAMVVDRCGCS.

Metabolic disorder: The term "metabolic disorder" is used interchangeably with the terms "metabolic disease" or "metabolic condition" and encompasses any conditions involving dysregulation of the body's metabolic function, resulting in perturbation of the normal physiological state of homeostasis due to an alteration in metabolism (anabolism and/or catabolism). Metabolic disorders may be inherited or acquired. Non-limiting examples of metabolic disorders include obesity or overweight, type 2 diabetes mellitus, type 2 diabetes mellitus associated with obesity, and metabolic syndrome.

Metabolic rate: The term "metabolic rate" refers to the amount of energy expended over a specific period of time. It is typically measured in calories, kilocalories, or joules. Metabolic rate may be expressed as oxygen consumed or carbon dioxide produced per unit time.

Metabolism: The term "metabolism" refers to the processes involved in the biosynthesis and breakdown of components that make up a body, such as fats (e.g., adipose tissue), muscle and bones. "Fat metabolism" therefore means the process of biosynthesis and breakdown of fats.

Myostatin: In the context of the present disclosure, unless explicitly defined otherwise, the term "myostatin" can refer to any forms of the myostatin protein, such as pro-myostatin, latent myostatin and mature myostatin, each of which exists in dimers in vivo.

Myostatin inhibitor As used herein, the term "myostatin inhibitor" refers to any agent that inhibits one or more forms of myostatin (e.g., pro-myostatin, latent myostatin, and/or mature myostatin). The term myostatin inhibitor encompasses any molecular modalities such as large molecules (biologics, such as antibodies and engineered protein constructs) and small molecules (such as structurally-defined low molecular weight chemical entities). The term myostatin inhibitor encompasses both selective inhibitors of myostatin and non-selective inhibitors of myostatin. A myostatin inhibitor may be an anti-myostatin antibody, or antigen-binding fragment thereof, that binds pro- and/or latent myostatin and/or mature myostatin. In some embodiments, the myostatin inhibitor may be an anti-pro/latent myostatin antibody, or antigen-binding fragment thereof, that preferentially (e.g., selectively) binds pro- and/or latent myostatin over mature myostatin. In various embodiments, the myostatin inhibitor may be an antibody (such as a neutralizing antibody), an activation inhibitor (e.g., an antibody that inhibits activation of pro- and/or latent-myostatin), an adnectin, a peptibody, a receptor trap, or a ligand trap. In some embodiments, the myostatin inhibitor is a small molecule inhibitor. In other embodiments, the myostatin inhibitor refers to a gene therapy.

Myostatin-selective inhibitor: The term "myostatin-selective inhibitor" is used interchangeably with a "selective myostatin inhibitor" and refers to myostatin inhibitor that inhibits myostatin but does not inhibit other members of TGFβ superfamily (e.g., GDF11 or Activin A). In some embodiments, a myostatin-selective inhibitor inhibits at least one activity of myostatin signaling (e.g., inhibits myostatin activation and/or inhibits or prevents subsequent downstream signaling by myostatin) with at least 100-fold, 200-fold, 500-fold, 1,000-fold, or greater potency (e.g., affinity) toward myostatin as compared to another member of the TGFβ superfamily (e.g., GDF11 or Activin A) at a biologically or clinically relevant concentration, as measured by any suitable in vitro assays, such as functional ELISA. In preferred embodiments, a myostatin-selective inhibitor exhibits no detectable binding towards other TGFβ family members. In some embodiments, myostatin-selective inhibitors are neutralizing antibodies that bind mature myostatin and inhibit its activity. In some embodiments, myostatin-selective inhibitors are antibodies that bind to pro/latent myostatin, and inhibit the activation step of myostatin. In some embodiments, the myostatin-selective inhibitor is an antibody or antigen-binding fragment provided herein (e.g. any one of Ab101-Ab141). In some embodiments, the myostatin-selective inhibitor is an antibody or antigen-binding fragment thereof comprising all six CDRs of any one of Ab101-Ab141, e.g., the set of SEQ ID NOs identified for a specific antibody in Tables 2d-f. In some embodiments, the myostatin-selective inhibitor is an antibody or antigen-binding fragment thereof comprising the heavy and light chain variable domains of any one of Ab101-Ab141, e.g., the pair of SEQ ID NOs identified for a specific antibody in Table 3. In some embodiments, the myostatin-selective inhibitor is an antibody comprising the heavy and light chains of any one of Ab101-Ab141, e.g., the pair of SEQ ID NOs identified for a specific antibody in Table 4. In some embodiments, the aforementioned antibody sequences are those of Ab109, Ab133 or Ab141 or an antigen-binding fragment thereof.

Overweight/obesity: A person whose weight is higher than what is considered as a normal weight adjusted for height is described as being overweight or having obesity. Using the BMI-based classification, for human adults (ages 20 and older), BMI of 18.5 to 24.9 is considered normal weight; BMI of 25 to 29.9 is considered overweight; BMI of 30+ is considered obese (including extreme obesity); and BMI of 40+ is considered extremely obese. For children and adolescents (ages 2-19), BMI at or above the $85^{th}$ percentile on the CDC growth chart is considered overweight or obese; BMI at or above the $95^{th}$ percentile on the CDC growth charts is considered obese (including extreme obesity); and, BMI at or above 120 percent of the $95^{th}$ percentile on the CDC growth chart is considered extremely obese.

Percent identity: The term "percent identity," as used herein, refers to the similarity between two amino acid sequences or between two nucleic acid sequences. Percent identity may be determined using any available alignment tool that attempts to match as many residues as possible across the full length of two sequences. For example, percent identity can be determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the BLASTN and BLASTX programs (version 2.0) of Altschul, et al. J. Mol. Biol. 215:403-10, 1990. BLAST protein alignment may be performed with the BLASTX program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) may be used. In embodiments where a percent identity of a cumulative or sum of sequence is required, the percent identity may be determined using the Needle algorithm in the European Molecular Biology Open Software Suite ("EMBOSS") program.

Potency: The term "potency" as used herein refers to activity of a drug, such as an antibody (or an antigen-binding fragment thereof) having inhibitory activity, with respect to concentration or amount of the drug to produce a defined effect. For example, an antibody capable of producing certain effects at a given dosage is more potent than another antibody that requires twice the amount (dosage) to produce equivalent effects. Potency may be measured using any suitable functional assays, such as functional ELISA and cell-based assays, in which the degree of myostatin activation, such as activation triggered by proteases (e.g., mTLL2), can be measured in the presence or absence of test article (e.g., inhibitory antibodies).

Prevent/preventing: The terms "preventing" and "prevent" as used herein refer to preventing or delaying the onset of a condition or disease in a subject or preventing or delaying the onset of at least one symptom of the condition or disease in the subject.

Pro/latent myostatin: As used herein, the term "pro/latent myostatin" refers to pro-myostatin, latent myostatin, or both (i.e., pro-forms or precursors of myostatin), but excludes a free form of mature myostatin that is not associated with the prodomain. Pro-myostatin and latent myostatin are dimers (e.g., homodimers) comprised of two pro-myostatin polypeptides. During biosynthesis, the N-terminal signal peptide is cleaved. The pro-myostatin homodimer is a proteolytic substrate for intracellular furin which cleaves between the prodomain and the growth factor domain. The furin-cleaved homodimer complex remains associated ("latent myostatin") until activation, which liberates the growth factor from the latent complex. The human sequence of each pro-myostatin polypeptide is provided as SEQ ID NO: 52.

The terms "pro-myostatin", "pro myostatin," or "promyostatin," also known as "proGDF8," refer to an inactive precursor of mature myostatin which comprises a disulfide-linked homodimer, each molecule of the homodimer comprising the amino terminal prodomain covalently bound to the carboxyl terminal mature myostatin domain. In one embodiment, "pro-myostatin" has not been cleaved by either a proprotein convertase, or a protease from the BMP/tolloid family. Exemplary pro-myostatin sequences, variants thereof, and methods of generating pro-myostatin are well known in the art and described in more detail herein. In the context of polypeptide sequences, the term "human proGDF8" or "human proMyostatin" refers to the amino acid sequence set forth in SEQ ID NO: 52, which reflects the single polypeptide chain.

As used herein the terms "latent myostatin" or "latent-myostatin" refer to an inactive precursor of mature myostatin which comprises a disulfide-linked homodimer, each molecule of the homodimer comprising the amino terminal prodomain non-covalently bound to the carboxyl terminal mature myostatin domain. In one embodiment, "latent myostatin" is generated from a pro-myostatin that has been cleaved by a proprotein convertase, but which has not been cleaved by a protease from the BMP/tolloid family. In another embodiment, "latent myostatin" can be generated by combining the prodomain and the carboxy terminal mature myostatin domain in vitro and allowing them to fold properly. See, for example, Sengle et al., J. Biol. Chem., 286(7): 5087-5099, 2011. Exemplary latent myostatin sequences, variants thereof, and methods of generating latent-myostatin are well known in the art and described in more detail herein.

```
proGDF8 (human):
                                                              (SEQ ID NO: 52)
NENSEQKENVEKEGLCNACTWRQNTKSSRIEAIKIQILSKLRLETAPNISKDVIRQLLPKAPPLRELIDQYDVQRDD

SSDGSLEDDDYHATTETIITMPTESDFLMQVDGKPKCCFFKFSSKIQYNKVVKAQLWIYLRPVETPTTVFVQILRLI

KPMKDGTRYTGIRSLKLDMNPGTGIWQSIDVKTVLQNWLKQPESNLGIEIKALDENGHDLAVTFPGPGEDGLNPF

LEVKVTDTPKRSRRDFGLDCDEHSTESRCCRYPLTVDFEAFGWDWIIAPKRYKANYCSGECEFVFLQKYPHTHL

VHQANPRGSAGPCCTPTKMSPINMLYFNGKEQIIYGKIPAMVVDRCGCS.

proGDF8 (rat):
                                                              (SEQ ID NO: 53)
NEDSEREANVEKEGLCNACAWRQNTRYSRIEAIKIQILSKLRLETAPNISKDAIRQLLPRAPPLRELIDQYDVQRDD

SSDGSLEDDDYHATTETIITMPTESDFLMQADGKPKCCFFKFSSKIQYNKVVKAQLWIYLRAVKTPTTVFVQILRLI

KPMKDGTRYTGIRSLKLDMSPGTGIWQSIDVKTVLQNWLKQPESNLGIEIKALDENGHDLAVTFPGPGEDGLNPF

LEVKVTDTPKRSRRDFGLDCDEHSTESRCCRYPLTVDFEAFGWDWIIAPKRYKANYCSGECEFVFLQKYPHTHL

VHQANPRGSAGPCCTPTKMSPINMLYFNGKEQIIYGKIPAMVVDRCGCS.

proGDF8 (mouse):
                                                              (SEQ ID NO: 54)
NEGSEREENVEKEGLCNACAWRQNTRYSRIEAIKIQILSKLRLETAPNISKDAIRQLLPRAPPLRELIDQYDVQRDD

SSDGSLEDDDYHATTETIITMPTESDFLMQADGKPKCCFFKFSSKIQYNKVVKAQLWIYLRPVKTPTTVFVQILRLI

KPMKDGTRYTGIRSLKLDMSPGTGIWQSIDVKTVLQNWLKQPESNLGIEIKALDENGHDLAVTFPGPGEDGLNPF

LEVKVTDTPKRSRRDFGLDCDEHSTESRCCRYPLTVDFEAFGWDWIIAPKRYKANYCSGECEFVFLQKYPHTHL

VHQANPRGSAGPCCTPTKMSPINMLYFNGKEQIIYGKIPAMVVDRCGCS.

proGDF8 (cynomolgus):
                                                              (SEQ ID NO: 55)
NENSEQKENVEKEGLCNACTWRQNTKSSRIEAIKIQILSKLRLETAPNISKDAIRQLLPKAPPLRELIDQYDVQRDD

SSDGSLEDDDYHATTETIITMPTESDFLMQVDGKPKCCFFKFSSKIQYNKVVKAQLWIYLRPVETPTTVFVQILRLI

KPMKDGTRYTGIRSLKLDMNPGTGIWQSIDVKTVLQNWLKQPESNLGIEIKALDENGHDLAVTFPGPGEDGLNPF

LEVKVTDTPKRSRRDFGLDCDEHSTESRCCRYPLTVDFEAFGWDWIIA
```

Exemplary proGDF8 sequences in the human, rat, mouse and *cynomolgus* are provided above. In these proGDF8 sequences, a proprotein convertase cleavage site is indicated in bold and a tolloid protease site is indicated by underlining. In some embodiments, the proprotein convertase cleavage site comprises amino acid residues 240 to 243 of SEQ ID NOs: 52-55. In some embodiments, the tolloid protease site comprises amino acid residues 74-75 of SEQ ID NOs: 52-55. It should be appreciated that the exemplary proGDF8 sequences provided herein are not intended to be limiting and additional proGDF8 sequences from other species, including any isoforms thereof, are within the scope of this disclosure.

The prodomain of the myostatin polypeptide is comprised of several structural domains as described previously (See, e.g., PCT/US2014/036933). These include, for example, Straight Jacket region, Fastner region, Arm region, Fingers region 1, Fingers region 2, Latency Loop, Alpha-1 Helical region, and Bowtie region. In some embodiments, preferred antibodies or fragments thereof that specifically bind to promyostatin bind an epitope within the Arm region of the myostatin prodomain. In some embodiments, the epitope includes at least one amino acid residue from the "KALDEN" (SEQ ID NO: 118) polypeptide stretch within the Arm region of the prodomain. In some embodiments, the amino acid residue within the Arm region of the prodomain making contact with the antibody when bound to the antigen is a residue that is not conserved between myostatin and GDF11. In some embodiments, such residue(s) is/are K, E, and/or N of the polypeptide stretch (shown in bold type above). In some embodiments, the epitope includes at least one amino acid residue from the "FVQILR-LIKPMKDGTRYTGIRSLK" (SEQ ID NO: 57) polypeptide stretch within the Arm region of the prodomain. In some embodiments, such residue(s) is/are F, Q, L, Y, R, S and/or K of the polypeptide stretch (shown in bold type above). See Dagbay et al. (J. Biol. Chem. (2020) 295(16): 5404-5418), the content of which is hereby incorporated in its entirety.

Serum clearance: As used herein, the term "serum clearance" or "clearance" refers to a relative pharmacokinetic/pharmacodynamic behavior pertaining to changes in serum concentrations (e.g., circulating levels) of an analyte (e.g., target protein or protein complex) over time. When the analyte being measured accumulates in the serum, it is said to have slow clearance. By contrast, when the analyte being measured is removed ("cleared") rapidly from the serum, it is said to have fast clearance. Serum clearance in vivo may occur via multiple mechanisms, including, for example, targeted degradation, Fc-mediated internalization, etc. For example, serum clearance of circulating myostatin may be measured with an assay for determining binding of an antibody to free myostatin in serum (circulating myostatin that is not bound by the antibody). Such an assay may involve immobilizing a biotinylated capture antibody known to bind pro and latent myostatin, before adding a sample comprising myostatin to test the ability of the antibody to bind to the free myostatin and adding a detection antibody with a detectable marker. The capture antibody known to bind myostatin may be a biotinylated antibody capable of binding latent myostatin, e.g., a biotinylated Ab2 or a biotinylated antibody of the present disclosure (e.g., biotinylated Ab109, Ab133 or Ab141), and the detection antibody may be a ruthenium labeled antibody known to bind both latent and mature myostatin.

Slow-twitch muscle: As used herein, the term "slow-twitch," "slow twitch Type 1" or "Type I" muscle refers to a muscle enriched in Type I muscle fibers and is used frequently, is more postural, and helps enable long-endurance feats such as distance running. As used herein, the term "fast-twitch," "fast twitch Type 2" or "Type II" muscle refers to a muscle that provides higher energy output and strength and is used in powerful bursts of movements like sprinting, but such a muscle fatigues faster and cannot be used repeatedly. Fast-twitch muscles break down into two categories of fiber types: moderate fast-twitch fibers (Type IIA) and fast-twitch fibers (Type IIB or IIx). Moderate fast-twitch fibers are thicker, quicker to contract, and wear out more rapidly than slow-twitch fibers. Fast-twitch fibers, the most powerful and lowest in endurance, are activated when the body nears maximum exertion. While most muscles tend to be comprised of a mixture of various fiber types, different muscles contain different ratios of fiber types. During development or in response to certain events (e.g., exercise, disease, injury, etc.), fiber types within a muscle or muscle group may undergo fiber type switching, resulting in an altered phenotype in muscle physiology.

Solution Equilibrium Titration (SET): SET is an assay whereby binding between two molecules (such as an antigen and an antibody that binds the antigen) can be measured at equilibrium in a solution. For example, Meso-Scale Discovery ("MSD")-based SET, or MSD-SET, is a mode of determining dissociation constants for particularly high-affinity protein-protein interactions at equilibrium, such as picomolar-affinity antibodies binding to their antigens (see, for example: Ducata et al. (2015) J Biomolecular Screening 20(10): 1256-1267). The SET-based assays may be particularly useful for determining KD values of antibodies with sub-nanomolar (e.g., picomolar) affinities.

Specific/specificity: The terms "specific" or "specificity" as used in the context of an interaction between members of a specific binding pair (e.g., a ligand and a binding site, an antibody and an antigen, biotin and avidin) refer to the selective reactivity of the interaction. The phrase "specifically binds to" and analogous phrases, in the context of antibodies, refer to the ability of antibodies (or antigenically reactive fragments thereof) to bind to an intended target antigen (or a fragment thereof) (i.e., "specific binding") as opposed to other entities. Specific binding is understood as a preference for binding a certain antigen, epitope, receptor ligand, or binding partner with, for example, at least 100-fold, 200-fold, 500-fold, or 1,000-fold preference over a control non-specific antigen, epitope, receptor ligand, or binding partner. "Specific binding" as used herein can also refer to binding pairs based on binding kinetics such as $K_{on}$, $K_{off}$, and $K_D$. For example, a ligand can be understood to bind specifically to its target site if it has a $K_{off}$ of $10^{-3}$ sec$^{-1}$ or less, $10^{-4}$ sec$^{-1}$ or less, $10^{-5}$ sec$^{-1}$ or less, or $10^{-6}$ sec$^{-1}$ or less; and/or a $K_D$ of $10^{-8}$ M or less, $10^{-9}$ M or less, $10^{-10}$ M or less, or $10^{-11}$ M or less, or $10^{-12}$ M or less, e.g., as measured by suitable in vitro binding assays such as BLI (e.g., Octet®), surface plasmon resonance (SPR) (e.g., Biacore™), and ELISA. It is understood that various proteins can share common epitopes or other binding sites (e.g., kinase reactive sites). In certain embodiments, binding sites may bind more than one ligand, but still can be considered to have specificity based on binding preference as compared to a non-specific antigen and/or by having certain binding kinetic parameters. Methods of selecting appropriate non-specific controls are within the ability of those of skill in the art. Binding assays are typically performed under physiological conditions.

Stoichiometry: As used herein, the term "stoichiometry" or "binding stoichiometry" refers to the configuration (e.g., a total mass of a complex comprised of components in certain ratios) with which an antibody (or antigen-binding fragment) interacts with its antigen under predetermined conditions. Binding stoichiometry between an antibody ("Ab") and antigen ("Ag") may be determined using, for example, whole immunoglobulin such as monoclonal antibody ("mAb"), or fragments such as Fab (monovalent) and F(ab')2 (bivalent). In the context of the present disclosure, the antigen is a pro/latent myostatin complex, which is a homodimer, containing two binding sites per antigen (one on each monomer). For example, a mAb (such as Ab2) may bind Ag with a 1:1 Ab:Ag configuration, such that a first arm of the mAb interacts with a first binding site on the Ag, and a second arm of the mAb interacts with a second binding site on the Ag (Dagbay et al. (J. Biol. Chem. (2020) 295(16): 5404-5418)). By contrast, in the 2:1 Ab:Ag configuration, on average, two molecules of the antibody can simultaneously interact with one molecule of the antigen. Similarly, in the 1:2 Ab:Ag configuration, on average, one molecule of the antibody can simultaneously interact with two molecules of the antigen. In some embodiments, in the context of protein complex formation (e.g., protein-protein interactions), such as an immune complex (e.g., antibody-antigen complex), the concept of stoichiometry takes into account both the ratio of the components that form the complex and the total mass of the complex. For example, mAb and antigen (pro/latent myostatin complex) may form an immune complex comprised of 1 mAb molecule and 1 antigen molecule; 1 mAb molecule and 2 antigen molecules; 2 mAb molecules and 2 antigen molecules, or mixtures thereof, when the mAb and the Ag are mixed in a solution attotal protein concentrations of about 3.5 to 8.0 mg/mL. Stoichiometry may be measured by analytical SEC-MALS. For example, the mAb and Ag may be present in a 1:1, 2:1 or 3:1 ratio (e.g., as a mAb:Ag mixture) or vice versa, with a total protein concentrations ranging between about 3.5 mg/mL (e.g., about 15 µM each of mAb and Ag) and about 8 mg/mL (e.g., about 45 µM of mAb and about 15 µM of Ag) and are allowed to form immune complexes at a neutral pH at room temperature for a suitable duration of time, such as 1-48 hours, preferably about 24 hours.

Subject: As used herein, the term "subject" is a target to whom the therapy or therapies described herein may be administered. In a clinical context, the terms "subject" and "patient" may be used interchangeably. In some embodiments, a subject is a mammalian subject, e.g., companion animals (e.g., dogs, cats and the like), farm animals (e.g., cows, pigs, horses, sheep, goats, poultry and the like), and laboratory animals (e.g., rats, mice, guinea pigs and the like). In preferred embodiments, the subject is a human subject.

Surface plasmon resonance (SPR): Surface plasmon resonance is an optical phenomenon that enables detection of unlabeled interactants in real time. SPR-based biosensors, such as those commercially available from Biacore™, can be employed to measure biomolecular interactions, including protein-protein interactions, such as antigen-antibody binding. The technology is widely known in the art and is useful for the determination of parameters such as binding affinities, kinetic rate constants and thermodynamics.

Total fat mass: The term "total fat mass" refers to the cumulative fat content in a subject's body. Total fat mass includes fat made up of various types of fat cells, such as white fat, brown fat, and beige fat, and includes fat storage in different body compartments, such as essential fat, subcutaneous fat, and visceral fat. Total fat mass may be measured or estimated by any method known in the art, including by skinfold measurements using calipers, measuring the circumference of certain body parts, dual-energy X-ray absorptiometry (DXA), hydrostatic weighing, air displacement plethysmography, bioelectric impedance analysis, bioimpedance spectroscopy, electrical impedance myography, 3-dimensional body scanners, multi-compartment models, or magnetic resonance imaging. The term "fat mass gain" or "fat mass loss" refers to a change in the amount of fat mass measured as compared to a baseline measurement. For example, a subject having a metabolic disorder may exhibit fat mass loss or visceral fat mass loss after a treatment for the metabolic disorder (e.g., treatment with a myostatin inhibitor). The term "subcutaneous fat" refers to fat found just beneath the skin. The term "visceral fat" refers to fat content that is predominantly made of fat found deep within the abdominal organs, e.g., in the abdominal area of a subject's body and around the subject's major organs, such as the liver, kidneys, pancreas, intestines, and heart.

Treating or preventing: The terms "treating," "treat," and "treatment" are used interchangeably herein. The term "treating" a condition or disease in a subject refers to the act of providing a therapeutic regimen aimed to cure, heal, alleviate, relieve, alter, remedy, delay progression, ameliorate, improve, or affect a medical condition or at least one symptom of the condition, including slowing or delaying its progression. Thus, the term treating does not necessarily require a complete treatment of the disease or disorder. In one embodiment, treating a subject alleviates symptoms of a disease or disorder by at least 5%, at least 10%, at least 20%, at least 30%, at least 40%, or at least 50%.

Weight loss: Weight loss refers to a reduction of body weight, irrespective of particular tissue(s) being lost. For example, weight loss per se does not distinguish between loss in fat mass vs muscle mass. Overall loss of total body weight does not necessarily reflect improved body composition, Weight management: As used herein, the term "weight management" encompasses measures taken to lose weight, sustain weight, as well as to reduce adipose tissue, increase lean mass, or otherwise to improve or sustain body composition. Successful weight management that is clinically meaningful may or may not accompany overall weight loss. Thus, weight management can include diet (e.g., a calorie restriction diet, e.g., reduced calorie intake or reduced absorption of calories), an exercise regimen, and/or medication (e.g., a treatment comprising a myostatin inhibitor) in order to reduce the amount of total body weight, reduce the amount of total fat mass, reduce the amount of visceral fat mass, increase the metabolic rate, increase the amount of lean mass, and/or increase the ratio of muscle to fat, or otherwise to improve body composition, in a subject.

Weight-related condition: The term "weight-related condition" or "weight-related problem" as used herein, refers to one or more medical condition(s) associated with excess fat mass (i.e., in addition to being overweight or obese), where the excess fat mass of the subject is a contributing factor. Non-limiting examples of weight-related conditions include type 2 diabetes mellitus, high blood pressure, high triglyceride or cholesterol level, heart disease, stroke, kidney disease, fatty liver (e.g., nonalcoholic fatty liver disease (NAFLD), nonalcoholic steatohepatitis (NASH) also known as metabolic dysfunction associated steatohepatitis (MASH)), and sleep apnea.

General Structural Features of the Novel Antibodies and Antigen-Binding Fragments Thereof The present disclosure provides a novel class of antibodies capable of inhibiting myostatin activation. Such antibodies bind pro/latent myostatin complex but do not bind free, mature myostatin that is not associated with the prodomain. In some embodiments, these antibodies bind to an epitope that includes one or more residues of the amino acid stretch FVQILRLIKPMKDGTRYTGIRSLK (SEQ ID NO: 57) (amino acid residues 147-170 of human proMyostatin) and/or KALDEN (SEQ ID NO: 118) (amino acid residues 205-210 of human proMyostatin). This is an epitope that was previously identified to confer inhibitory activity towards protease-induced activation of myostatin, e.g., in the previously identified myostatin inhibitor (Ab2). In some embodiments, these antibodies bind to a conformational epitope in the Arm Region of the prodomain distinct from the proteolytic sites. See Dagbay et al. (J. Biol. Chem. (2020) 295(16): 5404-5418).

Whilst retaining the general binding region, in some embodiments, the novel antibodies and antigen-binding fragments disclosed herein share no more than 70% of sequence identify to Ab2, when the VH and VL sequences are combined. Notably, in some embodiments, 2, 3, 4, or 5 out of the 6 CDRs of the novel antibody or the fragment share less than 50% sequence identity to the corresponding CDRs in Ab2.

In some embodiments, the antibodies and fragments disclosed herein share no greater than 70% cumulative VH+VL sequence identity with Ab2. In some embodiments, the VL sequence of the antibody shares less than 50% identity with that of Ab2. In some embodiments, the L-CDR1 of the antibody shares 25% or less sequence identity with that of Ab2 (preferably no more than 20%). In some embodiments, the L-CDR2 of the antibody shares less than 30% sequence identity with that of Ab2. In some embodiments, the L-CDR3 of the antibody shares no more than 20% sequence identity with that of Ab2 (preferably no more than 10%). Preferred antibodies or fragments according to the present disclosure are fully human antibodies/fragments. In various embodiments, preferred antibodies and fragments disclosed herein exhibit at least the property in category 1 from Table 1 below. In some embodiments, the preferred antibodies and fragments exhibit the property in category 1 and at least the property in one additional category from Table 1 below. In some embodiments, the preferred antibodies and fragments exhibit the property in category 1 and at least the property in two additional categories from Table 1 below. In some embodiments, the preferred antibodies and fragments exhibit the property in category 1 and at least the property in three additional categories from Table 1 below. In some embodiments, the preferred antibodies and fragments exhibit the property in category 1 and at least the property in four additional categories from Table 1 below. In some embodiments, the preferred antibodies and fragments exhibit the property in category 1 and at least the property in five additional categories from Table 1 below. In some embodiments, the preferred antibodies and fragments exhibit the properties in all of the categories from Table 1 below.

TABLE 1

Antibody features and characterizations.

| Category | Features, characterizations | Exemplary antibodies disclosed herein |
|---|---|---|
| 1 | An antibody that selectively binds human pro/latent myostatin and is capable of inhibiting its activation; wherein the antibody cross-blocks with Ab2 and/or binds the sequence FVQILRLIKPMKDGTRYTGIRSLK (SEQ ID NO: 57) (aa147-170 of human proMyostatin) and/or KALDEN (SEQ ID NO: 118) (aa205-210 of human proMyostatin); wherein, optionally, the antibody shares no greater than 70% cumulative VH + VL sequence identity with Ab2; wherein, further optionally, the antibody comprises: a) a VL sequence of the antibody that is less than 50% identical to the VL sequence of Ab2; b) a L-CDR1 sequence that is no more than 25% (preferably no more than 20%) identical to the L-CDR1 sequence of Ab2; c) a L-CDR2 sequence that is less than 30% identical to the L-CDR2 of Ab2; and/or d) a L-CDR3 sequence that is no more than 20% (preferably no more than 10%) identical to the L-CDR3 of Ab2. | Ab101, Ab102, Ab103, Ab104, Ab105, Ab106, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140, Ab141 |
| 2 | An antibody that satisfies category (1) and binds pro/latent myostatin with a bivalent KD of less than 1 nM as measured by a SPR-based in vitro binding assay (e.g., Biacore ™), e.g., as described in Example 1; | Ab101, Ab102, Ab103, Ab104, Ab105, Ab106, Ab107, Ab108, Ab109, Ab112, Ab121, Ab127, Ab128, Ab133, Ab136, Ab137, Ab138, Ab139, Ab140, Ab141 |
| 2a | wherein, optionally, the antibody binds pro/latent myostatin with a KD of 0.1 nM or below. | Ab101, Ab102, Ab104, Ab105, Ab107, Ab133, Ab141 |
| 3 | An antibody that satisfies category (1) and is capable of inhibiting mTLL-2-induced activation with IC50 of less than 1 nM, as measured by functional ELISA, e.g., as described in Example 1, wherein, optionally, the antibody also satisfies category (2). | Ab102, Ab105, Ab109, Ab123, Ab112, Ab130, Ab131, Ab132, Ab133, Ab134, Ab135, Ab136, Ab137, Ab138, Ab139, Ab140, Ab141 |
| 4 | An antibody that satisfies category (1) and binds the antigen in a pH-dependent manner as measured by a BLI-based in vitro binding assay (e.g., Octet ®); optionally the pH dependency is greater than 10x, as determined by comparing dissociation rates at pH 5.5/7.4 (described in Example 1); wherein, optionally, the antibody also satisfies category (2) and/or (3). | Ab102, Ab109, Ab130, Ab132, Ab133, Ab137, Ab138, Ab139, Ab140, Ab141 |

TABLE 1-continued

Antibody features and characterizations.

| Category | Features, characterizations | Exemplary antibodies disclosed herein |
|---|---|---|
| 5 | An antibody that satisfies category (1) and binds pro/latent myostatin with a 1:2 mAb to antigen binding stoichiometry as measured by analytical SEC-MALS (e.g., as described in Example 1); wherein, optionally, the antibody also satisfies category (2), (3), and/or (4). | Ab105, Ab109, Ab130, Ab133, Ab141 |
| 6 | An antibody that satisfies category (1) and does not cause accumulation or is capable of reducing total serum myostatin levels as compared to background when dosed at 1, 3, and/or 10 mg/kg of Ab2 (described in Example 2); wherein, optionally, the antibody also satisfies category (2), (3), (4), and/or (5). | Ab109, Ab132 |
| 7 | An antibody having a HCDR1 of SEQ ID NO: 201, HCDR2 of any one of SEQ ID NOs: 219 or 226, HCDR3 of SEQ ID NO: 220, LCDR1 of SEQ ID NO: 216, LCDR2 of SEQ ID NO: 222, and LCDR3 of any one of SEQ ID NOs: 223, 225, or 227 as numbered according to the Kabat numbering system. | Ab109, Ab132, Ab133 |
| 8 | An antibody having a HCDR1 of SEQ ID NO: 201, HCDR2 of SEQ ID NO: 214, HCDR3 of SEQ ID NO: 215, LCDR1 of SEQ ID NO: 216, LCDR2 of SEQ ID NO: 217, and LCDR3 of any one of SEQ ID NOs: 218 or 224 as numbered according to the Kabat numbering system. | Ab102, Ab130 |
| 9 | An antibody having a HCDR1 of SEQ ID NO: 201; HCDR2 of SEQ ID NO: 202, wherein $X_1$ is T or A; HCDR3 of SEQ ID NO: 203; LCDR1 of SEQ ID NO: 204; LCDR2 of SEQ ID NO: 205; and LCDR3 of SEQ ID NO: 206, wherein $X_1$ is M or Q and $X_2$ is P or G, as numbered according to the Kabat numbering system. | Ab109, Ab133, Ab141 |

Characterization of the Novel Antibodies and Antigen-binding Fragments

A. Binding Selectivity

In determining binding selectivity, any suitable in vitro binding assay techniques, such as BLI (e.g., Octet®), SPR (e.g., Biacore™), or ELISA may be employed to measure antibody-antigen interactions. Typically, recombinantly expressed and purified proteins are used as antigens to carry out binding assays (see, e.g., PCT/US2014/036933). As demonstrated herein, the novel antibodies and antigen-binding fragments disclosed herein selectively target pro- and/or latent myostatin dimer complex but do not bind to free mature myostatin when the growth factor is not associated with the prodomain. There is no detectable binding to proGDF11, proActivin A, proActivin B, mature GDF11, mature Activin A or mature Activin B. In some embodiments, the antibody or the antigen-binding fragment selectively binds pro- and latent myostatin but does not bind mature GDF11 as measured by ELISA.

In preferred embodiments, selective binding for pro/latent myostatin over mature myostatin, e.g., as provided by any one of Ab101-141, preemptively prevents activation, while antibodies that bind mature myostatin only exert their effect after an activation event and/or may exhibit more off-target binding.

In some embodiments, preferred antibodies show species cross-reactivity to the human, *cynomolgus* monkey, rat, and/or mouse pro/latent myostatin with similar binding characteristics. Most preferably, such antibodies show species cross-reactivity to the human, *cynomolgus* and mouse pro/latent myostatin with similar binding characteristics.

B. Binding Regions, Epitopes

In certain embodiments, the disclosure encompasses an antibody or an antigen-binding fragment thereof that binds a region of the prodomain of the pro/latent myostatin complex at an epitope that comprises one or more amino acid residues of the sequence FVQILRLIKPMKDGTRYT-GIRSLK (SEQ ID NO: 57) (amino acid positions 147-170 of human proMyostatin, as numbered according to SEQ ID NO: 52) and/or KALDEN (SEQ ID NO: 118) (amino acid positions 205-210 of human proMyostatin, as numbered according to SEQ ID NO: 52).

In some embodiments, binding to one or more of the residues mentioned above is determined by evaluating cross-blocking with an antibody known to bind at that epitope, e.g., Ab2. A cross-blocking antibody pair is indicative of having substantially overlapping binding regions between the two antibodies. In some embodiments, epitope binning may be carried out to determine whether two antibodies cross-block one another. In some embodiments, epitope binning may be determined using a pre-mix binning assay in which a first antibody or antigen-binding fragment is immobilized onto a biosensor and binding between the first antibody or antigen-binding fragment is determined using a pre-mixed complex comprising a second antibody or antigen-binding fragment bound to the antigen. In some embodiments, epitope binning may employ a sandwich binning assay in which a first antibody or antigen-binding fragment is immobilized onto a biosensor, after which a stepwise binding of the antigen and a second antibody or antigen-binding fragment is measured. In some embodiments, a cross-blocking antibody of the disclosure binds to one or more of the amino acid residues mentioned above.

C. Binding Affinity

In some embodiments, anti-pro/latent-myostatin antibodies or antigen-binding fragments thereof suitable for use in carrying out various embodiments of the present disclosure comprise an antibody or antigen-binding fragment thereof that binds to pro/latent myostatin with high affinity, as determined by SPR (e.g., Biacore™), by measuring equilibrium dissociation constant by solution equilibrium titration (SET), or by determining KD using a BLI-based assay (e.g., Octet®). In some embodiments, the binding affinity is determined by a BLI-based assay (e.g., Octet®). In some embodiments, the binding affinity is determined by SET. In some embodiments, SET may be used to measure levels of circulating myostatin (e.g., see Example 3). Preferably, the binding affinity is determined by SPR (e.g., Biacore™).

In some embodiments, an antibody or antigen-binding fragment provided herein binds to pro/latent myostatin with an equilibrium dissociation constant ($K_D$) of less than $10^{-8}$ M, $10^{-9}$ M, $10^{-10}$ M, $10^{-11}$ M or lower, preferably as measured by a SPR-based in vitro binding assay, such as Biacore™. In some embodiments, the antibody or antigen-binding fragment binds pro/latent-myostatin with a nanomolar or subnanomolar $K_D$. For example, anti-pro/latent-myostatin antibodies, or antigen-binding fragments thereof, can bind to pro/latent-myostatin with an affinity between 5 pM and 500 nM, e.g., between 50 pM and 100 nM, e.g., between 500 pM and 50 nM, e.g., between 50 pM and 5 nM, e.g., between 0.5 nM to 2 nM. In some embodiments, the disclosure encompasses antibodies or antigen-binding fragments that compete or cross-compete with any of the antibodies described herein for binding to pro/latent-myostatin and that have an affinity of 50 nM or lower (e.g., 20 nM or lower, 10 nM or lower, 5 nM or lower, or 1 nM or lower). In preferred embodiments, the antibody binds pro- or latent myostatin with a KD of less than 1.0 nM as measured by a SPR-based in vitro binding assay, such as Biacore™.

In some embodiments, an antibody or antigen-binding fragment thereof provided herein binds to human pro/latent myostatin with a $K_D$ in a range from $10^{-11}$ M to $10^{-8}$ M, preferably as measured by a SPR-based in vitro binding assay, such as Biacore™. In some embodiments, the antibody or antigen-binding fragment thereof binds to pro/latent myostatin with a $K_D$ of less than 5 nM. In some embodiments, the antibody or antigen-binding fragment thereof binds to pro/latent myostatin with a $K_D$ of less than 1 nM. In some embodiments, the antibody or antigen-binding fragment thereof binds to pro/latent myostatin with a KD of less than 0.5 nM. In some embodiments, the antibody or antigen-binding fragment thereof binds to pro/latent myostatin with a KD of less than 0.1 nM. In some embodiments, the antibody or antigen-binding fragment thereof binds to pro/latent myostatin with at least a 10-fold lower $K_D$ as compared to Ab2 disclosed in PCT/US2015/059468. In some embodiments, the affinity or binding kinetics are determined by a BLI-based in vitro binding assay. When such binding profiles are measured with the use of Octet® or Biacore™, the assay is performed in accordance with the manufacturer's instructions, unless otherwise specified. In some embodiments, the antibody or antigen-binding fragment thereof is an antibody or antigen-binding fragment provided herein that binds to pro/latent myostatin with a KD of less than 1 nM, e.g., selected from Ab101, Ab102, Ab103, Ab104, Ab105, Ab106, Ab107, Ab108, Ab109, Ab121, Ab123, Ab125, Ab127, Ab128, Ab133, Ab134, Ab135, Ab136, Ab137, Ab138, Ab139, Ab140, and Ab141. In some embodiments, the antibody or antigen-binding fragment thereof is an antibody or antigen-binding fragment provided herein that binds to pro/latent myostatin with a KD of less than 0.7 nM, e.g., less than 0.6 nM (e.g., selected from Ab102, Ab105, Ab109, Ab130, Ab131, Ab133, Ab138, Ab139, and Ab140). In some embodiments, the antibody or antigen-binding fragment thereof is an antibody or antigen-binding fragment provided herein that binds to pro/latent myostatin with a KD of less than 0.5 nM, e.g., selected from Ab102, Ab105, Ab109, Ab130, Ab131, Ab133, Ab138, Ab139, and Ab140). In some embodiments, the antibody or antigen-binding fragment thereof is an antibody or antigen-binding fragment provided herein that binds to pro/latent myostatin with a KD of less than 0.2 nM, e.g., Ab109, Ab133, Ab138, Ab139, or Ab140. In some embodiments, the antibody or antigen-binding fragment thereof is an antibody or antigen-binding fragment provided herein that binds to pro/latent myostatin with a $K_D$ of less than 0.1 nM, e.g., Ab133.

In some embodiments, the novel antibodies or antigen-binding fragments thereof encompassed by the present disclosure bind recombinant human pro/latent myostatin with a bivalent KD of less than 1 nM (i.e., <1 nM), as measured by a SPR-based in vitro binding assay, such as Biacore™ according to the manufacturer's instructions (e.g., using the exemplary protocol shown in Example 1). In some embodiments, the novel anti-pro/latent-myostatin antibodies or antigen-binding fragments thereof bind recombinant human pro/latent myostatin with a KD of less than or equal to 1 nM, e.g., less than 0.1 nM.

In some embodiments, KD may be determined by Bio-layer Interferometry (BLI)-based assays (such as Octet®), surface plasmon resonance (SPR)-based assays (such as Biacore™), MesoScale Discovery (MSD) immunoassays (such as MSD-solution equilibrium titration or MSD-SET). In some embodiments, KD is determined by a BLI-based assay, e.g., by Octet®. In preferred embodiments, KD is determined by an SPR-based assay, e.g., by Biacore™.

D. Inhibitory Potency

In some embodiments, antibodies or antigen-binding fragments thereof described herein are capable of binding to a pro/latent-myostatin, and thereby inhibiting the proteolytic activation of pro/latent-myostatin into mature myostatin. In some instances, antibodies, or antigen-binding fragments thereof, described herein can inhibit the proteolytic activation of pro/latent-myostatin by at least 20%, e.g., 30%, 40%, 50%, 60%, 70%, 80%, 90%, 95%, or higher. In some instances, antibodies described herein can inhibit the proteolytic cleavage of pro-myostatin by a proprotein convertase (e.g., furin) by at least 20%, e.g., 30%, 40%, 50%, 60%, 70%, 80%, 90%, 95%, or higher. In some instances, antibodies, or antigen-binding fragments thereof, described herein can inhibit the proteolytic cleavage of pro-myostatin or latent myostatin by a tolloid protease (e.g., mTLL2) by at least 20%, e.g., 30%, 40%, 50%, 60%, 70%, 80%, 90%, 95%, or higher. In some embodiments, the antibodies (e.g., Ab109 and Ab130) can inhibit the proteolytic cleavage of pro/latent myostatin by a tolloid protease (e.g., mTLL2) with an IC50 of less than 0.4 nM.

In some embodiments, antibodies, or antigen-binding fragments thereof described herein are capable of binding to a pro/latent-myostatin, and inhibiting myostatin activity. In some embodiments, the antibodies or antigen-binding fragments thereof described herein can inhibit myostatin signaling by at least 20%, e.g., 30%, 40%, 50%, 60%, 70%, 80%, 90%, 95%, or higher. In some embodiments, inhibition of myostatin signaling can be measured by routine methods, for example, using a myostatin activation assay as described in PCT/US2015/059468, the entire contents of which are expressly incorporated herein by reference. However, it should be appreciated that additional methods may be used for measuring myostatin signaling activity.

It should be appreciated that the extent of proteolytic cleavage of myostatin, e.g., by a proprotein convertase and/or a tolloid protease, can be measured and/or quantified using any suitable method. In some embodiments, the extent of proteolytic cleavage of myostatin is measured and/or quantified using an enzyme-linked immunosorbent assay (ELISA). For example, an ELISA may be used to measure the level of released growth factor (e.g., mature myostatin). As another example, an antibody, or antigen-binding fragment thereof, that specifically binds to pro-myostatin, latent myostatin and/or mature myostatin can be used in an ELISA to measure the level of a specific form of myostatin (e.g., pro/latent/mature-myostatin), or to quantify the extent of proteolytic cleavage of myostatin. In some embodiments, the extent of proteolytic cleavage of myostatin is measured and/or quantified using immunoprecipitation followed by SDS-PAGE or mass spectrometry of tryptic peptides, fluorescence anisotropy-based techniques, FRET assays, hydrogen-deuterium-exchange mass spectrometry, and/or NMR spectroscopy.

The novel antibodies and antigen-binding fragments thereof according to the present disclosure, e.g., any of Ab101-Ab141, are highly potent in inhibiting the activation step of myostatin from the latent complex. Such antibody or fragment inhibits myostatin activation with an IC50 of less than 1 nM as measured by functional ELISA, an exemplary use of which is provided in the Example section below. In some embodiments, any one of Ab102, Ab105, Ab109, Ab123, Ab112, Ab130, Ab131, Ab132, Ab133, Ab134, Ab135, Ab136, Ab137, Ab138, Ab139, Ab140, or Ab141, or an antigen binding fragment thereof, may be used to inhibit myostatin activation with an IC50 of less than 1 nM as measured by functional ELISA. More generally, to measure inhibitory potency of a myostatin activation inhibitor, such as those disclosed herein, in some embodiments, an ELISA-based in vitro potency assay ("functional ELISA") may be employed. In some embodiments, a test article (such as test antibodies) can be preincubated with recombinant human latent myostatin to let immune complexes form. Subsequently, a Tolloid protease, preferably mTLL-2, may be added to the immune mixture to trigger the release of mature myostatin by proteolytic cleavage. If the test antibody is capable of blocking mTLL-2-induced activation, mature myostatin is not released from the latent myostatin complex. On the other hand, if the test antibody does not inhibit myostatin activation, mTLL-2 treatment causes myostatin to be released from the latent myostatin complex. Following the Tolloid/mTLL-2 treatment step, the amount of free (released) mature myostatin in the presence of test antibodies may be measured by ELISA. The ELISA assay may comprise plates coated with a myostatin capture reagent. In some embodiments, the myostatin capture reagent is an antibody or fusion construct that binds mature myostatin. In some embodiments, the fusion construct is an ActRII-Fc fusion protein, which is a ligand trap. Free mature myostatin present in the assay mixture is captured on the ELISA plate, and the amount of bound mature myostatin may be measured by any suitable methods, such as biotin-streptavidin-based detection reagents. Functional ELISA experiments may be carried out at room temperature (e.g. 20-25° C.).

In some embodiments, the highly potent antibodies and antigen-binding fragments thereof comprise Ab102, Ab109, Ab130, Ab132, Ab133 and Ab141.

E. Binding Stoichiometry

In some embodiments, anti-pro/latent-myostatin antibodies or antigen-binding fragments thereof suitable for use in carrying out various embodiments of the present disclosure comprises an antibody that is capable of binding to pro/latent myostatin with about a 1:2 antibody:pro/latent myostatin stoichiometry. The antibody: pro/latent myostatin stoichiometry can be determined using any method known in the art, including SEC-MALS (size-exclusion chromatography with multi-angle light scattering).

In some embodiments, a monoclonal antibody of the disclosure binds to human pro/latent myostatin in a 1:2 antibody to antigen stoichiometry. In some embodiments, a monoclonal antibody of the disclosure binds to human pro/latent myostatin in both a 1:2 antibody to antigen configuration and in a daisy chain formation. In some embodiments, a monoclonal antibody of the disclosure binds to human pro/latent myostatin in a daisy chain formation. In some embodiments, a Fab fragment of a monoclonal antibody of the disclosure binds to human pro/latent myostatin in a 2:1 Fab to antigen stoichiometry. In some embodiments, the antibody binds to human pro/latent myostatin with a 1:2 mAb:Ag binding stoichiometry as measured by analytical SEC-MALS, wherein the mAb and Ag are preset in a 1:1, 2:1 or 3:1 stoichiometry (e.g., as a mAb:Ag mixture) with a total protein concentrations ranging between about 3.5 mg/mL (e.g., about 15 μM each of mAb and Ag) and about 8 mg/mL (e.g., about 45 μM of mAb and about 15 μM of Ag) and are allowed to form immune complexes at a neutral pH at room temperature for 24 hours. In some embodiments, the mAb:Ag mixture further comprises oligomeric complexes comprising a 2:1 mAb:Ab complex and/or a 2:2 mAb:Ag complex. In some embodiments, the mAb:Ag mixture does not comprise a detectable level of poly daisy-chains as measured by analytical SEC-MALS.

In some embodiments, an antibody or antigen-binding fragment disclosed herein is capable of reducing total serum myostatin levels in a subject as compared to a background level wherein the total serum myostatin comprises antibody-antigen immune complex. Whilst myostatin is thought to function locally, as opposed to through a circulating pool, it is conceivable that high levels of circulating immune complexes (therapeutic antibody bound to latent myostatin) may reach tissues where the bound latent myostatin may at some point dissociate from the inhibitory antibody, causing inadvertent activation at the tissue. In such a scenario, antibodies that are capable of fast serum clearance of myostatin may reduce the risk of inadvertent myostatin activation.

In some embodiments, the antibody binds to human pro/latent myostatin with a 1:2 mAb:Ag binding stoichiometry as measured by analytical SEC-MALS, wherein the mAb and Ag are present in a 1:1, 2:1 or 3:1 stoichiometry with a total protein concentrations ranging between about 3.5 mg/mL and about 8 mg/mL and are allowed to form complexes at room temperature for, e.g., 24 hours. In some embodiments, the antibodies or antigen binding fragments disclosed herein form larger immune complexes with pro/latent myostatin (e.g., 1:2 mAb:Ag or greater). In some embodiments, these larger complexes may comprise oligomers of greater than 1 mAb to antigen but smaller than daisy chains (e.g., an oligomer of 500 kDa or less). Such larger immune oligomer complexes may be advantageous, e.g., in promoting faster clearance and/or better target binding in tissues with higher local concentrations of myostatin. In some embodiments, larger immune complexes (e.g., poly daisy-chains) comprise complexes greater than 500 kDa in size and, e.g., may promote, faster serum clearance. Without being bound by a particular theory, it is contemplated that larger immune complex formation (e.g., oligomers or daisy chains) may facilitate clearance by, for example, increased FcRn interactions.

F. pH-Dependency

In some embodiments, anti-pro/latent-myostatin antibodies or antigen-binding fragments thereof suitable for use in carrying out various embodiments of the present disclosure comprise an antibody or antigen-binding fragment thereof that displays pH-sensitive binding to pro/latent myostatin, such that the antibody or antigen-binding fragment thereof binds to pro/latent myostatin with higher affinity at a pH ranging from 7.0 to 7.6 (e.g., physiological pH, e.g., pH 7.4) as compared to binding at a pH ranging from 4.0 to 6.5 (e.g., acidic pH, e.g., pH 5.5). In some embodiments, the antibody or antigen-binding fragment displays pH-sensitive affinities such that the off-rate (i.e., dissociation rate or Kd) is at least 10-fold greater at an acidic pH than the off-rate at a neutral pH. In one embodiment, the pH sensitive binding feature of the antibody or antigen-binding fragment thereof can be measured using a BLI-based assay such as Octet® (e.g., Octet Red384®). In some embodiments, pH sensitivity may be measured by comparing the off rates ($K_{off}$; dissociation rates) of the antibody at two or more pH levels. In some embodiments, the antibody or the fragment that is bound to pro/latent myostatin dissociates from the antigen with a faster rate at an acidic pH (e.g., pH 5.5) than at a neutral pH (e.g., pH 7.4).

In some embodiments, pH dependency may be expressed as a ratio of a first dissociation rate at a first pH level and a second dissociation rate at a second pH level. In some embodiments, the first pH level is an acidic pH level such as pH 5.5. In some embodiments, the second pH level is a neutral pH level such as pH 7.4. In some embodiments, the pH sensitivity of the antibody may be expressed as the first dissociation rate divided by the second dissociation rate.

In some embodiments, e.g., the embodiment shown in Example 1, dissociation rates are measured by known in vitro binding techniques, such as BLI-based assays (e.g., Octet®).

In some embodiments, the antibody or antigen-binding fragment thereof according to the present disclosure is a pH-dependent binder characterized in that the ratio of dissociation rates at acidic as compared to neutral pH levels, as determined by the dissociation rate at pH 5.5 divided by the dissociation rate at pH 7.4, as measured by a BLI-based binding assay, is 9 or greater, e.g., 9, 10, 11, 12, 13, 14, 15, 16, 17, 18, 19, 20, 21, 22, 23, 24, 25, 26 or greater.

In some embodiments, antibodies with high pH sensitivity (e.g., faster dissociation at acidic conditions as compared to neutral conditions) may facilitate more robust recycling capabilities in vivo as compared to antibodies with lower pH sensitivity, which may contribute to increased serum half-life of the antibody in vivo, Accordingly, the present disclosure includes an antibody that selectively binds human pro/latent myostatin binds at an epitope comprising one or more amino acid residues of the sequence FVQILRLIKPMKDGTRYTGIRSLK (SEQ ID NO: 57) (amino acid residues 147-170 of human proMyostatin) and/or KALDEN (SEQ ID NO: 118) (amino acid residues 205-210 of human proMyostatin) and thereby inhibits myostatin activation with a IC50 of less than 1 nM as measured by a functional ELISA that measures the inhibition of myostatin by mTLL2, wherein the antibody dissociates from pro/latent myostatin with a $K_{off}$ rate at least 10-fold greater at an acidic pH than at a neutral pH, wherein optionally the acidic pH is 5.5. and the neutral pH is 7.4.

G. Developability

With respect to antibody engineering design, an antibody or antigen binding fragment disclosed herein may be a fully human antibody of IgG1 subtype or IgG4 subtype. For the latter, in some embodiments, the antibody comprises an Adair mutation (S228P). This provides a hinge-stabilized backbone to reduce binding to Fc gamma receptors aimed to minimize effector function. In some embodiments, variable regions used are on preferred frameworks utilizing only germline amino acids, aimed to reduce potential for unwanted immunogenicity.

With respect to expression profile, in some embodiments, candidate antibodies are selected at least in part on the basis of their ability for high transient expression (e.g., 100-200 mg/L), e.g., using suitable mammalian cells such as 293 Expi cells at research scale in shake flasks. In addition, preferred antibodies may show high monomeric content after protein A purification. In preferred embodiments, protein A-purified antibody samples show >85% monomer based on small scale, transient expression.

Developability profiles may be assessed by well-known parameters. In some embodiments, the antibody shows no measurable polyreactivity as measured by baculovirus particle ELISA or a polyspecificity reagent (PSR). In some embodiments, antibodies are tested for aggregation behavior by affinity capture self-interaction nanoparticle spectroscopy (AC-SINS). In some embodiments, the antibody shows no measurable self-association as measured by affinity capture self-interaction nanoparticle spectroscopy (AC-SINS) ($\Delta\lambda$max (nM)<5). Typically, gold nanoparticles are coated with polyclonal antibodies that are specific for human monoclonal antibodies and the monoclonal antibodies are captured by the conjugates. The polyvalency of the monoclonal antibody conjugates amplifies the attractive self-interactions, i.e., aggregation between the adsorbed antibodies. This leads to reduced inter-particle separation distances and is detected by a change in color of the gold colloid solution, which may be quantified by a change in the wavelength of maximum absorbance (plasmon wavelength). Plasmon wavelength of 530 nm may be used as the reported value for unaggregated gold nanoparticles. Antibodies with a tendency to self-aggregate shift the plasmon wavelength toward the red end of the spectrum. In some embodiments, a shift of greater than 5 nm (i.e., >5 nm) in plasmon wavelength may be used as the cutoff indicative of self-interacting antibodies. In some embodiments, the antibody which shows no measurable self-association (e.g., aggregation) as measured by AC-SINS is selected from Ab101, Ab102, Ab103, Ab134, Ab104, Ab105, Ab106, Ab107, Ab108, Ab109, Ab133, Ab135, and Ab141.

In some embodiments, poly-specificity of the novel antibodies may be evaluated using ELISA detection of non-specific binding to baculovirus particles (BV-ELISA). In some embodiments, an arbitrary cutoff of 1000 RFU may be set based on average+5× standard deviation of control IgG and no antibody. Antibodies that show no measurable poly-reactivity using baculovirus particle ELISA include, but are not limited to: Ab101, Ab102, Ab103, Ab134, Ab104, Ab105, Ab106, Ab107, Ab108, Ab109, Ab133, Ab135, and Ab141.

In some embodiments, the antibody shows relatively low hydrophobic interactions as determined by retention time in a hydrophobic chromatography column, indicative of low probability of self-interaction. In some embodiments, minimal aggregation is observed in a 4-week accelerated degradation/stability study.

With respect to in vivo disposition, in some embodiments, a pharmacokinetic study in non-human primates (e.g., *cynomolgus* monkeys) predicts a half-life in humans. Preferably, such study predicts a half life of about 28 days in humans. In some embodiments an assay suitable for determining pharmacokinetics of the myostatin inhibiting antibodies can be used. The assay may be performed by immobilizing promyostatin on a surface, e.g., a microplate, and detecting the binding of the antibody to the promyostatin with a detection agent. Suitable detection agents include a goat anti-human antibody coupled to horseradish peroxidase (HRP) or, to increase specificity, particularly for human clinical use, a mouse anti human IgG4 Fc fragment coupled to a suitable detection agent, e.g., ruthenium red, can be used.

In some embodiments, the novel antibodies and antigen-binding fragments thereof according to the present disclosure are modified to reduce susceptibility to deamidation and oxidation. In some embodiments, such modifications include one or more modifications at or around a region of the protein containing the amino acid residues NG. In some embodiments, the novel antibodies and antigen-binding fragments thereof according to the present disclosure are modified to reduce susceptibility to isomerization. In some embodiments, such modifications include one or more modifications at or around a region of the protein containing the amino acid residues DG.

H. Reducing or Preventing Serum Accumulation

Previously, it was observed that certain myostatin-selective activation inhibitor such as apitegromab can cause elevated levels of circulating latent myostatin (e.g., latent myostatin-antibody immune complex) in subjects treated with the antibody. See, e.g., PCT/US2016/052014, the contents of which are hereby incorporated in their entirety. The accumulation of serum latent myostatin over baseline was in fact used as a pharmacodynamic biomarker for apitegromab. However, certain antibodies disclosed herein (e.g., Ab102, Ab130, Ab109, Ab132, Ab133, Ab141) unexpectedly showed enhanced serum clearance, as evidenced by little or no accumulation of total myostatin (e.g., latent myostatin) in serum samples collected from subjects dosed with the antibody (e.g. Ab109, Ab132), or reduced accumulation of circulating latent myostatin in serum samples from subjects dosed with the antibody (e.g. Ab102, Ab130, Ab133, Ab141), as compared to the increased accumulation seen with apitegromab. Without wishing to be bound by theory, it is contemplated that the enhanced serum clearance of latent myostatin associated with certain antibodies disclosed herein (e.g., Ab102, Ab130, Ab109, Ab132, Ab133, Ab141) may be due in part to the greater pH differential exhibited by the certain antibodies disclosed herein (e.g., Ab102, Ab130, Ab109, Ab132, Ab133, Ab141). It is also contemplated that a difference in binding stoichiometry may contribute to the enhanced serum clearance of latent myostatin. In some embodiments, the higher-order stoichiometry of certain antibodies disclosed herein may contribute to their enhanced serum clearance or reduced serum accumulation. For instance, it is contemplated that, in some embodiments, the single 1:2 antibody-to-antigen stoichiometry peak observed when measuring stoichiometry of Ab109 and Ab132 may contribute to their enhanced serum clearance of latent myostatin as compared to apitegromab, which binds with a 1:1 antibody-to-antigen stoichiometry, preventing accumulation of circulating latent myostatin above baseline levels. In some embodiments, the dual 1:2 and 2:1 antibody-to-antigen stoichiometries of Ab102, Ab130, Ab133, and Ab141 may contribute to their enhanced serum clearance of latent myostatin as compared to apitegromab, preventing accumulation of circulating latent myostatin levels in serum samples from subjects does with the antibody as compared to apitegromab.

Despite the observation of higher order stoichiometries of antibody:Pro-myostatin (e.g. 1:2 and/or 2:1) with certain antibodies of the present disclosure (e.g. Ab102, Ab130, Ab109, Ab132, Ab133, Ab141), negative stain electron microscopy done at lower protein concentrations (e.g. 0.01-0.015 mg/ml) demonstrates that certain antibodies (e.g. Ab2, Ab102, Ab130, Ab109, Ab132, Ab133, Ab141) can also form 1:1 stoichiometry. In some embodiments, certain of these antibodies (Ab102, Ab130, Ab109, Ab132, Ab133, Ab141) can form higher-order stoichiometries and a 1:1 stoichiometry (the antibodies are capable of forming both). Without wishing to be bound by theory, in circulation it is anticipated that subjects dosed with Ab109 would have circulating levels of the myostatin:antibody complex that can promote formation of the 1:1 stoichiometry; and in other instances where target myostatin concentrations are higher, e.g. target tissues such as muscle and other depots, and on cell surfaces where antibody is being cleared and local concentrations of the immune complex are formed, the 1:2 and 2:1 stoichiometries would be favored and promote target clearance and/or prevent target accumulation.]

In some embodiments, antibodies disclosed herein are capable of reducing serum concentrations of total myostatin or latent myostatin. In some embodiments, the antibody may comprise Ab102, Ab130, or an antigen binding fragment thereof (e.g., to provide higher clearance and lower accumulation than Ab2). In some embodiments, the antibody may comprise Ab133, Ab141, or an antigen binding fragment thereof (e.g., to provide higher clearance and lower accumulation than Ab2). In some embodiments, the antibody may comprise Ab109, Ab132, or an antigen binding fragment thereof (e.g., to provide even higher clearance and lower accumulation than Ab102, Ab130, Ab133, or Ab141). Without wishing to be bound by theory, it is contemplated that faster serum clearance may correlate with larger immune complexes (e.g., poly daisy-chains) formed in vivo and that larger immune complex formation (e.g., oligomers) may facilitate clearance by, for example, increasing FcRn interactions. In some embodiments, such enhanced clearance of total or latent myostatin associated with the antibodies disclosed herein is achieved without engineering (e.g., introducing mutations to) the Fc region (see, e.g., Muramatsu et al. Sci Rep. 2021; 11: 2160), thereby minimizing the risk of unwanted immunogenicity.

In some embodiments, anti-pro/latent-myostatin antibodies or antigen-binding fragments thereof suitable for use in carrying out various embodiments of the present disclosure comprise an antibody or antigen-binding fragment that reduces circulating total or latent myostatin. In some embodiments, administration of an antibody or antigen-binding fragment provided herein to a subject can reduce the subject's circulating total latent myostatin by at least 10% (e.g., at least 20%, 30%, 40%, 50%, 75%, 80%, 90% or more) as compared to baseline.

In some embodiments, anti-pro/latent-myostatin antibodies or antigen-binding fragments thereof suitable for use in carrying out various embodiments of the present disclosure comprise an antibody or antigen-binding fragment that increases clearance of myostatin in the serum. In some embodiments, administration of an antibody or antigen-binding fragment provided herein to a subject can increase the clearance of myostatin in the subject's serum by at least 10% (e.g., at least 20%, at least 30%, at least 40%, at least 50%, at least 75%, at least 80%, at least 90% or more) as compared to before the administration. In some embodiments, administering an anti-pro/latent-myostatin antibodies or antigen-binding fragments thereof provided herein can provide higher clearance of myostatin (e.g., at least 10%, 20%, 30%, 40%, 50%, 75%, 80%, 90%, or higher clearance) in the serum of the subject as compared to administering a similar dose of another anti-pro/latent-myostatin antibody or antigen-binding fragment known in the art (e.g., as compared to Ab2 as provided in PCT/US2015/059468).

In some embodiments, the inventors have discovered that certain antibodies or antigen-binding fragments of the disclosure that share common features with Ab2, such as selectivity for binding toward pro/latent myostatin, pH-dependent binding, and the binding region (i.e., epitope), can surprisingly provide a distinct serum clearance profile in vivo (e.g., faster clearance of immune complexes as compared to Ab2), such antibodies include, e.g., Ab109 and Ab130.

An assay of the target engagement of the antibodies, i.e., a pharmacodynamic assay, can be performed by measuring the binding of the antibodies to myostatin. In some embodiments, myostatin is detected as described by Lakshman et al. (Mol. Cell. Endocrinol. (2009) 302(1): 26-32), the contents of which are incorporated herein in their entirety. In some embodiments, samples are treated with acid to convert all latent myostatin forms to the mature growth factor; a biotinylated capture antibody that is specific for mature myostatin is added to a streptavidin coated plate and detected with a labeled antibody that is specific for mature myostatin.

In another embodiment, a pharmacodynamic assay, can be performed by measuring the binding of the antibodies to serum free latent myostatin (i.e., circulating latent myostatin that is not bound by the antibody). Such an assay may immobilize streptavidin, bind a biotinylated antibody known to bind latent myostatin, add latent myostatin, and test the ability of an antibody to bind to the free latent myostatin by labeling the test antibody with a detectable marker. In an embodiment, the biotinylated antibody known to bind latent myostatin is biotinylated Ab2, and the test antibody is a ruthenium labeled antibody of the disclosure. In such an embodiment, the detection range of the assay may be in the nanogram range, e.g., 0.1 ng/ml-750 ng/ml, 1.0 ng/ml-500 ng/ml, or 3.0 ng/ml-500 ng/ml, e.g., 3.9-500 ng/mL. Upon administration of a single dose of the novel myostatin inhibitor disclosed herein (e.g., at 2-20 mg/kg) to mice, a rapid reduction in serum free latent myostatin is observed within one day, which remains at undetectable or nearly undetectable levels for at least 42 days, indicating durable target engagement and inhibitory activity of the antibodies.

I. In Vivo Efficacy

In some embodiments, anti-pro/latent-myostatin antibodies or antigen-binding fragments thereof suitable for use in carrying out various embodiments of the present disclosure comprise an antibody or antigen-binding fragment that can result in one or more the following effects in vivo: 1) preventing muscle atrophy; 2) preserving or increasing muscle mass; and/or 3) preserving overall body weight. In some embodiments, the one or more effects may be tested in vivo using a dexamethasone-induced injury model of atrophy (for example as described in Example 2 of the present disclosure). In some embodiments, administration of one of the novel anti-pro/latent-myostatin antibodies or antigen-binding fragments thereof disclosed herein can result in one or more of the following effects: 1) inducing overall body weight loss; 2) attenuating weight gain; 3) maintaining or increasing lean muscle mass; 4) decreasing fat mass; and/or 5) altering the ratio of muscle to fat.

In some embodiments, administration of one of the novel anti-pro/latent-myostatin antibodies or antigen-binding fragments thereof disclosed herein in conjunction with a standard-of-care treatment for diabetes and/or obesity (e.g., a GLP-1 pathway activator, e.g., semaglutide, tirzepatide, AMG-133 (a GLP-1 receptor agonist/GIP-1 receptor antagonist being developed by Amgen), or danuglipron (an oral GLP-1 receptor agonist being developed by Pfizer)) can result in greater efficacy than administration of the standard-of-care treatment alone. For instance, administration of the combination therapy results in increased weight loss or more attenuated weight gain, increased lean muscle mass or attenuated lean muscle mass loss, and/or decreased fat mass as compared to administration of the standard-of-care treatment alone.

Non-Limiting Examples of Novel Antibodies and Antigen-Binding Fragments Thereof

In some embodiments, anti-pro/latent-myostatin antibodies or antigen-binding fragments thereof suitable for use in carrying out various embodiments of the present disclosure comprise an antibody or antigen-binding fragment that exhibits one or more surprisingly distinct property, e.g., as compared to a prior art antibody such as Ab2 as provided in PCT/US2015/059468. In some embodiments, the properties include one or more (e.g. all of): 1) binding to pro/latent myostatin with a bivalent KD (e.g., F(ab')2 or mAb) of less than 1 nM as measured by an SPR-based in vitro binding assay, e.g., Biacore™; 2) pH-sensitive binding to pro/latent myostatin, e.g., such that the binding affinity to pro/latent myostatin at physiological pH (e.g., pH 7.0-7.5, e.g., pH 7.4) is at least 9-fold, e.g., at least 10-fold, greater than the binding rate at acidic pH (pH 4.0-6.5, e.g., pH 5.5); 3) capable of binding to pro/latent myostatin with a 1:2 mAb:pro/latent myostatin stoichiometry; 4) ability to inhibit protease-induced activation of myostatin in vitro with an IC50 of less than 1 nM as measured by Functional ELISA described herein; 5) not causing serum accumulation of total or latent myostatin levels or reducing circulating total or latent myostatin levels (e.g., enhancing serum clearance of myostatin); and/or 6) ability to bind latent myostatin monovalently with a KD of less than 50 nM as measured by an SPR-based in vitro binding assay, e.g., Biacore™. In some embodiments, the antibody or antigen-binding fragment further comprises an IgG4 constant domain.

In some embodiments, anti-myostatin antibodies or antigen-binding fragments thereof suitable for use in carrying out various embodiments of the present disclosure comprise an antibody or antigen-binding fragment that exhibits one of the six distinct features described above. In some embodiments, the antibody or antigen-binding fragment thereof exhibits two of the distinct features described above. In some embodiments, the antibody or antigen-binding fragment thereof exhibits three of the distinct features described above. In some embodiments, the antibody or antigen-binding fragment thereof exhibits four of the distinct features described above. In some embodiments, the antibody or antigen-binding fragment thereof exhibits five of the distinct features described above. In some embodiments, the antibody or antigen-binding fragment thereof exhibits all six of the distinct features described above. Combinations of any grouping of the six features are contemplated herein.

The inventors have made the surprising discovery that a subset of antibodies derived from or binding to the same epitope as Ab2 as provided in PCT/US2015/059468 possess all six of the above-described features. These antibodies, described in further detail below, are particularly useful for carrying out the various embodiments of the present disclosure. In some embodiments, the antibodies or antigen-binding fragments thereof comprise Ab102, Ab109, Ab130, Ab132, Ab133, or Ab141 (e.g., as defined by their respective heavy chain and light chain sequences) or the set of six CDRs and/or the set of variable domains from any of those antibodies.

In some embodiments, anti-pro/latent-myostatin antibodies or antigen-binding fragments thereof suitable for use in carrying out various embodiments of the present disclosure include an antibody or antigen-binding fragment that binds specifically to pro/latent myostatin. In some embodiments, such antibody and antigen-binding fragment binds an epitope within the prodomain, wherein the epitope comprises one or more (e.g., all of) amino acid residues F147, Q149, L151, Y183, S168, Q149, L151, Y163, S168, K170, K205 and L207, as numbered according to SEQ ID NO: 52 (Dagbay et al. J Biol Chem. 2020 Apr. 17; 295(16):5404-5418). In some embodiments, such antibody and antigen-binding fragment binds an epitope within the prodomain, wherein the epitope comprises one or more of (e.g., all of) amino acid residues F147, Q149, L151, Y186, S168, K170, K205, and/or L207, as numbered according to SEQ ID NO: 52.

In some embodiments, the antibody or antigen-binding fragment has an off rate at least 10-fold greater than the on-rate. In some embodiments, the antibody or antigen-binding fragment thereof is an antibody or antigen-binding fragment provided herein, e.g., Ab109, Ab130, Ab132, Ab133, or Ab141.

In some embodiments, the antibody or antigen-binding fragment has a 1:2 antibody:pro/latent myostatin binding stoichiometry. In some embodiments, the antibody is an antibody provided herein, e.g., Ab105, Ab109, Ab130 Ab133 or Ab141.

In some embodiments, the antibody or antigen-binding fragment binds to pro/latent myostatin with a Kd of less than or equal to 0.1 nM binding, as measured by a SPR-based in vitro binding assay, such as Biacore™. In some embodiments, the antibody is an antibody provided herein, e.g., Ab101, Ab102, Ab104, Ab105, Ab107, Ab109, Ab133, or Ab141.

In some embodiments, anti-pro/latent-myostatin antibodies or antigen-binding fragments thereof suitable for use in carrying out various embodiments of the present disclosure comprise an antibody or antigen-binding fragment comprising a constant domain of IgG1 subtype or IgG4 subtype. In some embodiments, the antibody comprising an IgG1 or IgG4 constant domain further comprises an Adair mutation (S228P). In some embodiments, the antibody or antigen-binding fragment thereof is an antibody or antigen-binding fragment provided herein, e.g., Ab102, Ab109, Ab130, Ab132, Ab133, or Ab141.

In any one of the embodiments disclosed herein, the antibody or antigen-binding fragment may comprise an HCDR1 of SEQ ID NO: 201; an HCDR2 of SEQ ID NO: 202, wherein $X_1$ is T or A; an HCDR3 of SEQ ID NO: 203; a LCDR1 of SEQ ID NO: 204; a LCDR2 of SEQ ID NO: 205; and a LCDR3 of SEQ ID NO: 206, wherein $X_1$ is M or Q and $X_2$ is P or G, as numbered according to the Kabat numbering system.

In any one of the embodiments disclosed herein, the antibody or antigen-binding fragment may comprise an HCDR1 of SEQ ID NO: 293; an HCDR2 of SEQ ID NO: 279; an HCDR3 of SEQ ID NO: 296; a LCDR1 of SEQ ID NO: 281; a LCDR2 of EVS; and a LCDR3 of SEQ ID NO: 297, wherein $X_1$ is P or G, as numbered according to the Chothia numbering system.

In any one of the embodiments disclosed herein, the antibody or antigen-binding fragment may comprise an HCDR1 of SEQ ID NO: 293; an HCDR2 of SEQ ID NO: 294, wherein $X_1$ is T or A; an HCDR3 of SEQ ID NO: 257; a LCDR1 of SEQ ID NO: 258; a LCDR2 of EVS; and a LCDR3 of SEQ ID NO: 292, wherein $X_1$ is M or Q and $X_2$ is P or G, as numbered according to the IMGT numbering system.

In some embodiments, antibodies, or antigen-binding fragments, for carrying out various embodiments of the present disclosure comprise an antibody or antigen-binding fragment comprising six complementarity determining regions (CDRs), CDRH1, CDRH2, CDRH3, CDRL1, CDRL2, and CDRL3, wherein CDRH1 comprises the sequence SYGMS (SEQ ID NO: 201), CDRH2 comprises the sequence SFTGSGGX$_1$YYPDSVKG (SEQ ID NO: 202) wherein $X_1$ is T or A, CDRH3 comprises the sequence DLLIRFLEWSHYYGMDV (SEQ ID NO: 203), CDRL1 comprises the sequence RSSQSLLHSSGHNFLH (SEQ ID NO: 204), CDRL2 comprises the sequence EVSNRVS (SEQ ID NO: 205), and CDRL3 comprises the sequence $X_1$QQTQYPX$_2$T (SEQ ID NO: 206), wherein $X_1$ is M or Q, $X_2$ is P or G, wherein the CDR sequences are numbered according to the Kabat numbering system.

In some embodiments, antibodies, or antigen-binding fragments, for carrying out various embodiments of the present disclosure comprise an antibody or an antigen-binding fragment comprising six complementarity determining regions (CDRs), CDRH1, CDRH2, CDRH3, CDRL1, CDRL2, and CDRL3, wherein CDRH1 comprises the sequence SYGMS (SEQ ID NO: 201), CDRH2 comprises the sequence SITGSGGETYYPDSVKG (SEQ ID NO: 207), CDRH3 comprises the sequence DLLVRFLEWSHYYGMDV (SEQ ID NO: 208), CDRL1 comprises the sequence RSSQSLLHSSGHNFLH (SEQ ID NO: 204), CDRL2 comprises the sequence of EVSNRVS (SEQ ID NO: 205), and CDRL3 comprises the sequence $X_1$QATQFPRP (SEQ ID NO: 210), wherein $X_1$ is M or Q, wherein the CDR sequences are numbered according to Kabat.

In some embodiments, antibodies, or antigen-binding fragments, for carrying out various embodiments of the present disclosure comprise an antibody or an antigen-binding fragment comprising six complementarity determining regions (CDRs), CDRH1, CDRH2, CDRH3, CDRL1, CDRL2, and CDRL3, wherein CDRH1 comprises the sequence SYGMS (SEQ ID NO: 201), CDRH2 comprises the sequence SINPSGGTTYYAQKFKG (SEQ ID NO: 211), CDRH3 comprises the sequence DLLVRFLEWSHYYGMDV (SEQ ID NO: 208), CDRL1 comprises the sequence RX$_1$SQSX$_2$LHSX$_3$X$_4$HNFLH (SEQ ID NO: 212), wherein $X_1$ is S or A; $X_2$ is I or L; $X_3$ is S or L; and $X_4$ is G or A, CDRL2 comprises the sequence EX$_1$SNX$_2$X$_3$S (SEQ ID NO: 213), wherein $X_1$ is A or V; $X_2$ is R or L; $X_3$ is V or A, and CDRL3 comprises the sequence QQX$_1$TQYPPT (SEQ ID NO: 214), wherein $X_1$ is Q or Y, wherein the CDR sequences are numbered according to Kabat.

In some embodiments, antibodies, or antigen-binding fragments, for carrying out various embodiments of the present disclosure comprise an antibody or an antigen-binding fragment comprising six complementarity determining regions (CDRs), CDRH1, CDRH2, CDRH3, CDRL1, CDRL2, and CDRL3, wherein CDRH1 comprises the sequence SYGMS (SEQ ID NO: 201), CDRH2 comprises the sequence SX$_1$TGSGGX$_2$X$_3$YX$_4$X$_5$X$_6$X$_7$X$_8$X$_9$ (SEQ ID NO: 512), wherein $X_1$ is I or F; $X_2$ is E, T, or A; $X_3$ is Y or T; $X_4$ is P or Y; $X_5$ is D or P; $X_6$ is S or D; $X_7$ is V or S; $X_8$ is K or V; $X_9$ is G or K, CDRH3 comprises the sequence DLLX$_1$RFLEWSHYYGMDV (SEQ ID NO: 513), wherein $X_1$ is V or I, CDRL1 comprises the sequence RSSQSLLHSSGHNFLH (SEQ ID NO: 204), CDRL2 comprises the sequence EX$_1$SNRX$_2$X$_3$ (SEQ ID NO: 514), wherein $X_1$ is T or V; $X_2$ is A or V; $X_3$ is P or S, and CDRL3 comprises the sequence X$^1$QX$^2$TQX$^3$PX$^4$X$^5$ (SEQ ID NO: 515), wherein $X_1$ is Q or M; $X_2$ is Q or A; $X_3$ is Y or F; $X_4$ is P or R or G; $X_5$ is P or T, wherein the CDR sequences are numbered according to Kabat.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence SYGMS (SEQ ID NO: 201), CDRH2 comprises the sequence $SX_1TGSGGX_2TYYPDSVKG$ (SEQ ID NO: 275) wherein $X_1$ is F or I, and $X_2$ is E or A, CDRH3 comprises the sequence $DLLX_1RFLEWSHYYGMDV$ (SEQ ID NO: 272) wherein $X_1$ is I or V, CDRL1 comprises the sequence RSSQSLLHSSGHNFLH (SEQ ID NO: 204), CDRL2 comprises the sequence $ETSNRX_1X_2$ (SEQ ID NO: 276) wherein $X_1$ is V or A and $X_2$ is P or S, and CDRL3 comprises the sequence $X_1QQX_2TQX_3PX_4X_5$ (SEQ ID NO: 277) wherein $X_1$ is M or Q, $X_2$ is Q or A, $X_3$ is Y or F, $X_4$ is R, P, or G, and $X_5$ is T or P, wherein the CDR sequences are numbered according to the Kabat numbering system.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence $GFTFX_1SY$ (SEQ ID NO: 278), wherein X is S or T, CDRH2 comprises the sequence TGSGG (SEQ ID NO: 279), CDRH3 comprises the sequence $LLX_1RFLEWSHYYGMD$ (SEQ ID NO: 280) wherein $X_1$ is I or V, CDRL1 comprises the sequence of SQSLLHSSGHNF (SEQ ID NO: 281), CDRL2 comprises the sequence $EX_1S$ wherein $X_1$ is T or V, and CDRL3 comprises the sequence $X_1X_2X_3X_4X_5X_6$ wherein $X_1$ is Q, R, or A, $X_2$ is T or P, $X_3$ is Q or F, $X_4$ is Y, F, or G, $X_5$ is P or G, and $X_6$ is G, P, or R, wherein the CDR sequences are numbered according to the Chothia numbering system.

In some embodiments, the antibody or antigen-binding fragment comprises six complementarity determining regions (CDRs): CDRH1, CDRH2, CDRH3, CDRL1, CDRL2, and CDRL3, wherein CDRH1 comprises the sequence GFTFTSSYG (SEQ ID NO: 284), CDRH2 comprises the sequence $X_1TGSGGX_2T$ (SEQ ID NO: 285) wherein $X_1$ is F or I and $X_2$ is E, T, or A, CDRH3 comprises the sequence ARDLLVRFLEWSHYYGMDV (SEQ ID NO: 286), CDRL1 comprises the sequence QSLLHSSGHNF (SEQ ID NO: 287), CDRL2 comprises the sequence $EX_1S$ wherein X is T or V, or the sequence EVSNRVS (SEQ ID NO: 205), and CDRL3 comprises the sequence $X_1QX_2TQX_3PX_4X_5$ (SEQ ID NO: 288) wherein $X_1$ is Q or M, $X_2$ is Q or A, $X_3$ is Y or F, $X_4$ is Y, P, or G, and $X_5$ is P or T, wherein the CDR sequences are numbered according to the IMGT numbering system.

In some embodiments, an anti-pro/latent-myostatin antibody or an antigen-binding portion thereof suitable for carrying out various embodiments of the present disclosure comprises the following six CDRs: a CDRH1 comprising GFTFSSYG (SEQ ID NO: 3); a CDRH2 comprising $FTGSGGX_1$ (SEQ ID NO: 291) wherein $X_1$ is selected from T and A; a CDRH3 comprising ARDLLIRFLEWSHY-YGMDV (SEQ ID NO: 257); a CDRL1 comprising QSLLHSSGHNF (SEQ ID NO: 258); a CDRL2 comprising EVSNRVS (SEQ ID NO: 289); and, a CDRL3 comprising $X_1QQTQYPX_2T$ (SEQ ID NO: 292), wherein $X_1$ is selected from M and Q, and $X_2$ is selected from P and G. In preferred embodiments, the CDRH2 comprises FTGSGGT (SEQ ID NO: 256) or FTGSGGA (SEQ ID NO: 262) and/or the CDRL3 comprises QQQTQYPGT (SEQ ID NO: 261), MQQTQYPPT (SEQ ID NO: 260), or MQQTQYPGT (SEQ ID NO: 290). In some embodiments, the CDRL3 comprises the sequence $QTQYPX_1$ (SEQ ID NO: 293), wherein $X_1$ is P or G.

In some embodiments, antibodies, or antigen-binding fragments, for carrying out various embodiments of the present disclosure comprise an antibody or antigen-binding fragment comprising six complementarity determining regions (CDRs), CDRH1, CDRH2, CDRH3, CDRL1, CDRL2, or CDRL3, or combinations thereof, wherein CDRH1 comprises SEQ ID NO: 201, CDRH2 comprises SEQ ID NO: 214, CDRH3 comprises SEQ ID No: 215, CDRL1 comprises SEQ ID NO: 216, CDRL2 comprises SEQ ID No: 217, and CDRL3 comprises any one of SEQ ID Nos: 218 or 224, as defined by the Kabat numbering system. In some embodiments, preferred antibodies, or antigen-binding fragments, for carrying out various embodiments of the present disclosure comprise an antibody or antigen-binding fragment comprising six complementarity determining regions (CDRs), CDRH1, CDRH2, CDRH3, CDRL1, CDRL2, or CDRL3, or combinations thereof, wherein CDRH1 comprises SEQ ID NO: 201, CDRH2 comprises any one of SEQ ID NOs: 219 or 226, CDRH3 comprises SEQ ID No: 220, CDRL1 comprises SEQ ID NO: 216, CDRL2 comprises SEQ ID No: 222, and CDRL3 comprises any one of SEQ ID Nos: 223, 225, or 227, as defined by the Kabat numbering system.

In some embodiments, antibodies or antigen-binding fragments for carrying out various embodiments of the disclosure comprise an antibody or antigen-binding fragment comprising six complementarity determining regions (CDRs), CDRH1, CDRH2, CDRH3, CDRL1, CDRL2, or CDRL3, or combinations thereof, wherein CDRH1 comprises SEQ ID NO: 228, CDRH2 comprises SEQ ID NO: 229, CDRH3 comprises SEQ ID No: 230, CDRL1 comprises SEQ ID NO: 231, CDRL2 comprises ETS, and CDRL3 comprises SEQ ID No: 233, as defined by the Chothia numbering system. In some embodiments, preferred antibodies or antigen-binding fragments for carrying out various embodiments of the disclosure comprise an antibody or antigen-binding fragment comprising six complementarity determining regions (CDRs), CDRH1, CDRH2, CDRH3, CDRL1, CDRL2, or CDRL3, or combinations thereof, wherein CDRH1 comprises SEQ ID NO: 234, CDRH2 comprises SEQ ID NO: 235, CDRH3 comprises SEQ ID No: 236, CDRL1 comprises SEQ ID NO: 237, CDRL2 comprises EVS, and CDRL3 comprises any one of SEQ ID Nos: 239 or 240, as defined by the Chothia numbering system.

In some embodiments, antibodies or antigen-binding fragments for carrying out various embodiments of the disclosure comprise an antibody or antigen-binding fragment comprising six complementarity determining regions (CDRs), CDRH1, CDRH2, CDRH3, CDRL1, CDRL2, or CDRL3, or combinations thereof, wherein CDRH1 comprises SEQ ID NO: 250, CDRH2 comprises SEQ ID NO: 251, CDRH3 comprises SEQ ID NO: 252, CDRL1 comprises SEQ ID NO: 253, CDRL2 comprises ETS, and CDRL3 comprises SEQ ID NO: 255 or 264, as defined by the IMGT numbering system. In some embodiments, preferred antibodies or antigen-binding fragments for carrying out various embodiments of the disclosure comprise an antibody or antigen-binding fragment comprising six complementarity determining regions (CDRs), CDRH1, CDRH2, CDRH3, CDRL1, CDRL2, or CDRL3, or combinations thereof, wherein CDRH1 comprises SEQ ID NO: 250, CDRH2 comprises SEQ ID NO: 256, CDRH3 comprises SEQ ID No: 257, CDRL1 comprises SEQ ID NO: 258, CDRL2 comprises EVS, and CDRL3 comprises any one of SEQ ID NOs: 260, 261, or 263, as defined by the IMGT numbering system.

In some embodiments, antibodies or antigen-binding fragments, for carrying out various embodiments of the present disclosure comprise an antibody or antigen-binding fragment comprising a heavy chain variable domain comprising any one of SEQ ID NOs: 400, 402, 409, 420 and a light chain variable domain comprising any one of SEQ ID NOs: 410, 412, 419, 421, 422.

In some embodiments, antibodies or antigen-binding fragments, for carrying out various embodiments of the present disclosure comprise an antibody or antigen-binding fragment comprising a heavy chain variable domain comprising SEQ ID NO: 400 and a light chain variable domain comprising SEQ ID NO: 410. In some embodiments, preferred antibodies or antigen-binding fragments, for carrying out various embodiments of the present disclosure comprise an antibody or antigen-binding fragment comprising a heavy chain variable domain comprising any one of SEQ ID NOs: 402, 409, or 420 and a light chain variable domain comprising any one of SEQ ID Nos: 412, 419, or 421. In some embodiments, preferred antibodies or antigen-binding fragments, for carrying out various embodiments of the present disclosure comprise an antibody or antigen-binding fragment comprising a heavy chain variable domain comprising SEQ ID NO: 402 and a light chain variable domain comprising SEQ ID NO: 412. In some embodiments, preferred antibodies or antigen-binding fragments, for carrying out various embodiments of the present disclosure comprise an antibody or antigen-binding fragment comprising a heavy chain variable domain comprising SEQ ID NO: 409 and a light chain variable domain comprising SEQ ID NO: 419. In some embodiments, preferred antibodies or antigen-binding fragments for carrying out various embodiments of the present disclosure comprise an antibody or antigen-binding fragment comprising a heavy chain variable domain comprising SEQ ID NO: 420 and a light chain variable domain comprising SEQ ID NO: 421. In some embodiments, preferred antibodies or antigen-binding fragments for carrying out various embodiments of the present disclosure comprise an antibody or antigen-binding fragment comprising a heavy chain variable domain comprising SEQ ID NO: 420 and a light chain variable domain comprising SEQ ID NO: 422.

In some embodiments, a preferred antibody or antigen-binding fragment for carrying out various embodiments of the present disclosure is Ab102, Ab109, Ab130, Ab132, Ab133, or Ab141. In some embodiments, a preferred antibody or antigen-binding fragment for carrying out various embodiments of the present disclosure is Ab109, Ab133, or Ab141.

In some embodiments, anti-pro/latent-myostatin antibodies, or antigen-binding portions thereof, comprise the CDRH1, CDRH2, CDRH3, CDRL1, CDRL2, and CDRL3 of any one of the antibodies shown in Tables 2a-f. The disclosure also includes any nucleic acid sequence that encodes a molecule comprising a CDRH1, CDRH2, CDRH3, CDRL1, CDRL2, or CDRL3 as provided for any one of the antibodies shown in Tables 2a-f.

In some embodiments, the consensus CDR sequences provided in Table 2a are based on antibodies Ab109, Ab132, and Ab133. In some embodiments, the consensus CDR sequences provided in Table 2a are based on antibodies Ab102 and Ab130. In some embodiments, the consensus CDR sequences provided in Table 2a are based on all antibodies shown in Table 2d.

In some embodiments, the consensus CDR sequences provided in Table 2b and Table 2c are based on antibodies Abs 102, 109, 130, 132, and 133. In some embodiments, the consensus CDR sequences provided in Table 2b and Table 2c are based on antibodies Ab109, Ab133, and Ab141.

TABLE 2a

Consensus CDR sequences based on Kabat numbering.

| Kabat H-CDR1 | Kabat H-CDR2 | Kabat H-CDR3 |
|---|---|---|
| SYGMS (SEQ ID NO: 201) | SFTGSGGX$_1$YYPDSVKG (SEQ ID NO: 202) | DLLIRFLEWSHYYGMDV (SEQ ID NO: 203) |
| SYGMS (SEQ ID NO: 201) | SITGSGGETYYPDSVKG (SEQ ID NO: 207) | DLLVRFLEWSHYYGMDV (SEQ ID NO: 208) |
| SYGMS (SEQ ID NO: 201) | SINPSGGTTYYAQKFKG (SEQ ID NO: 211) | DLLVRFLEWSHYYGMDV (SEQ ID NO: 208) |
| SYGMS (SEQ ID NO: 201) | SX$_1$TGSGGX$_2$X$_3$YX$_4$X$_5$X$_6$X$_7$X$_8$X$_9$ (SEQ ID NO: 512) | DLLX$_1$RFLEWSHYYGMDV (SEQ ID NO: 513) |
| SYGMS (SEQ ID NO: 201) | SIGGTGATYYPDSVKG (SEQ ID NO: 520) | DLLVRFLEWGHYYGMDV (SEQ ID NO: 521) |

| Kabat L-CDR1 | Kabat L-CDR2 | Kabat L-CDR3 |
|---|---|---|
| RSSQSLLHSSGHNFLH (SEQ ID NO: 204) | EVSNRVS (SEQ ID NO: 205) | X$_1$QQTQYPX$_2$T (SEQ ID NO: 206) |
| RSSQSLLHSSGHNFLH (SEQ ID NO: 204) | EVSNRVS (SEQ ID NO: 205) | X$_1$QATQFPRP (SEQ ID NO: 210) |
| RX$_1$SQSX$_2$LHSX$_3$X$_4$HNFLH (SEQ ID NO: 212) | EX$_1$SNX$_2$X$_3$S (SEQ ID NO: 213) | QQX$_1$TQYPPT (SEQ ID NO: 214) |
| RSSQSLLHSSGHNFLH (SEQ ID NO: 204) | EX$_1$SNRX$_2$X$_3$ (SEQ ID NO: 514) | X$^1$QX$^2$TQX$^3$PX$^4$X$^5$ (SEQ ID NO: 515) |
| RSSQSLLHSSGYNFLH (SEQ ID NO: 522) | AASSRAP (SEQ ID NO: 523) | X$_1$HGGQGPT (SEQ ID NO: 14) |

TABLE 2b

Consensus CDR sequences based on Chothia numbering.

| Chothia H-CDR1 | Chothia H-CDR2 | Chothia H-CDR3 |
|---|---|---|
| GFTFX$_1$SY (SEQ ID NO: 278) | TGSGG (SEQ ID NO: 279) | LLX$_1$RFLEWSHYYGMD (SEQ ID NO: 280) |
| GFTFSSY (SEQ ID NO: 234) | TGSGG (SEQ ID NO: 279) | LLIRFLEWSHYYGMD (SEQ ID NO: 296) |

TABLE 2b-continued

Consensus CDR sequences based on Chothia numbering.

| Chothia L-CDR1 | Chothia L-CDR2 | Chothia L-CDR3 |
|---|---|---|
| SQSLLHSSGHNF (SEQ ID NO: 281) | EX$_1$S | X$_1$X$_2$X$_3$X$_4$X$_5$X$_6$ |
| SQSLLHSSGHNF (SEQ ID NO: 281) | EVS | QTQYPX$_1$ (SEQ ID NO: 297) |

TABLE 2c

Consensus CDR sequences based on IMGT numbering.

| IMGT H-CDR1 | IMGT H-CDR2 | IMGT H-CDR3 |
|---|---|---|
| GFTFTSYG (SEQ ID NO: 250) | X$_1$TGSGGX$_2$T (SEQ ID NO: 285) | ARDLLVRFLEWSHYYGMDV (SEQ ID NO: 286) |
| GFTFSSYG (SEQ ID NO: 3) | FTGSGGX$_1$ (SEQ ID NO: 291) | ARDLLIRFLEWSHYYGMDV (SEQ ID NO: 257) |
| GFTFSSY (SEQ ID NO: 234) | FTGSGGX$_1$ (SEQ ID NO: 294) | ARDLLIRFLEWSHYYGMDV (SEQ ID NO: 257) |
| GSAFSSYG (SEQ ID NO: 759) | IGGTGAT (SEQ ID NO: 765) | ARDLLVRFLEWGHYYGMDV (SEQ ID NO: 766) |
| IMGT L-CDR1 | IMGT L-CDR2 | IMGT L-CDR3 |
| QSLLHSSGHNF (SEQ ID NO: 258) | EX$_1$S | X$_1$QX$_2$TQX$_3$PX$_4$X$_5$ (SEQ ID NO: 288) |
| QSLLHSSGHNF (SEQ ID NO: 258) | EVSNRVS (SEQ ID NO: 289) | X$_1$QQTQYPX$_2$T (SEQ ID NO: 292) |
| QSLLHSSGHNF (SEQ ID NO: 258) | EVS | X$_1$QQTQYPX$_2$T (SEQ ID NO: 292) |
| QSLLHSSGYNF (SEQ ID NO: 767) | AAS | X$_1$HGGQGPT (SEQ ID NO: 15) |

TABLE 2d

CDR sequences based on Kabat numbering.

| Name | H-CDR1 | H-CDR2 | H-CDR3 |
|---|---|---|---|
| Ab101 | SYGMS (SEQ ID NO: 201) | SINSNGGSTYYPDSVKG (SEQ ID NO: 516) | DLLVRFLEWSHYYGMDV (SEQ ID NO: 10) |
| Ab102 | SYGMS (SEQ ID NO: 201) | SITGSGGETYYPDSVKG (SEQ ID NO: 207) | DLLVRFLEWSHYYGMDV (SEQ ID NO: 215) |
| Ab103 | SYGMS (SEQ ID NO: 201) | SITGDAGRTYYPDSVKG (SEQ ID NO: 517) | DTLVRFLEWSHYYGMDV (SEQ ID NO: 518) |
| Ab104 | SYGMS (SEQ ID NO: 201) | SINSNGGSTYYPDSVKG (SEQ ID NO: 516) | DLLVKFLSWSHYYGMDV (SEQ ID NO: 519) |
| Ab105 | SYGMS (SEQ ID NO: 201) | SIGGTGATYYPDSVKG (SEQ ID NO: 520) | DLLVRFLEWGHYYGMDV (SEQ ID NO: 521) |
| Ab106 | SYGMS (SEQ ID NO: 201) | SINSNGGSTYYPDSVKG (SEQ ID NO: 516) | DLLVRFLEWAGYYGMDV (SEQ ID NO: 525) |
| Ab107 | SYGMS (SEQ ID NO: 201) | SINSNGGSTYYPDSVKG (SEQ ID NO: 516) | DQLVRFLEWSHYYGMDV (SEQ ID NO: 526) |
| Ab108 | SYGMS (SEQ ID NO: 201) | SINSNGGSTYYPDSVKG (SEQ ID NO: 516) | DLLVGFLQWSHYYGMDV (SEQ ID NO: 528) |
| Ab109 | SYGMS (SEQ ID NO: 201) | SFTGSGGTYYPDSVKG (SEQ ID NO: 219) | DLLIRFLEWSHYYGMDV (SEQ ID NO: 220) |

TABLE 2d-continued

CDR sequences based on Kabat numbering.

| | | | |
|---|---|---|---|
| Ab110 | NYDIH (SEQ ID NO: 529) | GISAYHGNAIYAQKFQG (SEQ ID NO: 530) | DRVRRDYYNFGMDV (SEQ ID NO: 531) |
| Ab111 | SNDIH (SEQ ID NO: 535) | GIFPIFGTTIYAQKFQG (SEQ ID NO: 536) | EGLGYDFDY (SEQ ID NO: 537) |
| Ab112 | IYAIH (SEQ ID NO: 541) | GTIPVFGTAIYAQKFQG (SEQ ID NO: 542) | LTGIAAAGTHPARGGMDV (SEQ ID NO: 543) |
| Ab113 | ELSIH (SEQ ID NO: 547) | GIIPSFGTAIYAQKFQG (SEQ ID NO: 548) | SYSGFDLLPLDK (SEQ ID NO: 549) |
| Ab114 | SYTIH (SEQ ID NO: 553) | GMNPSSGHTIYAQKFQG (SEQ ID NO: 554) | GLDYGEGYYYYGMDV (SEQ ID NO: 555) |
| Ab115 | NYNIH (SEQ ID NO: 559) | GINPRTGGTIYAQKFQG (SEQ ID NO: 560) | DIYTGVAVAGSGMDY (SEQ ID NO: 561) |
| Ab116 | RPAIH (SEQ ID NO: 565) | GINPNAATTIYAQKFQG (SEQ ID NO: 566) | GRLLREWELRPYDT (SEQ ID NO: 567) |
| Ab117 | SHDIH (SEQ ID NO: 571) | GINPSDASTIYAQKFQG (SEQ ID NO: 572) | DLRGYSYGAETWHFQH (SEQ ID NO: 573) |
| Ab118 | GYNIH (SEQ ID NO: 577) | GMNPKSGDTIYAQKFQG (SEQ ID NO: 578) | DPGPYGSPLYYYGMDV (SEQ ID NO: 579) |
| Ab119 | KDHIH (SEQ ID NO: 583) | GITPSSGDTIYAQKFQG (SEQ ID NO: 584) | DHMVRGLPNYYYGMDL (SEQ ID NO: 585) |
| Ab120 | TFHIH (SEQ ID NO: 589) | GISAYSGSTIYAQKFQG (SEQ ID NO: 590) | ARYVDDAFDI (SEQ ID NO: 591) |
| Ab121 | TSGMVVN (SEQ ID NO: 595) | MIDWDADNIVYNSALKS (SEQ ID NO: 596) | DTGSGWFDAFDI (SEQ ID NO: 597) |
| Ab122 | SGGSYVN (SEQ ID NO: 601) | MTDWDADNIVYNSALK (SEQ ID NO: 602) | RQNVDSYGYWGDAFDI (SEQ ID NO: 603) |
| Ab123 | KYDMS (SEQ ID NO: 607) | SISSSGGTRYYPDSVKG (SEQ ID NO: 608) | DLWVASPGYGMDV (SEQ ID NO: 609) |
| Ab124 | SSPYS (SEQ ID NO: 613) | IGYVDLAGSTDYNPSLKS (SEQ ID NO: 614) | RASQSIGINLA (SEQ ID NO: 615) |
| Ab125 | DYWMN (SEQ ID NO: 618) | NIYPGYSDATYNRKFKGQ (SEQ ID NO: 619) | GRDGYNYFAAFDI (SEQ ID NO: 620) |
| Ab126 | NYAMD (SEQ ID NO: 624) | YISSDASTTYYADSVKG (SEQ ID NO: 625) | DGGYNPGIFDY (SEQ ID NO: 626) |
| Ab127 | SYPMD (SEQ ID NO: 630) | YISGRGDVTYYADSVKG (SEQ ID NO: 631) | VQSPSELLWFGELLPVD (SEQ ID NO: 632) |
| Ab128 | SYSMD (SEQ ID NO: 636) | YITGSGDTTYYADSVKG (SEQ ID NO: 637) | GFGWISGWAEDYFDY (SEQ ID NO: 638) |
| Ab129 | RSAIH (SEQ ID NO: 641) | GINPSGEATIYAQKFQG (SEQ ID NO: 642) | DSSPQWLVTAGVYFYGMDV (SEQ ID NO: 643) |
| Ab130 | SYGMS (SEQ ID NO: 201) | SITGSGGETYYPDSVKG (SEQ ID NO: 207) | DLLVRFLEWSHYYGMDV (SEQ ID NO: 215) |
| Ab131 | SYGMS (SEQ ID NO: 201) | SIGGTGATYYPDSVKG (SEQ ID NO: 520) | DLLVRFLEWGHYYGMDV (SEQ ID NO: 521) |
| Ab132 | SYGMS (SEQ ID NO: 201) | SFTGSGGTYYPDSVKG (SEQ ID NO: 219) | DLLIRFLEWSHYYGMDV (SEQ ID NO: 220) |
| Ab133 | SYGMS (SEQ ID NO: 201) | SFTGSGGAYYPDSVKG (SEQ ID NO: 226) | DLLIRFLEWSHYYGMDV (SEQ ID NO: 220) |
| Ab134 | SYGMS (SEQ ID NO: 201) | SINSNGGSTYYPDSVKG (SEQ ID NO: 516) | DLLVEFLKWSHYYGMDV (SEQ ID NO: 944) |
| Ab135 | SYGMS (SEQ ID NO: 201) | SINSNGGSTYYPDSVKG (SEQ ID NO: 516) | DLLVTFLRWSHYYGMDV (SEQ ID NO: 945) |

TABLE 2d-continued

CDR sequences based on Kabat numbering.

| | | | |
|---|---|---|---|
| Ab136 | SYGMS (SEQ ID NO: 201) | SIGGTGATYYPDSVKG (SEQ ID NO: 520) | DLLVRFLEWSHYYGMDV (SEQ ID NO: 10) |
| Ab137 | SYGMS (SEQ ID NO: 201) | SFTGSGGTYYPDSVKG (SEQ ID NO: 219) | DLLIRFLEWGHYYGMDV (SEQ ID NO: 946) |
| Ab138 | SYGMS (SEQ ID NO: 201) | SITGSKGETYYPDSVKG (SEQ ID NO: 947) | DLLVRFLEWSHYYGMDV (SEQ ID NO: 10) |
| Ab139 | SYGMS (SEQ ID NO: 201) | SFTGSGAAYYPDSVKG (SEQ ID NO: 948) | DLLIRFLEWSHYYGMDV (SEQ ID NO: 203) |
| Ab140 | SYGMS (SEQ ID NO: 201) | SFTGSGGTYYPDSVKG (SEQ ID NO: 219) | DNLIRFLEWSHYYGMDV (SEQ ID NO: 950) |
| Ab141 | SYGMS (SEQ ID NO: 201) | SFTGSGGAYYPDSVKG (SEQ ID NO: 226) | DLLIRFLEWSHYYGMDV (SEQ ID NO: 220) |

| Name | L-CDR1 | L-CDR2 | LCDR3 |
|---|---|---|---|
| Ab101 | RSSQSLLHSSGHNFLH (SEQ ID NO: 204) | EVSNRVS (SEQ ID NO: 205) | MQQTQYPPT (SEQ ID NO: 223) |
| Ab102 | RSSQSLLHSSGHNFLH (SEQ ID NO: 216) | ETSNRAP (SEQ ID NO: 217) | MQATQFPRP (SEQ ID NO: 218) |
| Ab103 | RSSQSLLHSSGHNFLH (SEQ ID NO: 204) | EVSNRVS (SEQ ID NO: 205) | MQQTQYPPT (SEQ ID NO: 223) |
| Ab104 | RSSQSLLHSSGHNFLH (SEQ ID NO: 204) | EVSNRVS (SEQ ID NO: 205) | MQQTQYPPT (SEQ ID NO: 223) |
| Ab105 | RSSQSLLHSSGYNFLH (SEQ ID NO: 522) | AASSRAP (SEQ ID NO: 523) | MHGGQGPT (SEQ ID NO: 524) |
| Ab106 | RSSQSLLHSSGHNFLH (SEQ ID NO: 204) | EVSNRVS (SEQ ID NO: 205) | MQQTQYPPT (SEQ ID NO: 223) |
| Ab107 | RSSQSLLHSSGHNFLH (SEQ ID NO: 204) | AGSNRPS (SEQ ID NO: 527) | AGSNRPS (SEQ ID NO: 527) |
| Ab108 | RSSQSLLHSSGHNFLH (SEQ ID NO: 204) | EVSNRVS (SEQ ID NO: 205) | MQQTQYPPT (SEQ ID NO: 223) |
| Ab109 | RSSQSLLHSSGHNFLH (SEQ ID NO: 216) | EVSNRVS (SEQ ID NO: 222) | MQQTQYPPT (SEQ ID NO: 223) |
| Ab110 | RASEDITSYLA (SEQ ID NO: 532) | DVSSLQS (SEQ ID NO: 533) | LQHNAYPYG (SEQ ID NO: 534) |
| Ab111 | RASQNIGNWLA (SEQ ID NO: 538) | SASALQS (SEQ ID NO: 539) | QQSYGAPMYS (SEQ ID NO: 540) |
| Ab112 | RASPSISSYLA (SEQ ID NO: 544) | AASRLQS (SEQ ID NO: 545) | QEYLSFPLT (SEQ ID NO: 546) |
| Ab113 | RASQHISTWLA (SEQ ID NO: 550) | YASSLQG (SEQ ID NO: 551) | LQTYTYPRT (SEQ ID NO: 552) |
| Ab114 | RASQGISESLA (SEQ ID NO: 556) | SASSLES (SEQ ID NO: 557) | QQGYSSPPYT (SEQ ID NO: 558) |
| Ab115 | RASQGISTHLA (SEQ ID NO: 562) | GASNLES (SEQ ID NO: 563) | QQANSFPWT (SEQ ID NO: 564) |
| Ab116 | RASQSIGKSLA (SEQ ID NO: 568) | SASNLRS (SEQ ID NO: 569) | QQYRDVPPIT (SEQ ID NO: 570) |
| Ab117 | RASQYISNYLA (SEQ ID NO: 574) | ETSRLES (SEQ ID NO: 575) | QQTSSTPLT (SEQ ID NO: 576) |
| Ab118 | RASQIITTHLA (SEQ ID NO: 580) | DASYLER (SEQ ID NO: 581) | QQYRTSSSLT (SEQ ID NO: 582) |
| Ab119 | RASRDIANYLA (SEQ ID NO: 586) | AASILQN (SEQ ID NO: 587) | QQAYTTPPT (SEQ ID NO: 588) |

TABLE 2d-continued

CDR sequences based on Kabat numbering.

| | | | |
|---|---|---|---|
| Ab120 | RASEDISNFLA (SEQ ID NO: 592) | AASDLLS (SEQ ID NO: 593) | QKYISAPS (SEQ ID NO: 594) |
| Ab121 | KSSQSVLYSSTNQNFLA (SEQ ID NO: 598) | QASTLQN (SEQ ID NO: 599) | QQYLTTPYT (SEQ ID NO: 600) |
| Ab122 | KSSQSVLYSADNKNYLA (SEQ ID NO: 604) | DASSLEN (SEQ ID NO: 605) | QQGHLFPYS (SEQ ID NO: 606) |
| Ab123 | RSSQSLLHSSGHNYLH (SEQ ID NO: 610) | LGSIRAP (SEQ ID NO: 611) | MQALLNPPT (SEQ ID NO: 612) |
| Ab124 | RASQSIGINLA (SEQ ID NO: 615) | GVSNRAT (SEQ ID NO: 616) | QQYGTARLT (SEQ ID NO: 617) |
| Ab125 | RASQSVASSYLA (SEQ ID NO: 621) | DTSSRAA (SEQ ID NO: 622) | HQYGSSLTT (SEQ ID NO: 623) |
| Ab126 | QASQSIGRWLN (SEQ ID NO: 627) | DASILQT (SEQ ID NO: 628) | QQSFTTPPLT (SEQ ID NO: 629) |
| Ab127 | QASQVIKTWLN (SEQ ID NO: 633) | DASNLQR (SEQ ID NO: 634) | QQSASTPIT (SEQ ID NO: 635) |
| Ab128 | GFGWISGWAEDYFDY (SEQ ID NO: 638) | GASRLEG (SEQ ID NO: 639) | QQHSTDQRT (SEQ ID NO: 640) |
| Ab129 | RASQSISNWLA (SEQ ID NO: 644) | HASTLQS (SEQ ID NO: 645) | QQYSSTPWT (SEQ ID NO: 646) |
| Ab130 | RSSQSLLHSSGHNFLH (SEQ ID NO: 216) | ETSNRAP (SEQ ID NO: 217) | QQATQFPRP (SEQ ID NO: 224) |
| Ab131 | RSSQSLLHSSGYNFLH (SEQ ID NO: 522) | AASSRAP (SEQ ID NO: 523) | QHGGQGPT (SEQ ID NO: 647) |
| Ab132 | RSSQSLLHSSGHNFLH (SEQ ID NO: 216) | EVSNRVS (SEQ ID NO: 222) | QQQTQYPPT (SEQ ID NO: 225) |
| Ab133 | RSSQSLLHSSGHNFLH (SEQ ID NO: 216) | EVSNRVS (SEQ ID NO: 222) | QQQTQYPGT (SEQ ID NO: 227) |
| Ab134 | RSSQSLLHSSGHNFLH (SEQ ID NO: 204) | EVSNRVS (SEQ ID NO: 205) | MQQTQYPPT (SEQ ID NO: 223) |
| Ab135 | RSSQSLLHSSGHNFLH (SEQ ID NO: 204) | EVSNRVS (SEQ ID NO: 205) | MQQTQYPPT (SEQ ID NO: 223) |
| Ab136 | RSSQSLLHSSGYNFLH (SEQ ID NO: 522) | AASSRAP (SEQ ID NO: 523) | MHGGQGPT (SEQ ID NO: 524) |
| Ab137 | RSSQSLLHSSGHNFLH (SEQ ID NO: 204) | EVSNRVS (SEQ ID NO: 205) | MQQTQYPPT (SEQ ID NO: 223) |
| Ab138 | RSSQSLLHSSGHNFLH (SEQ ID NO: 204) | ETSNRAP (SEQ ID NO: 217) | QQATQFPRP (SEQ ID NO: 224) |
| Ab139 | RSSQSLLHSSGHNFLH (SEQ ID NO: 204) | ESSNRVS (SEQ ID NO: 949) | QQQTQYPPT (SEQ ID NO: 225) |
| Ab140 | RSSQSLLHSSGHNFLH (SEQ ID NO: 204) | EVSNRES (SEQ ID NO: 951) | QQQTQYPPT (SEQ ID NO: 225) |
| Ab141 | RSSQSLLHSSGHNFLH (SEQ ID NO: 216) | EVSNRVS (SEQ ID NO: 222) | MQQTQYPGT (SEQ ID NO: 298) |

TABLE 2e

CDR sequences based on Chothia numbering.

| Name | H-CDR1 | H-CDR2 | H-CDR3 |
|---|---|---|---|
| Ab101 | GSAFSSY (SEQ ID NO: 648) | NSNGGS (SEQ ID NO: 649) | LLVRFLEWSHYYGMD (SEQ ID NO: 230) |

TABLE 2e-continued

CDR sequences based on Chothia numbering.

| | | | |
|---|---|---|---|
| Ab102 | GFTFTSY (SEQ ID NO: 228) | TGSGGE (SEQ ID NO: 229) | LLVRFLEWSHYYGMD (SEQ ID NO: 230) |
| Ab103 | GYTFSSY (SEQ ID NO: 650) | TGDAGR (SEQ ID NO: 651) | TLVRFLEWSHYYGMD (SEQ ID NO: 652) |
| Ab104 | GSAFSSY (SEQ ID NO: 648) | NSNGGS (SEQ ID NO: 649) | LLVKFLSWSHYYGMD (SEQ ID NO: 653) |
| Ab105 | GSAFSSY (SEQ ID NO: 648) | GGTGA (SEQ ID NO: 654) | LLVRFLEWGHYYGMD (SEQ ID NO: 655) |
| Ab106 | GSAFSSY (SEQ ID NO: 648) | NSNGGS (SEQ ID NO: 649) | LLVRFLEWAGYYGMD (SEQ ID NO: 658) |
| Ab107 | GSAFSSY (SEQ ID NO: 648) | NSNGGS (SEQ ID NO: 649) | QLVRFLEWSHYYGMD (SEQ ID NO: 659) |
| Ab108 | GSAFSSY (SEQ ID NO: 648) | NSNGGS (SEQ ID NO: 649) | LLVGFLQWSHYYGMD (SEQ ID NO: 661) |
| Ab109 | GFTFSSY (SEQ ID NO: 234) | TGSGG (SEQ ID NO: 235) | LLIRFLEWSHYYGMD (SEQ ID NO: 236) |
| Ab110 | EYTFTNY (SEQ ID NO: 662) | SAYHGN (SEQ ID NO: 663) | RVRRDYYNFGMD (SEQ ID NO: 664) |
| Ab111 | GYTFTSN (SEQ ID NO: 667) | FPIFGT (SEQ ID NO: 668) | GLGYDED (SEQ ID NO: 669) |
| Ab112 | GGTFGIY (SEQ ID NO: 672) | IPVFGT (SEQ ID NO: 673) | TGIAAAGTHPARGGMD (SEQ ID NO: 674) |
| Ab113 | GYLLTEL (SEQ ID NO: 677) | IPSFGT (SEQ ID NO: 678) | YSGFDLLPLD (SEQ ID NO: 679) |
| Ab114 | GGTFRSY (SEQ ID NO: 682) | NPSSGH (SEQ ID NO: 683) | LDYGEGYYYYGMD (SEQ ID NO: 684) |
| Ab115 | GYAFTNY (SEQ ID NO: 686) | NPRTGG (SEQ ID NO: 687) | IYTGVAVAGSGMD (SEQ ID NO: 688) |
| Ab116 | GFTFSRP (SEQ ID NO: 691) | NPNAAT (SEQ ID NO: 692) | RLLREWELRPYD (SEQ ID NO: 693) |
| Ab117 | GGTFSSH (SEQ ID NO: 696) | NPSDAS (SEQ ID NO: 697) | LRGYSYGAETWHFQ (SEQ ID NO: 698) |
| Ab118 | GYTSTGY (SEQ ID NO: 701) | NPKSGD (SEQ ID NO: 702) | PGPYGSPLYYYGMD (SEQ ID NO: 703) |
| Ab119 | GYTFTK (SEQ ID NO: 706) | TPSSGD (SEQ ID NO: 707) | HMVRGLPNYYYGMD (SEQ ID NO: 708) |
| Ab120 | GGTFSTF (SEQ ID NO: 711) | SAYSGS (SEQ ID NO: 712) | RYVDDAFD (SEQ ID NO: 713) |
| Ab121 | GFSFSTSGM (SEQ ID NO: 716) | DWDADN (SEQ ID NO: 717) | TGSGWFDAFD (SEQ ID NO: 718) |
| Ab122 | GGSLSSGGS (SEQ ID NO: 721) | DWDADN (SEQ ID NO: 717) | QNVDSYGYWGDAF (SEQ ID NO: 722) |
| Ab123 | GFTFSKY (SEQ ID NO: 725) | SSSGGT (SEQ ID NO: 726) | LWVASPGYGMD (SEQ ID NO: 727) |
| Ab124 | GGSISSS (SEQ ID NO: 730) | YVDLAGS (SEQ ID NO: 731) | LSSRSSEWLLDQYTMD (SEQ ID NO: 732) |
| Ab125 | GNRISDY (SEQ ID NO: 735) | YPGYSDA (SEQ ID NO: 736) | RDGYNYFAAFD (SEQ ID NO: 737) |
| Ab126 | SFTFSNY (SEQ ID NO: 740) | SSDAST (SEQ ID NO: 741) | GGYNPGIFD (SEQ ID NO: 739) |
| Ab127 | GFTFGSY (SEQ ID NO: 744) | SGRGDV (SEQ ID NO: 745) | QSPSELLWFGELLPVD (SEQ ID NO: 746) |

TABLE 2e-continued

CDR sequences based on Chothia numbering.

| | | | |
|---|---|---|---|
| Ab128 | GFTLSSY (SEQ ID NO: 749) | TGSGDT (SEQ ID NO: 750) | FGWISGWAEDYFD (SEQ ID NO: 751) |
| Ab129 | GFNYPRS (SEQ ID NO: 754) | NPSGEA (SEQ ID NO: 755) | SSPQWLVTAGVYFYGMD (SEQ ID NO: 756) |
| Ab130 | GFTFTSY (SEQ ID NO: 228) | TGSGGE (SEQ ID NO: 229) | LLVRFLEWSHYYGMD (SEQ ID NO: 230) |
| Ab131 | GSAFSSY (SEQ ID NO: 648) | GGTGA (SEQ ID NO: 654) | LLVRFLEWGHYYGMD (SEQ ID NO: 655) |
| Ab132 | GFTFSSY (SEQ ID NO: 234) | TGSGG (SEQ ID NO: 235) | LLIRFLEWSHYYGMD (SEQ ID NO: 236) |
| Ab133 | GFTFSSY (SEQ ID NO: 234) | TGSGG (SEQ ID NO: 235) | LLIRFLEWSHYYGMD (SEQ ID NO: 236) |
| Ab134 | GSAFSSY (SEQ ID NO: 648) | NSNGGS (SEQ ID NO: 649) | LLVEFLKWSHYYGMD (SEQ ID NO: 952) |
| Ab135 | GSAFSSY (SEQ ID NO: 648) | NSNGGS (SEQ ID NO: 649) | LLVTFLRWSHYYGMD (SEQ ID NO: 954) |
| Ab136 | GSAFSSY (SEQ ID NO: 648) | GGTGA (SEQ ID NO: 654) | DLLVRFLEWSHYYGMDV (SEQ ID NO: 10) |
| Ab137 | GFTFSSY (SEQ ID NO: 234) | TGSGG (SEQ ID NO: 235) | DLLIRFLEWGHYYGMDV (SEQ ID NO: 946) |
| Ab138 | GFTFTSY (SEQ ID NO: 228) | TGSKGE (SEQ ID NO: 955) | DLLVRFLEWSHYYGMDV (SEQ ID NO: 10) |
| Ab139 | GFTFSSY (SEQ ID NO: 234) | TGSGA (SEQ ID NO: 956) | DLLIRFLEWSHYYGMDV (SEQ ID NO: 203) |
| Ab140 | GFTFSSY (SEQ ID NO: 234) | TGSGG (SEQ ID NO: 235) | DNLIRFLEWSHYYGMDV (SEQ ID NO: 950) |
| Ab141 | GFTFSSY (SEQ ID NO: 234) | TGSGG (SEQ ID NO: 235) | LLIRFLEWSHYYGMD (SEQ ID NO: 236) |
| Name | L-CDR1 | L-CDR2 | L-CDR3 |
| Ab101 | SQSLLHSSGHNF (SEQ ID NO: 231) | EVS | QTQYPP (SEQ ID NO: 239) |
| Ab102 | SQSLLHSSGHNF (SEQ ID NO: 231) | ETS | ATQFPR (SEQ ID NO: 233) |
| Ab103 | SQSLLHSSGHNF (SEQ ID NO: 231) | EVS | QTQYPP (SEQ ID NO: 239) |
| Ab104 | SQSLLHSSGHNF (SEQ ID NO: 231) | EVS | QTQYPP (SEQ ID N 239) |
| Ab105 | SQSLLHSSGYNF (SEQ ID NO: 656) | AAS | GGQGP (SEQ ID NO: 657) |
| Ab106 | SQSLLHSSGHNF (SEQ ID NO: 231) | EVS | QTQYPP (SEQ ID NO: 239) |
| Ab107 | SQSLLHSSGHNF (SEQ ID NO: 231) | AGS | ATQLPH (SEQ ID NO: 660) |
| Ab108 | SQSLLHSSGHNF (SEQ ID NO: 231) | EVS | QTQYPP (SEQ ID NO: 239) |
| Ab109 | SQSLLHSSGHNF (SEQ ID NO: 237) | EVS | QTQYPP (SEQ ID NO: 239) |
| Ab110 | SEDITSY (SEQ ID NO: 665) | DVS | HNAYPY (SEQ ID NO: 666) |
| Ab111 | SQNIGNW (SEQ ID NO: 670) | SAS | SYGAPMY (SEQ ID NO: 671) |

TABLE 2e-continued

CDR sequences based on Chothia numbering.

| | | | |
|---|---|---|---|
| Ab112 | SPSISSY (SEQ ID NO: 675) | AAS | YLSFPL (SEQ ID NO: 676) |
| Ab113 | SQHISTW (SEQ ID NO: 680) | YAS | TYTYPR (SEQ ID NO: 681) |
| Ab114 | LDYGEGYYYYGMD (SEQ ID NO: 684) | SAS | GYSSPPY (SEQ ID NO: 685) |
| Ab115 | SQGISTH (SEQ ID NO: 689) | GAS | ANSFPW (SEQ ID NO: 690) |
| Ab116 | SQSIGKS (SEQ ID NO: 694) | SAS | YRDVPPI (SEQ ID NO: 695) |
| Ab117 | SQYISNY (SEQ ID NO: 699) | ETS | TSSTPL (SEQ ID NO: 700) |
| Ab118 | SQIITTH (SEQ ID NO: 704) | DAS | YRTSSSL (SEQ ID NO: 705) |
| Ab119 | SRDIANY (SEQ ID NO: 709) | AAS | AYTTPP (SEQ ID NO: 710) |
| Ab120 | SEDISNF (SEQ ID NO: 714) | AAS | YISAP (SEQ ID NO: 715) |
| Ab121 | SQSVLYSSTNQNF (SEQ ID NO: 719) | QAS | YLTTPY (SEQ ID NO: 720) |
| Ab122 | SQSVLYSADNKNY (SEQ ID NO: 723) | DAS | GHLFPY (SEQ ID NO: 724) |
| Ab123 | SQSLLHSSGHNY (SEQ ID NO: 728) | LGS | ALLNPP (SEQ ID NO: 729) |
| Ab124 | SQSIGIN (SEQ ID NO: 733) | GVS | YGTARL (SEQ ID NO: 734) |
| Ab125 | YGSSLT (SEQ ID NO: 738) | DTS | GGYNPGIFD (SEQ ID NO: 739) |
| Ab126 | SQSIGRW (SEQ ID NO: 742) | DAS | SFTTPPL (SEQ ID NO: 743) |
| Ab127 | SQVIKTW (SEQ ID NO: 747) | DAS | SASTPI (SEQ ID NO: 748) |
| Ab128 | SQSVYSY (SEQ ID NO: 752) | GAS | HSTDQR (SEQ ID NO: 753) |
| Ab129 | SQSISNW (SEQ ID NO: 757) | HAS | YSSTPW (SEQ ID NO: 758) |
| Ab130 | SQSLLHSSGHNF (SEQ ID NO: 231) | ETS | ATQFPR (SEQ ID NO: 233) |
| Ab131 | SQSLLHSSGYNF (SEQ ID NO: 656) | AAS | GGQGP (SEQ ID NO: 657) |
| Ab132 | SQSLLHSSGHNF (SEQ ID NO: 237) | EVS | QTQYPP (SEQ ID NO: 239) |
| Ab133 | SQSLLHSSGHNF (SEQ ID NO: 237) | EVS | QTQYPG (SEQ ID NO: 240) |
| Ab134 | SQSLLHSSGHNF (SEQ ID NO: 231) | EVS | PTFGGG (SEQ ID NO: 953) |
| Ab135 | SQSLLHSSGHNF (SEQ ID NO: 231) | EVS | QTQYPP (SEQ ID NO: 239) |
| Ab136 | RSSQSLLHSSGYNFLH (SEQ ID NO: 522) | AAS | MHGGQGPT (SEQ ID NO: 524) |
| Ab137 | RSSQSLLHSSGHNFLH (SEQ ID NO: 204) | EVS | MQQTQYPPT (SEQ ID NO: 223) |

TABLE 2e-continued

CDR sequences based on Chothia numbering.

| | | | |
|---|---|---|---|
| Ab138 | RSSQSLLHSSGHNFLH (SEQ ID NO: 204) | ETS | QQATQFPRP (SEQ ID NO: 224) |
| Ab139 | RSSQSLLHSSGHNFLH (SEQ ID NO: 204) | ESS | QQQTQYPPT (SEQ ID NO: 225) |
| Ab140 | RSSQSLLHSSGHNFLH (SEQ ID NO: 204) | EVS | QQQTQYPPT (SEQ ID NO: 225) |
| Ab141 | SQSLLHSSGHNF (SEQ ID NO: 237) | EVS | QTQYPG (SEQ ID NO: 240) |

TABLE 2f

CDR sequences based on IMGT numbering.

| Name | H-CDR1 | H-CDR2 | H-CDR3 |
|---|---|---|---|
| Ab101 | GSAFSSYG (SEQ ID NO: 759) | INSNGGST (SEQ ID NO: 760) | ARDLLVRFLEWSHYYGMDV (SEQ ID NO: 252) |
| Ab102 | GFTFTSYG (SEQ ID NO: 250) | ITGSGGET (SEQ ID NO: 251) | ARDLLVRFLEWSHYYGMDV (SEQ ID NO: 252) |
| Ab103 | GYTFSSYG (SEQ ID NO: 761) | ITGDAGRT (SEQ ID NO: 762) | ARDTLVRFLEWSHYYGMDV (SEQ ID NO: 763) |
| Ab104 | GSAFSSYG (SEQ ID NO: 759) | INSNGGST (SEQ ID NO: 760) | ARDLLVKFLSWSHYYGMDV (SEQ ID NO: 764) |
| Ab105 | GSAFSSYG (SEQ ID NO: 759) | IGGTGAT (SEQ ID NO: 765) | ARDLLVRFLEWGHYYGMDV (SEQ ID NO: 766) |
| Ab106 | GSAFSSYG (SEQ ID NO: 759) | INSNGGST (SEQ ID NO: 760) | ARDLLVRFLEWAGYYGMDV (SEQ ID NO: 768) |
| Ab107 | GSAFSSYG (SEQ ID NO: 759) | INSNGGST (SEQ ID NO: 760) | ARDQLVRFLEWSHYYGMDV (SEQ ID NO: 769) |
| Ab108 | GSAFSSYG (SEQ ID NO: 759) | INSNGGST (SEQ ID NO: 760) | ARDLLVGFLQWSHYYGMDV (SEQ ID NO: 771) |
| Ab109 | GFTFSSYG (SEQ ID NO: 3) | FTGSGGT (SEQ ID NO: 256) | ARDLLIRFLEWSHYYGMDV (SEQ ID NO: 257) |
| Ab110 | EYTFTNYD (SEQ ID NO: 772) | ISAYHGNA (SEQ ID NO: 773) | ARDRVRRDYYNFGMDV (SEQ ID NO: 774) |
| Ab111 | GYTFTSND (SEQ ID NO: 776) | IFPIFGTT (SEQ ID NO: 777) | AREGLGYDFDY (SEQ ID NO: 778) |
| Ab112 | GGTFGIYA (SEQ ID NO: 780) | TIPVFGTA (SEQ ID NO: 781) | ASLTGIAAAGTHPARGGMDV (SEQ ID NO: 782) |
| Ab113 | GYLLTELS (SEQ ID NO: 784) | IIPSFGTA (SEQ ID NO: 785) | AISYSGFDLLPLDK (SEQ ID NO: 786) |
| Ab114 | GGTFRSYT (SEQ ID NO: 788) | MNPSSGHT (SEQ ID NO: 789) | ARGLDYGEGYYYYGMDV (SEQ ID NO: 790) |
| Ab115 | GYAFTNYN (SEQ ID NO: 792) | INPRTGGT (SEQ ID NO: 793) | AKDIYTGVAVAGSGMDY (SEQ ID NO: 794) |
| Ab116 | GFTFSRPA (SEQ ID NO: 796) | INPNAATT (SEQ ID NO: 797) | ARGRLLREWELRPYDT (SEQ ID NO: 798) |
| Ab117 | GGTFSSHD (SEQ ID NO: 800) | INPSDAST (SEQ ID NO: 801) | ARDLRGYSYGAETWHFQH (SEQ ID NO: 802) |
| Ab118 | GYTSTGYN (SEQ ID NO: 804) | MNPKSGDT (SEQ ID NO: 805) | ARDPGPYGSPLYYYGMDV (SEQ ID NO: 806) |
| Ab119 | GYTFTKDH (SEQ ID NO: 808) | ITPSSGDT (SEQ ID NO: 809) | ARDHMVRGLPNYYYGMDL (SEQ ID NO: 810) |

TABLE 2f-continued

CDR sequences based on IMGT numbering.

| | | | |
|---|---|---|---|
| Ab120 | GGTFSTFH (SEQ ID NO: 812) | ISAYSGST (SEQ ID NO: 813) | ARARYVDDAFDI (SEQ ID NO: 814) |
| Ab121 | GFSFSTSGMV (SEQ ID NO: 816) | IDWDADNI (SEQ ID NO: 817) | AKDTGSGWFDAFDI (SEQ ID NO: 818) |
| Ab122 | GGSLSSGGSY (SEQ ID NO: 820) | TDWDADNI (SEQ ID NO: 821) | AHRQNVDSYGYWGDAFDI (SEQ ID NO: 822) |
| Ab123 | GFTFSKYD (SEQ ID NO: 824) | ISSSGGTR (SEQ ID NO: 825) | AKDLWVASPGYGMDV (SEQ ID NO: 826) |
| Ab124 | GGSISSSPYS (SEQ ID NO: 828) | VDLAGST (SEQ ID NO: 829) | ARALSSRSSEWLLDQYTMDV (SEQ ID NO: 830) |
| Ab125 | GNRISDYW (SEQ ID NO: 832) | IYPGYSDA (SEQ ID NO: 833) | ARGRDGYNYFAAFDI (SEQ ID NO: 834) |
| Ab126 | SFTFSNYA (SEQ ID NO: 836) | ISSDASTT (SEQ ID NO: 837) | ARDGGYNPGIFDY (SEQ ID NO: 838) |
| Ab127 | GFTFGSYP (SEQ ID NO: 840) | ISGRGDVT (SEQ ID NO: 841) | AKVQSPSELLWFGELLPVDY (SEQ ID NO: 842) |
| Ab128 | GFTLSSYS (SEQ ID NO: 844) | ITGSGDTT (SEQ ID NO: 845) | ARGFGWISGWAEDYFDY (SEQ ID NO: 846) |
| Ab129 | GFNYPRSA (SEQ ID NO: 848) | INPSGEAT (SEQ ID NO: 849) | ARDSSPQWLVTAGVYFYGMDV (SEQ ID NO: 850) |
| Ab130 | GFTFTSYG (SEQ ID NO: 250) | ITGSGGET (SEQ ID NO: 251) | ARDLLVRFLEWSHYYGMDV (SEQ ID NO: 252) |
| Ab131 | GSAFSSYG (SEQ ID NO: 759) | IGGTGAT (SEQ ID NO: 765) | ARDLLVRFLEWGHYYGMDV (SEQ ID NO: 766) |
| Ab132 | GFTFSSYG (SEQ ID NO: 3) | FTGSGGT (SEQ ID NO: 256) | ARDLLIRFLEWSHYYGMDV (SEQ ID NO: 257) |
| Ab133 | GFTFSSYG (SEQ ID NO: 3) | FTGSGGA (SEQ ID NO: 262) | ARDLLIRFLEWSHYYGMDV (SEQ ID NO: 257) |
| Ab134 | GSAFSSYG (SEQ ID NO: 759) | INSNGGST (SEQ ID NO: 760) | ARDLLVEFLKWSHYYGMDV (SEQ ID NO: 957) |
| Ab135 | GSAFSSYG (SEQ ID NO: 759) | INSNGGST (SEQ ID NO: 760) | ARDLLVTFLRWSHYYGMDV (SEQ ID NO: 958) |
| Ab136 | GSAFSSYG (SEQ ID NO: 759) | IGGTGAT (SEQ ID NO: 765) | ARDLLVRFLEWSHYYGMDV (SEQ ID NO: 252) |
| Ab137 | GFTFSSYG (SEQ ID NO: 3) | FTGSGGT (SEQ ID NO: 256) | ARDLLIRFLEWGHYYGMDV (SEQ ID NO: 959) |
| Ab138 | GFTFTSYG (SEQ ID NO: 250) | ITGSKGET (SEQ ID NO: 960) | RDLLVRFLEWSHYYGMDV (SEQ ID NO: 961) |
| Ab139 | GFTFSSYG (SEQ ID NO: 3) | FTGSGAA (SEQ ID NO: 962) | ARDLLIRFLEWSHYYGMDV (SEQ ID NO: 257) |
| Ab140 | GFTFSSYG (SEQ ID NO: 3) | FTGSGGT (SEQ ID NO: 256) | ARDNLIRFLEWSHYYGMDV (SEQ ID NO: 963) |
| Ab141 | GFTFSSYG (SEQ ID NO: 3) | FTGSGGA (SEQ ID NO: 262) | ARDLLIRFLEWSHYYGMDV (SEQ ID NO: 257) |
| Name | L-CDR1 | L-CDR2 | L-CDR3 |
| Ab101 | QSLLHSSGHNF (SEQ ID NO: 253) | EVS | QTQYPP (SEQ ID NO: 223) |
| Ab102 | QSLLHSSGHNF (SEQ ID NO: 253) | ETS | MQATQFPRP (SEQ ID NO: 255) |
| Ab103 | QSLLHSSGHNF (SEQ ID NO: 253) | EVS | MQQTQYPPT (SEQ ID NO: 223) |

TABLE 2f-continued

CDR sequences based on IMGT numbering.

| | | | |
|---|---|---|---|
| Ab104 | QSLLHSSGHNF (SEQ ID NO: 253) | EVS | MQQTQYPPT (SEQ ID NO: 223) |
| Ab105 | QSLLHSSGYNF (SEQ ID NO: 767) | AAS | MHGGQGPT (SEQ ID NO: 524) |
| Ab106 | QSLLHSSGHNF (SEQ ID NO: 253) | EVS | MQQTQYPPT (SEQ ID NO: 223) |
| Ab107 | QSLLHSSGHNF (SEQ ID NO: 253) | AGS | AHATQLPHT (SEQ ID NO: 770) |
| Ab108 | QSLLHSSGHNF (SEQ ID NO: 253) | EVS | MQQTQYPPT (SEQ ID NO: 223) |
| Ab109 | QSLLHSSGHNF (SEQ ID NO: 258) | EVS | MQQTQYPPT (SEQ ID NO: 260) |
| Ab110 | EDITSY (SEQ ID NO: 775) | DVS | LQHNAYPYG (SEQ ID NO: 534) |
| Ab111 | QNIGNW (SEQ ID NO: 779) | SAS | QQSYGAPMYS (SEQ ID NO: 540) |
| Ab112 | PSISSY (SEQ ID NO: 783) | AAS | QEYLSFPLT (SEQ ID NO: 546) |
| Ab113 | QHISTW (SEQ ID NO: 787) | YAS | LQTYTYPRT (SEQ ID NO: 552) |
| Ab114 | QGISES (SEQ ID NO: 791) | SAS | QQGYSSPPYT (SEQ ID NO: 558) |
| Ab115 | QGISTH (SEQ ID NO: 795) | GAS | QQANSFPWT (SEQ ID NO: 564) |
| Ab116 | QSIGKS (SEQ ID NO: 799) | SAS | QQYRDVPPIT (SEQ ID NO: 570) |
| Ab117 | QYISNY (SEQ ID NO: 803) | ETS | QQTSSTPLT (SEQ ID NO: 576) |
| Ab118 | QIITTH (SEQ ID NO: 807) | DAS | QQYRTSSSLT (SEQ ID NO: 582) |
| Ab119 | RDIANY (SEQ ID NO: 811) | AAS | QQAYTTPPT (SEQ ID NO: 588) |
| Ab120 | EDISNF (SEQ ID NO: 815) | AAS | QKYISAPS (SEQ ID NO: 594) |
| Ab121 | QSVLYSSTNQNF (SEQ ID NO: 819) | QAS | QQYLTTPYT (SEQ ID NO: 600) |
| Ab122 | QSVLYSADNKNY (SEQ ID NO: 823) | DAS | QQGHLFPYS (SEQ ID NO: 606) |
| Ab123 | QSLLHSSGHNY (SEQ ID NO: 827) | LGS | MQALLNPPT (SEQ ID NO: 612) |
| Ab124 | QSIGIN (SEQ ID NO: 831) | GVS | QQYGTARLT (SEQ ID NO: 617) |
| Ab125 | QSVASSY (SEQ ID NO: 835) | DTS | HQYGSSLTT (SEQ ID NO: 623) |
| Ab126 | QSIGRW (SEQ ID NO: 839) | DAS | QQSFTTPPLT (SEQ ID NO: 629) |
| Ab127 | QVIKTW (SEQ ID NO: 843) | DAS | QQSASTPIT (SEQ ID NO: 635) |
| Ab128 | QSVYSY (SEQ ID NO: 847) | GAS | QQHSTDQRT (SEQ ID NO: 640) |
| Ab129 | QSISNW (SEQ ID NO: 851) | HAS | QQYSSTPWT (SEQ ID NO: 646) |

TABLE 2f-continued

CDR sequences based on IMGT numbering.

| | | | |
|---|---|---|---|
| Ab130 | QSLLHSSGHNF (SEQ ID NO: 253) | ETS | QQATQFPRP (SEQ ID NO: 264) |
| Ab131 | QSLLHSSGYNF (SEQ ID NO: 767) | AAS | QHGGQGPT (SEQ ID NO: 647) |
| Ab132 | QSLLHSSGHNF (SEQ ID NO: 258) | EVS | QQQTQYPPT (SEQ ID NO: 225) |
| Ab133 | QSLLHSSGHNF (SEQ ID NO: 258) | EVS | QQQTQYPGT (SEQ ID NO: 263) |
| Ab134 | QSLLHSSGHNF (SEQ ID NO: 253) | EVS | MQQTQYPPT (SEQ ID NO: 223) |
| Ab135 | QSLLHSSGHNF (SEQ ID NO: 253) | EVS | MQQTQYPPT (SEQ ID NO: 223) |
| Ab136 | QSLLHSSGYNF (SEQ ID NO: 767) | AAS | MHGGQGPT (SEQ ID NO: 524) |
| Ab137 | QSLLHSSGHNF (SEQ ID NO: 253) | EVS | MQQTQYPPT (SEQ ID NO: 223) |
| Ab138 | QSLLHSSGHNF (SEQ ID NO: 253) | ETS | QQATQFPRP (SEQ ID NO: 224) |
| Ab139 | QSLLHSSGHNF (SEQ ID NO: 253) | ESS | QQQTQYPPT (SEQ ID NO: 225) |
| Ab140 | QSLLHSSGHNF (SEQ ID NO: 253) | EVS | QQQTQYPPT (SEQ ID NO: 225) |
| Ab141 | QSLLHSSGHNF (SEQ ID NO: 258) | EVS | MQQTQYPGT (SEQ ID NO: 290) |

In some embodiments, an anti-pro/latent-myostatin antibody or an antigen-binding portion thereof suitable for carrying out various embodiments of the disclosure comprises a CDRH1 comprising a sequence as set forth in SEQ ID NO: 201, a CDRH2 comprising a sequence as set forth in SEQ ID NO: 214, a CDRH3 comprising a sequence as set forth in SEQ ID NO: 215, a CDRL1 comprising a sequence as set forth in SEQ ID NO: 216, a CDRL2 comprising a sequence as set forth in SEQ ID NO: 217, and a CDRL3 comprising a sequence as set forth in SEQ ID NO: 218 or 224, as defined by the Kabat numbering system.

In some embodiments, an anti-pro/latent-myostatin antibody or an antigen-binding portion thereof suitable for carrying out various embodiments of the disclosure comprises a CDRH1 comprising a sequence as set forth in SEQ ID NO: 228, a CDRH2 comprising a sequence as set forth in SEQ ID NO: 229, a CDRH3 comprising a sequence as set forth in SEQ ID NO: 230, a CDRL1 comprising a sequence as set forth in SEQ ID NO: 231, a CDRL2 comprising the amino acid sequence ETS, and a CDRL3 comprising a sequence as set forth in SEQ ID NO: 233 or 224, as defined by the Chothia numbering system.

In some embodiments, an anti-pro/latent-myostatin antibody or an antigen-binding portion thereof suitable for carrying out various embodiments of the disclosure comprises a CDRH1 comprising a sequence as set forth in SEQ ID NO: 201, a CDRH2 comprising a sequence as set forth in SEQ ID NO: 219 or 226, a CDRH3 comprising a sequence as set forth in SEQ ID NO: 220, a CDRL1 comprising a sequence as set forth in SEQ ID NO: 216, a CDRL2 comprising a sequence as set forth in SEQ ID NO: 222, and a CDRL3 comprising a sequence as set forth in SEQ ID NO: 223, 227, or 298, as defined by the Kabat numbering system.

In some embodiments, an anti-pro/latent-myostatin antibody or an antigen-binding portion thereof suitable for carrying out various embodiments of the disclosure comprises a CDRH1 comprising a sequence as set forth in SEQ ID NO: 234, a CDRH2 comprising a sequence as set forth in SEQ ID NO: 235, a CDRH3 comprising a sequence as set forth in SEQ ID NO: 236, a CDRL1 comprising a sequence as set forth in SEQ ID NO: 237, a CDRL2 comprising the amino acid sequence EVS, and a CDRL3 comprising a sequence as set forth in SEQ ID NO: 239 or 240, as defined by the Chothia numbering system.

In some embodiments, anti-pro/latent-myostatin antibody or an antigen-binding portion thereof suitable for carrying out various embodiments of the disclosure comprises a CDRH1 comprising a sequence as set forth in SEQ ID NO: 250, a CDRH2 comprising a sequence as set forth in SEQ ID NO: 256 or 262, a CDRH3 comprising a sequence as set forth in SEQ ID NO: 257, a CDRL1 comprising a sequence as set forth in SEQ ID NO: 258, a CDRL2 comprising a sequence as set forth in EVS, and a CDRL3 comprising a sequence as set forth in SEQ ID NO: 260, 262, 290, as defined by the IMGT numbering system.

In some embodiments, an anti-pro/latent-myostatin antibody or an antigen-binding portion thereof suitable for carrying out various embodiments of the disclosure comprises a CDRH1 comprising a sequence as set forth in SEQ ID NO: 201, a CDRH2 comprising a sequence as set forth in SEQ ID NO: 520, a CDRH3 comprising a sequence as set forth in SEQ ID NO: 521, a CDRL1 comprising a sequence as set forth in SEQ ID NO: 522, a CDRL2 comprising a sequence as set forth in SEQ ID NO: 523, and a CDRL3 comprising a sequence as set forth in SEQ ID NO: 524 or 647, as defined by the Kabat or IMGT numbering system.

In some embodiments, an anti-pro/latent-myostatin antibody or an antigen-binding portion thereof suitable for carrying out various embodiments of the disclosure comprises a CDRH1 comprising a sequence as set forth in SEQ ID NO: 648, a CDRH2 comprising a sequence as set forth in SEQ ID NO: 654, a CDRH3 comprising a sequence as set forth in SEQ ID NO: 655, a CDRL1 comprising a sequence as set forth in SEQ ID NO: 656, a CDRL2 comprising the amino acid sequence AAS, and a CDRL3 comprising a sequence as set forth in SEQ ID NO: 657, as defined by the Chothia numbering system.

In some embodiments, the present disclosure encompasses an anti-pro/latent-myostatin antibody or antigen-binding portions thereof having one or more CDR sequences containing up to 5, 4, 3, 2, or 1 variation(s) in amino acid residue as compared to the corresponding CDR region in any one of the SEQ ID NOs shown in Tables 2a-f (e.g., 1 or 2 or 3 substitutions, insertions, and/or deletions). In some embodiments, the present disclosure encompasses an anti-pro/latent-myostatin antibody or antigen-binding portions thereof comprising one or more CDR sequences, e.g., a set of all six CDRs corresponding to a set of CDRs specified in any one of the SEQ ID NOs shown in Tables 2a-f, e.g., the set of SEQ ID NOs from the table identified for a specific antibody in the table.

TABLE 3

Variable domain sequences of exemplary antibodies.

| Name | Heavy Chain Variable Region Amino Acid Sequence (SEQ ID NO) | Light Chain Variable Region Amino Acid Sequence (SEQ ID NO) |
| --- | --- | --- |
| Ab101 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVRFL EWSHYYGMDVWGQGTTVTVSS (SEQ ID NO: 852) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |
| Ab102 | EVQLVESGGGLVQPGGSLRLSCAASGFTFTSYGM SWVRQAPGKGLELVASITGSGGETYYPDSVKGRFT ISRDNAKNSLYLQMNSLRAEDTAVYYCARDLLVRFL EWSHYYGMDVWGQGTTVTVSS (SEQ ID NO: 400) | DIVMTQSPLSLPVTPGEPASISCRSSQSLLHSSGH NFLHWYLQKPGQSPQLLIYETSNRAPGIPDRFSGS GSGTDFTLKISRVEAEDVGVYYCMQATQFPRPFG GGTKVEIK (SEQ ID NO: 410) |
| Ab103 | EVQLVESGGGLVQPGGSLRLSCAASGYTFSSYGM SWVRQAPGKGLELVASITGDAGRTYYPDSVKGRFT ISRDNAKNSLYLQMNSLRAEDTAVYYCARDTLVRFL EWSHYYGMDVWGQGTTVTVSS (SEQ ID NO: 853) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |
| Ab104 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVKFL SWSHYYGMDVWGQGTTVTVSS (SEQ ID NO: 854) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |
| Ab105 | EVQLVESGGGLVQPGGSLRLSCAASGSAFSSYGM SWVRQAPGKGLELVASIGGTGATYYPDSVKGRFTI SRDNAKNSLYLQMNSLRAEDTAVYYCARDLLVRFL EWGHYYGMDVWGQGTTVTVSS (SEQ ID NO: 401) | DIVMTQSPLSLPVTPGEPASISCRSSQSLLHSSGY NFLHWYLQKPGQSPQLLIYAASSRAPGIPDRFSGS GSGTDFTLKISRVEAEDVGVYYCMHGGQGPTFG GGTKVEIK (SEQ ID NO: 411) |
| Ab106 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVRFL EWAGYYGMDVWGQGTTVTVSS (SEQ ID NO: 855) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |
| Ab107 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDQLVRF LEWSHYYGMDVWGQGTTVTVSS (SEQ ID NO: 856) | DIVMTQSPLSLPVTPGEPASISCRSSQSLLHSSGH NFLHWYLQKPGQSPQLLIYAGSNRPSGVPDRFSG SGSGTDFTLKISRVEAEDVGVYYCAHATQLPHTFG GGTKVEIK (SEQ ID NO: 857) |
| Ab108 | EVQLVESGGGLVQPGGSLRLSCAASGSAFSSYGM SWVRQAPGKGLELVASINSGGSTYYPDSVKGRFTI SRDNAKNSLYLQMNSLRAEDTAVYYCARDLLVGFL QWSHYYGMDVWGQGTTVTVSS (SEQ ID NO: 858) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |
| Ab109 | EVQLVESGGGLVQPGGSLRLSCAASGFTFSSYGM SWVRQAPGKGLELVASFTGSGGTYYPDSVKGRFTI SRDNAKNSLYLQMNSLRAEDTAVYYCARDLLIRFLE WSHYYGMDVWGQGTTVTVSS (SEQ ID NO: 402) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |
| Ab110 | QVQLVQSGAEVKKPGASVKVSCKVSEYTFTNYDIH WVRQAPGKGLEWMGGISAYHGNAIYAQKFQGRVT MTEDTSTDTAYMELSSLKSEDTAVYYCARDRVRRD YYNFGMDVWGQGTTVTVSS (SEQ ID NO: 859) | DIQMTQSPSSVSASVGDRVTITCRASEDITSYLAW YQQKPGKAPKLLIYDVSSLQSGVPSRFSGSGSGT DFTLTISSLQPEDFANYYCLQHNAYPYGFGGGTKV EIK (SEQ ID NO: 860) |

TABLE 3-continued

Variable domain sequences of exemplary antibodies.

| Name | Heavy Chain Variable Region Amino Acid Sequence (SEQ ID NO) | Light Chain Variable Region Amino Acid Sequence (SEQ ID NO) |
|---|---|---|
| Ab111 | QVQLVQSGAEVKKPGASVKVSCKVSGYTFTSNDIH WVRQAPGKGLEWMGGIFPIFGTTIYAQKFQGRVTM TEDTSTDTAYMELSSLKSEDTAVYYCAREGLGYDF DYWGQGTLVTVSS (SEQ ID NO: 861) | DIQMTQSPSSVSASVGDRVTITCRASQNIGNWLA WYQQKPGKAPKLLIYSASALQSGVPSRFSGSGSG TDFTLTISSLQPEDFANYYCQQSYGAPMYSFGGG TKVEIK (SEQ ID NO: 862) |
| Ab112 | QVQLVQSGAEVKKPGASVKVSCKVSGGTFGIYAIH WVRQAPGKGLEWMGGTIPVFGTAIYAQKFQGRVT MTEDTSTDTAYMELSSLKSEDTAVYYCASLTGIAAA GTHPARGGMDVWGQGTTVTVSS (SEQ ID NO: 403) | DIQMTQSPSSVSASVGDRVTITCRASPSISSYLAW YQQKPGKAPKLLIYAASRLQSGVPSRFSGSGSGT DFTLTISSLQPEDFANYYCQEYLSFPLTFGGGTKV EIK (SEQ ID NO: 413) |
| Ab113 | QVQLVQSGAEVKKPGASVKVSCKVSGYLLTELSIH WVRQAPGKGLEWMGGIIPSFGTAIYAQKFQGRVT MTEDTSTDTAYMELSSLKSEDTAVYYCAISYSGFDL LPLDKWGQGTLVTVSS (SEQ ID NO: 863) | DIQMTQSPSSVSASVGDRVTITCRASQHISTWLA WYQQKPGKAPKLLIYYASSLQGGVPSRFSGSGSG TDFTLTISSLQPEDFANYYCLQTYTYPRTFGGGTK VEIK (SEQ ID NO: 864) |
| Ab114 | QVQLVQSGAEVKKPGASVKVSCKVSGGTFRSYTIH WVRQAPGKGLEWMGGMNPSSGHTIYAQKFQGRV TMTEDTSTDTAYMELSSLKSEDTAVYYCARGLDYG EGYYYYGMDVWGQGTTVTVSS (SEQ ID NO: 865) | DIQMTQSPSSVSASVGDRVTITCRASQGISESLAW YQQKPGKAPKLLIYSASSLESGVPSRFSGSGSGT DFTLTISSLQPEDFANYYCQQGYSSPPYTFGGGT KVEIK (SEQ ID NO: 866) |
| Ab115 | QVQLVQSGAEVKKPGASVKVSCKVSGYAFTNYNIH WVRQAPGKGLEWMGGINPRTGGTIYAQKFQGRVT MTEDTSTDTAYMELSSLKSEDTAVYYCAKDIYTGVA VAGSGMDYWGQGTLVTVSS (SEQ ID NO: 867) | DIQMTQSPSSVSASVGDRVTITCRASQGISTHLAW YQQKPGKAPKLLIYGASNLESGVPSRFSGSGSGT DFTLTISSLQPEDFANYYCQQANSFPWTFGGGTK VEIK (SEQ ID NO: 868) |
| Ab116 | QVQLVQSGAEVKKPGASVKVSCKVSGFTFSRPAIH WVRQAPGKGLEWMGGINPNAATTIYAQKFQGRVT MTEDTSTDTAYMELSSLKSEDTAVYYCARGRLLRE WELRPYDTWGQGTLVTVSS (SEQ ID NO: 869) | DIQMTQSPSSVSASVGDRVTITCRASQSIGKSLAW YQQKPGKAPKLLIYSASNLRSGVPSRFSGSGSGT DFTLTISSLQPEDFANYYCQQYRDVPPITFGGGTK VEIK (SEQ ID NO: 870) |
| Ab117 | QVQLVQSGAEVKKPGASVKVSCKVSGGTFSSHDIH WVRQAPGKGLEWMGGINPSDASTIYAQKFQGRVT MTEDTSTDTAYMELSSLKSEDTAVYYCARDLRGYS YGAETWHFQHWGQGTLVTVSS (SEQ ID NO: 871) | DIQMTQSPSSVSASVGDRVTITCRASQYISNYLAW YQQKPGKAPKLLIYETSRLESGVPSRFSGSGSGT DFTLTISSLQPEDFANYYCQQTSSTPLTFGGGTKV EIK (SEQ ID NO: 872) |
| Ab118 | QVQLVQSGAEVKKPGASVKVSCKVSGYTSTGYNIH WVRQAPGKGLEWMGGMNPKSGDTIYAQKFQGRV TMTEDTSTDTAYMELSSLKSEDTAVYYCARDPGPY GSPLYYYGMDVWGQGTTVTVSS (SEQ ID NO: 873) | DIQMTQSPSSVSASVGDRVTITCRASQIITTHLAWY QQKPGKAPKLLIYDASYLERGVPSRFSGSGSGTD FTLTISSLQPEDFANYYCQQYRTSSSLTFGGGTKV EIK (SEQ ID NO: 874) |
| Ab119 | QVQLVQSGAEVKKPGASVKVSCKVSGYTFTKDHIH WVRQAPGKGLEWMGGITPSSGDTIYAQKFQGRVT MTEDTSTDTAYMELSSLKSEDTAVYYCARDHMVR GLPNYYYGMDLWGQGTTVTVSS (SEQ ID NO: 875) | DIQMTQSPSSVSASVGDRVTITCRASRDIANYLAW YQQKPGKAPKLLIYAASILQNGVPSRFSGSGSGTD FTLTISSLQPEDFANYYCQQAYTTPPTFGGGTKVE IK (SEQ ID NO: 876) |
| Ab120 | QVQLVQSGAEVKKPGASVKVSCKVSGGTFSTFHIH WVRQAPGKGLEWMGGISAYSGSTIYAQKFQGRVT MTEDTSTDTAYMELSSLKSEDTAVYYCARARYVDD AFDIWGQGTMVTVSS (SEQ ID NO: 877) | DIQMTQSPSSVSASVGDRVTITCRASEDISNFLAW YQQKPGKAPKLLIYAASDLLSGVPSRFSGSGSGT DFTLTISSLQPEDFANYYCQKYISAPSFGGGTKVEI K (SEQ ID NO: 878) |
| Ab121 | QVTLRESGPALVKPTQTLTLTCTVSGFSFSTSGMV VNWIRQPPGKALEWLAMIDWDADNIVYNSALKSRL TISKDTSKNQVVLTMTNMDPVDTATYYCAKDTGSG WFDAFDIWGQGTMVTVSS (SEQ ID NO: 404) | DIVMTQSPDSLAVSLGERATINCKSSQSVLYSSTN QNFLAWYQQKPGQPPKLLIYQASTLQNGVPDRFS GSGSGTDFTLTISSLQAEDVAVYYCQQYLTTPYTF GGGTKVEIK (SEQ ID NO: 414) |
| Ab122 | QVTLRESGPALVKPTQTLTLTCTVSGGSLSSGGSY VNWIRQPPGKALEWLAMTDWDADNIVYNSALKSR LTISKDTSKNQVVLTMTNMDPVDTATYYCAHRQN VDSYGYWGDAFDIWGQGTMVTVSS (SEQ ID NO: 879) | DIVMTQSPDSLAVSLGERATINCKSSQSVLYSADN KNYLAWYQQKPGQPPKLLIYDASSLENGVPDRFS GSGSGTDFTLTISSLQAEDVAVYYCQQGHLFPYSF GGGTKVEIK (SEQ ID NO: 880) |
| Ab123 | EVQLVESGGGLVQPGGSLRLSCAASGFTFSKYDM SWVRQAPGKGLELVASISSSGGTRYYPDSVKGRFT ISRDNAKNSLYLQMNSLRAEDTAVYYCAKDLWVAS PGYGMDVWGQGTTVTVSS (SEQ ID NO: 405) | EVQLVESGGGLVQPGGSLRLSCAASGFTFSKYDM SWVRQAPGKGLELVASISSSGGTRYYPDSVKGRF TISRDNAKNSLYLQMNSLRAEDTAVYYCAKDLWV ASPGYGMDVWGQGTTVTVSS (SEQ ID NO: 415) |
| Ab124 | QVQLQESGPGLVKPSQTLSLTCTVSGGSISSSPYS WSWIRQPPGKGLEWIGYVDLAGSTDYNPSLKSRVT MSVDTSKNQFSLKVNSVTAADTAVYYCARALSSRS SEWLLDQYTMDVWGQGTTVTVSS (SEQ ID NO: 881) | EIVMTQSPATLSLSPGERATLSCRASQSIGINLAW YQQKPGQAPRLLIYGVSNRATGIPARFSGSGSGT DFTLTISSLEPEDFAVYYCQQYGTARLTFGGGTKV EIK (SEQ ID NO: 882) |

TABLE 3-continued

Variable domain sequences of exemplary antibodies.

| Name | Heavy Chain Variable Region Amino Acid Sequence (SEQ ID NO) | Light Chain Variable Region Amino Acid Sequence (SEQ ID NO) |
| --- | --- | --- |
| Ab125 | EVQLVQSGAEVKKPGESLKISCKGSGNRISDYWMN WVRQVPGKGLEWMGNIYPGYSDATYNRKFKGQVT ISADKSISTAYLQWSSLKASDTAIYYCARGRDGYNY FAAFDIWGQGTMVTVSS (SEQ ID NO: 883) | EIVLTQSPATLSLSPGERATLSCRASQSVASSYLA WYQQKPGQAPRLLIYDTSSRAAGIPARFSGSGSG TDFTLTISSLEPEDFAVYYCHQYGSSLTTFGGGTK VEIK (SEQ ID NO: 884) |
| Ab126 | EVQLVESGGGLVQPGGSLRLSCTASSFTFSNYAM DWVRQAPGKGLEWVSYISSDASTTYYADSVKGRF TISRDNAKNTLYLQMNSLRAEDTAVYYCARDGGYN PGIFDYWGQGTLVTVSS (SEQ ID NO: 885) | DIQMTQSPSSLSASVGDRVTITCQASQSIGRWLN WYQQKPGKAPKLLIYDASILQTGVPSRFSGSGSG TDFTFTISSLQPEDIATYYCQQSFTTPPLTFGGGTK VEIK (SEQ ID NO: 886) |
| Ab127 | EVQLVESGGGLVQPGGSLRLSCTASGFTFGSYPM DWVRQAPGKGLEWVSYISGRGDVTYYADSVKGRF TISRDNAKNTLYLQMNSLRAEDTAVYYCAKVQSPS ELLWFGELLPVDYWGQGTLVTVSS (SEQ ID NO: 406) | EVQLVESGGGLVQPGGSLRLSCTASGFTFGSYPM DWVRQAPGKGLEWVSYISGRGDVTYYADSVKGR FTISRDNAKNTLYLQMNSLRAEDTAVYYCAKVQSP SELLWFGELLPVDYWGQGTLVTVSS (SEQ ID NO: 416) |
| Ab128 | EVQLVESGGGLVQPGGSLRLSCTASGFTLSSYSM DWVRQAPGKGLEWVSYITGSGDTTYYADSVKGRF TISRDNAKNTLYLQMNSLRAEDTAVYYCARGFGWI SGWAEDYFDYWGQGTLVTVSS (SEQ ID NO: 887) | DIQMTQSPSSLSASVGDRVTITCQASQSVYSYLN WYQQKPGKAPKLLIYGASRLEGGVPSRFSGSGSG TDFTFTISSLQPEDIATYYCQQHSTDQRTFGGGTK VEIK (SEQ ID NO: 888) |
| Ab129 | QVQLVQSGAEVKKPGASVKVSCKVSGFNYPRSAIH WVRQAPGKGLEWMGGINPSGEATIYAQKFQGRVT MTEDTSTDTAYMELSSLKSEDTAVYYCARDSSPQ WLVTAGVYFYGMDVWGQGTTVTVSS (SEQ ID NO: 889) | DIQMTQSPSSVSASVGDRVTITCRASQSISNWLA WYQQKPGKAPKLLIYHASTLQSGVPSRFSGSGSG TDFTLTISSLQPEDFANYYCQQYSSTPWTFGGGT KVEIK (SEQ ID NO: 890) |
| Ab130 | EVQLVESGGGLVQPGGSLRLSCAASGFTFTSYGM SWVRQAPGKGLELVASITGSGGETYYPDSVKGRFT ISRDNAKNSLYLQMNSLRAEDTAVYYCARDLLVRFL EWSHYYGMDVWGQGTTVTVSS (SEQ ID NO: 407) | DIVMTQSPLSLPVTPGEPASISCRSSQSLLHSSGH NFLHWYLQKPGQSPQLLIYETSNRAPGIPDRFSGS GSGTDFTLKISRVEAEDVGVYYCQQATQFPRPFG GGTKVEIK (SEQ ID NO: 417) |
| Ab131 | EVQLVESGGGLVQPGGSLRLSCAASGSAFSSYGM SWVRQAPGKGLELVASIGGTGATYYPDSVKGRFTI SRDNAKNSLYLQMNSLRAEDTAVYYCARDLLVRFL EWGHYYGMDVWGQGTTVTVSS (SEQ ID NO: 408) | DIVMTQSPLSLPVTPGEPASISCRSSQSLLHSSGY NFLHWYLQKPGQSPQLLIYAASSRAPGIPDRFSGS GSGTDFTLKISRVEAEDVGVYYCQHGGQGPTFGG GTKVEIK (SEQ ID NO: 418) |
| Ab132 | EVQLVESGGGLVQPGGSLRLSCAASGFTFSSYGM SWVRQAPGKGLELVASFTGSGGTYYPDSVKGRFTI SRDNAKNSLYLQMNSLRAEDTAVYYCARDLLIRFLE WSHYYGMDVWGQGTTVTVSS (SEQ ID NO: 409) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCQQQTQYPPTF GGGTKVEIK (SEQ ID NO: 419) |
| Ab133 | EVQLVESGGGLVQPGGSLRLSCAASGFTFSSYGM SWVRQAPGKGLELVASFTGSGGAYYPDSVKGRFTI SRDNAKNSLYLQMNSLRAEDTAVYYCARDLLIRFLE WSHYYGMDVWGQGTTVTVSS (SEQ ID NO: 420) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCQQQTQYPGTF GGGTKVEIK (SEQ ID NO: 421) |
| Ab134 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVEFL KWSHYYGMDVWGQGTTVTVS (SEQ ID NO: 981) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |
| Ab135 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVTFL RWSHYYGMDVWGQGTTVTVSS (SEQ ID NO: 964) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |
| Ab136 | EVQLVESGGGLVQPGGSLRLSCAASGSAFSSYGM SWVRQAPGKGLELVASIGGTGATYYPDSVKGRFT ISRDNAKNSLYLQMNSLRAEDTAVYYCARDLLVRFL EWSHYYGMDVWGQGTTVTVSS (SEQ ID NO: 965) | DIVMTQSPLSLPVTPGEPASISCRSSQSLLHSSGY NFLHWYLQKPGQSPQLLIYAASSRAPGIPDRFSGS GSGTDFTLKISRVEAEDVGVYYCMHGGQGPTFG GGTKVEIK (SEQ ID NO: 411) |
| Ab137 | EVQLVESGGGLVQPGGSLRLSCAASGFTFSSYGM SWVRQAPGKGLELVASFTGSGGTYYPDSVKGRFTI SRDNAKNSLYLQMNSLRAEDTAVYYCARDLLIRFLE WGHYYGMDVWGQGTTVTVSS (SEQ ID NO: 966) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIK (SEQ ID NO: 412) |

TABLE 3-continued

Variable domain sequences of exemplary antibodies.

| Name | Heavy Chain Variable Region<br>Amino Acid Sequence (SEQ ID NO) | Light Chain Variable Region<br>Amino Acid Sequence (SEQ ID NO) |
|---|---|---|
| Ab138 | EVQLVESGGGLVQPGGSLRLSCAASGFTFTSYGM<br>SWVRQAPGKGLELVASITGSKGETYYPDSVKGRFT<br>ISRDNAKNSLYLQMNSLRAEDTAVYYCARDLLVRFL<br>EWSHYYGMDVWGQGTTVTVSS<br>(SEQ ID NO: 967) | DIVMTQSPLSLPVTPGEPASISCRSSQSLLHSSGH<br>NFLHWYLQKPGQSPQLLIYETSNRAPGIPDRFSGS<br>GSGTDFTLKISRVEAEDVGVYYCQQATQFPRPFG<br>GGTKVEIK<br>(SEQ ID NO: 417) |
| Ab139 | EVQLVESGGGLVQPGGSLRLSCAASGFTFSSYGM<br>SWVRQAPGKGLELVASFTGSGAAYYPDSVKGRFTI<br>SRDNAKNSLYLQMNSLRAEDTAVYYCARDLLIRFLE<br>WSHYYGMDVWGQGTTVTVSS<br>(SEQ ID NO: 968) | DIVMTQSPLSLPVTPGEPASISCRSSQSLLHSSGH<br>NFLHWYLQKPGQSPQLLIYESSNRVSGVPDRFSG<br>SGSGTDFTLKISRVEAEDVGVYYCQQQTQYPPTF<br>GGGTKVEIK<br>(SEQ ID NO: 969) |
| Ab140 | EVQLVESGGGLVQPGGSLRLSCAASGFTFSSYGM<br>SWVRQAPGKGLELVASFTGSGGTYYPDSVKGRFTI<br>SRDNAKNSLYLQMNSLRAEDTAVYYCARDNLIRFL<br>EWSHYYGMDVWGQGTTVTVSS<br>(SEQ ID NO: 970) | DIVMTQSPLSLPVTPGEPASISCRSSQSLLHSSGH<br>NFLHWYLQKPGQSPQLLIYEVSNRESGVPDRFSG<br>SGSGTDFTLKISRVEAEDVGVYYCQQQTQYPPTF<br>GGGTKVEIK<br>(SEQ ID NO: 971) |
| Ab141 | EVQLVESGGGLVQPGGSLRLSCAASGFTFSSYGM<br>SWVRQAPGKGLELVASFTGSGGAYYPDSVKGRFTI<br>SRDNAKNSLYLQMNSLRAEDTAVYYCARDLLIRFLE<br>WSHYYGMDVWGQGTTVTVSS<br>(SEQ ID NO: 420) | DIVMTQSPLSLPVTPGEPASISCRSSQSLLHSSGH<br>NFLHWYLQKPGQSPQLLIYEVSNRVSGVPDRFSG<br>SGSGTDFTLKISRVEAEDVGVYYCMQQTQYPGTF<br>GGGTKVEIK<br>(SEQ ID NO: 422) |

TABLE 4

Full chain sequences of exemplary antibodies.

| Description | Heavy Chain Amino Acid Sequence (SEQ ID NO) | Light Chain Amino Acid Sequence (SEQ ID NO) |
|---|---|---|
| Ab101 | EVQLVESGGGLVQPGGSLRLSCAASGSAFSSYGM<br>SWVRQAPGKGLELVASINSNGGSTYYPDSVKGRFT<br>ISRDNAKNSLYLQMNSLRAEDTAVYYCARDLLVRFL<br>EWSHYYGMDVWGQGTTVTVSSASTKGPSVFPLAP<br>CSRSTSESTAALGCLVKDYFPEPVTVSWNSGALTS<br>GVHTFPAVLQSSGLYSLSSVVTVPSSSLGTKTYTC<br>NVDHKPSNTKVDKRVESKYGPPCPPCPAPEFLGG<br>PSVFLFPPKPKDTLMISRTPEVTCVVVDVSQEDPEV<br>QFNWYVDGVEVHNAKTKPREEQFNSTYRVVSVLT<br>VLHQDWLNGKEYKCKVSNKGLPSSIEKTISKAKGQ<br>PREPQVYTLPPSQEEMTKNQVSLTCLVKGFYPSDI<br>AVEWESNGQPENNYKTTPPVLDSDGSFFLYSRLTV<br>DKSRWQEGNVFSCSVMHEALHNHYTQKSLSLSLG<br>(SEQ ID NO: 891) | DIVMTQSPLSLPVTPGEPASISCRSSQSLLHSSGH<br>NFLHWYLQKPGQSPQLLIYEVSNRVSGVPDRFSG<br>SGSGTDFTLKISRVEAEDVGVYYCMQQTQYPPTF<br>GGGTKVEIKRTVAAPSVFIFPPSDEQLKSGTASVV<br>CLLNNFYPREAKVQWKVDNALQSGNSQESVTEQ<br>DSKDSTYSLSSTLTLSKADYEKHKVYACEVTHQGL<br>SSPVTKSFNRGEC (SEQ ID NO: 504) |
| Ab102 | EVQLVESGGGLVQPGGSLRLSCAASGFTFTSYGM<br>SWVRQAPGKGLELVASITGSGGETYYPDSVKGRFT<br>ISRDNAKNSLYLQMNSLRAEDTAVYYCARDLLVRFL<br>EWSHYYGMDVWGQGTTVTVSSASTKGPSVFPLAP<br>CSRSTSESTAALGCLVKDYFPEPVTVSWNSGALTS<br>GVHTFPAVLQSSGLYSLSSVVTVPSSSLGTKTYTC<br>NVDHKPSNTKVDKRVESKYGPPCPPCPAPEFLGG<br>PSVFLFPPKPKDTLMISRTPEVTCVVVDVSQEDPEV<br>QFNWYVDGVEVHNAKTKPREEQFNSTYRVVSVLT<br>VLHQDWLNGKEYKCKVSNKGLPSSIEKTISKAKGQ<br>PREPQVYTLPPSQEEMTKNQVSLTCLVKGFYPSDI<br>AVEWESNGQPENNYKTTPPVLDSDGSFFLYSRLTV<br>DKSRWQEGNVFSCSVMHEALHNHYTQKSLSLSLG<br>(SEQ ID NO: 501) | DIVMTQSPLSLPVTPGEPASISCRSSQSLLHSSGH<br>NFLHWYLQKPGQSPQLLIYETSNRAPGIPDRFSGS<br>GSGTDFTLKISRVEAEDVGVYYCMQATQFPRPFG<br>GGTKVEIKRTVAAPSVFIFPPSDEQLKSGTASVVC<br>LLNNFYPREAKVQWKVDNALQSGNSQESVTEQD<br>SKDSTYSLSSTLTLSKADYEKHKVYACEVTHQGLS<br>SPVTKSFNRGEC<br>(SEQ ID NO: 502) |
| Ab103 | EVQLVESGGGLVQPGGSLRLSCAASGYTFSSYGM<br>SWVRQAPGKGLELVASITGDAGRTYYPDSVKGRFT<br>ISRDNAKNSLYLQMNSLRAEDTAVYYCARDTLVRFL<br>EWSHYYGMDVWGQGTTVTVSSASTKGPSVFPLAP<br>CSRSTSESTAALGCLVKDYFPEPVTVSWNSGALTS<br>GVHTFPAVLQSSGLYSLSSVVTVPSSSLGTKTYTC<br>NVDHKPSNTKVDKRVESKYGPPCPPCPAPEFLGG<br>PSVFLFPPKPKDTLMISRTPEVTCVVVDVSQEDPEV<br>QFNWYVDGVEVHNAKTKPREEQFNSTYRVVSVLT<br>VLHQDWLNGKEYKCKVSNKGLPSSIEKTISKAKGQ<br>PREPQVYTLPPSQEEMTKNQVSLTCLVKGFYPSDI | DIVMTQSPLSLPVTPGEPASISCRSSQSLLHSSGH<br>NFLHWYLQKPGQSPQLLIYEVSNRVSGVPDRFSG<br>SGSGTDFTLKISRVEAEDVGVYYCMQQTQYPPTF<br>GGGTKVEIKRTVAAPSVFIFPPSDEQLKSGTASVV<br>CLLNNFYPREAKVQWKVDNALQSGNSQESVTEQ<br>DSKDSTYSLSSTLTLSKADYEKHKVYACEVTHQGL<br>SSPVTKSFNRGEC (SEQ ID NO: 504) |

TABLE 4-continued

Full chain sequences of exemplary antibodies.

| Description | Heavy Chain Amino Acid Sequence (SEQ ID NO) | Light Chain Amino Acid Sequence (SEQ ID NO) |
|---|---|---|
| | AVEWESNGQPENNYKTTPPVLDSDGSFFLYSRLTV DKSRWQEGNVFSCSVMHEALHNHYTQKSLSLSLG (SEQ ID NO: 892) | |
| Ab104 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVKFL SWSHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 893) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 504) |
| Ab105 | EVQLVESGGGLVQPGGSLRLSCAASGSAFSSYGM SWVRQAPGKGLELVASIGGTGATYYPDSVKGRFTI SRDNAKNSLYLQMNSLRAEDTAVYYCARDLLVRFL EWGHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 894) | DIVMTQSPLSLPVTPGEPASISCRSSQSLLHSSGY NFLHWYLQKPGQSPQLLIYAASSRAPGIPDRFSGS GSGTDFTLKISRVEAEDVGVYYCMHGGQGPTFG GGTKVEIKRTVAAPSVFIFPPSDEQLKSGTASVVC LLNNFYPREAKVQWKVDNALQSGNSQESVTEQD SKDSTYSLSSTLTLSKADYEKHKVYACEVTHQGLS SPVTKSFNRGEC (SEQ ID NO: 895) |
| Ab106 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVRFL EWAGYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 896) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 504) |
| Ab107 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDQLVRF LEWSHYYGMDVWGQGTTVTVSSASTKGPSVFPLA PCSRSTSESTAALGCLVKDYFPEPVTVSWNSGALT SGVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 897) | DIVMTQSPLSLPVTPGEPASISCRSSQSLLHSSGH NFLHWYLQKPGQSPQLLIYAGSNRPSGVPDRFSG SGSGTDFTLKISRVEAEDVGVYYCAHATQLPHTFG GGTKVEIKRTVAAPSVFIFPPSDEQLKSGTASVVC LLNNFYPREAKVQWKVDNALQSGNSQESVTEQD SKDSTYSLSSTLTLSKADYEKHKVYACEVTHQGLS SPVTKSFNRGEC (SEQ ID NO: 898) |
| Ab108 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVGFL QWSHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 504) |

TABLE 4-continued

Full chain sequences of exemplary antibodies.

| Description | Heavy Chain Amino Acid Sequence (SEQ ID NO) | Light Chain Amino Acid Sequence (SEQ ID NO) |
|---|---|---|
| | AVEWESNGQPENNYKTTPPVLDSDGSFFLYSRLTV DKSRWQEGNVFSCSVMHEALHNHYTQKSLSLSLG (SEQ ID NO: 899) | |
| Ab109 | EVQLVESGGGLVQPGGSLRLSCAASGFTFSSYGM SWVRQAPGKGLELVASFTGSGGTYYPDSVKGRFTI SRDNAKNSLYLQMNSLRAEDTAVYYCARDLLIRFLE WSHYYGMDVWGQGTTVTVSSASTKGPSVFPLAPC SRSTSESTAALGCLVKDYFPEPVTVSWNSGALTSG VHTFPAVLQSSGLYSLSSVVTVPSSSLGTKTYTCNV DHKPSNTKVDKRVESKYGPPCPPCPAPEFLGGPS VFLFPPKPKDTLMISRTPEVTCVVVDVSQEDPEVQF NWYVDGVEVHNAKTKPREEQFNSTYRVVSVLTVL HQDWLNGKEYKCKVSNKGLPSSIEKTISKAKGQPR EPQVYTLPPSQEEMTKNQVSLTCLVKGFYPSDIAV EWESNGQPENNYKTTPPVLDSDGSFFLYSRLTVDK SRWQEGNVFSCSVMHEALHNHYTQKSLSLSLG (SEQ ID NO: 503) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 504) |
| Ab110 | QVQLVQSGAEVKKPGASVKVSCKVSEYTFTNYDIH WVRQAPGKGLEWMGGISAYHGNAIYAQKFQGRVT MTEDTSTDTAYMELSSLKSEDTAVYYCARDRVRRD YYNFGMDVWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNVD HKPSNTKVDKRVESKYGPPCPPCPAPEFLGGPSVF LFPPKPKDTLMISRTPEVTCVVVDVSQEDPEVQFN WYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG (SEQ ID NO: 900) | DIQMTQSPSSVSASVGDRVTITCRASEDITSYLAW YQQKPGKAPKLLIYDVSSLQSGVPSRFSGSGSGT DFTLTISSLQPEDFANYYCLQHNAYPYGFGGGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC (SEQ ID NO: 901) |
| Ab111 | QVQLVQSGAEVKKPGASVKVSCKVSGYTFTSNDIH WVRQAPGKGLEWMGGIFPIFGTTIYAQKFQGRVTM TEDTSTDTAYMELSSLKSEDTAVYYCAREGLGYFG DYWGQGTLVTVSSASTKGPSVFPLAPCSRSTSEST AALGCLVKDYFPEPVTVSWNSGALTSGVHTFPAVL QSSGLYSLSSVVTVPSSSLGTKTYTCNVDHKPSNT KVDKRVESKYGPPCPPCPAPEFLGGPSVFLFPPKP KDTLMISRTPEVTCVVVDVSQEDPEVQFNWYVDGV EVHNAKTKPREEQFNSTYRVVSVLTVLHQDWLNG KEYKCKVSNKGLPSSIEKTISKAKGQPREPQVYTLP PSQEEMTKNQVSLTCLVKGFYPSDIAVEWESNGQP ENNYKTTPPVLDSDGSFFLYSRLTVDKSRWQEGNV FSCSVMHEALHNHYTQKSLSLSLG (SEQ ID NO: 902) | DIQMTQSPSSVSASVGDRVTITCRASQNIGNWLA WYQQKPGKAPKLLIYSASALQSGVPSRFSGSGSG TDFTLTISSLQPEDFANYYCQQSYGAPMYSFGGG TKVEIKRTVAAPSVFIFPPSDEQLKSGTASVVCLLN NFYPREAKVQWKVDNALQSGNSQESVTEQDSKD STYSLSSTLTLSKADYEKHKVYACEVTHQGLSSPV TKSFNRGEC (SEQ ID NO: 903) |
| Ab112 | QVQLVQSGAEVKKPGASVKVSCKVSGGTFGIYAIH WVRQAPGKGLEWMGGTIPVFGTAIYAQKFQGRVT MTEDTSTDTAYMELSSLKSEDTAVYYCASLTGIAAA GTHPARGGMDVWGQGTTVTVSSASTKGPSVFPLA PCSRSTSESTAALGCLVKDYFPEPVTVSWNSGALT SGVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 904) | DIQMTQSPSSVSASVGDRVTITCRASPSISSYLAW YQQKPGKAPKLLIYAASRLQSGVPSRFSGSGSGT DFTLTISSLQPEDFANYYCQEYLSFPLTFGGGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC (SEQ ID NO: 905) |
| Ab113 | QVQLVQSGAEVKKPGASVKVSCKVSGYLLTELSIH WYRQAPGKGLEWMGGIIPSFGTAIYAQKFQGRVT MTEDTSTDTAYMELSSLKSEDTAVYYCAISYSGFDL LPLDKWGQGTLVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKP SNTKVDKRVESKYGPPCPPCPAPEFLGGPSVFLFP PKPKDTLMISRTPEVTCVVVDVSQEDPEVQFNWYV DGVEVHNAKTKPREEQFNSTYRVVSVLTVLHQDW LNGKEYKCKVSNKGLPSSIEKTISKAKGQPREPQVY TLPPSQEEMTKNQVSLTCLVKGFYPSDIAVEWESN | DIQMTQSPSSVSASVGDRVTITCRASQHISTWLA WYQQKPGKAPKLLIYYASSLQGGVPSRFSGSGSG TDFTLTISSLQPEDFANYYCLQTYTYPRTFGGGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVTK SFNRGEC (SEQ ID NO: 907) |

TABLE 4-continued

Full chain sequences of exemplary antibodies.

| Description | Heavy Chain Amino Acid Sequence (SEQ ID NO) | Light Chain Amino Acid Sequence (SEQ ID NO) |
|---|---|---|
| | GQPENNYKTTPPVLDSDGSFFLYSRLTVDKSRWQ EGNVFSCSVMHEALHNHYTQKSLSLSLG (SEQ ID NO: 906) | |
| Ab114 | QVQLVQSGAEVKKPGASVKVSCKVSGGTFRSYTIH WVRQAPGKGLEWMGGMNPSSGHTIYAQKFQGRV TMTEDTSTDTAYMELSSLKSEDTAVYYCARGLDYG EGYYYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 908) | DIQMTQSPSSVSASVGDRVTITCRASQGISESLAW YQQKPGKAPKLLIYSASSLESGVPSRFSGSGSGT DFTLTISSLQPEDFANYYCQQGYSSPPYTFGGGT KVEIKRTVAAPSVFIFPPSDEQLKSGTASVVCLLNN FYPREAKVQWKVDNALQSGNSQESVTEQDSKDS TYSLSSTLTLSKADYEKHKVYACEVTHQGLSSPVT KSFNRGEC (SEQ ID NO: 909) |
| Ab115 | QVQLVQSGAEVKKPGASVKVSCKVSGYAFTNYNIH WVRQAPGKGLEWMGGINPRTGGTIYAQKFQGRVT MTEDTSTDTAYMELSSLKSEDTAVYYCAKDIYTGVA VAGSGMDYWGQGTLVTVSSASTKGPSVFPLAPCS RSTSESTAALGCLVKDYFPEPVTVSWNSGALTSGV HTFPAVLQSSGLYSLSSVVTVPSSSLGTKTYTCNVD HKPSNTKVDKRVESKYGPPCPPCPAPEFLGGPSVF LFPPKPKDTLMISRTPEVTCVVVDVSQEDPEVQFN WYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG (SEQ ID NO: 910) | DIQMTQSPSSVSASVGDRVTITCRASQGISTHLAW YQQKPGKAPKLLIYGASNLESGVPSRFSGSGSGT DFTLTISSLQPEDFANYYCQQANSFPWTFGGGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVTK SFNRGEC (SEQ ID NO: 911) |
| Ab116 | QVQLVQSGAEVKKPGASVKVSCKVSGTFSRPAIH WVRQAPGKGLEWMGGINPNAATTIYAQKFQGRVT MTEDTSTDTAYMELSSLKSEDTAVYYCARGRLLRE WELRPYDTWGQGTLVTVSSASTKGPSVFPLAPCS RSTSESTAALGCLVKDYFPEPVTVSWNSGALTSGV HTFPAVLQSSGLYSLSSVVTVPSSSLGTKTYTCNVD HKPSNTKVDKRVESKYGPPCPPCPAPEFLGGPSVF LFPPKPKDTLMISRTPEVTCVVVDVSQEDPEVQFN WYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG (SEQ ID NO: 912) | DIQMTQSPSSVSASVGDRVTITCRASQSIGKSLAW YQQKPGKAPKLLIYSASNLRSGVPSRFSGSGSGT DFTLTISSLQPEDFANYYCQQTSSTPLTFGGGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVTK SFNRGEC (SEQ ID NO: 913) |
| Ab117 | QVQLVQSGAEVKKPGASVKVSCKVSGGTFSSHDIH WVRQAPGKGLEWMGGINPSDASTIYAQKFQGRVT MTEDTSTDTAYMELSSLKSEDTAVYYCARDLRGYS YGAETWHFQHWGQGTLVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 914) | DIQMTQSPSSVSASVGDRVTITCRASQYISNYLAW YQQKPGKAPKLLIYETSRLESGVPSRFSGSGSGT DFTLTISSLQPEDFANYYCQQTSSTPLTFGGGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC (SEQ ID NO: 915) |
| Ab118 | QVQLVQSGAEVKKPGASVKVSCKVSGYTSTGYNIH WVRQAPGKGLEWMGGMNPKSGDTIYAQKFQGRV TMTEDTSTDTAYMELSSLKSEDTAVYYCARDPGPY GSPLYYYGMDVWGQGTTVTVSSASTKGPSVFPPLA PCSRSTSESTAALGCLVKDYFPEPVTVSWNSGALT SGVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI | DIQMTQSPSSVSASVGDRVTITCRASQIITTHLAWY QQKPGKAPKLLIYDASYLERGVPSRFSGSGSGTD FTLTISSLQPEDFANYYCQQYRTSSSLTFGGGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC (SEQ ID NO: 917) |

TABLE 4-continued

Full chain sequences of exemplary antibodies.

| Description | Heavy Chain Amino Acid Sequence (SEQ ID NO) | Light Chain Amino Acid Sequence (SEQ ID NO) |
|---|---|---|
| | AVEWESNGQPENNYKTTPPVLDSDGSFFLYSRLTV DKSRWQEGNVFSCSVMHEALHNHYTQKSLSLSLG (SEQ ID NO: 916) | |
| Ab119 | QVQLVQSGAEVKKPGASVKVSCKVSGYTFTKDHIH WVRQAPGKGLEWMGGITPSSGDTIYAQKFQGRVT MTEDTSTDTAYMELSSLKSEDTAVYYCARDHMVR GLPNYYYGMDLWGQGTTVTVSSASTKGPSVFPLA PCSRSTSESTAALGCLVKDYFPEPVTVSWNSGALT SGVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 918) | DIQMTQSPSSVSASVGDRVTITCRASRDIANYLAW YQQKPGKAPKLLIYAASILQNGVPSRFSGSGSGTD FTLTISSLQPEDFANYYCQQAYTTPPTFGGGTKVE IKRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKSF NRGEC (SEQ ID NO: 919) |
| Ab120 | QVQLVQSGAEVKKPGASVKVSCKVSGGTFSTFHIH WVRQAPGKGLEWMGGISAYSGSTIYAQKFQGRVT MTEDTSTDTAYMELSSLKSEDTAVYYCARARYVDD AFDIWGQGTMVTVSSASTKGPSVFPLAPCSRSTSE STAALGCLVKDYFPEPVTVSWNSGALTSGVHTFPA VLQSSGLYSLSSVVTVPSSSLGTKTYTCNVDHKPS NTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWL NGKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQE GNVFSCSVMHEALHNHYTQKSLSLSLG (SEQ ID NO: 920) | DIQMTQSPSSVSASVGDRVTITCRASEDISNFLAW YQQKPGKAPKLLIYAASDLLSGVPSRFSGSGSGT DFTLTISSLQPEDFANYYCQKYISAPSFGGGTKVEI KRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKSF NRGEC (SEQ ID NO: 921) |
| Ab121 | QVTLRESGPALVKPTQTLTLTCTVSGFSFSTSGMV VNWIRQPPGKALEWLAMIDWDADNIVYNSALKSRL TISKDTSKNQVVLTMTNMDPVDTATYYCAKDTGSG WFDAFDIWGQGTMVTVSSASTKGPSVFPLAPCSR STSESTAALGCLVKDYFPEPVTVSWNSGALTSGVH TFPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFNW YVDGVEVHNAKTKPREEQFNSTYRVVSVLTVLHQD WLNGKEYKCKVSNKGLPSSIEKTISKAKGQPREPQ VYTLPPSQEEMTKNQVSLTCLVKGFYPSDIAVEWE SNGQPENNYKTTPPVLDSDGSFFLYSRLTVDKSRW QEGNVFSCSVMHEALHNHYTQKSLSLSLG (SEQ ID NO: 922) | DIVMTQSPDSLAVSLGERATINCKSSQSVLYSSTN QNFLAWYQQKPGQPPKLLIYQASTLQNGVPDRFS GSGSGTDFTLTISSLQAEDVAVYYCQQYLTTPYTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 923) |
| Ab122 | QVTLRESGPALVKPTQTLTLTCTVSGGSLSSGGSY VNWIRQPPGKALEWLAMTDWDADNIVYNSALKSRL TISKDTSKNQVVLTMTNMDPVDTATYYCAHRQNVD SYGYWGDAFDIWGQGTMVTVSSASTKGPSVFPLA PCSRSTSESTAALGCLVKDYFPEPVTVSWNSGALT SGVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 924) | DIVMTQSPDSLAVSLGERATINCKSSQSVLYSADN KNYLAWYQQKPGQPPKLLIYDASSLENGVPDRFS GSGSGTDFTLTISSLQAEDVAVYYCQQGHLFPYSF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGE (SEQ ID NO: 925) |
| Ab123 | EVQLVESGGGLVQPGGSLRLSCAASGFTFSKYDM SWVRQAPGKGLELVASISSSGGTRYYPDSVKGRFT ISRDNAKNSLYLQMNSLRAEDTAVYYCAKDLWVAS PGYGMDVWGQGTTVTVSSASTKGPSVFPLAPCSR STSESTAALGCLVKDYFPEPVTVSWNSGALTSGVH TFPAVLQSSGLYSLSSVVTVPSSSLGTKTYTCNVDH KPSNTKVDKRVESKYGPPCPPCPAPEFLGGPSVFL FPPKPKDTLMISRTPEVTCVVVDVSQEDPEVQFNW YVDGVEVHNAKTKPREEQFNSTYRVVSVLTVLHQD WLNGKEYKCKVSNKGLPSSIEKTISKAKGQPREPQ VYTLPPSQEEMTKNQVSLTCLVKGFYPSDIAVEWE | DIVMTQSPLSLPVTPGEPASISCRSSQSLLHSSGH NYLHWYLQKPGQSPQLLIYLGSIRAPGVPDRFSGS GSGTDFTLKISRVEAEDVGVYYCMQALLNPPTFG GGTKVEIKRTVAAPSVFIFPPSDEQLKSGTASVVC LLNNFYPREAKVQWKVDNALQSGNSQESVTEQD SKDSTYSLSSTLTLSKADYEKHKVYACEVTHQGLS SPVTKSFNRGEC (SEQ ID NO: 927) |

TABLE 4-continued

Full chain sequences of exemplary antibodies.

| Description | Heavy Chain Amino Acid Sequence (SEQ ID NO) | Light Chain Amino Acid Sequence (SEQ ID NO) |
|---|---|---|
| | SNGQPENNYKTTPPVLDSDGSFFLYSRLTVDKSRW QEGNVFSCSVMHEALHNHYTQKSLSLSLG (SEQ ID NO: 926) | |
| Ab124 | QVQLQESGPGLVKPSQTLSLTCTVSGGSISSSPYS WSWIRQPPGKGLEWIGYVDLAGSTDYNPSLKSRVT MSVDTSKNQFSLKVNSVTAADTAVYYCARALSSRS SEWLLDQYTMDVWGQGTTVTVSSASTKGPSVFPL APCSRSTSESTAALGCLVKDYFPEPVTVSWNSGAL TSGVHTFPAVLQSSGLYSLSSVVTVPSSSLGTKTYT CNVDHKPSNTKVDKRVESKYGPPCPPCPAPEFLG GPSVFLFPPKPKDTLMISRTPEVTCVVVDVSQEDPE VQFNWYVDGVEVHNAKTKPREEQFNSTYRVVSVL TVLHQDWLNGKEYKCKVSNKGLPSSIEKTISKAKG QPREPQVYTLPPSQEEMTKNQVSLTCLVKGFYPSD IAVEWESNGQPENNYKTTPPVLDSDGSFFLYSRLT VDKSRWQEGNVFSCSVMHEALHNHYTQKSLSLSL G (SEQ ID NO: 928) | EIVMTQSPATLSLSPGERATLSCRASQSIGINLAW YQQKPGQAPRLLIYGVSNRATGIPARFSGSGSGT DFTLTISSLEPEDFAVYYCQQYGTARLTFGGGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC (SEQ ID NO: 929) |
| Ab125 | EVQLVQSGAEVKKPGESLKISCKGSGNRISDYWMN WVRQVPGKGLEWMGNIYPGYSDATYNRKFKGQVT ISADKSISTAYLQWSSLKASDTAIYYCARGRDGYNY FAAFDIWGQGTMVTVSSASTKGPSVFPLAPCSRST SESTAALGCLVKDYFPEPVTVSWNSGALTSGVHTF PAVLQSSGLYSLSSVVTVPSSSLGTKTYTCNVDHK PSNTKVDKRVESKYGPPCPPCPAPEFLGGPSVFLF PPKPKDTLMISRTPEVTCVVVDVSQEDPEVQFNWY VDGVEVHNAKTKPREEQFNSTYRVVSVLTVLHQD WLNGKEYKCKVSNKGLPSSIEKTISKAKGQPREPQ VYTLPPSQEEMTKNQVSLTCLVKGFYPSDIAVEWE SNGQPENNYKTTPPVLDSDGSFFLYSRLTVDKSRW QEGNVFSCSVMHEALHNHYTQKSLSLSLG (SEQ ID NO: 930) | EIVLTQSPATLSLSPGERATLSCRASQSVASSYLA WYQQKPGQAPRLLIYDTSSRAAGIPARFSGSGSG TDFTLTISSLEPEDFAVYYCHQYGSSLTTFGGGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVTK SFNRGEC (SEQ ID NO: 931) |
| Ab126 | EVQLVESGGGLVQPGGSLRLSCTASSFTFSNYAM DWVRQAPGKGLEWVSYISSDASTTYYADSVKGRF TISRDNAKNTLYLQMNSLRAEDTAVYYCARDGGYN PGIFDYWGQGTLVTVSSASTKGPSVFPLAPCSRST SESTAALGCLVKDYFPEPVTVSWNSGALTSGVHTF PAVLQSSGLYSLSSVVTVPSSSLGTKTYTCNVDHK PSNTKVDKRVESKYGPPCPPCPAPEFLGGPSVFLF PPKPKDTLMISRTPEVTCVVVDVSQEDPEVQFNWY VDGVEVHNAKTKPREEQFNSTYRVVSVLTVLHQD WLNGKEYKCKVSNKGLPSSIEKTISKAKGQPREPQ VYTLPPSQEEMTKNQVSLTCLVKGFYPSDIAVEWE SNGQPENNYKTTPPVLDSDGSFFLYSRLTVDKSRW QEGNVFSCSVMHEALHNHYTQKSLSLSLG (SEQ ID NO: 932) | DIQMTQSPSSLSASVGDRVTITCQASQSIGRWLN WYQQKPGKAPKLLIYDASILQTGVPSRFSGSGSG TDFTFTISSLQPEDIATYYCQQSFTTPPLTFGGGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVTK SFNRGEC (SEQ ID NO: 933) |
| Ab127 | EVQLVESGGGLVQPGGSLRLSCTASGFTFGSYPM DWVRQAPGKGLEWVSYISGRGDVTYYADSVKGRF TISRDNAKNTLYLQMNSLRAEDTAVYYCAKVQSPS ELLWFGELLPVDYWGQGTLVTVSSASTKGPSVFPL APCSRSTSESTAALGCLVKDYFPEPVTVSWNSGAL TSGVHTFPAVLQSSGLYSLSSVVTVPSSSLGTKTYT CNVDHKPSNTKVDKRVESKYGPPCPPCPAPEFLG GPSVFLFPPKPKDTLMISRTPEVTCVVVDVSQEDPE VQFNWYVDGVEVHNAKTKPREEQFNSTYRVVSVL TVLHQDWLNGKEYKCKVSNKGLPSSIEKTISKAKG QPREPQVYTLPPSQEEMTKNQVSLTCLVKGFYPSD IAVEWESNGQPENNYKTTPPVLDSDGSFFLYSRLT VDKSRWQEGNVFSCSVMHEALHNHYTQKSLSLSL G (SEQ ID NO: 934) | DIQMTQSPSSLSASVGDRVTITCQASQVIKTWLNW YQQKPGKAPKLLIYDASNLQRGVPSRFSGSGSGT DFTFTISSLQPEDIATYYCQQSASTPITFGGGTKVE IKRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKSF NRGEC (SEQ ID NO: 935) |
| Ab128 | EVQLVESGGGLVQPGGSLRLSCTASGFTLSSYSM DWVRQAPGKGLEWVSYITGSGDTTYYADSVKGRF TISRDNAKNTLYLQMNSLRAEDTAVYYCARGFGWI SGWAEDYFDYWGQGTLVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI | DIQMTQSPSSLSASVGDRVTITCQASQSVYSYLN WYQQKPGKAPKLLIYGASRLEGGVPSRFSGSGSG TDFTFTISSLQPEDIATYYCQHSTDQRTFGGGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVTK SFNRGEC (SEQ ID NO: 937) |

TABLE 4-continued

Full chain sequences of exemplary antibodies.

| Description | Heavy Chain Amino Acid Sequence (SEQ ID NO) | Light Chain Amino Acid Sequence (SEQ ID NO) |
|---|---|---|
| | AVEWESNGQPENNYKTTPPVLDSDGSFFLYSRLTV DKSRWQEGNVFSCSVMHEALHNHYTQKSLSLSLG (SEQ ID NO: 936) | |
| Ab129 | QVQLVQSGAEVKKPGASVKVSCKVSGFNYPRSAIH WVRQAPGKGLEWMGGINPSGEATIYAQKFQGRVT MTEDTSTDTAYMELSSLKSEDTAVYYCARDSSPQ WLVTAGVYFYGMDVWGQGTTVTVSSASTKGPSVF PLAPCSRSTSESTAALGCLVKDYFPEPVTVSWNSG ALTSGVHTFPAVLQSSGLYSLSSVVTVPSSSLGTKT YTCNVDHKPSNTKVDKRVESKYGPPCPPCPAPEFL GGPSVFLFPPKPKDTLMISRTPEVTCVVVDVSQED PEVQFNWYVDGVEVHNAKTKPREEQFNSTYRVVS VLTVLHQDWLNGKEYKCKVSNKGLPSSIEKTISKAK GQPREPQVYTLPPSQEEMTKNQVSLTCLVKGFYPS DIAVEWESNGQPENNYKTTPPVLDSDGSFFLYSRL TVDKSRWQEGNVFSCSVMHEALHNHYTQKSLSLS LG (SEQ ID NO: 938) | DIQMTQSPSSVSASVGDRVTITCRASQSISNWLA WYQQKPGKAPKLLIYHASTLQSGVPSRFSGSGSG TDFTLTISSLQPEDFANYYCQQYSSTPWTFGGGT KVEIKRTVAAPSVFIFPPSDEQLKSGTASVVCLLNN FYPREAKVQWKVDNALQSGNSQESVTEQDSKDS TYSLSSTLTLSKADYEKHKVYACEVTHQGLSSPVT KSFNRGEC (SEQ ID NO: 939) |
| Ab130 | EVQLVESGGGLVQPGGSLRLSCAASGFTFTSYGM SWVRQAPGKGLELVASITGSGGETYYPDSVKGRFT ISRDNAKNSLYLQMNSLRAEDTAVYYCARDLLVRFL EWSHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 505) | DIVMTQSPLSLPVTPGEPASISCRSSQSLLHSSGH NFLHWYLQKPGQSPQLLIYETSNRAPGIPDRFSGS GSGTDFTLKISRVEAEDVGVYYCQQATQFPRPFG GGTKVEIKRTVAAPSVFIFPPSDEQLKSGTASVVC LLNNFYPREAKVQWKVDNALQSGNSQESVTEQD SKDSTYSLSSTLTLSKADYEKHKVYACEVTHQGLS SPVTKSFNRGEC (SEQ ID NO: 506) |
| Ab131 | EVQLVESGGGLVQPGGSLRLSCAASGSAFSSYGM SWVRQAPGKGLELVASIGGTGATYYPDSVKGRFTI SRDNAKNSLYLQMNSLRAEDTAVYYCARDLLVRFL EWGHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 894) | DIVMTQSPLSLPVTPGEPASISCRSSQSLLHSSGY NFLHWYLQKPGQSPQLLIYAASSRAPGIPDRFSGS GSGTDFTLKISRVEAEDVGVYYCQQATQFPRPFG GTKVEIKRTVAAPSVFIFPPSDEQLKSGTASVVCLL NNFYPREAKVQWKVDNALQSGNSQESVTEQDSK DSTYSLSSTLTLSKADYEKHKVYACEVTHQGLSSP VTKSFNRGEC (SEQ ID NO: 940) |
| Ab132 | EVQLVESGGGLVQPGGSLRLSCAASGFTFSSYGM SWVRQAPGKGLELVASFTGSGGTYYPDSVKGRFTI SRDNAKNSLYLQMNSLRAEDTAVYYCARDLLIRFLE WSHYYGMDVWGQGTTVTVSSASTKGPSVFPLAPC SRSTSESTAALGCLVKDYFPEPVTVSWNSGALTSG VHTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQFN WYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG (SEQ ID NO: 507) | DIVMTQSPLSLPVTPGEPASISCRSSQSLLHS SGHNFLHWYLQKPGQSPQLLIYEVSNRVSG VPDRFSGSGSGTDFTLKISRVEAEDVGVYYC QQQTQYPPTFGGGTKVEIKRTVAAPSVFIFP PSDEQLKSGTASVVCLLNNFYPREAKVQWK VDNALQSGNSQESVTEQDSKDSTYSLSSTLT LSKADYEKHKVYACEVTHQGLSSPVTKSFNR GEC (SEQ ID NO: 508) |
| Ab133 | EVQLVESGGGLVQPGGSLRLSCAASGFTFSSYGM SWVRQAPGKGLELVASFTGSGGAYYPDSVKGRFTI SRDNAKNSLYLQMNSLRAEDTAVYYCARDLLIRFLE WSHYYGMDVWGQGTTVTVSSASTKGPSVFPLAPC SRSTSESTAALGCLVKDYFPEPVTVSWNSGALTSG VHTFPAVLQSSGLYSLSSVVTVPSSSLGTKTYTCNV DHKPSNTKVDKRVESKYGPPCPPCPAPEFLGGPS VFLFPPKPKDTLMISRTPEVTCVVVDVSQEDPEVQF NWYVDGVEVHNAKTKPREEQFNSTYRVVSVLTVL HQDWLNGKEYKCKVSNKGLPSSIEKTISKAKGQPR EPQVYTLPPSQEEMTKNQVSLTCLVKGFYPSDIAV | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCQQQTQYPGTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 510) |

TABLE 4-continued

Full chain sequences of exemplary antibodies.

| Description | Heavy Chain Amino Acid Sequence (SEQ ID NO) | Light Chain Amino Acid Sequence (SEQ ID NO) |
|---|---|---|
| | EWESNGQPENNYKTTPPVLDSDGSFFLYSRLTVDK SRWQEGNVFSCSVMHEALHNHYTQKSLSLSLG (SEQ ID NO: 509) | |
| Ab134 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVEFL KWSHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 972) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 504) |
| Ab135 | EVQLVESGGGLVQPGGSLRLSCAASGSAFSSYGM SWVRQAPGKGLELVASINSNGGSTYYPDSVKGRFT ISRDNAKNSLYLQMNSLRAEDTAVYYCARDLLVTFL RWSHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 973) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 504) |
| Ab136 | EVQLVESGGGLVQPGGSLRLSCAASGSAFSSYGM SWVRQAPGKGLELVASIGGTGATYYPDSVKGRFTI SRDNAKNSLYLQMNSLRAEDTAVYYCARDLLVRFL EWSHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 974) | DIVMTQSPLSLPVTPGEPASISCRSSQSLLHSSGY NFLHWYLQKPGQSPQLLIYAASSRAPGIPDRFSGS GSGTDFTLKISRVEAEDVGVYYCMQQTQYPPTFG GGTKVEIKRTVAAPSVFIFPPSDEQLKSGTASVVC LLNNFYPREAKVQWKVDNALQSGNSQESVTEQD SKDSTYSLSSTLTLSKADYEKHKVYACEVTHQGLS SPVTKSFNRGEC (SEQ ID NO: 895) |
| Ab137 | EVQLVESGGGLVQPGGSLRLSCAASGFTFSSYGM SWVRQAPGKGLELVASFTGSGGTYYPDSVKGRFTI SRDNAKNSLYLQMNSLRAEDTAVYYCARDLLIRFLE WGHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG (SEQ ID NO: 975) | DIVMTQSPLSLPVTPGEPASISCRSSQSLLHSSGH NFLHWYLQKPGQSPQLLIYEVSNRVSGVPDRFSG SGSGTDFTLKISRVEAEDVGVYYCMQQTQYPPTF GGGTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQGL SSPVTKSFNRGEC (SEQ ID NO: 504) |
| Ab138 | EVQLVESGGGLVQPGGSLRLSCAASGFTFTSYGM SWVRQAPGKGLELVASITGSKGETYYPDSVKGRFT ISRDNAKNSLYLQMNSLRAEDTAVYYCARDLLVRFL EWSHYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI | DIVMTQSPLSLPVTPGEPASISCRSSQSLLHSSGH NFLHWYLQKPGQSPQLLIYETSNRAPGIPDRFSGS GSGTDFTLKISRVEAEDVGVYYCQQATQYFPRPFG GGTKVEIKRTVAAPSVFIFPPSDEQLKSGTASVVC LLNNFYPREAKVQWKVDNALQSGNSQESVTEQD SKDSTYSLSSTLTLSKADYEKHKVYACEVTHQGLS SPVTKSFNRGEC (SEQ ID NO: 506) |

TABLE 4-continued

Full chain sequences of exemplary antibodies.

| Description | Heavy Chain Amino Acid Sequence (SEQ ID NO) | Light Chain Amino Acid Sequence (SEQ ID NO) |
|---|---|---|
| | AVEWESNGQPENNYKTTPPVLDSDGSFFLYSRLTV<br>DKSRWQEGNVFSCSVMHEALHNHYTQKSLSLSLG<br>(SEQ ID NO: 976) | |
| Ab139 | EVQLVESGGGLVQPGGSLRLSCAASGFTFSSYGM<br>SWVRQAPGKGLELVASFTGSGAAYYPDSVKGRFTI<br>SRDNAKNSLYLQMNSLRAEDTAVYYCARDLLIRFLE<br>WSHYYGMDVWGQGTTVTVSSASTKGPSVFPLAPC<br>SRSTSESTAALGCLVKDYFPEPVTVSWNSGALTSG<br>VHTFPAVLQSSGLYSLSSVVTVPSSSLGTKTYTCNV<br>DHKPSNTKVDKRVESKYGPPCPPCPAPEFLGGPS<br>VFLFPPKPKDTLMISRTPEVTCVVVDVSQEDPEVQF<br>NWYVDGVEVHNAKTKPREEQFNSTYRVVSVLTVL<br>HQDWLNGKEYKCKVSNKGLPSSIEKTISKAKGQPR<br>EPQVYTLPPSQEEMTKNQVSLTCLVKGFYPSDIAV<br>EWESNGQPENNYKTTPPVLDSDGSFFLYSRLTVDK<br>SRWQEGNVFSCSVMHEALHNHYTQKSLSLSLG<br>(SEQ ID NO: 977) | DIVMTQSPLSLPVTPGEPASISCRSSQSLLHSSGH<br>NFLHWYLQKPGQSPQLLIYESSNRVSGVPDRFSG<br>SGSGTDFTLKISRVEAEDVGVYYCQQQTQYPPTF<br>GGGTKVEIKRTVAAPSVFIFPPSDEQLKSGTASVV<br>CLLNNFYPREAKVQWKVDNALQSGNSQESVTEQ<br>DSKDSTYSLSSTLTLSKADYEKHKVYACEVTHQGL<br>SSPVTKSFNRGEC<br>(SEQ ID NO: 978) |
| Ab140 | EVQLVESGGGLVQPGGSLRLSCAASGFTFSSYGM<br>SWVRQAPGKGLELVASFTGSGGTYYPDSVKGRFTI<br>SRDNAKNSLYLQMNSLRAEDTAVYYCARDNLIRFL<br>EWSHYYGMDVWGQGTTVTVSSASTKGPSVFPLAP<br>CSRSTSESTAALGCLVKDYFPEPVTVSWNSGALTS<br>GVHTFPAVLQSSGLYSLSSVVTVPSSSLGTKTYTC<br>NVDHKPSNTKVDKRVESKYGPPCPPCPAPEFLGG<br>PSVFLFPPKPKDTLMISRTPEVTCVVVDVSQEDPEV<br>QFNWYVDGVEVHNAKTKPREEQFNSTYRVVSVLT<br>VLHQDWLNGKEYKCKVSNKGLPSSIEKTISKAKGQ<br>PREPQVYTLPPSQEEMTKNQVSLTCLVKGFYPSDI<br>AVEWESNGQPENNYKTTPPVLDSDGSFFLYSRLTV<br>DKSRWQEGNVFSCSVMHEALHNHYTQKSLSLSLG<br>(SEQ ID NO: 979) | DIVMTQSPLSLPVTPGEPASISCRSSQSLLHSSGH<br>NFLHWYLQKPGQSPQLLIYEVSNRESGVPDRFSG<br>SGSGTDFTLKISRVEAEDVGVYYCQQQTQYPPTF<br>GGGTKVEIKRTVAAPSVFIFPPSDEQLKSGTASVV<br>CLLNNFYPREAKVQWKVDNALQSGNSQESVTEQ<br>DSKDSTYSLSSTLTLSKADYEKHKVYACEVTHQGL<br>SSPVTKSFNRGEC<br>(SEQ ID NO: 980) |
| Ab141 | EVQLVESGGGLVQPGGSLRLSCAASGFTFSSYGM<br>SWVRQAPGKGLELVASFTGSGGAYYPDSVKGRFTI<br>SRDNAKNSLYLQMNSLRAEDTAVYYCARDLLIRFLE<br>WSHYYGMDVWGQGTTVTVSSASTKGPSVFPLAPC<br>SRSTSESTAALGCLVKDYFPEPVTVSWNSGALTSG<br>VHTFPAVLQSSGLYSLSSVVTVPSSSLGTKTYTCNV<br>DHKPSNTKVDKRVESKYGPPCPPCPAPEFLGGPS<br>VFLFPPKPKDTLMISRTPEVTCVVVDVSQEDPEVQF<br>NWYVDGVEVHNAKTKPREEQFNSTYRVVSVLTVL<br>HQDWLNGKEYKCKVSNKGLPSSIEKTISKAKGQPR<br>EPQVYTLPPSQEEMTKNQVSLTCLVKGFYPSDIAV<br>EWESNGQPENNYKTTPPVLDSDGSFFLYSRLTVDK<br>SRWQEGNVFSCSVMHEALHNHYTQKSLSLSLG<br>(SEQ ID NO: 509) | DIVMTQSPLSLPVTPGEPASISCRSSQSLLHSSGH<br>NFLHWYLQKPGQSPQLLIYEVSNRVSGVPDRFSG<br>SGSGTDFTLKISRVEAEDVGVYYCMQQTQYPGTF<br>GGGTKVEIKRTVAAPSVFIFPPSDEQLKSGTASVV<br>CLLNNFYPREAKVQWKVDNALQSGNSQESVTEQ<br>DSKDSTYSLSSTLTLSKADYEKHKVYACEVTHQGL<br>SSPVTKSFNRGEC<br>(SEQ ID NO: 511) |

In some examples, the present disclosure encompasses an anti-pro/latent-myostatin antibody or antigen-binding portions thereof comprising a heavy chain variable domain, a light chain variable domain, or a paired heavy and light chain variable domain from Table 3 above.

In various embodiments, the anti-pro/latent myostatin antibody or antigen-binding fragment thereof comprises a heavy chain variable region comprising an amino acid sequence of SEQ ID NO: 400 or a sequence that is at least 95% identical thereto, and/or a light chain variable region comprising an amino acid sequence of SEQ ID NO: 410 or a sequence that is at least 95% identical thereto.

In various embodiments, the anti-pro/latent myostatin antibody or antigen-binding fragment thereof comprises a heavy chain variable region comprising an amino acid sequence of SEQ ID NO: 402 or a sequence that is at least 95% identical thereto, and/or a light chain variable region comprising an amino acid sequence of SEQ ID NO: 412 or a sequence that is at least 95% identical thereto.

In various embodiments, the anti-pro/latent myostatin antibody or antigen-binding fragment thereof comprises a heavy chain variable region comprising an amino acid sequence of SEQ ID NO: 409 or a sequence that is at least 95% identical thereto, and/or a light chain variable region comprising an amino acid sequence of SEQ ID NO: 419 or a sequence that is at least 95% identical thereto.

In various embodiments, the anti-pro/latent myostatin antibody or antigen-binding fragment thereof comprises a heavy chain variable region comprising an amino acid sequence of SEQ ID NO: 420 or a sequence that is at least 95% identical thereto, and/or a light chain variable region comprising an amino acid sequence of SEQ ID NO: 421 or a sequence that is at least 95% identical thereto.

In various embodiments, the anti-pro/latent myostatin antibody or antigen-binding fragment thereof is Ab102 or Ab130. In various embodiments, the anti-pro/latent myostatin antibody or antigen-binding fragment thereof is Ab109, Ab132, or Ab133.

In one embodiment, the anti-pro/latent myostatin antibody or antigen-binding fragment thereof comprises a heavy chain region comprising an amino acid sequence of SEQ ID NO: 501 or a sequence that is at least 95% identical thereto, and/or a light chain region comprising an amino acid sequence of SEQ ID NO: 502 or a sequence that is at least 95% identical thereto.

In another embodiment, the anti-pro/latent myostatin antibody or antigen-binding fragment thereof comprises a heavy chain region comprising an amino acid sequence of SEQ ID NO: 503 or a sequence that is at least 95% identical thereto, and/or a light chain region comprising an amino acid sequence of SEQ ID NO: 504 or a sequence that is at least 95% identical thereto.

In another embodiment, the anti-pro/latent myostatin antibody or antigen-binding fragment thereof comprises a heavy chain region comprising an amino acid sequence of SEQ ID NO: 505 or a sequence that is at least 95% identical thereto, and/or a light chain region comprising an amino acid sequence of SEQ ID NO: 506 or a sequence that is at least 95% identical thereto.

In another embodiment, the anti-pro/latent myostatin antibody or antigen-binding fragment thereof comprises a heavy chain region comprising an amino acid sequence of SEQ ID NO: 507 or a sequence that is at least 95% identical thereto, and/or a light chain region comprising an amino acid sequence of SEQ ID NO: 508 or a sequence that is at least 95% identical thereto.

In yet another embodiment, the anti-pro/latent myostatin antibody or antigen-binding fragment thereof comprises a heavy chain region comprising an amino acid sequence of SEQ ID NO: 509 or a sequence that is at least 95% identical thereto, and/or a light chain region comprising an amino acid sequence of SEQ ID NO: 510 or a sequence that is at least 95% identical thereto.

In some embodiments, anti-pro/latent-myostatin antibodies or antigen-binding fragments thereof, of the disclosure include any antibody or an antigen-binding fragment thereof comprising a heavy chain variable domain of any one of SEQ ID NOs: 400-409, 420 and a light chain variable domain of any one of SEQ ID NOs: 410-419, 421. In some embodiments, anti-pro/latent-myostatin antibodies or antigen-binding fragments thereof of the disclosure include any antibody comprising the heavy chain variable domain and the light chain variable domain of SEQ ID NOs: 400 and 410; 401 and 411; 402 and 412; 403 and 413; 404 and 414; 405 and 415; 406 and 416; 407 and 417; 408 and 418; 409 and 419; 420 and 421.

In some embodiments, the present disclosure encompasses anti-pro/latent-myostatin antibodies or antigen-binding fragments thereof comprising a heavy chain variable domain and/or a light chain variable domain comprising amino acid sequences that are homologous to any one of the sequences described herein. In some embodiments, the anti-pro/latent-myostatin antibody or antigen-binding fragment thereof comprises a heavy chain variable domain sequence that is at least 80%, 85% or 90% identical to the heavy chain variable domain sequence of any one of SEQ ID NOs: 400-409, 420. In some embodiments, the anti-pro/latent-myostatin antibody or antigen-binding fragment thereof comprises a light chain variable domain sequence that is at least 80%, 85% or 90% identical to the light chain variable sequence of any one of SEQ ID NOs: 410-419, 421. In some embodiments, the heavy chain variable domain that is at least 90% identical does not comprise any variation within any of the CDR sequences provided herein. In some embodiments, the light chain variable domain that is at least 90% identical does not comprise any variation within any of the CDR sequences provided herein. For example, in some embodiments, sequence variations in the heavy chain or light chain variable domain (e.g., 90%, 95%, 98%, or 99%) occur outside of the CDR sequences.

In some embodiments, the present disclosure encompasses an anti-pro/latent-myostatin antibody or antigen-binding fragment thereof comprising variable domain sequences (i.e., a sum of the heavy chain variable domain and a light chain variable domain combined) that are less than 70% identical to the variable domain sequences of Ab2 provided in PCT/US2015/059468. In some embodiments, the present disclosure encompasses an anti-pro/latent-myostatin antibody comprising a heavy chain sequence that is less than 70% identical to the heavy chain of Ab2 as provided in PCT/US2015/059468. In some embodiments, these antibodies comprise heavy chain variable domains that are also at least 80%, 85% or 90% identical to the heavy chain variable domain sequence of any one of SEQ ID NOs: 400-409, 420. In some embodiments, the anti-pro/latent-myostatin antibody or antigen-binding fragment thereof comprises a light chain variable domain sequence that is at least 80%, 85% or 90% identical to the light chain variable sequence of any one of SEQ ID NOs: 410-419, 421.

In some embodiments, an antibody encompassed by the disclosure comprises any one of the heavy chain variable domain sequences and/or any one of the light chain variable domain sequences provided in Table 3 and any IgG constant domain sequence. In some embodiments, the antibody comprises an IgG1 constant domain subtype or IgG4 subtype. For the latter, in some embodiments, the antibody comprises an Adair mutation (S228P).

In some embodiments, the antibodies or antigen-binding fragments thereof provided herein comprise IgG constant domains or mutations to constant domains that confer desirable properties. For example, to avoid potential complications due to Fab-arm exchange, which is known to occur with native IgG4 mAbs, the antibodies or antigen-binding fragments thereof provided herein may comprise an IgG1 constant domain or a stabilizing 'Adair' mutation, e.g., in a native IgG4 (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like (CPPCP (SEQ ID NO: 58)) hinge sequence. Accordingly, any of the antibodies may include a stabilizing 'Adair' mutation or the amino acid sequence CPPCP (SEQ ID NO: 58).

In some embodiments, anti-pro/latent-myostatin antibodies or antigen-binding portions thereof of this disclosure may comprise antibody constant regions or parts thereof. For example, a VL domain may be attached at its C-terminal end to a light chain constant domain like Cκ or Cλ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this disclosure may include VH and VL domains, or an antigen binding portion thereof, combined with any suitable constant regions.

In certain embodiments, the VH and/or VL domains may be reverted to germline sequence, e.g., the framework region (FR) of these domains are mutated using conventional molecular biology techniques to match those produced by the germline cells. For example, the VH and/or VL domains may be reverted to germline sequence of IgHV3-30 (SEQ ID NO: 36) and/or IgLV1-44 (SEQ ID NO: 37), respectively. It should be appreciated that any of the VH and/or VL domains may be reverted to any suitable germline sequence. In other embodiments, the FR sequences remain diverged from the consensus germline sequences.

In some embodiments, anti-pro/latent-myostatin antibodies or antigen-binding fragments may or may not include the framework region of the antibodies shown in SEQ ID NOs: 400-421. In some embodiments, anti-pro-latent-myostatin antibodies are murine antibodies and include murine framework region sequences.

In some embodiments, the antibodies or antigen-binding fragments thereof disclosed herein specifically bind pro/latent-myostatin. In some embodiments, any of the antibodies or antigen-binding fragments thereof provided herein bind at or near a tolloid cleavage site or at or near a tolloid docking site of pro/latent-myostatin. In some embodiments, an antibody binds near a tolloid cleavage site or near a tolloid docking site if it binds within 15 or fewer amino acid residues of the tolloid cleavage site or tolloid docking site. In some embodiments, any of the antibodies, or antigen-binding fragments thereof, provided herein bind within 1, 2, 3, 4, 5, 6, 7, 8, 9, 10, 11, 12, 13, 14 or 15 amino acid residues of a tolloid cleavage site or tolloid docking site. In some embodiments, an antibody binds at or near a tolloid cleavage site of GDF8. For example, an antibody may bind an amino acid sequence as set forth in SEQ ID NO: 62 PKAPPL-RELIDQYDVQRDDSSDGSLEDDDYHAT (SEQ ID NO: 62). In other embodiments, antibodies or antigen-binding fragments thereof provided herein may bind at or near a proprotein convertase cleavage site or at or near a proprotein convertase docking site of pro/latent-myostatin. In some embodiments, an antibody or antigen binding fragment thereof binds near a proprotein convertase cleavage site or near a proprotein convertase docking site if it binds within 15 or fewer amino acid residues of the proprotein convertase cleavage site or proprotein convertase docking site. In some embodiments, any of the antibodies, or antigen-binding fragments thereof, provided herein bind within 1, 2, 3, 4, 5, 6, 7, 8, 9, 10, 11, 12, 13, 14 or 15 amino acid residues of a proprotein convertase cleavage site or proprotein convertase docking site. In some embodiments, an antibody binds at or near a proprotein convertase cleavage site of GDF8. For example, an antibody may bind an amino acid sequence as set forth in SEQ ID NO: 63 (GLNP-FLEVKVTDTPKRSRRDFGLDCDEHSTESRC).

In some embodiments, the antibodies or antigen-binding fragments thereof disclosed herein bind an epitope that includes at least one amino acid residue of KALDEN (SEQ ID NO: 118) and/or FVQILRLIKPMKDGTRYTGIRSLK (SEQ ID NO: 57).

In some embodiments, an antibody or antigen binding fragment thereof disclosed herein binds an epitope that includes one or more amino acid residues of F147, Q149, L151, Y163, R167, S168, K170, K205, L207, E209 and N210, based on the numbering of the human proGDF8 sequence as set forth in SEQ ID NO; 52, which correspond to: F170, Q172, L174, Y186, R190, S191, K193, K228, L230, E232, and N233, respectively, based on the numbering of Dagbay et al. J. Biol. Chem. (2020), 295(16): 5404-5418. In some embodiments, such antibody or antigen-binding fragment binds an epitope within the prodomain of human myostatin, wherein the epitope comprises one or more (e.g., all of) amino acid residues F147, Q149, L151, Y186, S168, Q149, L151, Y163, S168, K170, K205, and/or L207, as numbered according to SEQ ID NO: 52 disclosed herein. In some embodiments, such antibody or antigen-binding fragment binds an epitope within the prodomain of human myostatin, wherein the epitope comprises one or more (e.g., all of) amino acid residues F147, Q149, L151, Y186, K170, K205, and/or L207, as numbered according to SEQ ID NO: 52. In some embodiments, such antibody binds an epitope that includes 7 or more, 6 or more, 5 or more, 4 or more, or 3 or more of the amino acid residues shown above. In some embodiments, the antibody is Ab102 or Ab130. In some embodiments, the antibody is Ab109, Ab132, or Ab133. In some embodiments, the antibody is Ab109, Ab133, or Ab141.

In some embodiments, the antibodies or antigen-binding fragments thereof disclosed herein specifically bind pro/latent-myostatin as compared to other forms of myostatin and/or other members of the TGFβ family of growth factors. Members of the TGFβ family of growth factors include, without limitation AMH, ARTN, BMP10, BMP15, BMP2, BMP3, BMP4, BMP5, BMP6, BMP7, BMP8A, BMP8B, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, NODAL, NRTN, PSPN, TGFβ1, TGFβ2, and TGFβ3 protein. In some embodiments, the antibodies or antigen-binding fragments thereof bind pro/latent-myostatin with a binding affinity that is at least 2-fold, 5-fold, 10-fold, 50-fold, 100-fold, 200-fold, 500-fold, or 1,000-fold higher as compared to other members of the TGFβ family of growth factors. In some embodiments, the antibodies or antigen-binding fragments thereof bind pro/latent-myostatin with an affinity of at least 1000-fold higher as compared to other members of the TGFβ family of growth factors. In some embodiments, the antibodies or antigen-binding fragments thereof provided herein bind to pro/latent-myostatin with a binding affinity that is at least 2-fold, 5-fold, 10-fold, 50-fold, 100-fold, 200-fold, 500-fold, or 1,000-fold higher as compared to one or more forms of GDF11 or mature myostatin. In some embodiments, antibodies or antigen-binding fragments thereof, provided herein bind to pro/latent-myostatin with an affinity of at least 1,000-fold higher as compared to one or more forms of GDF11 (e.g., proGDF11, latent GDF11 or mature GDF11) or mature myostatin. In some embodiments, antibodies or antigen-binding fragments thereof provided herein exhibit an inhibitory activity against proteolytic cleavage of pro/latent-myostatin (e.g., by a proprotein convertase or tolloid protease) that is at least 2-fold, 5-fold, 10-fold, 50-fold, 100-fold, 200-fold, 500-fold, 1,000-fold higher as compared with other members of the TGFβ family, such as pro/latent GDF11. In another embodiment, the antibodies or antigen-binding fragments thereof disclosed herein do not bind to GDF11. Without wishing to be bound by theory, the antibodies or antigen-binding fragments thereof as provided herein have improved safety profiles due to reduced toxicity associated with cross-reactivity with other TGFβ family members (e.g., as compared to antibodies that cross-react with both myostatin and GDF11). An example of one such potential toxicity relates to impaired bone strength associated with GDF11 inhibition as recently reported in Suh et al. Proceedings of the National Academy of Sciences March 2020, 117 (9) 4910-4920, the content of which is hereby incorporated in its entirety.

Sweeping Antibodies

Certain embodiments of the disclosure relate to sweeping antibodies. As used herein "sweeping antibodies" or antigen-binding fragments thereof refer to antibodies, or antigen-binding fragments thereof, having both pH-sensitive antigen binding and at least a threshold level of binding to cell surface neonatal Fc receptor (FcRn) at neutral or physiological pH. In some embodiments, sweeping antibodies, or an antigen-binding portion thereof, bind to the neonatal Fc receptor FcRn at neutral pH. For example, sweeping antibodies may bind to the FcRn at a pH ranging from 7.0 to 7.6. In some embodiments, sweeping antibodies, or an antigen-binding portion thereof, can bind to an antigen at an antigen binding site and bind to a cellular FcRn via an Fc portion of the antibody. In some embodiments, sweeping antibodies, or an antigen-binding portion thereof, may then be internalized, releasing antigen in an acidic endosome, which may be degraded. In some embodiments, a sweeping antibody, or an antigen-binding portion thereof, no longer bound to the antigen, may then be released (e.g., by exocytosis) by the cell back into the serum.

In some embodiments, FcRn in the vascular endothelia (e.g., of a subject) extends the half-life of a sweeping antibody, or an antigen-binding portion thereof. In some embodiments, vascular endothelial cells internalize sweeping antibodies, or antigen-binding portions thereof, which in some embodiments are bound to an antigen such as myostatin (e.g., pro-myostatin, latent myostatin or primed myostatin). In some embodiments, a sweeping antibody, or an antigen-binding portion thereof, is recycled back into the bloodstream. In some embodiments, a sweeping antibody, or an antigen-binding portion thereof, has an increased half-life (e.g., in the serum of a subject) as compared to its conventional counterpart. In some embodiments, a conventional counterpart of a sweeping antibody refers the antibody, or an antigen-binding portion thereof, from which the sweeping antibody, or an antigen-binding portion thereof, was derived (e.g., prior to engineering the Fc portion of the conventional antibody to bind FcRn with greater affinity at pH 7). In some embodiments, a sweeping antibody, or an antigen-binding portion thereof, has a half-life in the serum of a subject that is at least 1%, 5%, 10%, 15%, 20%, 25%, 35%, 50%, 75%, 100%, 150%, 200% or 250% longer as compared to its conventional counterpart.

In some embodiments, an Fc portion of a sweeping antibody binds FcRn. In some embodiments, the Fc portion of a sweeping antibody binds to FcRn at a pH of 7.4 with a $K_D$ ranging from $10^{-3}$ M to $10^{-8}$ M. In some embodiments, a sweeping antibody binds to FcRn at a pH of 7.4 with a $K_D$ ranging from $10^{-3}$ M to $10^{-7}$ M, from $10^{-3}$ M to $10^{-6}$ M, from $10^{-3}$ M to $10^{-5}$ M, from $10^{-3}$ M to $10^{-4}$ M, from $10^{-4}$ M to $10^{-8}$ M, from $10^{-4}$ M to $10^{-7}$ M, from $10^{-4}$ M to $10^{-6}$ M, from $10^{-4}$ M to $10^{-5}$ M, from $10^{-5}$ M to $10^{-8}$ M, from $10^{-5}$ M to $10^{-7}$ M, from $10^{-5}$ M to $10^{-6}$ M, from $10^{-6}$ M to $10^{-8}$ M, from $10^{-6}$ M to $10^{-7}$ M, or from $10^{-7}$ M to $10^{-8}$ M. In some embodiments, FcRn binds to the CH2-CH3 hinge region of a sweeping antibody. In some embodiments, FcRn binds to the same region as protein A or protein G. In some embodiments, FcRn binds to a different binding site from FcγRs. In some embodiments, the amino acid residues AA of a sweeping antibody Fc region are required for binding to FcRn. In some embodiments, the amino acid residues AA of a sweeping antibody Fc region affect binding to FcRn.

In some embodiments, any of the antibodies, or antigen-binding fragments thereof, provided herein are engineered to bind FcRn with greater affinity. In some embodiments, any of the antibodies, or antigen-binding fragments thereof, provided herein are engineered to bind FcRn with greater affinity at pH 7.4. In some embodiments, the affinity of antibodies, or antigen-binding fragments thereof, to FcRn is increased to extend their pharmacokinetic (PK) properties as compared to their conventional counterparts. For example, in some embodiments, sweeping antibodies elicit less adverse reactions due to their efficacy at lower doses. In some embodiments, sweeping antibodies, or an antigen-binding portion thereof, are administered less frequently. In some embodiments, transcytosis of sweeping antibodies, or an antigen-binding portion thereof, to certain tissue types are increased. In some embodiments, sweeping antibodies, or antigen-binding portions thereof, enhance efficiency of trans-placental delivery. In some embodiments, sweeping antibodies, or antigen-binding portions thereof, are less costly to produce.

In some embodiments, any of the antibodies, or antigen-binding fragments thereof, provided herein are engineered to bind FcRn with lower affinity. In some embodiments, any of the antibodies, or antigen-binding fragments thereof, provided herein are engineered to bind FcRn with lower affinity at pH 7.4. In some embodiments, the affinity of sweeping antibodies, or an antigen-binding portion thereof, to FcRn is decreased to shorten their pharmacokinetic (PK) properties as compared to their conventional counterparts. For example, in some embodiments, sweeping antibodies, or an antigen-binding portion thereof, are more rapidly cleared for imaging and/or radioimmunotherapy. In some embodiments, sweeping antibodies, or an antigen-binding portion thereof, promote clearance of endogenous pathogenic antibodies as a treatment for autoimmune diseases. In some embodiments, sweeping antibodies, or antigen-binding portions thereof, reduce the risk of adverse pregnancy outcome, which may be caused by trans-placental transport of material fetus-specific antibodies.

In some embodiments, sweeping antibodies, or an antigen-binding portion thereof, have decreased affinity to an antigen at low pH as compared to a neutral or physiological pH (e.g., pH 7.4). In some embodiments, sweeping antibodies, or an antigen-binding portion thereof, have a decreased affinity to an antigen at an acidic pH (e.g., a pH ranging from 5.5 to 6.5) as compared to a physiological pH (e.g., pH 7.4).

It should be appreciated that any of the antibodies, or antigen-binding fragments thereof, provided herein can be engineered to dissociate from the antigen depending on changes in pH (e.g., pH-sensitive antibodies). In some embodiments, sweeping antibodies, or an antigen-binding portion thereof, provided herein are engineered to bind antigen in a pH-dependent manner. In some embodiments, sweeping antibodies, or an antigen-binding portion thereof, provided herein are engineered to bind FcRn in a pH-dependent manner. In some embodiments, sweeping antibodies, or an antigen-binding portion thereof, provided herein are internalized by endocytosis. In some embodiments, sweeping antibodies, or an antigen-binding portion thereof, provided here are internalized by FcRn binding. In some embodiments, endocytosed sweeping antibodies, or antigen-binding portion thereof, release antigen in an endosome. In some embodiments, sweeping antibodies, or antigen-binding portions thereof, are recycled back to the cell surface. In some embodiments, sweeping antibodies remain attached to cells. In some embodiments, endocytosed sweeping antibodies, or an antigen-binding portion thereof, are recycled back to the plasma. It should be appreciated that the Fc portion of any of the antibodies, or antigen-binding fragments thereof, provided herein may be engineered to have different FcRn binding activity. In some embodiments, FcRn binding activity affects the clearance time of an antigen by a sweeping antibody. In some embodiments, sweeping antibodies may be long-acting or rapid-acting sweeping antibodies.

In some embodiments, converting a conventional therapeutic antibody, or an antigen-binding portion thereof, into a sweeping antibody, or an antigen-binding portion thereof, reduces the efficacious dose. In some embodiments, converting a conventional therapeutic antibody, or an antigen-binding portion thereof, into a sweeping antibody, or an antigen-binding portion thereof, reduces the efficacious dose by at least 1%, 2%, 5%, 10%, 20%, 30%, 40%, 50%, 60%, 70%, 80%, 90%, 95%, or 99%. In some embodiments, converting a conventional therapeutic antibody, or an antigen-binding portion thereof, into a sweeping antibody, or an antigen-binding portion thereof, reduces the efficacious dose by at least 1.5-fold, 2-fold, 3-fold, 4-fold, 5-fold, 6-fold, 8-fold, 10-fold, 15-fold, 20-fold, 50-fold, or 100-fold.

In some embodiments, selecting an appropriate dose of a sweeping antibody, or an antigen-binding portion thereof, for therapy may be performed empirically. In some embodiments, a high dose of a sweeping antibody, or an antigen-binding portion thereof, may saturate FcRn, resulting in antibodies which stabilize antigen in serum without being internalized. In some embodiments, sweeping antibodies, or antigen-binding portions thereof, are administered once a day, once a week, once every two weeks, once every three weeks, once every four weeks, once every 6 weeks, once every 8 weeks, once every 10 weeks, once every 12 weeks, once every 16 weeks, once every 20 weeks, or once every 24 weeks.

In some embodiments, any of the antibodies, or antigen-binding fragments thereof, provided herein may be modified or engineered to be sweeping antibodies. In some embodiments, any of the antibodies, or antigen-binding fragments thereof, provided herein may be converted into a sweeping antibody using any suitable method. For example, suitable methods for making sweeping antibodies, or antigen-binding portions thereof, have been previously described in Igawa et al., (2013) "Engineered Monoclonal Antibody with Novel Antigen-Sweeping Activity In vivo," PLoS ONE 8(5): e63236; and Igawa et al., "pH-dependent antigen-binding antibodies as a novel therapeutic modality," Biochimica et Biophysica Acta 1844 (2014) 1943-1950; the contents of each of which are hereby incorporated by reference. It should be appreciated, however, that the methods for making sweeping antibodies, or an antigen-binding portion thereof, as provided herein are not meant to be limiting. Thus, additional methods for making sweeping antibodies, or an antigen-binding portion thereof, are within the scope of this disclosure.

Some aspects of the disclosure are based on the recognition that the affinity (e.g., as expressed as $K_D$) of any of the anti-pro/latent-myostatin antibodies, or antigen-binding fragments thereof, provided herein are sensitive to changes in pH. In some embodiments, the antibodies, or antigen-binding fragments thereof, provided herein have an increased $K_D$ of binding to pro/latent-myostatin at a relatively low pH (e.g., a pH ranging from 4.0-6.5, e.g., pH 5.5) as compared to a relatively high pH (e.g., a pH ranging from 7.0-7.6, e.g., pH 7.4). In some embodiments, the antibodies, or antigen-binding fragments thereof, provided herein have a $K_D$ of binding to pro/latent-myostatin ranging from $10^{-3}$ M, $10^{-4}$ M, $10^{-5}$ M, $10^{-6}$ M, $10^{-7}$ M, $10^{-8}$ M when the pH is between 4.0 and 6.5 (e.g., pH 5.5). In some embodiments, the antibodies, or antigen-binding fragments thereof, provided herein have a $K_D$ of binding to pro/latent-myostatin ranging from $10^{-6}$ M, $10^{-7}$ M, $10^{-8}$ M, $10^{-9}$ M, $10^{-10}$ M, $10^{-11}$ M when the pH is between 7.0 and 7.6 (e.g., pH 7.4). In some embodiments, the antibodies, or antigen-binding fragments thereof, provided herein have a $K_D$ of binding to pro/latent-Myostatin that is at least 2-fold, at least 10-fold, at least 20-fold, at least 25-fold, at least 50-fold, at least 75-fold, at least 100-fold, at least 200-fold, at least 250-fold, at least 500-fold, at least 1000-fold, at least 5000-fold, or at least 10000-fold greater at a pH between 4.0 and 6.5 (e.g., pH 5.5) as compared to a pH between 7.0 and 7.6 (e.g., pH 7.4).

Antibodies and Antigen-Binding Fragments that Compete for Antigen Binding with the Novel Anti-Pro/Latent-Myostatin Antibodies or Antigen-Binding Fragments Thereof Certain embodiments of the disclosure relate to antibodies, and antigen-binding fragments thereof, that compete or cross-compete for antigen binding with any of the antibodies, or antigen-binding fragments thereof, provided herein. Preferably, the antigen is human latent myostatin.

In some embodiments, an antibody, or an antigen-binding portion thereof, binds at or near the same epitope as any of the antibodies provided herein. In some embodiments, an antibody, or an antigen-binding portion thereof, binds near an epitope if it binds within 15 or fewer amino acid residues of the epitope. In some embodiments, any of the antibodies, or antigen-binding fragments thereof, provided herein bind within 1, 2, 3, 4, 5, 6, 7, 8, 9, 10, 11, 12, 13, 14 or 15 amino acid residues of an epitope that is bound by any of the antibodies, or antigen-binding fragments thereof, provided herein. In preferred embodiments, such antibody or antigen-binding fragment cross-competes with Ab2 or apitegromab for binding to human pro/latent myostatin. The antibody or antigen-binding fragment may cross-compete with Ab2, as described herein, for binding to human pro/latent myostatin. In some embodiments, such antibody or antigen-binding fragment binds an epitope within the prodomain of human myostatin, wherein the epitope comprises one or more (e.g., all of) amino acid residues F147, Q149, L151, Y186, S168, Q149, L151, Y163, S168, K170, K205, and/or L207, as numbered according to SEQ ID NO: 52 disclosed herein. In some embodiments, such antibody or antigen-binding fragment binds an epitope within the prodomain of human myostatin, wherein the epitope comprises one or more (e.g., all of) amino acid residues F147, Q149, L151, Y186, K170, K205, and/or L207, as numbered according to SEQ ID NO: 52. In some embodiments, such antibody or antigen-binding fragment comprises an HCDR3 paratope that contains up to two amino acid differences as compared to SEQ ID NO: 220. In some embodiments, such antibody or antigen-binding fragment comprises an HCDR3 sequence comprising a leucine at amino acid position 3 and a tryptophan at amino acid position 9, as numbered according to SEQ ID NO: 220. In some embodiments, such antibody or antigen-binding fragment comprises an HCDR3 sequence comprising a leucine at amino acid position 3, a valine or isoleucine at amino acid position 4, a leucine at amino acid position 7, a glutamic acid at amino acid position 8, and/or a tryptophan at amino acid position 9, as numbered according to SEQ ID NO: 220.

In another embodiment, an antibody, or an antigen-binding portion thereof, competes or cross-competes for binding to any of the antigens provided herein (e.g., pro/latent-myostatin) with an equilibrium dissociation constant, $K_D$, between the antibody and the protein of less than $10^{-8}$ M. In other embodiments, an antibody, or an antigen-binding portion thereof, competes or cross-competes for binding to any of the antigens provided herein with a $K_D$ in a range from $10^{-11}$ M to $10^{-8}$ M. In preferred embodiments, the antibody has a bivalent $K_D$ of less than 1 nM, as measured by a SPR-based in vitro binding assay, such as Biacore™.

Certain embodiments of the disclosure relate to antibodies, or antigen-binding portions thereof, that compete for binding to pro/latent-myostatin with any of the antibodies, or antigen-binding fragments thereof, provided herein. In some embodiments, the antibody, or an antigen-binding portion thereof, binds to pro/latent-myostatin at the same epitope as any of the antibodies, or antigen-binding portions thereof, provided herein. In another embodiment, an antibody, or an antigen-binding portion thereof, competes for binding to pro/latent-myostatin with an equilibrium dissociation constant, $K_D$, between the antibody, or antigen-binding portion thereof, and pro/latent-myostatin of less than $10^{-6}$ M. In other embodiments, the antibody, or antigen-binding portion thereof, that competes with any of the antibodies, or antigen-binding portions thereof, provided herein binds to pro/latent-myostatin with a $K_D$ in ranging from $10^{-11}$ M to $10^{-8}$ M.

Any of the antibodies, or antigen-binding fragments thereof, provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody, or an antigen-binding portion thereof, binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody, or an antigen-binding portion thereof, binds can be determined in a systematic screen by using overlapping peptides derived from the target antigen sequence and determining binding by the antibody, or an antigen-binding portion thereof. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody, or an antigen-binding portion thereof, to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody, or an antigen-binding portion thereof, in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the pro/latent-myostatin polypeptide have been replaced (swapped) with sequences from a closely related, but antigenically distinct protein, such as another member of the TGFβ protein family (e.g., GDF11). By assessing binding of the antibody, or antigen-binding portion thereof, to the mutant pro/latent-myostatin, the importance of the particular antigen fragment to antibody, or antigen-binding portion thereof, binding can be assessed.

Alternatively, competition assays can be performed using other antibodies known to bind to the same antigen ("reference antibodies") to determine whether an antibody, or an antigen-binding portion thereof ("test antibody"), binds to the same epitope as the other antibodies, or antigen-binding portions thereof. Competition assays are well known to those of skill in the art. When a test antibody blocks a reference antibody from binding to an antigen, and the reference antibody blocks the test antibody from binding to the antigen, the reference antibody and the test antibody are said to cross-block or cross-compete each other for antigen binding. It is well understood in the art that such antibodies bind to the same or overlapping epitope within the antigen.

Any of the suitable methods, e.g., the epitope mapping methods as described herein, can be applied to determine whether an anti-pro/latent-myostatin antibody, or an antigen-binding portion thereof, binds one or more of the specific residues/segments in pro/latent-myostatin as described herein. Further, the interaction of the antibody, or an antigen-binding portion thereof, with one or more of those defined residues in pro/latent-myostatin can be determined by routine technology. For example, a crystal structure can be determined, and the distances between the residues in pro/latent-myostatin and one or more residues in the antibody, or antigen-binding portion thereof, can be determined accordingly. Based on such distance, whether a specific residue in pro/latent-myostatin interacts with one or more residues in the antibody, or antigen-binding portion thereof, can be determined. Further, suitable methods, such as competition assays and target mutagenesis assays can be applied to determine the preferential binding of a candidate anti-pro/latent-myostatin antibody, or an antigen-binding portion thereof, to pro/latent-myostatin as compared to another target such as a mutant pro/latent-myostatin.

In one embodiment, the present disclosure encompasses a method for identifying an antibody or an antigen-binding fragment thereof for competitive binding with one or more of the antibodies provided herein, wherein the method comprises screening for an antibody or antigen-binding fragment that competes or cross-competes with one or more of the antibodies provided herein (e.g., any of Ab101-141, e.g., any of Ab102, Ab109, Ab130, Ab132, or Ab133) and assaying the antibody or antigen-binding fragment that exhibits one or more (e.g., all of) the following properties: binding to pro/latent myostatin with a $K_D$ of less than 5 nM (e.g., less than 4 nM, 3 nM, 2 nM, 1 nM or 0.5 nM, as measured by a SPR-based in vitro binding assay, such as Biacore™), high pH sensitivity binding to pro/latent myostatin (e.g., greater than 10× as determined by comparing dissociation rates at pH 5.5/7.4), and/or 2:1 Fab: promyostatin homodimer binding stoichiometry. In some embodiments, the disclosure encompasses an antibody identified and/or prepared according to the disclosed method.

Modifications

In some embodiments, antibodies and antigen-binding fragments of the disclosure may be modified, e.g., by attachment to a therapeutic agent (e.g., as a bispecific antibody or an antibody-drug conjugate), or a detectable agent, e.g., a detectable label. Such labels include, but are not limited to, an enzyme, prosthetic group, fluorescent material, luminescent material, bioluminescent material, radioactive material, positron emitting metal, nonradioactive paramagnetic metal ion, and affinity label for detection and isolation of pro/latent-myostatin. The detectable substance may be coupled or conjugated either directly to the polypeptides of the disclosure or indirectly, through an intermediate (such as, for example, a linker) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine (131I, 125I, 123I, 121I), carbon (14C), sulfur (35S), tritium (3H), indium (115mIn, 113mIn, 112In, 111In), and technetium (99Tc, 99mTc), thallium (201Ti), gallium (68Ga, 67Ga), palladium (103Pd), molybdenum (99Mo), xenon (133Xe), fluorine (18F), 153Sm, Lu, 159Gd, 149Pm, 140La, 175Yb, 166Ho, 90Y, 47Sc, 86R, 188Re, 142Pr, 105Rh, 97Ru, 68Ge, 57Co, 65Zn, 85Sr, 32P, 153Gd, 169Yb, 51Cr, 54Mn, 75Se, and tin (113Sn, 117Sn). The detectable substance may be coupled or conjugated either directly to the anti-pro/latent-myostatin antibodies, or antigen-binding portions thereof, of the disclosure or indirectly, through an intermediate (such as, for example, a linker) using suitable techniques. Anti-pro/latent-myostatin antibodies, or antigen-binding portions thereof, conjugated to a detectable substance may be used for diagnostic assays as described herein.

As shown herein, the present disclosure includes novel antibodies and antigen-binding fragments thereof that are capable of selectively inhibiting myostatin activation. Unlike the inhibitors previously described in PCT/US2016/052014, however, at least some of the novel antibodies disclosed herein (e.g., Ab109, Ab105, Ab130, and Ab133) bind to latent myostatin with sufficiently high monovalent affinities such that one arm (e.g., the Fab) of the antibody is capable of interacting with the antigen. Without wishing to be bound by theory, it is contemplated that such high monovalent binding affinity enables flexibility for designing myostatin inhibitors that incorporate the six CDRs, variable domains (VH and/or VL), or corresponding Fab domains into engineered constructs, such as bispecific antibodies and other modalities containing an antigen-binding portion of the antibody. Such recombinantly engineered constructs are encompassed by the disclosure.

Pharmaceutical Compositions

Antibodies or antigen binding fragments thereof described herein may be formulated into pharmaceutical compositions suitable for administration in human or non-human subjects. Such pharmaceutical compositions may be intended for therapeutic use, or prophylactic use. In some embodiments, the pharmaceutical composition is suitable for subcutaneous administration. One or more of the myostatin inhibitors, e.g., anti-pro/latent-myostatin antibodies can be mixed with a pharmaceutically acceptable carrier (excipient), including buffer, to form a pharmaceutical composition for administering to a patient who may benefit from reduced myostatin signaling in vivo. "Pharmaceutically acceptable" means that the carrier is compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In one example, a pharmaceutical composition described herein contains more than one myostatin inhibitor, e.g., more than one anti-pro/latent-myostatin antibody, or antigen-binding portion thereof, that recognize different epitopes/residues of the target antigen.

In some examples, the pharmaceutical composition described herein comprises emulsion-based or lipid-based formulations, such as liposomes containing a myostatin inhibitor, e.g., anti-pro/latent-myostatin antibody or antigen-binding portion thereof, which can be prepared by any suitable method, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-pro/latent-myostatin antibody or antigen-binding portion thereof may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, or antigen-binding portion thereof, which matrices are in the form of shaped articles, e.g., films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Kits

The present disclosure also provides kits for use in alleviating diseases/disorders associated with myopathy or metabolic disorders, e.g., diabetes, obesity, or metabolic syndrome. Such kits can include one or more containers comprising any of the anti-pro/latent-myostatin antibodies or antigen binding fragments thereof disclosed herein, e.g., Ab102, Ab109, Ab130, Ab132, Ab133, or Ab141. In some embodiments, such kits may further comprise one or more additional therapeutic reagent, e.g., one or more GLP-1 receptor agonist. In some embodiments, such kits may further comprise one or more diagnostic reagent.

In some embodiments, the kit can comprise instructions for use in accordance with any of the methods described herein. The included instructions can comprise a description of administration of any of the anti-pro/latent-myostatin antibodies or antigen binding fragments thereof disclosed herein, e.g., Ab102, Ab109, Ab130, Ab132, Ab133 or Ab141 to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of any of the anti-pro/latent-myostatin antibodies, or antigen binding fragments thereof disclosed herein, e.g., Ab102, Ab109, Ab130, Ab132, Ab133 or Ab141 to treat, generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with a muscle disorder, e.g., a myopathy or associated with a metabolic disorder, e.g., diabetes, obesity, and/or metabolic syndrome. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-pro/latent-myostatin antibody, or antigen binding fragment thereof, as those described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

Production of Anti-Pro/Latent-Myostatin Antibodies or Antigen-Binding Fragments Thereof Numerous methods may be used for obtaining antibodies, or antigen-binding fragments thereof, of the disclosure. For example, antibodies, and antigen-binding fragments thereof, can be produced using recombinant DNA methods. Monoclonal antibodies, and antigen-binding fragments thereof, may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and BLI or SPR (e.g., Octet® or Biacore™) analysis, to identify one or more hybridomas that produce an antibody, or an antigen-binding portion thereof, that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies, and antigen-binding portions thereof, includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597; WO92/18619; WO 91/17271; WO 92/20791; WO 92/15679; WO 93/01288; WO 92/01047; WO 92/09690; and WO 90/02809.

In addition to the use of display libraries, the specified antigen (e.g., pro-myostatin) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., chimeric, using suitable recombinant DNA techniques. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal, or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue. In some embodiments, a host cell, e.g., an NSO and CHO cell, may be transformed with a polynucleotide or vector encoding any one of the antibodies disclosed herein (e.g., Ab101-Ab141) or an antigen binding fragment thereof, or with a portion thereof (e.g., a first cell may be transformed with a polynucleotide or vector encoding the heavy chain of any one of Ab101-Ab141 or an antigen binding fragment thereof and a second cell may be transformed with a polynucleotide or vector encoding the light chain of any one of Ab101-Ab141 or an antigen binding fragment thereof).

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen-binding fragments or other immunoglobulin forms may follow; see, Beychok, Cells of Immunoglobulin Synthesis, Academic Press, N.Y. (1979). Thus, polynucleotides or vectors are introduced into the cells which in turn produce the antibody or antigen-binding fragments. For example, the host cells, e.g., NSO or CHO cells, comprising a polynucleotide or vector encoding any one of the antibodies disclosed herein (e.g., Ab101-Ab141) or an antigen binding fragment thereof, or with a portion thereof may express the antibody or antigen binding fragment (or a heavy or light chain of the antibody). Furthermore, transgenic animals, preferably mammals, comprising the aforementioned host cells may be used for the large-scale production of the antibody or antibody fragments. Large-scale production typically refers to 250 liters or greater of bioreactor (e.g., cell culture), e.g., 250 L, 500 L, 1000 L, 1500 L, 2000 L, 3000 L, 4000 L, 5000 L, 6000 L, or larger.

The transformed host cells can be grown in fermenters and cultured using any suitable techniques to achieve optimal cell growth. Once expressed, the whole antibodies, their dimers, individual light and heavy chains, other immunoglobulin forms, or antigen-binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen-binding fragments can then be isolated from the growth medium, cellular lysates, or cellular membrane fractions. The isolation and purification of the, e.g., microbially expressed antibodies or antigen-binding fragments may be by any conventional means such as, for example, preparative chromatographic separations and immunological separations such as those involving the use of monoclonal or polyclonal antibodies directed, e.g., against the constant region of the antibody. Any one of any one of Ab101-Ab141 or an antigen binding fragment thereof produced by the host cell may be harvested, or heavy and light chains of the antibody or antigen binding fragment may be harvested from separate cells and then combined to form the complete antibodies or antigen binding fragments thereof.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, a heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies, and antigen-binding portions thereof.

In some embodiments, an appropriate nucleic acid that encodes variable regions of a heavy and/or light chain is obtained and inserted into an expression vector that can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen-binding fragment may be undertaken by culturing a modified recombinant host under culture conditions appropriate for the growth of the host cells and the expression of the coding sequences. The antibodies or antigen-binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein, e.g. any one of Ab101-Ab141 or an antigen binding fragment thereof. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen-binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX$_1$ or GAL1 promoter in yeast or the CMV-promoter, SV40-promoter, RSV-promoter (Rous sarcoma virus), CMV-enhancer (cytomegalovirus), SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation, and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, a polynucleotide(s) may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen-binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen-binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Myostatin

In some embodiments, the human pro/latent myostatin is wild type human pro/latent myostatin with a human kappa signal peptide that is cleaved when it is expressed and an N-terminal His6-tag (SEQ ID NO: 941) (pro-myostatin). Pro-myostatin undergoes incomplete furin cleavage during expression. In some embodiments, the human pro/latent myostatin has the amino acid sequence of SEQ ID NO: 135, shown below:

(SEQ ID NO: 135)
MDMRVPAQLLGLLLLWFSGVLGHHHHHHNENSEQKENVEKEGLCNACTW

RQNTKSSRIEAIKIQILSKLRLETAPNISKDVIRQLLPKAPPLRELIDQ

YDVQRDDSSDGSLEDDDYHATTETIITMPTESDFLMQVDGKPKCCFFKF

SSKIQYNKVVKAQLWIYLRPVETPTTVFVQILRLIKPMKDGTRYTGIRS

LKLDMNPGTGIWQSIDVKTVLQNWLKQPESNLGIEIKALDENGHDLAVT

FPGPGEDGLNPFLEVKVTDTPKRSRRDFGLDCDEHSTESRCCRYPLTVD

FEAFGWDWIIAPKRYKANYCSGECEFVFLQKYPHTHLVHQANPRGSAGP

CCTPTKMSPINMLYFNGKEQIIYGKIPAMVVDRCGCS.

In some embodiments, the sequence encoding the human immunoglobulin kappa signal peptide is MDMRVPAQLLGLLLLWFSGVLG (SEQ ID NO: 136).

In some embodiments, the His6 tag (SEQ ID NO: 941) of human pro-myostatin has the underlined sequence (HHHHHH (SEQ ID NO: 942)) in SEQ ID NO: 135.

In some embodiments, the sequence encoding the human myostatin prodomain is SEQ ID NO: 137, shown below:

(SEQ ID NO: 137)
NENSEQKENVEKEGLCNACTWRQNTKSSRIEAIKIQILSKLRLETAPNI

SKDVIRQLLPKAPPLRELIDQYDVQRDDSSDGSLEDDDYHATTETIITM

PTESDFLMQVDGKPKCCFFKFSSKIQYNKVVKAQLWIYLRPVETPTTVF

VQILRLIKPMKDGTRYTGIRSLKLDMNPGTGIWQSIDVKTVLQNWLKQP

ESNLGIEIKALDENGHDLAVTFPGPGEDGLNPFLEVKVTDTPK.

In some embodiments, the RSRR furin cleavage site (SEQ ID NO: 943) of human pro-myostatin is the bolded sequence in SEQ ID NO: 135.

In some embodiments, the sequence encoding the mature human myostatin growth factor is SEQ ID NO: 138, shown below:

(SEQ ID NO: 138)
DFGLDCDEHSTESRCCRYPLTVDFEAFGWDWIIAPKRYKANYCSGECEF

VFLQKYPHTHLVHQANPRGSAGPCCTPTKMSPINMLYFNGKEQIIYGKI

PAMVVDRCGCS.

In some embodiments, the DNA sequence encoding human pro-myostatin is SEQ ID NO: 139, shown below:

(SEQ ID NO: 139)
ATGGACATGAGAGTGCCCGCCCAGCTGCTGGGACTTCTGCTGCTGTGGTTTAGCGGCGTGCTGGGCCACC

ACCACCATCACCACAACGAGAACAGCGAGCAGAAAGAAAACGTGGAAAAAGAGGGCCTGTGCAACGCCTG

CACCTGGCGGCAGAATACCAAGAGCAGCCGGATCGAGGCCATCAAGATCCAGATCCTGAGCAAGCTGCGG

CTGGAAACCGCCCCCAACATCAGCAAGGACGTGATCAGACAGCTGCTGCCCAAGGCCCCACCCCTGAGAG

AGCTGATCGACCAGTACGACGTGCAGCGGGACGATAGCTCCGATGGCAGCCTGGAAGATGACGACTACCA

CGCCACCACCGAGACAATCATCACCATGCCTACCGAGAGCGACTTCCTGATGCAAGTGGACGGCAAGCCCA

AGTGCTGCTTCTTCAAGTTCAGCTCTAAGATCCAGTACAACAAGGTCGTGAAGGCCCAGCTGTGGATCTACC

TGCGGCCCGTGGAAACCCCCACCACCGTGTTTGTGCAGATCCTGCGGCTGATCAAGCCCATGAAGGACGG

CACCCGGTACACCGGCATCCGGTCCCTGAAGCTGGACATGAATCCCGGCACAGGCATCTGGCAGAGCATC

GACGTGAAAACCGTGCTGCAGAACTGGCTGAAGCAGCCCGAGAGCAACCTGGGCATCGAGATCAAGGCCC

TGGACGAGAACGGCCACGACCTGGCCGTGACATTTCCTGGCCCTGGCGAGGATGGCCTGAACCCATTCCT

GGAAGTGAAAGTGACCGACACCCCCAAGCGGAGCAGACGGGATTTCGGCCTGGATTGCGACGAGCACAGC

ACCGAGTCCAGATGCTGCAGATACCCCCTGACCGTGGACTTCGAGGCCTTCGGCTGGGACTGGATCATTGC

CCCCAAGAGATACAAGGCCAACTACTGCAGCGGCGAGTGCGAGTTCGTGTTCCTGCAGAAGTACCCCCACA

CCCACCTGGTGCATCAGGCCAACCCTAGAGGCTCTGCCGGCCCTTGCTGTACCCCTACCAAGATGAGCCCC

ATCAACATGCTGTACTTCAACGGCAAAGAGCAGATCATCTACGGCAAGATCCCCGCCATGGTGGTGGACAG

ATGCGGCTGCAGCTGATGA.

In some embodiments, the signal peptide is cleaved from the rest of the molecule when the protein is expressed.

In some embodiments, an antibody or antigen-binding fragment thereof disclosed herein binds an epitope on pro-myostatin. In some embodiments, the antibody or antigen-binding fragment is one disclosed herein that competes for antigen binding with Ab2. The variable domain and full-length antibody sequences for Ab2 are disclosed in PCT/US2015/059468 and PCT/US2016/052014.

Role of Myostatin in Muscle Homeostasis and Metabolic Regulation

Skeletal muscle accounts for approximately 40% of body mass and is a dynamic organ, turning over at a rate of 1-2% per day. Myostatin is believed to play a pivotal role in maintaining the homeostasis of muscle both in healthy and disease conditions. Myostatin is capable of inducing muscle atrophy via its inhibition of myoblast proliferation, increasing ubiquitin-proteasomal activity and downregulating activity of the IGF-Akt pathway. These well-recognized effects are seen in multiple atrophy-causing situations, including injury, diseases such as cachexia, disuse and space flight, demonstrating the importance of the myostatin signaling mechanism. Based on this central role, significant work has been pursued to inhibit myostatin's actions in vivo. Indeed, inhibition of the myostatin pathway has been shown to promote muscle growth and maintain muscle mass.

In addition, muscle is known to be the major protein reservoir of the body and therefore contributes to amino acid homeostasis and metabolism. Along with glucose (made and stored as glycogen primarily in the liver and the muscles) and lipids (stored in fat tissues), proteins in muscles can act as an energy source (i.e., broken down to generate energy). Impairment or imbalance in the utilization or mobilization of these energy sinks in the body may, at least in part, contribute to various types of metabolic dysregulation. It is therefore contemplated that myostatin may play a direct role in the regulation of metabolism by coordinating the balance between breakdown vs. synthesis/storage of glucose, fat, and/or muscle in the body (e.g., enhancing "metabolic adaptability") such as adaptability or flexibility with respect to fuel sources, ability to change metabolism in to meet organismal or tissue needs in states of exercise or based on available fuels), thereby contributing to overall metabolic regulation, e.g., energy expenditure, in the body. Indeed, while myostatin has been primarily considered as a key regulator of muscle metabolism since its discovery in 1997, effects of myostatin as a metabolic regulator have been shown in more recent findings. See, e.g., PCT/US2018/012686. Accordingly, it is contemplated here that myostatin inhibition, e.g., by an antibody or antigen-binding fragment disclosed herein, may be useful in certain embodiments for treating a variety of conditions relating to muscle and/or metabolic dysregulation, as discussed in more detail below.

Therapeutic Use

In various embodiments, pharmaceutical compositions comprising an antibody or antigen binding fragment disclosed herein, e.g., compositions comprising any one of Ab101-Ab141 or an antigen binding fragment thereof, are suitable for administration to human patients for the treatment or prevention of diseases and conditions associated with myostatin signaling, e.g., conditions where reduced myostatin signaling is desirable. In some embodiments, the antibodies and antigen-binding fragments disclosed herein may be used to improve metabolic health in patients. Suitable diseases and conditions include, for example, muscle disorders such as muscle atrophies and myopathies, metabolic disorders such as obesity and diabetes, bone and connective tissue disorders or conditions such as bone loss, anterior cruciate ligament (ACL) repair and osteogenesis imperfecta (OI), cardiovascular diseases such as heart disease (e.g., heart failure, e.g., in patients with type 2 diabetes or obesity), and chronic inflammation and inflammatory diseases, such as chronic kidney disease (CKD), idiopathic pulmonary fibrosis (IPF), and fatty liver disease (e.g, NAFLD, NASH). Thus, the present disclosure encompasses therapeutic use of such antibodies and antigen-binding fragments thereof (e.g., engineered constructs that incorporate such fragments) to treat one or more of these diseases and conditions. In some embodiments, the myostatin-selective inhibitor is an antibody or antigen-binding fragment thereof comprising all six CDRs of any one of Ab101-Ab141, e.g., the set of SEQ ID NOs identified for a specific antibody in Tables 2d-f. In some embodiments, the myostatin-selective inhibitor is an antibody or antigen-binding fragment thereof comprising the heavy and light chain variable domains of any one of Ab101-Ab141, e.g., the pair of SEQ ID NOs identified for a specific antibody in Table 3. In some embodiments, the myostatin-selective inhibitor is an antibody comprising the heavy and light chains of any one of Ab101-Ab141, e.g., the pair of SEQ ID NOs identified for a specific antibody in Table 4. In some embodiments, the antibody sequences are those of Ab109, Ab133 or Ab141 or an antigen-binding fragment thereof. In some embodiments, the antibody is selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen-binding fragment thereof. In preferred embodiments, the antibody is selected from Ab109, Ab133, and Ab141. The antibody or antigen binding fragment may also be administered in combination with one or more additional agent disclosed herein, e.g., a GLP-1 pathway activator (e.g., GLP-1 receptor agonists) or biguanide (e.g., metformin), to treat any of the diseases or disorders.

The diseases and conditions encompassed by the disclosure include, but are not limited to, metabolic disorders such as metabolic syndrome, obesity, type 2 diabetes mellitus (T2DM) (e.g., adult-onset diabetes), pre-diabetes, and T2DM associated with obesity. T2DM is a chronic and progressive metabolic disease characterized by raised glucose levels in the blood, which if left untreated, can damage various organs leading to complications such as cardiovascular disease, neuropathy, nephropathy (e.g., diabetic nephropathy), and retinopathy (e.g., diabetic retinopathy). Obesity is a risk factor for many serious medical conditions including cardiovascular disease, pre-diabetes, T2DM, NAFLD, NASH, certain types of cancers, Alzheimer's, and others. Accordingly, treating obesity can treat or ameliorate these conditions. In some embodiments of the present disclosure, the patients are not treated with a TGFβ inhibitor, such as TGFβ1 inhibitor. In some embodiments, the patients suffer from a metabolic liver disorder, wherein optionally the metabolic liver disorder comprises NAFLD, wherein further optionally the metabolic liver disorder has not progressed to NASH, wherein optionally the metabolic liver disease has not progressed to fibrosis, or wherein optionally the metabolic liver disease has not progressed to cirrhosis.

In some embodiments, preferred myostatin inhibitors for therapeutic use are myostatin-selective inhibitors, such as any one of the myostatin-selective antibodies or antigen-binding fragments disclosed herein, e.g., an antibody or antigen-binding fragment that binds selectively to pro/latent myostatin, such as any one of Ab101-Ab141. Without wishing to be bound by theory, it may be beneficial to use a myostatin-selective inhibitor to provide a desired therapeutic effect while avoiding undesired adverse effects, e.g., those associated with non-selective myostatin inhibition. In some embodiments, the desired therapeutic effect includes at least one, e.g., all, of: preferential loss of fat mass over lean mass; maintaining fat mass loss; prevention of muscle loss; increased muscle mass; increased endurance; reduced fatigue; prevention of bone loss; improved blood glucose levels; and/or improved liver health. In some embodiments, it may be beneficial to avoid inhibition of GDF11, which has been reported to promote metabolic health but has also been associated with adverse effects. See, e.g., Frohlich et al. (Cell Prolif. 2022 October; 55(10): e13310); Lu et al. (J Transl Med. 2019; 17: 422); Walker et al. (Sci Rep 10, 4561 (2020); and Muramatsu et al. (Sci Rep. 2021 Jan. 25; 11(1):2160), the contents of which are hereby incorporated in their entirety.

In some embodiments, combining a selective inhibitor of myostatin activation with a GLP-1 pathway activator, GIP activator or antagonist, or glucagon modulator may provide additive or synergistic effects on the metabolic health of a subject, e.g., by preventing muscle loss during weight loss, a greater amount of fat, including visceral fat, may be lost. Combining a selective inhibitor of myostatin activation with a GLP-1 pathway activator (e.g., GLP-1 receptor agonists) may also increase the durability of the therapeutic effect, e.g., maintaining muscle mass may promote the durability of the metabolic benefits.

Exemplary conditions for which the compositions and methods of the present disclosure may be useful are further described below.

Metabolic Disorders and Diseases

In various embodiments, disclosed herein are methods for treating or preventing a metabolic disease in a subject. A metabolic disease (also referred to as a metabolic disorder or metabolic condition) is generally associated with aberrant glucose, lipid/fat and/or protein/nitrogen metabolism, or osmotic dysregulation, and has pathological consequences arising from such a condition. A number of metabolic disorders of the disclosure share certain characteristics, e.g., they are associated with a loss of fat-free or lean muscle mass, an excess of fat mass, a lower metabolic rate, insulin resistance, lack of ability to regulate blood sugar, weight gain, and/or increase in body mass index. In some cases, such metabolic diseases or disorders may be triggered or exacerbated by medication that the patients receive.

The present disclosure is based, at least in part, on the discovery that administration of a myostatin inhibitor described herein (e.g., an anti-myostatin antibody or antigen-binding fragment thereof disclosed herein) to a subject having a metabolic disease, e.g., via a subcutaneous route, may improve both the physiological and the functional characteristics of the subject.

Further examples of metabolic diseases that may be treated or prevented by the methods of the present disclosure include but are not limited to, pre-diabetes and diabetes (e.g., type 1 or type 2 diabetes, or diabetes associated with obesity), obesity (e.g., adult-onset obesity, diet-induced obesity, pediatric obesity, etc.), obesity syndrome (e.g., diet-associated or diet-induced obesity), insulin resistance, insulin insufficiency, hyperinsulinemia, impaired glucose tolerance (IGT), abnormal glycogen metabolism, hyperlipidemia, hypoalbuminemia, hypertriglyceridemia, kidney disease, e.g., chronic kidney disease, syndrome X, fatty liver disease, metabolic bone diseases. Spinal cord injury (SCI) (e.g., complete or incomplete/partial SCI), hypo-metabolic states, double diabetes, and Cushing's disease (also referred to as Cushing's syndrome). In some embodiments, metabolic diseases include diseases associated with impaired neurological signaling or partial denervation. In some embodiments, metabolic diseases include conditions triggered by or associated with certain medication (e.g., side effects).

Additional diseases or conditions related to metabolic disorders and/or body composition that would be apparent to the skilled artisan and are within the scope of this disclosure.

As discussed in more detail herein, metabolic disorders can occur secondarily to, or occur as a result of, a muscle condition or disorder. Because muscle homeostasis is correlated with amino acid/protein metabolism, it is further contemplated that myostatin inhibition may in turn regulate nitrogen metabolism and nitrogen mobilization in the body. In muscle catabolism, a muscle tissue breaks down into its building blocks, amino acids, which may be considered as a major reservoir (and thus a source) of nitrogen. Nitrogen is an element of ammonia, which is highly toxic to the body and is excreted in a form of urea in humans. When nitrogen metabolism is dysregulated, a possible outcome includes an imbalance of fluid retention, which may manifest as systemic or local edema (e.g., congestion or fluid overload).

Diabetes is a prevalent metabolic disease that refers to a group of metabolic diseases characterized by high blood sugar (glucose) levels which result from defects in insulin secretion or action, or both. Insulin is a hormone released by the pancreas in response to increased levels of blood sugar (glucose) in the blood. There are two most common types of diabetes, namely type 1 diabetes and type 2 diabetes, which both result from the body's inability to regulate insulin.

In type 2 diabetes mellitus (T2DM), also referred to as noninsulin-dependent diabetes mellitus, NDDM), the pancreas continues to manufacture insulin, sometimes even at higher-than-normal levels. However, the body develops resistance to its effects, resulting in a relative insulin deficiency. As the pancreas continues to manufacture insulin and the body becomes insulin-resistant, the insulin-producing cells in the Islets of Langerhans in the pancreas may wear out, limiting or losing their ability to continue to produce insulin. Type 2 diabetes may occur in children and adolescents but usually begins after age 30 and becomes progressively more common with age: about 15 percent of people over age 70 have type II diabetes. Obesity is a risk factor for type 2 diabetes, and 80 to 90 percent of the people with this disorder are obese.

In some embodiments, diabetes includes pre-diabetes. "Pre-diabetes" refers to one or more early diabetic conditions including impaired glucose utilization, abnormal or impaired fasting glucose levels, impaired glucose tolerance, impaired insulin sensitivity and insulin resistance. Prediabetes is a major risk factor for the development of type 2 diabetes mellitus, cardiovascular disease, and mortality. Much focus has been given to developing therapeutic interventions that prevent the development of or progression to type 2 diabetes by effectively treating prediabetes.

In some embodiments, diabetes includes double diabetes, which is a combination of type 1 diabetes with features of insulin resistance and type 2 diabetes.

Diabetes and prediabetes can be diagnosed by the administration of a glucose tolerance test, which can be determined by venous blood draws from a fasting or non-fasting subject. They can also be diagnosed by measuring blood levels of hemoglobin A1C (A1C), a glycosylated form of hemoglobin that reflects the average amount of glucose in the blood over the past two to three months. Normal, prediabetic, and diabetic A1C levels are known in the art and can vary with age. In some embodiments, the expected values for normal fasting blood glucose concentration can be between about 70 mg/dL (3.9 mmol/L) and about 100 mg/dL (5.6 mmol/L). In some embodiments, pre-diabetes is associated with hemoglobin A1C levels of about 100 mg/dL to about 125 mg/dL or about 5.6 mmol/L to about 6.9 mmol/L. In some embodiments, diabetes is associated with fasted glucose levels above about 125 mg/dL or hemoglobin A1C levels above about 6.9 mmol/L.

Clinically, diabetes is often divided into several basic categories. Primary examples of these categories include, autoimmune diabetes mellitus, non-insulin-dependent diabetes mellitus (type 1 NDDM), insulin-dependent diabetes mellitus (type 2 IDDM), non-autoimmune diabetes mellitus, non-insulin-dependent diabetes mellitus (type 2 NIDDM), and maturity-onset diabetes of the young (MODY). A further category, often referred to as secondary, refers to diabetes brought about by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes. (see e.g., Harrison's (1996) 14$^{th}$ ed., New York, McGraw-Hill).

Obesity is another prevalent metabolic disease that can be treated or prevented by the methods of the present disclosure. "Obesity" refers to a chronic condition defined by an excess amount of body fat. The normal amount of body fat (expressed as percentage of body weight) is between 25-30% in women and 18-23% in men. Women with over 30% body fat and men with over 25% body fat are considered obese. Obesity can be defined using any clinically relevant definitions. For example, in adults, body mass index (BMI, kg/m2) is frequently used as a measure of overweight and obesity, with overweight being defined as a BMI 25-29.9 kg/m2, obesity as a BMI equal to or greater than 30 kg/m2, and morbid obesity being defined as BMIs over 40 kg/m2. Obesity can also be defined in adults by central adiposity as measured by waist circumference, with raised waist circumference defined as equal to or greater than 102 cm in men and equal to or greater than 88 cm in women.

Subjects with obesity may exhibit other symptoms such as increased fasting plasma glucose, glucose intolerance, heart failure, hypertension, insulin resistance, increased fasting plasma triglycerides, decreased fasting high density lipoprotein (HDL) level, prediabetes, increased blood pressure, stroke, heart failure, obstructive sleep apnea, reproductive hormone impairment, obstructive sleep apnea, osteoarthritis, gallstones, gastroesophageal reflux, or renal disease. Obesity may also cause various orthopedic problems, skin disorders and swelling of the feet and ankles. Severe complications of obesity include a much higher risk of coronary artery disorder and of its major risk factors type II diabetes, hyperlipidemia and hypertension. Much of the morbidity associated with obesity is associated with type II diabetes, as poorly controlled diabetes and obesity lead to a constellation of symptoms that are together known as syndrome X, or metabolic syndrome. In some embodiments, the obesity is sarcopenic obesity. In some embodiments, the subject having obesity is on a caloric restriction regimen.

In an aspect, the methods of the present disclosure are suitable for treating all forms of obesity. Obesity includes obesity associated with diabetes, obesity associated with metabolic syndrome, obesity associated with a monogenetic disorder, obesity associated with anti-psychotic drug use, glucocorticoid-associated obesity, and hypothalamic obesity.

In another aspect, the methods of the present disclosure are suitable for treating or preventing metabolic disease such as obesity syndromes. The term "obesity syndrome" refers to any disorder or condition causing a subject to be grossly fat or overweight. Like other metabolic diseases, people with obesity syndrome are usually associated a loss of fat-free or lean muscle mass, an excess of fat mass, a lower metabolic rate, insulin resistance, lack of ability to regulate blood sugar, weight gain, and increase in body mass index. In some embodiments, the obesity syndrome is selected from the group consisting of Prader Willi, an obesity syndrome associated with a genetic disorder, and an obesity syndrome associated with a hypothalamic disorder.

The methods of the present disclosure are also suitable for treating or preventing metabolic disease such as metabolic syndromes. As used herein, "metabolic syndrome" refers to the concept of a clustering of metabolic risk factors that come together in a single individual and lead to a high risk of developing diabetes and/or cardiovascular diseases. The main features of metabolic syndrome include insulin resistance, hypertension (high blood pressure), cholesterol abnormalities, dyslipidemia, triglyceride abnormalities, an increased risk for clotting and excess body weight, especially in the abdomen, or obesity. In some embodiments, metabolic syndrome can be diagnosed by the presence of three or more of the following components: (1) an elevated waist circumference (men, equal to or greater than 40 inches (102 cm); women, equal to or greater than 35 inches (88 cm)); (2) elevated triglycerides (equal to or greater than 150 mg/dL); (3) reduced high density lipoprotein cholesterol (HDL) (men, less than 40 mg/dL; women, less than 50 mg/dL); (4) elevated blood pressure (equal to or greater than 130/85 mm Hg); and (5) elevated fasting glucose (equal to or greater than 100 mg/dL).

Body composition may be measured by a variety of methods, including dual energy X-ray absorptiometry (DEXA). Total body scans using DEXA provide generally accurate and precise measurements of body composition, including bone mineral content, bone mineral density, lean tissue mass, fat tissue mass, and fractional contribution of fat.

Obesity is a risk factor for the development of cardiovascular disease. Obese individuals experience cardiovascular disease events at an earlier age, live with cardiovascular disease for a greater proportion of their lifetime and have a shorter average lifespan than individuals with normal weight. Obesity contributes directly to cardiovascular risk factors, including dyslipidemia, type 2 diabetes, hypertension, and sleep disorders. Obesity accelerates atherosclerotic changes through multiple mechanisms, including insulin resistance and inflammation. Obesity also leads to the development of cardiovascular disease and cardiovascular disease mortality independently of other cardiovascular risk factors. Visceral adiposity promotes systemic and vascular inflammation, which is fundamental to the atherosclerotic process. Inflammation induced by obesity increases the likelihood of LDL oxidation, which in turn promotes atherogenesis. Insulin resistance is associated with dyslipidemia and metabolic syndrome, which are linked to atherosclerosis. Endothelial function in obesity, e.g., due to decreased bioavailability of nitric oxide in the setting of inflammation and oxidative stress also contributes to the progression of atherosclerosis. Obesity also has been linked to abnormalities in the coronary microvasculature and on epicardial coronary vessels. Another aspect of the disclosure includes a method of treating a subject having a metabolic disease or condition related to aging. Exemplary diseases and conditions related to ageing include, without limitation, sarcopenia (age-related muscle loss), frailty, and androgen deficiency.

Accordingly, the methods of the present disclosure are suitable for treating or preventing metabolic diseases such as cardiovascular disease, e.g., cardiovascular disease associated with metabolic syndrome. The term "cardiovascular disease" refers to any disease of the heart or blood vessels. Cardiovascular or heart disease includes but is not limited to, for example, angina, arrhythmia, coronary artery disease (CAD), coronary heart disease, cardiomyopathy (including dilated cardiomyopathy, restrictive cardiomyopathy, arrhythmogenic right ventricular cardiomyopathy, and diabetic cardiomyopathy), heart attack (myocardial infarction), heart failure (e.g., acute heart failure (AHF), chronic heart failure (CHF) or heart failure with preserved ejection fraction (HfpEF)), hypertrophic cardiomyopathy, mitral regurgitation, mitral valve prolapse, pulmonary stenosis, etc. Blood vessel disease includes but is not limited to, for example, peripheral vascular disease, artery disease, carotid artery disease, deep vein thrombosis, venous diseases, and atherosclerosis. In some embodiments, a subject having heart failure is resistant to diuretic therapy. In another embodiment, a subject having heart failure responds poorly to diuretic therapy. It is contemplated herein that myostatin inhibitors may provide beneficial effects in reducing risk of major cardiovascular events particularly in patients with metabolic disorders, such as obesity and diabetes. Such effects may be synergistic when used in conjunction with a GLP-1 pathway activator, such as GLP-1 receptor agonists. In preferred embodiments, the myostatin inhibitor is a myostatin-selective inhibitor. In particularly preferred embodiments, the myostatin inhibitor is selected from the novel antibodies disclosed herein, e.g., any one of Ab101-Ab141. In most preferred embodiments, the myostatin inhibitor is selected from Ab109, Ab133 and Ab141.

Pulmonary edema, as well as renal congestion, for example, is frequently observed in patients with heart failure, associated with decreased cardiac output. Pulmonary congestion is in fact the most frequent cause of hospitalization in this clinical setting and correlates with poor prognosis. Similarly, in pathologic conditions that involve impaired osmoregulation, the affected individual may be particularly sensitive to salt intake, which may cause or exacerbate fluid overload. Therefore, for subjects with fluid retention or volume-overload, such as subjects having impaired osmoregulation and subjects with heart failure, e.g., chronic heart failure, current guidelines suggest that decongestion should be attempted using diuretic therapy (see, e.g., Regolisti et al., Nephrology@Point of Care 2016; 2(1):e73-e87). However, in many cases, diuretic treatment is ineffective, or the subject is refractory to diuretic therapy. Myostatin inhibition according to the present disclosure may provide such patients with clinical benefits. Specifically, the methods of the present disclosure are suitable for increasing responsiveness of subjects who are refractory to diuretic treatment, or poorly responsive to diuretic treatment. For example, administration of a myostatin inhibitor reduces the diuretic dose needed and/or offers improved control of symptoms, such as CHF symptoms; improves cardiac function; and/or prevents pathologic cardiac remodeling or other worsening of cardiac function chronically. Myostatin inhibition using an inhibitor described herein also reduces the risk of CHF exacerbations, such as episodes of acute pulmonary edema.

For subjects at higher risk for developing acute pulmonary edema, such as subjects receiving IV fluids, blood transfusions, or fluid shifts, the myostatin inhibitors disclosed herein may be administered prophylactically. For example, a subject with congestive heart failure who needs to receive a blood transfusion can be prophylactically administered a myostatin inhibitor during the blood transfusion to prevent the onset of acute pulmonary edema during the transfusion. For subjects having CHF and/or other volume-overload states who develop hyponatremia, either due to the volume-overload, itself, or from diuretics used to treat the volume-overload, myostatin inhibitors disclosed herein can be administered to treat the hyponatremia and/or enable higher doses of diuretics to be used, when diuretic dosing is limited by hyponatremia as a side effect. Generally speaking, however, the myostatin inhibitors disclosed herein may be used to treat hyponatremia, irrespective of the underlying etiology.

For other volume-overload states, e.g., renal failure or liver disease, which require high-dose diuretics, a myostatin inhibitor disclosed herein reduces the diuretic dose needed; offer improved control of symptoms, such as peripheral edema or congestion within the body internally (including pleural effusions, ascites, hepatic congestion, or volume overload within the eyes, which can lead to retinal detachment, and/or reduce the risk of pulmonary edema.

Metabolic disorders and diseases for treatment according to the methods provided herein also include metabolic conditions that affect the liver. Nonalcoholic fatty liver disease (NAFLD) is a spectrum of hepatic diseases associated with metabolic and cardiovascular disorders and is strongly associated with metabolic syndrome (Godoy-Matos (2020) Diabetes Metab Synd 12:50). Metabolic conditions that affect the liver include non-alcoholic steatohepatitis (NASH), NAFLD, hereditary hemochromatosis, alpha-1 antitrypsin deficiency, and Wilson disease. Fibrosis, a thickening of connective tissues occurs in both NASH and the later stages of NAFLD, as excess tissue deposits lead to fibrotic scarring. Fibroblast growth factor 21 (FGF21) and FGF19 have been observed to decrease hepatic steatosis. Accordingly, in some embodiments, the subject receives an FGF21 or FGF19 receptor agonist as well as a myostatin inhibitor of the invention. Zhao et al., Signal Transduction and Targeted Therapy (2022) 7:206. In some embodiments, the subject also receives, or has received, one or more of the following therapeutics to treat the liver disease: Hydronidone, BIO89-100, Efruxifermin, Pegbelfermin, Aldafermin, MK-3655, PRI-724, Selonsertib, CC-90001, Epeleuton, Elafibranor, Saroglitazar, Lanifibranor, Pemafibrate, ZSP0678, Obeticholic Acid, Cilofexor, Nidufexor, TERN-101, Vonafexor, EDP-305, Tropifexor, JKB-121, JKB-122, Semaglutide, Tirzepatide, Cotadutide, HM-15211, Resmetirom, VK2809, Cenicriviroc, Belapectin, GB1211, Azemiglitazone potassium, Deuterium-Stabilized I-Pioglitazone, Aramchol, PF-05221304, Firsocostat, ZSP1601, Epeleuton, PXL-770, ALS-L1023, Namodenoson, TVB-2640, LPCN 1144, HepaStem, BMS-986263, Foralumab, Elobixibat, Apararenone, PF-06835919, ARO-HSD, and CB4211.

The compositions and methods of the present disclosure are also suitable for treating or preventing metabolic diseases associated with a hypo-metabolic state. The term "a hypo-metabolic state" refers to a state of reduced metabolism or metabolic activity, where the body is not producing enough energy. Patients with a hypo-metabolic state generally have a lower metabolic rate, a loss of fat-free or lean muscle mass, an excessive gain of fat mass, insulin resistance, lack of ability to regulate blood sugar, weight gain, and an increase in body mass index. In some embodiments, the hypo-metabolic state is selected from the group consisting of a state associated with prolonged immobilization, a state associated with bed rest, a state associated with casting, a state associated with a stroke, a state associated with amputation, and a post-surgery state. In some embodiments, the hypo-metabolic state is a post-surgery state, e.g., paraspinal muscle atrophy after lumbar spine surgery. In one embodiment, the paraspinal muscle atrophy is a nerve injury-dependent muscle atrophy. In one embodiment, the surgery is a spinal surgery. In one embodiment, the spinal surgery is a lumbar spine surgery or a lumbar spine procedure, e.g., a lumbar fusion procedure, a lumbar nonfusion procedure, a posterior lumbar fusion procedure, an anterior lumbar fusion procedure, a minimally invasive (MIS) posterior lumbar decompression procedure, a minimally invasive (MIS) posterior lumbar fusion procedure, a non-MIS equivalent procedure, etc.

In some embodiments, the myostatin inhibitors of the invention may be used to attenuate spinal cord injury (SCI)-induced reduction in sub-lesional muscle mass and overall body mass and, while at the same time reducing the mass of undesirable adipose tissue such as white and visceral adipose tissue. Subjects treated with the myostatin inhibitor therapy may also exhibit a significant improvement in their locomotor function, muscle strength, as well as motor coordination and balance skills.

In another aspect, the methods of the present disclosure are suitable for treating or preventing metabolic diseases such as Cushing's disease, which is also referred to as Cushing's syndrome or hypercortisolism. The term "Cushing's disease" refers to a collection of signs and symptoms due to prolonged exposure to cortisol. In some embodiments, the Cushing's disease is selected from the group consisting of corticosteroid-induced Cushing's disease and tumor-induced Cushing's disease. In some embodiments, the antibodies or antigen-binding fragments disclosed herein may be useful as an alternative or additive treatment option to the current standard-of-care treatments for patients suffering from Cushing's disease.

Accordingly, the present disclosure provides methods for treating or preventing metabolic diseases in a human subject. The methods include selecting a human subject suffering from a metabolic disease and administering to the human subject an effective amount of a myostatin inhibitor (e.g., Ab102, Ab109, Ab130, Ab132, or Ab133), thereby treating or preventing the metabolic disease in the human subject. Preferably, the myostatin inhibitor is a myostatin-selective inhibitor. More preferably, the myostatin-selective inhibitor is an antibody, or antigen-binding fragment thereof, that specifically binds to pro/latent myostatin, but does not bind to GDF11, e.g., Ab102, Ab109, Ab130, Ab132, or Ab133. Antibodies that specifically recognize pro/latent myostatin, but not GDF11, are beneficial and avoid undesirable toxicity caused by off-target binding of antibodies to GDF11 in the subject. In one embodiment, the subject is a pediatric subject. In one embodiment, the subject is a subject aged 2-19 years, inclusive of endpoints. In one embodiment, the subject is a subject aged 12 years or older (e.g., 12-17 years), inclusive of endpoints.

In one embodiment, the monoclonal antibody specifically binds and inhibits the activation step of myostatin/GDF8. In some embodiments, such antibodies bind pro-myostatin and/or latent myostatin, and inhibit activation and subsequent release of mature myostatin, but do not bind mature myostatin that is not associated with a latent (inactive) complex. In some embodiments, the antibodies or fragments thereof bind tethered forms (e.g., intramuscular) of inactive myostatin (e.g., pro-myostatin), which have the ability to locally act upon tissue-associated myostatin within a disease niche. In some embodiments, the antibodies or fragments thereof bind soluble forms (e.g., in circulation) of inactive myostatin (e.g., latent-myostatin), which have the ability to act upon circulating latent myostatin that may have endocrine or systemic effects. In any of such embodiments, preferred inhibitors of myostatin for carrying out the methods of the present disclosure are those that are selective for myostatin that do not antagonize other members of the TGFβ superfamily of growth factors/cytokines, such as GDF11. Such selectivity is advantageous particularly in pediatric patient populations and/or patient populations requiring a long-term care (e.g., chronic therapy), where inhibiting other pathways, such as GDF11, may produce harmful or unwanted side effects or adverse events. In any of such embodiments, preferred inhibitors of myostatin for carrying out the methods of the present disclosure comprise Ab102, Ab109, Ab130, Ab132, or Ab133.

Weight Management

Currently available obesity treatment, such as GLP-1 receptor agonists, almost exclusively focuses on weight loss. By comparison, the present disclosure takes into consideration the quality of weight management beyond mere weight loss to achieve improved metabolic health. To this end, it is contemplated that incorporating myostatin inhibitors into a weight management regimen may achieve one or more of the following: preferential loss of fat mass over lean mass; maintaining fat mass loss; prevention of muscle loss; increased muscle mass; increased endurance; reduced fatigue; prevention of bone loss; improved blood glucose levels; and/or improved liver health. Thus, myostatin inhibitors such as the novel antibodies and antigen-binding fragments disclosed herein, may contribute to safe and sustainable weight management, particularly when used in conjunction with another therapy aimed to address metabolic dysregulation.

The present disclosure further provides methods for promoting robust weight loss (e.g., loss of fat mass (i.e., the weight of fat in the body) without concomitant loss of lean muscle mass) in both healthy subjects, e.g., bodybuilders, or in subjects having metabolic diseases, such as obesity, e.g., diet-induced obesity, metabolic syndrome, and/or type 2 diabetes mellitus (T2DM). As compared to dieting alone (e.g., dieting by caloric restriction, low-carbohydrate diet, ketogenic diet, vegan diet, etc.), where weight loss occurs in both fat stores and muscle during dieting, administration of a myostatin inhibitor disclosed herein (e.g., an anti-myostatin antibody or antigen-binding fragment thereof disclosed herein, e.g., Ab102, Ab109, Ab130, Ab132, Ab133, or Ab141) leads to weight loss in fat stores, while sparing the muscle. In some embodiments, administration of the myostatin inhibitor results in about a 5%, about 10%, about 15%, or about 20% or greater loss of fat mass in the subject during the course of treatment.

Body fat mass increases with age in both men and women through middle age. Abdominal fat in particular is associated with higher risk of cardiovascular disease, metabolic syndrome, hypertension, diabetes, or dyslipidemia in a subject when compared to the risk in individuals without abdominal obesity. Fat mass or abdominal fat mass may be measured directly by dual energy X-ray absorptiometry, ultrasound, computed tomography, or magnetic resonance imaging (e.g., qNMR). Clinically, abdominal obesity is defined as a waist circumference of 102 cm or greater in men, and 88 cm or greater in women.

In some embodiments, administration of a myostatin inhibitor disclosed herein (e.g., an anti-myostatin antibody or antigen-binding fragment thereof disclosed herein, e.g., Ab102, Ab109, Ab130, Ab132, Ab133, or Ab141) may result in more robust weight loss due to the maintenance of a higher metabolic rate; improved cardiometabolic benefits (such as lipid profile, glucose metabolism, cardiovascular risk, etc.); and higher reduction in fat (e.g., total fat or visceral fat and/or other deleterious fat levels) as compared to dieting or administration of another standard therapy alone. Additionally, administration of the myostatin inhibitor therapy may prevent or reduce muscle atrophy and/or bone loss which can occur concomitantly with a diet, e.g., a caloric restriction diet, a low-carbohydrate diet, a ketogenic diet, etc. Overall, administration of a myostatin inhibitor disclosed herein (e.g., an anti-myostatin antibody or antigen-binding fragment thereof disclosed herein, e.g., Ab102, Ab109, Ab130, Ab132, Ab133, or Ab141) may increase the ratio of muscle to fat in the subject.

In subjects with a metabolic disease, e.g., obesity, metabolic syndrome and/or diabetes, e.g., T2DM, administering a myostatin inhibitor disclosed herein (e.g., an anti-myostatin antibody or antigen-binding fragment thereof disclosed herein, e.g., Ab102, Ab109, Ab130, Ab132, Ab133, or Ab141) enables prevention or mitigation of lowering of the metabolic rate in a subject, and prevention or reduction of lean muscle loss. The myostatin inhibitor therapy may be combined with another standard therapy, e.g., a diet, e.g., a caloric restriction diet. In some embodiments, a moderate calorie restriction diet is recommended, as this provides for better patient compliance and better long-term outcomes since subjects do not have to adhere to austere, aggressive diets, e.g., aggressive caloric restriction diets.

Such treatments are particularly useful for subjects who have limitations on physical activity, e.g., subjects having an orthopedic injury, spinal cord injury, musculoskeletal disease, a pulmonary disorder, a cardiovascular disorder, a neurologic disorder, severe obesity, etc. In such subjects, administration of the myostatin inhibitor therapy prevents muscle atrophy and/or bone loss which are more prominent in these subjects due to their limitations on physical activity. In some embodiments, such a treatment enables subjects with limitations on physical activity to undergo a more robust diet, e.g., caloric restriction diet, because they are no longer limited by concerns regarding muscle loss or bone loss due to the administration of the myostatin inhibitor.

In some embodiments, the subject is on a diet regimen, but is not on an exercise regimen. In some embodiments, the subject is on an exercise regimen, but is not on a diet regimen. In some embodiments, the subject is on a diet regimen, and an exercise regimen. Examples of a diet regimen include, but are not limited to, caloric restriction (e.g., reduced calorie intake or reduced absorption of calories), diets with modified nutrient content (e.g., high protein, low fat, low carbohydrate, keto, paleo, etc.) or modified timing of food intake (e.g., intermittent fasting, increased frequency of feeding, etc.) or a combination of modified timing, portion size, and nutrient content (e.g., more frequent meals of smaller portions containing high protein, low fat, and/or other nutrient content restrictions).

While the availability of GLP-1 receptor agonists has made a tremendous impact on the treatment of obesity in recent years, rapid weight loss is associated with reduced bone density. Applicant previously showed that selective inhibition of myostatin can enhance bone (PCT/US2018/012686, the contents of which are hereby incorporated by reference in their entirety). This, coupled with the observation that GDF11 can exert a beneficial effect on the bone, suggests that the myostatin-selective approach may provide advantages over non-selective approaches in preventing bone loss during obesity treatment. For instance, Suh et al. reports that GDF11 promotes osteogenesis and that follistatin increases muscle mass but weakens bone (Proc Natl Acad Sci USA. 2020 Mar. 3; 117(9):4910-4920; doi: 10.1073/pnas.1916034117). As such, it is contemplated that inhibition of GDF11 may be detrimental to bone health and that selectivity of myostatin inhibition (e.g., over Activin A or GDF11 inhibition) may be beneficial in preventing bone loss.

Accordingly, the present disclosure encompasses methods of using a myostatin-selective inhibitor for preventing bone loss, e.g., during weight loss and/or treatment of a metabolic disorder. In some embodiments, the myostatin-selective inhibitor does not cause a reduction in bone mineral density as compared to baseline, as measured by dual-energy x-ray absorptiometry. In some embodiments, the myostatin-selective inhibitor is an antibody or antigen-binding fragment thereof that inhibits myostatin but does not inhibit GDF11 or Activin A. In some embodiments, the myostatin-selective inhibitors include but are not limited to neutralizing antibodies that bind mature myostatin and thereby prevent or interfere with receptor binding, and activation antibodies that bind pro/latent myostatin, and inhibit activation of myostatin. In some embodiments, the myostatin-selective inhibitor is any one of the antibodies or antigen-binding fragments disclosed herein. In preferred embodiments, the myostatin inhibitor is an inhibitor that selectively targets pro/latent myostatin, e.g., Ab109, Ab133, or Ab141. In a preferred embodiment, the myostatin inhibitor is Ab109.

Diseases Associated with Impaired Neurological Signaling

The antibodies and antigen binding fragments disclosed herein may be useful for the intervention of conditions involving defects in communication between muscle and its innervating neurons. The spinal cord houses major nerves that control motor function. Thus, the disclosure provides methods for treating or preventing diseases associated with impaired neurological signaling between a neuron and a target tissue that expresses myostatin in subjects, e.g., human subjects. A disorder may be, for example, injury-based (e.g., a spinal cord injury) or genetic (e.g., resulting from a genetic mutation, e.g., SMA).

In some embodiments, the methods include administering to a subject suffering from a disease associated with an impaired neurological signaling between a neuron and a target tissue an effective amount of a myostatin inhibitor, e.g., an antibody, or antigen binding fragment thereof, that specifically binds myostatin and inhibits myostatin signaling, thereby treating or preventing the disease associated with the impaired neurological signaling in the subject. Preferably, the antibody, or antigen binding fragment thereof, specifically binds to pro/latent myostatin, but does not bind to mature GDF11. In some embodiments, such antibody or fragment does not bind mature myostatin/GDF8. In some embodiments, the antibodies suitable for carrying out these embodiments include Ab102, Ab109, Ab130, Ab132, Ab133, and Ab141.

As used herein, term "disease with an impaired neurological signaling" refers to any disease or disorder that is caused by, or associated with, a disrupted signal transduction or a breakdown in communication between a neuron and its target tissue(s), e.g., a muscle tissue, a brain tissue, a liver tissue, a blood vessel tissue, or an adipose tissue. In some embodiments, the impaired neurological signaling occurs due to a damage in the neuron structure, where neurons are incapable of transmitting signals towards their targets. In other embodiments, the structures of neurons remain intact, but there are functional disruption or defects, for example, a blockage at the neuromuscular junction, such that the ability of neurons to transmit signals is affected.

In some embodiments, "disease with an impaired neurological signaling" refers to disease or condition associated with denervation, e.g., a partial loss or perturbation of nerve supply or neuronal input to its target, such as muscle. In some embodiments, denervation is induced by injury. In some embodiments, denervation is associated with a disease, such as a genetic disease. In cases of genetic diseases, in some embodiments, the patient may be diagnosed with the genetic disease by genetic screening. In some embodiments, such genetic screening may be performed in a fetal, neonatal or pediatric subject. Non-limiting examples of diseases with an impaired neurological signaling include, for example, vocal cord paresis/paralysis, spinal cord injury (SCI), myasthenia gravis, amyotrophic lateral sclerosis (ALS), Alzheimer's disease, Parkinson's disease, bulbar muscular atrophy, and spinal muscular atrophy (SMA).

Spinal Cord Injury

The methods of the present disclosure are suitable for treating or preventing conditions with an impaired neurological signaling due to nerve injury. In some embodiments, such condition is spinal cord injury (SCI). As used herein, the term "spinal cord injury" refers to damage to any part of the spinal cord or nerves at the end of the spinal canal. Spinal cord injury often causes permanent changes in strength, sensation and other body functions below the site of the injury. There are no therapies in development directed at reversing or reducing muscle atrophy in SCI and this represents a large unmet need. Additionally, therapies to treat metabolic conditions that develop as a consequence of SCI are also needed.

SCI patients are stratified based on the level (paraplegia vs. tetraplegia) and the completeness of the lesion (complete vs incomplete). This stratification has been developed into the American Spinal Injury Association (ASIA) Impairment scale (Roberts, et al. ((2017) Clin Orthop Relat Res 475: 1499), with two broad groups based on level of paralysis: complete (AIS grades A/B) and incomplete (AIS grades C/D/E). There are 7 cervical (neck), 12 thoracic (chest), 5 lumbar (back), and 5 sacral (tail) vertebrae. A lesion in SCI may occur at any location along the vertebrae. With a complete spinal cord injury, the cord is unable to send signals below the level of the injury. As a result, patients are paralyzed below the injury. With an incomplete injury, patients will have some movement and sensation below the injury.

There are multiple phases associated with spinal cord injury. Subjects may be in an acute spinal cord injury phase immediately after injury, where diagnosis between complete and incomplete injury is generally difficult, due in part to the trauma and associated inflammation. Typically, the acute phase is defined as the initial in-hospital period following the event/injury in acute medical/surgical care, which is generally around ~2 weeks A subject may be in a sub-acute spinal cord injury phase, where there is a distinction between complete and incomplete spinal cord injury, and recovery is possible through ongoing rehab. Typically, the sub-acute phase constitutes ~2 weeks up to ~18 months post injury (e.g., 3-6 months post-injury). Yet further, a subject may be in a chronic spinal cord injury phase which generally starts around 6-12 months after the time of injury, where patients have demonstrated substantial decrease in rate of recovery or when rehab efforts have reached a stable phase (e.g., plateau) despite the ongoing standard of care efforts.

Muscle strength may be graded according to the maximum strength attained, no matter how briefly that strength is maintained during the examination. The muscles are tested with the patient supine. Motor level is determined by the most caudal key muscles that have muscle strength of 3 or above while the segment above is normal (=5). Motor index scoring uses the 0-5 scoring of each key muscle, with total points being 25 per extremity and with the total possible score being 100. Lower extremities motor score (LEMS) uses the ASIA key muscles in both lower extremities, with a total possible score of 50 (i.e., maximum score of 5 for each key muscle [L2, L3, L4, L5, and S1] per extremity). A LEMS of 20 or less indicates that the patient is likely to be a limited ambulator. A LEMS of 30 or more suggests that the individual is likely to be a community ambulator.

Monitoring functional outcomes and quality of life in SCI patients is a complex task as selection of the appropriate functional measure depends upon the completeness and level of injury. One common measure which is applicable to all patients is the functional independence measure (FIM) which is a 7-point scale designed to quantify the dependence of a patient on a caregiver. An additional metric for measuring quality of life which has had recent attention is the SCI-QOL, which integrates both functional skills and emotional health of the patient (Tulsky 2015, J Spinal Cord Med. 38(3): 257-69). Many other functional outcome measures have been outlined by the SCIRE project.

In some embodiments, meaningful clinical effects achieved by administration of an effective amount of the myostatin inhibitor described herein to SCI patients may correspond to at least a 6 point (>6) increase from baseline in total motor score of ASIA at, e.g., week 24. In some embodiments, meaningful clinical effects achieved by administration of an effective amount of the myostatin inhibitor described herein to SCI patients may correspond to statistically significant difference in the mean total SCIM III score between treated and untreated/control groups at Day 112 (+/−7 days). In some embodiments, meaningful clinical effects achieved by administration of an effective amount of the myostatin inhibitor described herein to SCI patients may correspond to greater than a 4 point (>4) increase in Functional Independence Measure for Locomotion (FIM-L) score.

Individuals with spinal cord injury have an increased prevalence of abnormalities in carbohydrate and lipid metabolism associated with immobilization, muscle atrophy, and increased adiposity. The body composition is substantially altered and typified by rapid and long-term decline in metabolically active muscle mass and bone with stark increases in central adiposity. The latter contributes to a maladaptive metabolic profile favoring substantial gain in body mass occurring 2-7 months following injury. Occurring together these co-morbid risk factors incite all-cause cardiovascular disease, diabetes, and risk clustering as cardiometabolic disease, the latter including component hazards for dyslipidemia, glucose intolerance and insulin resistance.

Rapid and profound muscle wasting affects those with a spinal cord injury and impacts the entire body, not just the denervated limbs. Muscle loss is believed to be due to a combination of factors including denervation (of the paretic limbs), immobilization, inflammation, factors released by the paralyzed muscle, steroid use, infections, and lack of nutrition. A large percentage (~30%) of lean muscle mass is lost in the first six weeks following injury (the acute phase). This accelerated rate of lean mass loss continues on into chronic conditions with a decrease in lean mass (per decade) of 3% for tetraplegia and 2.4% for paraplegia (as compared to a decline of 1% seen in healthy controls) (Spungen 2003). This accelerated muscle atrophy contributes to premature sarcopenia.

An SCI patient experiences profound changes in total body composition. In particular, lean muscle mass is replaced with fat mass, on average an SCI patient has 13% more fat tissue per unit BMI than a healthy control, with a significant increase in intramuscular fat (Spungen 2003, Gorgey 2007). This whole-body change in composition (~60-70% are obese) has profound impacts on metabolism which is evidenced by increased prevalence of cardiovascular disease, type II diabetes, and thyroid disorders.

Mechanical unloading following spinal cord injury also translates into disruptions in bone homeostasis. SCI patients have reduced bone mineral content, develop osteoporosis, and suffer from increased rates of fractures (as many as 50% of SCI patients will experience a fracture post injury) (Battaglino 2013). A fracture leads to hospitalization and can have profound consequences by increasing the risk for developing pressure ulcers, contractures of the knee and hip, and for experiencing a hypertensive crisis.

Overall increases in lean mass and decrease in fat mass in SCI patients can be monitored by several well-validated methods, such as thigh or upper arm muscle volume by magnetic resonance imaging, or total body composition by dual-energy x-ray absorptiometry or DEXA. Such measurements are routinely performed in the field.

Outcome or progress of therapy (e.g., overall clinical effects) may be measured by using any of well-characterized tests commonly employed for evaluating SCI clinical practice. These tests are useful for i) providing information on each measure's clinical utility and psychometric properties; ii) assisting clinicians to select appropriate measures tailored to particular patient(s); iii) identifying individuals who may benefit from a certain therapy; iv) monitoring progress; v) evaluating whether treatments are effective; and/or, vi) help programs improve services to patients and medical professionals.

Based on the effects of myostatin on muscle mass and metabolism, a myostatin inhibitor, e.g., an anti-myostatin antibody or antigen-binding portion thereof, can potentiate a number of long-term health consequences (which may be measured by one or more standardized tests/tools such as those listed above) which affect those living with SCI, and would cause clinically meaningful benefits to patients at the time of injury and/or in chronic conditions. Indeed, the present inventors surprisingly discovered that specific inhibition of myostatin activation by a myostatin inhibitor, e.g., an anti-pro/latent myostatin antibody had a positive impact on muscle function in the subjects, including in muscles below the injury or lesion. Specifically, administration of the myostatin inhibitor, e.g., anti-pro/latent myostatin antibody, to a partial denervation animal model not only prevented muscle atrophy and increased muscle mass in the injured subjects, but also enhanced the function of the injured muscle, as well as prevented metabolic dysregulation associated with neuron injuries and, thus, improving the overall metabolic health of the subjects which may provide significant long term benefits.

Whilst myostatin inhibition is effective in treating muscle atrophy and metabolic dysfunction caused by partial/incomplete SCI (such as severe contusion SCI) as described above, where the function of innervating motor neurons is at least partially intact, the inventors of the present disclosure further contemplate the use of a myostatin inhibitor, such as those described herein, in the treatment of complete SCI (e.g., complete transection), used in conjunction with a nerve stimulator.

Previously published work indicated that myostatin inhibition was ineffective in ameliorating complete transection injuries of the spinal cord or sciatic nerve. For example, it has been reported that prophylactic administration of a soluble ActRIIB ligand trap showed no therapeutic effect on muscle atrophy or bone loss in sublesional hind limbs in a complete transection model of SCI in mice (Graham 2015). The same study still showed increased mass of supralesional muscle, suggesting that myostatin inhibition is ineffective in the context of denervated muscle. In support of this, a separate study showed that prophylactic administration of soluble ActRIIB ligand trap failed to prevent muscle atrophy following complete transection of the sciatic nerve (MacDonald 2014).

Nevertheless, based on Applicant's previous recognition that effectiveness of myostatin inhibition at least in part depends on neuronal signaling from the innervating motor neurons (see, for example, PCT/US2017/037332), it is contemplated that myostatin inhibitor therapy, in conjunction with neuronal stimulation, may enhance therapeutic effects in complete SCI. Studies in rats and human patients with complete transection SCI suggest that a therapeutic neuronal stimulation regimen may protect against sublesional muscle atrophy, the conversion from slow twitch to fast fatigable muscle, and bone loss, while increasing muscle strength and decreasing blood glucose and insulin compared to control (Wu 2013; Adams 2011; Shields 2006; Griffin 2007). Thus, contrary to the general consensus in the art that myostatin inhibition appears ineffective in treating complete transection nerve injuries, it is contemplated herein to use a myostatin inhibitor, preferably an inhibitor of myostatin activation, in the treatment of patients inflicted with complete SCI to enhance clinical benefits of nerve stimulation.

Spinal Muscular Atrophy (SMA)

Myostatin inhibition has been shown to be an effective approach to enhance motor function in SMA, which is a genetic disease associated with impaired neuromuscular signaling due to mutations in the Smn1 gene. This concept is captured in more detail in, for example, PCT/US2017/012606, PCT/US2017/037332, and PCT/US2021/056517, the contents of which are hereby incorporated in their entirety. Clinical benefits of myostatin inhibition in SMA may further include prevention or amelioration of bone loss or fracture. In some embodiments, subjects with SMA who receive myostatin inhibitor therapy, such as those described herein, may show beneficial clinical effects.

The present disclosure includes the use of myostatin inhibitors in the treatment of SMA in an amount effective to protect against (e.g., prevent or retard) bone loss, and/or reduce the frequency and/or degree of bone fracture in these patients. In some embodiments, SMA patients include those on neuronal corrector therapy. In some embodiments, SMA patients have not received or are not candidates for a neuronal corrector therapy. In some embodiments, the SMA patients who are not candidates for a neuronal corrector therapy have undergone a spinal fusion procedure. In some embodiments, SMA patients have ambulatory SMA (such as Type III). In some embodiments, SMA patients are non-ambulatory (such as Type I and severe forms of Type II).

Other Muscle Conditions and Disorders

In some embodiments, the antibodies and antigen-binding fragments of the disclosure are suitable for treating or preventing muscle conditions and disorders. As used herein, the term "muscle condition" or "muscle disorder" refers to a disease, condition, or disorder, where the muscle does not function normally, or a disease, condition, or disorder, where the function of muscle is normal, but there are less force generated by the muscle due to a reduced amount of muscle available. A muscle condition or disorder may include, without limitation, a myopathy, muscular atrophy, a muscular dystrophy, etc. Such conditions may be caused by a defect or defects in a motor neuron, a genetic mutation, or an injury, such as a nerve injury.

In one embodiment, the muscle condition is a muscular atrophy or muscle dystrophy. Muscle atrophies can result from conditions such as, but not limited to an adult motor neuron disease, aging, amyotrophic lateral sclerosis (AML), autoimmune motor neuropathy, cancer, fasting, immobilization due to trauma, nutritional insufficiency, prolonged bed rest, spinal muscular atrophy, space travel, stroke, or thyroid disorder. Muscle dystrophies include, but are not limited to, Duchenne's, Becker's, facioscapulohumeral (FSH), and Limb-Girdle muscular dystrophies.

In one embodiment, the muscle condition is a myopathy. As used herein, the term "myopathy" refers to a muscular condition characterized by impaired muscle structure or function, typically resulting in muscular weakness. A "myopathy" may also include a muscular condition characterized by normal muscle structure but impaired or abnormal neuronal input, which in turn affects muscle function. A "myopathy" may also include inflammatory myopathies and/or autoimmune myopathies, e.g., myasthenia gravis.

Myopathies include muscular conditions that are neuromuscular or musculoskeletal in nature. In some embodiments, the myopathy is an inherited myopathy. Inherited myopathies include, without limitation, dystrophies, myotonias, congenital myopathies (e.g., nemaline myopathy, multi/minicore myopathy, and centronuclear myopathy), mitochondrial myopathies, familial periodic myopathies, inflammatory myopathies and metabolic myopathies (e.g., glycogen storage diseases and lipid storage disorder). In some embodiments, the myopathy is an acquired myopathy. Acquired myopathies include, without limitation, external substance induced myopathy (e.g., drug-induced myopathy and glucocorticoid myopathy (i.e., induced by treatment with a glucocorticoid, e.g., dexamethasone, cortisol, betamethasone, prednisone, prednisolone, or methylprednisolone), alcoholic myopathy, and myopathy due to other toxic agents), myositis (e.g., dermatomyositis, polymyositis and inclusion body myositis), myositis ossificans, rhabdomyolysis, and myoglobinurias, and disuse atrophy. In some embodiments, the myopathy is disuse atrophy, which may be caused by prolonged disuse of muscles, leading to deterioration of normal muscle function. Disuse atrophy may be a result of hospitalization, bone fracture (e.g., a hip fracture) or by nerve injury. In some embodiments the myopathy is related to a disease or disorder such as amyotrophic lateral sclerosis (ALS), spinal muscular atrophy (SMA), cachexia syndromes due to renal failure, AIDS, cardiac conditions and/or cancer. In some embodiments the myopathy is a myotonia. In some embodiments the myopathy is related to ageing. In some embodiments the myopathy is related to sarcopenia. In some embodiments, the myopathy is related to paraspinal muscle atrophy (PMA).

In some embodiments, the myopathy is a primary myopathy. In one embodiment, a primary myopathy comprises disuse atrophy. In some embodiments, the disuse atrophy is associated with hip fracture, elective joint replacement, critical care myopathy, spinal cord injury or stroke. In some embodiments, the myopathy is a genetic muscle weakness associated with, for example, a muscular dystrophy.

In some embodiments, the myopathy is a secondary myopathy, in which muscle loss or dysfunction is secondary to a disease pathology. In some embodiments, secondary myopathy comprises denervation or cachexia. In some embodiments, the secondary myopathy is caused by a denervation associated with monitor neuron dysfunction. In some embodiments, motor neuron dysfunction is due to genetic mutation(s) that affect motor neurons. Diseases known to involve mutations in motor neurons include, but are not limited to, amyotrophic lateral sclerosis (ALS) and spinal muscular atrophy (SMA). In some embodiments, the secondary myopathy is a cachexia associated with renal failure, AIDS, a cardiac condition, cancer or aging. In some embodiments, the secondary myopathy is caused by a nerve injury, including unwanted nerve injury sustained during a medical procedure, such as surgeries. Detrimental effects of such injury to the function of a target tissue (e.g., target muscle) may be effectively treated by administration of a myostatin inhibitor described herein. For example, such administration may prevent and/or alleviate myopathy, and/or facilitate recovery.

In some embodiments, the methods of the present disclosure are suitable for treating or preventing muscle conditions and disorders, including vocal cord paresis/paralysis. As used herein, the term "vocal cord paresis/paralysis" refers to a condition that results from abnormal nerve input into the voice box muscles (laryngeal muscles). Paralysis may involve the total interruption of nerve impulse, resulting in no movement; paresis may involve the partial interruption of nerve impulse, resulting in weak or abnormal motion of laryngeal muscles. In some embodiments, the anti-myostatin antibody, or antigen binding fragment thereof, is administered locally, for example, via direct local injection into the affected vocal cord muscle(s). Unilateral injection is needed when only one side of the vocal cord is affected, for example, due to a nerve injury on one side. In other embodiments, both sides of the vocal cord are affected when nerves on both sides are injured and, thus, bilateral injection is preferred. In some embodiments, the anti-myostatin antibodies or antigen binding fragments thereof disclosed herein may increase the vocal cord muscle mass locally to close the gap between the two vocal cord folds to restore function. In severe cases, where the gap is too large, surgery may be required to correct it. In such cases of severe vocal cord paresis/paralysis, anti-myostatin antibody, or antigen binding fragment thereof, may be used as an adjunctive therapy with surgery to further close the gap. In some embodiments, the methods of the present disclosure are suitable for treating or preventing mild vocal cord paresis/paralysis for which vocalization function is affected but where a corrective surgery is not necessary. In other embodiments, the methods of the present disclosure are suitable for treating or preventing severe vocal cord paresis/paralysis as an adjunct to surgery or as a primary therapy in situations when surgery is not feasible or too risky.

In some embodiments, the methods of the present disclosure are suitable for treating or preventing muscle conditions and disorders, including paraspinal muscle atrophy (PMA).

In one embodiment, the antibodies, or antigen binding fragments thereof, described herein are used in methods of treatment of a paraspinal muscle atrophy that is a postoperative paraspinal muscle atrophy, i.e., a paraspinal muscle atrophy after a surgery. In one embodiment, the methods of treatment include treating a nerve injury-dependent muscle atrophy. In one embodiment, the methods of treatment as described herein include treating a postoperative nerve injury-dependent muscle atrophy. In one embodiment, the methods of treatment include treating a postoperative muscle atrophy, in which the surgery is a spinal surgery. In one embodiment, the methods of treatment include treating a postoperative muscle atrophy, in which the spinal surgery is a lumbar spine surgery or a lumbar spine procedure, e.g., a lumbar fusion procedure, a lumbar nonfusion procedure, a posterior lumbar fusion procedure, an anterior lumbar fusion procedure, a minimally invasive (MIS) posterior lumbar decompression procedure, a minimally invasive (MIS) posterior lumbar fusion procedure, a non-MIS equivalent procedure, etc. In one embodiment, the methods of treatment include treating a paraspinal muscle atrophy after a lumbar spine fusion procedure. In one embodiment, the methods of treatment include treating a paraspinal muscle atrophy after a posterior lumbar spine fusion procedure. In one embodiment, the methods of treatment include treating a paraspinal muscle atrophy after a non-MIS lumbar fusion procedure. In one embodiment, methods of treatment with the myostatin inhibitors, e.g., antibodies, or antigen binding fragments thereof, described herein results in at least 1%, 2%, 3%, 4%, 5%, 6%, 7%, 8%, 9%, 10%, 12%, 15%, 18%, 20%, or 25% decrease in postoperative paraspinal muscle atrophy. In one embodiment, methods of treatment with the myostatin inhibitors, e.g., antibodies, or antigen binding fragments thereof, described herein results in at least 1%, 2%, 3%, 4%, 5%, 6%, 7%, 8%, 9%, 10%, 12%, 15%, 18%, 20%, or 25% decrease in postoperative nerve injury-dependent paraspinal muscle atrophy.

Another aspect of the disclosure includes a method of treating a subject having a disease or condition related to congenital myopathies or musculoskeletal disease. Exemplary congenital myopathies include, without limitation, hereditary distal myopathy, X-linked myotubular myopathy, autosomal dominant centronuclear myopathy, autosomal recessive centronuclear myopathy, nemaline myopathy, and congenital fiber-type disproportion myopathy. Exemplary musculoskeletal diseases include, without limitation, osteoporosis, a bone fracture, short stature, and dwarfism.

Another aspect of the disclosure includes a method of treating a subject having a muscle disease or condition related to muscular dystrophies. Exemplary muscular dystrophies include, without limitation, Duchenne's, Becker's, facioscapulohumeral (FSHD), Emery-Dreifuss, oculopharyngeal, scapulohumeral, Fukuyama, and limb-girdle muscular dystrophies.

Chronic Inflammation

It has been observed that chronic inflammation can lead to muscle atrophy and/or bone loss (e.g., reduced bone density), and this process may at least be mediated by myostatin signaling.

For example, IPF is characterized by chronic inflammation of the lung and associated fibrosis. Skeletal muscle atrophy is a common complication of IPF. See, for example, Ito et al. Respir Investig 2023 61(4):371-378.

Similarly, chronic inflammation is a hallmark of chronic kidney disease (CKD), which is often associated with kidney fibrosis and inflammation-induced anemia. In mice with CKD, myostatin expression is elevated by 2 to 3-fold in muscle, which is at least in part mediated by increased levels of inflammatory cytokines. In a murine model of CKD, myostatin inhibition has been shown to suppress systemic inflammation and muscle atrophy (Zhang et al. 2011. FASEB J. 25(5):1653-1663).

In rheumatoid arthritis (RA), which is an autoimmune condition characterized by chronic inflammation and progressive joint destruction, myostatin is overexpressed in the joint, which is the primary site of inflammation and impaired bone homeostasis. It is postulated that elevated levels of inflammatory cytokines such as IL-6 and TNF-α, may be involved in this process. Dankbar et al (Ann Rheum Dis. 2011. 70(Suppl 2):A1-A94) reported that myostatin is highly expressed in RA synovial tissues as compared to wild type, which may induce osteoclast development. Conversely, lack of myostatin ameliorated the clinical severity of arthritis and improved joint damage, displayed less bone erosion and inflammation in mouse models.

Similarly, patients with inflammatory bowel disease (IBD), including Crohn's disease (CD) and ulcerative colitis (UC), which are autoimmune conditions, commonly suffer from muscle impairment (e.g., weak muscle) and are characterized by increased circulating levels of pro-inflammatory cytokines, such as TNF-alpha, IL-6, and myostatin. It is reported that 42% of IBD patients suffer from sarcopenia (reviewed in: Front. Immunol., 13 Jul. 2021 Sec. Autoimmune and Autoinflammatory Disorders, Volume 12-2021).

Obesity may also constitute a form of chronic inflammation. The excess of macronutrients in the adipose tissues stimulates them to release inflammatory cytokines such as IL-6 and TNF-α, leading to a pro-inflammatory environment and oxidative stress (reviewed in: Ellulu et al. 2017. Arch Med Sci. 13(4):851-863), which are associated with metabolic dysregulation, such as insulin resistance, diabetes, as well as cardiovascular disease. Notably, in diabetic patients, high blood sugar over time causes damage to the kidney, impairing its function. As a result, one in three adult diabetic patients also suffer from CKD. CKD may comprise diabetic nephropathy.

Taken together, these observations suggest that myostatin inhibition may mitigate bone destruction and muscle atrophy associated with chronic inflammation. It is therefore contemplated herein that myostatin may function as a common link between metabolic regulation and inflammation.

Accordingly, the present disclosure encompasses therapeutic use of myostatin inhibitors to treat chronic inflammation. In some embodiments, a myostatin inhibitor is used in the treatment of chronic inflammation in a subject, wherein the treatment comprises administration of a myostatin inhibitor in an amount sufficient to alleviate the inflammation and associated dysregulation, such as muscle atrophy and bone metabolism. Chronic inflammation may include, without limitation, inflammation associated with CKD, inflammation associated with NASH, inflammation associated with NAFLD, inflammation associated with IPF, inflammation associated with autoimmune disorders such as RA and IBD, inflammation associated with pancreatitis, inflammation associated with muscle disorders (e.g., inflammatory myopathies, myositis), inflammation associated with diabetes, inflammation associated with diabetic retinopathy, inflammation associated with ocular myositis, inflammation associated with eye muscle weakness such as with myasthenia gravis, inflammation associated with age-related macular degeneration, and inflammation associated with obesity. In some embodiments, inflammation associated with diabetes is diabetic nephropathy. In some embodiments, inflammation associated with diabetes is diabetic retinopathy. In preferred embodiments, the myostatin inhibitor is a myostatin-selective inhibitor (i.e., agents that selectively inhibit myostatin signaling, as opposed to agents that also inhibit additional growth factor signaling such as GDF11 and Activin A). Examples of myostatin-selective inhibitors include, without limitation, the antibodies and antigen-binding fragments of the novel myostatin inhibitors disclosed herein, apitegromab, trevogrumab, GYM329, and any variants thereof. In preferred embodiments, the myostatin selective inhibitor is an antibody or antigen binding fragment selective for pro/latent myostatin, e.g., any one of Ab101-141 or an antigen binding fragment thereof.

Other Diseases and Disorders

In some embodiments, the present disclosure encompasses a method of treating a brain disease or disorder related to improvement of glucose tolerance and/or insulin sensitivity, such as Alzheimer's disease, Parkinson's disease, stroke or diabetic neuropathy.

Another aspect of the disclosure includes a method of treating a subject having a urogynecological related disease or condition, glottic disorder, e.g., stenosis, extraocular myopathy, carpal tunnel, Guillain-Barre, or osteosarcoma.

In some embodiments, the present disclosure encompasses a method of treating a subject having a disease or condition related to cachexia. Exemplary diseases and conditions related to cachexia include, without limitation, cancer, chronic heart failure (CHF), acquired immune deficiency syndrome (AIDS), chronic obstructive pulmonary disease (COPD), and chronic kidney disease (CKD).

In some embodiments, a myostatin inhibitor is used in the treatment of CKD in a subject, wherein the treatment comprises administration of a myostatin inhibitor to treat CKD (e.g., slow the progression of CKD and/or improve kidney function). In some embodiments, the subject has dialysis-dependent CKD. In other embodiments, the subject has dialysis-independent CKD. In some embodiments, the myostatin inhibitor is used in combination with or adjunct to a GLP-1 receptor agonist (e.g., semaglutide). In some embodiments, the myostatin inhibitor is used to treat patients who are on a GLP-1 receptor agonist therapy. In some embodiments, the subject may further receive a therapy for anemia, such as HIF-PH inhibitors (HIF stabilizers) and RGMc inhibitors. In some embodiments, the patient is prediabetic, diabetic, and/or obese/overweight. In some embodiments, the diabetic patient has stage 1 kidney disease (e.g., there is mild kidney damage but kidney function is normal with an estimated glomerular filtration rate (eGFR) of >90 mL/min/1.73 m$^2$). In some embodiment, the diabetic patient has stage 2 kidney disease (e.g., kidney damage with some loss of function and an eGFR of 60-89 mL/min/1.73 m$^2$). In some embodiments, the diabetic patient has stage 3 kidney disease (e.g., mild to severe loss of function and a GFR of 30-59 mL/min/1.73 m$^2$). In some embodiments, the diabetic patient has stage 4 kidney disease (e.g., severe loss of function and a GFR of 15-29 mL/min/ 1.73 m$^2$).

In some embodiments, myostatin inhibitor is used in combination with or adjunct to a SGLT2 inhibitor for treating CKD in a subject. In some embodiments, the subject has lower estimated glomerular filtration rate (eGFR) (e.g., eGFR<60 mL/min/1.73 m$^2$) and/or higher urine albumin-creatinine ratio (uACR) (e.g., uACR>300 mg/g) than a healthy subject. In some embodiments, the subject has diabetes. In other embodiments, the subject does not have diabetes.

In some embodiments, myostatin inhibitor is used in combination with or adjunct to a SGLT2 inhibitor for treating Type 2 diabetes, for slowing the progression of kidney disease, for reducing heart failure, and/or for lowering the risk of kidney failure and death.

A significant fraction of cancer patients suffers from cachexia and/or bone loss/frequent bone fractures. In some embodiments, the present disclosure encompasses myostatin inhibitors such as those described herein for use in treating cancer patients, wherein the treatment to not only prevents muscle loss but also prevents bone loss and reduces the frequency and/or severity of bone fractures.

In some embodiments, any metabolic bone diseases or diseases associated with bone loss (such as cancer) may be treated with a combination of a myostatin inhibitor and at least one other therapy, such as TGFβ inhibitor (preferably a TGFβ1 inhibitor) and/or other bone-protective agents, e.g., bisphosphonates, calcium, vitamin D, RANKL inhibitors, etc.

In some embodiments, the present disclosure encompasses a method of treating a subject having a disease or condition related to rare diseases. Exemplary rare diseases and conditions include, without limitation, osteogenesis imperfecta, sporadic inclusion body myositis, and acute lymphoblastic leukemia.

In some embodiments, the present disclosure encompasses a method of treating a subject having a lysosomal storage disorder comprising administering to the subject an effective amount of a myostatin inhibitor described herein. In some embodiments, the lysosomal storage disorder is a glycogen storage disease, wherein optionally the glycogen storage disease is Pompe disease.

Use of various agents (e.g., medications), such as glucocorticoids, immunologic drugs and antimicrobials, is associate with myopathies. Examples of such agents known to cause myopathy include: alcohol and toluene; checkpoint inhibitor immunotherapy (e.g., pembrolizumab, nivolumab); corticosteroids (e.g., prednisone); cholesterol-lowering drugs (e.g., statins); amiodarone; colchicine; chloroquine; antivirals and protease inhibitors used in the treatment of HIV infection; and omeprazole. Accordingly, it is contemplated herein that a myostatin inhibitor, such as those disclosed herein, may be used in the treatment of drug-induced myopathy in a subject.

In some embodiments, the drug-induced myopathy is associated with the use of statin (i.e., statin-induced myopathy). In some embodiments, the drug-induced myopathy is associated with the use of SGLT2 inhibitor (i.e., SGLT2 inhibitor-induced myopathy). See, for example: Gupta et al. Myopathy Associated With Statins and SGL-2—A Review of Literature. Curr Probl Cardiol. 2021 April; 46(4):100765.

In preferred embodiments, the myostatin inhibitor used to treat drug-induced myopathy in a subject is a myostatin-selective inhibitor, wherein optionally the myostatin-selective inhibitor is selected from Ab101-Ab141 disclosed herein, trevogrumab and GYM329. In most preferred embodiments, the myostatin selective inhibitor is an antibody or antigen binding fragment selective for pro/latent myostatin, e.g., any one of Ab101-141. In any of the embodiments, the subject is treated with or is on a therapy known to cause myopathy. Administration of the myostatin inhibitor is aimed to ameliorate the drug-induced myopathy.

Use of Myostatin Inhibitors in Conjunction with One or More Additional Therapies The disclosure encompasses pharmaceutical compositions and related methods used in combination or as adjunct therapies for treating subjects who may benefit from myostatin inhibition in vivo. In any of these embodiments, such subjects may receive therapies that include a first composition comprising a myostatin inhibitor (e.g., an antibody or antigen-binding fragment thereof as described herein) in conjunction with a second composition comprising at least one additional therapeutic intended to treat the same or overlapping disease or clinical condition. Alternatively, in some embodiments, the myostatin inhibitor may be the second composition in the therapy. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for simultaneous or sequential administration of the therapies. The term "concurrent administration," as used herein, may include co-formulated therapeutics being administered together, or separately formulated therapeutics being administered at the same time, e.g., simultaneously, or, in some embodiments, on the same day. The term "sequential administration," as used herein, includes therapeutic regimens in which therapeutics are administered at separate times. In some embodiments, a subject receives concurrent administration of two or more therapies when subject is on one or more first therapeutic(s) at the beginning of the treatment regimen and one or more second therapeutic(s) is/are added to the regimen at a specific point during the treatment.

In some embodiments, the myostatin pathway inhibitor used in the combination or adjunct therapy is an antibody or antigen-binding fragment thereof which bind mature myostatin (e.g., trevogrumab), pro/latent myostatin (e.g., apitegromab, GYM329, any one of the novel antibodies disclosed herein), or its receptors (e.g., ActRIIB and/or ActRIIA) (e.g., bimagrumab); small molecule antagonist of a receptor (e.g., Alk4 inhibitor), ligand trap comprising a soluble fragment(s) of ligand-binding portions of receptor(s); anti-myostatin adnectin (e.g., taldefgrobep alfa), follistatin or variant thereof, etc. In some embodiments, the myostatin pathway inhibitor is a myostatin inhibitor that does not cause a reduction in bone mineral density as compared to baseline, as measured by dual-energy x-ray absorptiometry. In preferred embodiments, the myostatin pathway inhibitor is a selective myostatin inhibitor, e.g., an antibody or antigen-binding fragment thereof that inhibits myostatin but does not inhibit GDF11 or Activin A. In some embodiments, the selective myostatin inhibitors include but are not limited to neutralizing antibodies that bind mature myostatin and thereby prevent or interfere with receptor binding (e.g., trevogrumab), and activation antibodies that bind pro/latent myostatin, and inhibit activation of myostatin (e.g., apitegromab and GYM329). In some embodiments, the myostatin-selective inhibitor is an antibody or antigen-binding fragment thereof comprising all six CDRs of any one of Ab101-Ab141, e.g., the set of SEQ ID NOs identified for a specific antibody in Tables 2d-f. In some embodiments, the myostatin-selective inhibitor is an antibody or antigen-binding fragment thereof comprising the heavy and light chain variable domains of any one of Ab101-Ab141, e.g., the pair of SEQ ID NOs identified for a specific antibody in Table 3. In some embodiments, the myostatin-selective inhibitor is an antibody comprising the heavy and light chains of any one of Ab101-Ab141, e.g., the pair of SEQ ID NOs identified for a specific antibody in Table 4. In preferred embodiments, the myostatin selective inhibitor is an antibody or antigen binding fragment selective for pro/latent myostatin, e.g., any one of Ab101-141. In most preferred embodiments, the myostatin inhibitor is an inhibitor that selectively and potently 99: targets pro/latent myostatin, e.g., Ab109, Ab133, or Ab141. In a preferred embodiment, the myostatin inhibitor is Ab109.

In some embodiments, pharmacologically targeting muscle can improve the effects (e.g., synergistic effects) of GLP-1 pathway activator-mediated weight loss and/or body composition improvement (e.g., GLP-1 receptor agonist-mediated weight loss and/or body composition improvement). In some embodiments, pharmacologically targeting the muscle can be achieved with a myostatin inhibitor, e.g., any agents that inhibit the myostatin signaling pathway, irrespective of the mechanism of action.

In some embodiments, the myostatin inhibitor is used in conjunction with (e.g., administered in combination with) one or more therapies other than a GLP-1 receptor agonist (i.e., treatment where a GLP-1 receptor agonist is not used). In some embodiments, the one or more additional therapies comprise a biguanide, e.g., metformin. In some embodiments, the one or more additional therapies comprises a chloride intracellular channel 1 (Clic1) inhibitor. In some embodiments, the one or more additional therapies comprises a clic inhibitor and/or metformin. In some embodiments, the one or more additional therapies comprise diet and/or exercise, wherein diet and/or exercise is administered as an adjunct therapy. In some embodiments, therapies comprising myostatin inhibitors, myostatin-selective inhibitors in particular, may serve as a backbone for treating obesity, not only to effectuate overall body weight loss, but to enhance metabolic health by improving body composition. In some embodiments, these therapies can achieve a greater degree of fat loss relative to lean mass in patients. In some embodiments, these therapies can maintain lean mass i.e., prevent lean mass loss) in patients going through weight loss. In some embodiments, the one or more additional therapies comprises a cell therapy, e.g., insulin-producing cells for treating diabetes.

A. Therapies Comprising a Myostatin Inhibitor and a GLP-1 Receptor Agonist

Glucagon-like peptide-1 (GLP-1), an incretin, is a potent stimulator of insulin secretion, an inhibitor of glucagon secretion, and a regulator of energy homeostasis. By increasing the synthesis and release of insulin, it decreases blood glucose. It also inhibits gastric mobility and plays a role in decreasing food intake and modulating the brain-based motivation/reward systems, e.g., to promote satiety (Smith et al. (2019) Neurochem Int 128:94.). GLP-1 is produced by the cleavage of proglucagon in pancreatic alpha cells and endocrine cells in the gastrointestinal tract. It has a short half-life, ranging from two to eleven minutes, thus, longer lasting analogues have been developed which delay its metabolism and increase its circulating half-life. These GLP-1 analogues can act as receptor agonists and improve the clinical efficacy of GLP-1 activity.

GLP-1 receptor agonists are widely in use for the treatment of weight loss, obesity and/or diabetes. Dulaglutide (Trulicity®), exenatide (Byetta®), exenatide extended release (Bydureon®), liraglutide (Saxenda®/Victoza®), lixisenatide (Adlyxin®), semaglutide (Ozempic®/Rybelsus®), and tirzepatide (Mounjaro®/Zepbound®)) have been approved by the United States Food and Drug Administration. However, both tolerability and durability are a concern. They require a prolonged, e.g., six-month, dose escalation in an attempt to improve tolerability and minimize side effects. Even so, gastrointestinal side effects such as nausea, vomiting, and diarrhea are common. In the SURPASS-2 trial, 40-45% of the subjects on semaglutide or tirzepatide reported mild to moderate gastrointestinal adverse events. Weiss et al (2022) BMJ Open Diabetes Res Care 10:e002517 reported a 45% discontinuation rate at 12 months and a 65% discontinuation rate at 24 months. Discontinuation leads to body weight regain and loss of cardiometabolic benefits, as evidenced by an increase in systolic blood pressure and an increase in HbA1c levels (STEP1 Trial, NCT03548935).

Furthermore, the FDA currently requires that GLP-1 receptor agonists carry a black box warning on the label regarding the risk of C-cell tumors. It recommends against using GLP-1 receptor agonists in patients with a personal or family history of medullary thyroid cell cancer or multiple endocrine neoplasia type 2a or 2b.

The well-known challenges that occur with weight loss treatment may also occur with the use of GLP-1 receptor agonist treatment. A substantial portion of weight loss is muscle rather than fat; as much as 20-30% of weight loss is estimated to be muscle and this percentage may be higher in individuals with rapid and significant weight loss (Cava et al. (2017) Adv Nutr 8:511). Also, weight loss is difficult to sustain because the basal metabolic rate declines to compensate for the body's calorie deficit. With this lower basal metabolic rate, the subject may need to maintain a reduced calorie intake and increased physical activity level to stay calorie budget neutral, but these lifestyle changes are not always sustainable. Moreover, significant rebound in weight has been reported in patients who discontinue GLP-1 receptor agonist treatment (see, e.g., Wilding et al. Diabetes Obes Metab. 2022 August; 24(8):1553-1564, reporting that participants regained two-thirds of their prior weight loss one year after discontinuing semaglutide treatment). Similarly, patients who discontinued tirzepatide treatment regained 70% of their lost weight one year after stopping tirzepatide treatment (see, e.g., Aronne et al, JAMA. Published online Dec. 11, 2023. doi:10.1001/jama.2023.24945).

The well-known challenges that occur with treatment of type 2 diabetes also may still occur with the use of GLP-1 receptor agonists. As a progressive disease, type 2 diabetes frequently requires multiple pharmacologic therapies.

GLP-1 receptor agonist therapies have been shown to be associated with unintended loss of lean mass and certain adverse events. For example, a sizable fraction of patients choose to discontinue the GLP-1 receptor agonist therapy due to side effects such as nausea. In addition, upon discontinuation, patients quickly regain most of the weight they lost during GLP-1 receptor agonists therapy. Moreover, a prolonged use of GLP-1 receptor agonists therapy may be associated with increased instances of certain cancers, such as thyroid cancer and pancreatic cancer.

To address these shortcomings, the present disclosure encompasses improved therapies comprising a GLP-1 receptor agonist and a myostatin inhibitor (e.g., myostatin-selective inhibitors) or alternative combinations with myostatin inhibitors such as biguanides (e.g., metformin) in lieu of a GLP-1 receptor agonist (as discussed in further detail in the next section below) as novel approaches to achieve synergistic effects for improving metabolic health. First, rather than focusing primarily on body weight (weight loss), the inventors sought to improve overall body composition through fat loss and maintained lean mass at the same time.

Second, incorporation of myostatin inhibition into a therapeutic regimen may reduce or slow the observed rebound effects associated with GLP-1 receptor agonists discontinuation. And third, this approach may allow reduced doses for the GLP-1 receptor agonists to achieve efficacy, which as monotherapy would be suboptimal or sub-efficacious, but may still provide efficacy in conjunction with a myostatin inhibitor. Thus, treatments comprising a GLP-1 receptor agonist and a myostatin inhibitor (e.g., a myostatin-selective inhibitor, e.g., an antibody disclosed herein) may reduce the risk, frequency, and/or degree of severity of certain side effects associated with the GLP-1 receptor agonists. In some embodiments, a combination of an antibody or antigen-binding fragment thereof, as disclosed herein, may less the need for multiple anti-diabetic therapies and/or augment the effect of GLP-1 in weight loss treatment by maintaining lean mass.

Accordingly, the present disclosure provides a myostatin inhibitor for use in conjunction with a GLP-1 receptor agonist in the treatment of obesity or for use in improving body composition in a subject. In some embodiments, the present disclosure provides a myostatin inhibitor and a GLP-1 receptor agonist for use in the treatment of obesity or for use in improving body composition in a subject, wherein the treatment comprises administration of a myostatin inhibitor in conjunction with a GLP-1 receptor agonist to the subject, optionally wherein the myostatin inhibitor is a selective myostatin inhibitor, e.g., an antibody disclosed herein or an antigen-binding fragment thereof (e.g., Ab109, Ab133, or Ab141). The disclosure also includes a myostatin inhibitor for use in the treatment of obesity or for use in improving body composition in a subject, wherein the treatment comprises administration of a myostatin inhibitor to the subject, wherein the subject is treated has been treated with a GLP-1 receptor agonist, optionally wherein the myostatin inhibitor is a selective myostatin inhibitor, e.g., an antibody disclosed herein or an antigen-binding fragment thereof. The disclosure further provides a GLP-1 receptor agonist for use in the treatment of obesity or for use in improving body composition in a subject, wherein the treatment comprises administration of a GLP-1 receptor agonist to the subject, wherein the subject is treated or has been treated with a myostatin inhibitor, optionally wherein the myostatin inhibitor is a selective myostatin inhibitor, e.g., an antibody disclosed herein or an antigen-binding fragment thereof. In any of these embodiments, the myostatin inhibitor may be a non-selective inhibitor of myostatin. In any of these embodiments, the GLP-1 receptor agonist may be semaglutide, liraglutide, tirzepatide, or retatrutide. In any of these embodiments, the myostatin inhibitor may be Ab109, Ab133, or Ab141 or a variant thereof, wherein, preferably, the myostatin inhibitor is Ab109 or a variant thereof.

In some embodiments, the myostatin inhibitor is an antibody that binds latent myostatin, e.g., GYM329 or a variant thereof. In some embodiments, the myostatin inhibitor is an antibody that binds mature myostatin, e.g., trevogrumab or a variant thereof. In some embodiments, the myostatin inhibitor is a non-selective inhibitor of myostatin, e.g., an antibody that binds ActRIIB, such as bimagrumab. In some embodiments, the non-selective inhibitor of myostatin is an anti-myostatin Adnectin®.

In preferred embodiments, the myostatin inhibitor is a myostatin-selective inhibitor, wherein further optionally, the myostatin-selective inhibitor is an antibody or antigen-binding fragment thereof that binds mature myostatin or latent myostatin (e.g., Ab109, Ab133, or Ab141) or a variant thereof. In a preferred embodiment, the antibody that binds latent myostatin is Ab109.

Without wishing to be bound by theory, it is contemplated that, by preventing muscle loss during weight loss, a greater amount of fat, including visceral fat, may be lost. Furthermore, maintaining muscle mass may attenuate the reductions in metabolic rate that limit the durability of the weight loss effect. In some embodiments, a myostatin inhibitor, e.g., a selective myostatin inhibitor antibody or antigen-binding fragment thereof, augments the effect of a lower dose of a GLP-1 receptor agonist, overcoming the tolerability issues by reducing the side effects of the GLP-1 receptor agonist treatment alone. In some embodiments, a myostatin inhibitor, e.g., a selective myostatin inhibitor antibody or antigen-binding fragment thereof, reduces the rebound effect on weight gain after GLP-1 receptor agonist withdrawal. In some embodiments, the present disclosure comprises use of a GLP-1 receptor agonist (e.g., semaglutide or liraglutide) and a myostatin-selective inhibitor (e.g., Ab109) for treating obesity or improving body composition, wherein the treatment is in amounts sufficient to reduce fat mass (e.g., visceral and/or subcutaneous fat mass) while maintaining lean muscle mass. In some embodiments, administration of the treatment comprising the GLP-1 receptor agonist and the myostatin-selective inhibitor (e.g., Ab109) reduces fat mass in the subject to a greater extent (e.g., at least 5%, 10%, 15%, 20%, or 25% more) than in a subject administered the GLP-1 receptor agonist alone. In some embodiments, administration of the treatment comprising the GLP-1 receptor agonist and the myostatin-selective inhibitor (e.g., Ab109) reduces subcutaneous fat mass in the subject to a greater extent (e.g., at least 5% or 10% more) than in a subject administered the GLP-1 receptor agonist alone. In some embodiments, administration of the treatment comprising the GLP-1 receptor agonist and the myostatin-selective inhibitor (e.g., Ab109) reduces visceral fat mass to a greater extent (e.g., at least 5% or 10% more) than in a subject administered the GLP-1 receptor agonist alone. In some embodiments, administration of the treatment comprising the GLP-1 receptor agonist and the myostatin-selective inhibitor (e.g., Ab109) prevents loss of lean muscle mass as compared to baseline.

In some embodiments, the present disclosure provides a method of treating obesity or improving body composition, comprising administering a myostatin-selective inhibitor to a subject who has discontinued treatment with a GLP-1 receptor agonist. In some embodiments, the subject was administered the GLP-1 receptor agonist for at least 12 weeks (e.g., at least 6 months), wherein, optionally, the GLP-1 receptor agonist comprises semaglutide. In some embodiments, administering the myostatin-selective inhibitor reduces fat mass by at least 10% relative to a subject not administered the myostatin-selective inhibitor after discontinuing the GLP-1 receptor agonist. In some embodiments, administering the myostatin-selective inhibitor prevents regain of fat mass by more than 20% for up to 6 months from the time of discontinuing the GLP-1 receptor agonist. In some embodiments, administering the myostatin-selective inhibitor prevents a decrease in the ratio of lean mass to fat mass by more than 20% for up to 6 months from the time of discontinuing the GLP-1 receptor agonist. In some embodiments, the subject is further administered metformin. In some embodiments, the myostatin-selective inhibitor is any one of the antibodies or antigen-binding fragments disclosed herein (e.g., Ab109).

In some embodiments, the present disclosure provides a method of reducing fat mass regain in a subject after discontinuing treatment with a GLP-1 receptor agonist, wherein the method comprises administering to the subject a myostatin-selective inhibitor (e.g., any one of the myostatin-selective antibodies or the antigen-binding fragments disclosed herein) in an amount effective to reduce fat mass gain as compared to a subject who has discontinued treatment with a GLP-1 receptor agonist but is not treated with the myostatin-selective inhibitor. In some embodiments, the administration reduces fat mass regain for at least 6 months after discontinuing the GLP-1 receptor agonist. In some embodiments, the administration reduces fat mass regain by at least 10% (e.g., at least 10%, 20%, 25%, or more). In some embodiments, the myostatin-selective inhibitor is administered prior to discontinuing the GLP-1 receptor agonist (e.g., in conjunction with the GLP-1 receptor agonist). In some embodiments, the myostatin-selective inhibitor is administered within 6 months of discontinuing the GLP-1 receptor agonist. In some embodiments, the myostatin-selective inhibitor is Ab109.

In some embodiments, administration of the myostatin-selective inhibitor (e.g., Ab109) after discontinuing the GLP-1 receptor agonist maintains fat loss and/or prevents loss of lean mass in the subject. In some embodiments, administration of the myostatin-selective inhibitor (e.g., Ab109) reduces the rate or degree of fat regain after discontinuing the GLP-1 receptor agonist.

In some embodiments, the present disclosure provides a method of improving liver health (e.g., reducing liver fat) in a subject, e.g., in an obese subject and/or a subject with fatty liver disease, comprising administering to the subject a myostatin-selective inhibitor in an amount effective to improve liver health. In some embodiments, administering the myostatin-selective inhibitor reduces liver weight by at least 10% (e.g., 10%, 20%, 25%, or more). In some embodiments, the subject is receiving or has received metformin. In some embodiments, the myostatin-selective inhibitor is any one of the antibodies or antigen-binding fragments disclosed herein (e.g., Ab109). In some embodiments, a myostatin-selective inhibitor is used in combination with a GLP-1 receptor agonist in the treatment of fatty liver in a subject, wherein the treatment comprises administration of a myostatin-selective inhibitor and a GLP-1 receptor agonist for at least 8 weeks to treat the fatty liver, wherein optionally the myostatin-selective inhibitor is Ab109, Ab133 or Ab141, and wherein further optionally the GLP-1 receptor agonist is selected from: albiglutide, taspoglutide, semaglutide, exenatide, BPI-3016, GW002, glutazumab, exendin-4, exenatide, GLP-1 (7-36)NH2, everestmab, liraglutide, lixisenatide, tirzepatide, dulaglutide, danuglipron (Pfizer), PF-07081532, or orforglipron. In some embodiments, other therapies comprising a GLP-1 receptor agonist include, but are not limited to, GLP-1 receptor agonist/GIP receptor antagonist combination such as AMG 133 (Amgen); GLP-1/GIP dual agonists such as tirzepatide (LY3298176; Eli Lilly), and CT-388; amylin/GLP-1 combination such as cagrilintide/semaglutide combination (Novo Nordisk); GLP-1/glucagon combination such as DD01 (Neuraly); GLP-1/glucagon receptor (GCG) agonist combinations such as ALT-801 (Altimmune), GLP-1/GIP such as CT-388 (Carmot); GLP-1/glucagon dual agonist such as IBI362 (LY-330567 (Innovent/Eli Lilly), cotadutide, DD01, danuglipron (PF-06882961) (Pfizer), mazdutide (IBI1362; LY-330567), MED10382; noiiglutide, oxyntomodulin, pemvidutide, setmelanotide (Rhythm), survodutide, and GLP-1/GIP/Glucagon triple receptor agonist such as retatrutide and LY343794.

Rapid weight loss is associated with reduced bone mineral density. Because GLP-1 receptor agonist therapy can trigger significant weight loss in relatively short periods, such weight loss may exert negative impact on the bone metabolism. Applicant previously showed that select inhibition of myostatin can have beneficial effects on the bone, such as increased bone cross section area, increased cortical thickness and increased bone mineral density. Accordingly, it is postulated that incorporating a myostatin-selective inhibitor therapy into weight management regimen may provide a protective effect on bone/joint metabolism, e.g., in RA and/or during weight loss. In some embodiments, the present disclosure provides a method of improving bone strength and/or preventing bone loss in a subject (e.g., an obese subject), comprising administering to the subject a myostatin-selective inhibitor in an amount effective to improve bone strength and/or prevent bone loss as compared to a subject (e.g., an obese subject) who has not been administered the myostatin-selective inhibitor. In some embodiments, administering the myostatin-selective inhibitor reduces bone fracture by at least 10% (e.g., 10%, 20%, 25%, or more) as compared to a subject who has not been administered the myostatin-selective inhibitor. In some embodiments, the subject is receiving or has received a GLP-1 receptor agonist and/or metformin, wherein, optionally, the GLP-1 receptor agonist comprises semaglutide. In some embodiments, the myostatin-selective inhibitor is any one of the antibodies or antigen-binding fragments disclosed herein (e.g., Ab109).

Moreover, GDF11 has been shown to have beneficial effects on bone metabolism. As such, use of myostatin inhibitors that also inhibit GDF11 (e.g., non-selective myostatin inhibitors) may dampen the protective effect of myostatin inhibition on bone. Accordingly, the present disclosure includes the use of a myostatin-selective inhibitor in the treatment of a metabolic disorder (e.g., obesity, metabolic syndrome, prediabetes, diabetes, etc.) in a patient who is on or has received a GDF11 inhibitor therapy (such as non-selective myostatin inhibitor that also inhibits GDF11) and a GLP-1 receptor agonist therapy as a replacement for the GDF11 therapy. Examples of GDF11 therapies to be replaced with a myostatin-selective inhibitor therapy include but are not limited to: ActRII receptor antagonists (e.g., bimagrumab), anti-myostatin Adnectins (e.g., taldefgrobep alfa), follistatin-based therapies, ligand traps, and neutralizing antibodies that bind mature myostatin as well as GDF11.

In some embodiments, the present disclosure provides a method of improving blood glucose or hemoglobin A1C (A1C) levels in a pre-diabetic or diabetic subject who is receiving or has received a GLP-1 receptor agonist, comprising administering to the subject a myostatin-selective inhibitor in an amount effective to reduce blood glucose or A1C levels as compared to before the administration of the myostatin-selective inhibitor. In some embodiments, administering of the myostatin-selective inhibitor reduces blood glucose or A1C levels by at least 10% (e.g., 10%, 20%, 25%, or more), wherein, optionally, the reduction in glucose is a reduction in fasted glucose. In some embodiments, the GLP-1 receptor agonist comprises semaglutide. In some embodiments, the subject is receiving or has received metformin. In some embodiments, the myostatin-selective inhibitor is any one of the antibodies or antigen-binding fragments disclosed herein (e.g., Ab109).

In any one of the embodiments provided herein, a GLP-1 gene therapy may be used in place of or in addition to a GLP-1 receptor agonist.

B. Therapies Comprising a Biguanide

Whilst the availability of GLP-1 receptor agonists has had a dramatic impact on the weight management options since approval, recent reports highlight certain risks and shortcomings of GLP-1 receptor agonists. A significant fraction of patients who receive GLP-1 receptor agonist therapy discontinue the treatment due to unwanted side effects. Upon discontinuation, most of the weight lost during the treatment is quickly regained. In addition, an increased risk of cancer (e.g., thyroid cancer) is associated with the use of GLP-1 receptor agonists. Furthermore, more recently, concerns are raised regarding a possible link between the use of GLP-1 receptor agonists and suicidal thoughts and self-injury, which, at the time of the filing date of the present application, remains under review by the EMA.

Therefore, as an alternative approach for improving metabolic health, the inventors of the present disclosure have sought weight management therapeutic regiments that do not rely on a GLP-1 receptor agonist. In particular, present disclosure includes novel use of biguanides such as metformin for treating obesity and for improving body composition, in patients who may or may not suffer from diabetes. In preferred embodiments, the biguanide-based therapy (e.g., metformin-based therapy) is used in conjunction with a non-GLP-1 receptor agonist to enhance or synergize effects on metabolic health. Such therapies may be administered as a combination therapy or add-on (adjunct) therapy. Preferably, the non-GLP-1 receptor agonist is a myostatin inhibitor; however, other non-GLP-1 receptor agonist agents aimed to improve metabolic heath can be used in conjunction with the biguanide (e.g., metformin).

Metformin, a biguanide, has been widely used as a first line oral treatment for type 2 diabetes since its approval in 1994. It lowers plasma glucose levels by reducing hepatic glucose production and lessens insulin resistance. It can be effective in treating type 2 diabetes when used alone or along with other hypoglycemic agents. Metformin acts as a GLP-1 pathway activator by increasing GLP-1 secretion. It has been shown to have both a direct and a 5'AMP-activated protein kinase (AMP kinase) dependent effect on GLP-1 secretion (Bahne et al (2018) JCI Insight https://doi.org/10.1172/jci.insight.93936).

In addition to its role in treating type 2 diabetes, metformin has been shown to have beneficial effects on other disorders acting through both AMP kinase-dependent and AMP kinase-independent pathways. It has been shown to have cardioprotective and neuroprotective effects by inhibiting inflammation. Metformin has been reported to limit osteoarthritis progression, inhibit tumorigenesis, and have a positive effect on polycystic ovary syndrome, which is a disorder associated with reproductive and metabolic abnormalities. (Du et al. (2022) Molec Biomed 3:41.)

While a meta-analysis of the effect of metformin in type 2 diabetics showed no effect on weight loss, metformin was found to mitigate the propensity of other antidiabetic agents to induce weight gain (Golay (2008) Int J Obesity 32:61).

Accordingly, the present disclosure provides a novel treatment (e.g., a novel combination or adjunct therapy) comprising a biguanide, e.g., metformin, for the treatment of obesity and/or diabetes. In some embodiments, the present disclosure encompasses use of metformin in conjunction with an additional therapy to achieve weight loss and/or improved body composition in obese subjects, wherein the additional therapy is not a GLP-1 receptor agonist. Examples of the additional therapy may include, for example, a myostatin inhibitor, a GIP agonist, an FGF receptor agonist, etc., as discussed further below.

Data presented herein demonstrate that metformin used in conjunction with a myostatin-selective inhibitor can synergistically cause weight loss in high-fat diet-induced obese mice that are not treated with a GLP-1 receptor agonist. Advantageously, the data indicate that the combination of a myostatin-selective inhibitor and metformin can improve body composition characterized by preferential loss of fat mass over lean mass. Surprisingly, myostatin-selective inhibition (i.e., without inhibiting related growth factors such as GDF11 and Activin A), is sufficient to achieve this effect with metformin even in the absence of a GLP-1 receptor agonist. Furthermore, this can lead to loss of fat mass (e.g., visceral fat) while preserving muscle mass (i.e., lean mass), contributing to an overall improvement in body composition. Thus, the therapy comprising a myostatin-selective inhibitor and a biguanide (e.g., metformin) can be used to cause preferential loss of fat mass over lean mass, thereby achieving improved body composition in obese subjects (e.g., patients suffering from diet-induced obesity), wherein optionally the subject is not on a GLP-1 receptor agonist therapy at the time of receiving the therapy. Relative changes (e.g., loss) in fat vs lean mass may be measured by any suitable techniques, such as qNMR and dual-energy X-Ray absorptiometry (DXA).

Accordingly, the present disclosure provides a myostatin-selective inhibitor and a biguanide for use in the treatment of obesity or for use in improving body composition in a subject, wherein the treatment comprises administration of a myostatin inhibitor (e.g., a myostatin-selective inhibitor, e.g., Ab109, Ab133, or Ab141) and a biguanide to the subject to treat the obesity or improve body composition, wherein optionally the biguanide is metformin. The disclosure also includes a myostatin inhibitor (e.g., a myostatin-selective inhibitor, e.g., Ab109, Ab133, or Ab141) for use in the treatment of obesity or for use in improving body composition in a subject, wherein the treatment comprises administration of the myostatin inhibitor (e.g., myostatin-selective inhibitor, e.g., Ab109, Ab133, or Ab141) to the subject, wherein the subject is treated with a biguanide, wherein optionally the biguanide is metformin.

The disclosure further provides a biguanide for use in the treatment of obesity or for use in improving body composition in a subject, wherein the treatment comprises administration of the biguanide to the subject, wherein the subject is treated with a myostatin inhibitor (e.g., a myostatin-selective inhibitor, e.g., Ab109, Ab133, or Ab141), wherein optionally the biguanide is metformin. In any of these embodiments, the myostatin inhibitor is an antibody or antigen-binding fragments thereof that binds mature myostatin but does not bind GDF11 or Activin A, wherein optionally the antibody is trevogrumab or a variant thereof. In some embodiments, the myostatin-selective inhibitor is an antibody or antigen-binding fragments thereof that binds pro/latent myostatin, wherein optionally the antibody is apitegromab or a variant thereof, GYM329 or a variant thereof, or an antibody disclosed herein, or a variant thereof. In some embodiments, the myostatin-selective inhibitor is an antibody disclosed herein or an antigen-binding fragment or variant thereof. In preferred embodiments, the myostatin-selective inhibitor is Ab109.

In some embodiments, a myostatin inhibitor and a biguanide (such as metformin) are used in conjunction for the treatment of a metabolic disorder in a non-diabetic subject, wherein preferably the metabolic disorder is obesity, and wherein the subject is not on a GLP-1 receptor agonist therapy at the time of receiving the myostatin inhibitor-biguanide therapy. The myostatin inhibitor may comprise a non-selective inhibitor of myostatin or selective inhibitor of myostatin. Examples of non-selective inhibitors of myostatin include anti-ActRIIB antibodies, anti-ActRIIA antibodies, anti-myostatin Adnectins, follistatins and variants, and so-called ligand traps which incorporate ligand-binding fragments of the ActRIIA/B receptors. Examples of selective inhibitors of myostatin (i.e., myostatin-selective inhibitors) include neutralizing antibodies that bind myostatin/GDF8 without binding GDF11 or Activins (such as trevogrumab) and anti-latent myostatin antibodies that inhibit activation of myostatin (such as apitegromab, GYM329 and the novel antibodies disclosed herein). In some embodiments, the subject previously received but poorly responded to a GLP-1 receptor agonist therapy. In some embodiments, the subject has or is at risk of developing cancer.

In some embodiments, the present disclosure comprises use of a biguanide (e.g., metformin) and a myostatin inhibitor (e.g., a myostatin-selective inhibitor) for treating obesity or improving body composition, wherein the treatment is in amounts sufficient to slow fat accumulation while maintaining lean muscle mass. In some embodiments, administration of the treatment slows fat accumulation in the subject by at least 10% as compared to the rate of fat accumulation in the subject before receiving the therapy. In some embodiments, administration of the treatment prevents more than 10% loss of lean muscle mass in the subject as compared to baseline. In some embodiments, the treatment increases lean mass in the subject as compared to baseline.

In some embodiments, administering a biguanide (e.g., metformin) in lieu of a GLP-1 receptor agonist may circumvent certain adverse events associated with use of the GLP-1 receptor agonist, which, in some embodiments, may provide an alternative therapeutic regimen for patients who have low tolerance to GLP-1 receptor agonist, as well as patients who are at risk of developing cancer. In some embodiments, administering a biguanide (e.g., metformin) in lieu of a GLP-1 receptor agonist may reduce the risk and/or degree of adverse events. In some embodiments, the subject has discontinued use of a GLP-1 receptor agonist therapy.

Accordingly, a biguanide (preferably metformin) may be used for treating obesity or improving body composition in a subject in conjunction with an additional agent which is not a GLP-1 receptor agonist (e.g., either as a combination therapy or add-on/adjunct therapy). Examples of the additional agents that are not GLP-1 receptor agonists which may be used in conjunction with a biguanide (e.g., metformin) include, without limitation: myostatin inhibitors (e.g., selective or non-selective inhibitors of myostatin), glucagon receptor agonists, GIP receptor agonists, peroxisome proliferator-activated receptor (PPAR) alpha agonists (such as fibrates), alpha-glucosidase inhibitors, dipeptidyl peptidase-4 (DPP-4) inhibitors, sodium-glucose transporter (SGLT) 2 inhibitors, sulfonylurea, meglitinide, thiazolidinedione, FGF21 receptor agonists, FGF19 receptor agonists, mucin-complexing polymers (such as GLY-200 being developed by Glyscend Tx), clic1 inhibitors and/or mitochondrial decoupling agents (e.g., controlled metabolic accelerators such as HU6 being developed by Rivus Pharma). In preferred embodiments, the additional agent used in conjunction with a biguanide (e.g., metformin) is a myostatin inhibitor. In most preferred embodiments, the myostatin inhibitor is a myostatin-selective inhibitor, such as an antibody disclosed herein or a variant thereof (e.g., Ab109, Ab133, or Ab141). In some embodiments, the therapy may be used to treat obesity in a patient, wherein optionally the patient is not on a GLP-1 receptor activator. In some embodiments, the subject is overweight or obese but is not diabetic. In some embodiments, the subject is pre-diabetic. In some embodiments, the subject has metabolic syndrome.

C. Various Embodiments of Treatments Comprising Two or More Therapies

Non-limiting embodiments of treatments comprising two or more therapies (e.g., combination or adjunct therapies) are encompassed by the present disclosure provided below. In any of the combination or add-on/adjunct regimen that includes a GLP-1 receptor agonist, the dosage for the GLP-1 receptor agonist may be reduced, as compared to a recommended dosage when used as monotherapy.

In some embodiments, treatments comprising two or more therapies produce synergistic effects in the treatment of a disease. The term "synergistic" refers to effects that are greater than additive effects (e.g., greater efficacy) of each monotherapy in aggregate. In some embodiments, treatments comprising two or more therapies produce additive effects in the treatment of a disease.

In some embodiments, the present disclosure provides a use of a myostatin inhibitor, e.g., a myostatin-selective inhibitor, e.g., an antibody or antigen-binding fragment thereof as described herein, and a second agent for treating or preventing a metabolic disease or a disease associated with impaired neurological signaling, wherein the treatment provides amelioration of at least one symptom of the disease with efficacy that is equivalent to or improved compared to the effect that is produced by the second agent alone. In some embodiments, the treatment is associated with fewer unwanted adverse effect or less severe toxicity as compared to those associated with the second agent alone. In some embodiments, the treatment allows lower dosage of the second agent but maintain overall efficacy. In some embodiments, the treatment may be particularly suitable for patient populations where a long-term treatment is warranted, optionally wherein the patient population is pediatric patients, patients aged 2-19 years, or patients aged 12 years or older (e.g., 12-17 years; inclusive of endpoints).

Accordingly, the disclosure provides pharmaceutical compositions and methods for use in therapies for the increasing the ratio of lean mass to fat mass, and/or for the treatment or prevention of metabolic diseases or diseases associated with an impaired neurological signaling, including metabolic syndrome, diabetes (e.g., T2DM), obesity, and spinal cord injury. In some embodiments, the methods or pharmaceutical compositions for use comprise a first therapy. In some embodiments, the methods or pharmaceutical compositions for use further comprise a second therapy.

In some embodiments, the first therapy includes a therapy useful in treating or preventing metabolic diseases or diseases associated with impaired neurological signaling. In some embodiments, exemplary first therapies include treatments suitable for a metabolic disease (e.g., metabolic syndrome, diabetes, and/or obesity), such as GLP-1 pathway activators (e.g., GLP-1 receptor agonists, e.g., GLP-1 analogs), biguanides (e.g., metformin), weight-loss agents, diet, and/or exercise regimen. In some embodiments, the second therapy is useful for increasing the ratio of lean mass to fat mass. In some embodiments, the first and second therapies are administered in any order (i.e., the second therapy is treated as the first therapy and vice versa).

In some embodiments, exemplary second therapies include a myostatin inhibitor. In some embodiments, the myostatin inhibitor is a myostatin-selective inhibitor, e.g., an antibody or antigen-binding fragments thereof that specifically binds to mature and/or pro/latent myostatin. In some embodiments, the antibody or antigen-binding fragments thereof specifically binds to pro/latent myostatin, e.g., an antibody or fragment as described herein, such as Ab102, Ab109, Ab130, Ab132, Ab133, or Ab141 or a variant thereof. In preferred embodiments, the myostatin inhibitor is Ab109, Ab133, or Ab141 or a variant thereof. In a preferred embodiment, the myostatin inhibitor is Ab109. In a preferred embodiment, the myostatin inhibitor (e.g., Ab109, Ab133, or Ab141 or a variant thereof) is used in conjunction with a biguanide (e.g., metformin). In another preferred embodiment, the myostatin inhibitor (e.g., Ab109, Ab133, or Ab141 or a variant thereof) is used in conjunction with a GLP-1 pathway activator (e.g., a GLP-1 receptor agonist or GLP-1 analog).

In some embodiments, the first and second therapies may exert their biological effects by similar mechanisms of action. In some embodiments, the first and second therapies may exert their biological effects by different mechanisms of action. In some embodiments, the first therapy is administered in conjunction with the second therapy. In some embodiments, the second therapy is administered to a subject who is receiving the first therapy. In some embodiments, the second therapy is administered to a subject who has not previously received the first therapy. In some embodiments, the first therapy and the second therapy are administered concurrently. In some embodiments, the first therapy and the second therapy are administered sequentially. In some embodiments, the first therapy and the second therapy are administered separately. It should be understood that the uses and pharmaceutical compositions described herein may comprise the first and second therapies in the same pharmaceutically acceptable carrier or in different pharmaceutically acceptable carriers for each described embodiment. It further should be understood that the first and second therapies may be administered simultaneously or sequentially or separately.

In some embodiments, the first therapy is used in conjunction with a myostatin inhibitor (e.g., a myostatin-selective inhibitor, e.g., an antibody or antigen-binding fragment thereof as described herein), wherein the first therapy comprises a therapy for treating a metabolic disease, e.g., metabolic syndrome, diabetes, and/or obesity. In some embodiments, the first therapy comprises a diet and/or exercise regimen. In some embodiments, the first therapy comprises a GLP-1 pathway activator, e.g., a GLP-1 receptor agonist, e.g., semaglutide, liraglutide, tirzepatide, retatrutide. In some embodiments, the first therapy comprises metformin. In some embodiments, the first therapy comprises an alpha-glucosidase inhibitor, a dopamine agonist, a dipeptidyl peptidase-4 (DPP-4) inhibitor, a sodium-glucose transporter (SGLT) 2 inhibitor, a sulfonylurea, a meglitinide, a thiazolidinedione, or a combination of any of the above.

In some embodiments, the first therapy may be a GLP-1 pathway activator known in the art (e.g., albiglutide, BPI-3016, danuglipron, DD01, dulaglutide, everestmab, exenatide, exendin-4, glutazumab, GLP-1 (7-36)NH2, GW002 (GLP1 mimetic with albumin moiety to extend half-life; see, e.g., Eur J Pharmacol. (2021) 890:173650), IBI362 liraglutide, lixisenatide, MEDI0382, metformin, noiiglutide orforglipron, pemvidutide, PF-07081532, semaglutide, taspoglutide, XW003, or tirzepatide). In some embodiments, the GLP-1 pathway activator is a GLP-1 receptor agonist (e.g., albiglutide, BPI-3016, danuglipron, dulaglutide, everestmab, exenatide, exendin-4, glutazumab, GLP-1 (7-36)NH2, GW002 Iiraglutide, lixisenatide, metformin, ecnoglutide, orforglipron, PF-07081532, semaglutide, taspoglutide, tirzepatide, or XW003).

In some embodiments, the GLP-1 pathway activator is a duel GLP-1/glucose-dependent insulinotropic polypeptide (GIP) receptor agonist known in the art (e.g., tirzepatide). In some embodiments, GLP-1 pathway activator is a duel GLP-1/glucagon receptor agonist known in the art (e.g., cotaditide, DD01 (Neuraly), IBI362 (LY330567), pemvidutide, or survodutide). In some embodiments, the GLP-1 pathway activator is a GLP-1/GIP/glucagon triple receptor agonist such as retatrutide.

In some embodiments, the GLP-1 pathway activator is a GLP-1 pathway activator that acts on the central nervous system (a central-acting GLP-1 pathway activator, e.g., a central-acting GLP-1 receptor agonist or a central-acting GLP-1 analog). In some embodiments, the GLP-1 pathway activator is a GLP-1 pathway activator that acts on peripheral tissues (a peripheral-acting GLP-1 pathway activator, e.g., a peripheral-acting GLP-1 receptor agonist or a peripheral-acting GL-1 analog). In some embodiments, the GLP-1 pathway activator is a GLP-1 pathway activator that acts on both the central nervous system and peripheral tissues. In some embodiments, the GLP-1 pathway activator is a combination of semaglutide and insulin icodec, such as IcoSema.

In some embodiments, the first therapy comprises a GIP or GIP receptor agonist or antagonist. In some embodiments, the therapy comprises administering GIP (both GLP-1 and GIP may also be referred to as an incretins). In some embodiments, the first therapy comprises a glucagon receptor agonist. In some embodiments, the first therapy comprises a dual GLP-1 receptor agonist and glucagon receptor agonist or a combination of a GLP-1 receptor agonist and a glucagon receptor agonist. In some embodiments, the first therapy comprises a GLP-1 receptor agonist and an amylin analog or a GLP-1 receptor agonist, an amylin analog, and insulin. In some embodiments, the first therapy comprises a dual GLP-1 receptor agonist and GIP receptor antagonist.

In some embodiments, the disclosure provides a method of treating a metabolic disorder in a subject in need thereof, comprising administering to the subject a GLP-1 pathway activator in conjunction with a myostatin inhibitor (e.g., a myostatin-selective inhibitor, e.g., an antibody disclosed herein or an antigen binding fragment thereof), wherein, optionally, the GLP-1 pathway activator is semaglutide, liraglutide, tirzepatide, retatrutide and the myostatin inhibitor is Ab109, Ab133, or Ab141, wherein, further optionally, the treatment comprises diet and/or exercise as an adjunct therapy. In some embodiments, the GLP-1 receptor agonist is or comprises ECC5004, CT-996, PF-07081532, orforglipron, semaglutide, liraglutide and/or tirzepatide (dual GLP-1 receptor agonist and GIP receptor agonist). In some embodiments, the GLP-1 receptor agonist is a GIP, GLP-1, and glucagon receptor agonist, such as retatrutide (LY3437943).

In some embodiments, the GLP-1 receptor agonist is a GLP-1 receptor agonist and a glucagon receptor dual agonist such as AZD9550, CT-388, CT-868, survodutide (BI456906), pemvidutide (ALT-801), NN1177, and/or efinopegdutide (MK-6024). In some embodiments, the GLP-1 pathway activator is a dual GLP-1/GLP-2 receptor agonist, such as Dapiglutide. In some embodiments, the GLP-1 receptor agonist is a GLP-1 receptor agonist and a GIP receptor antagonist such as AMG133 (maridebart cafraglutide).

In some embodiments, the disclosure provides a method of treating a metabolic disorder in a subject in need thereof, comprising administering to the subject a GIP-1 receptor agonist in conjunction with a myostatin inhibitor (e.g., a myostatin-selective inhibitor, e.g., an antibody disclosed herein or an antigen binding fragment thereof), wherein optionally the GIP receptor agonist is ZP6590.

In some embodiments, the disclosure provides a method of treating a metabolic disorder in a subject in need thereof, comprising administering to the subject an amylin analog in conjunction with a myostatin inhibitor (e.g., a myostatin-selective inhibitor, e.g. an antibody disclosed herein or an antigen binding fragment thereof), wherein optionally the amylin analog is AZD6234 and/or petrelintide (ZP8396). In some embodiments, the amylin analog is a co-agonist of GLP-1R and amylin, such as amycretin. In some embodiments, the amylin analog is a combination of an amylin analogue and semaglutide, such as CagriSema.

In some embodiments, the first therapy is used in conjunction with a myostatin inhibitor (e.g., a myostatin-selective inhibitor, e.g., an antibody or antigen-binding fragment thereof as described herein), wherein the first therapy is a weight-loss agent. In some embodiments, the weight loss agent is an appetite suppressant (e.g., phentermine, benzphetamine, diethylpropion, or phendimetrazine); a biguanide (e.g., metformin, phenformin, or buformin); a sulfonyurea (e.g. glimepiride, -rosiglitazone, or bromocriptine); a dipeptidyl peptidase 4 inhibitor (e.g., alogliptin, linagliptin, saxagliptin, sitagliptin, saxagliptin-metformin, sitagliptin-metformin, sitagliptin-simvastatin); a meglitinide (e.g., nateglinide or repaglinide); a sodium-glucose cotransporter-2 (SGLT2) inhibitor (e.g., canagliflozin, dapagliflozin, ertugliflozin, empagliflozin, empagliflozin-linagliptin, or empagliflozin-metformin); a thiazolidinedione (e.g., tosiglitazone or pioglitazone); chloride intracellular channel 1 (Clic1), or a combination of any of the above.

In some embodiments, the first therapy is used in conjunction with a myostatin inhibitor (e.g., a myostatin-selective inhibitor, e.g., an antibody or antigen-binding fragment thereof as described herein), wherein the first therapy is a peroxisome proliferator-activated receptor alpha (PPARα) agonist, such as a fibrate (Staels et al. Nat Clin Pract Cardiovasc Med. 2008 September; 5(9):542-53). In some embodiments, the disclosure provides a method of treating a metabolic disorder in a subject in need thereof, comprising administering a myostatin inhibitor (e.g., a myostatin-selective inhibitor, e.g., an anti-myostatin antibody disclosed herein or an antigen binding fragment thereof) in conjunction with a PPARα agonist, e.g., a fibrate.

In some embodiments, the first therapy is used in conjunction with a myostatin inhibitor (e.g., a myostatin-selective inhibitor, e.g., an antibody or antigen-binding fragment thereof as described herein), wherein the first therapy provides embryonic stem cell derived islet cells comprising functional beta cells (Butler and Gale (2022) J Clin Invest 132(3):e158305) to a subject in need thereof, e.g., is insulin resistant.

In some embodiments, wherein the metabolic disease is a liver disease, e.g., nonalcoholic steatohepatitis (NASH) or nonalcoholic fatty liver disease (NAFLD), the first therapy is a glucagon/GLP-1 receptor co-agonist such as NN1177, Efinopegdutide (MK-6024), or a thyroid hormone receptor-beta (THR-beta) selective agonist (e.g., an aryloxyphenyl based thyromimetic such as resmetirom or eprotirome), or a diphenylmethane based thyromimetic (e.g., sobetirome, Sob-AM2, VK2809 (MB08711), MB07344, IS25, or TG68). In some embodiments, a subject having NAFLD or NASH or is at risk of developing NASH is not receiving and/or has not been treated with a TGFβ inhibitor (e.g., TGFβ1 inhibitor). In some embodiments, use of a myostatin inhibitor (e.g., a myostatin-selective inhibitor, e.g., an antibody or antigen-binding fragment thereof as described herein) reduces fat mass surrounding the subject's liver. In some embodiments, use of the myostatin inhibitor in conjunction with a GLP-1 receptor agonist results in synergistic effects on reducing fat mass surrounding the subject's liver. In some embodiments, use of the myostatin inhibitor in conjunction with a GLP-1 receptor agonist results in reduced liver weight.

In some embodiments, the disclosure provides a method of treating a metabolic disorder in a subject who is or has been treated with a GLP-1 pathway activator comprising administering to the subject a myostatin inhibitor (e.g., a myostatin-selective inhibitor, e.g., an antibody disclosed herein or an antigen binding fragment thereof) in conjunction with the GLP-1 pathway activator.

In some embodiments, the disclosure provides a method of treating a metabolic disorder in a subject in need thereof, comprising administering to the subject a myostatin inhibitor (e.g., a myostatin-selective inhibitor, e.g., an antibody disclosed herein or an antigen binding fragment thereof) in conjunction with diet and/or exercise.

GLP-1 receptor agonist therapy is commonly associated with side effects, which include GI adverse effects such as nausea, vomiting and diarrhea. A sizable fraction of patients who receive GLP-1 receptor agonist therapy discontinue the therapy due at least in part to such side effects. Upon discontinuation, patients typically quickly regain much of the weight they lost during the GLP-1 receptor agonist therapy. To counter this fat mass regain triggered by discontinuation of GLP-1 receptor agonist therapy, a myostatin inhibitor may be used to reduce the degree of fat regain or slow the rate of fat regain.

In some embodiments, the present disclosure provides a method of reducing fat mass regain in a subject in a subject after the subject discontinues treatment with a GLP-1 receptor agonist, wherein the method comprises administering to the subject a myostatin-selective inhibitor (e.g., any one of the myostatin-selective antibodies or the antigen-binding fragments disclosed herein) in an amount effective to reduce fat mass gain as compared to a subject who has discontinued treatment with a GLP-1 receptor agonist but is not treated with the myostatin-selective inhibitor. In some embodiments, the administration reduces fat mass regain in the subject for at least 6 months after discontinuing the GLP-1 receptor agonist. In some embodiments, the administration slows or reduces fat mass regain in the subject by at least 10% (e.g., at least 10%, 20%, 25%, or more). In some embodiments, the administration retains lean mass to fat mass ratio for at least 6 months after discontinuing the GLP-1 receptor agonist. In some embodiments, the administration retains lean mass to fat mass ratio by slowing or reducing fat mass regain at least 10% (e.g., at least 10%, 20%, 25%, or more) and/or preventing loss of lean mass by more than 10%. In some embodiments, the myostatin-selective inhibitor is administered prior to discontinuing the GLP-1 receptor agonist (e.g., in conjunction with the GLP-1 receptor agonist). In some embodiments, the myostatin-selective inhibitor is administered within 6 months of discontinuing the GLP-1 receptor agonist.

In some embodiments, the present disclosure encompasses the use of a myostatin inhibitor (e.g., a myostatin-selective inhibitor, e.g., an antibody or antigen-binding fragments thereof that specifically binds to pro/latent myostatin as described herein such as Ab102, Ab109, Ab130, Ab132, Ab133, or Ab141 or a variant thereof) in conjunction with one or more of additional therapy including, but are not limited to, diabetes mellitus-treating agents, diabetic complication-treating agents, cardiovascular diseases-treating agents, anti-hyperlipemic agents, hypotensive or antihypertensive agents, anti-obesity agents, chemotherapeutic agents, immunotherapeutic agents, immunosuppressive agents, and the like. Such therapies may advantageously utilize lower dosages of the additional therapeutic agent, thus avoiding possible toxicities or complications associated with the various monotherapies.

In some embodiments, the disclosure provides use of a myostatin inhibitor (e.g., a myostatin-selective inhibitor, e.g., an antibody or antigen-binding fragments thereof that specifically binds to pro/latent myostatin as described herein such as Ab109, Ab133, or Ab141 or a variant thereof) in conjunction with one or more additional therapy selected from one or more of (e.g., two or more of, e.g., all of) diet and/or exercise, metformin, and/or a GLP-1 receptor agonist such as semaglutide, liraglutide, tirzepatide, and/or retatrutide. In some embodiment, the use of the myostatin inhibitor may advantageously allow usage of lower dosages of a GLP-1 receptor agonist (e.g., semaglutide, liraglutide, tirzepatide, retatrutide), e.g., to avoid adverse events, toxicities, or other complications associated with use of the GLP-1 receptor agonist as a single agent.

In some embodiments, the myostatin inhibitor (e.g., an antibody or antigen-binding fragments thereof that specifically binds to pro/latent myostatin as described herein such as Ab101-Ab141 or a variant thereof, e.g., Ab109 or a variant thereof) is administered in the same treatment regimen as the additional therapy. In some embodiments, the myostatin inhibitor is administered to a subject who is already receiving one or more therapies such as any one of the additional therapies described above. In some embodiments, administering the treatment comprising the myostatin inhibitor and the additional therapy results in a reduction of at least one symptom of type 2 diabetes in the subject. In some embodiments, administering the treatment comprising the myostatin inhibitor and the additional therapy results in slowing or halting the progression type 2 diabetes in the subject (e.g., partial or complete remission), or reversing diabetic symptoms. In some embodiments, administering the treatment comprising the myostatin inhibitor and the additional therapy results in remission of type 2 diabetes in the subject (i.e., returning of the blood sugar levels of the subject to normal or healthy levels, i.e., blood sugar level of someone without diabetes, e.g., an A1C level of less than 6.5%). In some embodiments, the additional therapy comprises a GLP-1 pathway activator (e.g., semaglutide, liraglutide, tirzepatide, retatrutide), metformin, diet, and/or exercise.

In any of the embodiments disclosed herein, the treatment comprising a myostatin inhibitor (e.g., a myostatin-selective inhibitor, e.g., an antibody or antigen-binding fragments thereof that specifically binds to pro/latent myostatin as described herein such as Ab102, Ab109, Ab130, Ab132, Ab133, or Ab141 or a variant thereof) may be used in conjunction with diet and exercise. In preferred embodiments, the myostatin inhibitor is Ab109, Ab133, or Ab141. In some embodiments, the treatment is administered to a subject who is on a diet and/or exercise regimen for weight loss or for improving or alleviating symptoms of one or more metabolic diseases or diseases associated with an impaired neurological signaling, including metabolic syndrome, diabetes (e.g., type 2 diabetes), obesity, and spinal cord injury. In some embodiments, the diet regimen includes, but is not limited to, caloric restriction (e.g., reduced calorie intake or reduced absorption of calories), diets with modified nutrient content (e.g., high protein, low fat, low carbohydrate, keto, paleo, etc.) or modified timing of food intake (e.g., intermittent fasting, increased frequency of feeding, etc.) or a combination of modified timing, portion size, and nutrient content (e.g., more frequent meals of smaller portions containing high protein, low fat, and/or other nutrient content restrictions).

In some embodiments, the disclosure encompasses use of a myostatin inhibitor (e.g., an anti-myostatin antibody or antigen-binding fragment thereof disclosed herein, e.g., Ab109, Ab133, or Ab141) in conjunction with an agent for treating diabetes mellitus (e.g., type 2 diabetes). Examples of agents for treating diabetes mellitus (e.g., type 2 diabetes) include insulin formulations known in the art (e.g., animal insulin formulations extracted from a pancreas of a cattle or a swine; a human insulin formulation synthesized by a gene engineering technology using microorganisms or methods); insulin sensitivity enhancing agents, pharmaceutically acceptable salts, hydrates, or solvates thereof (e.g., pioglitazone, troglitazone, rosiglitazone, netoglitazone, balaglitazone, rivoglitazone, tesaglitazar, farglitazar, CLX-0921, R-483, NIP-221, NIP-223, DRF-2189, GW-7282TAK-559, T-131, RG-12525, LY-510929, LY-519818, BMS-298585, DRF-2725, GW-1536, GI-262570, KRP-297, TZD18 (Merck), DRF-2655, and the like); alpha-glycosidase inhibitors (e.g., voglibose, acarbose, miglitol, emiglitate, and the like), biguanides (e.g., phenformin, metformin, buformin and the like); or sulfonylureas (e.g., tolbutamide, glibenclamide, gliclazide, chlorpropamide, tolazamide, acetohexamide, glyclopyramide, glimepiride, and the like) as well as other insulin secretion-promoting agents (e.g., repaglinide, senaglinide, nateglinide, mitiglinide, and the like); GLP-1 pathway activators as described above, amyrin agonists (e.g., pramlintide and the like); and phosphotyrosine phosphatase inhibitors (e.g., vanadic acid and the like).

In some embodiments, the disclosure encompasses use of a myostatin inhibitor (e.g., an anti-myostatin antibody or antigen-binding fragment thereof disclosed herein, e.g., Ab109, Ab133, or Ab141) in conjunction with a GLP-1-pathway activator, such as those described above. Additional examples of GLP1R pathway activators include DPP-4 inhibitors, non-limiting examples of which are sitagliptin, vildagliptin, saxagliptin, linagliptin, gemigliptin, anagliptin, teneligliptin, alogliptin, alogliptin-metformin, alogliptin-pioglitazone, trelagliptin, omarigliptin, evogliptin, gosogliptin, dutogliptin, and berberine. Examples of agents for treating diabetic complications include, but are not limited to, aldose reductase inhibitors (e.g., tolrestat, epalrestat, zenarestat, zopolrestat, minalrestat, fidareatat, SK-860, CT-112 and the like), neurotrophic factors (e.g., NGF, NT-3, BDNF and the like), PKC inhibitors (e.g., LY-333531 and the like), advanced glycation end-product (AGE) inhibitors (e.g., ALT946, pimagedine, pyradoxamine, phenacylthiazolium bromide (ALT766) and the like), active oxygen quenching agents (e.g., thioctic acid or derivative thereof, a bioflavonoid including flavones, isoflavones, flavonones, procyanidins, anthocyanidins, pycnogenol, lutein, lycopene, vitamins E, coenzymes Q, and the like), and cerebrovascular dilating agents (e.g., tiapride, mexiletene and the like).

In some embodiments, the disclosure encompasses use of a myostatin inhibitor (e.g., an anti-myostatin antibody or antigen-binding fragment thereof disclosed herein, e.g., Ab109, Ab133, or Ab141) in conjunction with a GLP-1-pathway activator, such as those described above, along with lifestyle interventions that support weight loss, such as diet and exercise. Upon cessation of the GLP-1 pathway activator, the anti-myostatin antibody or antigen-binding fragment thereof disclosed herein maintains some or all of the previous weight loss and maintains or gains lean muscle mass. (See, e.g., NCT04657016 and NCT04660643.)

In some embodiments, remission of diabetes can be induced by administration of a myostatin inhibitor (e.g., an anti-myostatin antibody or antigen-binding fragment thereof disclosed herein, e.g., Ab109, Ab133, or Ab141 or a variant thereof) in conjunction with a GLP-1 pathway activator, optionally in conjunction with a caloric restriction diet, or other diet. In some embodiments, an exercise routine is included depending on the subject's physical capabilities. In some embodiments, treatment comprising a myostatin inhibitor (an anti-myostatin antibody or antigen-binding fragment thereof disclosed herein, e.g., Ab109, Ab133, or Ab141) to a subject having type 2 diabetes that is in remission may advantageously allow the subject to reduce or eliminate other diabetes medication(s). In some embodiments, the myostatin inhibitor therapy may achieve partial or complete remission of type 2 diabetes.

In some embodiments, a myostatin inhibitor of the disclosure (e.g., an anti-myostatin antibody or antigen-binding fragment thereof disclosed herein, e.g., Ab109, Ab133, or Ab141 or a variant thereof) may be used in conjunction with one or more of a hyperlipidemic agent, an immunotherapeutic agent, an anti-obesity agent, a chemotherapeutic agent, an immunotherapeutic agent, an immunosuppressive agent, or an agent that improves cachexia.

Examples of anti-hyperlipemic agents include, for example, statin-based compounds which are cholesterol synthesis inhibitors (e.g., pravastatin, simvastatin, lovastatin, atorvastatin, fluvastatin, rosuvastatin and the like), squalene synthetase inhibitors or fibrate compounds having a triglyceride-lowering effect (e.g., fenofibrate, gemfibrozil, bezafibrate, clofibrate, sinfibrate, clinofibrate and the like), niacin, PCSK9 inhibitors, triglyceride lowering agents or cholesterol sequestering agents.

Examples of hypotensive agents include, for example, thiazide-type diuretics (e.g., hydrochlorothiazide, chlorthalidone, indapamide, and the like), angiotensin converting enzyme inhibitors (e.g., captopril, enalapril, delapril, benazepril, cilazapril, enalapril, enalaprilat, fosinopril, lisinopril, moexipril, perindopril, quinapril, ramipril, trandolapril and the like), angiotensin II antagonists (e.g., losartan, candesartan cilexetil, olmesartan medoxomil, eprosartan, valsartan, telmisartan, irbesartan, tasosartan, pomisartan, ripisartan forasartan, and the like), calcium channel blockers (e.g., amlodipine), or aspirin.

Examples of anti-obesity agents include, for example, agents that increase energy expenditure and/or fat metabolism and weight loss by neural and chemical regulation. Anti-obesity agents include biologic agents, such as antibodies, fusion proteins, nanobodies, and the like, as well as small molecule agents. Agents include those targeting GLP-1 and its receptor (GLP-1R), including GLP-1R agonists or other GLP-1 pathway activators, including biologics such as albiglutide, BPI-3016, danuglipron, DD01, dulaglutide, everestmab, exenatide, exendin-4, glutazumab, GLP-1 (7-36)NH2, GW002, IBI362 liraglutide, lixisenatide, MEDI0382, metformin, noiiglutide, orforglipron, pemvidutide, PF-07081532, semaglutide, taspoglutide, XW003, or tirzepatide; small molecules such as topiramate, dexfenfluramine, fenfluramine, phentermine, phenmetrazine, sibutramine, amfepramone, dexamphetamine, mazindol, diethylpropion, orlistat, cathine, oleoyl-estrone, perflubron, benfluorex, setmelanotide, aclimostat, cetilistat, amlintide, rimonabant, phenylpropanolamine, clobenzorex and the like. Anti-obesity agents also include insulin and insulin-secretion promoting agents, gastrointestinal lipase inhibitors (e.g., orlistat and the like), sodium glucose cotransporter 2 (SGLT-2) inhibitors, beta 3-adrenoceptor agonists (e.g., CL-316243, SR-58611-A, UL-TG-307, SB-226552, AJ-9677, BMS-196085 and the like), peptide-based, appetite-suppressing agents (e.g., leptin, CNTF, and the like), cholecystokinin agonists (e.g., lintitript, FPL-15849 and the like), oxytocin and oxytocin analogs (such as carbetocin), and the like.

Examples of chemotherapeutic agents include, for example, alkylating agents (e.g., cyclophosphamide, iphosphamide and the like), metabolism antagonists (e.g., methotrexate, 5-fluorouracil and the like), anticancer antibiotics (e.g., mitomycin, adriamycin and the like), vegetable-derived anticancer agents (e.g., vincristine, vindesine, taxol, and the like), cisplatin, carboplatin, etoposide, and the like. Among these substances, 5-fluorouracil derivatives such as furtulon and neofurtulon are preferred.

Examples of immunotherapeutic agents include, for example, microorganisms or bacterial components (e.g., muramyl dipeptide derivatives, picibanil and the like), polysaccharides having immune potentiating activity (e.g., lentinan, sizofilan, krestin and the like), cytokines obtained by a gene engineering technology (e.g., interferon, interleukin (IL) and the like), colony stimulating factors (e.g., granulocyte colony stimulating factor, erythropoietin and the like); among these substances, those preferred are IL-1, IL-2, IL-12 and the like.

Examples of immunosuppressive agents include, for example, calcineurin inhibitor/immunophilin modulators such as cyclosporine (Sandimmune, Gengraf, Neoral), tacrolimus (Prograf, FK506), ASM 981, sirolimus (RAPA, rapamycin, (Rapamune) or its derivative SDZ-RAD, glucocorticoids (prednisone, prednisolone, methylprednisolone, dexamethasone and the like), purine synthesis inhibitors (mycophenolate mofetil, MMF, CellCept®, azathioprine, cyclophosphamide), interleukin antagonists (basiliximab, daclizumab, deoxyspergualin), lymphocyte-depleting agents such as antithymocyte globulin (Thymoglobulin, Lymphoglobuline), anti-CD3 antibody (OKT3), and the like.

In addition, agents whose cachexia-improving effect has been established in an animal model or at a clinical stage, such as cyclooxygenase inhibitors (e.g., indomethacin and the like), progesterone derivatives (e.g., megestrol acetate), glucosteroids (e.g., dexamethasone and the like), metoclopramide-based agents, tetrahydrocannabinol-based agents, lipid metabolism improving agents (e.g., eicosapentanoic acid and the like), growth hormones, IGF-1, antibodies against TNF-α, LIF, IL-6 and oncostatin M may also be employed concomitantly with a myostatin inhibitor (e.g., e.g., an anti-myostatin antibody or antigen-binding fragment thereof disclosed herein). Additional therapeutic agents for use in the treatment of diseases or conditions related to metabolic disorders and/or impaired neurological signaling would be apparent to the skilled artisan and are within the scope of this disclosure.

In some embodiments, the present disclosure provides use of a myostatin inhibitor (e.g., a myostatin-selective inhibitor, e.g., an antibody or antigen-binding fragments thereof that specifically binds to pro/latent myostatin as described herein such as Ab102, Ab109, Ab130, Ab132, Ab133, or Ab141) in conjunction with additional agents such as TGFβ1 inhibitors, modulators (e.g., agonists and antagonists) of certain members of the TGFβ super family, such as BMP6, BMP7, GDF11, TGFβ2, TGFβ3, and/or an inhibitor of RGMc, such as anti-RGMc antibodies. In some embodiments, where the subject has NASH or NAFLD, the myostatin inhibitor is not used in conjunction with a TGFβ1 inhibitor.

Any of the above-mentioned agents can be administered in conjunction with a myostatin inhibitor disclosed herein (e.g., an anti-myostatin antibody or antigen-binding fragment thereof disclosed herein) to treat a metabolic disease or disorder, e.g., metabolic syndrome, obesity, type 2 diabetes, or type 2 diabetes associated with obesity. In some embodiments, any of the above-mentioned agents may be administered in conjunction with a myostatin inhibitor (e.g., an anti-myostatin antibody or antigen-binding fragment thereof disclosed herein) to treat a metabolic disease or disorder, e.g., metabolic syndrome, obesity, type 2 diabetes, or type 2 diabetes associated with obesity, wherein the agents are administered in conjunction with a diet and/or exercise regimen. Examples of the diet regimen include, but are not limited to, caloric restriction (e.g., reduced calorie intake or reduced absorption of calories), diets with modified nutrient content (e.g., high protein, low fat, low carbohydrate, keto, paleo, etc.) or modified timing of food intake (e.g., intermittent fasting, increased frequency of feeding, etc.) or a combination of modified timing, portion size, and nutrient content (e.g., more frequent meals of smaller portions containing high protein, low fat, and/or other nutrient content restrictions).

Biological Effects of Myostatin Inhibitors

Methods or treatments comprising administering a myostatin inhibitor are encompassed by the present disclosure. In some embodiments, the myostatin inhibitor may be a myostatin-selective inhibitor, e.g., an anti-myostatin antibody or antigen-binding fragment thereof disclosed herein, e.g., Ab102, Ab109, Ab130, Ab132, Ab133, or Ab141. In some embodiments, the myostatin inhibitor is administered in an effective amount to effectuate one or more beneficial effects (e.g., therapeutic effects) in a subject. Exemplary biologically beneficial effects are provided herein. In some embodiments, beneficial biological effects in a subject can be achieved by administration of a myostatin inhibitor, e.g., an antibody or antigen-binding fragments thereof that specifically binds to pro/latent myostatin as described herein, e.g., Ab102, Ab109, Ab130, Ab132, Ab133, or Ab141. In some embodiments, beneficial biological effects in a subject can be achieved by administration of myostatin inhibitor alone. In other embodiments, the myostatin inhibitor may be used in conjunction with at least one additional therapeutic agent or regimen to achieve one or more of the beneficial biological effects discussed herein, wherein, optionally, the at least one additional therapeutic agent or regimen may include one or more approved agents for treating a metabolic disorder such as diabetes. obesity, or a liver disease, wherein, optionally, the one or more approved agents include, e.g., a diet and/or exercise regimen, a GLP-1 pathway activator (e.g., dulaglutide, exenatide, semaglutide, liraglutide, lixisenatide, PF-07081532, or orforglipron), a biguanide (e.g., metformin), a sulfonyurea (e.g., glipizide, glimepiride, or glyburide), a bile acid-metformin, sequestrant, a dopamine-2 agonist (e.g., bromocriptine), a dipeptidyl peptidase 4 inhibitor (e.g., alogliptin, linagliptin, linagliptin-empagliflozin, linagliptin saxagliptin, or sitagliptin), a meglitinide (e.g., nateglinide, repaglinide, or repaglinide-metformin), a sodium-glucose cotransporter-2 (SGLT2) inhibitor (canagliflozin, canagliflozin-metformin, dapagliflozin, dapagliflozin-metformin or empagliflozin), a thiazolidinediones (e.g., tosiglitazone or pioglutazone), a weight-loss drug such as phentermine, benzphetamine, diethylpropion, or phendimetrazine, or a thyroid hormone receptor-beta (THR-beta) selective agonist, e.g., an aryloxyphenyl based thyromimetic such as resmetirom or eprotirome, or a diphenylmethane based thyromimetic such as sobetirome, Sob-AM2, VK2809 (MB08711), MB07344, IS25, and TG68. In some embodiments, the myostatin inhibitor (e.g., an antibody or antigen-binding fragments thereof that specifically binds to pro/latent myostatin as described herein, e.g., Ab102, Ab109, Ab130, Ab132, Ab133, or Ab141) may be used in conjunction with a GLP-1 pathway activator to achieve one or more of the biological effects discussed herein. In some embodiments, the myostatin inhibitor (e.g., an antibody or antigen-binding fragments thereof that specifically binds to pro/latent myostatin as described herein, e.g., Ab102, Ab109, Ab130, Ab132, Ab133, or Ab141) may be used in conjunction with a GLP-1 pathway activator and a diet and/or exercise regimen to achieve one or more of the biological effects discussed herein.

In some embodiments, the myostatin inhibitor (e.g., a selective myostatin inhibitor, e.g., an anti-myostatin antibody or antigen-binding fragment thereof disclosed herein, e.g., Ab102, Ab109, Ab130, Ab132, Ab133, or Ab141) is administered in an amount effective to cause two or more of the biological effects described below. In some embodiments, the myostatin inhibitor is administered in an amount effective to cause three or more of the biological effects described below. In some embodiments, the myostatin inhibitor is administered in an amount effective to cause four or more of the biological effects described below. In some embodiments, the myostatin inhibitor is administered in an amount effective to cause five or more of the biological effects described below. In some embodiments, the myostatin inhibitor is administered in an amount effective to cause six or more of the biological effects described below. In some embodiments, the myostatin inhibitor is administered in an amount effective to cause seven or more of the biological effects described below. In some embodiments, the myostatin inhibitor is administered in an amount effective to cause eight, nine, ten, eleven, twelve, thirteen, fourteen, fifteen, or sixteen of the biological effects described below. In some embodiments, the myostatin-selective inhibitor is an antibody or antigen-binding fragment thereof comprising all six CDRs of any one of Ab101-Ab141, e.g., the set of SEQ ID NOs identified for a specific antibody in Tables 2d-f. In some embodiments, the myostatin-selective inhibitor is an antibody or antigen-binding fragment thereof comprising the heavy and light chain variable domains of any one of Ab101-Ab141, e.g., the pair of SEQ ID NOs identified for a specific antibody in Table 3. In some embodiments, the myostatin-selective inhibitor is an antibody comprising the heavy and light chains of any one of Ab101-Ab141, e.g., the pair of SEQ ID NOs identified for a specific antibody in Table 4. In some embodiments, the myostatin-selective inhibitor antibody or antigen-binding fragment is selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141. In preferred embodiments, the antibody or antigen-binding fragment thereof is Ab109, Ab133 or Ab141.

In some embodiments, the myostatin inhibitor is administered in conjunction with at least one additional therapeutic agent (e.g., an approved therapeutic agent for treating a metabolic disorder, e.g., diabetes and/or obesity), wherein the administration is sufficient to cause two or more of the biological effects described herein.

A. Effect on Mass and/or Function of Muscle Tissue in the Human Subject

In some embodiments, administration of a myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) increases mass and/or function of a muscle tissue in the human subject. In some embodiments, the muscle tissue is selected from the group consisting of a smooth muscle tissue, a skeletal muscle tissue and a cardiac muscle tissue. Smooth muscle tissue is made up from long tapering cells, generally involuntary and differs from striated muscle in the much higher actin/myosin ratio, the absence of conspicuous sarcomeres and the ability to contract to a much smaller fraction of its resting length. Smooth muscle cells are found particularly in blood vessel walls, surrounding the intestine and in the uterus. Cardiac muscle tissue is a striated but involuntary tissue responsible for the pumping activity of the vertebrate heart. The individual cardiac muscle cells are not fused together into multinucleate structures as they are in striated muscle tissue. Skeletal muscle tissue is under voluntary control. The muscle fibers are syncytial and contain myofibrils, tandem arrays of sarcomeres. There are two general types of skeletal muscle fibers: slow-twitch (type I) and fast-twitch (type II) according to the expression of their particular myosin heavy chain (MHC) isoform. Slow-twitch muscles are better equipped to work aerobically and help enable long-endurance feats such as distance running, while fast-twitch muscles fatigue faster but are better equipped to work anaerobically and are used in powerful bursts of movements like sprinting. The differentiation between slow and fast twitch muscle fibers is based on histochemical staining for myosin adenosine-triphosphatase (ATPase) and the type of myosin heavy chain. The slow twitch muscle fiber (type I fiber) is MHC isoform I and the three fast twitch isoforms (type II fibers) are MHC isoform IIa, MHC isoform IId, and MHC isoform IIb (S. Schiaffino, J. Muscle Res. Cell. Motil., 10 (1989), pp. 197-205).

In some embodiments, the mass and/or function of a fast twitch muscle tissue in the human subject is increased. In other embodiments, the mass and/or function of a slow twitch muscle tissue in the human subject is increased. In some embodiments, maintaining muscle mass in the context of treating obesity provides beneficial effects for weight loss, e.g., as observed by resistance training. In some embodiments, administration of a myostatin inhibitor according to the present disclosure (e.g., Ab102, Ab109, Ab130, Ab132, Ab133, or Ab141) preferentially preserves fast-twitch fibers.

In some embodiments, the biological effects of administering an effective amount of the pharmaceutical compositions and therapeutic methods provided herein may be associated with a phenotypic change of muscle fiber types, which is a process referred to as fiber type switch. In some embodiments, fiber type switch is triggered by an event, such as an injury and starvation.

In one embodiment, the disclosure provides a method for promoting fiber type switch in a subject. The method comprises administering to the subject a composition comprising an antibody or antigen-binding fragment thereof (e.g., Ab102, Ab109, Ab130, Ab132, Ab133, or Ab141) that specifically binds pro/latent-myostatin and blocks release of mature myostatin in an amount effective to promote fiber type switch, thereby promoting fiber type switch in the subject.

In another embodiment, the disclosure provides a method for preferentially increasing type II or fast twitch fibers overtype I or slow twitch fibers in a subject. The method comprises administering to the subject a composition comprising a myostatin inhibitor, e.g., an antibody or antigen-binding fragment thereof that binds specifically to pro/latent myostatin as disclosed herein (e.g., Ab102, Ab109, Ab130, Ab132, Ab133, or Ab141), in an amount effective to preferentially increase type II or fast twitch fibers over type I or slow twitch fibers fiber type switch, thereby preferentially increasing type II or fast twitch fibers over type I or slow twitch fibers in the subject.

In some embodiments, administration of an effective amount of a myostatin inhibitor, e.g., an antibody or antigen-binding fragment thereof that binds specifically to pro/latent myostatin as disclosed herein, e.g., Ab102, Ab109, Ab130, Ab132, or Ab133, can cause an increase in muscle mass and/or muscle function. Preferably, such an increase in muscle mass is clinically meaningful to benefit or otherwise improve the health status of the subject. For example, clinically meaningful changes in muscle mass may improve the patient's mobility, self-care, metabolism, etc. In some embodiments, the increase in muscle mass is an increase in lean muscle or lean muscles. In some embodiments, such increase in muscle mass is a systemic effect such that muscles in the whole body or substantially whole body show the measurable effect. In some embodiments, lean muscle is muscle that is densely packed with contractile tissue and has low fat and connective tissue content. In other embodiments, effects are localized to certain group/type of muscles. In some embodiments, the mass of the muscle tissue, e.g., lean muscle tissue, is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue, e.g., lean muscle tissue, is increased by at least 1-5%, 5-10%, 10-20%, 1-30%, 1-40%, 1-50%, 10-50%, 20-30%, 20-60%, 30-80%, 40-90%, or 50-100%. Such increase in muscle mass may be deduced or measured by any suitable known methods, including measurement of cross-sectional area via MRI (e.g., forearm cross section), circumference, diaphragm width (e.g., via ultrasound), qNMR, DXA, etc.

In some embodiments, administration of an effective amount of a myostatin inhibitor, e.g., an antibody or antigen-binding fragment thereof that binds specifically to pro/latent myostatin as disclosed herein, e.g., an antibody selected from Ab101, Ab102, Ab103, Ab104, Ab105, Ab106, Ab107, Ab108, Ab109, Ab110, Ab111, Ab112, Ab113, Ab114, Ab115, Ab116, Ab117, Ab118, Ab119, Ab120, Ab121, Ab122, Ab123, Ab124, Ab125, Ab126, Ab127, Ab128, Ab129, Ab130, Ab131, Ab132, Ab133, Ab134, Ab135, Ab136, Ab137, Ab138, Ab139, Ab140 and Ab141 or an antigen binding fragment thereof, preferably Ab102, Ab109, Ab130, Ab132, or Ab133 or an antigen binding fragment thereof, can cause an enhancement in muscle function. Muscle function may be assessed by a variety of measures, including, without limitation: force generation, grip strength (e.g., maximum grip strength), endurance, muscle oxidative capacity, dynamic grip endurance, etc. In some embodiments, biomarkers indicative of myostatin inhibition may include a gene or protein expression marker described in PCT/US2018/012686, the contents of which are hereby incorporated by reference. In some embodiments, the biomarkers comprise one or more downregulated marker of adipogenesis, adipocytes, or adipokines. The biomarker change observed after administration may indicate an improvement in cardiovascular health, e.g., an increase in Actc1. In some embodiments, the biomarker change indicates a change in fatty acid synthesis, e.g., a reduction in Acc1, Pdk4, and/or an increase in PDP1. In some embodiments, serum creatinine levels are used as a biomarker indicative of muscle mass, e.g., an increase in serum creatinine following administration.

In some embodiments, the biomarker change observed after administration of a myostatin inhibitor may indicate a reduction in inflammation. In some embodiments, administration results in a reduction in one or more catabolic markers and/or an increase in one or more anabolic markers, e.g., when measuring protein synthesis, and the opposite when measuring fat synthesis. In some embodiments, administration results in reduced intramuscular fat.

In various embodiments, one or more biomarker change affected by administering an antibody disclosed herein may comprise (1) a decrease in the expression of pyruvate dehydrogenase kinase 4 (PDK4) and an increase in the expression of pyruvate dehydrogenase phosphatase 1 (PDP1); (2) a decrease in the expression of one or more of acetyl-CoA carboxylase (ACC1), adipogenin (ADIG), CCAAT/enhancer-binding protein delta (CEBPD), fatty acid binding protein 5 (FABP5), fatty acid synthase (FASN), lipase E (LIPE), perilipin 1 (PLIN1), perilipin 4 (PLIN4), angiotensinogen (AGT), angiopoietin-like 14 (ANGPTL14), apolipoprotein C1 (APOC1), adiponectin (ADIPOQ), Leptin (LEP), Resistin (RES), and Haptoglobin (HP); (3) an increase in the expression of Sharp1; (4) a decrease in the expression of MYOG, MYL2, MYL4, and/or TNNC1; (5) an increase in expression in actin alpha cardiac muscle 1 (ACTC1); and/or, (6) a decrease in the expression of PGC1A, NOR1, UCP1, and/or NUR77. In some embodiments, biomarker change affected by administering an antibody disclosed herein may comprise a decrease in the expression level of one or more regulators of adipogenesis, adipocyte markers, and adipokines (e.g., AGT, ANGPTL14, APOC1, ADIPOQ, ACC1, ADIG, LEP, RES, and HP). In some embodiments, biomarker change affected by administering an antibody disclosed herein may comprise a decrease in low-density lipoprotein (LDL) levels and/or decrease in the expression levels of apolipoprotein B (APOB). In some embodiments, biomarker change affected by administering an antibody disclosed herein may comprise an increase in high-density lipoprotein (DHL) levels and/or increase in the expression levels of apolipoprotein A-1 (APOA-1). In some embodiments, biomarker change affected by administering an antibody disclosed herein may comprise a decrease in the expression level of one or more inflammatory markers (e.g., IL-6, IL1Ra, IL1β, fibrinogen, and TNFα). In some embodiments, biomarker change affected by administering an antibody disclosed herein may comprise a decrease in the expression level of GlycA, high-sensitivity C-reactive protein (hs-CRP), and/or N-terminal prohormone of brain natriuretic peptide (NT-proBNP). In some embodiments, biomarker change affected by administering an antibody disclosed herein may comprise reduced intramuscular fat. In some embodiments, biomarker change affected by administering an antibody disclosed herein may comprise an increase in expression levels of insulin-like growth factor 1 (IGF-1), procollagen type III N-terminal peptide (P3NP), and/or fibroblast growth factor 21 (FGF-21). In some embodiments, biomarker change affected by administering an antibody disclosed herein may comprise an increase in the level of Ghrelin, total testosterone, growth hormone, and/or dehydroepiandrosterone sulfate (DHEA-S). In some embodiments, biomarker change affected by administering an antibody disclosed herein may comprise a decrease in the expression level of creatine kinase (CK) and/or an increase in serum creatinine levels. In some embodiments, biomarker changes affected by administering an antibody disclosed herein may comprise a decrease in markers previously identified as targets of myostatin signaling (e.g. ubiquitin ligases Fbxo32 (Atrogin-1) and/or Trim63 (MuRF) and/or ubiquitin protein Ubc (polyubiquitin C). In some embodiments, biomarker change affected by administering an antibody disclosed herein may comprise a decrease in the expression level of plasminogen activator inhibitor 1 (PAI-1). In some embodiments, biomarker change affected by administering an antibody disclosed herein may comprise a decrease in the level of 1,5-anhydroglucitol, fructosamine, and/or hemoglobin A1c (HBA1C). In some embodiments, biomarker change affected by administering an antibody disclosed herein may comprise a decrease in serum insulin. In some embodiments, biomarker change affected by administering an antibody disclosed herein may comprise a decrease in cortisol levels. In some embodiments, biomarker change affected by administering an antibody disclosed herein may comprise a decrease in expression level of pancreatic polypeptide family. In some embodiments, biomarker change affected by administering an antibody disclosed herein may comprise an increase in expression level of chromatin assembly factor 1 (CAF-1). In some embodiments, biomarker change affected by administering an antibody disclosed herein may comprise a decrease in leptin and fasting glucose. In some embodiments, treatment is continued if a listed change is detected. In some embodiments, dosages or treatment frequencies are increased if a listed change is not detected. In some embodiments, treatment is discontinued if a listed change is not detected. In some embodiments, the biomarker change is detected in samples collected 1-10, e,g., 2-7, e.g., 3 days after administration of an antibody disclosed herein. In some embodiments, the biomarker change is detected in a sample collected 7 days after administration of an antibody disclosed herein. In some embodiments, the biomarker change is detected in a sample collected 28 days after administration of an antibody disclosed herein. In some embodiments, the biomarker change serves as a pharmacodynamic biomarker for myostatin inhibition.

In some embodiments, the function of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the function of the muscle tissue is increased by at least about 1-5%, 5-10%, 10-20%, 1-30%, 1-40%, 1-50%, 10-50%, 20-30%, 20-60%, 30-80%, 40-90%, or 50-100%. In some embodiments, increased muscle function comprises improved rating, for example, from 1 to 2, 2 to 3, 3 to 4, 4 to 5, 5 to 6, 6 to 7, 7 to 8, 8 to 9, or 9 to 10.

In some embodiments, use of a myostatin inhibitor, e.g., an antibody or antigen-binding fragment thereof that binds specifically to pro/latent myostatin as disclosed herein, e.g., Ab102, Ab109, Ab130, Ab132, Ab133, or Ab141, in the methods of the present disclosure may increase the mass and/or function of the muscle tissue in the subject suffering from a lesion, e.g., due to a spinal cord injury. In some embodiments, the subject is in an acute spinal cord injury phase immediately after injury, where diagnosis between complete and incomplete injury is generally difficult. In other embodiments, the subject is in a sub-acute spinal cord injury phase, where there is a distinction between complete and incomplete spinal cord injury, and recovery is possible through ongoing rehab. In yet another embodiment, the subject is in a chronic spinal cord injury phase. The chronic SCI phase occurs around 4 or 6 months from the date of injury, where patients have demonstrated substantial decrease in rate of recovery or when rehab efforts have reached a plateau despite the ongoing standard of care efforts.

In some embodiments, the mass and/or function of the muscle tissue below a lesion is increased in a subject suffering from a lesion, e.g., a spinal cord injury. In other embodiments, the mass and/or function of the muscle tissue above a lesion is increased in a subject suffering from a lesion, e.g., a spinal cord injury. In some embodiments, the muscle is selected from the group consisting of a soleus muscle, a gastrocnemius muscle, a bicep muscle and a tricep muscle. In some embodiments, the mass of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue is increased by at least about 1-5%, 5-10%, 10-20%, 1-30%, 1-40%, 1-50%, 10-50%, 20-30%, 20-60%, 30-80%, 40-90%, or 50-100%. In some embodiments, the function of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the function of the muscle tissue is increased by at least 1-5%, 5-10%, 10-20%, 1-30%, 1-40%, 1-50%, 10-50%, 20-30%, 20-60%, 30-80%, 40-90%, or 50-100%.

In some embodiments, administration of a myostatin inhibitor, e.g., an antibody or antigen-binding fragment thereof that binds specifically to pro/latent myostatin as disclosed herein, e.g., Ab102, Ab109, Ab130, Ab132, Ab133, or Ab141, increases locomotor function in the human subject, e.g., in a subject suffering from a lesion. In some embodiments, the locomotor function of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the locomotor function of the human subject is increased by at least 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor, e.g., an antibody or antigen-binding fragment thereof that binds specifically to pro/latent myostatin as disclosed herein, e.g., Ab102, Ab109, Ab130, Ab132, Ab133, or Ab141, increases the motor coordination and balance in the human subject, e.g., in a subject suffering from a lesion. In some embodiments, the motor coordination and balance of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the motor coordination and balance of the human subject is increased by at least 1-5%, 5-10%, 10-20%, 1-30%, 1-40%, 1-50%, 10-50%, 20-30%, 20-60%, 30-80%, 40- 90%, or 50-100%.

In another embodiment, the myostatin inhibitor, e.g., an antibody or antigen-binding fragment thereof that binds specifically to pro/latent myostatin as disclosed herein, e.g., Ab102, Ab109, Ab130, Ab132, Ab133, or Ab141, is administered to a human subject suffering from a lesion. In some embodiments, the muscle strength of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the muscle strength of the human subject is increased by at least 1-5%, 5-10%, 10-20%, 1-30%, 1-40%, 1-50%, 10-50%, 20-30%, 20-60%, 30-80%, 40- 90%, or 50-100%.

In some embodiments, administration of a myostatin inhibitor e.g., an antibody or antigen-binding fragment thereof that binds specifically to pro/latent myostatin as disclosed herein, e.g., Ab102, Ab109, Ab130, Ab132, Ab133, or Ab141, can cause clinically meaningful changes in muscle function which corresponds to enhanced functionality of the patient. In some embodiments, enhanced functionality includes improvement in the patient's mobility, self-care, metabolism, etc. In some embodiments, administration of an effective amount of the myostatin inhibitor facilitates or accelerates recovery from a condition, such as injuries, surgeries, and other medical procedures. Suitable such conditions may involve a condition that is associated with a nerve damage (whether resulting from an injury or a surgical or other clinical procedure).

For example, suitable subjects include generally healthy individuals, such as a patient who: i) has sustained an acute injury involving a nerve damage that affects muscle function; ii) is scheduled to undergo a surgical procedure (therapeutic or corrective) that may cause an unintended nerve injury (e.g., motor neuron injury); iii) has undergone a surgical procedure that has caused an unintended muscle dysfunction; iv) receives a treatment that involves immobilization of a particular muscle or muscle groups (e.g., cast, etc.); v) is on ventilator (e.g., as a result of acute injury). The administration of a myostatin inhibitor described herein (e.g., Ab102, Ab109, Ab130, Ab132, Ab133, or Ab141) may accelerate recovery in such patients. In some embodiments, such administration may be prophylactic. For example, prior to undergoing or immediately following a surgical procedure that may cause a nerve damage and associated muscle dysfunction, the antibody may be administered to prevent muscle dysfunction. Prevention includes alleviating or lessening the severity of such dysfunction. In these embodiments, administration may be a local administration at or near the site of the affected area, e.g., injury, surgery, etc.

B. Effect on Muscle Catabolism of Protein and/or Muscle Release of Amino Acids in the Human Subject In some embodiments, administration of a myostatin inhibitor, e.g., an antibody or antigen-binding fragment thereof that binds specifically to pro/latent myostatin as disclosed herein, e.g., Ab102, Ab109, Ab130, Ab132, Ab133, or Ab141, to a human subject decreases muscle catabolism of protein and/or muscle release of amino acids in the human subject. In some embodiments, muscle catabolism of protein and/or muscle release of amino acids is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, muscle catabolism of protein and/or muscle release of amino acids is decreased by at least 1-5%, 5-10%, 10-20%, 1-30%, 1-40%, 1-50%, 10-50%, 20-30%, 20-60%, 30-80%, 40-90%, or 50-100%.

C. Effect on Preventing Muscle Loss or Atrophy in the Human Subject

In some embodiments, administration of an effective amount of a myostatin inhibitor, e.g., an antibody or antigen-binding fragment thereof that binds specifically to pro/latent myostatin as disclosed herein, e.g., Ab102, Ab109, Ab130, Ab132, Ab133, or Ab141, to a human subject prevents muscle loss or atrophy wherein the subject is at risk of developing muscle loss and/or atrophy. In some embodiments, muscle loss or atrophy is decreased or prevented by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In some embodiments, muscle loss or atrophy is decreased or prevented by at least 1-5%, 5-10%, 10-20%, 1-30%, 1-40%, 1-50%, 10-50%, 20-30%, 20-60%, 30-80%, 40-90%, or 50-100%. In some embodiments, muscle mass is retained (i.e., no muscle mass gain or loss) as a result of the administration. In some embodiments, muscle mass is retained while fat mass is reduced as a result of the administration. In some embodiments, a subject receiving the myostatin inhibitor may exhibit an increase in muscle mass. In some embodiments, administration of the myostatin inhibitor maintains the gain in muscle mass relative to muscle mass prior to treatment.

In some embodiments, a suitable subject is a human subject who has not yet developed atrophy but is considered at risk of developing atrophy. In some embodiments, the subject is on a weight loss program, such as a program comprising diet restriction and/or an exercise regimen. In some embodiments, the subject is on a weight loss program comprising a diet restriction regimen of at least 20%, e.g., at least 30%, 35%, 40%, 45%, or 50%, calorie reduction. In some embodiments, the subject has type 2 diabetes. In some embodiments, the subject is obese. In some embodiments, the subject is obese and has type 2 diabetes. In some embodiments, the subject has cardiovascular disease.

In some embodiments, a suitable subject is a human subject who has a disease or condition associated with a neurological defect that impairs motor neuron function. In some embodiments, such disease or condition is caused by muscular dystrophy or atrophy. In some embodiments, the neurological defect is caused by a nerve injury. In some embodiments, the nerve injury involves partial denervation of motor neurons, which causes partial impairment of function in the affected muscle. In some embodiments, such disease or condition is caused by SCI. In some embodiments, the subject with SCI is in an acute or sub-acute phase of SCI (e.g., not yet reached a chronic phase).

In some embodiments, when a composition comprising a myostatin inhibitor, e.g., an antibody or antigen-binding fragment thereof that binds specifically to pro/latent myostatin as disclosed herein, e.g., Ab102, Ab109, Ab130, Ab132, or Ab133, is administered to a population of patients who are at risk of developing muscle atrophy associated with partial denervation of motor neurons, the administration is capable of i) preventing onset or progression of the muscle atrophy in a statistically significant fraction of the patient population; or, ii) reducing the severity of the muscle atrophy in the statistically significant fraction of the patient population. In some embodiments, the myostatin inhibitor is administered at a dose and frequency sufficient to prevent onset or progression of muscle atrophy or reduce the severity of muscle atrophy.

Prevention of muscle loss or atrophy by the use of a myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) can be readily monitored or assessed by any suitable methods to evaluate muscle mass or motor function involving affected muscles.

In some embodiments, administration of an effective amount of a myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) prevents or lessens neuropathy, e.g., diabetic neuropathy, or an early-onset axonal polyneuropathy in affected limbs.

D. Effect on Intramuscular Fat Infiltration in the Human Subject

In some embodiments, administration of a myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) decreases intramuscular fat infiltration in the human subject. In some embodiments, intramuscular fat infiltration is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, intramuscular fat infiltration is decreased by at least 1-5%, 5-10%, 10-20%, 1-30%, 1-40%, 1-50%, 10-50%, 20-30%, 20-60%, 30-80%, 40-90%, or 50-100%.

E. Effect on the Level of Adipose Tissue in the Human Subject

Brown adipose tissue (BAT) is known to function in the dissipation of chemical energy in response to cold or excess feeding, and also has the capacity to modulate energy balance. Activation of brown adipose tissue has been shown to improve glucose homeostasis and insulin sensitivity in humans suggesting that anyone with impaired insulin function might benefit from BAT activation (Stanford et al., J Clin Invest. 2013, 123(1): 215-223).

Beige adipose tissue is generated as a result of browning of white adipose tissue (WAT), also known as "beiging." This occurs when adipocytes within WAT depots develop features of BAT. Beige adipocytes take on a multilocular appearance (containing several lipid droplets) and increase expression of uncoupling protein 1 (UCP1). In doing so, these normally energy-storing white adipocytes become energy-releasing adipocytes (Harms et al. Nature Medicine. 2013, 19 (10): 1252-63).

Visceral fat or abdominal fat (also known as organ fat or intra-abdominal fat) is located inside the abdominal cavity, packed between the organs (stomach, liver, intestines, kidneys, etc.). Visceral fat is different from subcutaneous fat underneath the skin, and intramuscular fat interspersed in skeletal muscles. Fat in the lower body, as in thighs and buttocks, is subcutaneous and is not consistently spaced tissue, whereas fat in the abdomen is mostly visceral and semi-fluid. An excess of visceral fat is known as central obesity, "central adiposity," or "belly fat," in which the abdomen protrudes excessively. Measurements such as the Body Volume Index (BVI) are specifically designed to measure abdominal volume and abdominal fat. Excess visceral fat is linked to type 2 diabetes, insulin resistance, inflammatory diseases and other obesity-related diseases (Mokdad et al., JAMA: The Journal of the American Medical Association. 2001, 289 (1): 76-9).

Mass of adipose tissue can be determined by any method known to a person of ordinary skill in the art. For example, adipose tissue may be measured by qNMR, dual-energy X-Ray absorptiometry (DXA), and other methods known in the art.

In some embodiments, administration of a myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) affects the level of adipose tissue in the human subject. As used herein, the term "adipose tissue" refers to fat including the connective tissue that stores fat. Adipose tissue is derived from preadipocytes. Its main role is to store energy in the form of lipids, although it also cushions and insulates the body. The two types of adipose tissue are white adipose tissue (WAT), which stores energy, and brown adipose tissue (BAT), which generates body heat.

In some embodiments, administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) increases the level of brown adipose tissue and/or the level of beige adipose tissue in the human subject. In some embodiments, the administration decreases the level of white adipose tissue and visceral adipose tissue in the human subject.

In some embodiments, administration of a myostatin inhibitor (e.g., an antibody or antigen-binding fragment thereof that binds specifically to pro/latent myostatin as disclosed herein, e.g., Ab102, Ab109, Ab130, Ab132, or Ab133) increases the level of brown or beige adipose tissue by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In some embodiments, the administration increases the level of brown or beige adipose tissue by at least 1-5%, 5-10%, 10-20%, 1-30%, 1-40%, 1-50%, 10-50%, 20-30%, 20-60%, 30-80%, 40-90%, or 50-100%.

In some embodiments, administration of a myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) decreases the level of white or visceral adipose tissue by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the administration decreases the level of white or visceral adipose tissue by at least 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) has different effects during the weight loss phase as compared to the weight maintenance phase. In some embodiments, administration of the myostatin inhibitor promotes more fat mass loss in the weight maintenance phase as compared to fat mass loss in the active weight loss phase. In some embodiments, administration of the myostatin inhibitor promotes more fat mass loss under moderate calorie restriction (e.g., 30% or less calorie restriction, e.g., 20% calorie restriction) as compared to extreme calorie restriction (e.g., 30% or more calorie restriction).

In some embodiments, administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) slows the rate of fat increase relative to the rate prior to starting the administration. In some embodiments, the administration maintains the reduced rate of fat increase. In some embodiments, the administration stops fat increase during the duration of the administration.

In some embodiments, the above effect(s) may be achieved with administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) alone or in conjunction with at least one additional agent (e.g., a standard of care therapeutic, e.g., for a metabolic disease). In some embodiments, the at least one additional agent is a GLP-1 pathway activator.

In some embodiments, administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141, e.g., Ab109) prevents the degree or rate of fat regain after discontinuation of a GLP-1 pathway activator.

In some embodiments, administration of the myostatin inhibitor, such as an antibody or antigen-binding fragment thereof that binds specifically to pro/latent myostatin as disclosed herein, e.g., Ab102, Ab109, Ab130, Ab132, Ab133 or Ab141, e.g., Ab109) reduces fat mass around the subject's liver.

F. Effect on the Ratio of Adipose-To-Muscle Tissue in the Human Subject

In some embodiments, administration of a myostatin inhibitor (e.g., a myostatin-selective inhibitor, e.g., an antibody or antigen-binding fragment thereof that binds specifically to pro/latent myostatin as disclosed herein, e.g., Ab102, Ab109, Ab130, Ab132, or Ab133) decreases the ratio of adipose-to-muscle tissue in the human subject. In some embodiments, the ratio of adipose-to-muscle tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the ratio of adipose-to-muscle tissue is decreased by at least 1-5%, 5-10%, 10-20%, 1-30%, 1-40%, 1-50%, 10-50%, 20-30%, 20-60%, 30-80%, 40-90%, or 50-100%. In some embodiments, administration of the myostatin inhibitor maintains the reduction in the ratio between adipose-to-muscle tissue in a human subject who has previously achieved a reduced ratio of adipose-to-muscle tissue.

In some embodiments, administration of a myostatin inhibitor (e.g., a myostatin-selective inhibitor, e.g., an antibody or antigen-binding fragment thereof that binds specifically to pro/latent myostatin as disclosed herein, e.g., Ab102, Ab109, Ab130, Ab132, Ab133, or Ab141) increases the ratio of muscle tissue to adipose in the human subject. In some embodiments, the ratio of muscle tissue-to-adipose is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the ratio of muscle tissue-to-adipose is increased by at least 1-5%, 5-10%, 10-20%, 1-30%, 1-40%, 1-50%, 10-50%, 20-30%, 20-60%, 30-80%, 40-90%, or 50-100%. In some embodiments, administration of the myostatin inhibitor maintains the increased ratio of muscle tissue to adipose tissue in a human subject who has previously achieved such an increased ratio.

In some embodiments, the above effect(s) may be achieved with administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) alone or in conjunction with at least one additional agent (e.g., a standard of care therapeutic, e.g., for a metabolic disease). In some embodiments, the at least one additional agent is a GLP-1 pathway activator.

G. Hormonal Control

Leptin is a hormone produced and secreted by adipose tissue that plays a role in regulating food intake and stimulating energy expenditure. Defects in leptin production have been reported to cause severe hereditary obesity in rodents and humans. In addition to its effects on body weight, leptin has a variety of other functions, including the regulation of hematopoiesis, angiogenesis, wound healing, and the immune and inflammatory response. Leptin acts through the leptin receptor, a single-transmembrane-domain receptor of the cytokine receptor family, which is found in many tissues in several alternatively spliced forms. The LEP gene is the human homolog of the gene (ob) mutant in the mouse 'obese' phenotype. The leptin level in a subject refers to the amount of circulating leptin in the body of the subject, e.g., a mammalian subject, and a reduction in leptin levels refers to a reduction in the amount of circulating leptin as compared to a baseline measurement, e.g., as a result of treatment.

In some embodiments, the therapeutic efficacy of treating a subject (e.g., a mammalian subject) with a myostatin inhibitor (e.g., e.g., a myostatin-selective inhibitor, e.g., an antibody or antigen-binding fragment thereof that binds specifically to pro/latent myostatin as disclosed herein, e.g., Ab102, Ab109, Ab130, Ab132, Ab133, or Ab141) may be determined by measuring a reduction in leptin levels in the blood of the subject after administering the myostatin inhibitor as compared to before the administration. In some embodiments, the therapeutic efficacy may be determined by (i) determining a blood level of leptin in the subject prior to administering the myostatin inhibitor; (ii) administering the myostatin inhibitor; and (iii) determining a blood level of leptin in the subject after administering the myostatin inhibitor; wherein a reduction in blood leptin level indicates therapeutic efficacy.

Adiponectin is an adipokine involved in the control of fat metabolism and insulin sensitivity with direct anti-diabetic, anti-atherogenic and anti-inflammatory activities. Adiponectin stimulates AMPK phosphorylation and activation in the liver and the skeletal muscle, enhancing glucose utilization and fatty-acid combustion and inhibits endothelial NF-kappa-B signaling through a cAMP-dependent pathway. Adiponectin may be involved in brown fat cell differentiation. As used herein, the term "adiponectin level" refers to the amount of circulating adiponectin, e.g., total adiponectin or glycosylated adiponectin. The plasma adiponectin level of a subject, e.g., a mammalian subject, may be measured by, e.g., the total adiponectin assay (ELISA kit EZHADP-61K, Millipore, St. Charles, Missouri, USA) which captures all forms of circulating adiponectin, with a sensitivity of 0.78 ng/mL and within-batch and between-batch coefficients of variation of 1.8% and 6.2%, respectively. An increase or decrease in adiponectin level refers to a higher or lower amount of circulating adiponectin detected in a subject (e.g., following a treatment for a metabolic disease or disorder) compared to a baseline measurement.

Ghrelin is an appetite-regulating hormone that has an appetite-stimulating effect, induces adiposity, and stimulates gastric secretion. Plasma ghrelin concentration is increased in fasting conditions and reduced after habitual feeding. The normal ghrelin concentration of plasma samples in humans is 10-20 fmol/ml for n-octanoyl ghrelin and 100-150 fmol/ml for total ghrelin, including both acyl-modified and des-acyl ghrelins. Ghrelin levels may be measured using, e.g., the Ghrelin Human ELISA kit, CAT #BMS2192 (Invitrogen).

In some embodiments, the above effect(s) may be achieved with administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) alone or in conjunction with at least one additional agent (e.g., a standard of care therapeutic, e.g., for a metabolic disease). In some embodiments, the at least one additional agent is a GLP-1 pathway activator.

H. Effect on the Metabolic Rate of the Human Subject

In some embodiments, administration of a myostatin inhibitor (e.g., a myostatin-selective inhibitor, e.g., an antibody or antigen-binding fragment thereof that binds specifically to pro/latent myostatin as disclosed herein, e.g., Ab102, Ab109, Ab130, Ab132, or Ab133) increases the metabolic rate of the human subject. In some embodiments, the administration can increase the basal metabolic rate in the subject. Metabolic rates can be calculated by any methods known in the art, for example, by examining the oxygen input and carbon dioxide output, or by indirect calorimetry. In some embodiments, the metabolic rate is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the metabolic rate is increased by at least 1-5%, 5-10%, 10-20%, 1-30%, 1-40%, 1-50%, 10-50%, 20-30%, 20-60%, 30-80%, 40-90%, or 50-100%.

In some embodiments, the above effect(s) may be achieved with administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) alone or in conjunction with at least one additional agent (e.g., a standard of care therapeutic, e.g., for a metabolic disease). In some embodiments, the at least one additional agent is a GLP-1 pathway activator.

I. Effect on Glucose Uptake in the Human Subject

In some embodiments, administration of a myostatin inhibitor (e.g., e.g., a myostatin-selective inhibitor, e.g., an antibody or antigen-binding fragment thereof that binds specifically to pro/latent myostatin as disclosed herein, e.g., Ab102, Ab109, Ab130, Ab132, or Ab133) affects glucose uptake by tissues in the human subject. In some embodiments, glucose uptake by muscle tissue is increased. In some embodiments, glucose uptake by the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In some embodiments, glucose uptake by the muscle tissue is increased by at least 1-5%, 5-10%, 10-20%, 1-30%, 1-40%, 1-50%, 10-50%, 20-30%, 20-60%, 30-80%, 40-90%, or 50-100%.

In other embodiments, glucose uptake by white adipose tissue, liver tissue and/or blood vessel tissue are reduced. In some embodiments, glucose uptake by white adipose tissue, liver tissue and/or blood vessel tissue are reduced by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, glucose uptake by white adipose tissue, liver tissue and/or blood vessel tissue are reduced by at least 1-5%, 5-10%, 10-20%, 1-30%, 1-40%, 1-50%, 10-50%, 20-30%, 20-60%, 30-80%, 40-90%, or 50-100%.

In some embodiments, treatment of a subject with a myostatin inhibitor (e.g., a myostatin-selective inhibitor, e.g., an antibody or antigen-binding fragment thereof that binds specifically to pro/latent myostatin as disclosed herein, e.g., Ab102, Ab109, Ab130, Ab132, or Ab133) reduces glucose levels (e.g., non-fasted glucose levels or fasted glucose levels) in the serum of the subject relative to baseline prior to treatment. In some embodiments, treatment of a subject comprising a GLP-1 receptor agonist and a myostatin inhibitor (e.g., a myostatin-selective inhibitor, e.g., an antibody or antigen-binding fragment thereof that binds specifically to pro/latent myostatin as disclosed herein, e.g., Ab102, Ab109, Ab130, Ab132, Ab133, or Ab141) reduces glucose levels (e.g., non-fasted glucose levels or fasted glucose levels) in the serum of the subject relative to a subject treatment with a GLP-1 receptor agonist alone. In some embodiments, the antibody or antigen-binding fragment thereof that binds specifically to pro/latent myostatin is Ab109 or comprises the CDRs and/or variable domains from Ab109.

The term "non-fasted glucose levels" refers to glucose content in a subject's blood as measured without having to fast or refraining from eating or drinking for a prolonged period of time, e.g., 8 hours. Blood glucose can be measured using a hemoglobin A1C test, also known as an A1C, HbA1C, glycated hemoglobin, or glycosylated hemoglobin test. Conventional home glucose monitoring can also be used to measure blood sugar. The term "postprandial insulin level" refers to the insulin concentration in a subject's blood shortly after eating (e.g., two hours after eating). The term "postprandial glucose level" refers to glucose concentrations in a subject's blood shortly after eating (e.g., two hours after eating). The postprandial insulin and glucose levels may be affected by carbohydrate absorption, insulin and glucagon secretion, and their coordinated effects on glucose metabolism in the liver and peripheral tissues. The magnitude and time of the peak plasma insulin or glucose concentration depend on a variety of factors, including the timing, quantity, and composition of the meal. In non-diabetic human subjects, plasma glucose concentrations peak about 60 min after the start of a meal and return to preprandial levels within 2-3 hour. Postprandial insulin levels may be measured using a postprandial insulin test, such as a two-hour postprandial insulin test. Postprandial glucose levels may be measured using a postprandial blood glucose test, such as a two-hour postprandial blood glucose test.

In some embodiments, the above effect(s) may be achieved with administration of the myostatin inhibitor (e.g., an antibody or antigen-binding fragment thereof that binds specifically to pro/latent myostatin as disclosed herein, e.g., Ab102, Ab109, Ab130, Ab132, Ab133, or Ab141) alone or in conjunction with at least one additional agent (e.g., a standard of care therapeutic, e.g., for a metabolic disease). In some embodiments, the at least one additional agent is a GLP-1 pathway activator.

J. Effect on Preventing Development of a Metabolic Disorder in the Subject

In some embodiments, administration of an effective amount of a myostatin inhibitor (e.g., a myostatin-selective inhibitor, e.g., an antibody or antigen-binding fragment thereof that binds specifically to pro/latent myostatin as disclosed herein, e.g., Ab102, Ab109, Ab130, Ab132, Ab133, or Ab141) may prevent development of a metabolic disorder in the subject, e.g., a human subject. In some embodiments, development of a metabolic disorder is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, development of a metabolic disorder is decreased by at least 1-5%, 5-10%, 10-20%, 1-30%, 1-40%, 1-50%, 10-50%, 20-30%, 20-60%, 30-80%, 40-90%, or 50-100%.

In some embodiments, administration of an effective amount of a myostatin inhibitor (e.g., a myostatin-selective inhibitor, e.g., an antibody or antigen-binding fragment thereof that binds specifically to pro/latent myostatin as disclosed herein, e.g., Ab102, Ab109, Ab130, Ab132, Ab133, or Ab141) reduces a risk of a cardiovascular disease, e.g., by reducing levels of cholesterol and or the LDL/HDL ratio. Cholesterol encompasses both low-density lipoprotein (LDL) cholesterol and high-density lipoprotein (HDL) cholesterol. Total cholesterol level refers to a measure of the total amount of cholesterol (e.g., LDL and HDL) in a blood sample collected from a subject. LDL cholesterol contains low-density lipoprotein that makes up most of the cholesterol found in the body. A high level of LDL may cause lipid deposits (e.g., plaques) in arteries and may be associated with or linked to increased risk for cardiovascular conditions, such as heart disease and stroke. By contrast, HDL cholesterol contains high-density lipoprotein, which absorbs cholesterol and carries it back to the liver. Generally, a high level of HDL cholesterol is associated with lower risk of heart disease and stroke. Cholesterol levels can be measured using a blood test, including blood tests commonly known as complete cholesterol tests, lipid panels, or lipid profiles.

In some embodiments, a suitable subject is a subject who has not fully developed a metabolic disease but is considered at risk of developing such a condition. In some embodiments, a subject has a disease or condition associated with muscle dysfunction. In some embodiments, the muscle dysfunction is associated with partial denervation of motor neurons, which causes partial impairment of function in the affected muscle. In some embodiments, such conditions are caused by muscular dystrophy or atrophy. In some embodiments, such condition is caused by SCI. In some embodiments, the subject with SCI is in an acute or sub-acute phase of SCI (e.g., not yet reached a chronic phase).

In some embodiments, when a composition comprising an effective amount of a myostatin inhibitor (e.g., a myostatin-selective inhibitor, e.g., an antibody or antigen-binding fragment thereof that binds specifically to pro/latent myostatin as disclosed herein, e.g., Ab102, Ab109, Ab130, Ab132, Ab133, or Ab141) is administered to a population of patients who are at risk of developing a metabolic disorder associated with muscle dysfunction, the composition i) prevents manifestation or aggravation of the metabolic disorder in a statistically significant fraction of the patient population; or, ii) lessens the severity of the metabolic disorder in the statistically significant fraction of the patient population. In some embodiments, myostatin inhibitor is administered alone or in conjunction with at least one additional agent (e.g., a standard of care therapeutic, e.g., for a metabolic disease). In some embodiments, the at least one additional agent is a GLP-1 pathway activator.

In some embodiments, effects on metabolism may be monitored or measured by insulin resistance, lipid panel/markers (e.g., leptin, adiponectin, ghrelin), inflammatory markers and oxidative stress markers, including, but are not limited to: IL-6, TNF, CRP, plasma total antioxidant status, lipid oxidation and erythrocyte glutathione peroxidase activity.

The Subject

Pharmaceutical compositions and therapeutic regimens described herein are suitable for administration in human or non-human subjects, e.g., mammalian subjects. Accordingly, the myostatin inhibitor, e.g., anti-pro/latent-myostatin antibodies, and antigen-binding portions thereof, described herein are useful as medicament for administering to a subject who is likely to benefit from reduced myostatin signaling. In some embodiments, the myostatin-selective inhibitor is an antibody or antigen-binding fragment thereof comprising all six CDRs of any one of Ab101-Ab141, e.g., the set of SEQ ID NOs identified for a specific antibody in Tables 2d-f. In some embodiments, the myostatin-selective inhibitor is an antibody or antigen-binding fragment thereof comprising the heavy and light chain variable domains of any one of Ab101-Ab141, e.g., the pair of SEQ ID NOs identified for a specific antibody in Table 3. In some embodiments, the myostatin-selective inhibitor is an antibody comprising the heavy and light chains of any one of Ab101-Ab141, e.g., the pair of SEQ ID NOs identified for a specific antibody in Table 4, or an antigen binding fragment thereof. In preferred embodiments, the antibody comprises Ab109, Ab133 or Ab141, or an antigen binding fragment thereof.

Selection of patients or patient populations who may benefit from myostatin inhibitor therapy according to the present disclosure are exemplified below, with the understanding that these categories are not intended to be limiting or mutually exclusive.

Patients with muscle disorders or muscle/motor impairment.

Patients suffering from muscle disorders or motor impairment, including primary myopathies and secondary myopathies, may benefit from myostatin inhibitor therapy. In some embodiments, the muscle disorders may be caused by inherent defects in the muscle itself (such as muscular dystrophies) or a result of neurological defects (such as SMA). In some embodiments, the myopathy may be caused by medication (i.e., drug-induced myopathies). In some embodiments, the myopathy may be caused by disuse.

Patients suffering from or at risk of manifesting bone loss.

Patients suffering from or prone to bone loss, e.g., reduced bone mineral density and increased frequency and/or severity of bone fractures, may benefit from myostatin inhibitor therapy. In some embodiments, bone loss or weak bone is caused by medication (i.e., drug-induced bone disorders). Certain drugs/pharmaceuticals have been reported to affect the microarchitecture of bone, leading to osteomalacia or osteoporosis.

Accordingly, in order to maintain or improve bone health, a myostatin inhibitor may be used in the treatment (e.g., prevention) of a bone disorder in a patient who is treated with a medication which may cause the dysregulation of bone metabolism. Examples of medications associated with impaired bone metabolism or bone mineral loss include: anti-epileptics, proton pump inhibitors, glucocorticoids, immunosuppressants (e.g., immune checkpoint inhibitors, calcineurin inhibitors), anticoagulants, glitazones, SGLT2 inhibitors, somatostatin analogs, anticancer medications, and protein kinase inhibitors. Thus, the myostatin inhibitor may be used as adjunct to (e.g., incorporated into; part of the treatment regimen) disclosed herein. In some embodiments, the patient is receiving a background therapy to maintain bone metabolism (prevent bone impairment).

Most of the currently available so-called myostatin inhibitors are in fact not selective for myostatin. Indeed, many also inhibit structurally similar growth factors such as GDF11. Notably, GDF11 has been implicated to play a role in the regulation of bone metabolism, and pharmacological inhibition of GDF11 may interfere with this process. Therefore, it is contemplated that a myostatin-selective inhibitor, such as those disclosed herein, should be considered particularly for patient populations that may be at risk of bone dysregulation, e.g., bone loss.

Examples of myostatin-selective inhibitors include antibodies and antigen-binding fragments thereof that specifically target pro/latent myostatin and inhibit its activation, such as Ab101-Ab141 disclosed herein, apitegromab (also known as SRK-015), and GYM329 (also known as R07204239); and antibodies and antigen-binding fragments thereof that selectively bind mature myostatin (i.e., growth factor) which interferes with ligand-receptor interaction, such as trevogrumab (also known as REGN1033). In more preferred embodiments, the myostatin-selective inhibitor is selected from Ab101-Ab141 of the present disclosure, such as Ab109, Ab133 and Ab141.

In some embodiments, suitable subjects include healthy individuals who may nonetheless benefit from enhanced muscle mass/function, as well as improved metabolism. In some embodiments, suitable subjects have an existing muscle condition and/or associated metabolic dysfunction. In some embodiments, suitable subjects are at risk of developing such condition(s). In some embodiments, suitable subjects are those on a therapy comprising another therapeutic agent to treat a muscle/metabolic condition, but which is associated with adverse effects or toxicity. In some embodiments, the subject is a pediatric subject, e.g., human patients of between birth and <18 years of age.

In some embodiments, preferred subjects meet at least two of the following criteria: i) the subject has a condition associated with partial denervation of a motor neuron; ii) the condition involves a muscle containing or enriched with fast twitch fibers; and iii) the subject retains an anabolic capability (e.g., generally healthy adults with injury) and/or is in a growth phase (e.g., young children, etc.). In some embodiments, preferred subjects has a metabolic disease or a metabolic condition associated with a neuromuscular disorder (e.g., a muscular atrophy/dystrophy, a myopathy, or spinal cord injury).

In some embodiments, treatment regimens comprising a myostatin inhibitor e.g., an anti-pro/latent-myostatin antibody, or antigen binding fragment thereof disclosed herein, e.g., any one of Ab101-Ab141, such as Ab102, Ab109, Ab130, Ab132, Ab133, or Ab141, are useful for administering to a subject who may be healthy but who may nonetheless benefit from enhanced muscle mass/function, as well as improved metabolism. In some embodiments, suitable subjects have an existing muscle condition and/or a metabolic condition that is associated with an existing muscle condition. In some embodiments, suitable subjects are at risk of developing such condition(s). In some embodiments, suitable subjects are those on a therapy comprising another therapeutic agent to treat a muscle/metabolic condition, but which is associated with adverse effects or toxicity. In some embodiments, the subject is a human subject who is less than 18 years of age. In some embodiments, the subject is a human subject (child or adolescent) aged 2-19 years, inclusive of endpoints. In some embodiments, the subject is a human subject aged 12 years or older (e.g., 12-17 years), inclusive of endpoints.

In some embodiments, a preferred subject is a human subject with obesity or who is overweight, e.g., a human subject with at least one weight-related condition such as diabetes mellitus type 2, high blood pressure, cardiovascular disease, or high cholesterol. In some embodiments, the subject is an overweight subject who has a body mass index (BMI) of 27 $kg/m^2$ or greater. In some embodiments, the subject has obesity and has a BMI of 28 to 40, inclusive of endpoints. In some embodiments, the subject has obesity and has a BMI of 30 $kg/m^2$ or greater. In some embodiments, a subject having a BMI of 27 $kg/m^2$ or greater is considered overweight according to European Medicines Agency Guideline on Clinical Evaluation of Medicinal Products Used in Weight Management. In some embodiments, a subject having a BMI of 30 $kg/m^2$ or greater is considered obese according to European Medicines Agency Guideline on Clinical Evaluation of Medicinal Products Used in Weight Management. In some embodiments, the subjects are on a reduced calorie diet and/or an exercise regimen. In some embodiments, the subject has a metabolic disorder. In some embodiments, the subject has an excess of abdominal fat.

In some embodiments, the subject has a body mass index of greater than or equal to 25, 26, 27, 28, 29, 30, or higher. In some embodiments, the subject has one or more obesity related comorbidities such as type II diabetes or cardiovascular disease. In some embodiments, the subject has a body mass index of greater than or equal to 30, or greater than or equal to 27, with one or more obesity related comorbidities such as type II diabetes or cardiovascular disease. In some embodiments, the subject is a pediatric subject.

In some embodiments, the subject is obese and diabetic. In some embodiments, the subject is obese and non-diabetic. In some embodiments, the subject is a pediatric subject.

Table 5 and Table 6 below show BMI ranges that may be used for overweight and obesity. An online tool for gauging the BMIs of adults can be found at: https://www.cdc.gov.

TABLE 5

BMI of adults ages 20 and older.
BMI of Adults Ages 20 and Older

| BMI | Classification |
|---|---|
| 18.5 to <25 | Normal weight |
| 25 to <30 | Overweight |
| 30 or higher | Obesity (including extreme obesity) |
| 40 or higher | Severe obesity |

Younger individuals (e.g., children and adolescents) grow at different rates at different times, so it is not always easy to tell if a child is overweight. The CDC BMI growth charts may be used to compare a child's or adolescent's BMI with other children or adolescents of the same sex and age. An online tool for gauging the BMIs of children and teens can be found at: https://www.cdc.gov/healthyweight/bmi/calculator.html.

TABLE 6

BMI of children and adolescents ages 2 to 19.
BMI of Children and Adolescents Ages 2 to 19

| BMI | Classification |
|---|---|
| At or above the 85th percentile on the CDC growth charts | Overweight or obesity |
| At or above the 95th percentile on the CDC growth charts | Obesity (including extreme obesity) |
| At or above 120 percent of the 95th percentile on the CDC growth charts | Extreme obesity |

In some embodiments, a subject having obesity is a subject who carries excess weight but does not have any comorbidities or risk factors for comorbid conditions and who does not experience any impairments in their daily feeling or functioning. In other embodiments, a subject having obesity is obese with risk factors, wherein the subject carries excess weight and does not yet have any comorbidities, but wherein the subject has measurable risk factors for comorbid conditions and/or impairments to their daily feeling or functioning. For instance, the subject may be at risk for insulin resistance, glucose intolerance, hypertension, cardiovascular disease, dyslipidemia, hyperuricemia, type 2 diabetes, stroke, fatty liver disease, kidney disease and other health issues. In other embodiments, a subject having obesity is obese and sick, wherein the subject carries excess weight and has one or more obesity-attributable comorbidities and impairments to their daily feeling or functioning. In some embodiments, the subject is overweight or obese but is not diabetic.

In some embodiments, a subject having obesity is evaluated using the Edmonton Obesity Staging System (EOSS), a 5-point ordinal classification system that considers comorbidity and functional status, as shown in Table 7.

TABLE 7

The Edmonton obesity staging system.

| Stage | Comorbidity and Functional Status |
|---|---|
| 0 | No apparent risk factors (e.g., blood pressure, serum lipid and fasting glucose levels within normal range), physical symptoms, psychopathology, functional limitations and/or impairment of well-being related to obesity |
| 1 | Presence of obesity-related subclinical risk factors (e.g., borderline hypertension, impaired fasting glucose levels, elevated levels of liver enzymes), mild physical symptoms (e.g., dyspnea on moderate exertion, occasional aches and pains, fatigue), mild psychopathology, mild functional limitations and/or mild impairment of well-being |
| 2 | Presence of established obesity-related chronic disease (e.g., hypertension, type 2 diabetes, sleep apnea, osteoarthritis), moderate limitations in activities of daily living and/or well-being |
| 3 | Established end-organ damage such as myocardial infarction, heart failure, stroke, significant psychopathology, significant functional limitations and/or impairment of well-being |
| 4 | Severe (potentially end-stage) disabilities from obesity-related chronic diseases, severe disabling psychopathology, severe functional limitations and/or severe impairment of well-being |

(See, e.g., Padwal et al, CMAJ. 2011 Oct 4; 183(14): e1059-e1066)

In some embodiments, a medicament disclosed herein is suitable for administration in a pediatric population, adult population, and/or an elderly population.

In some embodiments, such medicament is suitable for administration in a subject aged 2-19 years, inclusive of endpoints.

In some embodiments, such medicament is suitable for administration in a subject aged 12 years or older (e.g., 12-17 years), inclusive of endpoints.

The population in need for a myostatin inhibitor (e.g., an anti-pro/latent myostatin antibody or antigen-binding fragment) described herein, may range between 0 and 6 months of age, between 0 and 12 months of age, between 0 and 18 months of age, between 0 and 24 months of age, between 0 and 36 months of age, between 0 and 72 months of age, between 6 and 36 months of age, between 6 and 36 months of age, between 6 and 72 months of age, between 12 and 36 months of age, between 12 and 72 months of age. In some embodiments, the pediatric population suitable for receiving the myostatin inhibitor, e.g., antibody or antigen-binding fragment, described herein who is likely to benefit from such treatment may range between 0 and 6 years of age, between 0 and 12 years of age, between 3 and 12 years of age, between 0 and 17 years of age. In some embodiments, the population has an age of at least 5 years, e.g., 6, 7, 8, 9, 10, 11, 12, 13, 14, 15, 16, or 17 years. In some embodiments, the pediatric population may be aged below 18 years old. In some embodiments, the pediatric population may be (a) at least 5 years of age and (b) below 18 years of age.

The adult population in need for therapy comprising a myostatin inhibitor (e.g., an anti-pro/latent myostatin antibody or antigen-binding fragment) described herein may have an age of at least 20 years, e.g., at least 20, 25, 30, 35, 40, 45, 50, 55, 60 or 65 years. In some embodiments, the adult population may be below 65 years of age. In some embodiments, the adult population may be below 75 years of age.

The elderly population in need for therapy comprising a myostatin inhibitor (e.g., an anti-pro/latent myostatin antibody or antigen-binding fragment) described herein may have an age of 65 years or older (i.e., >65 years old), e.g., at least 70, 75 or 80 years.

In some embodiments, a human subject who is likely to benefit from the treatment comprising a myostatin inhibitor (e.g., an anti-pro/latent myostatin antibody or antigen-binding fragment) describe herein may be a human patient having, at risk of developing, or suspected of having a metabolic disease. In some embodiments, a human subject who is likely to benefit from the treatment comprising a myostatin inhibitor (e.g., an anti-pro/latent myostatin antibody or antigen-binding fragment) describe herein may be a human patient having a metabolic condition associated with a muscle disorder (e.g., spinal muscular atrophy, spinal cord injury, a muscle dystrophy). A subject having a metabolic disease or condition (e.g., obesity, type 2 diabetes mellitus (T2DM), etc.) can be identified by routine medical examination, e.g., laboratory tests, organ functional tests, CT scans, or ultrasounds. A subject suspected of having a metabolic disease or condition might show one or more symptoms of the metabolic disease or condition. A subject at risk for a metabolic disease or condition can be a subject having one or more of the risk factors for the metabolic disease or condition.

In some embodiments, a human subject who is likely to benefit from the treatment comprising a myostatin inhibitor may be a human subject having T2DM with a hemoglobin A1C (HbA1C) between 5% and 15% (e.g., between 6.5% and 10%, inclusive of endpoints).

In some embodiments, a human subject who is likely to benefit from the treatment comprising a myostatin inhibitor (e.g., an anti-pro/latent myostatin antibody or antigen-binding fragment) describe herein may be a human subject having T2DM who has been on an anti-diabetic treatment for at least 3 months. In some embodiments, the subject has been on an anti-diabetic treatment for approximately 3 months. In some embodiments, the subject has been on an anti-diabetic treatment for at least 6 months.

In some embodiments, a human subject who is likely to benefit from the treatment comprising a myostatin inhibitor (e.g., an anti-pro/latent myostatin antibody or antigen-binding fragment) describe herein may be a human subject having a body weight of at least 70 kg. In some embodiments, the subject has a body weight of at least 80 kg. In some embodiments, the subject has a body weight of 80 to 140 kg, inclusive of endpoints. In some embodiments, the subject has a body weight of more than 140 kg.

A control subject, as described herein, is a subject who provides an appropriate reference for evaluating the effects of a particular treatment or intervention of a test subject or subject. Control subjects can be of similar age, race, gender, weight, height, and/or other features, or any combination thereof, to the test subjects.

In some embodiments, a myostatin assay (e.g., myostatin ELISA) is used to identify a subject requiring treatment of a myostatin inhibitor (e.g., an anti-pro/latent myostatin antibody or antigen-binding fragment) describe herein. Methods for assaying myostatin include the total ELISA kit (EMD Millipore, Billerica, MA, USA), with the microplate absorbance reader (Bio-Rad) set to 450 nm. Additional methods can be found in Lakshman et al. Molecular and Cell Endocrinology (2009) 302:26-32 (myostatin ELISA) and Bergen et al. Skeletal Muscle (2015) 5:21 (liquid chromatography with tandem mass spectrometry, both of which are incorporated by reference herein.

In some embodiments, methods are provided for improving muscle performance in a subject. The subject may or may not have or be at risk of having a condition associated with decreased muscle mass and/or decreased muscle function. As used herein, the term "muscle performance" generally refers to the capacity of the muscle to contract and/or to apply a force (e.g., to an external object). In some embodiments, muscle performance may relate to the capacity of the muscle to consume energy. For example, in some embodiments, muscle performance may relate to the capacity of the muscle to produce and/or consume adenosine triphosphate (ATP) molecules to facilitate muscle contraction. In some embodiments, muscle performance refers to the capacity of the muscle to contract repeatedly for a particular duration of time. In some embodiments, muscle performance refers to the capacity of the muscle to apply a force to an object, e.g., to move the object over a measurable distance. In some embodiments, muscle performance refers to the capacity of the muscle to apply a force to an object for a particular duration of time (e.g., to move the object over a measurable distance for a particular duration of time).

In some embodiments, a myostatin inhibitor (e.g., an anti-pro/latent myostatin antibody or antigen-binding fragment) described herein is administered to a subject in need of the treatment at an amount sufficient to inhibit the proteolytic activation of pro/latent-myostatin to active myostatin by at least 20% (e.g., 30%, 40%, 50%, 60%, 70%, 80%, 90% or greater) in vivo. In other embodiments, a myostatin inhibitor, e.g., antibody or antigen-binding portion thereof, is administered in an amount effective in reducing the pro/latent-myostatin or latent myostatin level by at least 20% (e.g., 30%, 40%, 50%, 60%, 70%, 80%, 90% or greater).

In some embodiments, a myostatin inhibitor (e.g., an anti-pro/latent myostatin antibody or antigen-binding fragment) described herein is administered to a subject in need of the treatment at an amount sufficient to inhibit the proteolytic activation of pro/latent-myostatin to active myostatin by at least 20% (e.g., 30%, 40%, 50%, 60%, 70%, 80%, 90% or greater) in vivo and/or at an amount sufficient to enhance insulin secretion or inhibit glucagon secretion by at least 0.5, 1.0, 1.5, 2.0. 2.5, 3.0, 3.5, 4.0, 4.5, 5.0, 5.5, 6.0, 6.5, 7.0, 7.5, 8.0, 8.5, 9.0, 9.5, or 10.0 fold.

In some embodiments, the myostatin inhibitor, e.g., anti-pro/latent-myostatin antibody or antigen-binding portion thereof, described herein is administered to a subject who will benefit from increased muscle mass. In some embodiments, the myostatin inhibitor, e.g., an anti-pro/latent-myostatin antibody or antigen-binding portion thereof described herein, is administered to a subject who will benefit from increased muscle-to-fat ratios. In some embodiments, the myostatin inhibitor, e.g., anti-pro/latent-myostatin antibody or antigen-binding portion thereof, described herein is administered to a subject who will benefit from increased muscle function. In some embodiments, the subject may or may not have or be at risk of having a condition associated with decreased muscle mass and/or decreased muscle function. In some embodiments, the subject has or is at risk of having a condition associated with decreased muscle mass and/or decreased muscle function.

The methods of the present disclosure further comprise selecting a patient (subject) or a patient population who is likely to benefit from the therapy described herein.

In some embodiments, the subject suffers from or is at risk of developing a muscle condition or disorder. In some embodiments, the subject suffers from or is at risk of developing a metabolic disorder. In some embodiment, the subject suffers or is at risk of developing a disease or disorder associated with impaired neurological signaling.

In some embodiments, a myostatin inhibitor (e.g., an anti-pro/latent-myostatin antibody or antigen-binding portion thereof) described herein may be used in conjunction with one or more additional therapies. In some embodiments, selection of a subject who may benefit from a therapy comprising a myostatin inhibitor (e.g., an anti-pro/latent-myostatin antibody or antigen-binding portion thereof) described herein may be based on the responsiveness of a subject to another therapy aimed to treat a metabolic disease such as obesity or type 2 diabetes. Patients who respond poorly to such therapy may have an enhanced response to the therapy when used in conjunction with, complementary to, as an adjunct therapy or as an add-on therapy with a myostatin inhibitor (e.g., an anti-pro/latent-myostatin antibody or antigen-binding portion thereof described herein, e.g., any one of Ab101-Ab141, such as Ab102, Ab109, Ab130, Ab132, Ab133, or Ab141).

Thus, in some embodiments, a myostatin inhibitor (e.g., an anti-pro/latent-myostatin antibody or antigen-binding portion thereof described herein, e.g., any one of Ab101-Ab141, such as Ab102, Ab109, Ab130, Ab132, Ab133, or Ab141) is used in the treatment of a metabolic disease in a patient, wherein the treatment comprises administration of the myostatin inhibitor to the patient who has received, is receiving, or will receive another therapy aimed to treat the metabolic disease but has failed to achieve an intended therapeutic goal or expected therapeutic outcome, wherein optionally, the metabolic disease is obesity/overweight and/or type 2 diabetes.

In some embodiments, said "another therapy aimed to treat the metabolic disease" is or comprises a GLP-1 receptor agonist. In some embodiments, the "another therapy" may include, without limitation, albiglutide, taspoglutide, semaglutide, exenatide, BPI-3016, GW002, glutazumab, exendin-4, exenatide, GLP-1 (7-36)NH2, everestmab, liraglutide, lixisenatide, tirzepatide, dulaglutide, danuglipron (Pfizer), PF-07081532, or orforglipron. In some embodiments, other therapies comprising a GLP-1 receptor agonist include, but are not limited to, GLP-1 receptor agonist/GIP receptor antagonist combination such as AMG 133 (Amgen); GLP-1/GIP dual agonists such as tirzepatide (LY3298176; Eli Lilly), and CT-388; amylin/GLP-1 combination such as cagrilintide/semaglutide combination (Novo Nordisk); GLP-1/glucagon combination such as DD01 (Neuraly); GLP-1/glucagon receptor (GCG) agonist combinations such as ALT-801 (Altimmune), GLP-1/GIP such as CT-388 (Carmot); GLP-1/glucagon dual agonist such as IBI362 (LY-330567 (Innovent/Eli Lilly), cotadutide, DD01, danuglipron (PF-06882961) (Pfizer), mazdutide (IB1I362; LY-330567), MEDI0382; noiiglutide, oxyntomodulin, pemvidutide, setmelanotide (Rhythm), survodutide, and GLP-1/GIP/Glucagon triple receptor agonist such as retatrutide and LY343794. In some embodiments, the intended therapeutic goal or expected therapeutic outcome is a reduction of body weight (percent change from baseline) of at least 5% or at least 10%, reduced BMI, reduced waist circumference, reduced fat mass, increased lean to fat mass ratio, and/or improved insulin sensitivity.

In some embodiments, said "additional therapy" or "another therapy" is or comprises a diet and/or exercise regimen. In some embodiments, the "additional therapy" or "another therapy" is or comprises a biguanide (e.g., metformin). In some embodiments, the "additional therapy" or "another therapy" is or comprises a sulfonyurea (e.g., glipizide, glimepiride, or glyburide), a bile acid sequestrant, a dopamine-2 agonist (e.g., bromocriptine), a dipeptidyl peptidase 4 inhibitor (e.g., alogliptin, linagliptin, saxagliptin, or sitagliptin), a meglitinide (e.g., nateglinide or repaglinide), a sodium-glucose cotransporter-2 (SGLT2) inhibitor (canagliflozin, dapagliflozin, or empagliflozin), a thiazolidinediones (e.g., tosiglitazone or pioglutazone), a weight-loss drug such as phentermine, benzphetamine, diethylpropion, or phendimetrazine.

In some embodiments, the "additional therapy" or "another therapy" comprises a healthy diet, exercise, or a thyroid hormone receptor-beta (THR-beta) selective agonist e.g., an aryloxyphenyl based thyromimetic such as resmetirom or eprotirome, or a diphenylmethane based thyromimetic such as sobetirome, Sob-AM2, VK2809 (MB08711), MB07344, IS25, and TG68, e.g., wherein the metabolic disease is a liver disease, e.g., nonalcoholic steatohepatitis (NASH) or nonalcoholic fatty liver disease (NAFLD).

In some embodiments, the "additional therapy" or "another therapy" is not a TGFβ inhibitor (e.g., TGFβ1 inhibitor) if the subject has or is at risk of having NASH or NAFLD. In some embodiments, a subject having NAFLD or NASH or is at risk of developing NAFLD or NASH is not receiving and/or has not been treated with a TGFβ inhibitor (e.g., TGFβ1 inhibitor).

Patient selection may be based on a patient's ability to perform or adhere to a therapeutic regimen for a weight management treatment. In some embodiments, a myostatin inhibitor is used in the treatment of a metabolic disease in a patient wherein the treatment comprises administration of the myostatin inhibitor to the patient who is on a weight management therapy (e.g., a GLP-1 pathway activator) and who cannot or fails to perform or continue a reduced calorie regimen and/or an exercise regimen intended as part of the weight management therapy.

Patient selection may be based at least in part on the patient's tolerability to GLP-1 receptor agonists. In some embodiments, patients with low tolerance to GLP-1 receptor agonists may be candidates for a combination therapy comprising a myostatin inhibitor and a reduced dose of GLP-1 receptor agonist aimed to achieve at least equivalent efficacy as GLP-1 receptor agonist monotherapy but with less side effects. In some embodiments, such patients may be candidates for a combination therapy comprising a myostatin-selective inhibitor and metformin, optionally wherein the metformin is used in lieu of the GLP-1 receptor agonist. Advantageously, patients who have or are at risk of developing cancer may benefit from the myostatin-selective inhibitor-metformin combination therapy so as to avoid increased risk of cancer associated with GLP-1 receptor agonist.

Patient selection may be based on the eligibility criteria for myostatin inhibitors. For example, broad-spectrum inhibitors such as anti-ActRII (e.g., bimagrumab) which are capable of inhibiting not only myostatin but also Activin A, and in some cases other growth factors, may have undesirable effects on reproductive hormone regulation. For this reason, when such myostatin inhibitor is used for treating patients, women of child-bearing potential (as defined as those who are not post-menopausal or post-surgical sterilization) are either ineligible for such therapy or are required to be on at least two lines of contraceptives. By comparison, myostatin-selective inhibitors (such as the antibodies disclosed herein) may be preferred for administration to a broader patient population, including women of child-bearing potential who are not on contraceptives and/or who otherwise may be ineligible for receiving non-selective inhibitors of myostatin.

Patient selection may be based on background therapy or therapies that the patient is receiving. The background therapies may be standard-of-care medications for weight management and/or diabetes. In some embodiments, a myostatin-selective inhibitor (e.g., an anti-pro/latent-myostatin antibody or antigen-binding portion thereof described herein, e.g., any one of Ab101-Ab141, such as Ab102, Ab109, Ab130, Ab132, Ab133, or Ab141) is used in the treatment of obesity/overweight in a patient, wherein the treatment comprises administration of the myostatin-selective inhibitor to the patient who is on a background therapy containing a biguanide such as metformin or a derivative thereof. Non-limiting examples of metformin include Fortamet, Glucophage, Glucophage XR, Glumetza, Riomet, Obimet, Gluformin, Dianben, Diabex, Diaformin, Metsol, Siofor, Metforgamma and Glifor, as well as metformin-containing medications that include additional active. Examples include, but are not limited to, thiazolidinediones (glitazones) and rosiglitazone.

In some embodiments, a myostatin selective inhibitor (e.g., an anti-pro/latent-myostatin antibody or antigen-binding portion thereof described herein, e.g., any one of Ab101-Ab141, such as Ab102, Ab109, Ab130, Ab132, Ab133, or Ab141) is used to treat an overweight or an obese patient wherein the treatment comprises administering the myostatin selective inhibitor to a patient who is on a medication for type 2 diabetes. In some embodiments, the medication for type 2 diabetes may be a biguanide (e.g., phenformin, metformin, buformin and the like); an alpha-glucosidase inhibitor; a dipeptidyl peptidase-4 (DPP-4) inhibitor such as alogliptin, linagliptin, saxagliptin or sitagliptin; a sodium-glucose cotransporter-2 (SGLT-2) inhibitor such as dapagliflozin, canagliflozin, empagliflozin, or ertugliflozin; a sulfonylurea; or a thiazolidinedione. In some embodiments, due to the progression of diabetes, with or without a decline in beta cell function, the medication for type 2 diabetes alone does not meet the treatment goal.

Accordingly, the present disclosure includes a myostatin-selective inhibitor for use in the treatment of obesity in a patient, wherein the treatment comprises administration of the myostatin-selective inhibitor in conjunction with a GLP-1 receptor agonist and/or metformin, wherein the patient is characterized as one or more of the following: i) the patient has low tolerance (or hypersensitivity) to a GLP-1 receptor agonist at a dose considered efficacious as monotherapy; ii) the patient is a female patient of child-bearing potential who is not on at least two lines of contraceptives for at least 3 months before receiving a myostatin inhibitor therapy; and/or, iii) the patient benefits from maintaining lean mass. In some embodiments, the myostatin-selective inhibitor is used in conjunction with metformin for treating obesity in a patient, wherein the patient is not on a GLP-1 receptor agonist therapy.

Assessment and Measures of Body Composition

Clinical effects of the therapies described herein may be measured by any suitable methods or criteria in order to assess benefits on pharmacologic management of excess adiposity and accompanying metabolic disturbances (Heymsfield et al. J Biol Chem. 2020 Apr. 17; 295(16):5404-5418.).

In some embodiments, various parameters of body composition can be measured, such as changes in total body fat mass, lean mass, waist circumference, HbA1c levels, and body weight. Any suitable techniques can be employed to assess body composition, including, without limitation, qNMR, dual energy x-ray absorptiometry (DXA), magnetic resonance imaging (MRI)-derived hepatic fat fraction, hydrodensitometry, air displacement plethysmography (ADP), bioelectrical impedance analysis (BIA), bioimpedance spectroscopy (BIS), electrical impedance myography (EIM), 3D body scanners, and multi-compartment models (e.g., 3-compartment and 4-compartment models).

In some embodiments, the combination and adjunct therapies described herein may result in a change in total body fat mass in a subject as compared to baseline. In some embodiments, total body fat mass is measured by dual energy x-ray absorptiometry (DXA) (Garito et al. Diabetes Obes Metab. 2018; 20(1):94-102). In some embodiments, the combination and adjunct therapies described herein may result in a change in diabetes status in a subject as compared to baseline. In some embodiments, diabetes status can be determined by measuring the subject's HbA1C level, homeostatic model assessment, quantitative insulin sensitivity check, Matsuda Index (Yokoyama et al. J Clin Endocrinol Metab. 2004; 89(3):1481-1484; Hrebicek et al. J Clin Endocrinol Metab. 2002; 87(1):144-147; Matsuda et al. Diabetes Care. 1999; 22(9):1462-1470). In some embodiments, the combination and adjunct therapies described herein may result in a change in a subject's body weight, BMI, waist circumference, and/or waist-to-hip ratio. In some embodiments, the combination and adjunct therapies described herein may result in a change in a subject's body composition. In some embodiments, the subject's body composition may be assessed by DXA-measurements of bone mineral-free lean mass, magnetic resonance imaging (MRI)-derived hepatic fat fraction (Mashood et al. J Magn Reson Imaging. 2013; 37(6):1359-1370), and/or subcutaneous and abdominal visceral adipose tissue (Fallah et al. MAGMA. 2017; 30 (2):139-151). In some embodiments, the combination and adjunct therapies described herein may result in a change in a subject's metabolic status (Garito et al. Diabetes Obes Metab. 2018; 20(1):94-102; Goyal et al. N Am J Med Sci. 2012; 4(4):180-184; Rossi et al. Obesity (Silver Spring). 2011; 19(9):1747-1754). In some embodiments, the subject's metabolic status may be assessed using metabolic biomarkers, non-limiting examples of such markers are discussed in, e.g., Robberecht et al., Metab Syndr Relat Disord. 2016 March; 14(2):47-93, and Belhayara et al., Nutrients. 2020 March; 12(3): 727, each of which is herein incorporated by reference in its entirety. In some embodiments, the subject's metabolic status may be assessed based on the subject's cardiovascular risk factors, including serum lipid levels, high-sensitivity C-reactive protein level, interleukin 6 level, leptin level, adiponectin level, and blood pressure. In some embodiments, the combination and adjunct therapies described herein may result in a change in a subject's physical performance. In some embodiments, the subject's physical performance may be assessed by measuring hand grip strength by dynamometry (Rooks et al. J Am Geriatr Soc. 2017; 65(9):1988-1995).

Routes of Administration

To practice the method disclosed herein, an effective amount of the pharmaceutical composition described above can be administered to a subject (e.g., a mammalian subject) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. In some embodiments, the administration is intravenous. In some embodiments, the administration is subcutaneous. In some embodiments, a preferred route of administration for a myostatin inhibitor (e.g., an anti-pro/latent-myostatin antibody or antigen-binding portion thereof described herein, e.g., any one of Ab101-Ab141, such as Ab102, Ab109, Ab130, Ab132, Ab133, or Ab141) is subcutaneous. The myostatin-selective inhibitor may be an antibody or antigen-binding fragment thereof comprising all six CDRs of any one of Ab101-Ab141, e.g., the set of SEQ ID NOs identified for a specific antibody in Tables 2d-f. The myostatin-selective inhibitor may be an antibody or antigen-binding fragment thereof comprising the heavy and light chain variable domains of any one of Ab101-Ab141, e.g., the pair of SEQ ID NOs identified for a specific antibody in Table 3. The myostatin-selective inhibitor may be an antibody comprising the heavy and light chains of any one of Ab101-Ab141, e.g., the pair of SEQ ID NOs identified for a specific antibody in Table 4.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

In preferred embodiments, the composition comprising a myostatin inhibitor (e.g., an anti-pro/latent-myostatin antibody or antigen-binding portion thereof described herein, e.g., any one of Ab101-Ab141, such as Ab102, Ab109, Ab130, Ab132, Ab133, or Ab141) is formulated for subcutaneous administration. In some embodiments, the antibodies and antigen binding fragments thereof disclosed herein (e.g., any one of Ab101-141, such as Ab102, Ab109, Ab130, Ab132, Ab133, or Ab141 or an antigen binding fragment thereof) provide improved bioavailability, e.g., at least 80%, 81%, 82%, 83%, 84%, or 85% bioavailability or greater following subcutaneous administration, as compared to intravenous administration. Notably, other myostatin inhibitors, including bimagrumab and taldefgrbep alfa are not suitable for subcutaneous administration at volumes that can be injected and/or with comparable bioavailability to intravenous dosing. As such, the antibodies and antigen binding fragments thereof disclosed herein may provide superior benefit for a subject whose treatment favors a subcutaneous administration, e.g., a subject suffering from a cardiometabolic disorder such as obesity or other chronic disorder necessitating repeated administration of a therapeutic agent.

In some embodiments, the composition may contain more than one agent, e.g., a myostatin inhibitor and at least one other pharmaceutically active ingredient in the same formulation. In some embodiments, e.g., for adjunct therapy, a myostatin inhibitor (e.g., an anti-pro/latent-myostatin antibody or antigen-binding portion thereof described herein, e.g., any one of Ab101-Ab141, such as Ab102, Ab109, Ab130, Ab132, Ab133, or Ab141) may be formulated in a separate formulation as one or more additional therapies.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically-acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as water-for-injection, 0.9% saline, or 5% glucose solution.

In one embodiment, a myostatin inhibitor, e.g., an anti-pro/latent-myostatin antibody or antigen-binding portion thereof disclosed herein, is administered via site-specific or targeted local delivery techniques. Examples of site-specific or targeted local delivery techniques include various implantable depot sources of the myostatin inhibitor, e.g., anti-pro/latent-myostatin antibody or antigen-binding portion thereof, or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

The particular dosage regimen, e.g., dose, timing, and repetition, used in the methods described herein will depend on the particular subject and that subject's medical history as well as the formulation and pharmacokinetic properties of the drug administered, e.g., the myostatin inhibitor.

In some embodiments, in the context of an increase in the level of pro-myostatin in the target muscle, the increase is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to a control level of pro-myostatin, wherein the level of pro-myostatin is measured by ELISA. In one embodiment, the increase in the level of pro-myostatin in the target muscle is an increase in a range of 1-fold to 3-fold, 1.2-fold to 10-fold, 2-fold to 9-fold, 3-fold to 8-fold, 4-fold to 7-fold, 2-fold to 7-fold, etc. compared to the control level of pro-myostatin.

The term "control level" refers to an accepted or predetermined level of a biological marker, e.g., a level of a marker obtained before treatment or the onset of disease or before administration of a drug, e.g., an antibody or an antigen-binding portion thereof. The level of a biological marker present in a subject or population of subjects having one or more particular characteristics, e.g., the presence or absence of a particular disease or condition.

In some embodiments, in the context of an increase in latent myostatin in the target muscle after the administering step, the increase is detectable within 4 hours, 24 hours, 48 hours, 7 days, 14 days, 21 days, 28 days or 30 days (or any time range bracketed by any of the listed duration of times) after the administering step. In one embodiment, an increase in latent myostatin in the target muscle after the administering step is detectable for at least 5 days, 7 days, 14 days, 21 days, 28 days, or 30 days (or any time range bracketed by any of the listed duration of times) after the administering step. In one embodiment, an increase in the level of latent myostatin in the target muscle after the administering step is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to the level of latent myostatin in the target muscle before the administering step. In one embodiment, an increase in the level of latent myostatin in the target muscle after the administering step is an increase in a range of 1-fold to 3-fold, 1.2-fold to 10-fold, 2-fold to 9-fold, 3-fold to 8-fold, 4-fold to 7-fold, 2-fold to 7-fold, etc., compared to the level of latent myostatin in the target muscle before the administering step.

In some embodiments, administration of the novel antibodies or antigen-binding fragments disclosed herein does not lead to accumulation of serum myostatin in a subject, as measured by total levels of myostatin or latent myostatin in serum. In some embodiments, in the context of a decrease in the level of latent myostatin in the circulation, the decrease is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to a control level of latent myostatin. In one embodiment, a decrease in the level of latent myostatin in the circulation is a decrease in a range of 1-fold to 3-fold, 1.2-fold to 10-fold, 2-fold to 9-fold, 3-fold to 8-fold, 4-fold to 7-fold, 2-fold to 7-fold, etc. compared to the control level of latent myostatin. In some embodiments, serum myostatin or latent myostatin can be measured using ELISA, e.g., according to Cote et al. (SLAS Discovery (2020) 25(1): 95-103) and (Lakshman (2009) Cellular Endocrinol 302:26).

In some embodiments, in the context of administering an effective amount of a myostatin inhibitor (e.g., an anti-pro/latent-myostatin antibody or antigen-binding portion thereof described herein) to a subject, an effective amount is an amount effective to increase the mass of a target muscle in the subject compared with a control muscle mass. In some embodiments, the mass of a muscle treated with an effective amount of the myostatin inhibitor therapy is increased by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, etc. as compared with a control muscle that is not treated with an effective amount of the combination. In some embodiments, such a muscle mass increase is achieved in a select group or type of muscles in the subject. In some embodiments, an effective amount is an amount effective to maintain muscle mass in a subject (e.g., a mammal) throughout treatment with a myostatin inhibitor e.g., an anti-pro/latent-myostatin antibody or antigen-binding portion thereof described herein. For example, a subject receiving the combination treatment may retain muscle mass as fat mass is reduced. In some embodiments, an effective amount is an amount effective to reduce loss of mass in a target muscle in a subject compared with a control muscle mass, during and/or after the treatment with the myostatin inhibitor therapy.

In some embodiments, an effective amount is administered subcutaneously, e.g., to a subject needing treatment for a cardiometabolic disorder such as obesity. In some embodiments, an effective amount administered subcutaneously is a dose equivalent to about 10 mg/kg or less when administered intravenously, e.g., equivalent to about 0.1 mg/kg to 10 mg/kg.

The term "control" in reference to a control sample refers to any clinically or scientifically relevant comparative sample or counterpart, including, for example, a sample from a healthy subject, a sample from a subject having a deficiency that can cause or make the subject susceptible to a certain disease or condition, a subject with a disease or condition of interest, a sample from a subject treated with a pharmaceutical carrier, a sample from a subject prior to treatment, a sham or buffer treated subject or sample, an untreated subject or sample, and the like.

In some embodiments, an effective amount of a myostatin inhibitor (e.g., an anti-pro/latent-myostatin antibody or antigen-binding portion thereof described herein) is an amount effective to reduce overall body weight. In some embodiments, body weight of a subject treated with an effective amount of the myostatin inhibitor therapy is decreased by at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, etc. as compared to untreated baseline. In some embodiments, the reduction in body weight of a subject treated with an effective amount of the myostatin inhibitor therapy is predominantly due to reduction of fat mass as determined by qNMR.

In some embodiments, an effective amount of a myostatin inhibitor (e.g., an anti-pro/latent-myostatin antibody or antigen-binding portion thereof described herein) is an amount effective to switch fiber types in the subject. In some embodiments, an effective amount of the myostatin inhibitor therapy can promote a fiber type switch from type I to type II. In some embodiments, an effective amount of the myostatin inhibitor therapy can promote a fiber type switch from type I to type IIB. In some embodiments, an effective amount of the myostatin inhibitor therapy can promote type II fibers, relative to other types of fibers. In some embodiments, an effective amount of the myostatin inhibitor therapy can promote type IIB fibers, relative to other types of fibers. In some embodiments, such phenotypic switch in fibers may occur without significant change in overall muscle mass. In other embodiments, such phenotypic switch in fibers may coincide with an increase in overall muscle mass.

In some embodiments, an effective amount of a myostatin inhibitor (e.g., an anti-pro/latent-myostatin antibody or antigen-binding portion thereof described herein) is an amount effective to increase diameter of muscle fiber in the subject compared with a control muscle fiber. In some embodiments, the increase in the diameter of the muscle fiber is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control muscle fiber. In some embodiments, the increase in the diameter of muscle fiber is an increase in a range of 1-fold to 5-fold, 2-fold to 10-fold, 1-fold to 1.5-fold, 1-fold to 2-fold, etc. compared with a control muscle fiber.

In some embodiments, an effective amount of a myostatin inhibitor (e.g., an anti-pro/latent-myostatin antibody or antigen-binding portion thereof described herein) is an amount effective to increase muscle-to-fat ratio in the subject compared with a control muscle mass. In some embodiments, the increase in the muscle-to-fat ratio is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control subject. In some embodiments, the increase in the muscle-to-fat ratio is an increase in a range of 1-fold to 5-fold, 2-fold to 10-fold, 1-fold to 1.5-fold, 1-fold to 2-fold, etc. compared with a control subject.

In some embodiments, an effective amount of a myostatin inhibitor (e.g., an anti-pro/latent-myostatin antibody or antigen-binding portion thereof described herein) is an amount effective to decrease intramuscular fat infiltration in the subject compared with a control muscle mass. In some embodiments, the decrease in the intramuscular fat infiltration is a decrease of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control subject. In some embodiments, the decrease in intramuscular fat infiltration is a decrease in a range of 1-fold to 5-fold, 2-fold to 10-fold, 1-fold to 1.5-fold, 1-fold to 2-fold, etc. compared with a control subject.

In some embodiments, a method of preventing a reduction of and/or increasing muscle mass in a human subject includes administering a myostatin inhibitor (e.g., an anti-pro/latent-myostatin antibody or antigen-binding portion thereof described herein) to a subject wherein the myostatin inhibitor inhibits proteolytic formation of mature myostatin by a tolloid protease. In one embodiment, inhibition of proteolytic cleavage of pro-myostatin or latent myostatin by a tolloid protease results in a progressive or sustained increase in muscle mass. In one embodiment, a subject exhibits a progressive increase in muscle mass for at least 2 weeks, 4 weeks, 6 weeks, 8 weeks, 10 weeks, 12 weeks, 14 weeks, 16 weeks, 18 weeks, or 20 weeks (or any range bracketed by any of the values). In some embodiments, a method of preventing a reduction of and/or increasing muscle mass in a human subject includes administering a myostatin inhibitor, e.g., a pro/latent-myostatin antibody, or antigen-binding fragment thereof, to a subject comprising more than two doses. In one embodiment, administering the myostatin inhibitor comprises at least a first dose and a second dose, the first dose and the second dose are administered to the subject at least about one week apart, 2 weeks apart, 4 weeks apart, 6 weeks apart, 8 weeks apart, or 12 weeks apart.

As used herein, the term "control muscle mass" refers to a reference standard useful for evaluating effects of a condition (e.g., treatment with a myostatin inhibitor on the mass of a target muscle in a subject). In some embodiments, the target muscle is a gastrocnemius muscle. In some embodiments, a control muscle mass is a predetermined value. In some embodiments, a control muscle mass is experimentally determined. In some embodiments, a control muscle mass is the mass of a target muscle in a subject who has not been administered the myostatin inhibitor, e.g., a pro/latent-myostatin antibody, or antigen-binding fragment thereof, as described herein. In some embodiments, a control muscle mass is the mass (e.g., the average mass) of a target muscle in a population of subjects who have not been administered the myostatin inhibitor. In some embodiments, a control muscle mass is the mass of a target muscle in a subject prior to (e.g., immediately prior to) being administered the myostatin inhibitor therapy. In some embodiments, a control muscle mass is the mass of a target muscle in a subject who has been administered, in place of the myostatin inhibitor, (e.g., an anti-myostatin antibody), a normal antibody (e.g., of the same isotype as the anti-myostatin antibody) that has been obtained from an animal that has not been exposed to the antigen to which the anti-myostatin antibody, or antigen-binding fragment thereof, is directed. In some embodiments, a control muscle mass is the mass of a target muscle in a subject who has been administered, in place of the myostatin inhibitor, e.g., pro/latent-myostatin antibody, or antigen-binding fragment thereof, a vehicle, e.g., saline.

Dosages

Empirical considerations, such as the half-life, generally will contribute to the determination of the dosage. For example, antibodies and antigen-binding portions thereof that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a disease/disorder associated with myopathy. Alternatively, sustained continuous release formulations of a myostatin inhibitor, e.g., an anti-pro/latent-myostatin antibody, or antigen-binding portion thereof, may be appropriate. The myostatin inhibitor may be an antibody or antigen-binding fragment thereof comprising all six CDRs of any one of Ab101-Ab141, e.g., the set of SEQ ID NOs identified for a specific antibody in Tables 2d-f. The myostatin inhibitor may be an antibody or antigen-binding fragment thereof comprising the heavy and light chain variable domains of any one of Ab101-Ab141, e.g., the pair of SEQ ID NOs identified for a specific antibody in Table 3. The myostatin inhibitor may be an antibody comprising the heavy and light chains of any one of Ab101-Ab141, e.g., the pair of SEQ ID NOs identified for a specific antibody in Table 4. Various formulations and devices for achieving sustained release would be apparent to the skilled artisan and are within the scope of this disclosure.

In some embodiments, dosages for a myostatin inhibitor, e.g., an anti-pro/latent-myostatin antibody, or antigen binding fragment thereof, as described herein may be determined empirically in individuals who have been given one or more administration(s) of the myostatin inhibitor, e.g., antibody, or antigen binding fragment thereof. Individuals are given incremental dosages of the antagonist. To assess efficacy of the antagonist, an indicator of the disease/disorder can be followed.

In some embodiments, dosages for a myostatin inhibitor, e.g., an anti-pro/latent-myostatin antibody, or antigen binding fragment thereof, as described herein may be selected for obtaining one or more of the desired effects discussed herein via subcutaneous administration.

For the purpose of the present disclosure, the appropriate dosage of a myostatin inhibitor, e.g., an anti-pro/latent-myostatin antibody, or antigen binding fragment thereof, will depend on the specific antibody (or compositions thereof) employed, the type and severity of the disease/disorder, whether the antibody is administered for preventive or therapeutic purposes, previous therapy, the patient's clinical history and response to the antagonist, and the discretion of the attending physician. In some embodiments, a clinician will administer a myostatin inhibitor, e.g., an anti-pro/latent-myostatin antibody or antigen-binding portion thereof, until a dosage is reached that achieves the desired result. Administration of a myostatin inhibitor, e.g., an anti-pro/latent-myostatin antibody or antigen-binding portion thereof, can be continuous or intermittent, depending, for example, upon the recipient's physiological condition, whether the purpose of the administration is therapeutic or prophylactic, and other factors known to skilled practitioners. The administration of a myostatin inhibitor, e.g., an anti-pro/latent-myostatin antibody, or antigen binding fragment thereof, may be essentially continuous over a preselected period of time or may be in a series of spaced dose, e.g., either before, during, or after developing a disease or disorder associated with pro/latent-myostatin.

The novel myostatin-selective inhibitory antibodies disclosed herein, e.g., any one of Ab101-141, e.g., Ab109, or an antigen binding fragment thereof, are highly potent (e.g., have IC50 of less than 1 nM as measured by functional ELISA as described herein) and have favorable developability and PK profiles, making them particularly suited for subcutaneous formulations. In some embodiments, effective doses of such antibodies are between about 0.1 mg/kg and 10 mg/kg per dose, e.g., between about 0.1 mg/kg and 5 mg/kg, between about 0.1 mg/kg and 3 mg/kg, between about 0.1 mg/kg and 2 mg/kg. In some embodiments, the antibodies and antigen binding fragments thereof disclosed herein (e.g., any one of Ab101-141, e.g., Ab109, or an antigen binding fragment thereof) provide improved subcutaneous bioavailability, e.g., at least 80%, 81%, 82%, 83%, 84%, or 85% bioavailability or greater, as compared to intravenous administration. Such antibodies may be formulated into a pharmaceutical composition with antibody concentrations at about 150-250 mg/mL, e.g., about 200 mg/mL. In some embodiments, such antibodies are administered subcutaneously every 4 weeks or monthly. In some embodiments, such antibodies are administered subcutaneously every 6 weeks, every 8 weeks (or every two months), or every 12 weeks (or every three months).

Alleviating a disease/disorder associated with pro/latent-myostatin includes delaying the development or progression of the disease, or reducing disease severity. Alleviating the disease does not necessarily require curative results. As used therein, "delaying" the development of a disease/disorder associated with pro/latent-myostatin means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

EXAMPLES

The present disclosure is further illustrated by the following examples, which are not intended to be limiting in any way. The entire contents of all references, patents and published patent applications cited throughout this application, as well as the Figures and Sequence Listing, are hereby incorporated herein by reference.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

Example 1: Antibody Characterization

A. Myostatin Inhibitory Potency

To measure inhibitory potency of the novel antibodies against myostatin activation, an ELISA-based in vitro potency assay ("functional ELISA") was carried out. First, each of the test antibodies was preincubated with recombinant human latent myostatin to let immune complexes form. Subsequently, mTLL-2 was added to the immune mixture to trigger the release of mature myostatin by proteolytic cleavage. If the test antibody is capable of blocking mTLL-2-induced activation, mature myostatin is not released from the latent myostatin complex. On the other hand, if the test antibody does not inhibit myostatin activation, mTLL-2 treatment causes myostatin to be released from the latent myostatin complex. Following mTLL-2 treatment, the amount of free (released) mature myostatin in the presence of test antibodies was measured by ELISA, in which the plates were coated with ActRII-Fc fusion protein, which is a ligand trap serving as the capture reagent. Free mature myostatin present in the assay mixture was captured on the ELISA plate, and the amount of bound mature myostatin was measured by biotin-streptavidin-based detection reagents in 11 data points.

As shown in FIG. 1A, Ab109 and Ab130 inhibited myostatin activation at lower concentrations than Ab2 as provided in PCT/US2015/059468. Ab109 inhibited myostatin activation with an IC50 of 0.38 nM, and Ab130 inhibited myostatin activation with an IC50 of 0.31 nM. In comparison, Ab2 was about 10-fold less potent at inhibiting myostatin activation, with an IC50 value of 5.37 nM. Similarly, FIG. 1B demonstrates that Ab109, Ab130, and Ab133 all inhibited myostatin activation at sub-nanomolar concentrations, where Ab109 inhibition had an IC50 of 0.33 nM, Ab130 had an IC50 of 0.30 nM, and Ab133 had an IC50 of 0.16 nM. The myostatin inhibitory activity of exemplary antibodies are shown below in Table 8. Antibodies that showed an IC50 of less than 1 nM in the functional ELISA were deemed highly potent and were selected for further evaluation.

TABLE 8

Myostatin inhibition activity.

| Antibody | $IC_{50}$ (nM) Latent + mTLL2 | $IC_{50}$ (nM) Pro + Furin |
|---|---|---|
| Ab2 | 2.87 ± 0.7 | 2.21 ± 0.88 |
| Ab101 | 0.128 | 0.251 |
| Ab102 | 0.162 | 0.211 |
| Ab103 | 0.506 | 0.413 |
| Ab104 | 0.22 | 0.363 |
| Ab105 | 0.25 | 0.356 |
| Ab106 | 0.163 | 0.233 |
| Ab107 | 0.135 | 0.195 |
| Ab108 | 0.237 | 0.27 |
| Ab109 | 0.145 | 0.214 |
| Ab112 | 9.22 ± 1.75 | 1.076 |
| Ab114 | 3.301 | 2.796 |
| Ab115 | 2.943 | 6.01 |
| Ab121 | 0.386 | 0.143 |
| Ab123 | 0.139 | 0.184 |
| Ab124 | 1.434 | 1.076 |
| Ab125 | 0.202 | 0.318 |
| Ab127 | 0.14 | 0.195 |
| Ab128 | 1.028 | 0.774 |
| Ab129 | 3.889 | 4.31 |
| Ab133 | 0.161 | |
| Ab134 | 0.631 | |
| Ab135 | 0.154 | |
| Ab141 | 0.139 | |

B. Binding Affinity

The Biacore™ 8 k SPR system was utilized to evaluate the binding affinity of myostatin antibodies to biotinylated human, murine, and cyno pro-myostatin. Biotin CAPture kit and sensor chips (Cytiva) were utilized in these experiments to immobilize the various antigens, followed by flowing a range of concentrations of each of the test antibodies.

Figure 3:
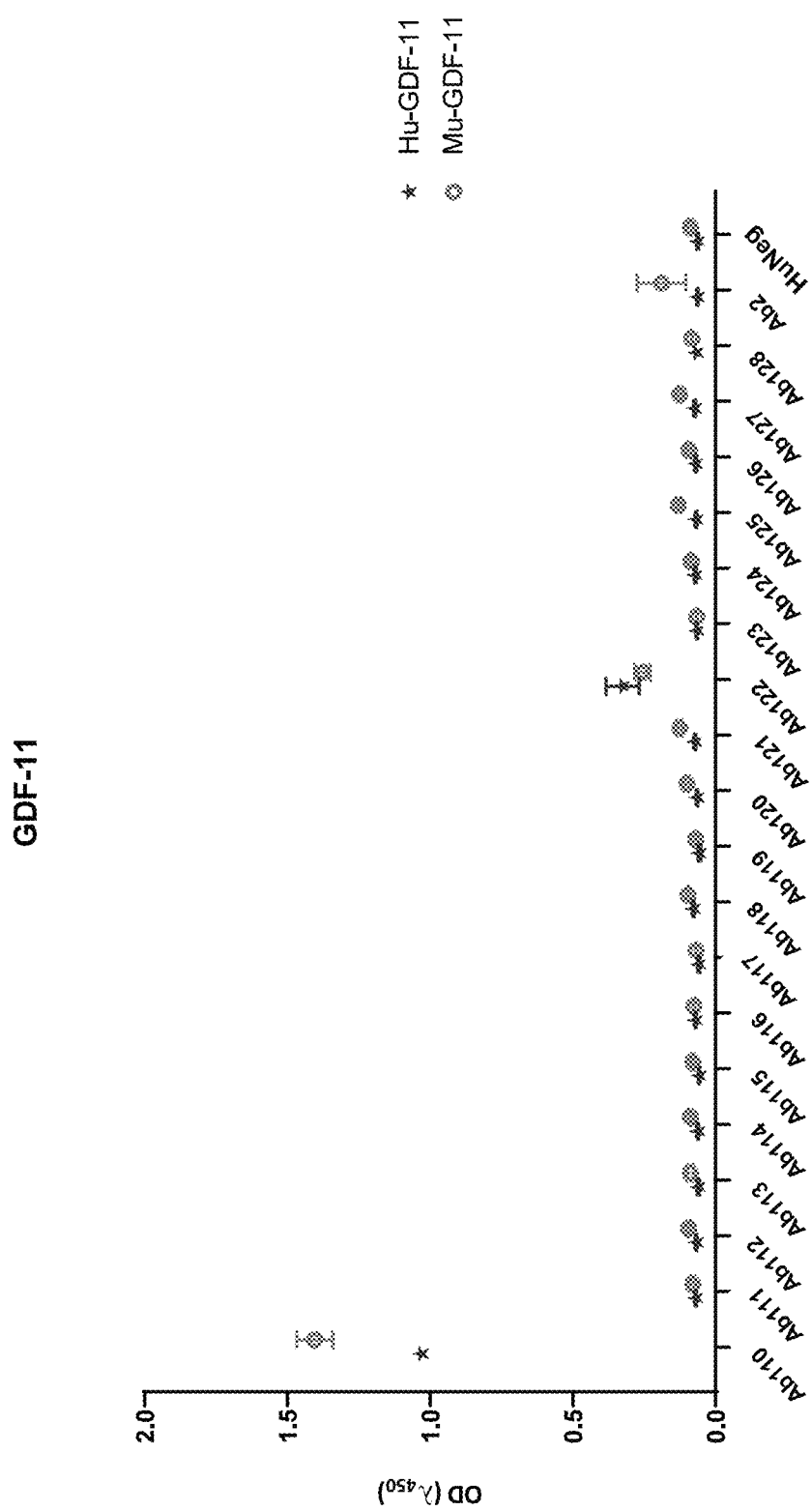
FIG. 3 shows binding of antibodies disclosed herein to human or mouse GDF-11.

Antibody binding affinities to antigen (e.g., human, mouse, or *cynomolgus* monkey pro-myostatin are shown in Table 9. Antibodies Ab102, Ab105, and Ab109 showed high binding affinities, expressed as the equilibrium dissociation constant (KD). Antibody binding to pro-myostatin from human, mouse, and *cynomolgus* monkey is shown in FIGS. 2A-D. Further, the lack of antibody binding to mouse or human GDF-11 is shown in FIG. 3.

TABLE 9

Binding affinities of antibodies.

| | Human Pro-Myostatin | | | Murine Pro-Myostatin | | | Cyno Pro-Myostatin | | |
|---|---|---|---|---|---|---|---|---|---|
| | Ka (1/Ms) | Kd (1/s) | KD (nM) | Ka (1/Ms) | Kd (1/s) | KD (nM) | Ka (1/Ms) | Kd (1/s) | KD (nM) |
| Ab2 | 7.77E+05 | 1.56E−03 | 2.013 | 7.67E+05 | 2.16E−03 | 2.816 | 8.63E+05 | 1.50E−03 | 1.795 |
| Ab101 | 4.37E+06 | 3.39E−04 | 0.078 | 4.34E+06 | 3.60E−04 | 0.083 | 4.84E+06 | 3.17E−04 | 0.065 |
| Ab102 | 6.49E+06 | 3.76E−04 | 0.058 | 6.11E+06 | 5.00E−04 | 0.082 | 6.80E+06 | 3.35E−04 | 0.049 |
| Ab103 | 5.78E+06 | 1.51 E−03 | 0.261 | 5.83E+06 | 2.21E−03 | 0.379 | 6.09E+06 | 1.54E−03 | 0.252 |
| Ab104 | 3.82E+06 | 3.81E−04 | 0.100 | 3.58E+06 | 5.18E−04 | 0.145 | 4.21E+06 | 3.22E−04 | 0.076 |
| Ab105 | 4.89E+06 | 2.47E−04 | 0.051 | 5.99E+06 | 2.76E−04 | 0.46 | 5.26E+06 | 2.33E−04 | 0.044 |
| Ab106 | 2.00E+06 | 2.24E−04 | 0.112 | 1.96E+06 | 3.17E−04 | 0.162 | 1.91E+06 | 2.91E−04 | 0.152 |
| Ab107 | 5.34E+06 | 3.19E−04 | 0.060 | 8.04E+06 | 4.55E−04 | 0.057 | 5.85E+06 | 3.16E−04 | 0.054 |
| Ab108 | 5.92E+06 | 1.05E−03 | 0.177 | 8.42E+06 | 1.83E−03 | 0.218 | 6.39E+06 | 1.02E−03 | 0.159 |
| Ab109 | 6.62E+06 | 1.96E−04 | 0.138 | 6.81E+06 | 1.34E−03 | 0.197 | 7.23E+06 | 9.25E−04 | 0.128 |
| Ab112 | 2.17E+05 | 1.22E−04 | 0.561 | 2.51E+05 | 1.88E−04 | 0.748 | 2.07E+05 | 1.24E−04 | 0.601 |
| Ab114 | 4.23E+06 | 7.35E−03 | 1.738 | 3.31E+06 | 2.08E−02 | 6.287 | 3.49E+06 | 9.08E−03 | 2.602 |
| Ab115 | 4.06E+05 | 1.23E−03 | 3.035 | 4.50E+05 | 1.37E−03 | 3.052 | 4.43E+05 | 1.39E−03 | 3.133 |
| Ab121 | 3.16E+06 | 3.18E−04 | 0.101 | 3.24E+06 | 6.08E−04 | 0.187 | 3.45E+06 | 3.65E−04 | 0.106 |
| Ab123 | 1.38E+06 | 5.43E−04 | 0.394 | 1.25E+06 | 7.72E−04 | 0.618 | 1.59E+06 | 5.39E−04 | 0.339 |
| Ab124 | 1.54E+06 | 2.85E−04 | 1.843 | 1.39E+05 | 4.54E−04 | 3.261 | 1.76E+05 | 2.77E−04 | 1.575 |
| Ab125 | 3.58E+06 | 3.71E−04 | 0.103 | 3.29E+06 | 4.11E−04 | 0.125 | 4.01 E+06 | 3.54E−04 | 0.088 |
| Ab127 | 8.13E+05 | 2.13E−04 | 0.262 | 8.15E+05 | 2.65E−04 | 0.325 | 8.21 E+05 | 2.69E−04 | 0.327 |
| Ab128 | 1.27E+06 | 4.63E−04 | 0.365 | 9.14E+05 | 6.55E−04 | 0.716 | 9.05E+05 | 7.36E−04 | 0.814 |
| Ab129 | 1.40E+05 | 3.07E−04 | 2.197 | 1.17E+05 | 4.96E−04 | 4.240 | 4.11E+05 | 5.34E−04 | 1.299 |
| Ab133 | 2.84E+06 | 1.16E−04 | 0.041 | 3.01E+06 | 1.62E−04 | 0.054 | 2.86E+06 | 1.09E−04 | 0.0383 |
| Ab138 | 5.27E+06 | 5.77E−04 | 0.110 | | | | | | |
| Ab139 | 1.90E+07 | 2.30E−03 | 0.121 | | | | | | |
| Ab140 | 6.53E+06 | 7.11E−04 | 0.109 | | | | | | |
| Ab141 | 2.79E+06 | 1.12E−04 | 0.040 | 2.93E+06 | 1.56E−04 | 0.0531 | 2.80E+06 | 1.03E−04 | 0.0369 |

C. pH Dependency

As shown in FIGS. 4A-B, some of the antibodies demonstrate pH-dependent binding. Binding was performed at pH 7.4 and dissociation at pH 5.5 in an Octet Red384® assay. Streptavidin biosensors were baselined in 1× kinetics buffer (KB) (Sartorius) for one minute, then loaded with 100 nM biotinylated human latent myostatin for five minutes, followed by another baseline step of one minute in 1×KB. Binding of test antibodies was performed for five minutes and then dissociation was performed in PBS at either pH 7.4 or pH 5.5 for five minutes. Analysis was performed using a partial fit, in which full dissociation was projected. Kd at pH 5.5 was divided by Kd at pH 7.4 to calculate pH sensitivity.

As shown in FIGS. 4A-B the pH dependency of binding of Ab102, Ab130, Ab109, Ab132, and Ab133 was much greater than that of Ab2, as evidenced by the larger difference in off-rates at the different pH values. Of these, Ab109 and Ab132 had the greatest difference at 24 to 25-fold. Ab133 demonstrated a 17.5-fold difference, Ab102 demonstrated a 9.3-fold difference, Ab130 demonstrated a 10.6-fold difference. Ab105 and Ab131 were not pH dependent binding antibodies, demonstrating a difference of 0.8 and 0.9-fold, respectively. Ab2 demonstrated a difference of 8-fold.

D. Stoichiometry

A combination of size exclusion chromatography and multi-angle light scattering (SEC-MALS) was used to determine the approximate mass and therefore the oligomeric state of the antibodies and their stoichiometry of binding to human promyostatin. The monoclonal antibody (mAb) or its Fab fragment was mixed with 50 µg of human pro-myostatin at a ratio of 1:1, 2:1 or 3:1 (antibody to antigen) for at least 24 hours at room temperature for immune complexes to form, filtered and injected into an analytical SEC column (Waters HPLC with a Superdex 200 10/300), flowed through a refractive index detector and then a miniDAWN® multi-angle light scattering detector to determine the mass. A full-length human-pro-myostatin with an N-terminal His6 tag (SEQ ID NO: 941) was used to express pro-myostatin in HEK cells. The signal peptide present in the construct is cleaved during biosynthesis. The resulting recombinant human pro myostatin was purified using the His6 tag (SEQ ID NO: 941) and used for the experiment.

As a control, antibody Ab2 having a known stoichiometry of binding to pro myostatin of 1:1, was examined by SEC-MALS at stoichiometric ratios of antibody to pro myostatin of 1:1, 1.1:1, and 3:1. The stoichiometry of binding of the Ab2 Fab fragment was previously shown to be 2:1 (Dagbay et al. J Biol Chem. 2020 Apr. 17; 295(16): 5404-5418). Further, stoichiometry binding of Ab2 Fab was examined by SEC-MALS as a control at ratios of 2:1 and 3:1 (Table 10a).

TABLE 10a

Stoichiometry of Ab2 binding to pro-myostatin.

| Input Ratio Ab2 mAb:pro-myostatin | SEC-MALS Result (kDa) | Input Ratio Ab2 Fab:pro-myostatin | SEC-MALS Result (kDa) |
|---|---|---|---|
| 1:1 | 239.5 | 2:1 | 171.1 |
| 1.1:1 | 233.7 | 3:1 | 175.9 |
| 3:1 | 246.1 | | |
| Controls | | Controls | |
| Ab2 | 153.1 | Ab2 Fab | 56 |
| pro-myostatin | 86.54 | pro-myostatin | 86.33 |
| BSA | 67.4 | BSA | 65.69 |

TABLE 10b

Concluded stoichiometry of Ab2 binding to pro-myostatin.

| Stoichiometry Ab2 (mAb:pro-myostatin) | Predicted Molecular Weight (KDa) | Observed Molecular Weight (kDa) | Difference Observed vs. Predicted (kDa) |
|---|---|---|---|
| 1 to 1 | 239.62 | 239.5 | <0.12 |

| Stoichiometry Ab2 (Fab:pro-myostatin) | Predicted Molecular Weight (KDa) | Observed Molecular Weight (kDa) | Difference Observed vs. Predicted (kDa) |
|---|---|---|---|
| 2 to 1 | 198.33 | 171.1 | <27.23 |

Consistent with our previous findings, the resulting binding stoichiometry for full-length Ab2 (mAb) as measured by SEC-MALS was confirmed to be 1:1 antibody:pro-myostatin. The predicted molecular weight of the complex was 239.62 kDa, the observed molecular weight was 239.5 kDa and the difference between the observed and the predicted was <0.12. Also as expected, the resulting stoichiometry of the Fab to antigen was 2:1 Fab:pro-myostatin. The predicted molecular weight of the 1:1 complex was 142.33 kDa, the observed molecular weight was 171.1 kDa and the difference between the observed and the predicted was >28.77. The predicted molecular weight of the 2:1 complex was 198.33 kDa, the observed molecular weight was 171.1 kDa and the difference between the observed and the predicted was <27.23, i.e., the difference between the observed and the predicted was approximately the same in either direction (Table 10b). Taking into account both the mAb and the Fab data and other biophysical measurements (Dagbay et al., J. Biol. Chem. 2020 Apr. 17; 295 (16):5404-5418), the Fab:pro-myostatin stoichiometry was concluded to be 2:1.

Another known antibody, MS1032L000SG1 (as disclosed in PCT/JP2015/006323), was analyzed as described above and found to bind pro-myostatin in a poly-daisy chain formation (Table 10c). The binding stoichiometry of Ab2 to human pro-myostatin is included as a reference to a known 1:1 ratio. The stoichiometry of the MS1032L000SG1 Fab fragment to pro-myostatin is 2:1, based on a MALS observed weight of 187.9 kDa. i.e., <2.5 kDa (a 1:1 ratio would have a MALS observed weight of 136.3 kDa. i.e., >48.5 kDa).

TABLE 10c

Stoichiometry of MS1032L000SG1 binding to pro-myostatin.

| Input Ratio MS1032L000SG1 (mAb:pro-myostatin) | SEC-MALS Result (kDa) | Input Ratio MS1032L000SG1 (Fab:pro-myostatin) | SEC-MALS Result (kDa) |
|---|---|---|---|
| 1:1 | 701.2 | 2:1 | 185.4 |
| 3:1 | 592.2 | 3:1 | 187.1 |
| Controls | | | |
| MS1032L000SG1 | 151.1 | MS1032L000SG1 | 50.96 |
| pro-myostatin | 86.7 | pro-myostatin | 85.97 |
| Ab2:pro-myostatin | 238.1 | n/a | n/a |
| BSA | 67.5 | BSA | 66.13 |

Figure 5A:
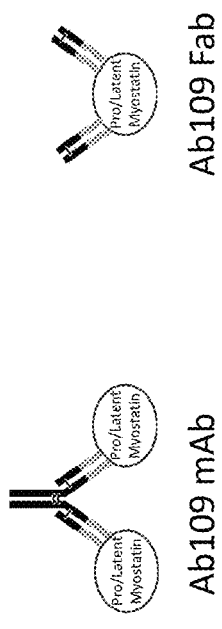
FIGS. 5A-F show binding stoichiometry of antibody:pro-myostatin or Fab:myostatin. Diagrams are simplified depictions and are not drawn to scale.

Antibodies of the disclosure were analyzed as described above. As shown below and illustrated by the diagram in FIG. 5A, the stoichiometry of Ab109 (molecular weight 146.8 kDa) to pro-myostatin (molecular weight 81.839 kDa) is 1:2 and the stoichiometry of the Fab fragment of Ab109 (molecular weight 49.25 kDa) to pro-myostatin is 2:1. (Tables 10d and 10e). The observed molecular weights are averages of the complexes across two exchanging species. This is consistent with the observed 2:1 (Fab:pro-myostatin) stoichiometry, where the Fab binding in this experiment does not account for steric hinderance that may be present for Fabs connected via a hinge (e.g., two Fab arms within a full length antibody).

TABLE 10d

Stoichiometry of Ab109 binding to pro-myostatin.

| Input Ratio Ab109 mAb:pro-myostatin | SEC-MALS Result (kDa) |
|---|---|
| 1:1 | 311.4 |
| 3:1 | 319.6 |
| Controls | |
| Ab109 | 153.6 |
| pro-myostatin | 86.33 |
| BSA | 65.69 |

TABLE 10e

Concluded stoichiometry of Ab109 binding to pro-myostatin.

| | Predicted Molecular Weight (kDa) | Observed Molecular Weight (kDa) | Difference Observed vs. Predicted (kDa) |
|---|---|---|---|
| Stoichiometry Ab109 (mAb:pro-myostatin) | | | |
| 1 to 2 | 317.3 | 311.4 | <5.9 |
| Stoichiometry Ab109 (Fab:pro-myostatin) | | | |
| 2 to 1 | 187.53 | 158.6 | <28.93 |

Figure 5B:
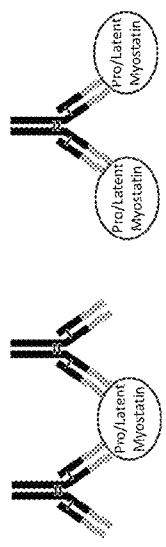

As shown in FIG. 5B, Ab130 has two observed stoichiometries: a 2:1 complex and a 1:2 (mAb:pro-myostatin) complex.

Figure 5C:
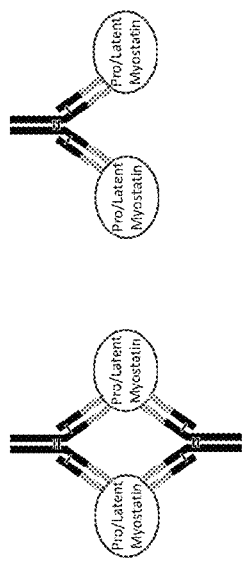

As shown in Tables 10f and 10g and illustrated by the diagram in FIG. 5C, Ab105 has two observed stoichiometries: a 2:2 complex and a 1:2 complex.

TABLE 10f

Stoichiometry of Ab105 binding to pro-myostatin.

| Input Ratio Ab105 mAb:pro-myostatin | SEC-MALS Result (kDa) |
|---|---|
| 1:1 (peak 1) | 500 |
| 1:1 (peak 2) | 298.9 |
| Controls | |
| Ab105 | 156 |
| pro-myostatin | 86.79 |
| BSA | 66.08 |

TABLE 10g

Concluded stoichiometry of Ab105 binding to pro-myostatin.

| Stoichiometry Ab105 (mAb:pro-myostatin) | Predicted Molecular Weight (KDa) | Observed Molecular Weight (kDa) | Difference Observed vs. Predicted (kDa) |
|---|---|---|---|
| Peak 1 - 2:2 complex | 485.58 | 500.0 | >14.4 |
| Peak 2 - 1:2 complex | 329.58 | 298.9 | <30.7 |

Figure 5D:
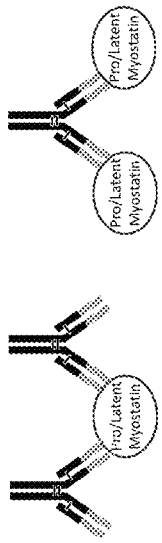

As shown below in Tables 10h and 10i and illustrated by the diagram in FIG. 5D, Ab133 has two observed stoichiometries: a 2:1 complex and a 1:2 complex.

TABLE 10h

Stoichiometry of Ab133 binding to pro-myostatin.

| Input Ratio Ab133 (mAb:pro-myostatin) | SEC-MALS Result (kDa) |
|---|---|
| 1:1 (peak 1) | 405 |
| 1:1 (peak 2) | 302.9 |
| Controls | |
| Ab105 | 156.1 |
| pro-myostatin | 86.79 |
| BSA | 66.08 |

TABLE 10i

Concluded stoichiometry of Ab133 binding to pro-myostatin.

| Stoichiometry Ab133 (mAb:pro-myostatin) | Predicted Molecular Weight (kDa) | Observed Molecular Weight (kDa) | Difference Observed vs. Predicted (kDa) |
|---|---|---|---|
| Peak 1 - 2:1 complex | 398.99 | 405.0 | >6.01 |
| Peak 2 - 1:2 complex | 329.58 | 302.9 | <26.68 |

Figure 5E:
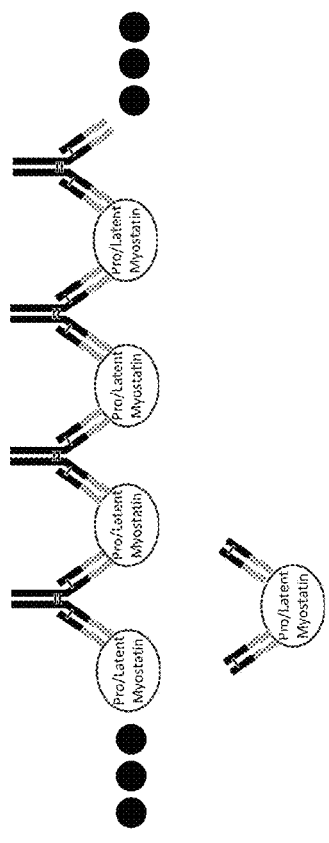

As shown in Table 10j and illustrated by the diagram in FIG. 5E, Ab112 forms large poly-daisy chains with the mAb and a 2:1 (Fab:pro-myostatin) stoichiometry. The binding stoichiometry of Ab2 to pro-myostatin was included as a reference to a known 1:1 stoichiometry. The stoichiometry of the Ab112 Fab fragment to pro-myostatin is 2:1, based on a MALS observed weight of 186.5 kDa. i.e., <9.6 kDa (a 1:1 ratio would have a MALS observed weight of 136.3 kDa. i.e., >50.2 kDa).

TABLE 10j

Stoichiometry of Ab112 binding to pro-myostatin.

| Input Ratio Ab112 (mAb:pro-myostatin) | SEC-MALS Result (kDa) | Input Ratio Ab112 (Fab:pro-myostatin) | SEC-MALS Result (kDa) |
|---|---|---|---|
| 1:1 | 2,519 | 2:1 | 176.9 |
| 3:1 | 699.6 | 3:1 | 180.9 |
| Controls | | | |
| Ab112 | 154.9 | Ab112 Fab | 50.28 |
| pro-myostatin | 90.71 | n/a | n/a |
| Ab2:pro-myostatin | 241 | pro-myostatin | 85.97 |
| BSA | 67.48 | BSA | 66.13 |

Figure 5F:

As shown in Table 10k and illustrated by the diagram in FIG. 5F, Ab123 forms a 1:1 complex with both the mAb and Fab, suggesting there is a single available epitope on the myostatin homodimer. The ratio of Ab2 to pro-myostatin was included as a reference to a known 1:1 ratio. The stoichiometry of the Ab123 Fab fragment to pro-myostatin is 1:1, based on a MALS observed weight of 137.5 kDa. i.e., >3.6 kDa (a 1:2 ratio would have a MALS observed weight of 188.9 kDa. i.e., <47.7 kDa).

TABLE 10k

Stoichiometry of Ab123 binding to pro-myostatin.

| Input Ratio Ab123 (mAb:pro-myostatin) | SEC-MALS Result (kDa) | Input Ratio Ab123 (Fab:pro-myostatin) | SEC-MALS Result (kDa) |
|---|---|---|---|
| 1:1 | 236.1 | 2:1 | 141.2 |
| 3:1 | 237.5 | 3:1 | 144.5 |
| Controls | | | |
| Ab123 | 151.7 | Ab123 | 51.48 |
| pro-myostatin | 88.4 | pro-myostatin | 85.97 |
| Ab2:pro-myostatin | 238.1 | n/a | n/a |
| BSA | 67.5 | BSA | 66.13 |

Ab105, Ab109, Ab130, and Ab133 have altered stoichiometry from the 1:1 (mAb:Myostatin) observed for Ab2 despite the presumably conserved/overlapping epitope at these concentrations. A hypothetical explanation for this observation is that the epitope has shifted and/or rotated and no longer allows the strong bivalent interaction with the myostatin homodimer. Rather, there is a tendency to primarily engage in a 1:2 (mAb:Myo) interaction with a latent ability to form discrete complexes up to 2:1 and 2:2 (mAb:Myo) but there is enough steric hinderance to prevent large poly daisy-chains to form.

Figure 23A:
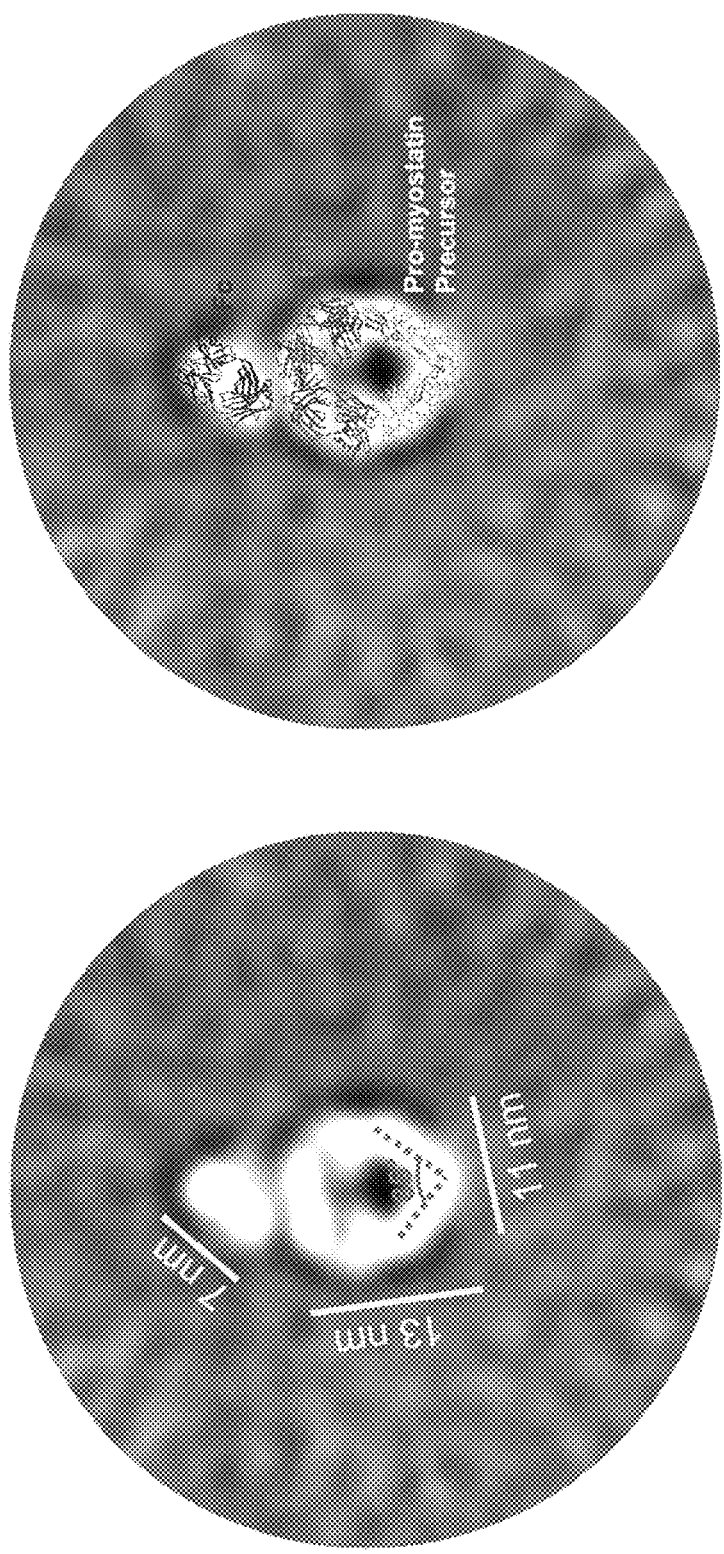
Figure 23B:
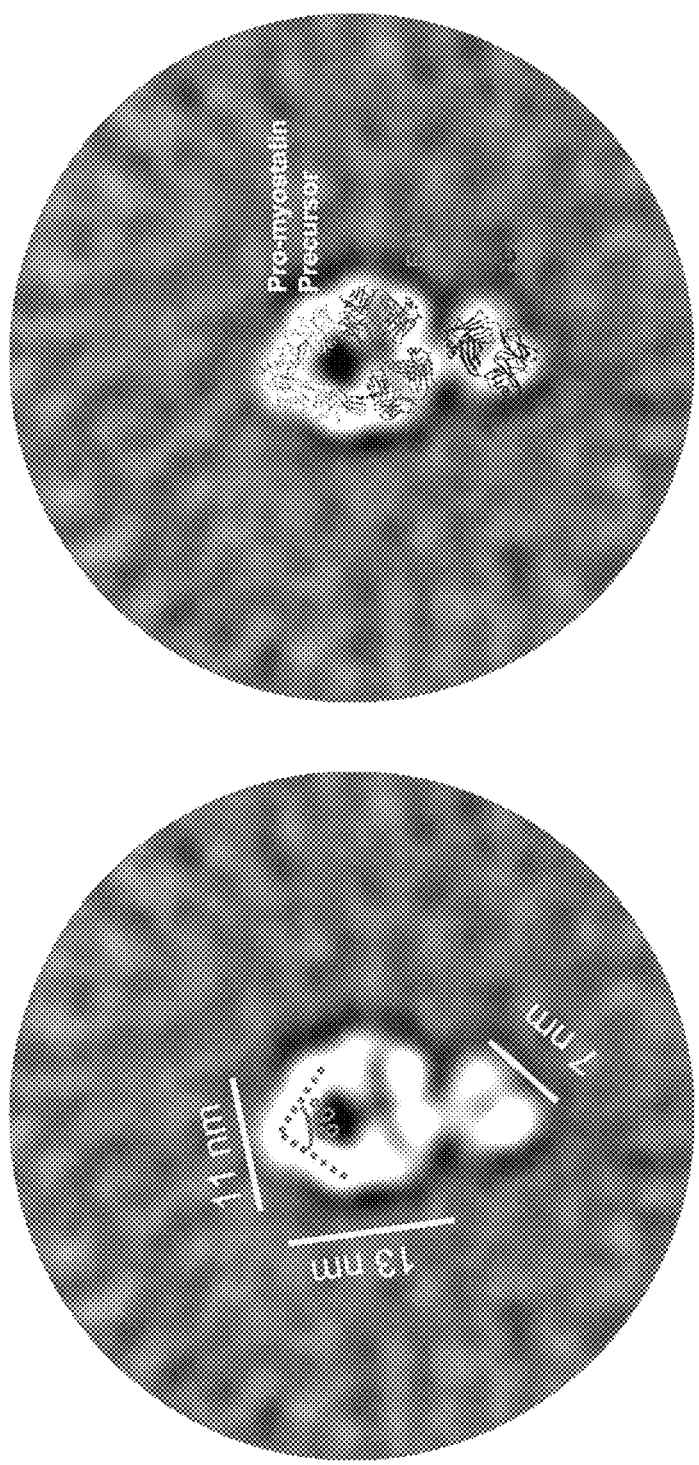

Additional experiments to investigate stoichiometry were carried out at lower concentrations using the technique of negative stain electron microscopy as shown in FIGS. 23A-C (showing 2D class average). FIG. 23A shows Ab2:Pro-Myostatin observed in a 1:1 complex from a 1:1 input sample. FIG. 23B shows Ab109:Pro-Myostatin observed in a 1:1 complex from a 1:2 input sample. FIG. 23C shows Ab133:Pro-Myostatin observed in a 1:1 complex from a 2:1 input sample. Samples of Ab2 Human IgG4:Pro-myostatin complex (1:1 stoichiometry fraction from size exclusion chromatography), Ab109 Human IgG4:Pro-myostatin complex (1:2 stoichiometry fraction from size exclusion chromatography), and Ab133 Human IgG4:Pro-myostatin complex (2:1 and 1:2 stoichiometry fractions from size exclusion chromatography) were obtained and diluted to 0.01-0.015 mg/ml prior to imaging. A 3 μl drop of sample suspension was applied to an EM grid that had been plasma-cleaned using a Gatan Solarus (Pleasanton, California). After blotting the sample away with filter paper, grids were immediately stained with a 1% uranyl formate solution. After ~30 seconds, the stain was blotted away with filter paper and the grids allowed to air-dry. If the buffer is expected to interfere with the staining, one or more 3 μl drop(s) of water can be used to wash the grid immediately prior to adding stain.

adopt the higher order stoichiometries observed at the higher complex concentrations of the SEC-MALS experiments above.

E. Summary of In Vitro Characteristics

A summary of in vitro characteristics for exemplary antibodies is shown in Table 11 below. The antibody MS1032L000SG1 is described in PCT/JP2015/006323.

TABLE 11

In vitro characteristics.

| Antibody | mTLL2 IC$_{50}$ (nM) | Ab KD (nM) | Fab KD (nM) | pH dep. | Stoichiometry By MALS (mAb:pro-myostatin) Leading peak | Main peak | Stoichiometry By MALS (Fab:pro-myostatin) |
|---|---|---|---|---|---|---|---|
| Ab2 | 2.86 | 2.3 | weak | + | n.a. | 1:1 | n.d. |
| Ab102 | 0.346 | 0.329 | 44.4 | ++ | 2:1 | 1:2 | n.d. |
| Ab130 | 0.33 | 0.350 | 53.8 | ++ | | | |
| Ab105 | 0.25 | 0.229 | 21.9 | − | 2:2 | 1:2 | n.d. |
| Ab131 | 0.208 | 0.155 | 17.4 | − | | | |
| Ab109 | 0.145 | 0.579 | 39.5 | +++ | n.a. | 1:2 | 2:1 |
| Ab132 | 0.144 | 0.926 | 61.4 | +++ | | | |
| Ab133 | 0.161 | 0.041 | 23 | +++ | 2:1 | 1:2 | n.d. |
| Ab141 | 0.139 | 0.040 | 19 | n.d. | n.d. | n.d. | n.d. |
| Ab112 | 9.22 | 3.56 | 6.19 | n.d. | n.a. | Poly daisy | 2:1 |
| Ab123 | 0.139 | 0.683 | 5.51 | n.d. | n.a. | 1:1 | 1:1 |
| MS1032L000SG1 | 0.231 | n.d | n.d | Yes | n.a. | Poly daisy | 2:1 |

Electron microscopy was performed using an FEI Tecnai T12 electron microscope (serial number D1100), operating at 120 keV and equipped with an FEI Eagle 4k×4k CCD camera. Negative stain grids were transferred into the electron microscope using a room temperature stage. Images of each grid were acquired at multiple scales to assess the overall distribution of the specimen. After identifying potentially suitable target areas for imaging at lower magnifications, high magnification images were acquired at nominal magnifications of 110,000× (0.10 nm/pixel) and 67,000× (0.16 nm/pixel). The contrast transfer function (CTF) was estimated for each micrograph using CTFfind4 (Rohou, et al. J Struct Biol. 2015, 192, 216-221). Particles must be identified in the high magnification images prior to alignment and classification. This was achieved by selecting individual particles in the high magnification images using automated picking protocols (Lander et al. J Struct Biol 2009, 166, 95-102.) and/or manual picking. These particles were then boxed out, and these individual subimages are combined into a stack. Particle images were CTF corrected by phase-flipping only. An initial round of alignments was done on each sample and from that alignment class averages that appeared to contain recognizable particles were selected for additional rounds of alignment. A reference-free alignment strategy based on the XMIPP (Sorzano et al. J Struct Biol. 2004, 148: 194-204.) processing package was used. Algorithms in this package align the selected particles and sort them into self-similar groups of classes.

Under these experimental conditions at lower mAb:myostatin protein complex concentrations the same 1:1 mAb:myostatin stoichiometry was observed for Ab2, Ab109, and Ab133, no matter the input stoichiometry (see FIGS. 23A-C). This suggests Ab109 and Ab133 can adopt this same 1:1 stoichiometry at lower complex concentrations but can also F. Binding Regions/Epitopes To identify novel and highly potent myostatin-selective inhibitors, antibody discovery campaigns were designed to preferentially select for antibodies and antigen-binding fragments that are capable of binding to the same or overlapping binding regions as Ab2, i.e., the regions of the prodomain of the pro/latent myostatin complex FVQILR-LIKPMKDGTRYTGIRSLK (SEQ ID NO: 57) (amino acid positions 147-170 of human proMyostatin, as numbered according to SEQ ID NO: 52) and/or KALDEN (SEQ ID NO: 118) (amino acid positions 205-210 of human proMyostatin, as numbered according to SEQ ID NO: 52). Epitope binning was carried out on Octet® using Ab2 as the reference, in a series of pairwise cross-blocking experiments performed in two different formats: the "pre-mix" format and the "sandwich" format of epitope binning. Among the antibodies shown to have high inhibitory potency (e.g., IC50 of less than 1 nM as measured by functional ELISA), all but Ab110 and Ab112 were found to cross-compete with Ab2 for antigen binding. Antibodies found to cross-block with Ab2 include, but are not limited to, Ab101, Ab102, Ab103, Ab104, Ab105, Ab106, Ab107, Ab108, Ab109, Ab111, Ab114, Ab115, Ab116, Ab117, Ab118, Ab121, Ab122, Ab123, Ab124, Ab125, Ab127, Ab128, Ab129, Ab133, and Ab141.

G. Developability

To minimize liabilities which may interfere with the developability of antibody-based therapeutics, novel antibodies disclosed herein were evaluated for developability studies as follows.

The antibodies were tested for aggregation behavior by affinity capture self-interaction nanoparticle spectroscopy (AC-SINS). Gold nanoparticles were coated with polyclonal antibodies that are specific for human monoclonal antibodies and the monoclonal antibodies are captured by the conjugates. The polyvalency of the monoclonal antibody conjugates amplifies the attractive self-interactions, i.e., aggregation between the adsorbed antibodies. This leads to reduced inter-particle separation distances and is detected by a change in color of the gold colloid solution, which was quantified by a change in the wavelength of maximum absorbance (plasmon wavelength). Plasmon wavelength of 530 nm was used as the reported value for unaggregated gold nanoparticles. Antibodies with a tendency to self-aggregate shift the plasmon wavelength toward the red end of the spectrum. A shift of greater than 5 nm (i.e., >5 nm) in plasmon wavelength was used as the cutoff indicative of self-interacting antibodies. Antibodies Ab111, and Ab113 the displayed aggregation behavior. Antibodies Ab101, Ab102, Ab103, Ab104, Ab105, Ab106, Ab107, Ab108, Ab109, Ab133, Ab134, and Ab141 did not display aggregation behavior.

In addition, poly-specificity of the novel antibodies was evaluated using ELISA detection of non-specific binding to baculovirus particles (BV-ELISA). For positive control, SR-ACSINS control, Myo29-ACSINS control and anti-BV particle positive control were used. For negative control, secondary antibody only was used. An arbitrary cutoff of 1000 RFU was set based on average+5× standard deviation of control IgG and no antibody. All antibodies tested (antibodies Ab101, Ab102, Ab103, Ab134, Ab104, Ab105, Ab106, Ab107, Ab108, Ab109, Ab133, Ab135, and Ab141) showed no poly-specificity as measured by BV-ELISA.

Example 2. Antibodies that Inhibit Myostatin Prevent Dexamethasone-Induced Muscle Atrophy To evaluate in vivo efficacy of the novel myostatin-selective inhibitors disclosed herein, the ability of the antibodies to preserve lean muscle mass was examined in a dexamethasone-induced atrophy mouse model. An excess of glucocorticoids directly stimulates myostatin production via interactions with a glucocorticoid response element in the myostatin promoter, thus inducing loss of muscle mass. As shown herein, antibodies of the disclosure prevented glucocorticoid-induced muscle atrophy.

C57BL6 male mice (n=8) at 13-14 weeks of age were given normal drinking water or water containing dexamethasone at a concentration of 2.5 mg/kg (17.5 grams dexamethasone per liter of drinking water) to induce atrophy. Mice were dosed at day 1 and day 7 with vehicle (PBS), human IgG control ("hIgG") or different doses of the test antibodies Ab2, Ab102, Ab105, Ab121, or Ab 123, as shown in Table 12. Body weight was measured daily. Body composition was measured by qNMR to determine lean mass pre-dosing, at day 7, and at day 14. After 14 days of dexamethasone exposure, the animals were terminated, and body weight and gastrocnemius weight were measured. Terminal blood for each animal was also collected.

TABLE 12

Ab102, Ab105, Ab121, and Ab123 attenuated dexamethasone-induced atrophy.

| Group | Dexamethasone | Treatment | Ab Dose |
| --- | --- | --- | --- |
| 1 | none | PBS | 0 mg/kg |
| 2 | 2.5 mg/kg/day | PBS | 0 mg/kg |
| 3 | 2.5 mg/kg/day | hIgG | 10 mg/kg |
| 4 | 2.5 mg/kg/day | Ab2 | 10 mg/kg |
| 5 | 2.5 mg/kg/day | Ab2 | 3 mg/kg |
| 6 | 2.5 mg/kg/day | Ab102 | 10 mg/kg |
| 7 | 2.5 mg/kg/day | Ab102 | 3 mg/kg |

TABLE 12-continued

Ab102, Ab105, Ab121, and Ab123 attenuated dexamethasone-induced atrophy.

| Group | Dexamethasone | Treatment | Ab Dose |
| --- | --- | --- | --- |
| 8 | 2.5 mg/kg/day | Ab105 | 10 mg/kg |
| 9 | 2.5 mg/kg/day | Ab105 | 3 mg/kg |
| 10 | 2.5 mg/kg/day | Ab121 | 10 mg/kg |
| 11 | 2.5 mg/kg/day | Ab121 | 3 mg/kg |
| 12 | 2.5 mg/kg/day | Ab123 | 10 mg/kg |
| 13 | 2.5 mg/kg/day | Ab123 | 3 mg/kg |

Figure 6A:
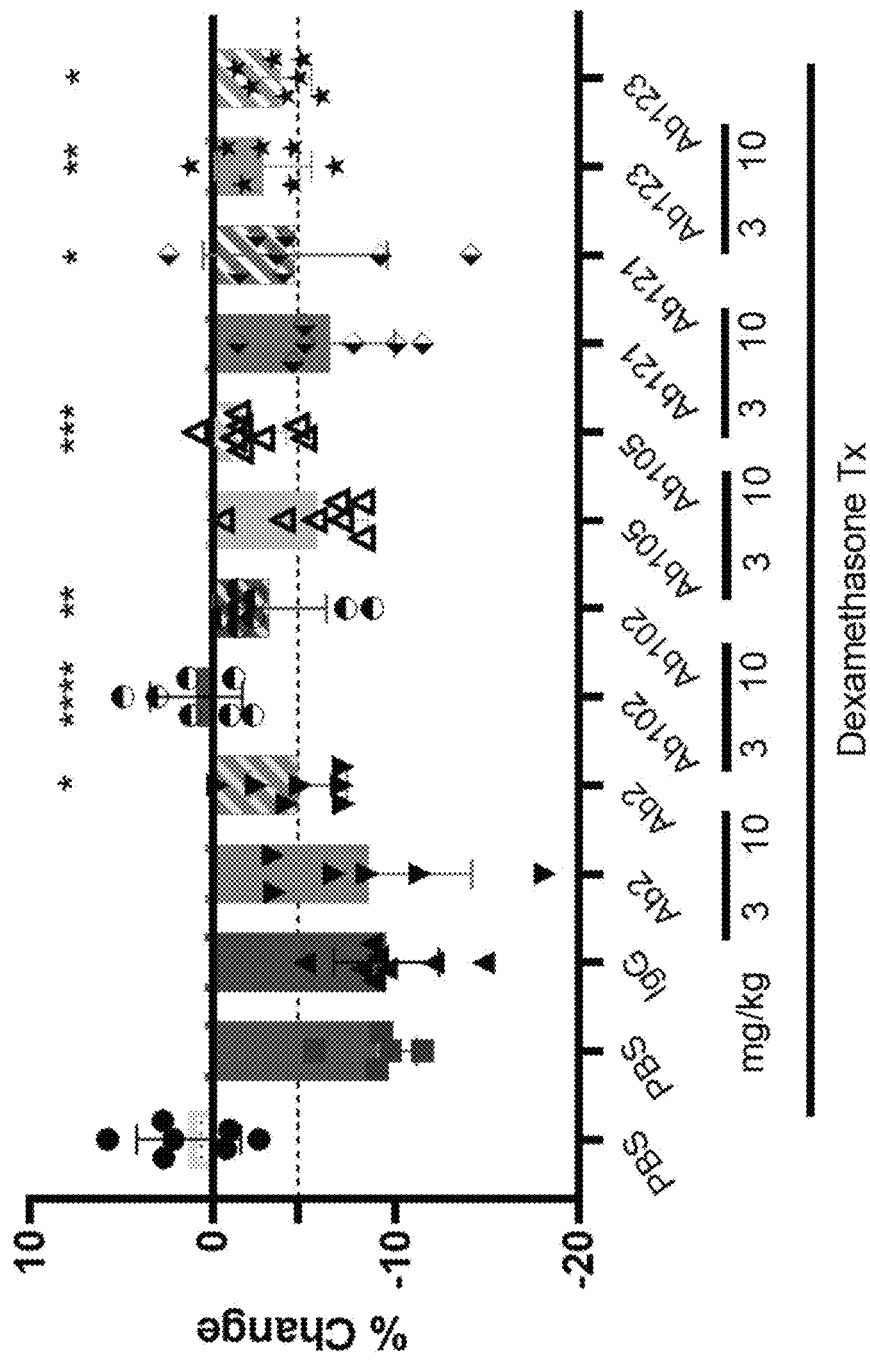
FIGS. 6A-C show in vivo effects of Ab2, Ab102, Ab105, Ab121, and Ab123 in mice with dexamethasone-induced muscle atrophy.

As shown in FIG. 6A, at a dose of 3 mg/kg/day, Ab102, Ab105, Ab 121, and Ab 123 maintained the body weight of the dexamethasone treated mice to a greater extent than Ab2. The effect of preventing the drug-induced loss of body weight was most pronounced with Ab 102. Compared to the immunoglobulin control, the percent body weight change induced by Ab102 at a dose of 3 mg/kg/day had a p value less than 0.0001 (one-way ANOVA). Compared to the immunoglobulin control, the % body weight change induced by 3 mg/kg/day Ab123 had a p value less than 0.01 (one-way ANOVA).

Figure 6B:
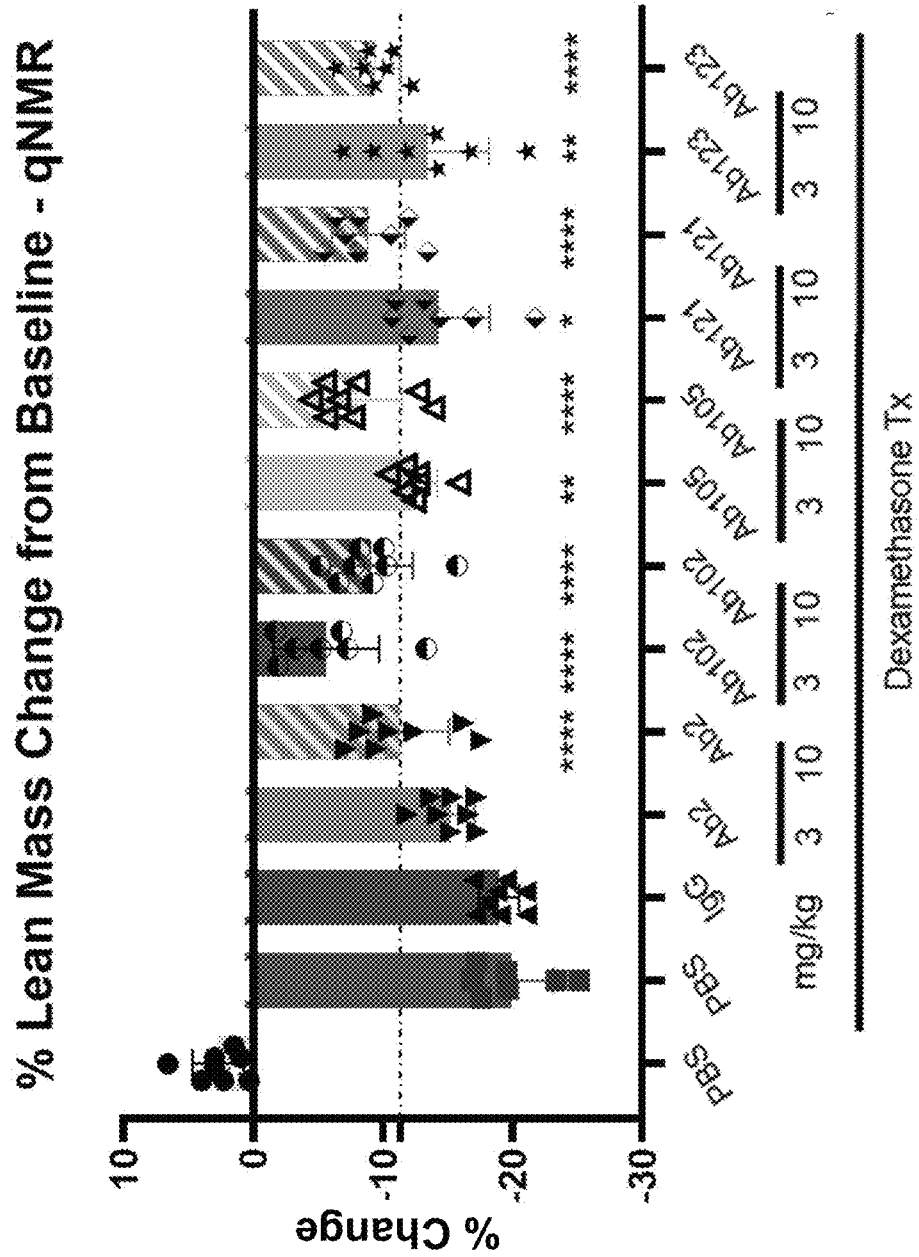
Figure 6C:
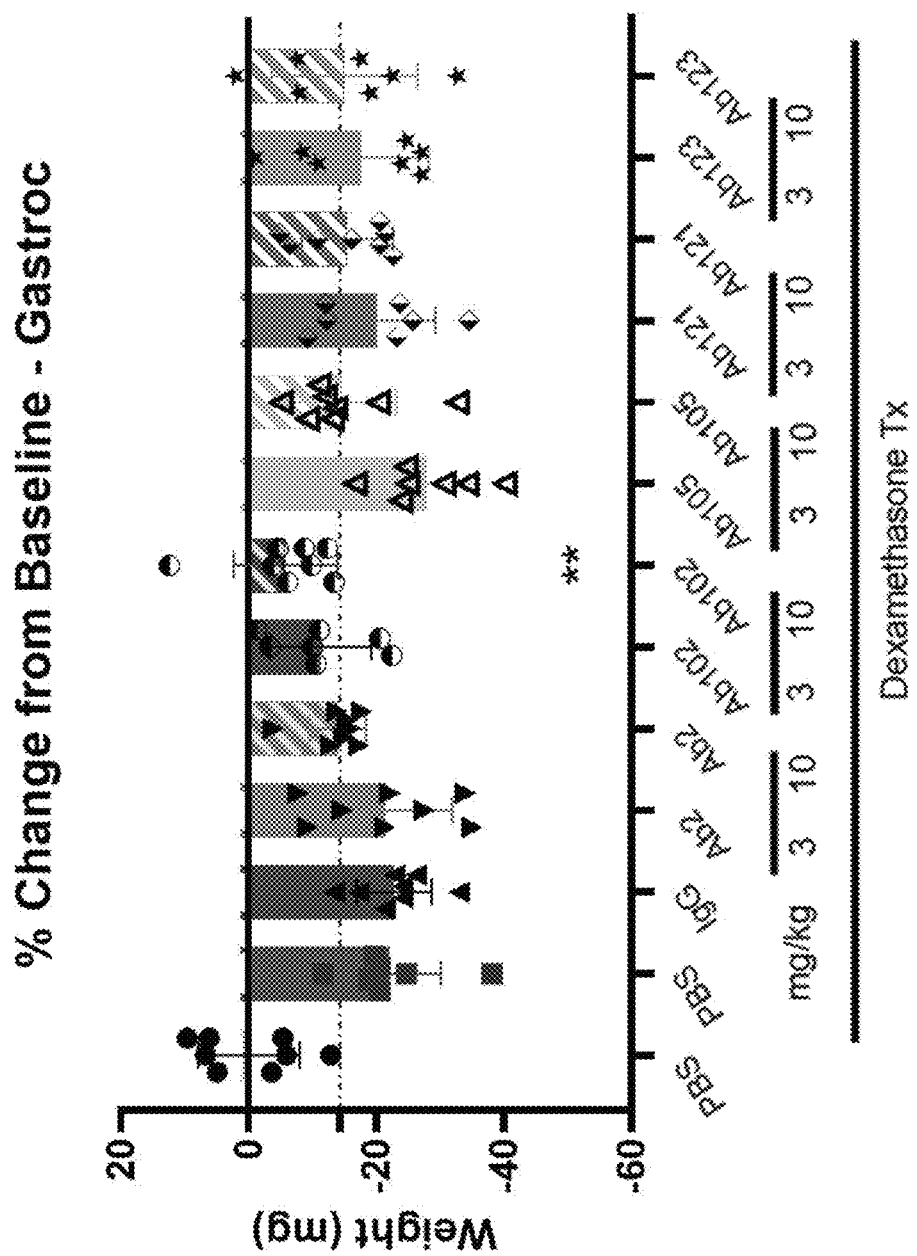

Ab102 also was superior to Ab 2 in preserving lean mass, as measured by qNMR. As shown in FIG. 6B, at a dose of 3 mg/kg/day, Ab102 preserved the lean mass of the mice to a greater degree than the 10 mg/kg/day dose of Ab2. This effect on lean mass was further demonstrated by measuring the percent loss of gastrocnemius muscle weight induced by dexamethasone treatment. As shown in FIG. 6C, Ab 102 at a dose of 3 mg/kg/day was highly effective in preserving gastrocnemius weight in the dexamethasone treated animals.

Having demonstrated the effectiveness of Ab102, Ab105, Ab121, and Ab123 in attenuating dexamethasone induced loss of body weight and lean mass, the effectiveness of additional antibodies, including lower antibody doses, were also evaluated.

C57BL6 male mice (n=8) at 13-14 weeks of age were given normal drinking water or water containing dexamethasone at a concentration of 2.5 mg/kg to induce atrophy. Mice were dosed at day 1 and day 7 with vehicle (PBS), IgG control ("hIgG") or different doses of the test antibodies, as shown in Table 13. Muscle mass at days −1, 6 and 13 was measured using qNMR. At the end of the study (day 14), serum from each animal was collected and changes in body weight, body composition (qNMR), left and right gastrocnemius weight, and left and right quadriceps weight were measured. Statistical analysis was performed by ANOVA (Dunnett's multiple comparison test).

TABLE 13

Ab109, Ab112, and Ab127 attenuated dexamethasone-induced atrophy.

| Group | Dexamethasone | Treatment | Dose |
| --- | --- | --- | --- |
| 1 | none | PBS | 0 |
| 2 | 2.5 mg/kg/day | PBS | 0 mg/kg |
| 3 | 2.5 mg/kg/day | hIgG | 10 mg/kg |
| 4 | 2.5 mg/kg/day | Ab2 | 10 mg/kg |
| 5 | 2.5 mg/kg/day | Ab2 | 3 mg/kg |
| 6 | 2.5 mg/kg/day | Ab112 | 10 mg/kg |
| 7 | 2.5 mg/kg/day | Ab112 | 3 mg/kg |
| 8 | 2.5 mg/kg/day | Ab109 | 10 mg/kg |
| 9 | 2.5 mg/kg/day | Ab109 | 3 mg/kg |
| 10 | 2.5 mg/kg/day | Ab127 | 10 mg/kg |
| 11 | 2.5 mg/kg/day | Ab127 | 3 mg/kg |

Figure 9A:
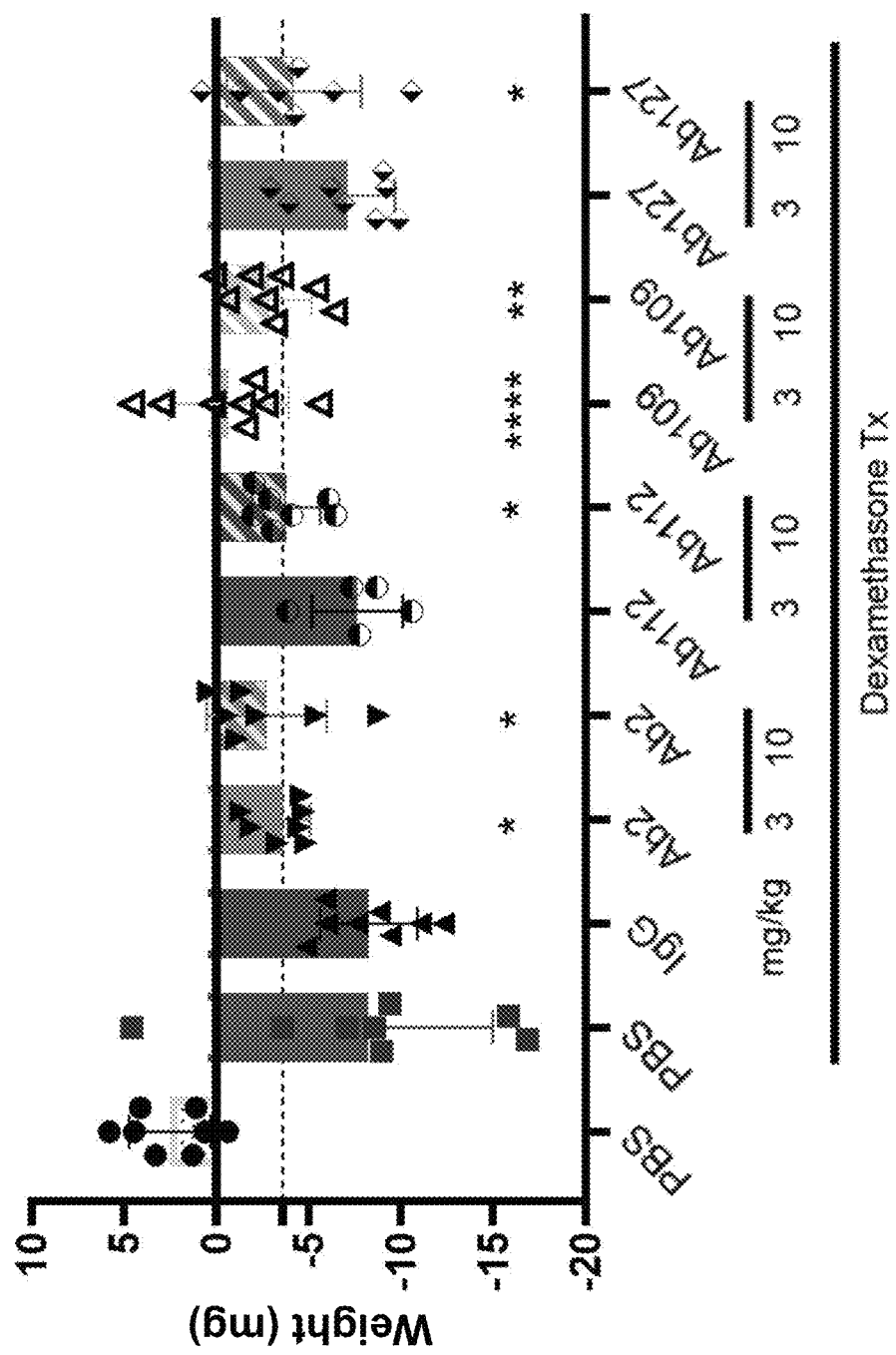
FIGS. 9A-D show in vivo effects of Ab2, Ab112, Ab109, and Ab127 in mice with dexamethasone-induced muscle atrophy.
Figure 9B:
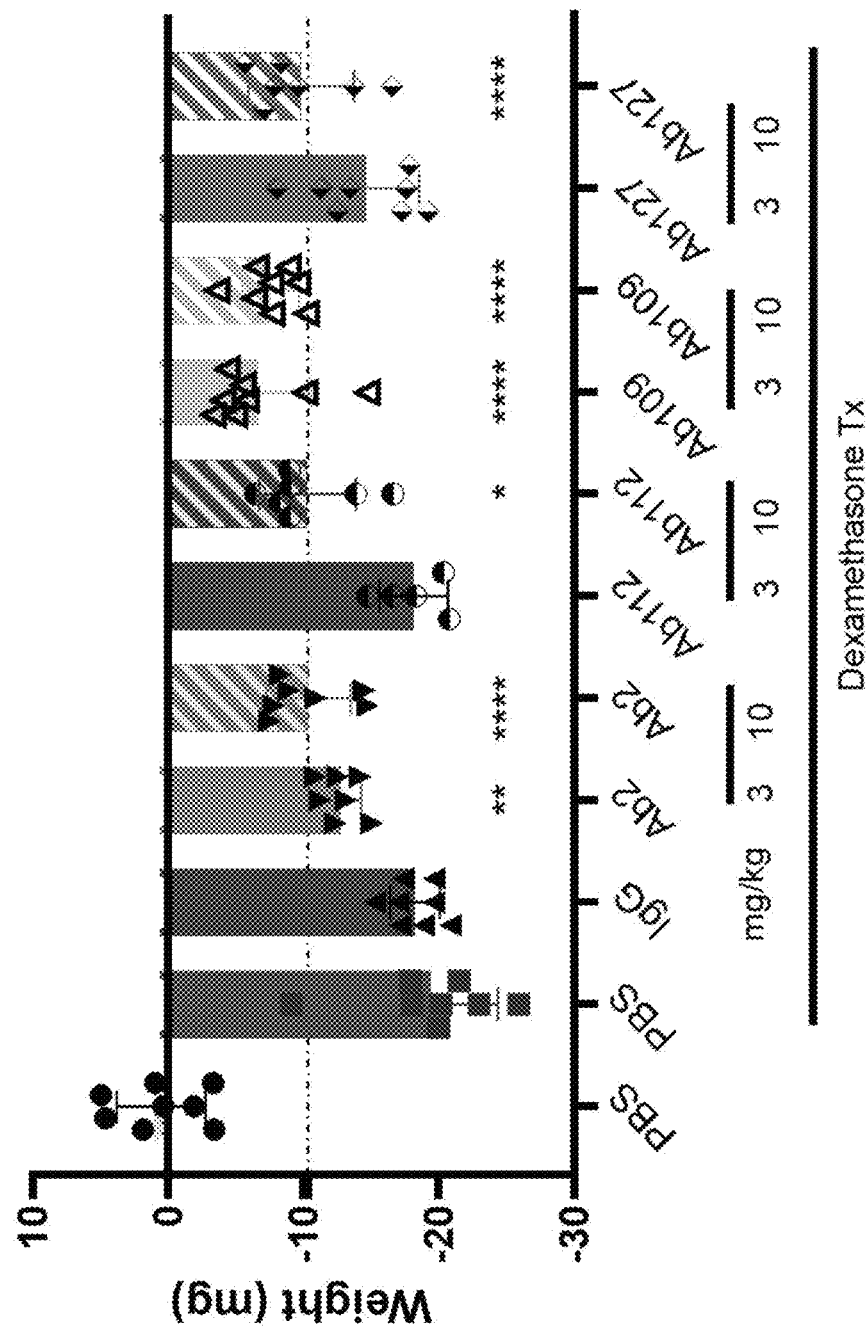
Figure 9C:
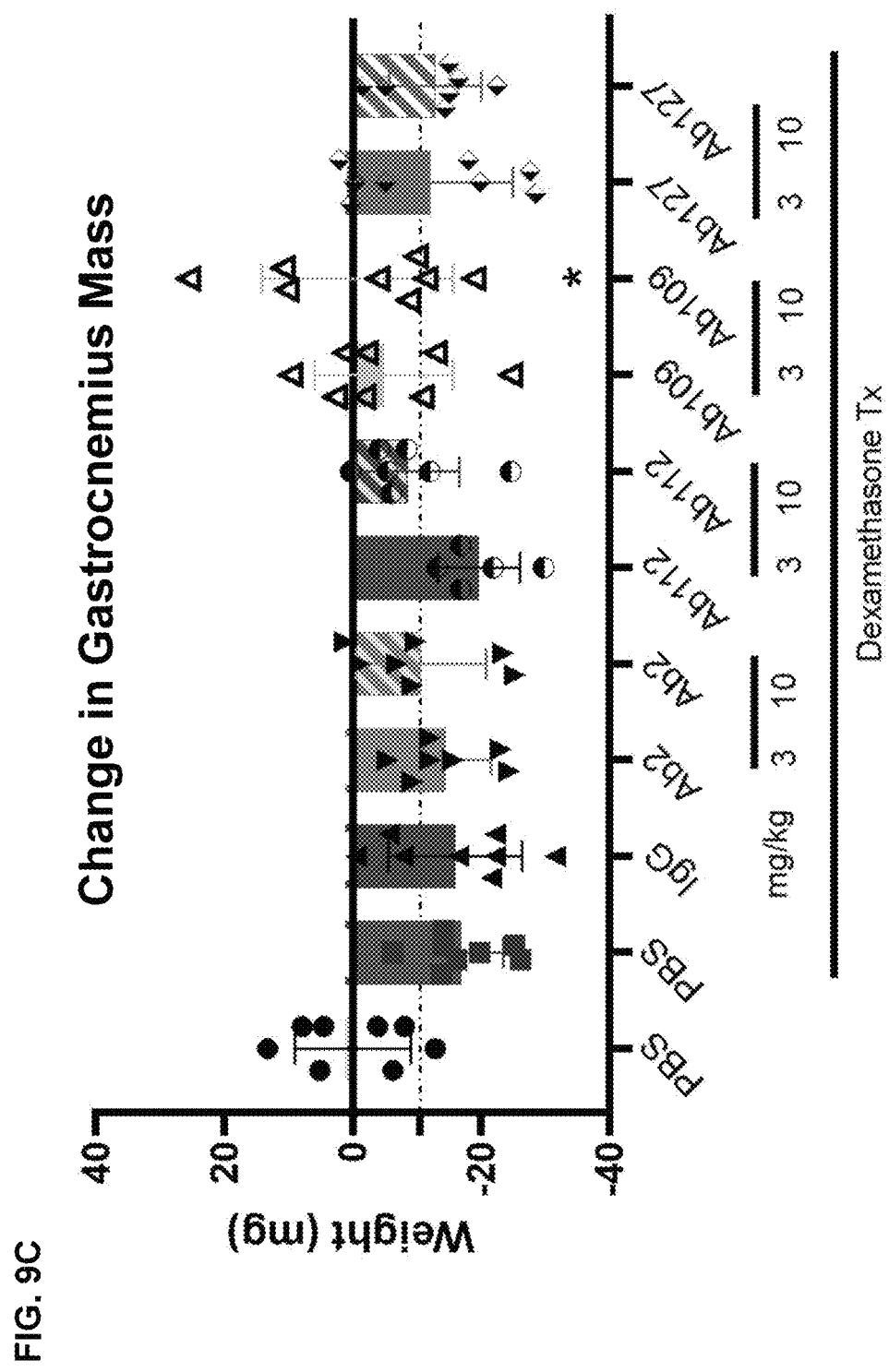
Figure 9D:
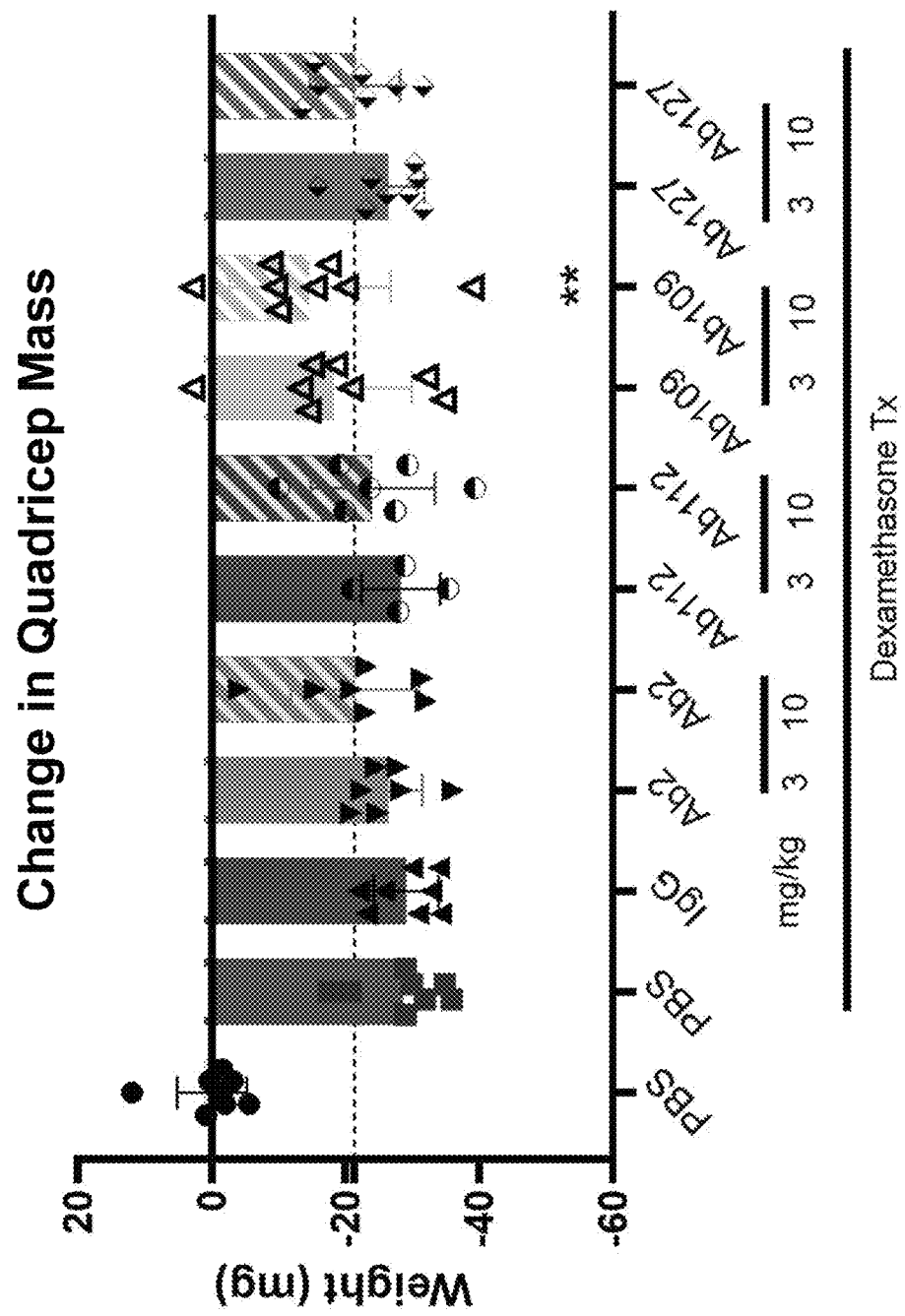

As shown in FIG. 9A, Ab109 maintained the body weight of the dexamethasone treated mice to a greater extent than Ab2. Compared to the immunoglobulin control, the percentage of body weight change induced by 3 mg/kg/day of Ab109 treatment had a p value less than 0.0001 (one-way ANOVA). Ab109 was also superior to Ab2 in preserving lean mass, as measured by qNMR. As shown in FIG. 9B, 3 mg/kg/day of Ab109 treatment preserved the lean mass of the mice to a greater degree than the 10 mg/kg/day Ab2 treatment. This effect on lean mass was further demonstrated by measuring the percent loss of gastrocnemius muscle weight induced by dexamethasone treatment. As shown in FIG. 9C, 3 mg/kg/day of Ab109 treatment was highly effective in preserving gastrocnemius weight in the dexamethasone treated animals. Ab109 was also highly effective in preserving quadriceps weight in the dexamethasone treated animals, as shown in FIG. 9D. Notably, Ab112 was less effective in preventing muscle-induced atrophy than Ab109 and Ab127, despite the sequence homology between Ab112, Ab109, and Ab 127.

In a third experiment, antibody doses ranging from 0.3 mg/kg to 10 mg/kg were compared for their effectiveness in attenuating dexamethasone-induced atrophy. C57BL6 male mice (n=8) at 13-14 weeks of age were given normal drinking water or water containing dexamethasone at a concentration of 2.5 mg/kg to induce atrophy. Mice were dosed at day 1 and day 7 with vehicle (PBS), human IgG control ("hIgG") or different doses of the test antibodies, as shown in Table 14 below. qNMR was used to measure muscle mass at days-1, 6 and 13. At day 14 the study ended, serum was collected and changes in body composition (qNMR), left and right gastrocnemius weight, and left and right quadriceps weight were determined. Circulating myostatin was measured in the serum of a terminal bleed taken at day 14. Statistical analysis was performed by ANOVA (Dunnett's multiple comparison test).

TABLE 14

Ab130 and Ab109 attenuated dexamethasone-induced atrophy.

| Group | Dexamethasone | Treatment | Dose |
|---|---|---|---|
| 1 | None | PBS | 0 mg/kg |
| 2 | 2.5 mg/kg/day | hIgG | 10 mg/kg |
| 3 | 2.5 mg/kg/day | Ab2 | 10 mg/kg |
| 4 | 2.5 mg/kg/day | Ab2 | 3 mg/kg |
| 5 | 2.5 mg/kg/day | Ab130 | 10 mg/kg |
| 6 | 2.5 mg/kg/day | Ab130 | 3 mg/kg |
| 7 | 2.5 mg/kg/day | Ab130 | 1 mg/kg |
| 8 | 2.5 mg/kg/day | Ab130 | 0.3 mg/kg |
| 9 | 2.5 mg/kg/day | Ab109 | 10 mg/kg |
| 10 | 2.5 mg/kg/day | Ab109 | 3 mg/kg |
| 11 | 2.5 mg/kg/day | Ab109 | 1 mg/kg |
| 12 | 2.5 mg/kg/day | Ab109 | 0.3 mg/kg |

Antibody exposure and circulating total myostatin levels were measured in the serum collected from the terminal bleeds after treatment with Ab2, Ab130 and Ab109. The results are shown in Table 15 and Table 16 respectively. Table 15 shows that the exposure of the antibody to the antigen are similar among the three antibodies.

TABLE 15

Terminal antibody exposure.

| Group | Treatment | Dose (mg/kg) | Exposure (ug/ml) | Std. Dev. | % CV | N |
|---|---|---|---|---|---|---|
| 1 | PBS | n/a | n/a | n/a | n/a | n/a |
| 2 | hIgG | n/a | n/a | n/a | n/a | n/a |

TABLE 15-continued

Terminal antibody exposure.

| Group | Treatment | Dose (mg/kg) | Exposure (ug/ml) | Std. Dev. | % CV | N |
|---|---|---|---|---|---|---|
| 3 | Ab2 | 10 | 444.7 | 399.9 | 90 | 8 |
| 4 | Ab2 | 3 | 51.7 | 42.3 | 82 | 8 |
| 5 | Ab130 | 10 | 488.4 | 787.2 | 161 | 8 |
| 6 | Ab130 | 3 | 93.1 | 52.8 | 57 | 8 |
| 7 | Ab130 | 1 | 4.7 | 1.7 | 36 | 8 |
| 8 | Ab130 | 0.3 | 1.2 | 0.7 | 60 | 8 |
| 9 | Ab109 | 10 | 470.2 | 229.0 | 49 | 8 |
| 10 | Ab109 | 3 | 67.3 | 43.7 | 65 | 8 |
| 11 | Ab109 | 1 | 104.9 | 42.5 | 41 | 8 |
| 12 | Ab109 | 0.3 | 2.8 | 3.5 | 127 | 8 |

Previously, Ab2 treatment had been shown to cause an accumulation of total myostatin in the serum of the dosed subject, presumably as a stable immune complex comprised of the antibody and its bound target (e.g., latent myostatin). To examine whether serum accumulation of total myostatin may be observed with the novel antibodies disclosed herein, similar to that observed with Ab2, serum samples were collected at endpoint (15 days), and total myostatin levels were measured by ELISA, as described above. Briefly, serum samples were acidified at low pH (e.g., pH ~2.5) to dissociate the bound antibody from the immune complex and to convert all myostatin in the sample to the active form of growth factor (i.e., mature myostatin). Samples were then neutralized and assayed for the presence of mature myostatin on ELISA plates coated with anti-mature myostatin antibodies as capture reagents.

Figure 8:
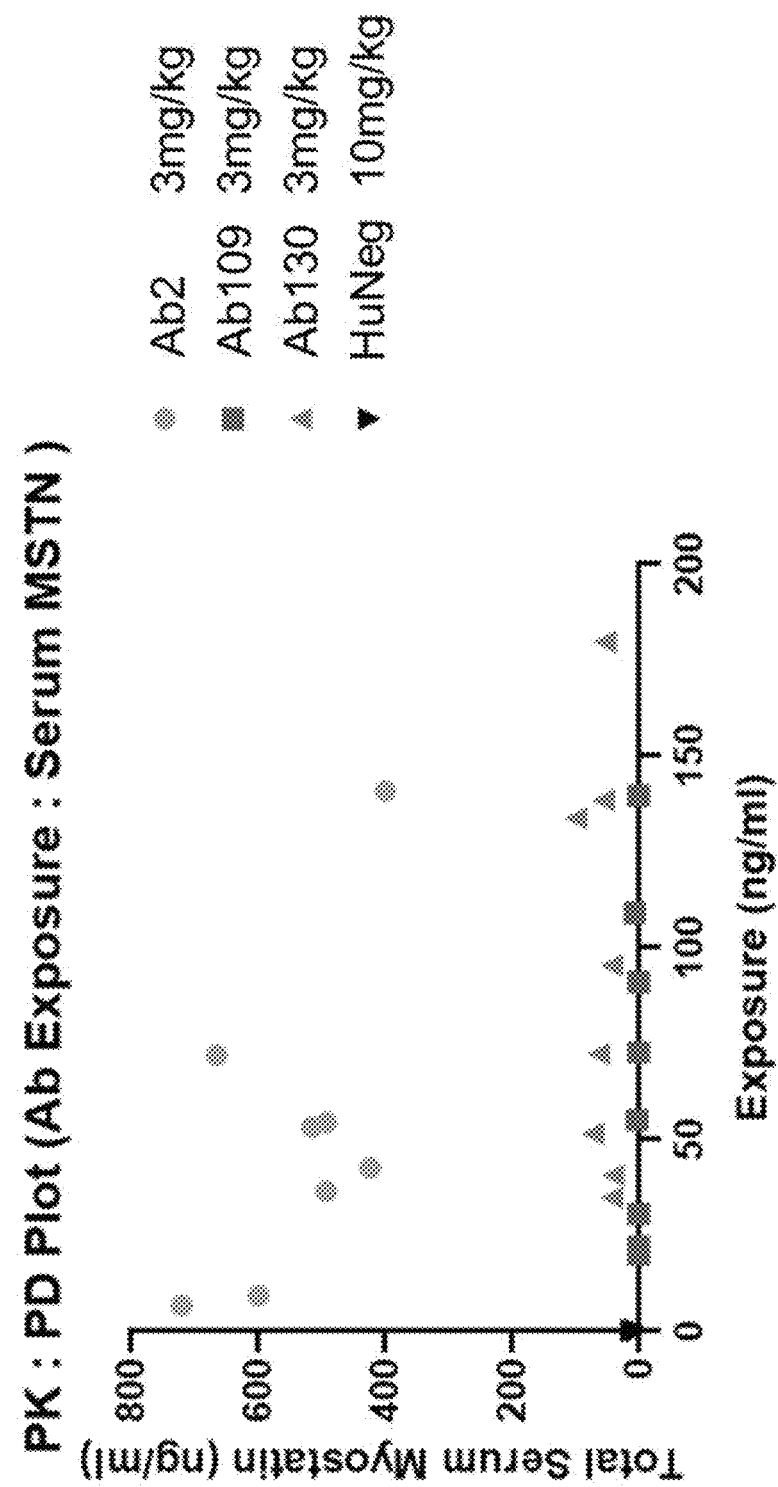
FIG. 8 shows the level of total serum myostatin in mice treated with Ab2, Ab109, or Ab130. Statistical analysis was done using one-way ANOVA (Dunnett's multiple comparisons test).

Results are summarized in Table 16, which shows that treatment with either Ab130 or Ab109 resulted in lower levels of total circulating myostatin as compared to Ab2 treatment. This effect is illustrated in FIG. 8, which shows the relationship of the exposure of the antibody to the antigen and the level of total myostatin in the serum. At a concentration of 3 mg/kg, both Ab130 and Ab109, decreased the level of total myostatin in the serum compared to Ab2. In addition, FIG. 17 also shows that 2 mg/kg and 20 mg/kg doses of Ab109 reduce free latent myostatin levels in the serum (i.e., latent myostatin that is not bound by the antibody). These findings suggest that while sharing common features with Ab2, such as selectivity, pH-dependent binding, and the binding region, Ab109 and Ab130 represent a unique subclass of antibodies that offers a distinct serum clearance behavior (e.g., faster clearance of immune complexes) in vivo.

TABLE 16

Circulating total myostatin levels.

| Group | Treatment | Dose (mg/kg) | Myostatin (ng/ml) | Std. Dev. | % CV | N* |
|---|---|---|---|---|---|---|
| 1 | PBS | n/a | 130.1 | 33.1 | 25 | 8 |
| 2 | hIgG | n/a | 73.6 | 33.8 | 46 | 8 |
| 3 | Ab2 | 10 | 8859.0 | 2569.0 | 29 | 7 |
| 4 | Ab2 | 3 | 5384.2 | 1134.1 | 21 | 8 |
| 5 | Ab130 | 10 | 325.2 | 61.0 | 19 | 8 |
| 6 | Ab130 | 3 | 585.6 | 194.7 | 33 | 8 |
| 7 | Ab130 | 1 | 567.3 | 56.0 | 10 | 8 |
| 8 | Ab130 | 0.3 | 473.8 | 63.9 | 13 | 8 |
| 9 | Ab109 | 10 | BLOQ | n/a | n/a | 0 |
| 10 | Ab109 | 3 | 48.4 | 30.1 | 62 | 2 |

TABLE 16-continued

Circulating total myostatin levels.

| Group | Treatment | Dose (mg/kg) | Myostatin (ng/ml) | Std. Dev. | % CV | N* |
|---|---|---|---|---|---|---|
| 11 | Ab109 | 1 | 45.7 | 17.8 | 39 | 7 |
| 12 | Ab109 | 0.3 | 159.6 | 56.6 | 35 | 8 |

*Number of samples that were not below the level of quantitation (BLOQ)

In a fourth experiment, antibodies Ab109 and Ab133 were compared to control human IgG and Ab2 in the same protocol as described above. Data are shown in Table 17.

TABLE 17

Ab109 and Ab133 attenuated dexamethasone-induced atrophy.

| Group | Dexamethasone | Treatment | DoseDIO |
|---|---|---|---|
| 1 | none | PBS | 0 |
| 2 | 2.5 mg/kg/day | hIgG | 10 mg/kg |
| 3 | 2.5 mg/kg/day | Ab2 | 10 mg/kg |
| 4 | 2.5 mg/kg/day | Ab2 | 3 mg/kg |
| 5 | 2.5 mg/kg/day | Ab133 | 10 mg/kg |
| 6 | 2.5 mg/kg/day | Ab133 | 3 mg/kg |
| 7 | 2.5 mg/kg/day | Ab133 | 1 mg/kg |
| 8 | 2.5 mg/kg/day | Ab133 | 0.3 mg/kg |
| 9 | 2.5 mg/kg/day | Ab109 | 10 mg/kg |
| 10 | 2.5 mg/kg/day | Ab109 | 3 mg/kg |
| 11 | 2.5 mg/kg/day | Ab109 | 1 mg/kg |
| 12 | 2.5 mg/kg/day | Ab109 | 0.3 mg/kg |

Figure 10A:
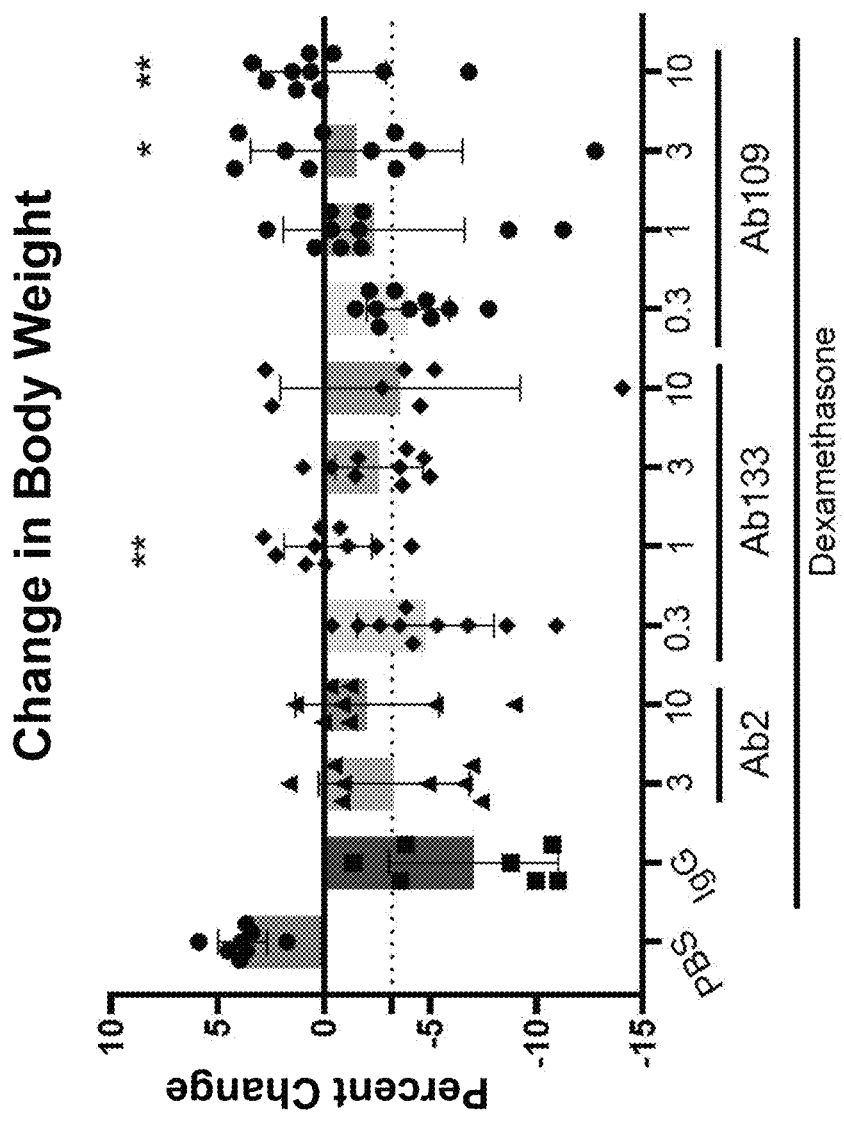
FIGS. 10A-F show in vivo effects of Ab2, Ab109, and Ab133 in mice with dexamethasone-induced muscle atrophy.
Figure 10B:
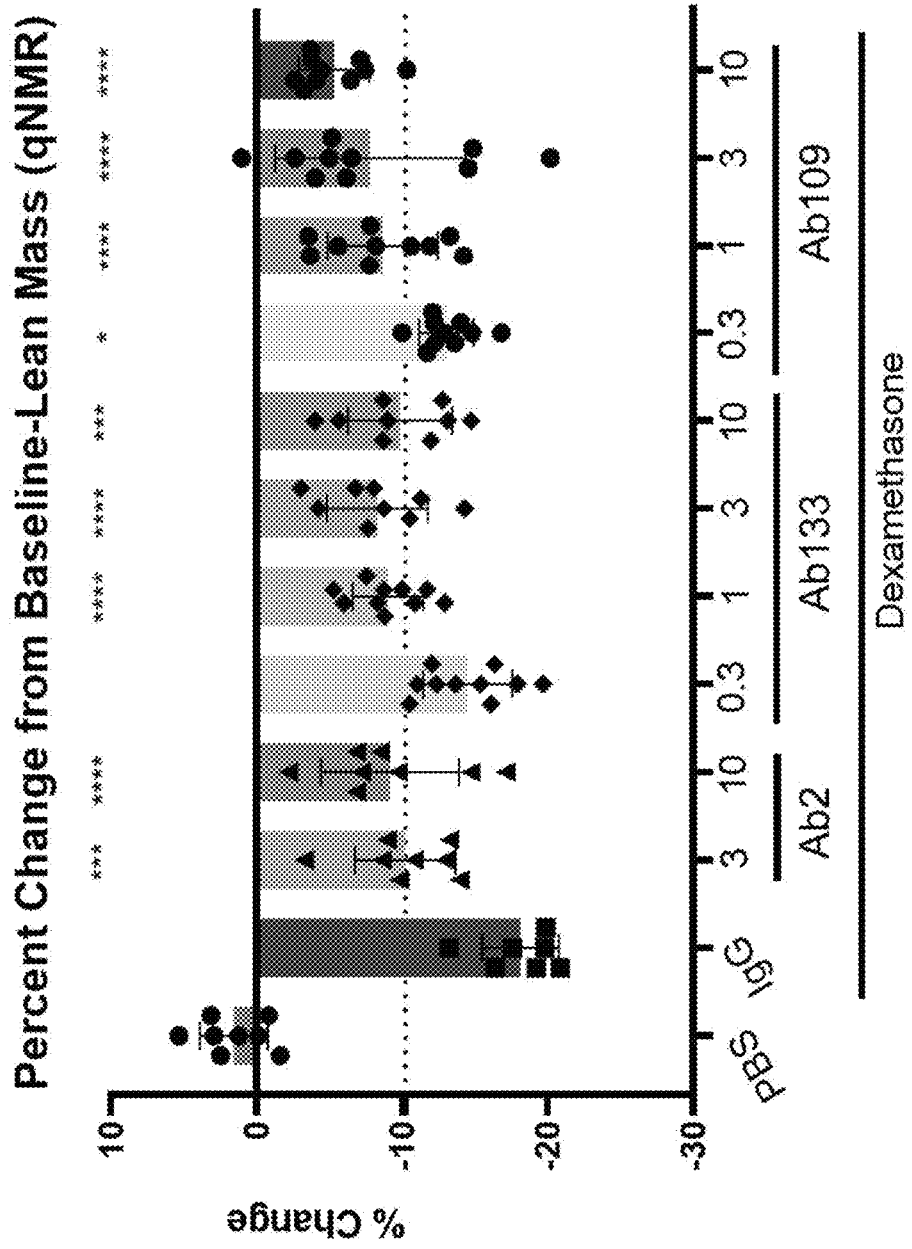
Figure 10C:
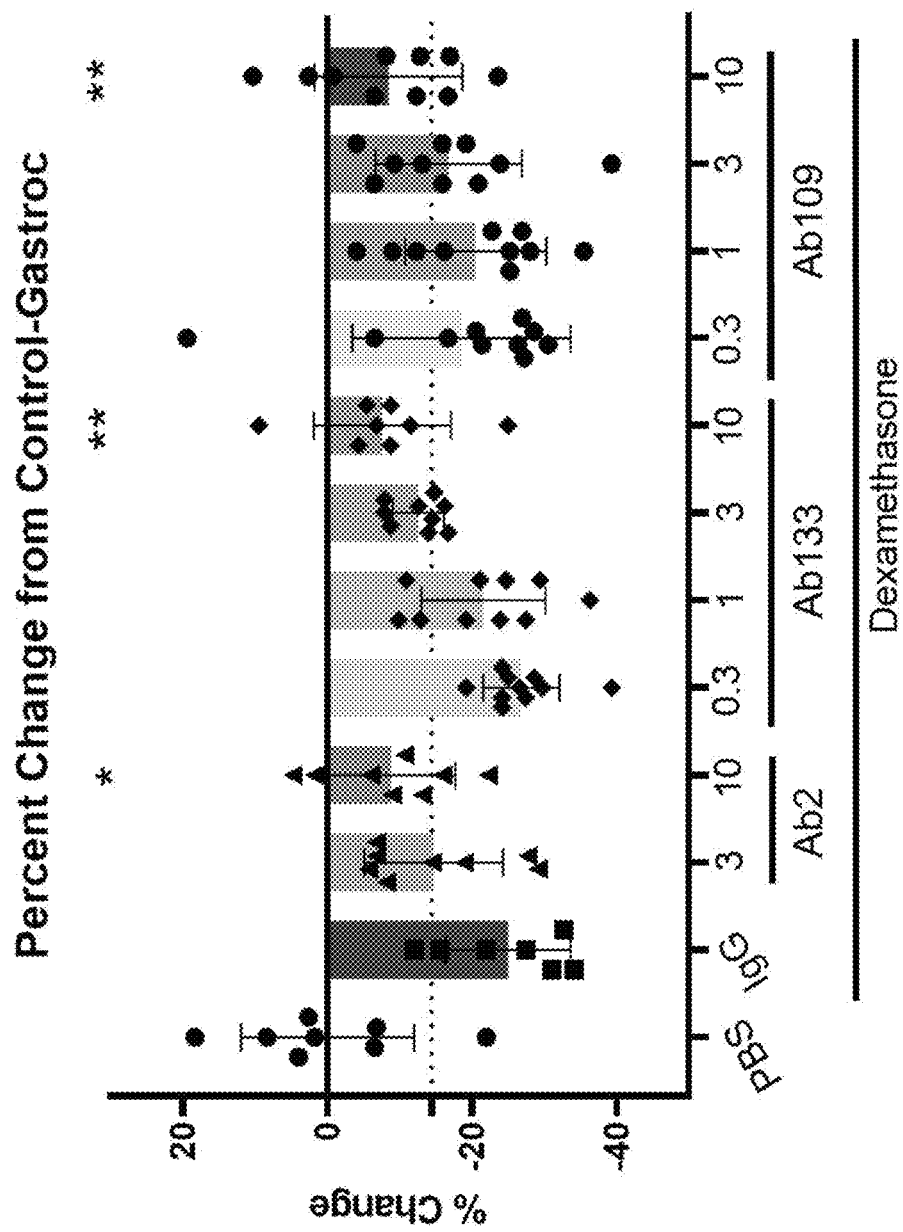
Figure 10D:
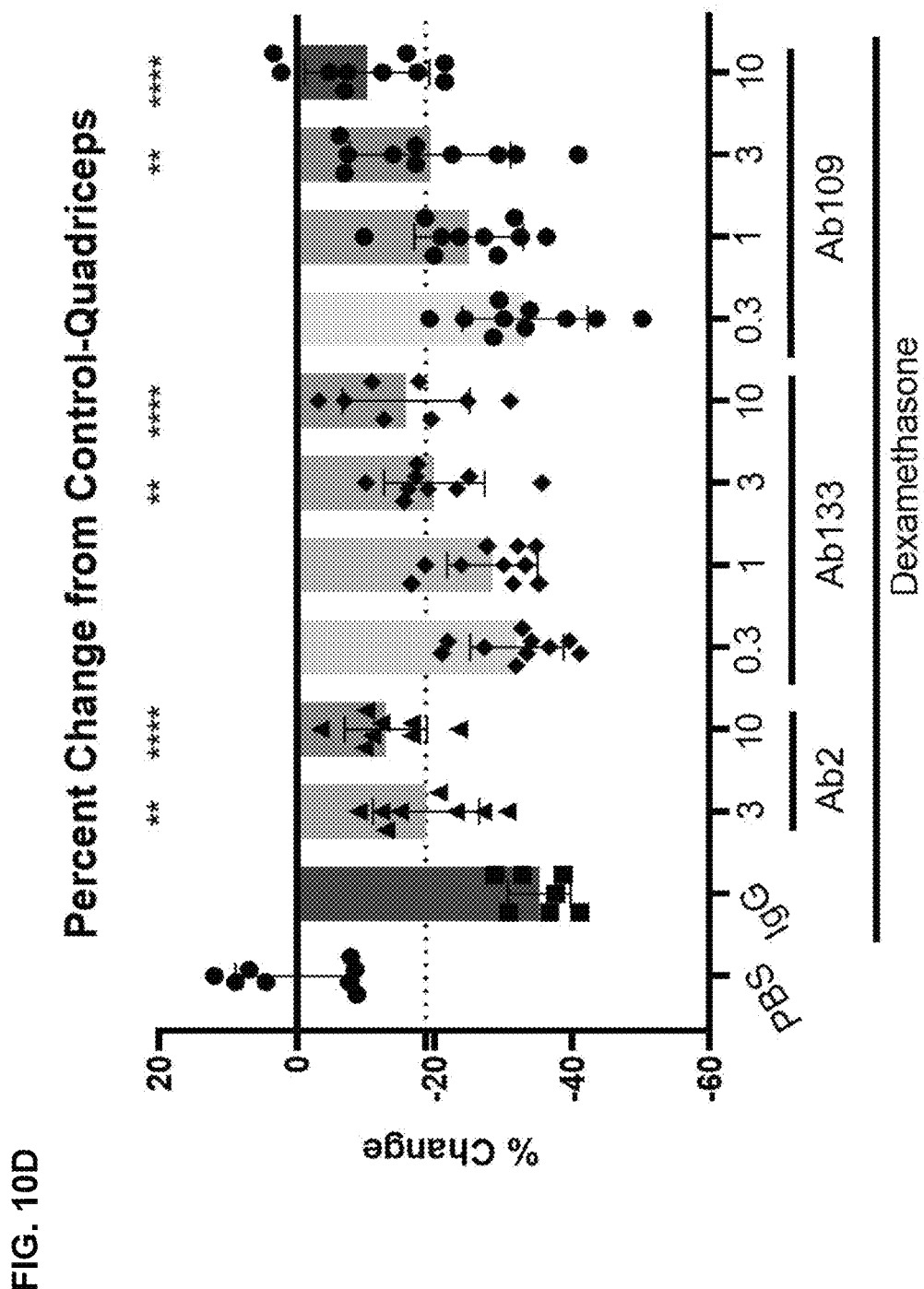
Figure 10E:
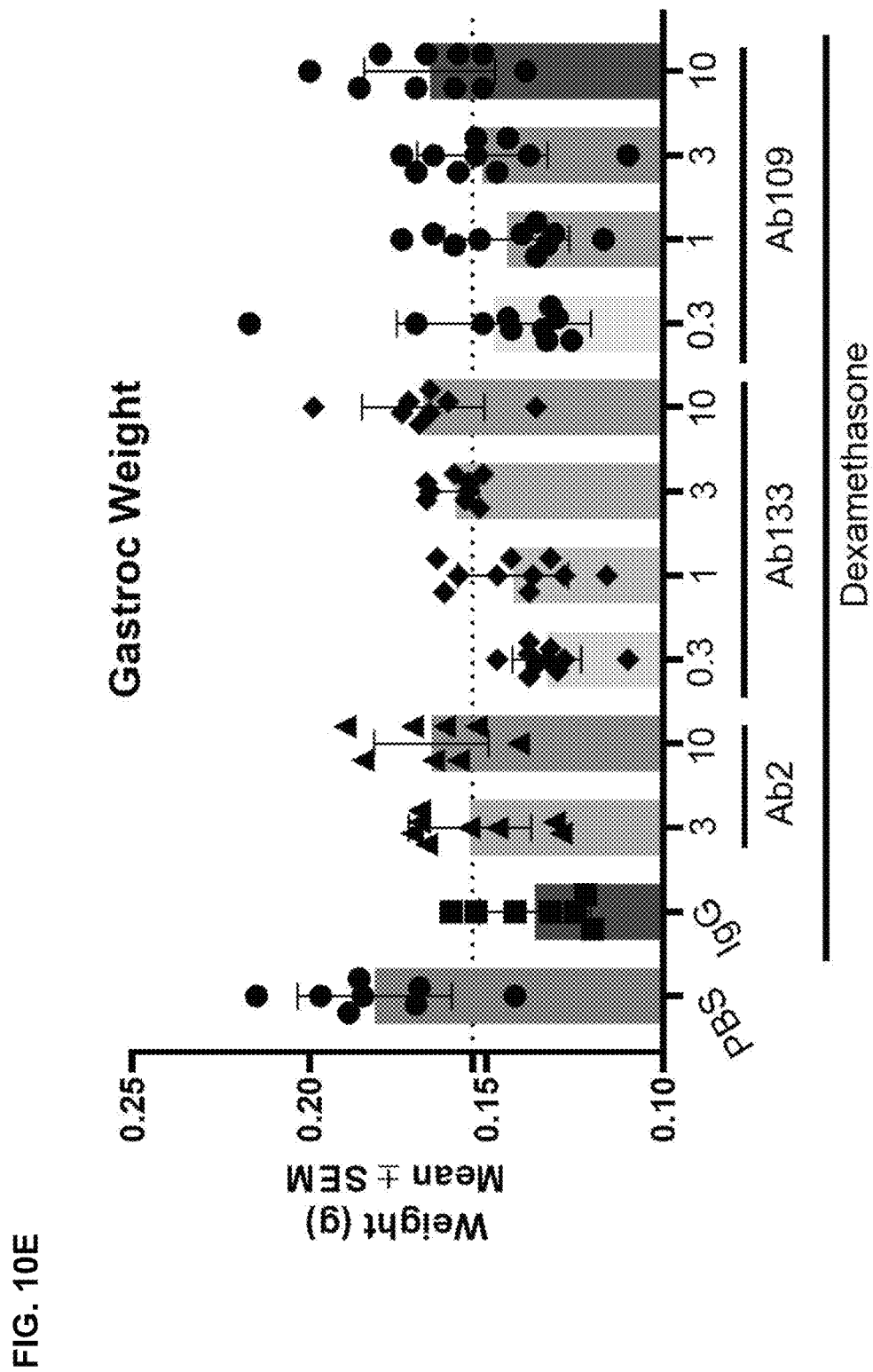
Figure 10F:
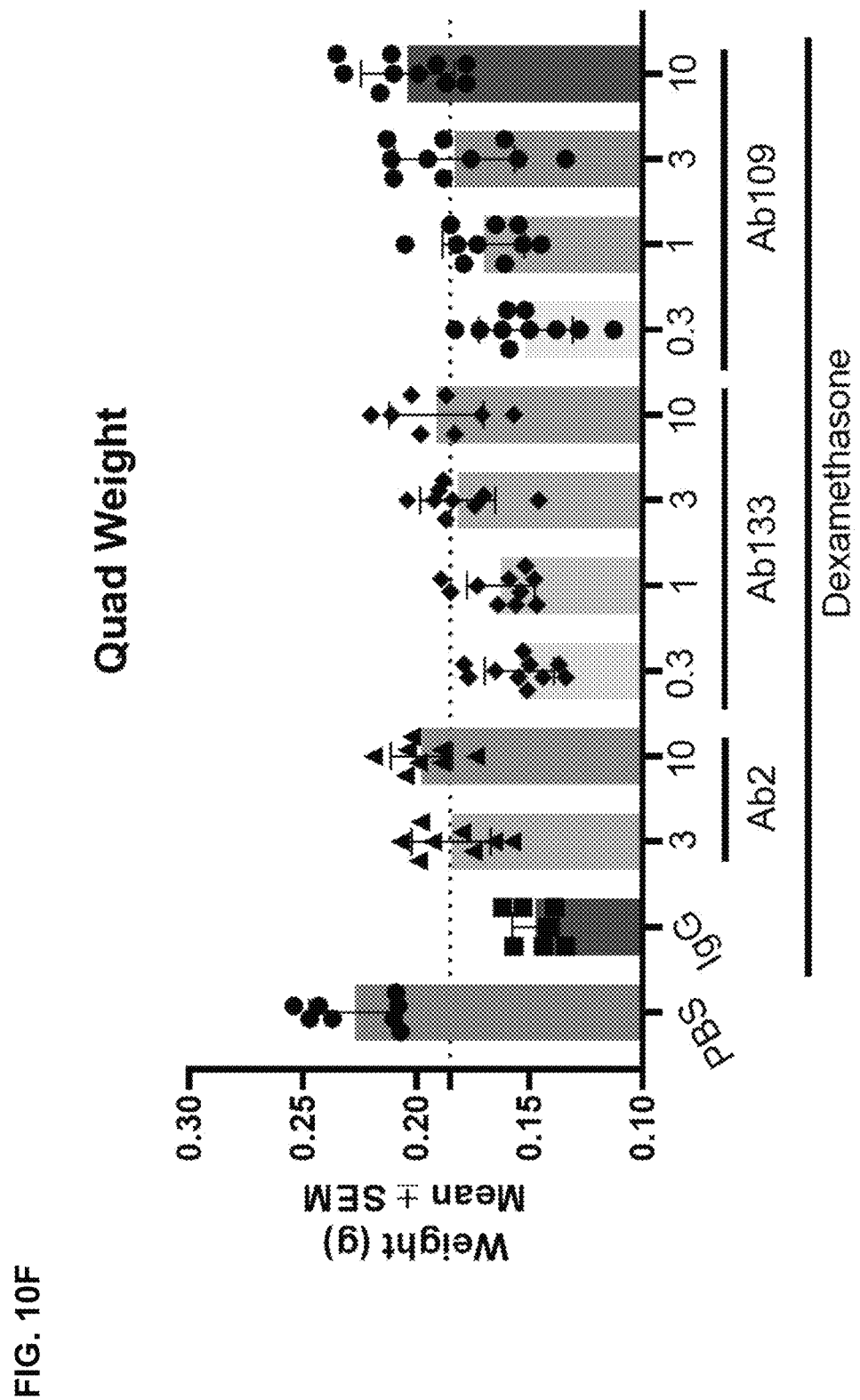

As shown in FIGS. 10A-10F, both Ab133 and Ab109 were effective in attenuating dexamethasone-induced muscle atrophy. FIG. 10A shows that Ab133 and Ab109 prevented dexamethasone-induced weight loss. Notably, the 1 mg/kg dose of Ab109 was equally as effective as the 10 mg/kg dose of Ab 2 in preventing weight loss in the dexamethasone-treated animals. Both Ab133 and Ab109 attenuated the loss of lean mass, as measured by qNMR, with Ab109 showing greater efficacy at both 3 mg/kg and 10 mg/kg compared to either Ab2 or Ab133 at 3 mg/kg and 10 mg/kg (FIG. 10B). Each of the antibodies also attenuated gastrocnemius muscle loss (FIG. 10C) and quadricep muscle loss (FIG. 10D). Both the gastrocnemius muscle weight and the quadricep muscle weight increased with antibody dose, i.e., showed a dose response, as shown in FIG. 10E and FIG. 10F.

FIGS. 7A-D and Table 18 further demonstrate the efficacy of Ab109 and Ab130 in attenuating dexamethasone-induced muscle atrophy as compared to Ab2.

TABLE 18

Ab109 and Ab130 attenuated dexamethasone-induced atrophy.

| Group | Dexamethasone | Treatment | Dose |
|---|---|---|---|
| 1 | none | PBS | 0 |
| 2 | 2.5 mg/kg/day | hIgG | 10 mg/kg |
| 3 | 2.5 mg/kg/day | Ab2 | 10 mg/kg |
| 4 | 2.5 mg/kg/day | Ab2 | 3 mg/kg |
| 5 | 2.5 mg/kg/day | Ab130 | 10 mg/kg |
| 6 | 2.5 mg/kg/day | Ab130 | 3 mg/kg |
| 7 | 2.5 mg/kg/day | Ab130 | 1 mg/kg |
| 8 | 2.5 mg/kg/day | Ab130 | 0.3 mg/kg |
| 9 | 2.5 mg/kg/day | Ab109 | 10 mg/kg |
| 10 | 2.5 mg/kg/day | Ab109 | 3 mg/kg |
| 11 | 2.5 mg/kg/day | Ab109 | 1 mg/kg |
| 12 | 2.5 mg/kg/day | Ab109 | 0.3 mg/kg |

Figure 7A:
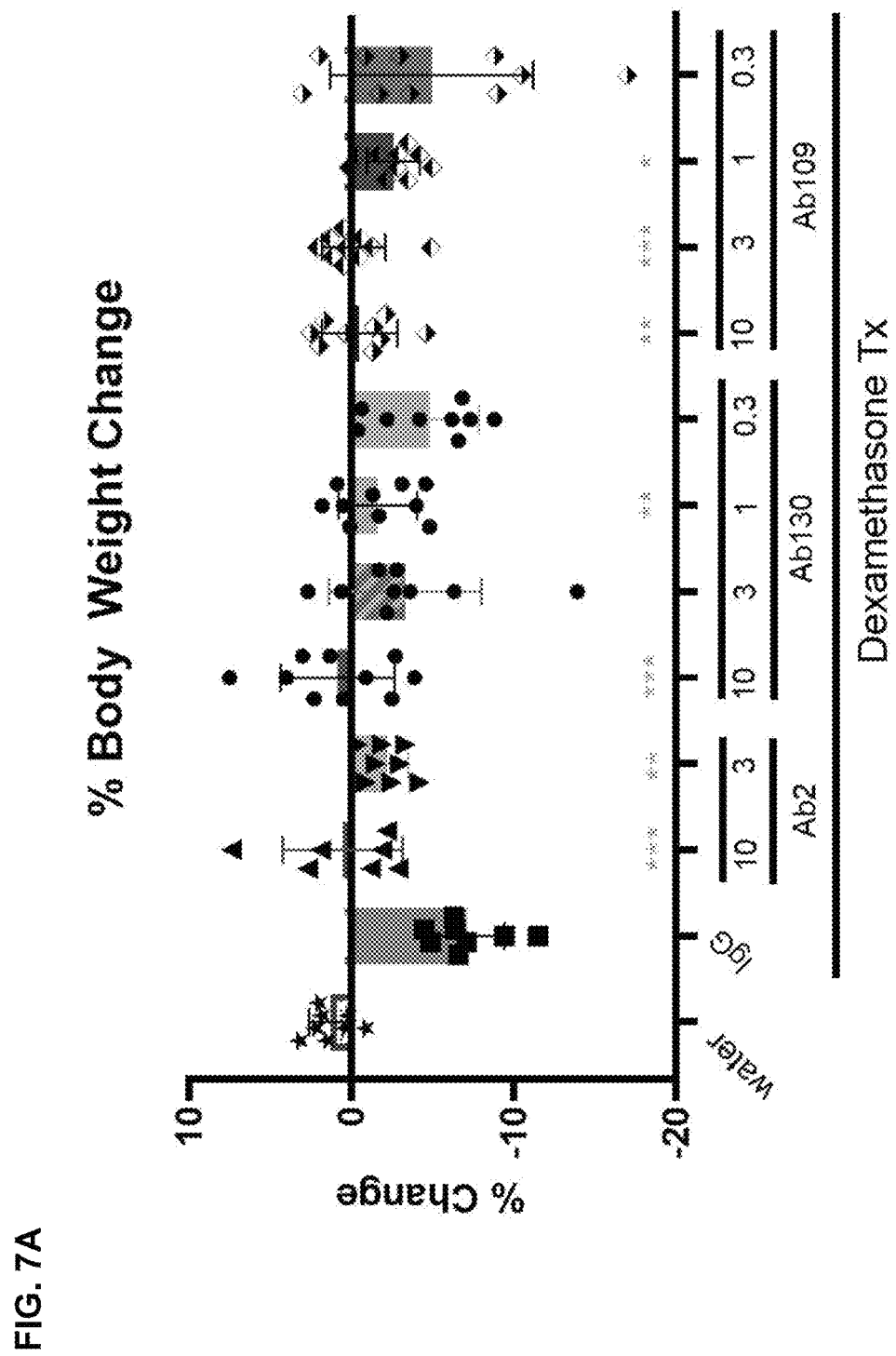
FIGS. 7A-D show in vivo effects of Ab2, Ab130, and Ab109 in mice with dexamethasone-induced muscle atrophy.

Dexamethasone induced body weight loss; animals treated with PBS or control antibody lost approximately 10% of their body weight. Antibodies of the disclosure mitigated the effect of dexamethasone on body weight loss (FIG. 7A). Ab130 and Ab109 were efficacious in preserving body weight. Surprisingly, both antibodies demonstrated efficacy at concentrations as low as 1 mg/kg and Ab109 demonstrated improved efficacy compared to Ab2 at 10, 3, and 1 mg/kg.

Figure 7B:
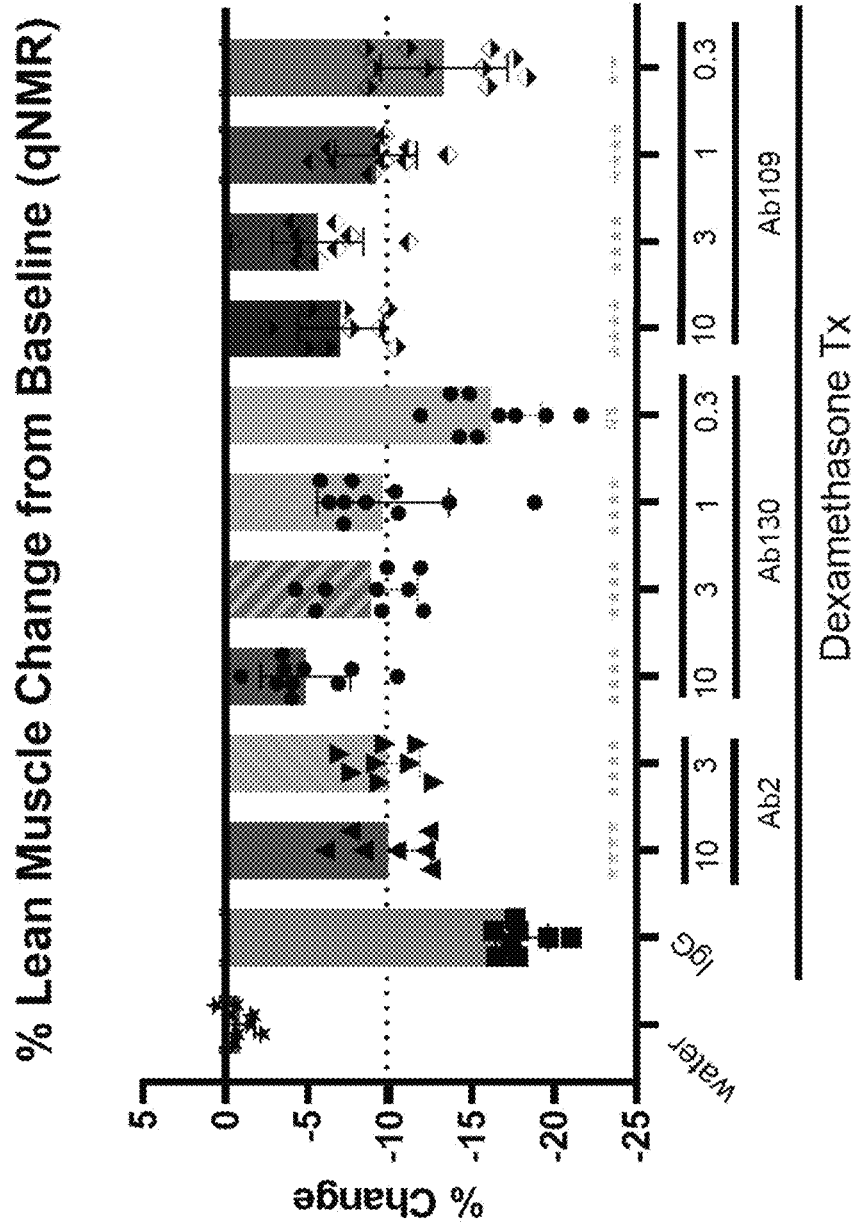

Dexamethasone also induced a loss in lean mass. Animals treated with dexamethasone and a sham IgG lost almost 20% of their lean muscle mass. FIG. 7B shows the effect of antibodies Ab130 and Ab109 on lean mass as compared to the average effect of Ab2 at 10 mg/kg (dashed line). At a dose of 10 mg/kg, Ab130 showed greater efficacy in preserving lean mass than Ab2. At doses of both 10 mg/kg and 3 mg/kg, Ab109 showed greater efficacy in preserving lean mass than Ab2.

Figure 7C:
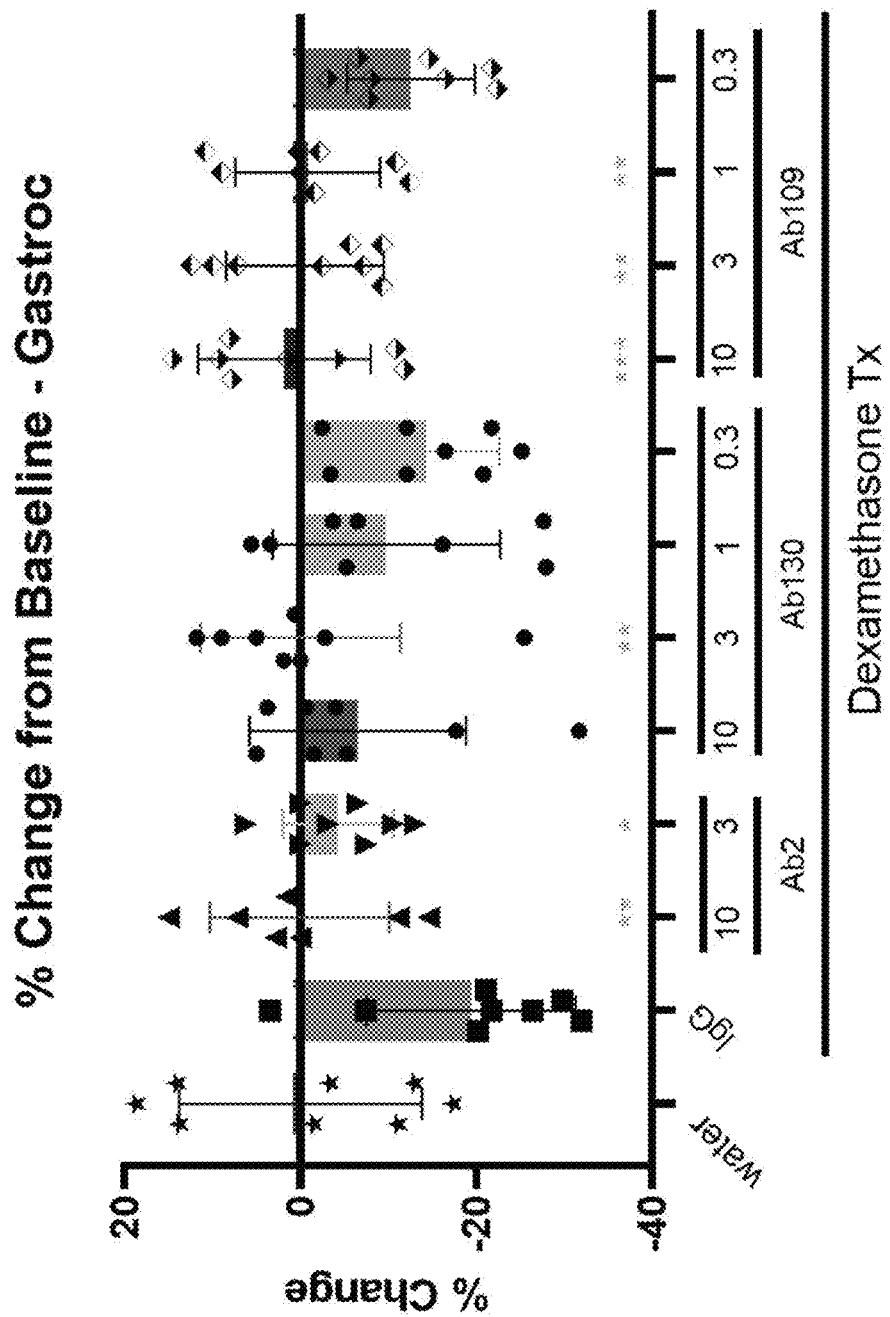

FIG. 7C illustrates the changes in gastrocnemius muscle weights after treatment with Ab130 or Ab109 at 0.3 mg/kg, 1 mg/kg, 3 mg/kg, or 10 mg/kg as compared to treatment with Ab2 at 3 mg/kg or 10 mg/kg. The percentage difference from the mean of the non-treated control is represented on the vertical axis. Both Ab130 and Ab109 were more efficacious than Ab2, with Ab130 showing more efficacy at 3 mg/kg than both doses of Ab2 and Ab109 showing more efficacy at all four doses as compared to Ab2 at 3 mg/kg (dashed line).

Figure 7D:
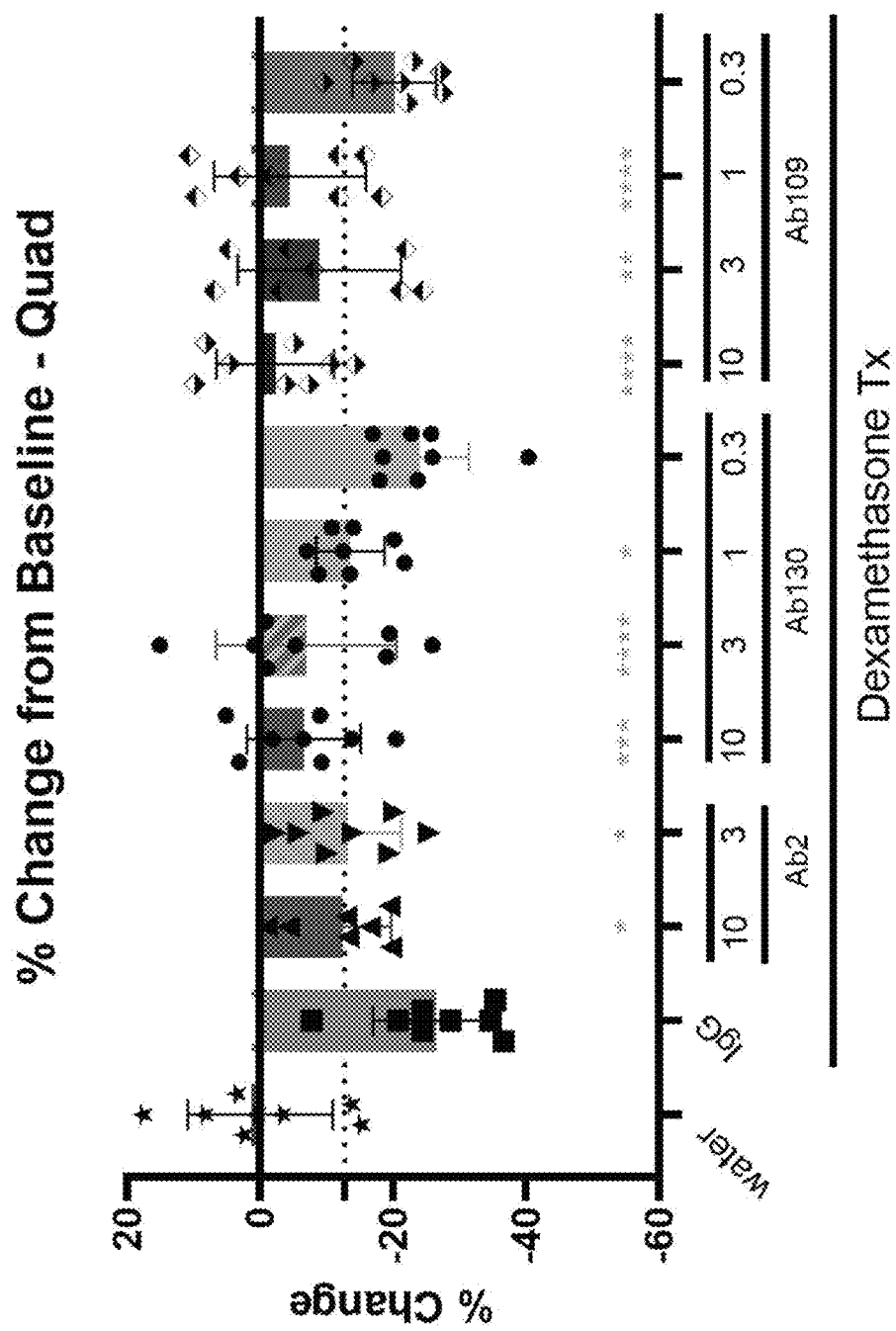

FIG. 7D illustrates the changes in quadriceps muscle weights after treatment with Ab130 or Ab109 at 0.3 mg/kg, 1 mg/kg, 3 mg/kg, or 10 mg/kg as compared to treatment with Ab2 at 3 mg/kg or 10 mg/kg. The percentage difference from the mean of the non-treated control is represented on the vertical axis. Both Ab130 and Ab109 were more efficacious than Ab2, with Ab130 showing more efficacy at 3 mg/kg than both doses of Ab2 and Ab109 showing more efficacy at all four doses as compared to Ab2 at 3 mg/kg (dashed line).

Both Ab130 and Ab109 were effective in attenuating dexamethasone-induced muscle atrophy. Both Ab130 and Ab109 prevented dexamethasone-induced weight loss and were effective at a dose as low as 1 mg/kg (FIG. 7A). Both Ab130 and Ab109 also attenuated the loss of lean mass, as measured by qNMR, and demonstrated superior efficacy in preserving lean mass than Ab2 (FIG. 7B). Specifically, the 10 mg/kg dose of Ab130 demonstrated superior efficacy in preserving lean muscle mass compared to the 10 mg/kg dose of Ab2; and Ab109 showed better efficacy of preserving lean muscle mass at both 3 mg/kg and 10 mg/kg compared to either 3 mg/kg or 10 mg/kg Ab2. Further, Ab109 preserved gastrocnemius muscle mass better at 1 mg/kg, 3 mg/kg, and 10 mg/kg doses than did Ab2 at 3 mg/kg (FIG. 7C); and Ab130 preserved lean muscle mass better at 3 mg/kg than Ab2 at either 3 mg/kg or 10 mg/kg. Similarly, Ab109 preserved quadricep muscle mass better at 1 mg/kg, 3 mg/kg, and 10 mg/kg doses than did Ab2 at 3 mg/kg or 10 mg/kg; and Ab130 preserved quadricep muscle mass better at 10 mg/kg than did Ab2 at 3 mg/kg (FIG. 7D).

In summary, Ab109 and Ab130 were both surprisingly more effective in preserving lean muscle mass, gastrocnemius muscle mass, and quadriceps muscle mass than Ab2 in an in vivo dexamethasone-induced muscle atrophy model.

Example 3. Antibodies that Inhibit Myostatin Activation Prevent Muscle Loss During Weight Loss Caloric restriction causes loss of both fat and lean mass; inhibiting myostatin maintains lean mass during weight loss. In this study, the GLP-1 analogue liraglutide, which induces weight loss, and the antibodies Ab130 and Ab109 were tested for their ability to improve body composition (e.g., reduce or prevent lean mass loss or increase muscle mass during weight loss). Changes in body composition were assessed by qNMR readout for fat mass and lean mass; gastrocnemius weight; and inguinal and perigonadal fat pad weight.

Ten-week-old male mice were fed formula D12492 ad lib, a high-calorie diet comprised of 60% fat, and remained on this diet throughout the study. At age 16 weeks the mice were dosed for four weeks with both antibody and liraglutide, as shown in Table 19. The antibodies were dosed weekly and liraglutide was dosed daily. Body composition and body weight were measured by qNMR prior to dosing, at 2 weeks, and at the end of the dosing period body weight. Gastrocnemius muscles were removed, and their weights were measured after the animals were terminated.

TABLE 19

GLP-1 analogue experimental design.

| Group | N | Antibody | Antibody Dose | GLP-1 Analogue | GLP-1 Analogue Dose |
|---|---|---|---|---|---|
| 1 | 8 | IgG | 20 mg/kg/week | vehicle | q.d. |
| 2 | 8 | Ab2 | 20 mg/kg/week | vehicle | q.d. |
| 3 | 8 | IgG | 20 mg/kg/week | liraglutide | 0.06 mg/kg q.d. |
| 4 | 8 | Ab130 | 20 mg/kg/week | liraglutide | 0.06 mg/kg q.d. |
| 5 | 8 | Ab130 | 10 mg/kg/week | liraglutide | 0.06 mg/kg q.d. |
| 6 | 8 | Ab130 | 3 mg/kg/week | liraglutide | 0.06 mg/kg q.d. |
| 7 | 8 | Ab130 | 1 mg/kg/week | liraglutide | 0.06 mg/kg q.d. |
| 8 | 8 | Ab109 | 20 mg/kg/week | liraglutide | 0.06 mg/kg q.d. |
| 9 | 8 | Ab109 | 10 mg/kg/week | liraglutide | 0.06 mg/kg q.d. |
| 10 | 8 | Ab109 | 3 mg/kg/week | liraglutide | 0.06 mg/kg q.d. |
| 11 | 8 | Ab109 | 1 mg/kg/week | liraglutide | 0.06 mg/kg q.d. |
| 12 | 8 | Ab2 | 20 mg/kg/week | liraglutide | 0.06 mg/kg q.d. |
| 13 | 8 | Ab2 | 10 mg/kg/week | liraglutide | 0.06 mg/kg q.d. |
| 14 | 8 | Ab2 | 3 mg/kg/week | liraglutide | 0.06 mg/kg q.d. |
| 15 | 8 | Ab2 | 1 mg/kg/week | liraglutide | 0.06 mg/kg q.d. |

Figure 11A:
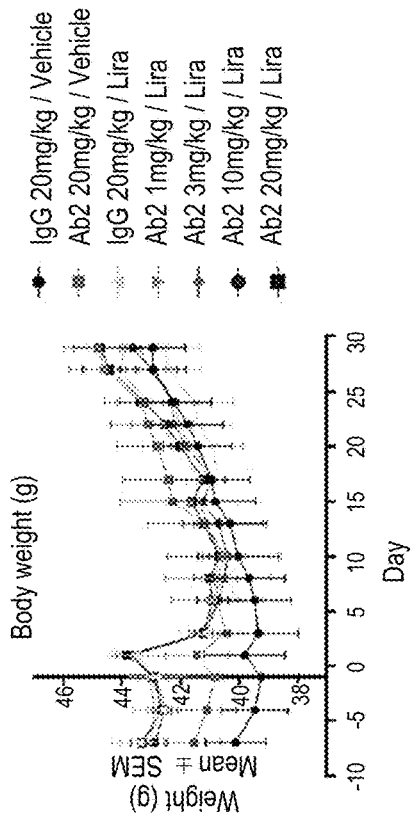
FIGS. 11A-H show in vivo effects in DIO mice treated with Ab2, Ab109, or Ab130 in conjunction with liraglutide.
Figure 11C:
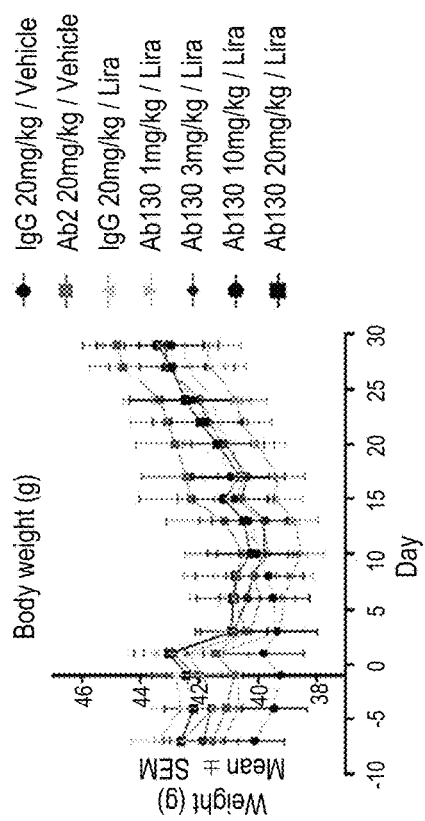
Figure 11B:
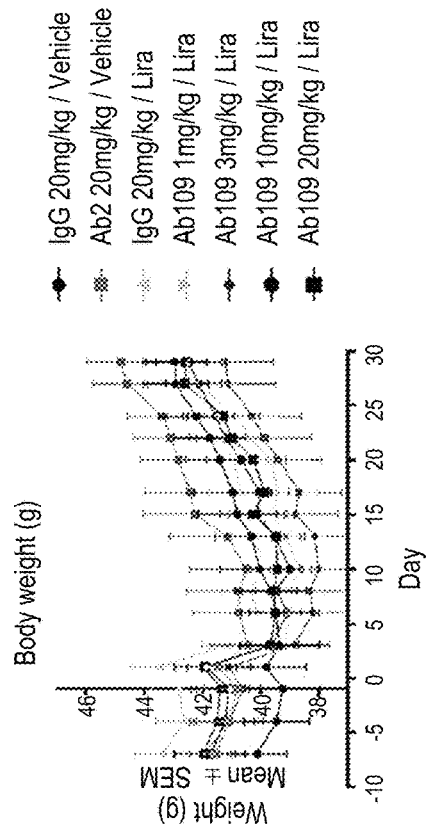

All animals on liraglutide initially lost body weight but began demonstrating a rebound weight gain after about two weeks, as they remained on the high fat diet. FIGS. 11A-C shows the effect of antibodies Ab109, Ab130, and the control antibody Ab2 on body weight gain, change in lean mass, change in gastrocnemius weight, and change in fat mass in animals on the high fat diet and treated with liraglutide.

As expected, liraglutide alone lowered the increase in body weight in the animals on the high fat diet. All animals lost body weight compared to the IgG control group. But surprisingly, animals treated with Ab2 gained more weight during the rebound stage and rebounded faster than those treated with Ab109 or with Ab130, as shown in FIGS. 11A-C. The animals treated with Ab109 or Ab130 lost more body weight compared to those treated with Ab2. FIG. 11A shows that animals treated with Ab2 initially lost body weight but rebounded and gained weight after about two weeks of treatment. FIG. 11B shows that Ab109 at concentrations of 1 mg/kg, 3 mg/kg, 10 mg/kg, and 20 mg/kg attenuated the increase in body weight compared to the Ig control in the presence of liraglutide. FIG. 11C shows that Ab130 at concentrations of 1 mg/kg, 3 mg/kg, and 10 mg/kg also attenuated the increase in body weight compared to liraglutide alone.

Figure 11D:
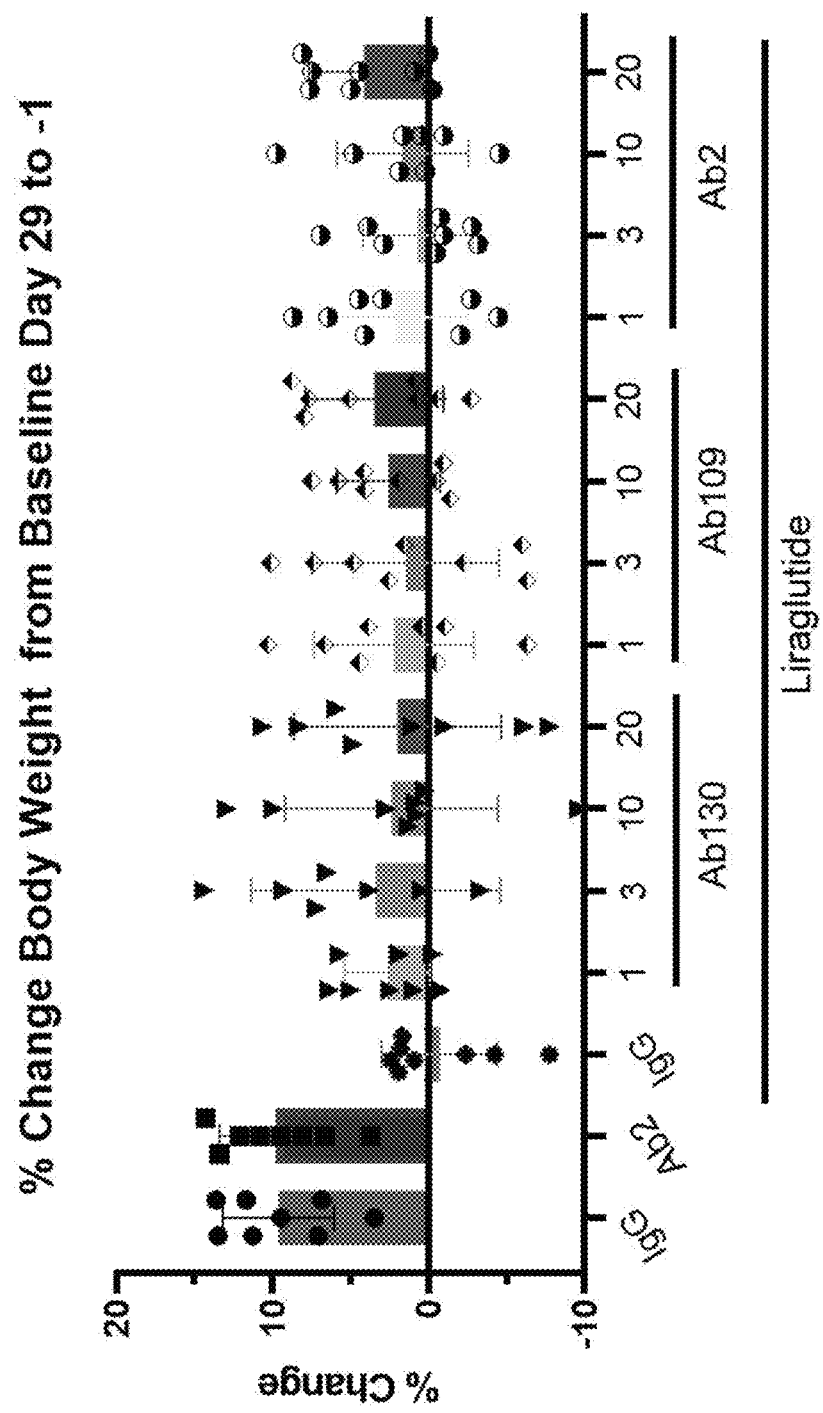

As shown in FIG. 11D, all animals treated with liraglutide and given an antibody of the disclosure lost body weight compared to animals who were not treated with liraglutide. The animals treated with Ab109 or Ab130 lost slightly less weight than those treated with liraglutide and an IgG control. This was accounted for by gains in lean mass by the animals treated with the antibodies that inhibit myostatin activation.

Figure 11E:
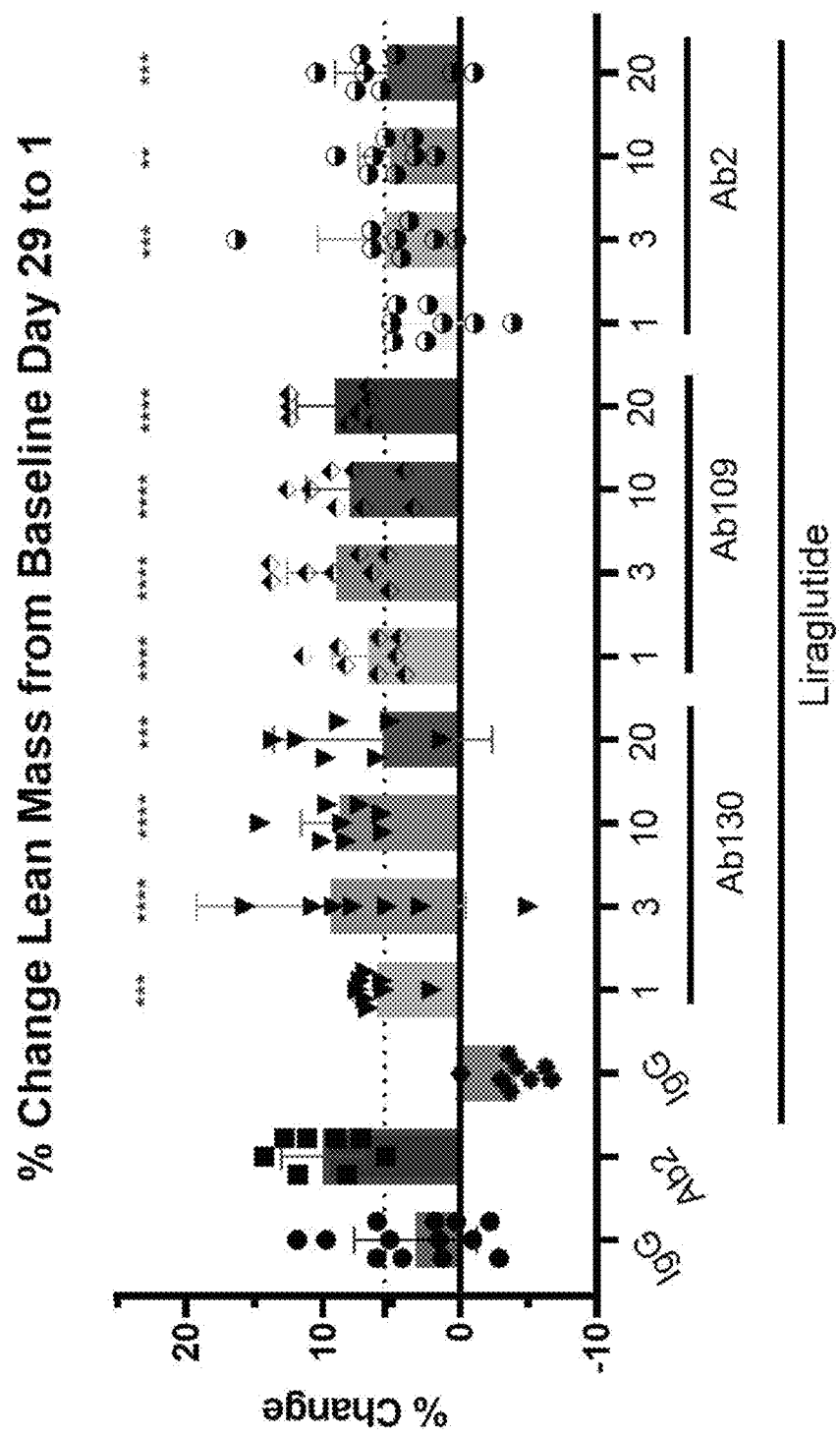

As shown in FIG. 11E, animals treated with liraglutide alone lost 4% of their lean mass. However, lean mass increased in the animals treated with Ab109, Ab130, or Ab2. Ab109 and Ab130 achieved greater increases in lean mass compared to Ab2. Ab109 and Ab130 were also more effective in increasing lean mass at lower doses than Ab2. All four doses of Ab109 increased lean mass compared to equivalent doses of Ab2. Doses of 1, 3, and 10 mg/kg Ab130 increased lean mass compared to Ab2.

Figure 11F:
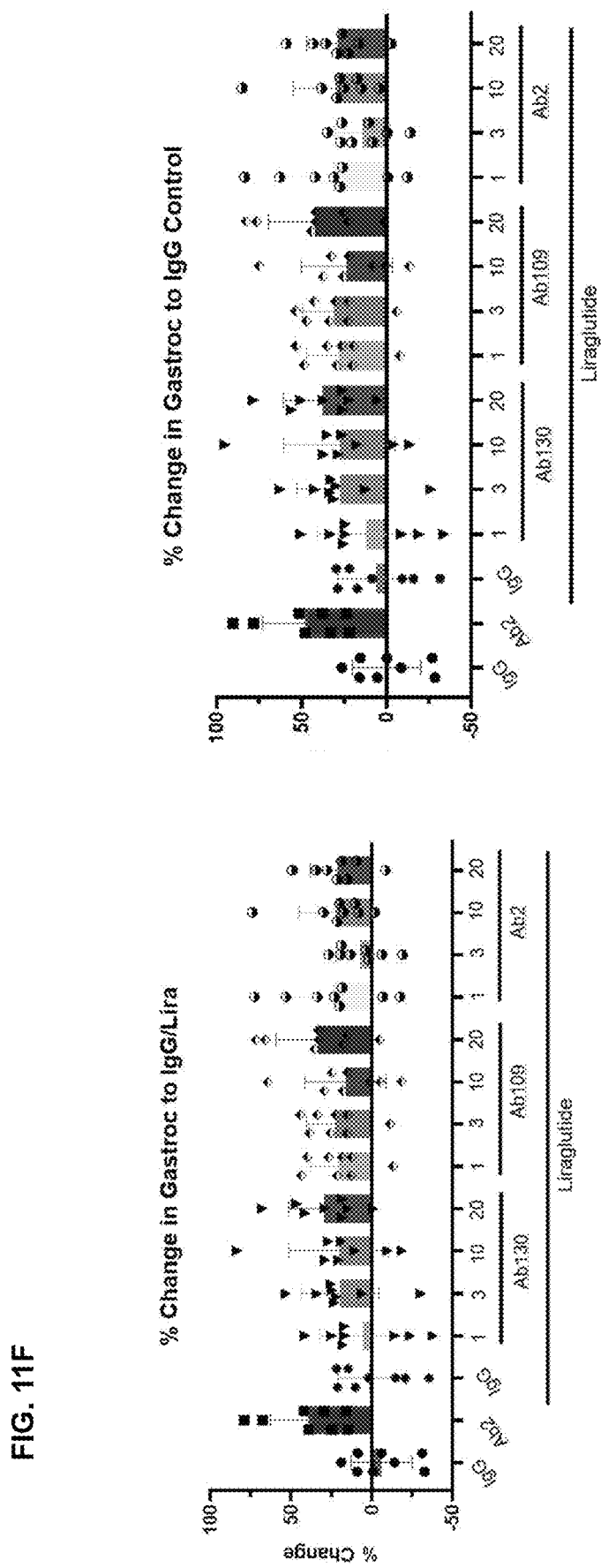

FIG. 11F shows the gains in gastrocnemius muscle caused by treatment with Ab109 and Ab130, further demonstrating lean muscle mass gain. FIG. 11F, left panel, demonstrates that all three antibodies increase gastrocnemius muscle mass compared to liraglutide alone. At a dose of 20 mg/kg, both Ab109 and Ab130 were more effective at increasing gastrocnemius mass than Ab2. FIG. 11F, right panel, demonstrates that all three antibodies increased gastrocnemius muscle mass compared to an IgG control. At a dose of 20 mg/kg, both Ab109 and Ab130 were more effective at increasing gastrocnemius mass than Ab2.

Figure 11G:
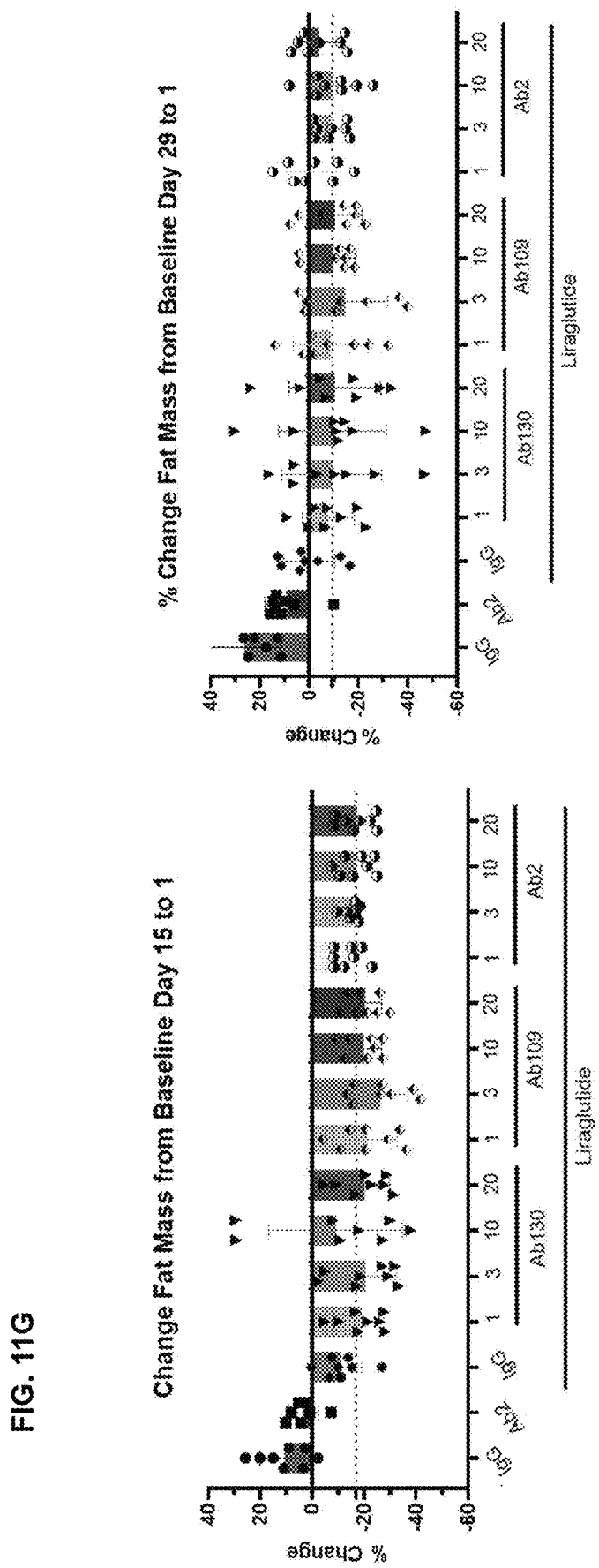

Animals treated with liraglutide initially lost fat mass, but the amount of fat mass began to rebound at about two weeks, as they remained on the high fat diet. FIG. 11G, left panel, shows the loss of fat mass during the first 15 days of treatment compared to FIG. 11G, right panel, which shows the loss of fat mass at 29 days, i.e., the end of the study. All three myostatin inhibitor antibodies decreased fat mass compared to liraglutide alone; equivalent doses of both Ab109 and Ab130 decreased fat mass to a greater extent than Ab2.

Despite the rebound in fat mass after around day 14, Ab 109 and Ab130 in combination with liraglutide reduced the fat mass in the subcutaneous inguinal fat pad and reduced the fat mass in the visceral perigonadal fat pad to a greater extent than the loss of the fat mass in the subcutaneous inguinal fat pad.

Figure 11H:
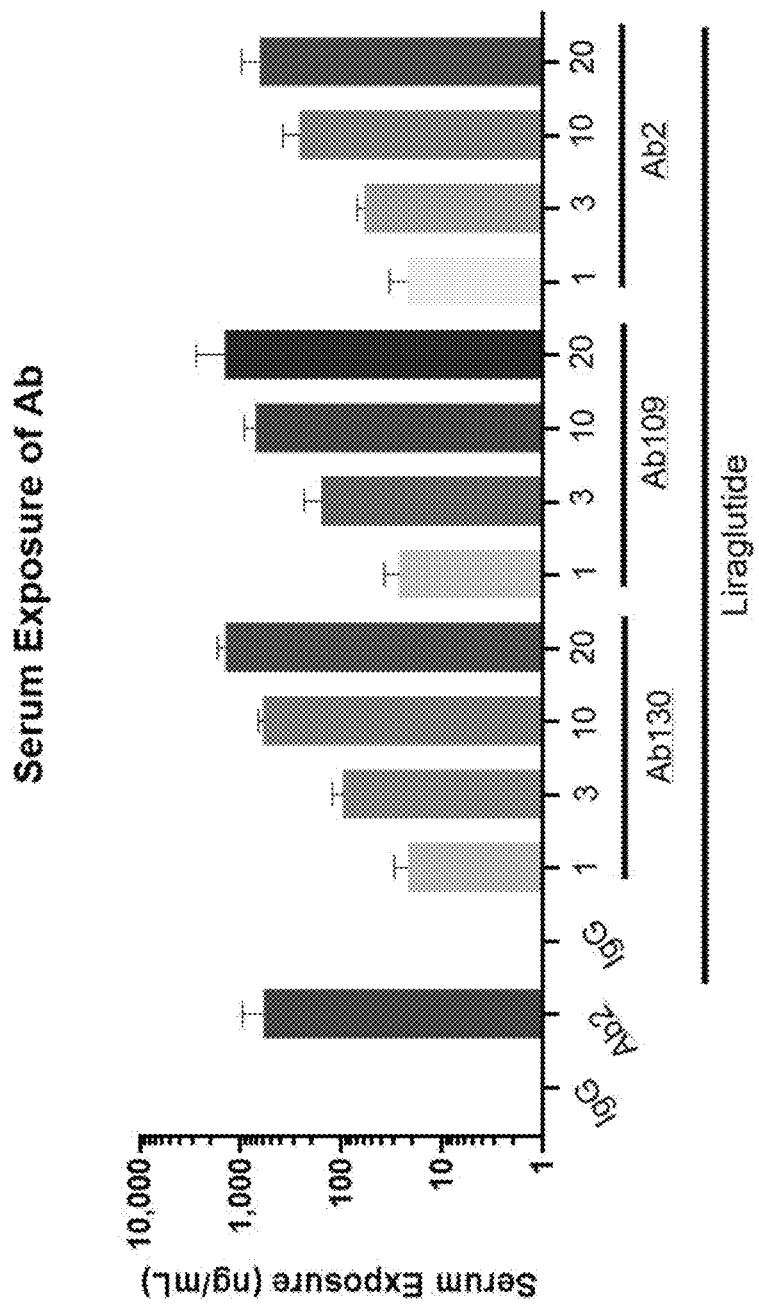

Table 20 and FIG. 11H show that Ab109 and Ab130 have higher exposure to their pro/latent myostatin ligand than Ab2. Pro myostatin was bound to a Costar plate at a concentration of 2 µg/ml then incubated in blocking solution. The antibody of interest was then added and its ability to bind pro myostatin was detected by horseradish peroxidase labeled anti IgG and a tetramethylbenzidine chromogenic substrate. Antibody exposure was measured as binding to the pro myostatin.

TABLE 20

Terminal antibody exposure.

| Group | Antibody | Antibody Dose | GLP-1 Analogue | GLP-1 Analogue Dose | Exposure (ng/ml) | Stnd. Dev. | % Coeff. Var. |
|---|---|---|---|---|---|---|---|
| 1 | IgG | 20 mg/kg/week | Vehicle | q.d. | BLOQ | n.a. | n.a. |
| 2 | Ab2 | 20 mg/kg/week | Vehicle | q.d. | 592.8 | 367.3 | 62 |

TABLE 20-continued

Terminal antibody exposure.

| Group | Antibody | Antibody Dose | GLP-1 Analogue | GLP-1 Analogue Dose | Exposure (ng/ml) | Stnd. Dev. | % Coeff. Var. |
|---|---|---|---|---|---|---|---|
| 3 | IgG | 20 mg/kg/week | Liraglutide | 0.06 mg/kg q.d. | BLOQ | n.a. | n.a. |
| 4 | Ab130 | 1 mg/kg/week | Liraglutide | 0.06 mg/kg q.d. | 21.6 | 8.3 | 39 |
| 5 | Ab130 | 3 mg/kg/week | Liraglutide | 0.06 mg/kg q.d. | 96.7 | 26.4 | 27 |
| 6 | Ab130 | 10 mg/kg/week | Liraglutide | 0.06 mg/kg q.d. | 599.0 | 70.9 | 12 |
| 7 | Ab130 | 20 mg/kg/week | Liraglutide | 0.06 mg/kg q.d. | 1418.2 | 274.6 | 19 |
| 8 | Ab109 | 1 mg/kg/week | Liraglutide | 0.06 mg/kg q.d. | 26.9 | 10.4 | 39 |
| 9 | Ab109 | 3 mg/kg/week | Liraglutide | 0.06 mg/kg q.d. | 159.2 | 76.0 | 48 |
| 10 | Ab109 | 10 mg/kg/week | Liraglutide | 0.06 mg/kg q.d. | 709.2 | 210.5 | 30 |
| 11 | Ab109 | 20 mg/kg/week | Liraglutide | 0.06 mg/kg q.d. | 1435.5 | 1323.2 | 92 |
| 12 | Ab2 | 1 mg/kg/week | Liraglutide | 0.06 mg/kg q.d. | 22.4 | 10.9 | 49 |
| 13 | Ab2 | 3 mg/kg/week | Liraglutide | 0.06 mg/kg q.d. | 58.7 | 10.7 | 18 |
| 14 | Ab2 | 10 mg/kg/week | Liraglutide | 0.06 mg/kg q.d. | 261.6 | 120.0 | 46 |
| 15 | Ab2 | 20 mg/kg/week | Liraglutide | 0.06 mg/kg q.d. | 650.6 | 332.6 | 51 |

Ab109 and Ab130 also reduced total serum myostatin concentrations compared to Ab2, as shown in Table 21. Levels of the antibodies' exposure to myostatin in the serum was measured by assaying for total myostatin in the serum (Lakshman (2009) Cellular Endocrinol 302:26). Terminal bleed serum samples were acidified at low pH (~2.5) to dissociate the antibody from its ligand, thus converting all forms of myostatin to the active growth factor. The samples were then neutralized and assayed for mature growth factor.

TABLE 21

Total serum myostatin exposure.

| Group | Antibody | Antibody Dose | GLP-1 Analogue | GLP-1 Analogue Dose | Myostatin (ng/ml) | Stnd. Dev. | % Coeff. Var. |
|---|---|---|---|---|---|---|---|
| 1 | IgG | 20 mg/kg/week | Vehicle | q.d. | 14.3 | 4.7 | 33 |
| 2 | Ab2 | 20 mg/kg/week | Vehicle | q.d. | 812.3 | 179.6 | 22 |
| 3 | IgG | 20 mg/kg/week | Liraglutide | 0.06 mg/kg q.d. | 10.7 | 4.9 | 46 |
| 4 | Ab130 | 1 mg/kg/week | Liraglutide | 0.06 mg/kg q.d. | 52.9 | 11.6 | 22 |
| 5 | Ab130 | 3 mg/kg/week | Liraglutide | 0.06 mg/kg q.d. | 41.5 | 15.4 | 37 |
| 6 | Ab130 | 10 mg/kg/week | Liraglutide | 0.06 mg/kg q.d. | 41.0 | 16.0 | 39 |
| 7 | Ab130 | 20 mg/kg/week | Liraglutide | 0.06 mg/kg q.d. | 42.4 | 8.9 | 21 |
| 8 | Ab109 | 1 mg/kg/week | Liraglutide | 0.06 mg/kg q.d. | 12.2 | 6.3 | 52 |
| 9 | Ab109 | 3 mg/kg/week | Liraglutide | 0.06 mg/kg q.d. | 4.7 | 2.6 | 55 |
| 10 | Ab109 | 10 mg/kg/week | Liraglutide | 0.06 mg/kg q.d. | 5.6 | 5.4 | 96 |
| 11 | Ab109 | 20 mg/kg/week | Liraglutide | 0.06 mg/kg q.d. | 4.5 | 3.4 | 76 |
| 12 | Ab2 | 1 mg/kg/week | Liraglutide | 0.06 mg/kg q.d. | 302.5 | 82.7 | 27 |
| 13 | Ab2 | 3 mg/kg/week | Liraglutide | 0.06 mg/kg q.d. | 884.2 | 410.5 | 46 |
| 14 | Ab2 | 10 mg/kg/week | Liraglutide | 0.06 mg/kg q.d. | 806.3 | 187.2 | 23 |
| 15 | Ab2 | 20 mg/kg/week | Liraglutide | 0.06 mg/kg q.d. | 943.9 | 343.5 | 36 |

Body weight and food intake were monitored three times per week throughout the study. On days 7, 35, 49, and 63, body composition was determined by qNMR, and glucose, ketones, and insulin were measured. At the end of the study on day 63, body composition was determined by qNMR; glucose, ketones, and insulin were measured, gastrocnemius muscle, whole liver, epididymal, and subcutaneous adipose tissue was collected and weighed.

Example 4: Antibodies that Inhibit Myostatin Activation Improve Body Composition in Animals Treated with Metformin Metformin treatment is herein shown to have a synergistic effect on improving body composition when combined with a myostatin activation inhibiting antibody of the disclosure.

Male C57/BL6 mice were fed a 60% high fat diet beginning at six weeks of age. At nineteen weeks of age (day 0), the mice were switched to a 45% high fat diet for 63 days. On day 35, the animals were randomized to receive either control IgG or Ab109 for the remainder of the study. These mice were further divided into groups that received either 50 mg/kg of metformin or no metformin (Table 22a). The 50 mg/kg metformin dose was selected based on a comparable dose given to human diabetic patients and is not expected to induce weight loss on its own.

TABLE 22a

Metformin and anti-myostatin Abs induce loss of fat mass in animals on a high fat diet.

| Group | Diet | Metformin | Antibody |
|---|---|---|---|
| 1 | 60% High Fat | none | IgG |
| 2 | 60% High Fat | none | Ab109 |
| 3 | 60% High Fat | 50 mg/kg | IgG |
| 4 | 60% High Fat | 50 mg/kg | Ab109 |
| 5 | 45% High Fat | None | IgG |
| 6 | 45% High Fat | None | Ab109 |
| 7 | 45% High Fat | 50 mg/kg | IgG |
| 8 | 45% High Fat | 50 mg/kg | Ab109 |

Figure 12A:
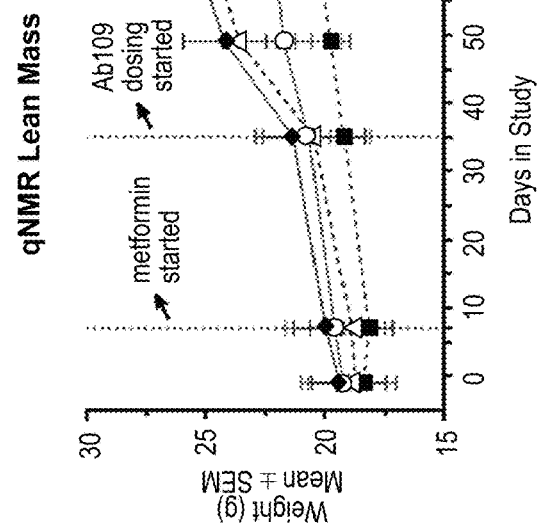
FIGS. 12A-B show in vivo effects of combination treatments of Ab 109 and metformin in mice fed with a high fat diet.

As shown in FIG. 12A, animals that were fed a 60% high fat diet and then switched to a 45% high fat diet continued to gain fat mass throughout the study, with the exception of the animals that received both metformin and Ab109. The combination of metformin and Ab109 stopped the fat mass gain, even while the animals continued to eat the 45% high fat diet (normal mouse chow is approximately 6%-12% fat). Neither metformin alone nor Ab109 alone showed this effect in this model, indicating that the effects of Ab109 and metformin are synergistic.

Figure 12B:
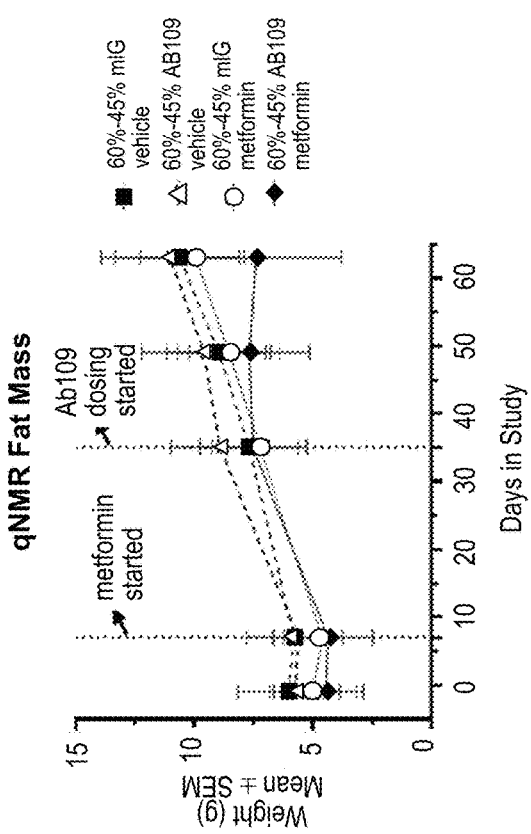

As shown in FIG. 12B, animals that were fed a 60% high fat diet and then switched to a 45% high fat diet showed a slight increase in lean mass throughout the study regardless of metformin treatment. These animals also gained weight throughout the study. Animals that received Ab109 gained more lean muscle mass regardless of whether they received metformin. This higher gain in lean muscle mass was observed upon starting Ab109 dosing.

Male C57/BL6 mice (n=8/group) were fed a 60% HFD until week 18, at which time they are switched to a 45% HFD for 7 days. At day 7, animals in group 3-6 were treated with 50 mg/kg/day metformin, given orally throughout the remainder of the study. At day 35 animals were treated with control human IgG (hIgG) or test antibodies at the doses and times indicated in TABLE 22b.

Body weight was measured three times per week; lean mass and fat mass were measured by qNMR on days 7, 35, 49, 63, and 77; serum glucose was also measured on days 7, 35, 49, 63, and 77; serum insulin was measured on days 49, 63, and 77. A glucose tolerance test (GTT) and an insulin tolerance test (ITT) was administered between day 56 and day 63.

TABLE 22b

Metformin and anti-myostatin Abs induce loss of fat mass in animals on a high fat diet.

| Group | Diet | N | Metformin | Antibody | Antibody Dose |
|---|---|---|---|---|---|
| 1 | 45% high fat: day 0-77 | 10 | 0 | mIgG | 10 mg/kg |
| 2 | 45% high fat: day 0-77 | 10 | 0 | Ab109 | 10 mg/kg |
| 3 | 45% high fat: day 0-77 | 10 | 50 mg/kg | mIgG | 10 mg/kg |
| 4 | 45% high fat: day 0-77 | 10 | 50 mg/kg | Ab109 | 10 mg/kg |
| 5 | 45% high fat: day 0-77 | 10 | 50 mg/kg | Ab109 | 3 mg/kg |
| 6 | 45% high fat: day 0-77 | 10 | 50 mg/kg | Ab141 | 10 mg/kg |

Example 5: Effect of Antibodies that Inhibit Myostatin Activation in Combination with Semaglutide in a Diet-Induced Obesity Model A study was conducted to assess the effect of myostatin antibodies Ab109 and Ab141 in combination with semaglutide in mice fed diets of varying fat content. Male C57/BL6 mice were a high-fat diet containing 60% fat then switched to a diet containing 45% fat. At 20 weeks of age, the mice were concurrently dosed with 0.040 mg/kg semaglutide daily and a myostatin inhibitor (Ab109 or Ab141) once weekly for three weeks (Table 23). Body weight and body composition determined by qNMR were recorded at days 7, 14, and 21 after dosing. Gastrocnemius weight, inguinal, and perigonadal fat pad weights were recorded at the end of the study. Liver and terminal blood were collected to measure the levels of glucose and insulin.

TABLE 23

Weight gain upon resuming a high fat diet.

| Group | Antibody | Antibody Dose | GLP-1 Receptor Agonist | GLP-1 Receptor Agonist Dose |
|---|---|---|---|---|
| 1 | Control hIgG | 3 mg/kg/week | Vehicle | 0 |
| 2 | Ab109 | 3 mg/kg/week | Vehicle | 0 |
| 3 | Ab141 | 3 mg/kg/week | Vehicle | 0 |
| 4 | Control hIgG | 3 mg/kg/week | Semaglutide | 0.040 mg/kg/day |
| 5 | Ab109 | 0.1 mg/kg/week | Semaglutide | 0.040 mg/kg/day |
| 6 | Ab109 | 0.3 mg/kg/week | Semaglutide | 0.040 mg/kg/day |
| 7 | Ab109 | 1.0 mg/kg/week | Semaglutide | 0.040 mg/kg/day |
| 8 | Ab109 | 3.0 mg/kg/week | Semaglutide | 0.040 mg/kg/day |
| 9 | Ab141 | 0.1 mg/kg/week | Semaglutide | 0.040 mg/kg/day |
| 10 | Ab141 | 0.3 mg/kg/week | Semaglutide | 0.040 mg/kg/day |
| 11 | Ab141 | 1.0 mg/kg/week | Semaglutide | 0.040 mg/kg/day |
| 12 | Ab141 | 3 mg/kg/week | Semaglutide | 0.040 mg/kg/day |

Figure 13B:
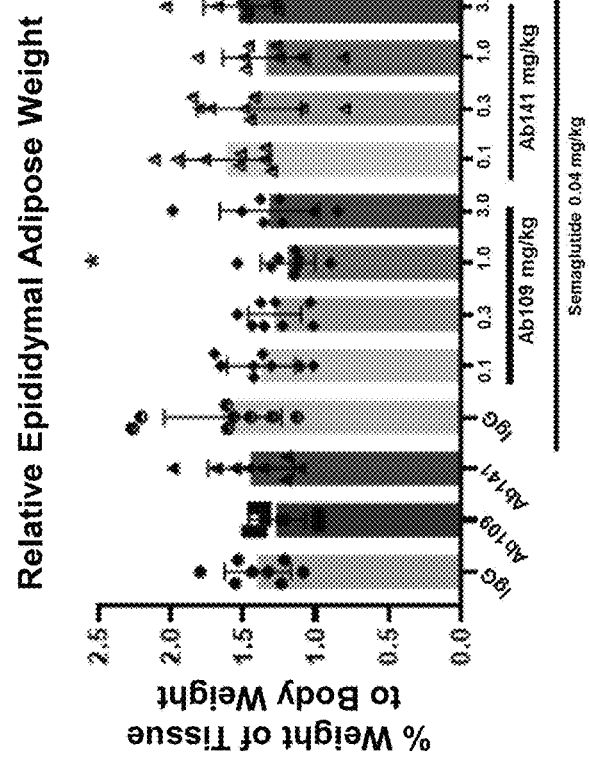
FIGS. 13A-B show in vivo effects of semaglutide treatment in combination with IgG control, Ab109, or Ab141 in mice fed with a high fat diet.
Figure 13A:
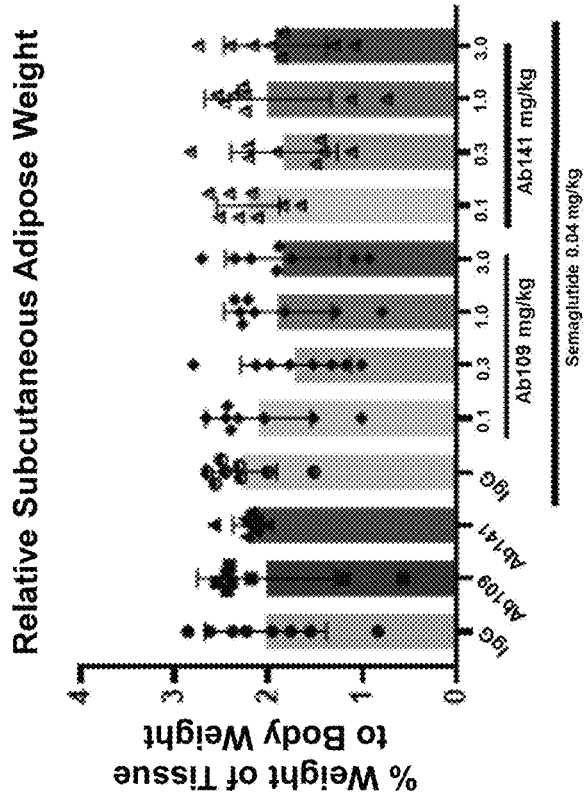

As shown in FIGS. 13A and 13B, the addition of semaglutide to treatment with Ab109 or Ab141 increased fat mass loss as compared to Ab109 or Ab141 alone.

Example 6: Effect of Antibodies that Inhibit Myostatin Activation in Combination with Semaglutide in a Diet-Induced Obesity Model Male C57/BL6 male mice (n=8/group) were either fed regular mouse chow (Group 1) or placed on a 60% high fat diet at six weeks of age and maintained on the 60% high fat diet until 21 weeks of age (Groups 2-8), at which time the study began (day 0). On day 0, animals in groups 2-8 were switched to a 45% high fat diet and maintained on the 45% high fat diet until the animals were terminated. On day 7, the animals were randomized and dosed subcutaneously with 0.04 mg/kg semaglutide once per week and dosed with either Ab109 or control human immunoglobulin (hIgG) as shown in Table 24. Body weight was measured three times per week and qNMR measurements of lean mass and fat mass were obtained on the days set forth.

TABLE 24

Semaglutide and myostatin inhibitor dosing.

| Group | Diet | Semaglutide | Antibody | qNMR | Termination |
|---|---|---|---|---|---|
| 1 | Chow | 0 | hIgG | Day 7, 21, 35, 49, 63 | Day 63 |
| 2 | 60%/45% high fat | 0 | hIgG | Day 7, 21, 35, 49, 63 | Day 63 |
| 3 | 60%/45% high fat | 0.04 mg/kg day 7-14 | hIgG | Day 7, 21 | Day 21 |
| 4 | 60%/45% high fat | 0.04 mg/kg day 7-14 | Ab109 | Day 7, 21 | Day 21 |
| 5 | 60%/45% high fat | 0.04 mg/kg day 7-35 (regain arm) | hIgG | Day 7, 21, 35, 49, 63 | Day 63 |
| 6 | 60%/45% high fat | 0.04 mg/kg day 7-35 (regain arm) | Ab109 | Day 7, 21, 35, 49, 63 | Day 63 |
| 7 | 60%/45% high fat | 0.04 mg/kg day 7-63 | hIgG | Day 7, 21, 35, 49, 63 | Day 63 |
| 8 | 60%/45% high fat | 0.04 mg/kg day 7-63 | Ab109 | Day 7, 21, 35, 49, 63 | Day 63 |

Animals in groups 3 and 4 were dosed with semaglutide weekly for 14 days, then terminated. Animals in groups 5 and 6 (weight regain groups), were treated with semaglutide for 35 days, then the semaglutide treatment was ended while the myostatin activation inhibiting antibody treatment continued until the animals were terminated on day 63. The animals in Groups 7 and 8 were treated with semaglutide for 63 days, i.e., they remained on semaglutide until the study terminated on day 63.

At termination, left and right gastrocnemius muscles were removed and frozen; the liver was weighed, one lobe was fixed, and the remainder was frozen; epididymal adipose tissue was removed and weighed; subcutaneous adipose tissue was removed and weighed; and a terminal serum bleed was obtained.

Figure 14A:
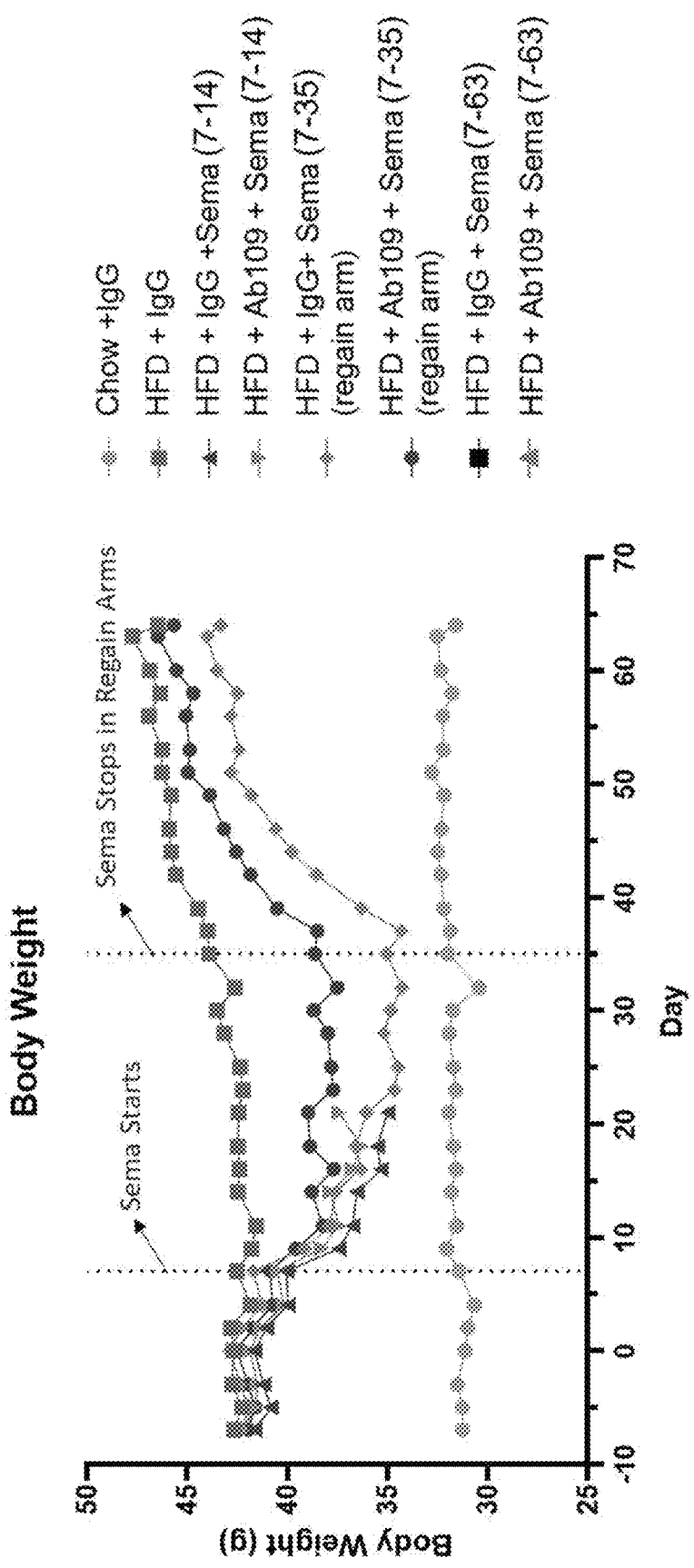

As expected, the animals fed the high fat diet weighed more than the animals fed standard chow. Also as expected, the animals that were fed the high fat diet and received semaglutide lost weight. The weight loss continued for about 20 days and then plateaued. The animals in groups 7 and 8, which remained on semaglutide, did not demonstrate an increase in body weight, despite an increase in lean mass. The animals in groups 5 and 6 (weight regain arm), which received semaglutide for four weeks and continued to eat a high fat diet for an additional four weeks without semaglutide, increased their body weight. These animals regained weight at the same rate whether they were treated with hIgG or Ab109 (FIG. 14A).

The animals that received semaglutide and hIgG throughout the duration of the study lost about 4% of their lean mass while on semaglutide. When semaglutide treatment was stopped, the mice began to regain lean mass. At the end of the study, the mice demonstrated a net 2.5% loss of their lean mass. In contrast, mice that received semaglutide and Ab109 continued to increase their lean mass throughout the duration of the study. That is, Ab109 treatment resulted in an increase in lean mass during semaglutide treatment and the increase in lean mass continued after withdrawal of semaglutide treatment.

Figure 14B:
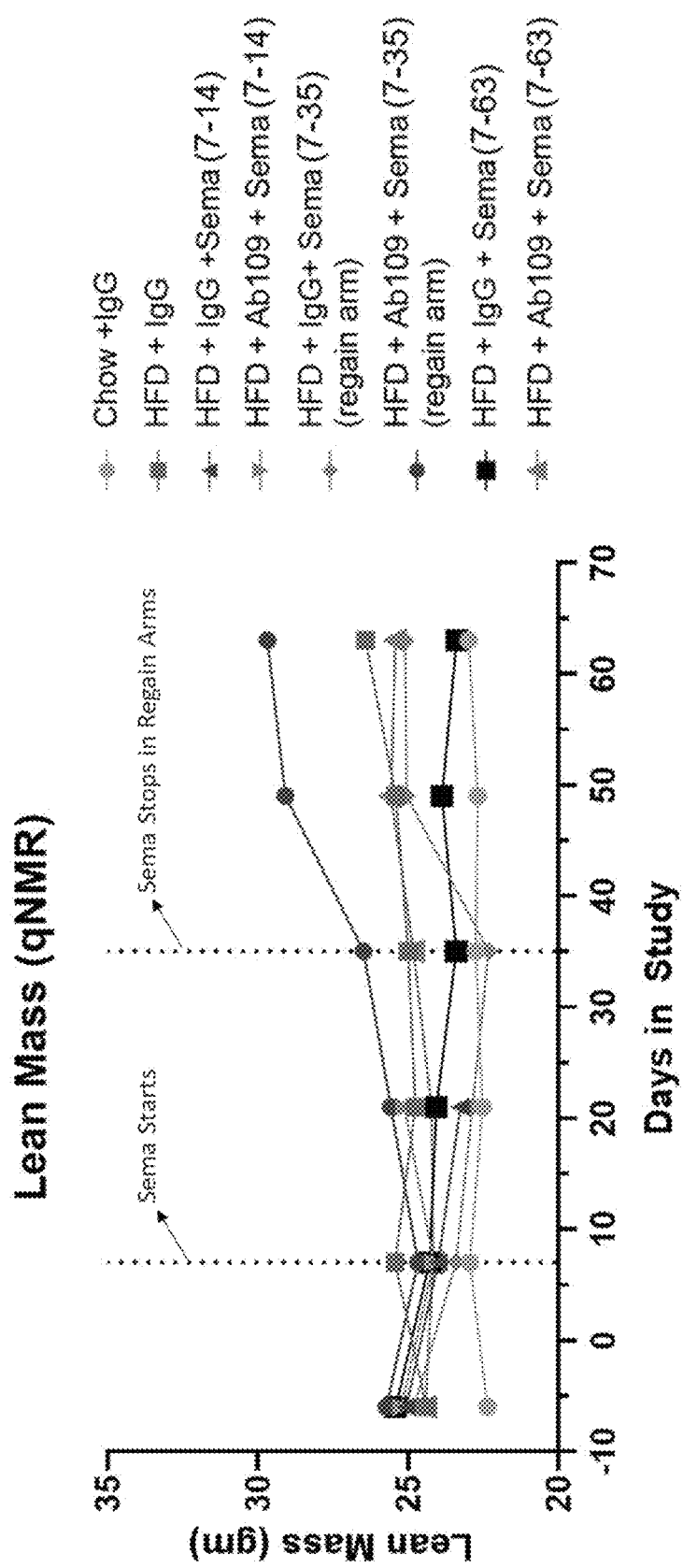

FIG. 14B shows the change in lean mass in the animals maintained on semaglutide for the duration of the study and in the animals where semaglutide treatment was withdrawn after four weeks of treatment. Animals maintained on semaglutide for the duration of the study maintained their lean mass. Animals that were treated with Ab109 and semaglutide for the entire duration of the study (group 8) had more lean mass than the animals treated with hIgG and semaglutide (group 7). In the "weight regain" groups 5 and 6, the animals treated with hIgG gained lean mass and gained body weight, but the animals treated with Ab109 gained more lean mass than those treated with hIgG after semaglutide was withdrawn.

Figure 14C:
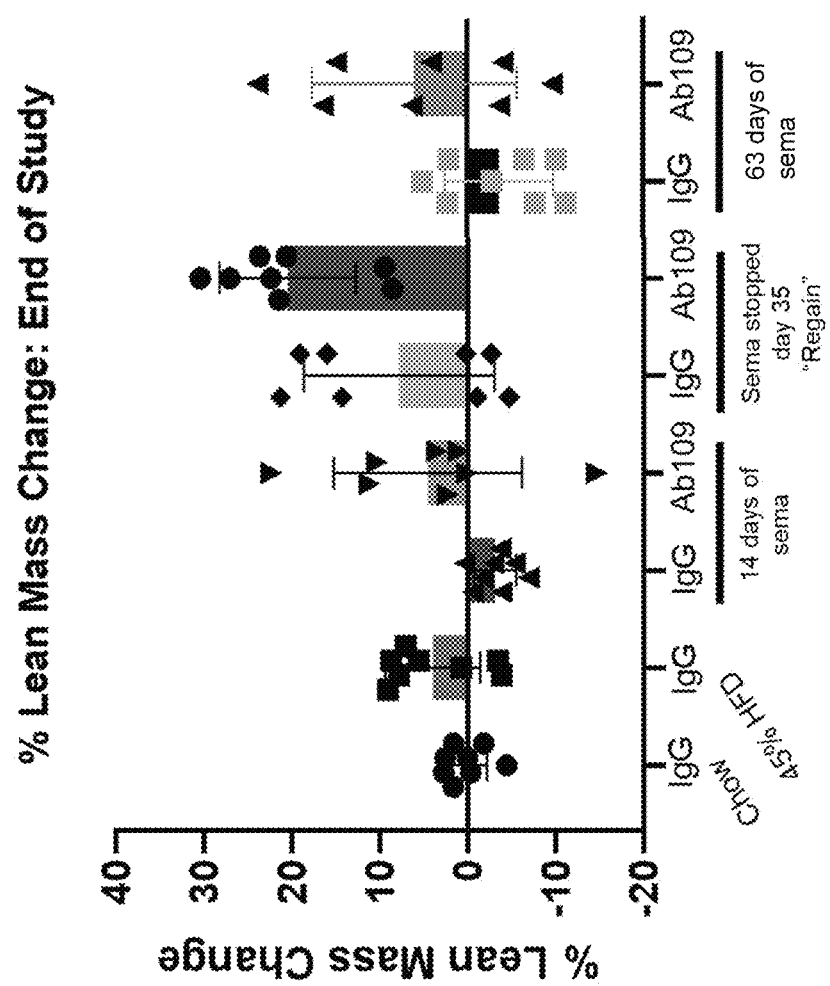

FIG. 14C shows the percent lean mass change in animals who completed the study to day 63. The bar graph shows that animals in groups 1 and 2 maintained their percentage of lean mass. Animals in group 3, which had only received semaglutide with hIgG control, had decreased lean mass, whereas animals in group 4, which were treated with Ab109, had increased lean mass. Animals in group 6 more than doubled their increase in percentage of lean mass compared to animals in group 5. Animals in group 8 also had increased percentage of lean mass as compared to animals in group 7. These data consistently show that animals treated with Ab109 were better at maintaining lean mass during weight loss and, in some cases, gained lean mass despite weight loss. The observed effect of Ab109 at maintaining or increasing lean mass was consistently superior to the effect observed with semaglutide treatment alone.

Figure 14D:
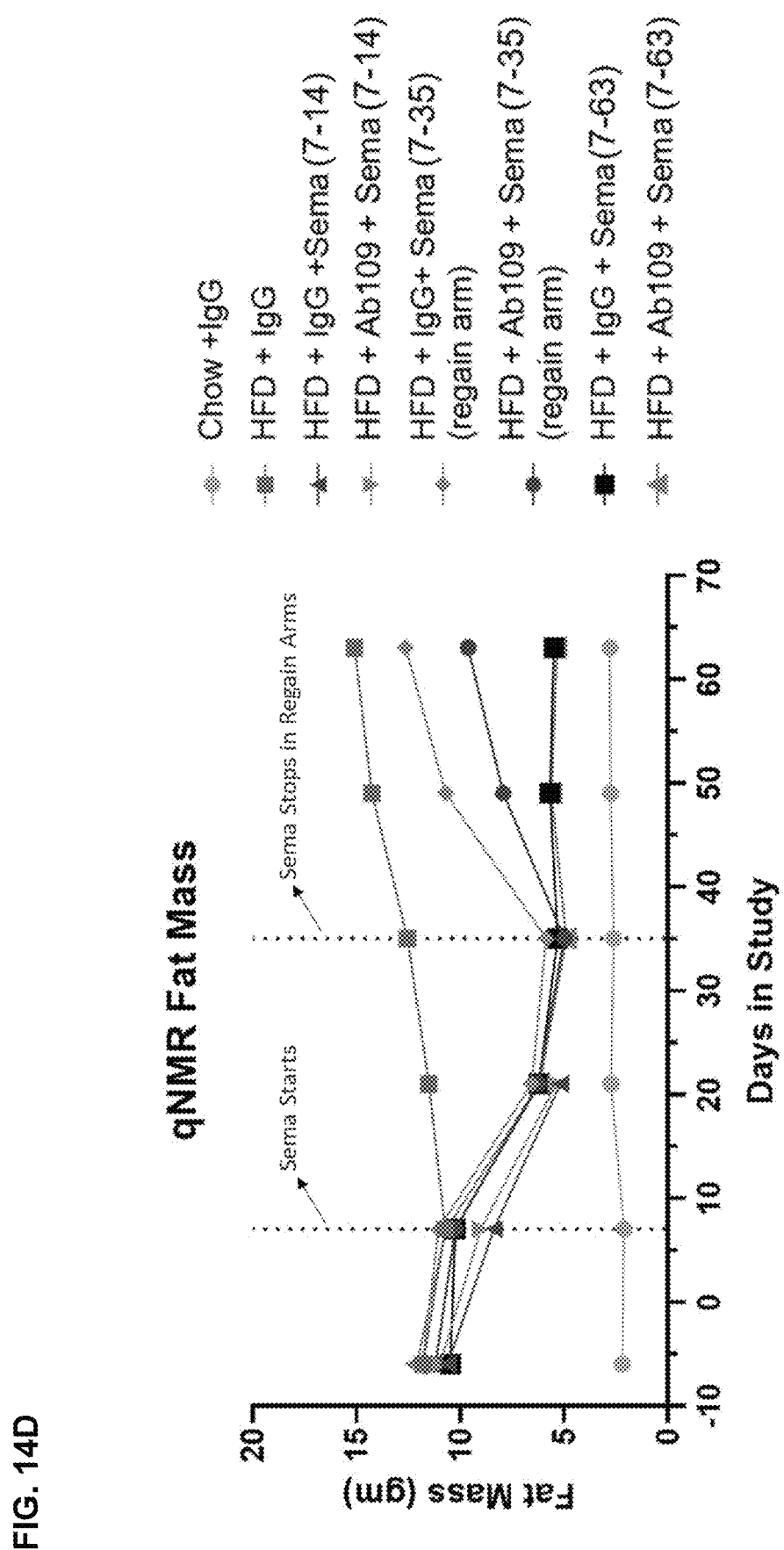

As expected, semaglutide induced fat mass loss in the animals, and the observed fat mass loss plateaued after about 35 days. When semaglutide was withdrawn, the animals treated with Ab109 regained less fat mass and regained it at a slower rate than those treated with control IgG (FIG. 14D).

The tissue weights of the gastrocnemius muscle and the inguinal and epididymal fat pads correspond to and corroborate the lean mass and fat mass qNMR measurements shown above.

Figure 14G:
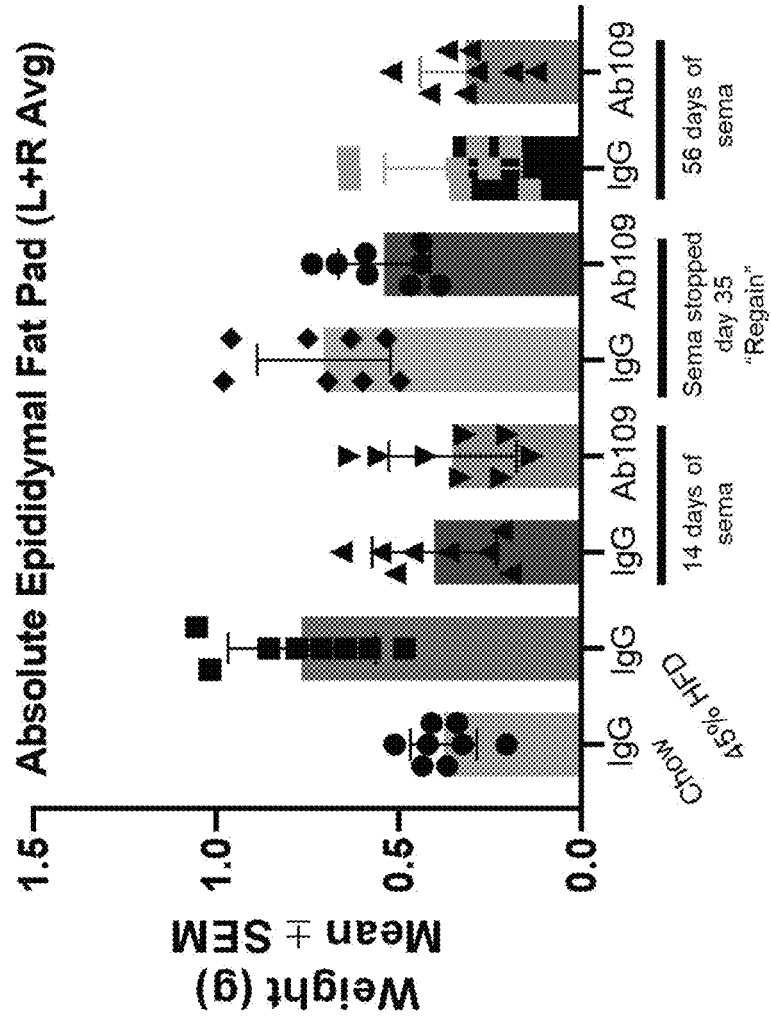

As shown in FIGS. 14A, 14E, and 14G, body weight and the gastrocnemius weight (lean muscle) were both increased in animals fed a high fat diet (group 2). After 14 days of semaglutide treatment, gastrocnemius weight decreased in the control animals (group 3) whereas Ab109 preserved the gastrocnemius muscle weight (group 4). A similar result was observed in animals treated with semaglutide for 35 days (groups 5 and 6), where the control animals (group 5) had decreased gastrocnemius weight as compared to Ab109-treated animals (group 6), which had higher gastrocnemius muscle weight. When the animals were continuously treated for 63 days with semaglutide in combination with a control antibody (group 7) or Ab109 (group 8), the effect of myostatin inhibition by Ab109 on maintaining lean mass was observed throughout the treatment period (FIG. 14E).

Figure 14H:
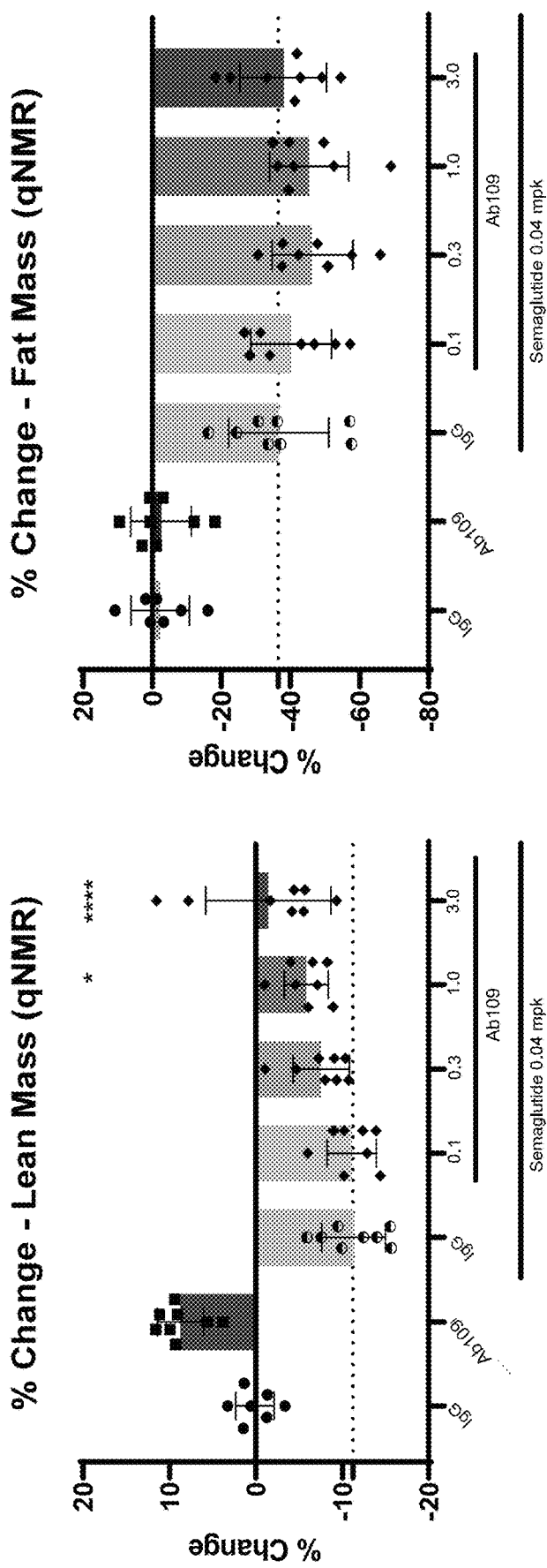
Figure 14I:
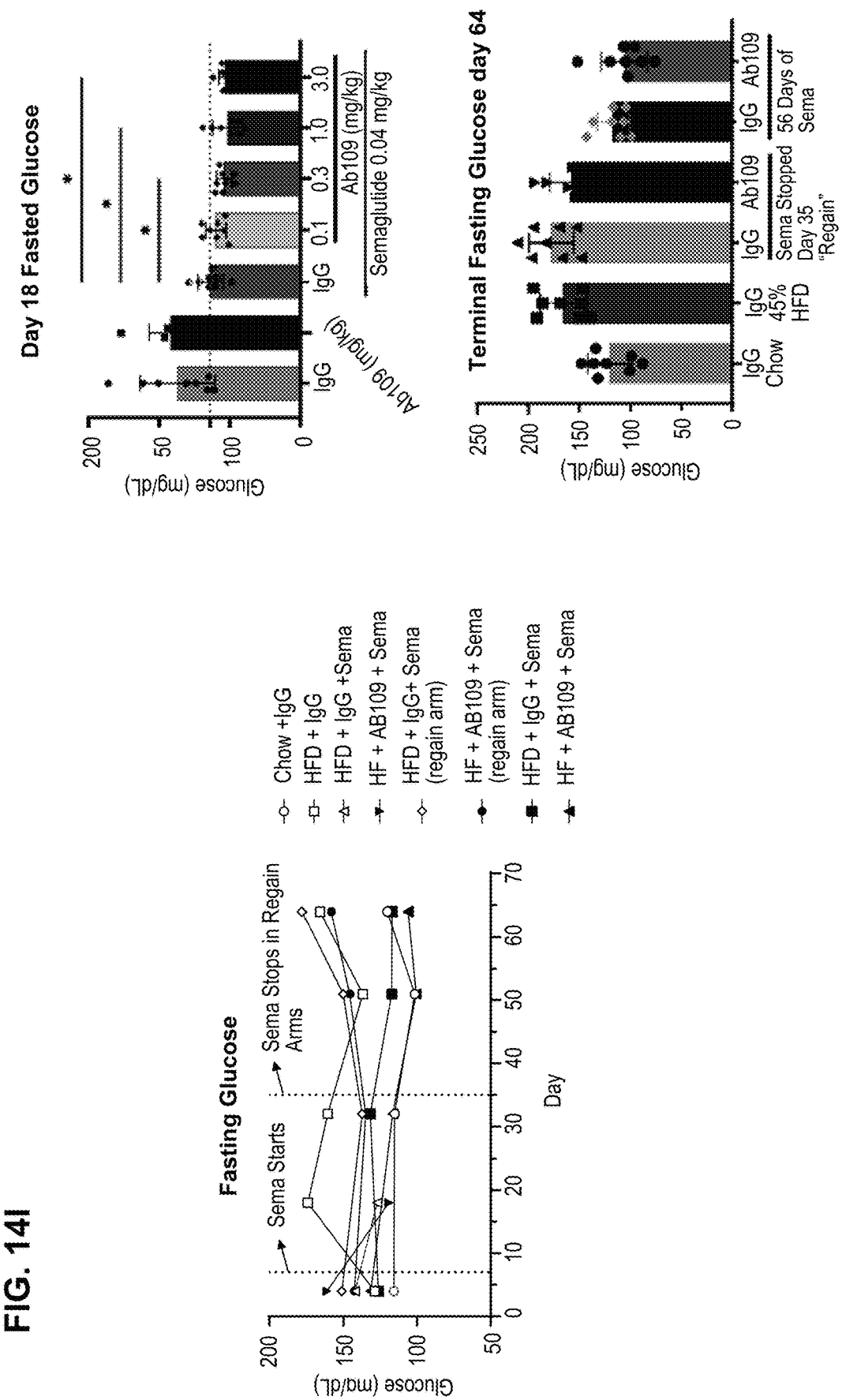

As shown in FIGS. 14A, 14F and 14G, the animals regained body weight and fat mass when semaglutide was withdrawn. FIG. 14F shows that there were no changes in the inguinal fat pads in groups 3, 4, 7, and 8. Only in groups 5 and 6, when semaglutide was stopped and antibody treatment was continued, was the inguinal fat reduced. FIG. 14G demonstrates similar results for epididymal fat pad weight, which is indicative of visceral fat levels. FIG. 14H shows Ab109 reversed lean mass loss and enhanced fat mass loss induced by semaglutide treatment. As shown in FIG. 14I, Ab109 treatment showed possible improvement in reducing fasting blood glucose in both regain and continuous semaglutide study cohorts. Ab109 treatment in conjunction with semaglutide further reduced fasting blood glucose by approximately 20% in a dose dependent manner, suggesting slight improvement in the metabolic profile of the treated mice.

Figure 14J:
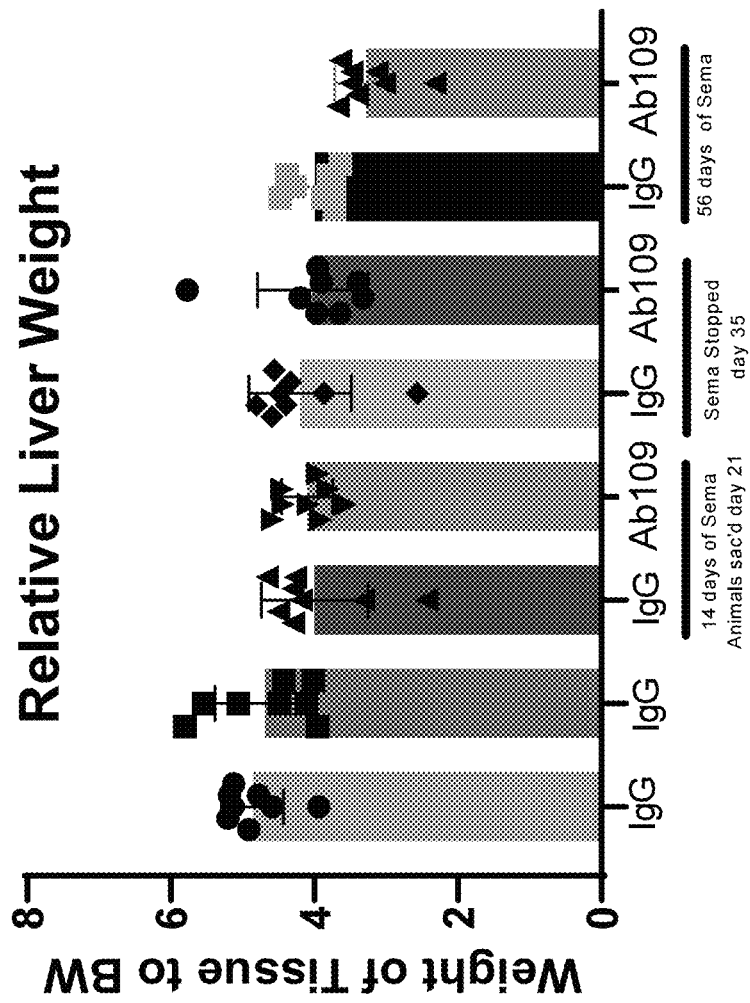

As shown in FIG. 14J, Ab109 treatment in conjunction with semaglutide reduced liver weight. Without wishing to be bound by theory, it is contemplated that GLP-1R agonist treatment in combination with myostatin inhibition may provide therapeutic benefits for reducing fat mass around the liver.

As shown in FIG. 14B and FIG. 14D, Ab109 treatment significantly enhanced lean mass gain and led to slower fat mass regain compared to treatment with control IgG. FIG. 14B shows that animals treated with semaglutide, then withdrawn from semaglutide at day 35, gained a significant amount of lean mass when treated with Ab109. FIG. 14D shows that, while reduction in fat mass plateaued with semaglutide treatment, animals treated with Ab109 in conjunction with semaglutide demonstrated attenuated regain of fat mass after discontinuation of semaglutide treatment at day 35 compared to IgG control.

Figure 14K:
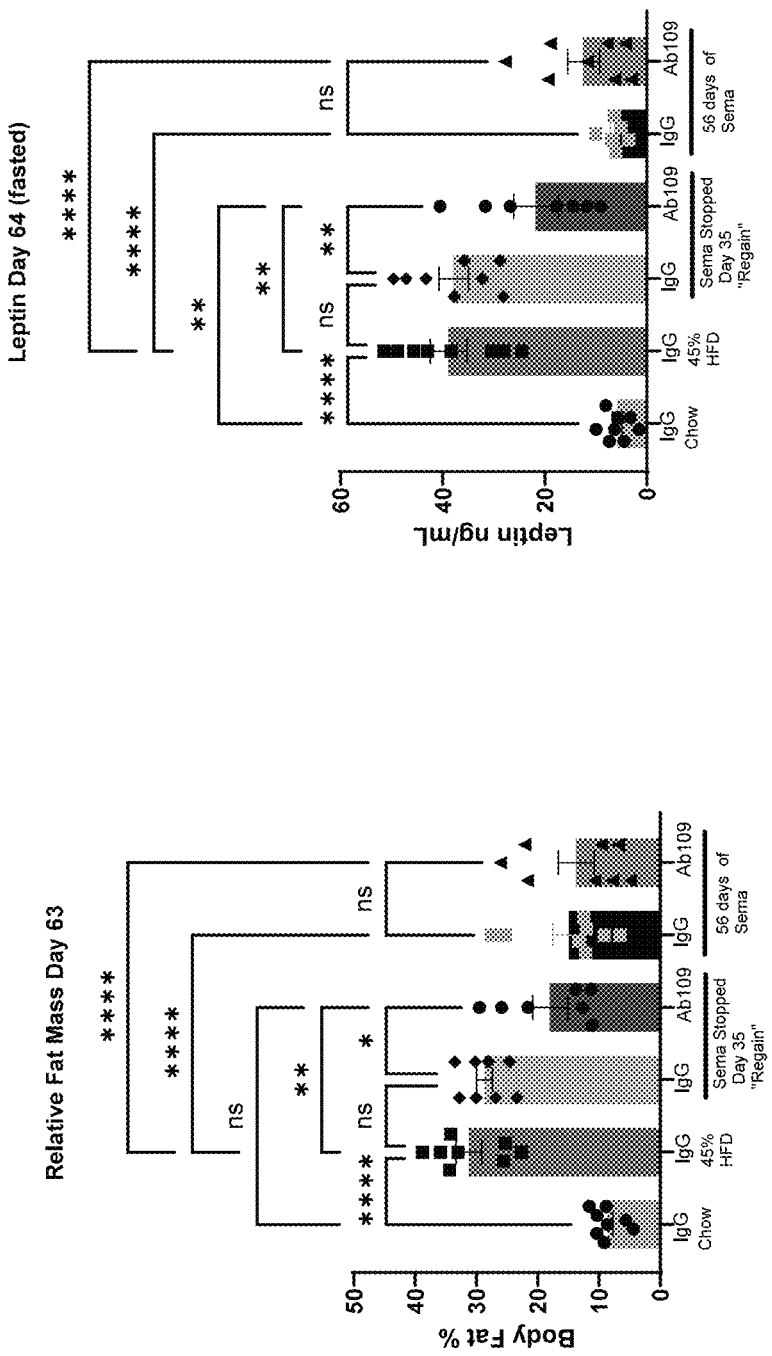

As shown in FIG. 14K and Table 24b, relative fat mass (body fat percent) is lower in animals treated with Ab109 after withdrawal of semaglutide when compared to animals treated with control IgG.

Circulating leptin was measured using the U-PLEX Metabolic Hormones Combo 1 (mouse) according to manufacturer's instructions (Meso Scale Diagnostics, #K15306K-2). As expected, circulating leptin was higher in animals fed the high fat diet than animals fed a standard chow. Continuous semaglutide administration lowered circulating leptin. Ab109 treatment decreased circulating leptin in the semaglutide withdrawal group compared to animals treated with control IgG (FIG. 14K and Table 24c).

TABLE 24b

Relative fat mass.

| Group | Diet | Semaglutide | Antibody | Relative Fat Mass Day 63 (% Body Fat) | S.E.M. | p-value vs Group 1 | p-value vs Group 2 | p-value vs hIgG control group |
|---|---|---|---|---|---|---|---|---|
| 1 | Chow | 0 | hIgG | 8.613 | 0.8678 | N/A | <0.0001 | N/A |
| 2 | 60%/45% high fat | 0 | hIgG | 31.24 | 2.073 | <0.0001 | N/A | N/A |
| 3 | 60%/45% high fat | 0.04 mg/kg day 7-14 | hIgG | N/A | N/A | N/A | N/A | N/A |
| 4 | 60%/45% high fat | 0.04 mg/kg day 7-14 | Ab109 | N/A | N/A | N/A | N/A | N/A |
| 5 | 60%/45% high fat | 0.04 mg/kg day 7-35 (regain arm) | hIgG | 28.69 | 1.284 | <0.0001 | 0.9621 | N/A |
| 6 | 60%/45% high fat | 0.04 mg/kg day 7-35 (regain arm) | Ab109 | 17.99 | 2.87 | 0.06 | 0.0023 | 0.0215 |
| 7 | 60%/45% high fat | 0.04 mg/kg day 7-63 | hIgG | 14.84 | 2.645 | 0.3589 | <0.0001 | N/A |
| 8 | 60%/45% high fat | 0.04 mg/kg day 7-63 | Ab109 | 13.73 | 2.907 | 0.5752 | <0.0001 | 0.9992 |

TABLE 24c

Circulating leptin.

| Group | Diet | Semaglutide | Antibody | Leptin Day 64 (ng/mL) | S.E.M. | p-value vs Group 1 | p-value vs Group 2 | p-value vs hIgG control group |
|---|---|---|---|---|---|---|---|---|
| 1 | Chow | 0 | hIgG | 5.864 | 0.958 | N/A | <0.0001 | N/A |
| 2 | 60%/45% high fat | 0 | hIgG | 38.83 | 3.578 | <0.0001 | N/A | N/A |
| 3 | 60%/45% high fat | 0.04 mg/kg day 7-14 | hIgG | N/A | N/A | N/A | N/A | N/A |
| 4 | 60%/45% high fat | 0.04 mg/kg day 7-14 | Ab109 | N/A | N/A | N/A | N/A | N/A |
| 5 | 60%/45% high fat | 0.04 mg/kg day 7-35 (regain arm) | hIgG | 37.87 | 2.889 | <0.0001 | 0.9999 | N/A |
| 6 | 60%/45% high fat | 0.04 mg/kg day 7-35 (regain arm) | Ab109 | 21.71 | 4.39 | 0.0072 | 0.0031 | 0.0059 |
| 7 | 60%/45% high fat | 0.04 mg/kg day 7-63 | hIgG | 6.357 | 0.8898 | >0.9999 | <0.0001 | N/A |

TABLE 24c-continued

Circulating leptin.

| Group | Diet | Semaglutide | Antibody | Leptin Day 64 (ng/mL) | S.E.M. | p-value vs Group 1 | p-value vs Group 2 | p-value vs hIgG control group |
|---|---|---|---|---|---|---|---|---|
| 8 | 60%/45% high fat | 0.04 mg/kg day 7-63 | Ab109 | 12.4 | 3.106 | 0.6044 | <0.0001 | 0.7451 |

Example 7: Effect of Ab109 on Serum Myostatin Levels

Figure 15B:
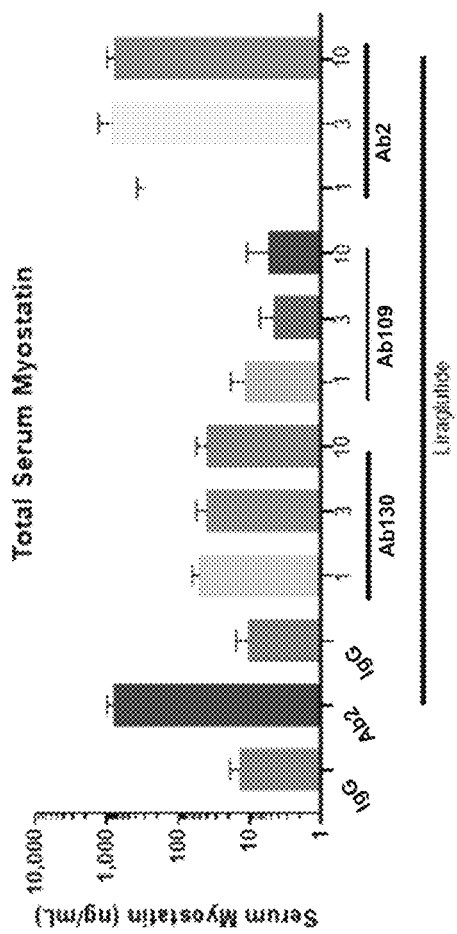
FIGS. 15A-B show total serum myostatin levels in mice treated with dexamethasone (FIG. 15A) or liraglutide (FIG. 15B) in combination with Ab2, Ab109, or Ab130.
Figure 15A:
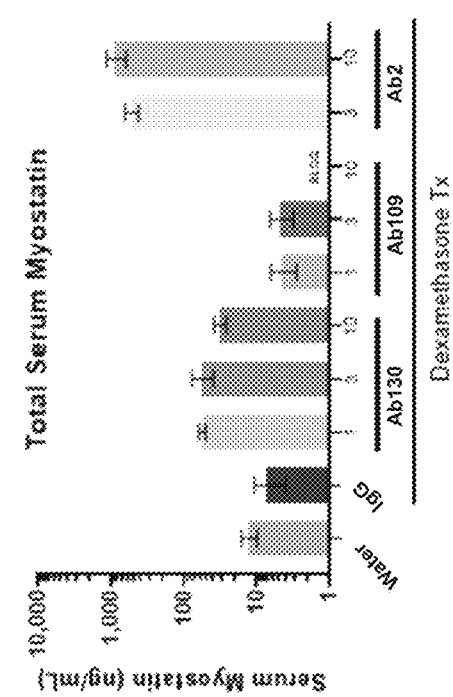

Serum from the dexamethasone-treated or the liraglutide-treated animals as described above was collected and total circulating myostatin levels were determined. As shown in FIGS. 15A and 15B, both Ab2 and Ab130 treatment resulted in an increase in serum myostatin levels, although the increase associated with Ab130 treatment was to a lesser extent than the increase associated with Ab2 treatment. In contrast, Ab109 treatment resulted in a decrease in serum myostatin, distinguishing its effect on circulating myostatin from that of Ab2. Without being bound by theory, the difference serum myostatin levels resulting from Ab2 and Ab109 treatments could be due in part to the greater pH differential exhibited by Ab109 (FIGS. 4A-B). Another potential explanation could be that Ab109 binds to myostatin with a 1:2 antibody-to-antigen ratio, in contrast to Ab2, which binds with a 1:1 antibody-to-antigen ratio (Tables 10b and 10d). These improved properties of Ab109 are unexpected, considering the sequence homology between Ab2 and Ab109 and the homology in the epitope region targeted by Ab2 and Ab109.

Example 8: Pharmacokinetics and Pharmacodynamics of Ab109 and Ab141 in Obese Mice Treated with a GLP-1 Receptor Agonist Male 19 week old C7/BL6 mice fed a high fat diet to induce obesity (DIO-B6-M mice, were evaluated for the effect of the combination of antibody and semaglutide on the exposure of the antibody to the target antigen (PK) and the total myostatin serum level (PD), as shown in Table 25. Animals were dosed with antibody intraperitoneally on days 0, 7, and 14 and were dosed with semaglutide subcutaneously daily throughout the study. Exposure of the antibody to immobilized promyostatin was determined by ELISA. Total serum myostatin was also measured by ELISA. The study concluded on day 22, when terminal bleeds were obtained.

TABLE 25

Effect of Semaglutide and Abs 109 and 141 on PK and PD.

| Group | Antibody | Antibody Dose | Semaglutide Dose |
|---|---|---|---|
| 1 | hIgG | 3 mg/kg | 0 |
| 2 | Ab109 | 3 mg/kg | 0 |
| 3 | Ab141 | 3 mg/kg | 0 |
| 4 | hIgG | 3 mg/kg | 0.04 mg/kg |
| 5 | Ab109 | 0.1 mg/kg | 0.04 mg/kg |
| 6 | Ab109 | 0.3 mg/kg | 0.04 mg/kg |
| 7 | Ab109 | 1 mg/kg | 0.04 mg/kg |
| 8 | Ab109 | 3 mg/kg | 0.04 mg/kg |
| 9 | Ab141 | Ab109 | 0.04 mg/kg |
| 10 | Ab141 | Ab109 | 0.04 mg/kg |
| 11 | Ab141 | Ab109 | 0.04 mg/kg |
| 12 | Ab141 | Ab109 | 0.04 mg/kg |

Figure 16B:
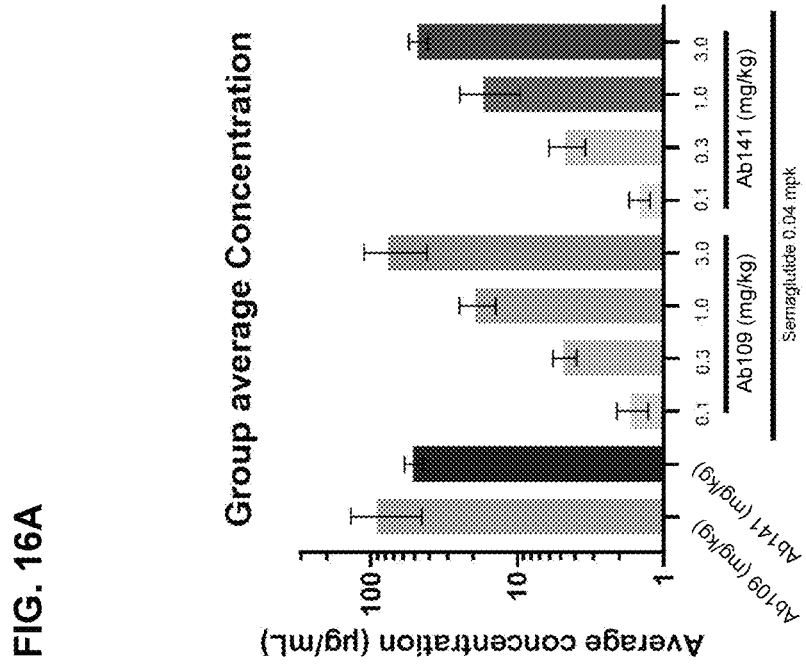
FIG. 16B shows total myostatin following treatment with Ab109 or Ab141 when dosed at between 0.1 and 3 mg/kg alone or in combination with semaglutide.
Figure 16A:
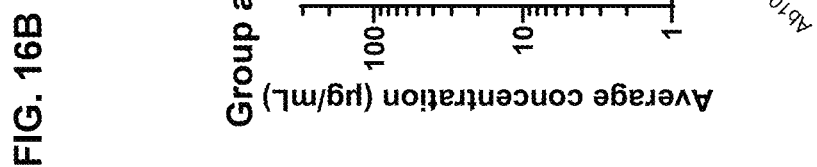
FIG. 16A shows dose-dependent serum exposure of Ab109 and Ab141 when dosed at between 0.1 and 3 mg/kg alone or in combination with semaglutide.

As shown in FIG. 16A, the exposure of Ab109 and Ab141 to pro/latent myostatin in serum (PK) was similar in the presence and absence of semaglutide. The serum exposure of Ab109 was dose proportional between 0.1 and 1 mg/kg and slightly exceeded dose proportionality at the highest dose of 3 mg/kg. The serum exposure of Ab141 was dose proportional between 0.1 and 3 mg/kg.

As shown in FIG. 16B, the levels of serum total myostatin in the presence of Ab109 or Ab141 were not affected by the presence of semaglutide. As depicted, increasing the dose of either antibody decreases the amount of circulating myostatin.

Figure 16C:
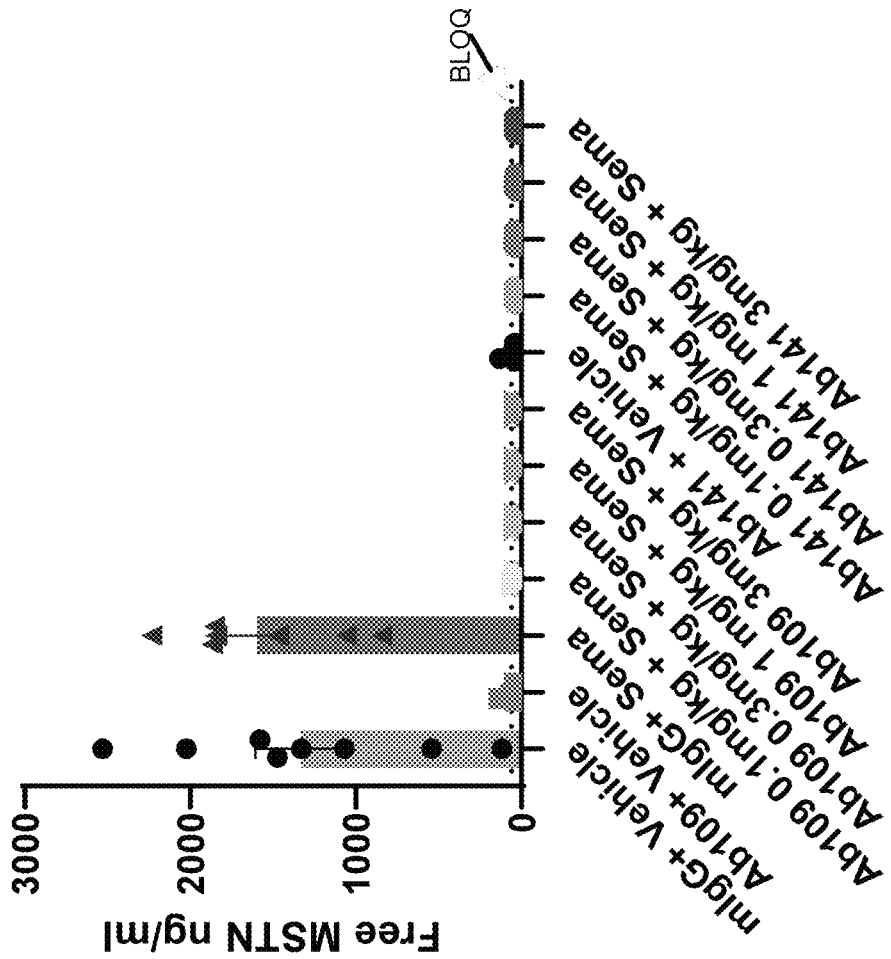
FIG. 16C shows free latent myostatin (latent myostatin not bound by antibody) levels following treatment for 22 days with Ab109 or Ab141 when dosed at 0.1 to 3 mg/kg alone or in combination with semaglutide.

As shown in FIG. 16C, levels of serum free latent myostatin (not bound by antibody) were reduced below the level of quantitation following treatment with Ab109 or Ab141 in presence or absence of semaglutide.

Figure 17:
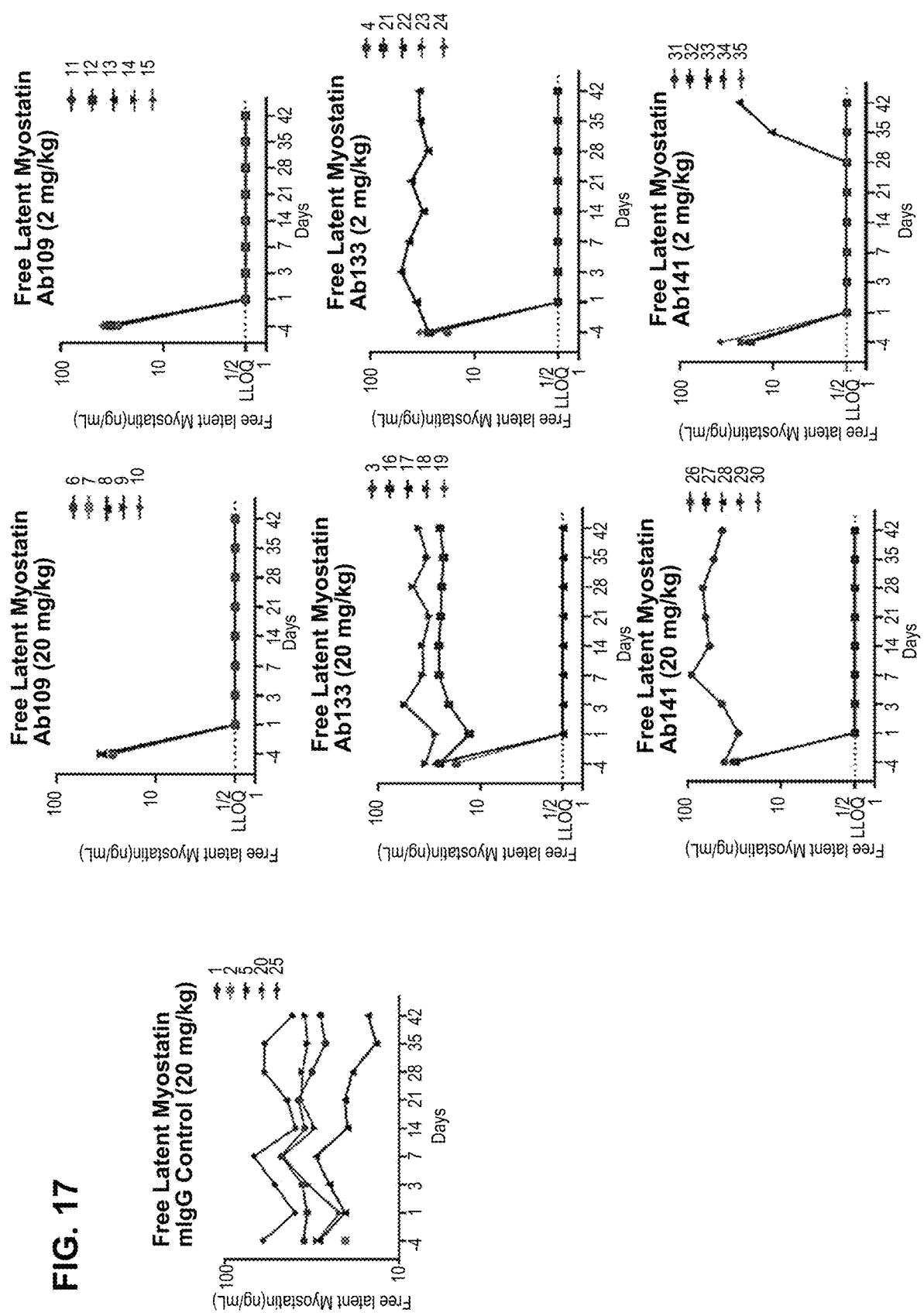
FIG. 17 shows the level of free latent myostatin in mice treated with Ab109, Ab133, and Ab141 compared to control mIgG antibody. Data for individual animals are shown in each plot.

FIG. 17 shows the level of free latent myostatin in mice treated with Ab109, Ab133, and Ab141. Data for individual animals are shown in each plot.

Example 9: Effects of A Treatment Comprising Ab109 and One of Two Dose Levels of Semaglutide Male C57/BL6 male mice (n=8/group) were placed on a 60% high fat diet at ~6 weeks of age and maintained on the 60% high fat diet until 21 weeks of age (Groups 1-12), at which time the study began (day −7). On day −7, animals in groups 1-12 were switched to a 45% high fat diet and maintained on the 45% high fat diet until the animals were terminated. On day 0, the animals were randomized and dosed subcutaneously with 0.01 mg/kg OR 0.04 mg/kg semaglutide once per day, and dosed at days 0, 7 and 14 with either Ab109 or control human immunoglobulin (hIgG) as shown in Table 26. Body weight was measured three times per week and qNMR measurements of lean mass and fat mass were obtained pre-dose on day 0 and on days 7, 14 and 21. Fasting glucose was measured on day 18 after a 4 hour fast.

TABLE 26

Semaglutide and myostatin inhibitor dosing.

| Group | N | TA #1 | TA #1 dose | TA #2 | TA #2 dose |
|---|---|---|---|---|---|
| 1 | 8 | IgG | 3 mg/kg/week | Vehicle | QD |
| 2 | 8 | Ab109 | 3 mg/kg/week | Vehicle | QD |

TABLE 26-continued

Semaglutide and myostatin inhibitor dosing.

| Group | N | TA #1 | TA #1 dose | TA #2 | TA #2 dose |
|---|---|---|---|---|---|
| 3 | 8 | IgG | 3 mg/kg/week | Semaglutide | 0.01 mg/kg QD |
| 4 | 8 | IgG | 3 mg/kg/week | Semaglutide | 0.04 mg/kg QD |
| 5 | 8 | Ab109 | 0.1 mg/kg/week | Semaglutide | 0.04 mg/kg QD |
| 6 | 8 | Ab109 | 1 mg/kg/week | Semaglutide | 0.04 mg/kg QD |
| 7 | 8 | Ab109 | 3 mg/kg/week | Semaglutide | 0.04 mg/kg QD |
| 8 | 8 | Ab109 | 10 mg/kg/week | Semaglutide | 0.04 mg/kg QD |
| 9 | 8 | Ab109 | 0.1 mg/kg/week | Semaglutide | 0.01 mg/kg QD |
| 10 | 8 | Ab109 | 1 mg/kg/week | Semaglutide | 0.01 mg/kg QD |
| 11 | 8 | Ab109 | 3 mg/kg/week | Semaglutide | 0.01 mg/kg QD |
| 12 | 8 | Ab109 | 10 mg/kg/week | Semaglutide | 0.01 mg/kg QD |

QD: once per day

Animals in groups 3-12 were dosed with semaglutide daily for 3 weeks, then terminated. Animals in groups 1, 3, and 4 were treated with IgG control antibody, and those in groups 2, 5-12 were treated with myostatin activation inhibiting antibody treatment, for 3 weeks.

At termination, left gastrocnemius and quadriceps muscles were removed and frozen; the liver was weighed, one lobe was frozen; epididymal (perigonadal) adipose tissue was removed and weighed; inguinal (subcutaneous) adipose tissue was removed and weighed; and a terminal serum bleed was obtained.

Figure 18A:
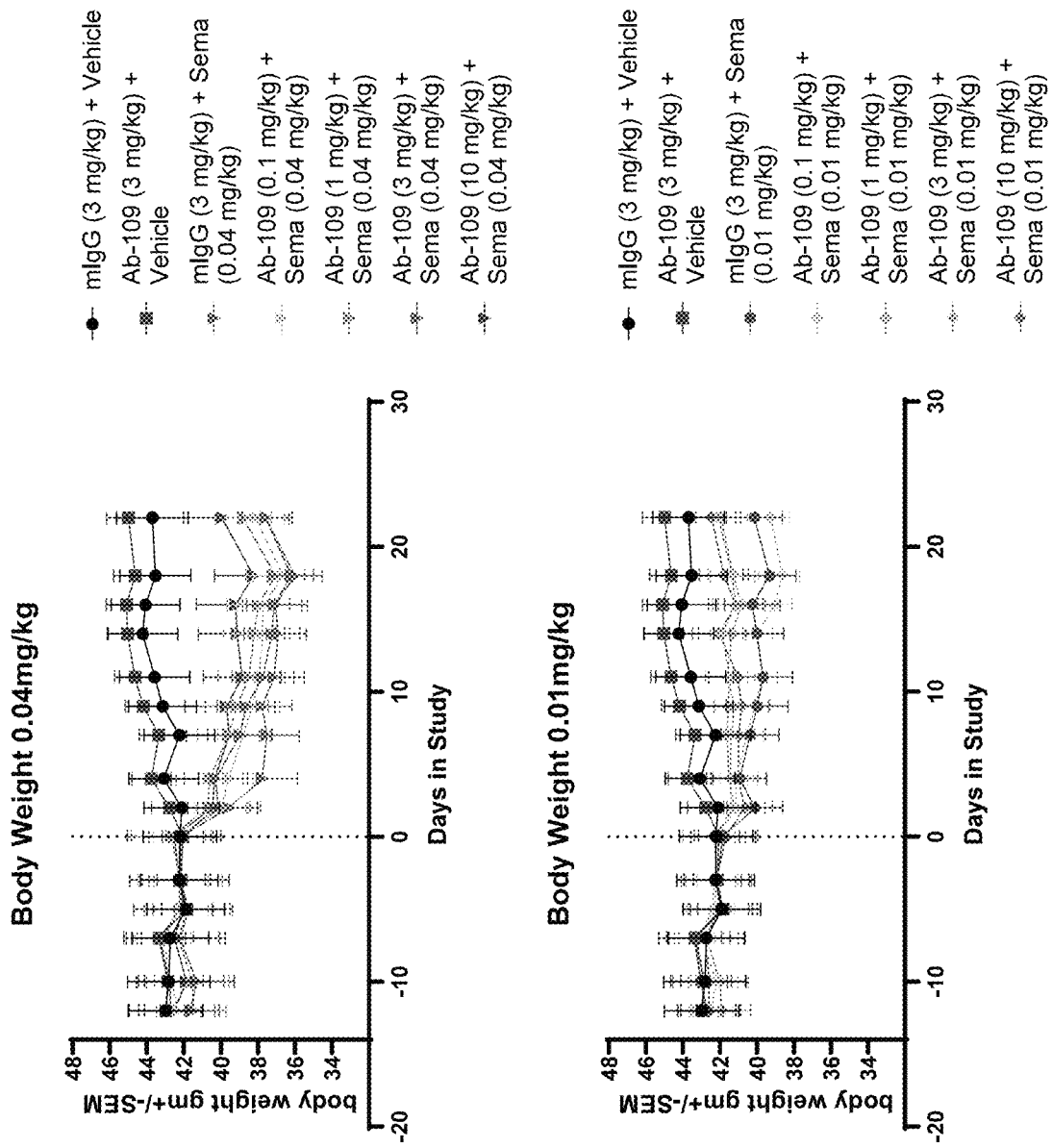
FIGS. 18A-B show body weight change (FIG. 18A) and percent body weight change (FIG. 18B) in mice treated with of Ab109 and semaglutide. The upper panel for each figure shows the effect for 0.04 mg/kg semaglutide dose; the lower panel for each figure shows the effect for 0.01 mg/kg semaglutide dose.
Figure 18B:
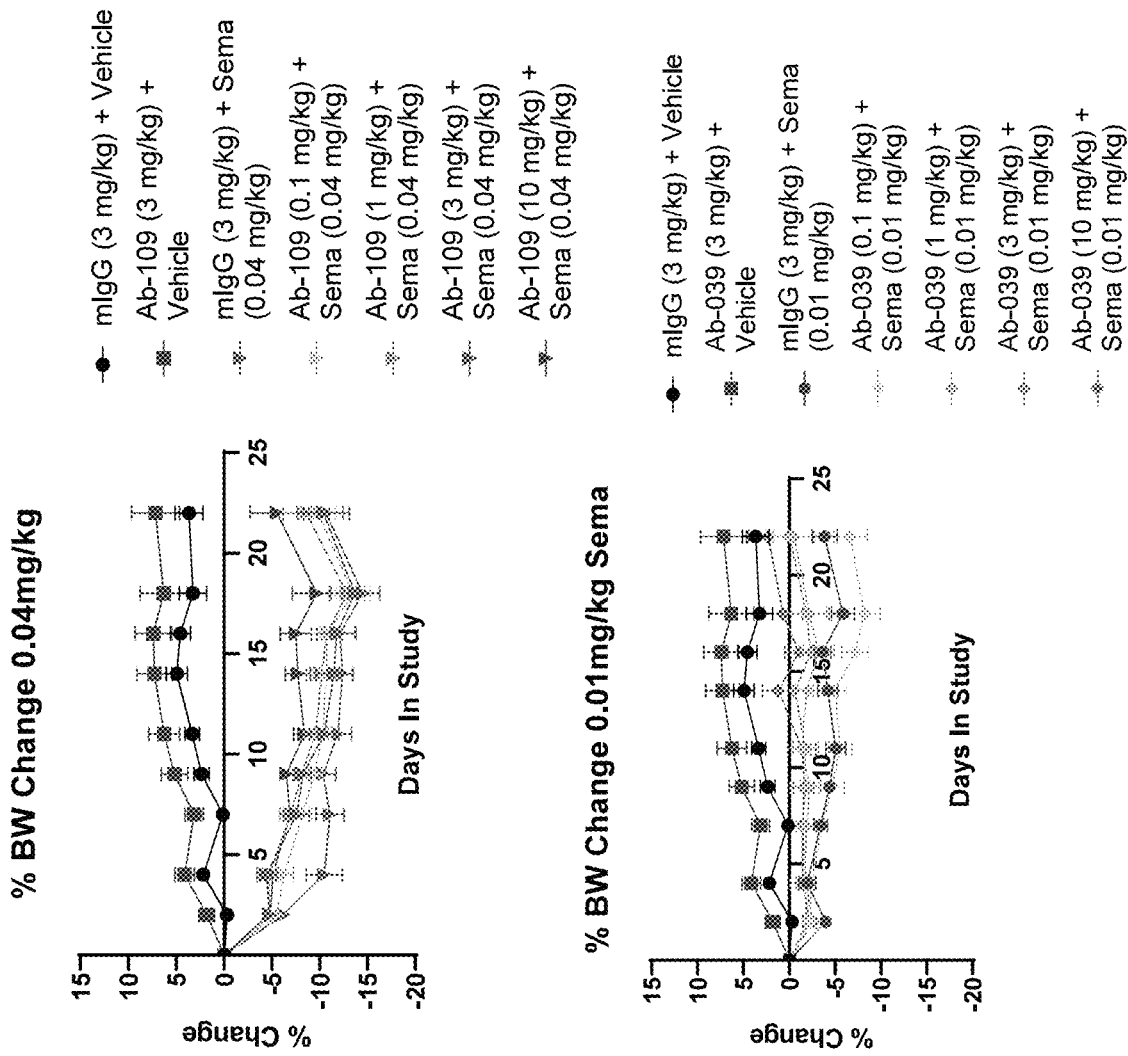

BODY WEIGHT: Animals that were fed the high fat diet and received semaglutide lost weight. The weight loss was greater for animals treated with the higher dose of semaglutide (0.04 mg/kg) than with the lower dose (0.01 mg/kg). Ab109 maintained steady body weight in animals treated with combination of Ab109 and the lower dose (0.01 mg/kg) of semaglutide (FIGS. 18A and 18B).

Figure 19A:
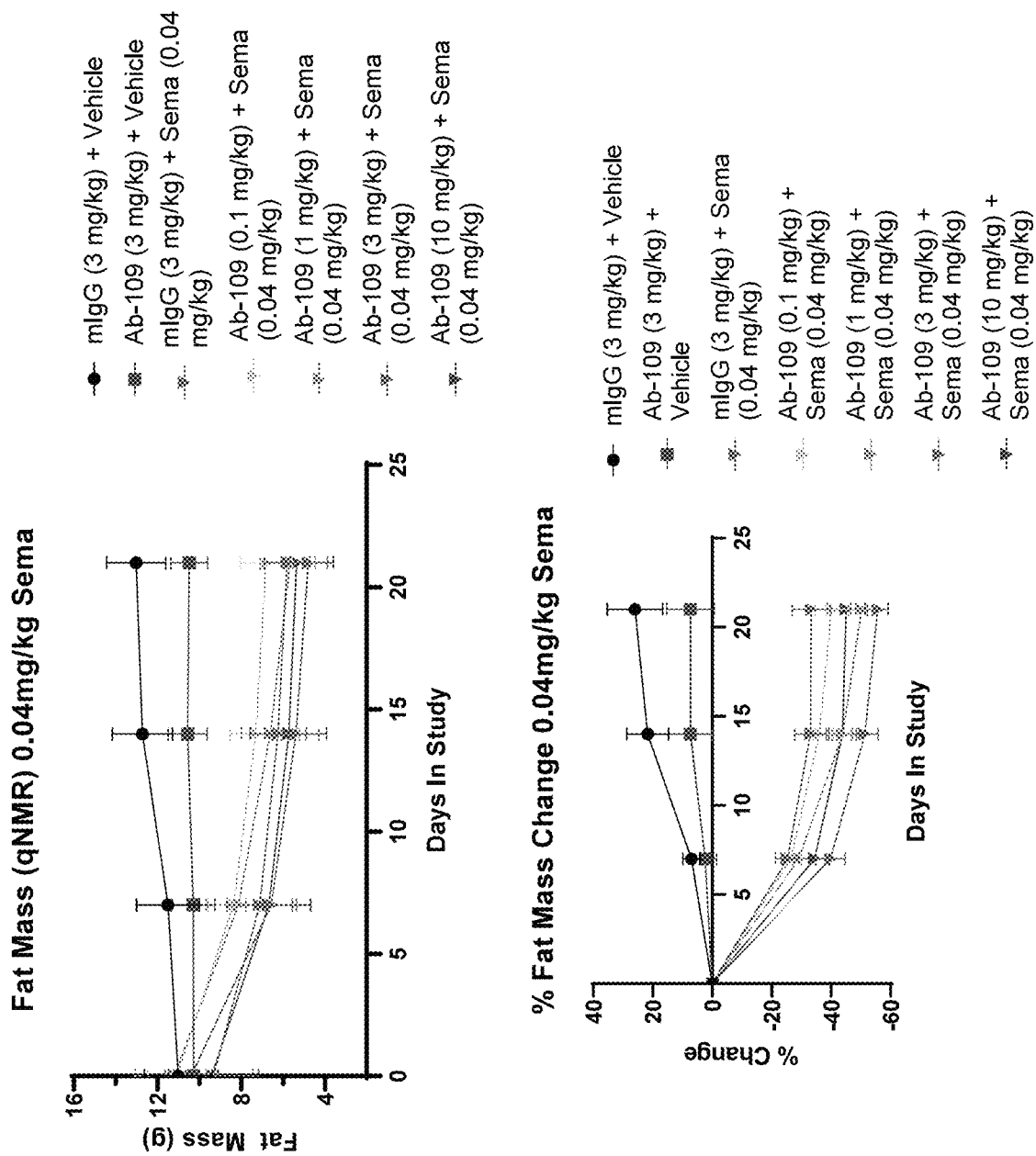
FIGS. 19A-B show fat mass change in mice treated with Ab109 and semaglutide.
Figure 19B:
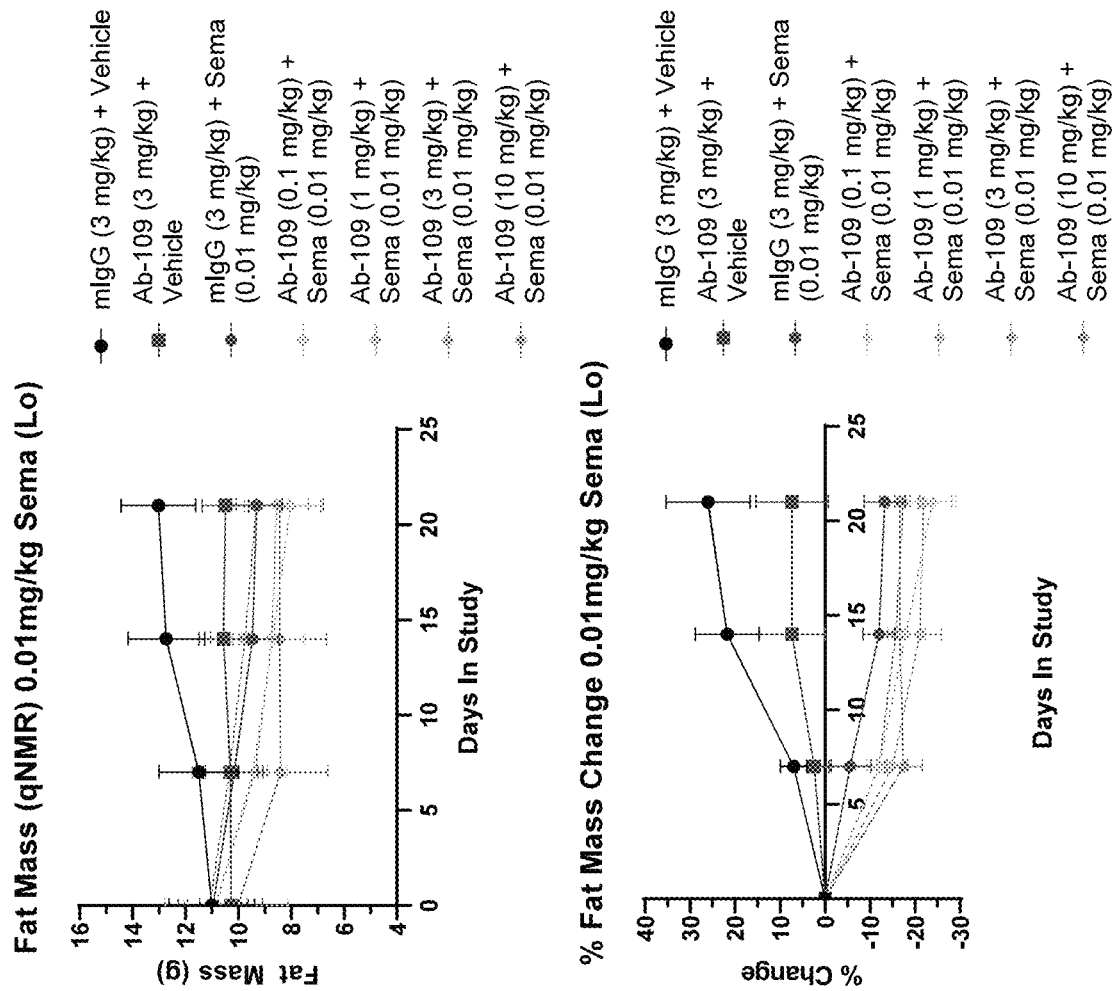
Figure 19C:
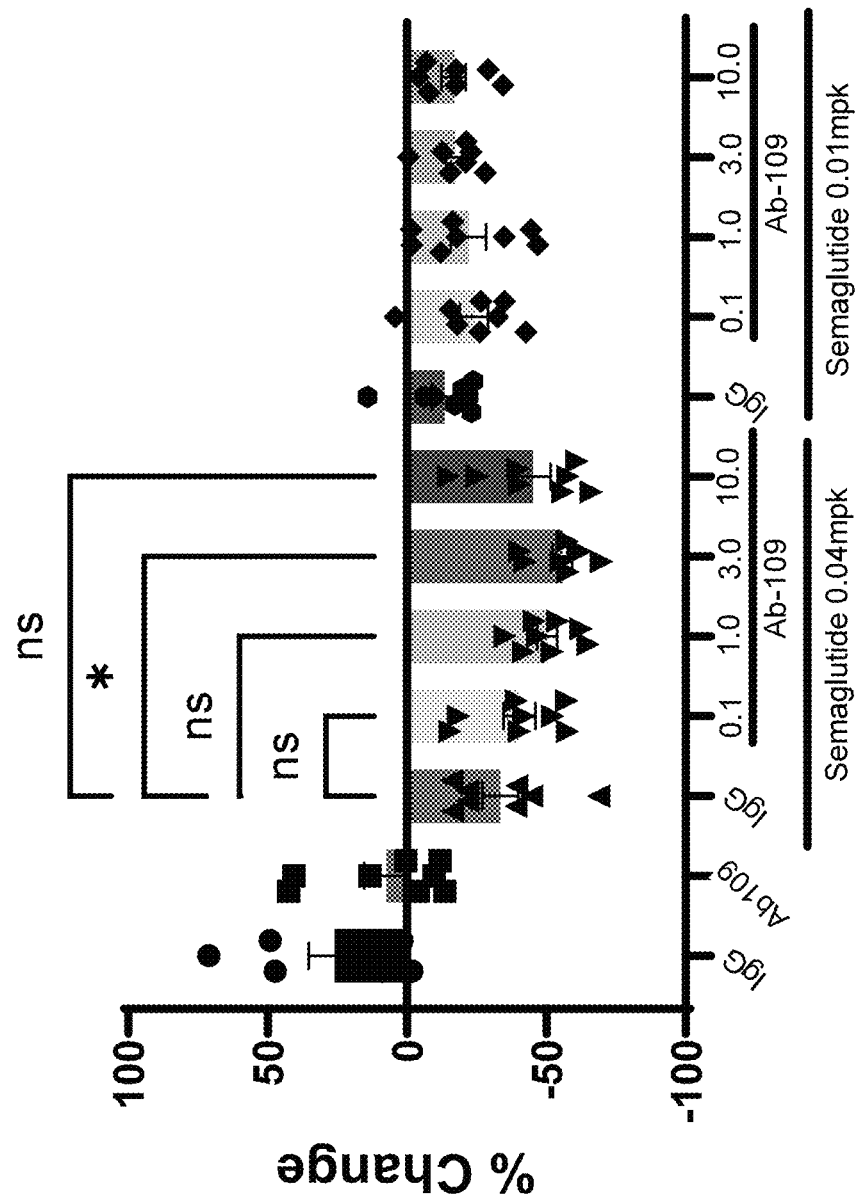
FIG. 19C compares percent fat mass changes between the semaglutide 0.04 mg/kg group and the semaglutide 0.01 mg/kg group.

FAT MASS LOSS: As expected, semaglutide treatment alone induced fat mass loss in the animals. All doses of Ab109 treatment in combination with 0.04 mg/kg semaglutide improved fat mass loss compared to IgG control with semaglutide. Lower fat mass gain was also observed with Ab109 monotherapy (without semaglutide: 7% compared to 23% for IgG control) (FIG. 19A). In animals treated with 0.01 mg/kg semaglutide, Ab109 in combination improved fat mass loss compared to those treated with 0.01 mg/kg semaglutide and IgG control. Lower fat mass gain was also observed with Ab109 monotherapy (without semaglutide) (FIG. 19B). In addition, Ab109 improved fat mass loss in a dose-dependent manner in combination with 0.04 mg/kg semaglutide (FIG. 19C).

Figure 20A:
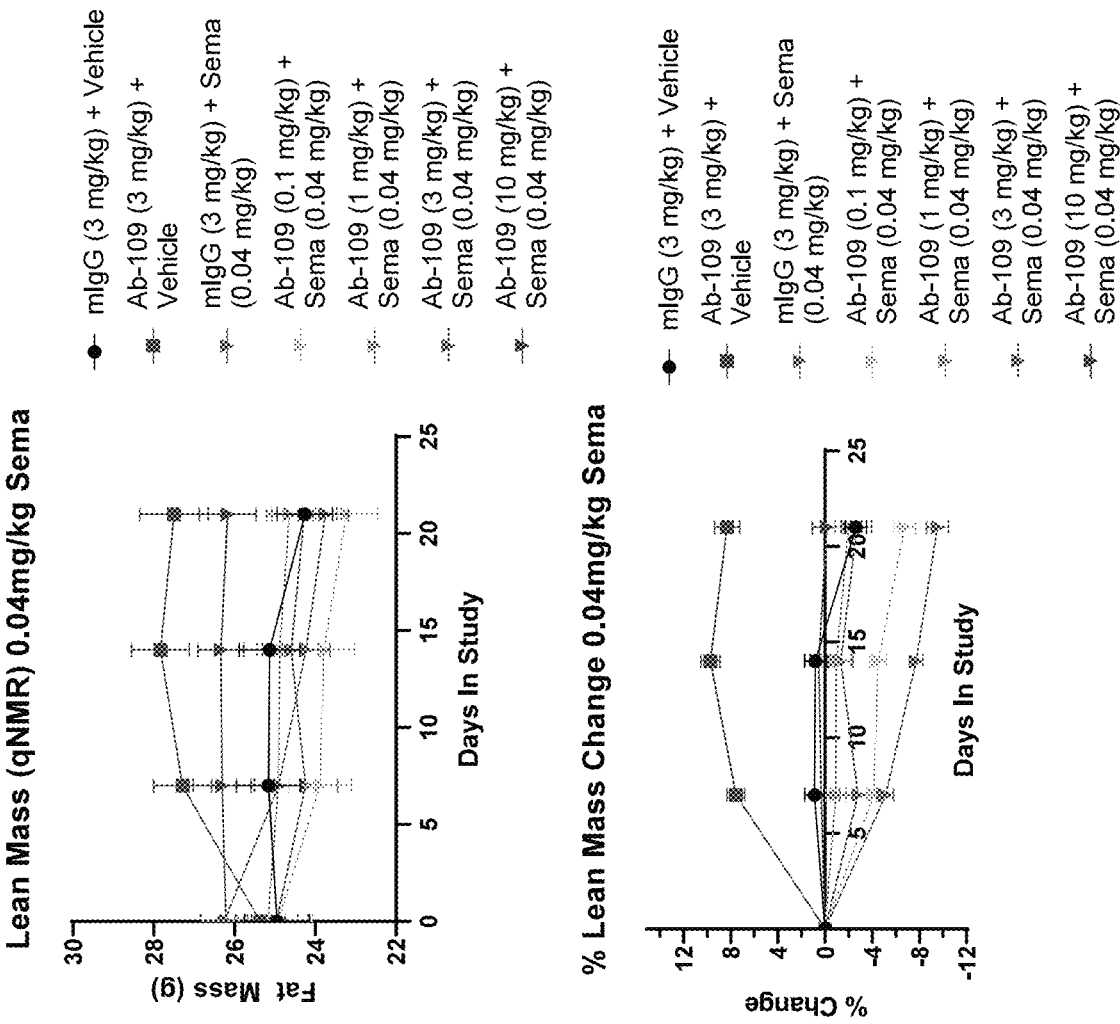
FIG. 20A-B show lean mass change and percent lean mass change in mice treated with Ab109 and semaglutide.

LEAN MASS: Animals that received 0.04 mg/kg semaglutide and hIgG throughout the duration of the study lost about 9.5% of their lean mass during the duration of the study (3 weeks). Addition of Ab109 blunted these lean mass losses and helped maintain a close-to-neutral lean mass change at 3 mg/kg and 10 mg/kg of Ab109. (FIG. 20A). Mice that received Ab109 without semaglutide exhibited increases in lean mass.

Figure 20B:
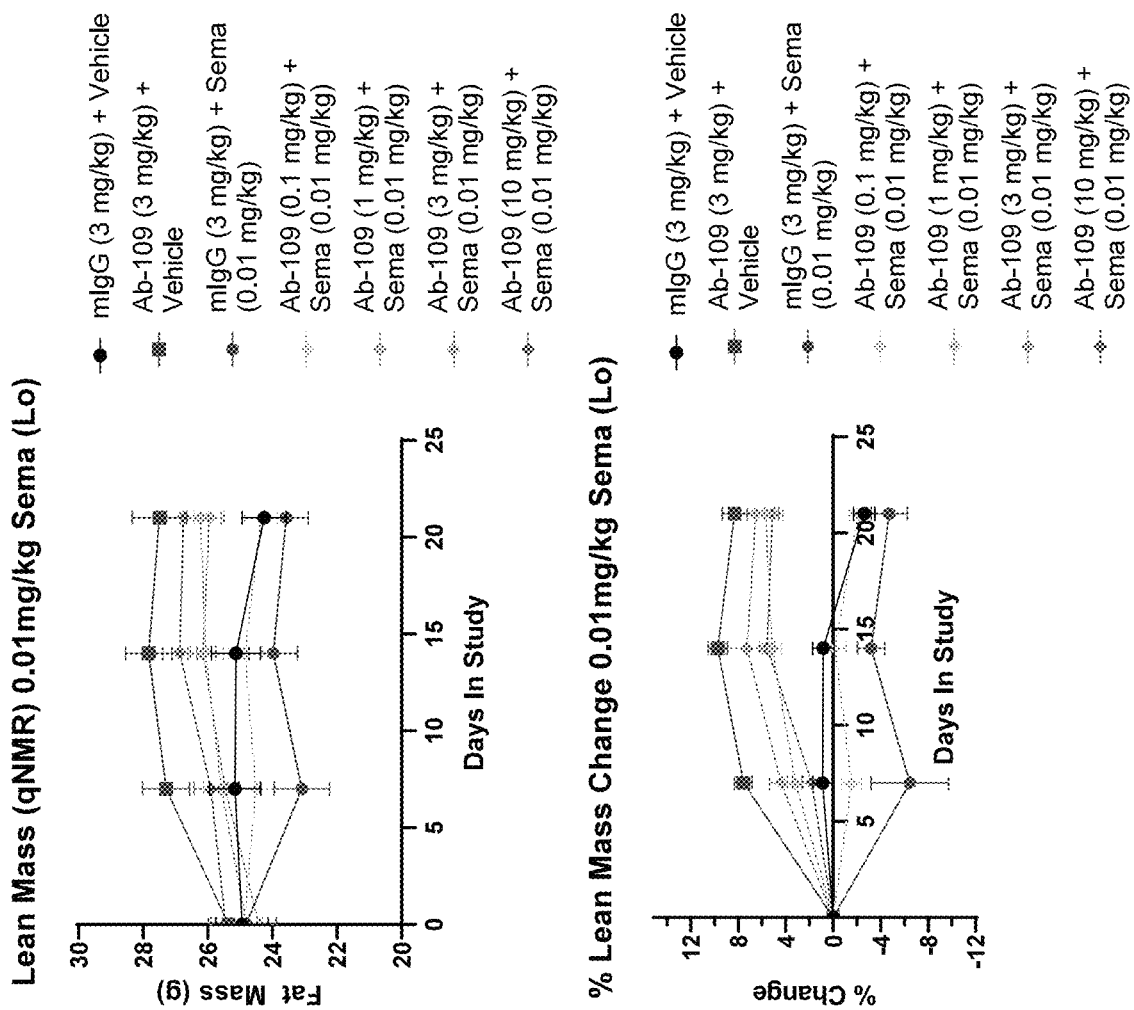
Figure 20C:
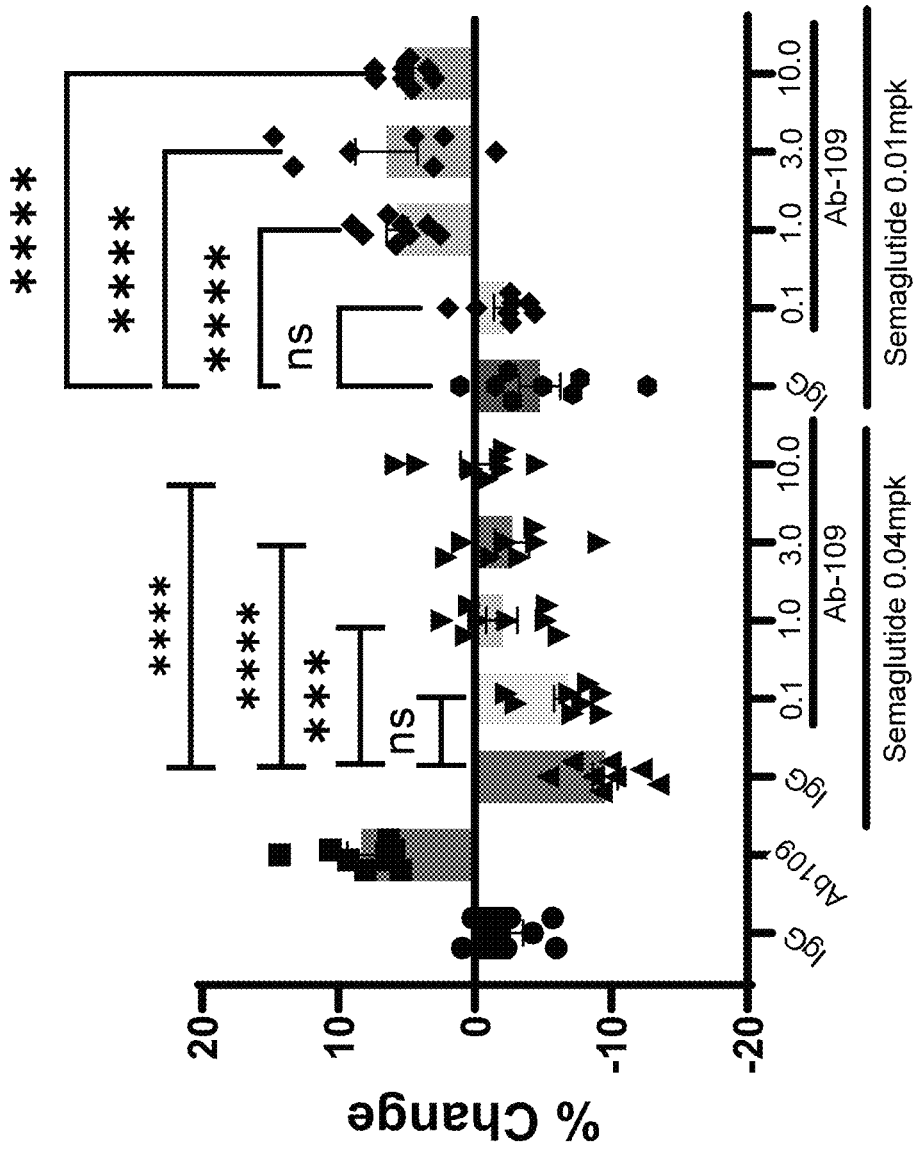
FIG. 20C compares percent lean mass changes between the semaglutide 0.04 mg/kg group and the semaglutide 0.01 mg/kg group.

Ab109 also helped preserve and improve lean mass during treatment with the lower dose of semaglutide (0.01 mg/kg). Semaglutide at this dose caused a 4.7% loss in lean mass over the duration of the study, and addition of Ab109 increased lean mass (4% to 6%), (FIG. 20B). In addition, Ab109 treatment alone increased lean mass by 8.3%, and in combination with semaglutide, Ab109 preserved lean mass at doses of 1, 3, and 10 mg/kg Ab109 (FIG. 20C).

The tissue weights of the gastrocnemius muscle and the inguinal and epididymal fat pads correspond to and corroborate the lean mass and fat mass qNMR measurements shown above.

Figure 21A:
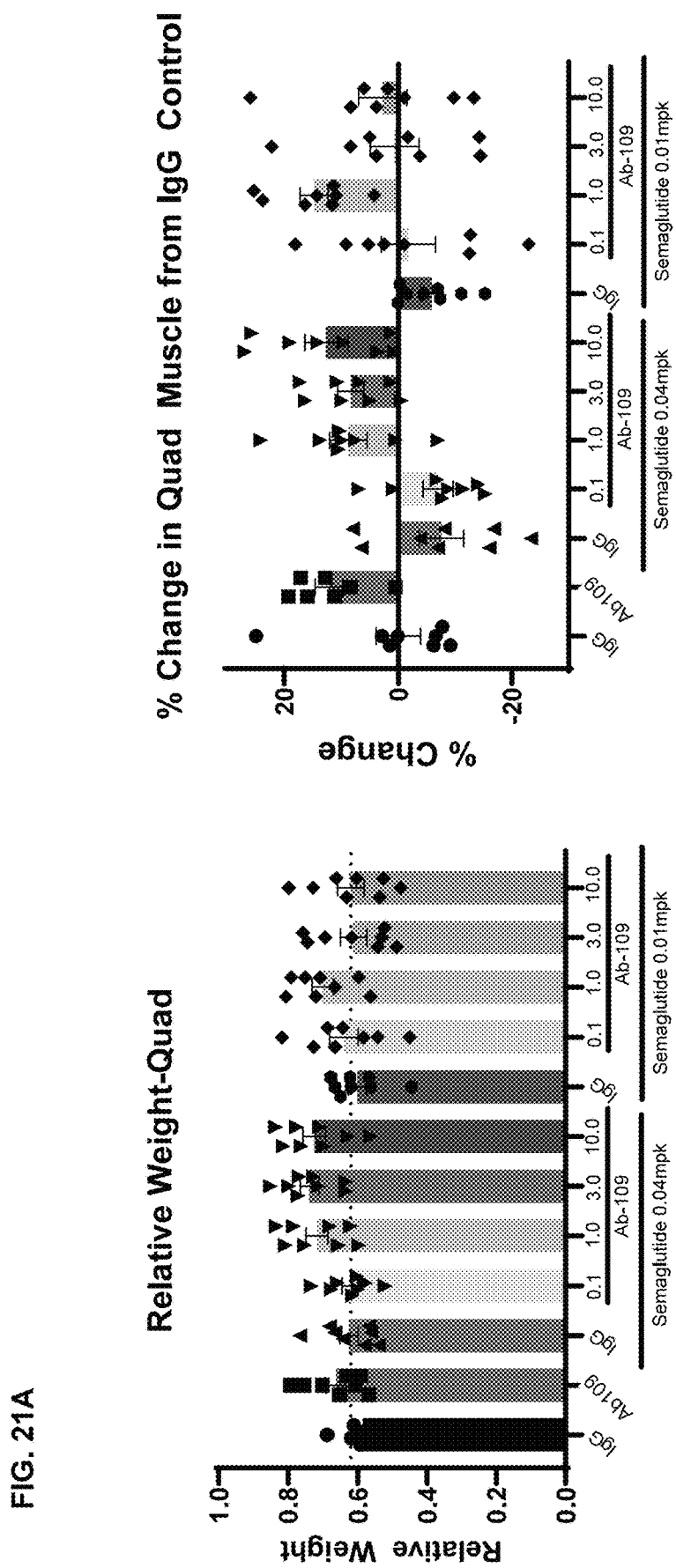
FIGS. 21A-B show the effect of Ab109 and semaglutide treatment on the weight of certain muscle tissues.
Figure 21B:
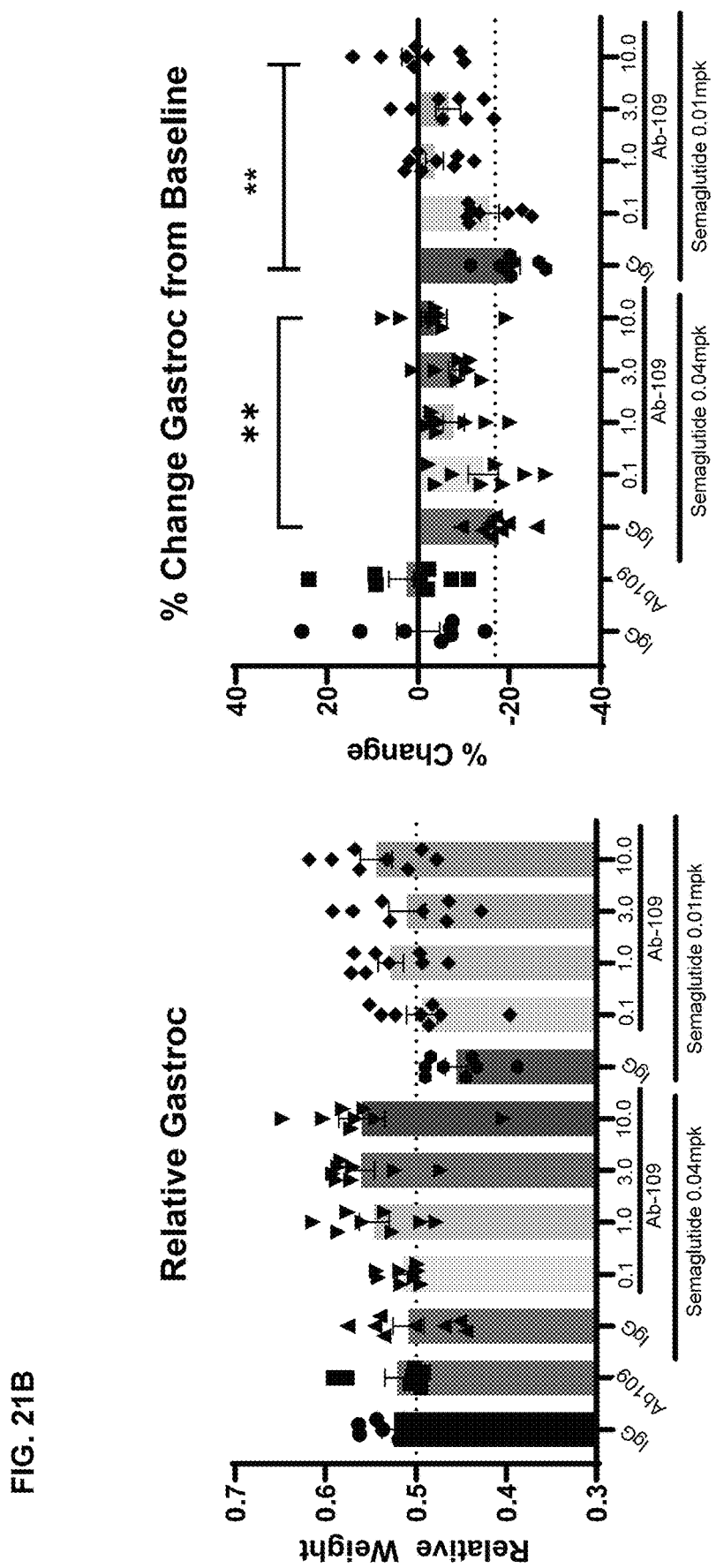

MUSCLE WEIGHTS: Semaglutide treatment at both the low and high doses caused loss in quadriceps weight of −4.8% and −7.6%, respectively, whereas Ab109 in combination with semaglutide prevented this muscle loss (FIG. 21A). A similar result was observed in gastrocnemius muscles: animals treated with semaglutide had −16.9% and −20.3% loss in gastrocnemius muscle weight, and Ab109 treatment in combination prevented this muscle loss (FIG. 21B).

Figure 22A:
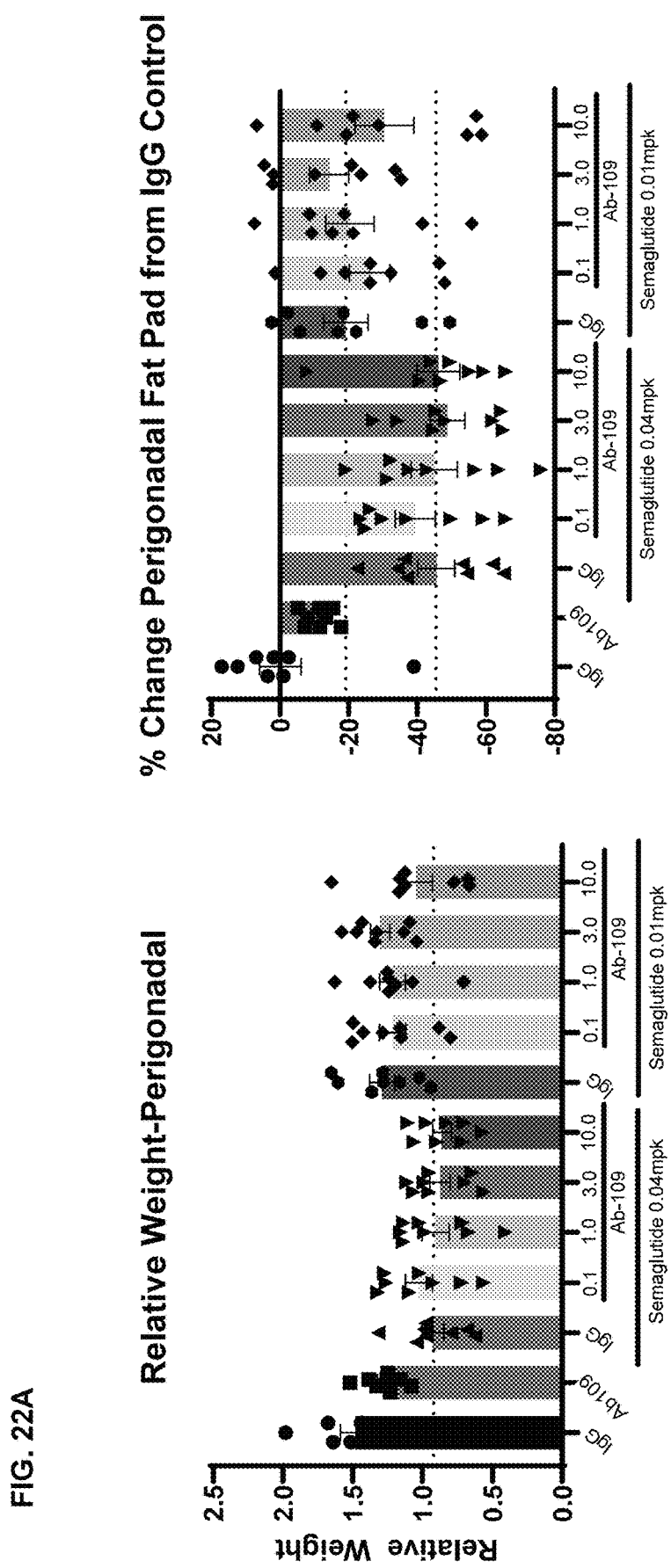
FIGS. 22A-B show the effect of Ab109 and semaglutide treatment on the weight of certain fat tissues.
Figure 22B:
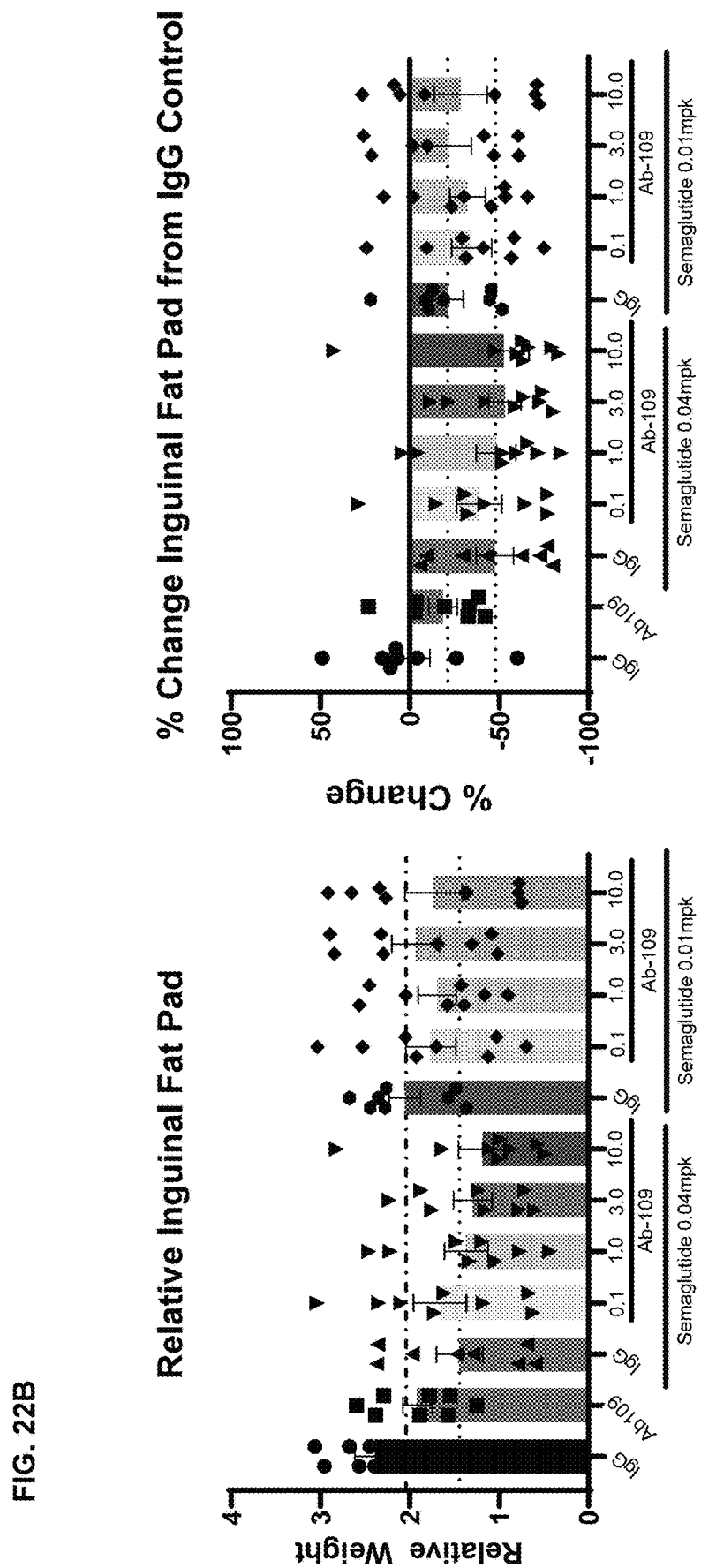

FAT PAD WEIGHTS: Semaglutide treatment also resulted in losses in perigonadal fat pad weights of −45.5% (at 0.04 mg/kg) and −19.1% (at 0.01 mg/kg). Treatment in combination with Ab109 only improved fat pad loss at select doses. This could be due to an already high fat mass loss for this fat pad in these animals treated with semaglutide (FIG. 22A). Similarly, semaglutide at both doses caused loss in the inguinal fat pads (−47.4% at 0.04 mg/kg and −21.4% at 0.01 mg/kg), and treatment in combination with Ab109 improved inguinal fat pad loss, especially with the lower dose (0.01 mg/kg) of semaglutide (FIG. 22B).

Combination with Ab109 improved fat mass loss at both concentrations of semaglutide (0.04 mg/kg and 0.01 mg/kg). Ab109 helped maintain baseline lean mass and/or prevent lean mass loss in presence of 0.04 mg/Ig semaglutide. Ab109 increased lean mass above baseline when combined with the low dose of semaglutide (0.01 mg/kg).

Ab109 preserved and/or increased lean mass and improved fat mass loss in combination with a lower dose of semaglutide (0.01 mg/kg). This may demonstrate benefit of Ab109 for patients who receive a sub-maximal dose of GLP-1 RA due tolerability issues.

Example 10: Preliminary Analysis of Ab109 Pharmacokinetics in Non-Human Primates

[1] A preliminary analysis of the pharmacokinetics of subcutaneous or intravenous dosing of Ab109 was determined in non-human primates following a single dose of Ab109 in five groups, each comprising three *Cynomolgus macaques*. Groups 1-4 were dosed subcutaneously with 0.3, 3, 10 or 30 mg/kg antibody, respectively. Group 5 was dosed intravenously with 10 mg/kg of Ab109. Samples were taken at day −1 (pre-dose), 1-hour and 8-hour post-dose, and at days 1, 3, 4, 5, 7, 10, 14, 17, 21, 28, 35, 42, 56 and 63 post-dose. An interim pharmacokinetic analysis was performed on samples up to 28 days post-dose.

TABLE 27

Groups, test articles, and dose/route.

| Group | Test article | Dosing Route | Dose (mg/kg) |
|---|---|---|---|
| 1 | Ab109 | SC | 0.3 |
| 2 | Ab109 | SC | 3 |
| 3 | Ab109 | SC | 10 |
| 4 | Ab109 | SC | 30 |
| 5 | Ab109 | IV | 10 |

Figure 24:
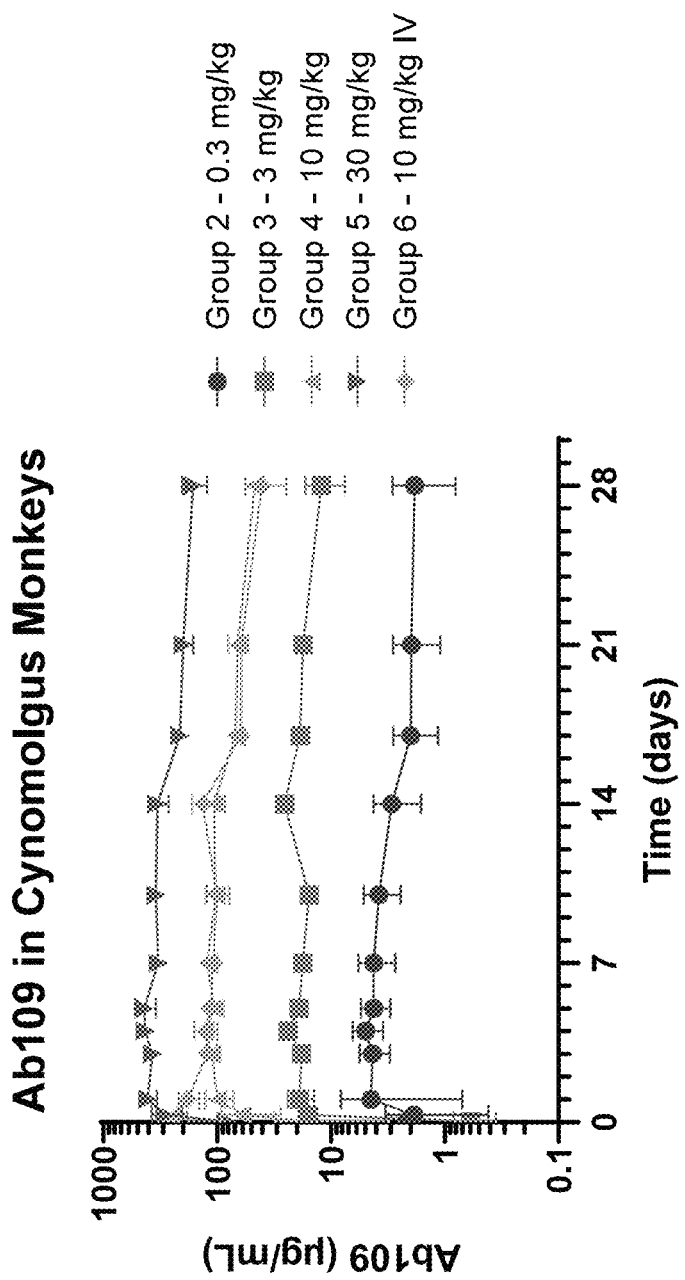
FIG. 24 shows the average serum concentrations of Ab109 up to 28 days post-dose in female *Cynomolgus macaques*.

[2] The preliminary results are shown in FIG. 24. The concentration of antibody in the serum was dose proportional for Ab109 across dose groups. Minimal variability was observed within each group.

[3] Based on the PK parameters determined in this interim analysis and a comparison of exposure between subcutaneous and intravenous administration of 10 mg/kg of Ab109 via $AUC_{0-28}$ (for days up to day 28 post-dose), the apparent bioavailability of Ab109 was calculated to be greater than 85%.

SEQUENCE LISTING

Sequence total quantity: 981

```
SEQ ID NO: 1            moltype =    length =
SEQUENCE: 1
000

SEQ ID NO: 2            moltype =    length =
SEQUENCE: 2
000

SEQ ID NO: 3            moltype = AA  length = 8
FEATURE                 Location/Qualifiers
source                  1..8
                        mol_type = protein
                        organism = synthetic construct
SEQUENCE: 3
GFTFSSYG                                                                 8

SEQ ID NO: 4            moltype =    length =
SEQUENCE: 4
000

SEQ ID NO: 5            moltype =    length =
SEQUENCE: 5
000

SEQ ID NO: 6            moltype =    length =
SEQUENCE: 6
000

SEQ ID NO: 7            moltype =    length =
SEQUENCE: 7
000

SEQ ID NO: 8            moltype =    length =
SEQUENCE: 8
000

SEQ ID NO: 9            moltype =    length =
SEQUENCE: 9
000

SEQ ID NO: 10           moltype = AA  length = 17
FEATURE                 Location/Qualifiers
source                  1..17
                        mol_type = protein
                        organism = synthetic construct
SEQUENCE: 10
DLLVRFLEWS HYYGMDV                                                       17

SEQ ID NO: 11           moltype =    length =
SEQUENCE: 11
000

SEQ ID NO: 12           moltype =    length =
SEQUENCE: 12
000

SEQ ID NO: 13           moltype =    length =
SEQUENCE: 13
000

SEQ ID NO: 14           moltype = AA  length = 8
FEATURE                 Location/Qualifiers
source                  1..8
                        mol_type = protein
                        organism = synthetic construct
VARIANT                 1
                        note = M or Q
SEQUENCE: 14
XHGGQGPT                                                                 8

SEQ ID NO: 15           moltype = AA  length = 8
FEATURE                 Location/Qualifiers
```

| | | |
|---|---|---|
| source | 1..8<br>mol_type = protein<br>organism = synthetic construct | |
| VARIANT | 1<br>note = M or Q | |
| SEQUENCE: 15 | | |
| XHGGQGPT | | 8 |
| SEQ ID NO: 16<br>SEQUENCE: 16<br>000 | moltype = length = | |
| SEQ ID NO: 17<br>SEQUENCE: 17<br>000 | moltype = length = | |
| SEQ ID NO: 18<br>SEQUENCE: 18<br>000 | moltype = length = | |
| SEQ ID NO: 19<br>SEQUENCE: 19<br>000 | moltype = length = | |
| SEQ ID NO: 20<br>SEQUENCE: 20<br>000 | moltype = length = | |
| SEQ ID NO: 21<br>SEQUENCE: 21<br>000 | moltype = length = | |
| SEQ ID NO: 22<br>SEQUENCE: 22<br>000 | moltype = length = | |
| SEQ ID NO: 23<br>SEQUENCE: 23<br>000 | moltype = length = | |
| SEQ ID NO: 24<br>SEQUENCE: 24<br>000 | moltype = length = | |
| SEQ ID NO: 25<br>SEQUENCE: 25<br>000 | moltype = length = | |
| SEQ ID NO: 26<br>SEQUENCE: 26<br>000 | moltype = length = | |
| SEQ ID NO: 27<br>SEQUENCE: 27<br>000 | moltype = length = | |
| SEQ ID NO: 28<br>SEQUENCE: 28<br>000 | moltype = length = | |
| SEQ ID NO: 29<br>SEQUENCE: 29<br>000 | moltype = length = | |
| SEQ ID NO: 30<br>SEQUENCE: 30<br>000 | moltype = length = | |
| SEQ ID NO: 31<br>SEQUENCE: 31<br>000 | moltype = length = | |
| SEQ ID NO: 32<br>SEQUENCE: 32<br>000 | moltype = length = | |
| SEQ ID NO: 33<br>SEQUENCE: 33<br>000 | moltype = length = | |

| | | |
|---|---|---|
| SEQ ID NO: 34 SEQUENCE: 34 000 | moltype = | length = |
| SEQ ID NO: 35 SEQUENCE: 35 000 | moltype = | length = |
| SEQ ID NO: 36 SEQUENCE: 36 000 | moltype = | length = |
| SEQ ID NO: 37 SEQUENCE: 37 000 | moltype = | length = |
| SEQ ID NO: 38 SEQUENCE: 38 000 | moltype = | length = |
| SEQ ID NO: 39 SEQUENCE: 39 000 | moltype = | length = |
| SEQ ID NO: 40 SEQUENCE: 40 000 | moltype = | length = |
| SEQ ID NO: 41 SEQUENCE: 41 000 | moltype = | length = |
| SEQ ID NO: 42 SEQUENCE: 42 000 | moltype = | length = |
| SEQ ID NO: 43 SEQUENCE: 43 000 | moltype = | length = |
| SEQ ID NO: 44 SEQUENCE: 44 000 | moltype = | length = |
| SEQ ID NO: 45 SEQUENCE: 45 000 | moltype = | length = |
| SEQ ID NO: 46 SEQUENCE: 46 000 | moltype = | length = |
| SEQ ID NO: 47 SEQUENCE: 47 000 | moltype = | length = |
| SEQ ID NO: 48 SEQUENCE: 48 000 | moltype = | length = |
| SEQ ID NO: 49 SEQUENCE: 49 000 | moltype = | length = |
| SEQ ID NO: 50 SEQUENCE: 50 000 | moltype = | length = |
| SEQ ID NO: 51 SEQUENCE: 51 000 | moltype = | length = |
| SEQ ID NO: 52 FEATURE source  SEQUENCE: 52 | moltype = AA   length = 352 Location/Qualifiers 1..352 mol_type = protein organism = Homo sapiens | |

```
NENSEQKENV EKEGLCNACT WRQNTKSSRI EAIKIQILSK LRLETAPNIS KDVIRQLLPK    60
APPLRELIDQ YDVQRDDSSD GSLEDDDYHA TTETIITMPT ESDFLMQVDG KPKCCFFKFS   120
SKIQYNKVVK AQLWIYLRPV ETPTTVFVQI LRLIKPMKDG TRYTGIRSLK LDMNPGTGIW   180
QSIDVKTVLQ NWLKQPESNL GIEIKALDEN GHDLAVTFPG PGEDGLNPFL EVKVTDTPKR   240
SRRDFGLDCD EHSTESRCCR YPLTVDFEAF GWDWIIAPKR YKANYCSGEC EFVFLQKYPH   300
THLVHQANPR GSAGPCCTPT KMSPINMLYF NGKEQIIYGK IPAMVVDRCG CS           352

SEQ ID NO: 53         moltype = AA  length = 352
FEATURE               Location/Qualifiers
source                1..352
                      mol_type = protein
                      organism = Rattus sp.
SEQUENCE: 53
NEDSEREANV EKEGLCNACA WRQNTRYSRI EAIKIQILSK LRLETAPNIS KDAIRQLLPR    60
APPLRELIDQ YDVQRDDSSD GSLEDDDYHA TTETIITMPT ESDFLMQADG KPKCCFFKFS   120
SKIQYNKVVK AQLWIYLRAV KTPTTVFVQI LRLIKPMKDG TRYTGIRSLK LDMSPGTGIW   180
QSIDVKTVLQ NWLKQPESNL GIEIKALDEN GHDLAVTFPG PGEDGLNPFL EVKVTDTPKR   240
SRRDFGLDCD EHSTESRCCR YPLTVDFEAF GWDWIIAPKR YKANYCSGEC EFVFLQKYPH   300
THLVHQANPR GSAGPCCTPT KMSPINMLYF NGKEQIIYGK IPAMVVDRCG CS           352

SEQ ID NO: 54         moltype = AA  length = 352
FEATURE               Location/Qualifiers
source                1..352
                      mol_type = protein
                      organism = Mus sp.
SEQUENCE: 54
NEGSEREENV EKEGLCNACA WRQNTRYSRI EAIKIQILSK LRLETAPNIS KDAIRQLLPR    60
APPLRELIDQ YDVQRDDSSD GSLEDDDYHA TTETIITMPT ESDFLMQADG KPKCCFFKFS   120
SKIQYNKVVK AQLWIYLRPV KTPTTVFVQI LRLIKPMKDG TRYTGIRSLK LDMSPGTGIW   180
QSIDVKTVLQ NWLKQPESNL GIEIKALDEN GHDLAVTFPG PGEDGLNPFL EVKVTDTPKR   240
SRRDFGLDCD EHSTESRCCR YPLTVDFEAF GWDWIIAPKR YKANYCSGEC EFVFLQKYPH   300
THLVHQANPR GSAGPCCTPT KMSPINMLYF NGKEQIIYGK IPAMVVDRCG CS           352

SEQ ID NO: 55         moltype = AA  length = 277
FEATURE               Location/Qualifiers
source                1..277
                      mol_type = protein
                      organism = Macaca fascicularis
SEQUENCE: 55
NENSEQKENV EKEGLCNACT WRQNTKSSRI EAIKIQILSK LRLETAPNIS KDAIRQLLPK    60
APPLRELIDQ YDVQRDDSSD GSLEDDDYHA TTETIITMPT ESDFLMQVDG KPKCCFFKFS   120
SKIQYNKVVK AQLWIYLRPV ETPTTVFVQI LRLIKPMKDG TRYTGIRSLK LDMNPGTGIW   180
QSIDVKTVLQ NWLKQPESNL GIEIKALDEN GHDLAVTFPG PGEDGLNPFL EVKVTDTPKR   240
SRRDFGLDCD EHSTESRCCR YPLTVDFEAF GWDWIIA                            277

SEQ ID NO: 56         moltype =    length =
SEQUENCE: 56
000

SEQ ID NO: 57         moltype = AA  length = 24
FEATURE               Location/Qualifiers
source                1..24
                      mol_type = protein
                      organism = Homo sapiens
SEQUENCE: 57
FVQILRLIKP MKDGTRYTGI RSLK                                           24

SEQ ID NO: 58         moltype = AA  length = 5
FEATURE               Location/Qualifiers
source                1..5
                      mol_type = protein
                      organism = synthetic construct
SEQUENCE: 58
CPPCP                                                                 5

SEQ ID NO: 59         moltype =    length =
SEQUENCE: 59
000

SEQ ID NO: 60         moltype =    length =
SEQUENCE: 60
000

SEQ ID NO: 61         moltype =    length =
SEQUENCE: 61
000

SEQ ID NO: 62         moltype = AA  length = 33
FEATURE               Location/Qualifiers
```

```
source                  1..33
                        mol_type = protein
                        organism = synthetic construct
SEQUENCE: 62
PKAPPLRELI DQYDVQRDDS SDGSLEDDDY HAT                            33

SEQ ID NO: 63           moltype = AA  length = 34
FEATURE                 Location/Qualifiers
source                  1..34
                        mol_type = protein
                        organism = synthetic construct
SEQUENCE: 63
GLNPFLEVKV TDTPKRSRRD FGLDCDEHST ESRC                           34

SEQ ID NO: 64           moltype =     length =
SEQUENCE: 64
000

SEQ ID NO: 65           moltype =     length =
SEQUENCE: 65
000

SEQ ID NO: 66           moltype =     length =
SEQUENCE: 66
000

SEQ ID NO: 67           moltype =     length =
SEQUENCE: 67
000

SEQ ID NO: 68           moltype =     length =
SEQUENCE: 68
000

SEQ ID NO: 69           moltype =     length =
SEQUENCE: 69
000

SEQ ID NO: 70           moltype =     length =
SEQUENCE: 70
000

SEQ ID NO: 71           moltype =     length =
SEQUENCE: 71
000

SEQ ID NO: 72           moltype =     length =
SEQUENCE: 72
000

SEQ ID NO: 73           moltype =     length =
SEQUENCE: 73
000

SEQ ID NO: 74           moltype =     length =
SEQUENCE: 74
000

SEQ ID NO: 75           moltype =     length =
SEQUENCE: 75
000

SEQ ID NO: 76           moltype =     length =
SEQUENCE: 76
000

SEQ ID NO: 77           moltype =     length =
SEQUENCE: 77
000

SEQ ID NO: 78           moltype =     length =
SEQUENCE: 78
000

SEQ ID NO: 79           moltype =     length =
SEQUENCE: 79
000

SEQ ID NO: 80           moltype =     length =
```

-continued

| | | |
|---|---|---|
| SEQUENCE: 80 000 | | |
| SEQ ID NO: 81 SEQUENCE: 81 000 | moltype = | length = |
| SEQ ID NO: 82 SEQUENCE: 82 000 | moltype = | length = |
| SEQ ID NO: 83 SEQUENCE: 83 000 | moltype = | length = |
| SEQ ID NO: 84 SEQUENCE: 84 000 | moltype = | length = |
| SEQ ID NO: 85 SEQUENCE: 85 000 | moltype = | length = |
| SEQ ID NO: 86 SEQUENCE: 86 000 | moltype = | length = |
| SEQ ID NO: 87 SEQUENCE: 87 000 | moltype = | length = |
| SEQ ID NO: 88 SEQUENCE: 88 000 | moltype = | length = |
| SEQ ID NO: 89 SEQUENCE: 89 000 | moltype = | length = |
| SEQ ID NO: 90 SEQUENCE: 90 000 | moltype = | length = |
| SEQ ID NO: 91 SEQUENCE: 91 000 | moltype = | length = |
| SEQ ID NO: 92 SEQUENCE: 92 000 | moltype = | length = |
| SEQ ID NO: 93 SEQUENCE: 93 000 | moltype = | length = |
| SEQ ID NO: 94 SEQUENCE: 94 000 | moltype = | length = |
| SEQ ID NO: 95 SEQUENCE: 95 000 | moltype = | length = |
| SEQ ID NO: 96 SEQUENCE: 96 000 | moltype = | length = |
| SEQ ID NO: 97 SEQUENCE: 97 000 | moltype = | length = |
| SEQ ID NO: 98 SEQUENCE: 98 000 | moltype = | length = |
| SEQ ID NO: 99 SEQUENCE: 99 000 | moltype = | length = |

| | | |
|---|---|---|
| SEQ ID NO: 100<br>SEQUENCE: 100<br>000 | moltype = | length = |
| SEQ ID NO: 101<br>SEQUENCE: 101<br>000 | moltype = | length = |
| SEQ ID NO: 102<br>SEQUENCE: 102<br>000 | moltype = | length = |
| SEQ ID NO: 103<br>SEQUENCE: 103<br>000 | moltype = | length = |
| SEQ ID NO: 104<br>SEQUENCE: 104<br>000 | moltype = | length = |
| SEQ ID NO: 105<br>SEQUENCE: 105<br>000 | moltype = | length = |
| SEQ ID NO: 106<br>SEQUENCE: 106<br>000 | moltype = | length = |
| SEQ ID NO: 107<br>SEQUENCE: 107<br>000 | moltype = | length = |
| SEQ ID NO: 108<br>SEQUENCE: 108<br>000 | moltype = | length = |
| SEQ ID NO: 109<br>SEQUENCE: 109<br>000 | moltype = | length = |
| SEQ ID NO: 110<br>SEQUENCE: 110<br>000 | moltype = | length = |
| SEQ ID NO: 111<br>SEQUENCE: 111<br>000 | moltype = | length = |
| SEQ ID NO: 112<br>SEQUENCE: 112<br>000 | moltype = | length = |
| SEQ ID NO: 113<br>SEQUENCE: 113<br>000 | moltype = | length = |
| SEQ ID NO: 114<br>SEQUENCE: 114<br>000 | moltype = | length = |
| SEQ ID NO: 115<br>SEQUENCE: 115<br>000 | moltype = | length = |
| SEQ ID NO: 116<br>FEATURE<br>source<br><br>SEQUENCE: 116<br>EGTFTSD | moltype = AA   length = 7<br>Location/Qualifiers<br>1..7<br>mol_type = protein<br>organism = synthetic construct | 7 |
| SEQ ID NO: 117<br>FEATURE<br>source<br><br><br>VARIANT | moltype = AA   length = 9<br>Location/Qualifiers<br>1..9<br>mol_type = protein<br>organism = synthetic construct<br>2<br>note = Any amino acid | |

-continued

| | | |
|---|---|---|
| VARIANT | 3 | |
| | note = Any amino acid | |
| VARIANT | 5 | |
| | note = Any amino acid | |
| VARIANT | 8 | |
| | note = Any amino acid | |
| SEQUENCE: 117 | | |
| HXXGXFTXD | | 9 |
| | | |
| SEQ ID NO: 118 | moltype = AA  length = 6 | |
| FEATURE | Location/Qualifiers | |
| source | 1..6 | |
| | mol_type = protein | |
| | organism = Homo sapiens | |
| SEQUENCE: 118 | | |
| KALDEN | | 6 |
| | | |
| SEQ ID NO: 119 | moltype =   length = | |
| SEQUENCE: 119 | | |
| 000 | | |
| | | |
| SEQ ID NO: 120 | moltype =   length = | |
| SEQUENCE: 120 | | |
| 000 | | |
| | | |
| SEQ ID NO: 121 | moltype =   length = | |
| SEQUENCE: 121 | | |
| 000 | | |
| | | |
| SEQ ID NO: 122 | moltype =   length = | |
| SEQUENCE: 122 | | |
| 000 | | |
| | | |
| SEQ ID NO: 123 | moltype =   length = | |
| SEQUENCE: 123 | | |
| 000 | | |
| | | |
| SEQ ID NO: 124 | moltype =   length = | |
| SEQUENCE: 124 | | |
| 000 | | |
| | | |
| SEQ ID NO: 125 | moltype =   length = | |
| SEQUENCE: 125 | | |
| 000 | | |
| | | |
| SEQ ID NO: 126 | moltype =   length = | |
| SEQUENCE: 126 | | |
| 000 | | |
| | | |
| SEQ ID NO: 127 | moltype =   length = | |
| SEQUENCE: 127 | | |
| 000 | | |
| | | |
| SEQ ID NO: 128 | moltype =   length = | |
| SEQUENCE: 128 | | |
| 000 | | |
| | | |
| SEQ ID NO: 129 | moltype =   length = | |
| SEQUENCE: 129 | | |
| 000 | | |
| | | |
| SEQ ID NO: 130 | moltype =   length = | |
| SEQUENCE: 130 | | |
| 000 | | |
| | | |
| SEQ ID NO: 131 | moltype =   length = | |
| SEQUENCE: 131 | | |
| 000 | | |
| | | |
| SEQ ID NO: 132 | moltype =   length = | |
| SEQUENCE: 132 | | |
| 000 | | |
| | | |
| SEQ ID NO: 133 | moltype =   length = | |
| SEQUENCE: 133 | | |
| 000 | | |
| | | |
| SEQ ID NO: 134 | moltype = AA  length = 109 | |
| FEATURE | Location/Qualifiers | |

```
source                       1..109
                             mol_type = protein
                             organism = unidentified
SEQUENCE: 134
DPFGLDCDEHS TESRCCRYPL TVDFEAFGWD WIIAPKRYKA NYCSGECEFV FLQKYPHTHL    60
VHQANPRGSA GPCCTPTKMS PINMLYFNGK EQIIYGKIPA MVVDRCGCS                109

SEQ ID NO: 135               moltype = AA   length = 380
FEATURE                      Location/Qualifiers
source                       1..380
                             mol_type = protein
                             organism = synthetic construct
SEQUENCE: 135
MDMRVPAQLL GLLLLWFSGV LGHHHHHHNE NSEQKENVEK EGLCNACTWR QNTKSSRIEA     60
IKIQILSKLR LETAPNISKD VIRQLLPKAP PLRELIDQYD VQRDDSSDGS LEDDDYHATT    120
ETIITMPTES DFLMQVDGKP KCCFFKFSSK IQYNKVVKAQ LWIYLRPVET PTTVFVQILR    180
LIKPMKDGTR YTGIRSLKLD MNPGTGIWQS IDVKTVLQNW LKQPESNLGI EIKALDENGH    240
DLAVTFPGPG EDGLNPFLEV KVTDTPKRSR RDFGLDCDEH STESRCCRYP LTVDFEAFGW    300
DWIIAPKRYK ANYCSGECEF VFLQKYPHTH LVHQANPRGS AGPCCTPTKM SPINMLYFNG    360
KEQIIYGKIP AMVVDRCGCS                                                380

SEQ ID NO: 136               moltype = AA   length = 22
FEATURE                      Location/Qualifiers
source                       1..22
                             mol_type = protein
                             organism = Homo sapiens
SEQUENCE: 136
MDMRVPAQLL GLLLLWFSGV LG                                              22

SEQ ID NO: 137               moltype = AA   length = 239
FEATURE                      Location/Qualifiers
source                       1..239
                             mol_type = protein
                             organism = Homo sapiens
SEQUENCE: 137
NENSEQKENV EKEGLCNACT WRQNTKSSRI EAIKIQILSK LRLETAPNIS KDVIRQLLPK     60
APPLRELIDQ YDVQRDDSSD GSLEDDDYHA TTETIITMPT ESDFLMQVDG KPKCCFFKFS    120
SKIQYNKVVK AQLWIYLRPV ETPTTVFVQI LRLIKPMKDG TRYTGIRSLK LDMNPGTGIW    180
QSIDVKTVLQ NWLKQPESNL GIEIKALDEN GHDLAVTFPG PGEDGLNPFL EVKVTDTPK     239

SEQ ID NO: 138               moltype = AA   length = 109
FEATURE                      Location/Qualifiers
source                       1..109
                             mol_type = protein
                             organism = Homo sapiens
SEQUENCE: 138
DPFGLDCDEHS TESRCCRYPL TVDFEAFGWD WIIAPKRYKA NYCSGECEFV FLQKYPHTHL    60
VHQANPRGSA GPCCTPTKMS PINMLYFNGK EQIIYGKIPA MVVDRCGCS                109

SEQ ID NO: 139               moltype = DNA   length = 1146
FEATURE                      Location/Qualifiers
source                       1..1146
                             mol_type = genomic DNA
                             organism = Homo sapiens
SEQUENCE: 139
atggacatga gagtgcccgc ccagctgctg ggacttctgc tgctgtggtt tagcggcgtg     60
ctgggccacc accaccatca ccacaacgag aacagcgagc agaaagaaaa cgtggaaaaa    120
gagggcctgt gcaacgcctg cacctggcgg cagaatacca gagcagccg gatcgaggcc    180
atcaagatcc agatcctgag caagctgcgg ctggaaaccg cccccaacat cagcaaggac    240
gtgatcagac agctgctgcc caaggcccca cccctgagag agctgatcga ccagtacgac    300
gtgcagcggg acgatagctc cgatggcagc ctggaagatg acgactacca cgccaccacc    360
gagacaatca tcaccatgcc taccgagagc gacttcctga tgcaagtgga cggcaagccc    420
aagtgctgct tcttcaagtt cagctctaag atccagtaca acaaggtcgt gaaggccag     480
ctgtggatct acctgcggcc cgtggaaacc cccaccgtg tgtttgtgca gatcctgcgg     540
ctgatcaagc ccatgaagga cggcacccgg tacaccggca tccggtccct gaagctggac    600
atgaatcccg gcacaggcat ctggcagagc atcgacgtga aaccgtgct gcagaactgg    660
ctgaagcagc ccgagagcaa cctgggcatc gagatcaagg ccctgacga gaacggccac    720
gacctggccg tgacatttcc tggccctggc gaggatggcc tgaacccatt cctggaagtg    780
aaagtgaccg acacccccaa gcggagcaga cgggatttcg gcctggattg cgacgagcac    840
agcaccgagt ccagatgctg cagataccc ctgaccgtgg acttcgaggc cttcggctgg    900
gactggatca ttgcccccaa gagatacaag gccaactact gcagcggcga gtgcgagttc    960
gtgttcctgc agaagtaccc ccacacccac ctggtgcatc aggccaaccc tagaggctct   1020
gccgccctt gctgtacccc taccaagatg agccccatca catgctgta cttcaacggc    1080
aaagagcaga tcatctacgg caagatcccc gccatgtgg tggacagatg cggctgcagc   1140
tgatga                                                             1146

SEQ ID NO: 140               moltype =    length =
SEQUENCE: 140
000
```

| | | |
|---|---|---|
| SEQ ID NO: 141 SEQUENCE: 141 000 | moltype = | length = |
| SEQ ID NO: 142 SEQUENCE: 142 000 | moltype = | length = |
| SEQ ID NO: 143 SEQUENCE: 143 000 | moltype = | length = |
| SEQ ID NO: 144 SEQUENCE: 144 000 | moltype = | length = |
| SEQ ID NO: 145 SEQUENCE: 145 000 | moltype = | length = |
| SEQ ID NO: 146 SEQUENCE: 146 000 | moltype = | length = |
| SEQ ID NO: 147 SEQUENCE: 147 000 | moltype = | length = |
| SEQ ID NO: 148 SEQUENCE: 148 000 | moltype = | length = |
| SEQ ID NO: 149 SEQUENCE: 149 000 | moltype = | length = |
| SEQ ID NO: 150 SEQUENCE: 150 000 | moltype = | length = |
| SEQ ID NO: 151 SEQUENCE: 151 000 | moltype = | length = |
| SEQ ID NO: 152 SEQUENCE: 152 000 | moltype = | length = |
| SEQ ID NO: 153 SEQUENCE: 153 000 | moltype = | length = |
| SEQ ID NO: 154 SEQUENCE: 154 000 | moltype = | length = |
| SEQ ID NO: 155 SEQUENCE: 155 000 | moltype = | length = |
| SEQ ID NO: 156 SEQUENCE: 156 000 | moltype = | length = |
| SEQ ID NO: 157 SEQUENCE: 157 000 | moltype = | length = |
| SEQ ID NO: 158 SEQUENCE: 158 000 | moltype = | length = |
| SEQ ID NO: 159 SEQUENCE: 159 000 | moltype = | length = |
| SEQ ID NO: 160 SEQUENCE: 160 | moltype = | length = |

000

SEQ ID NO: 161         moltype =     length =
SEQUENCE: 161
000

SEQ ID NO: 162         moltype =     length =
SEQUENCE: 162
000

SEQ ID NO: 163         moltype =     length =
SEQUENCE: 163
000

SEQ ID NO: 164         moltype =     length =
SEQUENCE: 164
000

SEQ ID NO: 165         moltype =     length =
SEQUENCE: 165
000

SEQ ID NO: 166         moltype =     length =
SEQUENCE: 166
000

SEQ ID NO: 167         moltype =     length =
SEQUENCE: 167
000

SEQ ID NO: 168         moltype =     length =
SEQUENCE: 168
000

SEQ ID NO: 169         moltype =     length =
SEQUENCE: 169
000

SEQ ID NO: 170         moltype =     length =
SEQUENCE: 170
000

SEQ ID NO: 171         moltype =     length =
SEQUENCE: 171
000

SEQ ID NO: 172         moltype =     length =
SEQUENCE: 172
000

SEQ ID NO: 173         moltype =     length =
SEQUENCE: 173
000

SEQ ID NO: 174         moltype =     length =
SEQUENCE: 174
000

SEQ ID NO: 175         moltype =     length =
SEQUENCE: 175
000

SEQ ID NO: 176         moltype =     length =
SEQUENCE: 176
000

SEQ ID NO: 177         moltype =     length =
SEQUENCE: 177
000

SEQ ID NO: 178         moltype =     length =
SEQUENCE: 178
000

SEQ ID NO: 179         moltype =     length =
SEQUENCE: 179
000

SEQ ID NO: 180         moltype =     length =

| | | |
|---|---|---|
| SEQUENCE: 180 000 | | |
| SEQ ID NO: 181 SEQUENCE: 181 000 | moltype = | length = |
| SEQ ID NO: 182 SEQUENCE: 182 000 | moltype = | length = |
| SEQ ID NO: 183 SEQUENCE: 183 000 | moltype = | length = |
| SEQ ID NO: 184 SEQUENCE: 184 000 | moltype = | length = |
| SEQ ID NO: 185 SEQUENCE: 185 000 | moltype = | length = |
| SEQ ID NO: 186 SEQUENCE: 186 000 | moltype = | length = |
| SEQ ID NO: 187 SEQUENCE: 187 000 | moltype = | length = |
| SEQ ID NO: 188 SEQUENCE: 188 000 | moltype = | length = |
| SEQ ID NO: 189 SEQUENCE: 189 000 | moltype = | length = |
| SEQ ID NO: 190 SEQUENCE: 190 000 | moltype = | length = |
| SEQ ID NO: 191 SEQUENCE: 191 000 | moltype = | length = |
| SEQ ID NO: 192 SEQUENCE: 192 000 | moltype = | length = |
| SEQ ID NO: 193 SEQUENCE: 193 000 | moltype = | length = |
| SEQ ID NO: 194 SEQUENCE: 194 000 | moltype = | length = |
| SEQ ID NO: 195 SEQUENCE: 195 000 | moltype = | length = |
| SEQ ID NO: 196 SEQUENCE: 196 000 | moltype = | length = |
| SEQ ID NO: 197 SEQUENCE: 197 000 | moltype = | length = |
| SEQ ID NO: 198 SEQUENCE: 198 000 | moltype = | length = |
| SEQ ID NO: 199 SEQUENCE: 199 000 | moltype = | length = |

| | | |
|---|---|---|
| SEQ ID NO: 200<br>SEQUENCE: 200<br>000 | moltype =    length = | |
| SEQ ID NO: 201<br>FEATURE<br>source | moltype = AA   length = 5<br>Location/Qualifiers<br>1..5<br>mol_type = protein<br>organism = synthetic construct | |
| SEQUENCE: 201<br>SYGMS | | 5 |
| SEQ ID NO: 202<br>FEATURE<br>source<br><br>VARIANT | moltype = AA   length = 16<br>Location/Qualifiers<br>1..16<br>mol_type = protein<br>organism = synthetic construct<br>8<br>note = T or A | |
| SEQUENCE: 202<br>SFTGSGGXYY PDSVKG | | 16 |
| SEQ ID NO: 203<br>FEATURE<br>source | moltype = AA   length = 17<br>Location/Qualifiers<br>1..17<br>mol_type = protein<br>organism = synthetic construct | |
| SEQUENCE: 203<br>DLLIRFLEWS HYYGMDV | | 17 |
| SEQ ID NO: 204<br>FEATURE<br>source | moltype = AA   length = 16<br>Location/Qualifiers<br>1..16<br>mol_type = protein<br>organism = synthetic construct | |
| SEQUENCE: 204<br>RSSQSLLHSS GHNFLH | | 16 |
| SEQ ID NO: 205<br>FEATURE<br>source | moltype = AA   length = 7<br>Location/Qualifiers<br>1..7<br>mol_type = protein<br>organism = synthetic construct | |
| SEQUENCE: 205<br>EVSNRVS | | 7 |
| SEQ ID NO: 206<br>FEATURE<br>source<br><br>VARIANT<br><br>VARIANT | moltype = AA   length = 9<br>Location/Qualifiers<br>1..9<br>mol_type = protein<br>organism = synthetic construct<br>1<br>note = M or Q<br>8<br>note = P or G | |
| SEQUENCE: 206<br>XQQTQYPXT | | 9 |
| SEQ ID NO: 207<br>FEATURE<br>source | moltype = AA   length = 17<br>Location/Qualifiers<br>1..17<br>mol_type = protein<br>organism = synthetic construct | |
| SEQUENCE: 207<br>SITGSGGETY YPDSVKG | | 17 |
| SEQ ID NO: 208<br>FEATURE<br>source | moltype = AA   length = 17<br>Location/Qualifiers<br>1..17<br>mol_type = protein<br>organism = synthetic construct | |
| SEQUENCE: 208<br>DLLVRFLEWS HYYGMDV | | 17 |
| SEQ ID NO: 209<br>SEQUENCE: 209<br>000 | moltype =    length = | |
| SEQ ID NO: 210 | moltype = AA   length = 9 | |

```
FEATURE                     Location/Qualifiers
source                      1..9
                            mol_type = protein
                            organism = synthetic construct
VARIANT                     1
                            note = M or Q
SEQUENCE: 210
XQATQFPRP                                                                        9

SEQ ID NO: 211              moltype = AA  length = 17
FEATURE                     Location/Qualifiers
source                      1..17
                            mol_type = protein
                            organism = synthetic construct
SEQUENCE: 211
SINPSGGTTY YAQKFKG                                                              17

SEQ ID NO: 212              moltype = AA  length = 16
FEATURE                     Location/Qualifiers
source                      1..16
                            mol_type = protein
                            organism = synthetic construct
VARIANT                     2
                            note = S or A
VARIANT                     6
                            note = I or L
VARIANT                     10
                            note = S or L
VARIANT                     11
                            note = G or A
SEQUENCE: 212
RXSQSXLHSX XHNFLH                                                               16

SEQ ID NO: 213              moltype = AA  length = 7
FEATURE                     Location/Qualifiers
source                      1..7
                            mol_type = protein
                            organism = synthetic construct
VARIANT                     2
                            note = A or V
VARIANT                     5
                            note = R or L
VARIANT                     6
                            note = V or A
SEQUENCE: 213
EXSNXXS                                                                          7

SEQ ID NO: 214              moltype = AA  length = 9
FEATURE                     Location/Qualifiers
source                      1..9
                            mol_type = protein
                            organism = synthetic construct
VARIANT                     3
                            note = Q or Y
SEQUENCE: 214
QQXTQYPPT                                                                        9

SEQ ID NO: 215              moltype = AA  length = 17
FEATURE                     Location/Qualifiers
source                      1..17
                            mol_type = protein
                            organism = synthetic construct
SEQUENCE: 215
DLLVRFLEWS HYYGMDV                                                              17

SEQ ID NO: 216              moltype = AA  length = 16
FEATURE                     Location/Qualifiers
source                      1..16
                            mol_type = protein
                            organism = synthetic construct
SEQUENCE: 216
RSSQSLLHSS GHNFLH                                                               16

SEQ ID NO: 217              moltype = AA  length = 7
FEATURE                     Location/Qualifiers
source                      1..7
                            mol_type = protein
                            organism = synthetic construct
SEQUENCE: 217
```

```
ETSNRAP                                                                          7

SEQ ID NO: 218         moltype = AA  length = 9
FEATURE                Location/Qualifiers
source                 1..9
                       mol_type = protein
                       organism = synthetic construct
SEQUENCE: 218
MQATQFPRP                                                                        9

SEQ ID NO: 219         moltype = AA  length = 16
FEATURE                Location/Qualifiers
source                 1..16
                       mol_type = protein
                       organism = synthetic construct
SEQUENCE: 219
SFTGSGGTYY PDSVKG                                                               16

SEQ ID NO: 220         moltype = AA  length = 17
FEATURE                Location/Qualifiers
source                 1..17
                       mol_type = protein
                       organism = synthetic construct
SEQUENCE: 220
DLLIRFLEWS HYYGMDV                                                              17

SEQ ID NO: 221         moltype =     length =
SEQUENCE: 221
000

SEQ ID NO: 222         moltype = AA  length = 7
FEATURE                Location/Qualifiers
source                 1..7
                       mol_type = protein
                       organism = synthetic construct
SEQUENCE: 222
EVSNRVS                                                                          7

SEQ ID NO: 223         moltype = AA  length = 9
FEATURE                Location/Qualifiers
source                 1..9
                       mol_type = protein
                       organism = synthetic construct
SEQUENCE: 223
MQQTQYPPT                                                                        9

SEQ ID NO: 224         moltype = AA  length = 9
FEATURE                Location/Qualifiers
source                 1..9
                       mol_type = protein
                       organism = synthetic construct
SEQUENCE: 224
QQATQFPRP                                                                        9

SEQ ID NO: 225         moltype = AA  length = 9
FEATURE                Location/Qualifiers
source                 1..9
                       mol_type = protein
                       organism = synthetic construct
SEQUENCE: 225
QQQTQYPPT                                                                        9

SEQ ID NO: 226         moltype = AA  length = 16
FEATURE                Location/Qualifiers
source                 1..16
                       mol_type = protein
                       organism = synthetic construct
SEQUENCE: 226
SFTGSGGAYY PDSVKG                                                               16

SEQ ID NO: 227         moltype = AA  length = 9
FEATURE                Location/Qualifiers
source                 1..9
                       mol_type = protein
                       organism = synthetic construct
SEQUENCE: 227
QQQTQYPGT                                                                        9

SEQ ID NO: 228         moltype = AA  length = 7
```

```
FEATURE                     Location/Qualifiers
source                      1..7
                            mol_type = protein
                            organism = synthetic construct
SEQUENCE: 228
GFTFTSY                                                                7

SEQ ID NO: 229              moltype = AA  length = 6
FEATURE                     Location/Qualifiers
source                      1..6
                            mol_type = protein
                            organism = synthetic construct
SEQUENCE: 229
TGSGGE                                                                 6

SEQ ID NO: 230              moltype = AA  length = 15
FEATURE                     Location/Qualifiers
source                      1..15
                            mol_type = protein
                            organism = synthetic construct
SEQUENCE: 230
LLVRFLEWSH YYGMD                                                       15

SEQ ID NO: 231              moltype = AA  length = 12
FEATURE                     Location/Qualifiers
source                      1..12
                            mol_type = protein
                            organism = synthetic construct
SEQUENCE: 231
SQSLLHSSGH NF                                                          12

SEQ ID NO: 232              moltype =     length =
SEQUENCE: 232
000

SEQ ID NO: 233              moltype = AA  length = 6
FEATURE                     Location/Qualifiers
source                      1..6
                            mol_type = protein
                            organism = synthetic construct
SEQUENCE: 233
ATQFPR                                                                 6

SEQ ID NO: 234              moltype = AA  length = 7
FEATURE                     Location/Qualifiers
source                      1..7
                            mol_type = protein
                            organism = synthetic construct
SEQUENCE: 234
GFTFSSY                                                                7

SEQ ID NO: 235              moltype = AA  length = 5
FEATURE                     Location/Qualifiers
source                      1..5
                            mol_type = protein
                            organism = synthetic construct
SEQUENCE: 235
TGSGG                                                                  5

SEQ ID NO: 236              moltype = AA  length = 15
FEATURE                     Location/Qualifiers
source                      1..15
                            mol_type = protein
                            organism = synthetic construct
SEQUENCE: 236
LLIRFLEWSH YYGMD                                                       15

SEQ ID NO: 237              moltype = AA  length = 12
FEATURE                     Location/Qualifiers
source                      1..12
                            mol_type = protein
                            organism = synthetic construct
SEQUENCE: 237
SQSLLHSSGH NF                                                          12

SEQ ID NO: 238              moltype =     length =
SEQUENCE: 238
000
```

-continued

| | | |
|---|---|---|
| SEQ ID NO: 239<br>FEATURE<br>source | moltype = AA  length = 6<br>Location/Qualifiers<br>1..6<br>mol_type = protein<br>organism = synthetic construct | |
| SEQUENCE: 239<br>QTQYPP | | 6 |
| SEQ ID NO: 240<br>FEATURE<br>source | moltype = AA  length = 6<br>Location/Qualifiers<br>1..6<br>mol_type = protein<br>organism = synthetic construct | |
| SEQUENCE: 240<br>QTQYPG | | 6 |
| SEQ ID NO: 241<br>SEQUENCE: 241<br>000 | moltype =   length = | |
| SEQ ID NO: 242<br>SEQUENCE: 242<br>000 | moltype =   length = | |
| SEQ ID NO: 243<br>SEQUENCE: 243<br>000 | moltype =   length = | |
| SEQ ID NO: 244<br>SEQUENCE: 244<br>000 | moltype =   length = | |
| SEQ ID NO: 245<br>SEQUENCE: 245<br>000 | moltype =   length = | |
| SEQ ID NO: 246<br>SEQUENCE: 246<br>000 | moltype =   length = | |
| SEQ ID NO: 247<br>SEQUENCE: 247<br>000 | moltype =   length = | |
| SEQ ID NO: 248<br>SEQUENCE: 248<br>000 | moltype =   length = | |
| SEQ ID NO: 249<br>SEQUENCE: 249<br>000 | moltype =   length = | |
| SEQ ID NO: 250<br>FEATURE<br>source | moltype = AA  length = 8<br>Location/Qualifiers<br>1..8<br>mol_type = protein<br>organism = synthetic construct | |
| SEQUENCE: 250<br>GFTFTSYG | | 8 |
| SEQ ID NO: 251<br>FEATURE<br>source | moltype = AA  length = 8<br>Location/Qualifiers<br>1..8<br>mol_type = protein<br>organism = synthetic construct | |
| SEQUENCE: 251<br>ITGSGGET | | 8 |
| SEQ ID NO: 252<br>FEATURE<br>source | moltype = AA  length = 19<br>Location/Qualifiers<br>1..19<br>mol_type = protein<br>organism = synthetic construct | |
| SEQUENCE: 252<br>ARDLLVRFLE WSHYYGMDV | | 19 |
| SEQ ID NO: 253<br>FEATURE<br>source | moltype = AA  length = 11<br>Location/Qualifiers<br>1..11 | |

```
                        mol_type = protein
                        organism = synthetic construct
SEQUENCE: 253
QSLLHSSGHN F                                                           11

SEQ ID NO: 254          moltype =    length =
SEQUENCE: 254
000

SEQ ID NO: 255          moltype = AA   length = 9
FEATURE                 Location/Qualifiers
source                  1..9
                        mol_type = protein
                        organism = synthetic construct
SEQUENCE: 255
MQATQFPRP                                                              9

SEQ ID NO: 256          moltype = AA   length = 7
FEATURE                 Location/Qualifiers
source                  1..7
                        mol_type = protein
                        organism = synthetic construct
SEQUENCE: 256
FTGSGGT                                                                7

SEQ ID NO: 257          moltype = AA   length = 19
FEATURE                 Location/Qualifiers
source                  1..19
                        mol_type = protein
                        organism = synthetic construct
SEQUENCE: 257
ARDLLIRFLE WSHYYGMDV                                                   19

SEQ ID NO: 258          moltype = AA   length = 11
FEATURE                 Location/Qualifiers
source                  1..11
                        mol_type = protein
                        organism = synthetic construct
SEQUENCE: 258
QSLLHSSGHN F                                                           11

SEQ ID NO: 259          moltype =    length =
SEQUENCE: 259
000

SEQ ID NO: 260          moltype = AA   length = 9
FEATURE                 Location/Qualifiers
source                  1..9
                        mol_type = protein
                        organism = synthetic construct
SEQUENCE: 260
MQQTQYPPT                                                              9

SEQ ID NO: 261          moltype = AA   length = 9
FEATURE                 Location/Qualifiers
source                  1..9
                        mol_type = protein
                        organism = synthetic construct
SEQUENCE: 261
QQQTQYPGT                                                              9

SEQ ID NO: 262          moltype = AA   length = 7
FEATURE                 Location/Qualifiers
source                  1..7
                        mol_type = protein
                        organism = synthetic construct
SEQUENCE: 262
FTGSGGA                                                                7

SEQ ID NO: 263          moltype = AA   length = 9
FEATURE                 Location/Qualifiers
source                  1..9
                        mol_type = protein
                        organism = synthetic construct
SEQUENCE: 263
QQQTQYPGT                                                              9

SEQ ID NO: 264          moltype = AA   length = 9
FEATURE                 Location/Qualifiers
```

-continued

```
source                  1..9
                        mol_type = protein
                        organism = synthetic construct
SEQUENCE: 264
QQATQFPRP                                                                    9

SEQ ID NO: 265          moltype =    length =
SEQUENCE: 265
000

SEQ ID NO: 266          moltype =    length =
SEQUENCE: 266
000

SEQ ID NO: 267          moltype =    length =
SEQUENCE: 267
000

SEQ ID NO: 268          moltype =    length =
SEQUENCE: 268
000

SEQ ID NO: 269          moltype =    length =
SEQUENCE: 269
000

SEQ ID NO: 270          moltype =    length =
SEQUENCE: 270
000

SEQ ID NO: 271          moltype =    length =
SEQUENCE: 271
000

SEQ ID NO: 272          moltype = AA   length = 17
FEATURE                 Location/Qualifiers
source                  1..17
                        mol_type = protein
                        organism = synthetic construct
VARIANT                 4
                        note = I or V
SEQUENCE: 272
DLLXRFLEWS HYYGMDV                                                          17

SEQ ID NO: 273          moltype =    length =
SEQUENCE: 273
000

SEQ ID NO: 274          moltype =    length =
SEQUENCE: 274
000

SEQ ID NO: 275          moltype = AA   length = 17
FEATURE                 Location/Qualifiers
source                  1..17
                        mol_type = protein
                        organism = synthetic construct
VARIANT                 2
                        note = F or I
VARIANT                 8
                        note = E or A
SEQUENCE: 275
SXTGSGGXTY YPDSVKG                                                          17

SEQ ID NO: 276          moltype = AA   length = 7
FEATURE                 Location/Qualifiers
source                  1..7
                        mol_type = protein
                        organism = synthetic construct
VARIANT                 6
                        note = V or A
VARIANT                 7
                        note = P or S
SEQUENCE: 276
ETSNRXX                                                                      7

SEQ ID NO: 277          moltype = AA   length = 10
FEATURE                 Location/Qualifiers
source                  1..10
```

```
                        mol_type = protein
                        organism = synthetic construct
VARIANT                 1
                        note = M or Q
VARIANT                 4
                        note = Q or A
VARIANT                 7
                        note = Y or F
VARIANT                 9
                        note = R, P, or G
VARIANT                 10
                        note = T or P
SEQUENCE: 277
XQQXTQXPXX                                                              10

SEQ ID NO: 278          moltype = AA  length = 7
FEATURE                 Location/Qualifiers
source                  1..7
                        mol_type = protein
                        organism = synthetic construct
VARIANT                 5
                        note = S or T
SEQUENCE: 278
GFTFXSY                                                                 7

SEQ ID NO: 279          moltype = AA  length = 5
FEATURE                 Location/Qualifiers
source                  1..5
                        mol_type = protein
                        organism = synthetic construct
SEQUENCE: 279
TGSGG                                                                   5

SEQ ID NO: 280          moltype = AA  length = 15
FEATURE                 Location/Qualifiers
source                  1..15
                        mol_type = protein
                        organism = synthetic construct
VARIANT                 3
                        note = I or V
SEQUENCE: 280
LLXRFLEWSH YYGMD                                                        15

SEQ ID NO: 281          moltype = AA  length = 12
FEATURE                 Location/Qualifiers
source                  1..12
                        mol_type = protein
                        organism = synthetic construct
SEQUENCE: 281
SQSLLHSSGH NF                                                           12

SEQ ID NO: 282          moltype =     length =
SEQUENCE: 282
000

SEQ ID NO: 283          moltype =     length =
SEQUENCE: 283
000

SEQ ID NO: 284          moltype = AA  length = 9
FEATURE                 Location/Qualifiers
source                  1..9
                        mol_type = protein
                        organism = synthetic construct
SEQUENCE: 284
GFTFTSSYG                                                               9

SEQ ID NO: 285          moltype = AA  length = 8
FEATURE                 Location/Qualifiers
source                  1..8
                        mol_type = protein
                        organism = synthetic construct
VARIANT                 1
                        note = F or I
VARIANT                 7
                        note = E, T, or A
SEQUENCE: 285
XTGSGGXT                                                                8
```

| | | |
|---|---|---|
| SEQ ID NO: 286 | moltype = AA   length = 19 | |
| FEATURE | Location/Qualifiers | |
| source | 1..19<br>mol_type = protein<br>organism = synthetic construct | |
| SEQUENCE: 286<br>ARDLLVRFLE WSHYYGMDV | | 19 |
| SEQ ID NO: 287 | moltype = AA   length = 11 | |
| FEATURE | Location/Qualifiers | |
| source | 1..11<br>mol_type = protein<br>organism = synthetic construct | |
| SEQUENCE: 287<br>QSLLHSSGHN F | | 11 |
| SEQ ID NO: 288 | moltype = AA   length = 9 | |
| FEATURE | Location/Qualifiers | |
| source | 1..9<br>mol_type = protein<br>organism = synthetic construct | |
| VARIANT | 1<br>note = Q or M | |
| VARIANT | 3<br>note = Q or A | |
| VARIANT | 6<br>note = Y or F | |
| VARIANT | 8<br>note = Y, P, or G | |
| VARIANT | 9<br>note = P or T | |
| SEQUENCE: 288<br>XQXTQXPXX | | 9 |
| SEQ ID NO: 289 | moltype = AA   length = 7 | |
| FEATURE | Location/Qualifiers | |
| source | 1..7<br>mol_type = protein<br>organism = synthetic construct | |
| SEQUENCE: 289<br>EVSNRVS | | 7 |
| SEQ ID NO: 290 | moltype = AA   length = 9 | |
| FEATURE | Location/Qualifiers | |
| source | 1..9<br>mol_type = protein<br>organism = synthetic construct | |
| SEQUENCE: 290<br>MQQTQYPGT | | 9 |
| SEQ ID NO: 291 | moltype = AA   length = 7 | |
| FEATURE | Location/Qualifiers | |
| source | 1..7<br>mol_type = protein<br>organism = synthetic construct | |
| VARIANT | 7<br>note = T or A | |
| SEQUENCE: 291<br>FTGSGGX | | 7 |
| SEQ ID NO: 292 | moltype = AA   length = 9 | |
| FEATURE | Location/Qualifiers | |
| source | 1..9<br>mol_type = protein<br>organism = synthetic construct | |
| VARIANT | 1<br>note = M or Q | |
| VARIANT | 8<br>note = P or G | |
| SEQUENCE: 292<br>XQQTQYPXT | | 9 |
| SEQ ID NO: 293 | moltype = AA   length = 6 | |
| FEATURE | Location/Qualifiers | |
| source | 1..6<br>mol_type = protein<br>organism = synthetic construct | |
| VARIANT | 6<br>note = P or G | |

```
SEQUENCE: 293
QTQYPX                                                                      6

SEQ ID NO: 294          moltype = AA  length = 7
FEATURE                 Location/Qualifiers
source                  1..7
                        mol_type = protein
                        organism = synthetic construct
VARIANT                 7
                        note = T or A
SEQUENCE: 294
FTGSGGX                                                                     7

SEQ ID NO: 295          moltype =     length =
SEQUENCE: 295
000

SEQ ID NO: 296          moltype = AA  length = 15
FEATURE                 Location/Qualifiers
source                  1..15
                        mol_type = protein
                        organism = synthetic construct
SEQUENCE: 296
LLIRFLEWSH YYGMD                                                           15

SEQ ID NO: 297          moltype = AA  length = 6
FEATURE                 Location/Qualifiers
source                  1..6
                        mol_type = protein
                        organism = synthetic construct
VARIANT                 6
                        note = T or A
SEQUENCE: 297
QTQYPX                                                                      6

SEQ ID NO: 298          moltype = AA  length = 9
FEATURE                 Location/Qualifiers
source                  1..9
                        mol_type = protein
                        organism = synthetic construct
SEQUENCE: 298
MQQTQYPGT                                                                   9

SEQ ID NO: 299          moltype =     length =
SEQUENCE: 299
000

SEQ ID NO: 300          moltype =     length =
SEQUENCE: 300
000

SEQ ID NO: 301          moltype =     length =
SEQUENCE: 301
000

SEQ ID NO: 302          moltype =     length =
SEQUENCE: 302
000

SEQ ID NO: 303          moltype =     length =
SEQUENCE: 303
000

SEQ ID NO: 304          moltype =     length =
SEQUENCE: 304
000

SEQ ID NO: 305          moltype =     length =
SEQUENCE: 305
000

SEQ ID NO: 306          moltype =     length =
SEQUENCE: 306
000

SEQ ID NO: 307          moltype =     length =
SEQUENCE: 307
000
```

| | | |
|---|---|---|
| SEQ ID NO: 308<br>SEQUENCE: 308<br>000 | moltype = | length = |
| SEQ ID NO: 309<br>SEQUENCE: 309<br>000 | moltype = | length = |
| SEQ ID NO: 310<br>SEQUENCE: 310<br>000 | moltype = | length = |
| SEQ ID NO: 311<br>SEQUENCE: 311<br>000 | moltype = | length = |
| SEQ ID NO: 312<br>SEQUENCE: 312<br>000 | moltype = | length = |
| SEQ ID NO: 313<br>SEQUENCE: 313<br>000 | moltype = | length = |
| SEQ ID NO: 314<br>SEQUENCE: 314<br>000 | moltype = | length = |
| SEQ ID NO: 315<br>SEQUENCE: 315<br>000 | moltype = | length = |
| SEQ ID NO: 316<br>SEQUENCE: 316<br>000 | moltype = | length = |
| SEQ ID NO: 317<br>SEQUENCE: 317<br>000 | moltype = | length = |
| SEQ ID NO: 318<br>SEQUENCE: 318<br>000 | moltype = | length = |
| SEQ ID NO: 319<br>SEQUENCE: 319<br>000 | moltype = | length = |
| SEQ ID NO: 320<br>SEQUENCE: 320<br>000 | moltype = | length = |
| SEQ ID NO: 321<br>SEQUENCE: 321<br>000 | moltype = | length = |
| SEQ ID NO: 322<br>SEQUENCE: 322<br>000 | moltype = | length = |
| SEQ ID NO: 323<br>SEQUENCE: 323<br>000 | moltype = | length = |
| SEQ ID NO: 324<br>SEQUENCE: 324<br>000 | moltype = | length = |
| SEQ ID NO: 325<br>SEQUENCE: 325<br>000 | moltype = | length = |
| SEQ ID NO: 326<br>SEQUENCE: 326<br>000 | moltype = | length = |
| SEQ ID NO: 327<br>SEQUENCE: 327<br>000 | moltype = | length = |

| | | |
|---|---|---|
| SEQ ID NO: 328  SEQUENCE: 328 | moltype = | length = 000 |
| SEQ ID NO: 329  SEQUENCE: 329 | moltype = | length = 000 |
| SEQ ID NO: 330  SEQUENCE: 330 | moltype = | length = 000 |
| SEQ ID NO: 331  SEQUENCE: 331 | moltype = | length = 000 |
| SEQ ID NO: 332  SEQUENCE: 332 | moltype = | length = 000 |
| SEQ ID NO: 333  SEQUENCE: 333 | moltype = | length = 000 |
| SEQ ID NO: 334  SEQUENCE: 334 | moltype = | length = 000 |
| SEQ ID NO: 335  SEQUENCE: 335 | moltype = | length = 000 |
| SEQ ID NO: 336  SEQUENCE: 336 | moltype = | length = 000 |
| SEQ ID NO: 337  SEQUENCE: 337 | moltype = | length = 000 |
| SEQ ID NO: 338  SEQUENCE: 338 | moltype = | length = 000 |
| SEQ ID NO: 339  SEQUENCE: 339 | moltype = | length = 000 |
| SEQ ID NO: 340  SEQUENCE: 340 | moltype = | length = 000 |
| SEQ ID NO: 341  SEQUENCE: 341 | moltype = | length = 000 |
| SEQ ID NO: 342  SEQUENCE: 342 | moltype = | length = 000 |
| SEQ ID NO: 343  SEQUENCE: 343 | moltype = | length = 000 |
| SEQ ID NO: 344  SEQUENCE: 344 | moltype = | length = 000 |
| SEQ ID NO: 345  SEQUENCE: 345 | moltype = | length = 000 |
| SEQ ID NO: 346  SEQUENCE: 346 | moltype = | length = 000 |
| SEQ ID NO: 347  SEQUENCE: 347 | moltype = | length = |

000

SEQ ID NO: 348        moltype =     length =
SEQUENCE: 348
000

SEQ ID NO: 349        moltype =     length =
SEQUENCE: 349
000

SEQ ID NO: 350        moltype =     length =
SEQUENCE: 350
000

SEQ ID NO: 351        moltype =     length =
SEQUENCE: 351
000

SEQ ID NO: 352        moltype =     length =
SEQUENCE: 352
000

SEQ ID NO: 353        moltype =     length =
SEQUENCE: 353
000

SEQ ID NO: 354        moltype =     length =
SEQUENCE: 354
000

SEQ ID NO: 355        moltype =     length =
SEQUENCE: 355
000

SEQ ID NO: 356        moltype =     length =
SEQUENCE: 356
000

SEQ ID NO: 357        moltype =     length =
SEQUENCE: 357
000

SEQ ID NO: 358        moltype =     length =
SEQUENCE: 358
000

SEQ ID NO: 359        moltype =     length =
SEQUENCE: 359
000

SEQ ID NO: 360        moltype =     length =
SEQUENCE: 360
000

SEQ ID NO: 361        moltype =     length =
SEQUENCE: 361
000

SEQ ID NO: 362        moltype =     length =
SEQUENCE: 362
000

SEQ ID NO: 363        moltype =     length =
SEQUENCE: 363
000

SEQ ID NO: 364        moltype =     length =
SEQUENCE: 364
000

SEQ ID NO: 365        moltype =     length =
SEQUENCE: 365
000

SEQ ID NO: 366        moltype =     length =
SEQUENCE: 366
000

SEQ ID NO: 367        moltype =     length =

| | | |
|---|---|---|
| SEQUENCE: 367<br>000 | | |
| SEQ ID NO: 368<br>SEQUENCE: 368<br>000 | moltype = | length = |
| SEQ ID NO: 369<br>SEQUENCE: 369<br>000 | moltype = | length = |
| SEQ ID NO: 370<br>SEQUENCE: 370<br>000 | moltype = | length = |
| SEQ ID NO: 371<br>SEQUENCE: 371<br>000 | moltype = | length = |
| SEQ ID NO: 372<br>SEQUENCE: 372<br>000 | moltype = | length = |
| SEQ ID NO: 373<br>SEQUENCE: 373<br>000 | moltype = | length = |
| SEQ ID NO: 374<br>SEQUENCE: 374<br>000 | moltype = | length = |
| SEQ ID NO: 375<br>SEQUENCE: 375<br>000 | moltype = | length = |
| SEQ ID NO: 376<br>SEQUENCE: 376<br>000 | moltype = | length = |
| SEQ ID NO: 377<br>SEQUENCE: 377<br>000 | moltype = | length = |
| SEQ ID NO: 378<br>SEQUENCE: 378<br>000 | moltype = | length = |
| SEQ ID NO: 379<br>SEQUENCE: 379<br>000 | moltype = | length = |
| SEQ ID NO: 380<br>SEQUENCE: 380<br>000 | moltype = | length = |
| SEQ ID NO: 381<br>SEQUENCE: 381<br>000 | moltype = | length = |
| SEQ ID NO: 382<br>SEQUENCE: 382<br>000 | moltype = | length = |
| SEQ ID NO: 383<br>SEQUENCE: 383<br>000 | moltype = | length = |
| SEQ ID NO: 384<br>SEQUENCE: 384<br>000 | moltype = | length = |
| SEQ ID NO: 385<br>SEQUENCE: 385<br>000 | moltype = | length = |
| SEQ ID NO: 386<br>SEQUENCE: 386<br>000 | moltype = | length = |

```
SEQ ID NO: 387           moltype =    length =
SEQUENCE: 387
000

SEQ ID NO: 388           moltype =    length =
SEQUENCE: 388
000

SEQ ID NO: 389           moltype =    length =
SEQUENCE: 389
000

SEQ ID NO: 390           moltype =    length =
SEQUENCE: 390
000

SEQ ID NO: 391           moltype =    length =
SEQUENCE: 391
000

SEQ ID NO: 392           moltype =    length =
SEQUENCE: 392
000

SEQ ID NO: 393           moltype =    length =
SEQUENCE: 393
000

SEQ ID NO: 394           moltype =    length =
SEQUENCE: 394
000

SEQ ID NO: 395           moltype =    length =
SEQUENCE: 395
000

SEQ ID NO: 396           moltype =    length =
SEQUENCE: 396
000

SEQ ID NO: 397           moltype =    length =
SEQUENCE: 397
000

SEQ ID NO: 398           moltype =    length =
SEQUENCE: 398
000

SEQ ID NO: 399           moltype =    length =
SEQUENCE: 399
000

SEQ ID NO: 400           moltype = AA  length = 126
FEATURE                  Location/Qualifiers
source                   1..126
                         mol_type = protein
                         organism = synthetic construct
SEQUENCE: 400
EVQLVESGGG LVQPGGSLRL SCAASGFTFT SYGMSWVRQA PGKGLELVAS ITGSGGETYY    60
PDSVKGRFTI SRDNAKNSLY LQMNSLRAED TAVYYCARDL LVRFLEWSHY YGMDVWGQGT   120
TVTVSS                                                              126

SEQ ID NO: 401           moltype = AA  length = 125
FEATURE                  Location/Qualifiers
source                   1..125
                         mol_type = protein
                         organism = synthetic construct
SEQUENCE: 401
EVQLVESGGG LVQPGGSLRL SCAASGSAFS SYGMSWVRQA PGKGLELVAS IGGTGATYYP    60
DSVKGRFTIS RDNAKNSLYL QMNSLRAEDT AVYYCARDLL VRFLEWGHYY GMDVWGQGTT   120
VTVSS                                                               125

SEQ ID NO: 402           moltype = AA  length = 125
FEATURE                  Location/Qualifiers
source                   1..125
                         mol_type = protein
                         organism = synthetic construct
SEQUENCE: 402
EVQLVESGGG LVQPGGSLRL SCAASGFTFS SYGMSWVRQA PGKGLELVAS FTGSGGTYYP    60
```

```
DSVKGRFTIS RDNAKNSLYL QMNSLRAEDT AVYYCARDLL IRFLEWSHYY GMDVWGQGTT    120
VTVSS                                                               125

SEQ ID NO: 403         moltype = AA  length = 127
FEATURE                Location/Qualifiers
source                 1..127
                       mol_type = protein
                       organism = synthetic construct
SEQUENCE: 403
QVQLVQSGAE VKKPGASVKV SCKVSGGTFG IYAIHWVRQA PGKGLEWMGG TIPVFGTAIY     60
AQKFQGRVTM TEDTSTDTAY MELSSLKSED TAVYYCASLT GIAAAGTHPA RGGMDVWGQG    120
TTVTVSS                                                             127

SEQ ID NO: 404         moltype = AA  length = 123
FEATURE                Location/Qualifiers
source                 1..123
                       mol_type = protein
                       organism = synthetic construct
SEQUENCE: 404
QVTLRESGPA LVKPTQTLTL TCTVSGFSFS TSGMVVNWIR QPPGKALEWL AMIDWDADNI     60
VYNSALKSRL TISKDTSKNQ VVLTMTNMDP VDTATYYCAK DTGSGWFDAF DIWGQGTMVT    120
VSS                                                                 123

SEQ ID NO: 405         moltype = AA  length = 122
FEATURE                Location/Qualifiers
source                 1..122
                       mol_type = protein
                       organism = synthetic construct
SEQUENCE: 405
EVQLVESGGG LVQPGGSLRL SCAASGFTFS KYDMSWVRQA PGKGLELVAS ISSSGGTRYY     60
PDSVKGRFTI SRDNAKNSLY LQMNSLRAED TAVYYCAKDL WVASPGYGMD VWGQGTTVTV    120
SS                                                                  122

SEQ ID NO: 406         moltype = AA  length = 127
FEATURE                Location/Qualifiers
source                 1..127
                       mol_type = protein
                       organism = synthetic construct
SEQUENCE: 406
EVQLVESGGG LVQPGGSLRL SCTASGFTFG SYPMDWVRQA PGKGLEWVSY ISGRGDVTYY     60
ADSVKGRFTI SRDNAKNTLY LQMNSLRAED TAVYYCAKVQ SPSELLWFGE LLPVDYWGQG    120
TLVTVSS                                                             127

SEQ ID NO: 407         moltype = AA  length = 126
FEATURE                Location/Qualifiers
source                 1..126
                       mol_type = protein
                       organism = synthetic construct
SEQUENCE: 407
EVQLVESGGG LVQPGGSLRL SCAASGFTFT SYGMSWVRQA PGKGLELVAS ITGSGGETYY     60
PDSVKGRFTI SRDNAKNSLY LQMNSLRAED TAVYYCARDL LVRFLEWSHY YGMDVWGQGT    120
TVTVSS                                                              126

SEQ ID NO: 408         moltype = AA  length = 125
FEATURE                Location/Qualifiers
source                 1..125
                       mol_type = protein
                       organism = synthetic construct
SEQUENCE: 408
EVQLVESGGG LVQPGGSLRL SCAASGSAFS SYGMSWVRQA PGKGLELVAS IGGTGATYYP     60
DSVKGRFTIS RDNAKNSLYL QMNSLRAEDT AVYYCARDLL VRFLEWGHYY GMDVWGQGTT    120
VTVSS                                                               125

SEQ ID NO: 409         moltype = AA  length = 125
FEATURE                Location/Qualifiers
source                 1..125
                       mol_type = protein
                       organism = synthetic construct
SEQUENCE: 409
EVQLVESGGG LVQPGGSLRL SCAASGFTFS SYGMSWVRQA PGKGLELVAS FTGSGGTYYP     60
DSVKGRFTIS RDNAKNSLYL QMNSLRAEDT AVYYCARDLL IRFLEWSHYY GMDVWGQGTT    120
VTVSS                                                               125

SEQ ID NO: 410         moltype = AA  length = 112
FEATURE                Location/Qualifiers
source                 1..112
                       mol_type = protein
                       organism = synthetic construct
SEQUENCE: 410
```

```
DIVMTQSPLS LPVTPGEPAS ISCRSSQSLL HSSGHNFLHW YLQKPGQSPQ LLIYETSNRA    60
PGIPDRFSGS GSGTDFTLKI SRVEAEDVGV YYCMQATQFP RPFGGGTKVE IK           112

SEQ ID NO: 411           moltype = AA  length = 111
FEATURE                  Location/Qualifiers
source                   1..111
                         mol_type = protein
                         organism = synthetic construct
SEQUENCE: 411
DIVMTQSPLS LPVTPGEPAS ISCRSSQSLL HSSGYNFLHW YLQKPGQSPQ LLIYAASSRA    60
PGIPDRFSGS GSGTDFTLKI SRVEAEDVGV YYCMHGGQGP TFGGGTKVEI K            111

SEQ ID NO: 412           moltype = AA  length = 112
FEATURE                  Location/Qualifiers
source                   1..112
                         mol_type = protein
                         organism = synthetic construct
SEQUENCE: 412
DIVMTQSPLS LPVTPGEPAS ISCRSSQSLL HSSGHNFLHW YLQKPGQSPQ LLIYEVSNRV    60
SGVPDRFSGS GSGTDFTLKI SRVEAEDVGV YYCMQQTQYP PTFGGGTKVE IK           112

SEQ ID NO: 413           moltype = AA  length = 107
FEATURE                  Location/Qualifiers
source                   1..107
                         mol_type = protein
                         organism = synthetic construct
SEQUENCE: 413
DIQMTQSPSS VSASVGDRVT ITCRASPSIS SYLAWYQQKP GKAPKLLIYA ASRLQSGVPS    60
RFSGSGSGTD FTLTISSLQP EDFANYYCQE YLSFPLTFGG GTKVEIK                 107

SEQ ID NO: 414           moltype = AA  length = 113
FEATURE                  Location/Qualifiers
source                   1..113
                         mol_type = protein
                         organism = synthetic construct
SEQUENCE: 414
DIVMTQSPDS LAVSLGERAT INCKSSQSVL YSSTNQNFLA WYQQKPGQPP KLLIYQASTL    60
QNGVPDRFSG SGSGTDFTLT ISSLQAEDVA VYYCQQYLTT PYTFGGGTKV EIK          113

SEQ ID NO: 415           moltype = AA  length = 122
FEATURE                  Location/Qualifiers
source                   1..122
                         mol_type = protein
                         organism = synthetic construct
SEQUENCE: 415
EVQLVESGGG LVQPGGSLRL SCAASGFTFS KYDMSWVRQA PGKGLELVAS ISSSGGTRYY    60
PDSVKGRFTI SRDNAKNSLY LQMNSLRAED TAVYYCAKDL WVASPGYGMD VWGQGTTVTV   120
SS                                                                  122

SEQ ID NO: 416           moltype = AA  length = 127
FEATURE                  Location/Qualifiers
source                   1..127
                         mol_type = protein
                         organism = synthetic construct
SEQUENCE: 416
EVQLVESGGG LVQPGGSLRL SCTASGFTFG SYPMDWVRQA PGKGLEWVSY ISGRGDVTYY    60
ADSVKGRFTI SRDNAKNTLY LQMNSLRAED TAVYYCAKVQ SPSELLWFGE LLPVDYWGQG   120
TLVTVSS                                                             127

SEQ ID NO: 417           moltype = AA  length = 112
FEATURE                  Location/Qualifiers
source                   1..112
                         mol_type = protein
                         organism = synthetic construct
SEQUENCE: 417
DIVMTQSPLS LPVTPGEPAS ISCRSSQSLL HSSGHNFLHW YLQKPGQSPQ LLIYETSNRA    60
PGIPDRFSGS GSGTDFTLKI SRVEAEDVGV YYCQQATQFP RPFGGGTKVE IK           112

SEQ ID NO: 418           moltype = AA  length = 111
FEATURE                  Location/Qualifiers
source                   1..111
                         mol_type = protein
                         organism = synthetic construct
SEQUENCE: 418
DIVMTQSPLS LPVTPGEPAS ISCRSSQSLL HSSGYNFLHW YLQKPGQSPQ LLIYAASSRA    60
PGIPDRFSGS GSGTDFTLKI SRVEAEDVGV YYCQHGGQGP TFGGGTKVEI K            111

SEQ ID NO: 419           moltype = AA  length = 112
FEATURE                  Location/Qualifiers
```

```
source                  1..112
                        mol_type = protein
                        organism = synthetic construct
SEQUENCE: 419
DIVMTQSPLS LPVTPGEPAS ISCRSSQSLL HSSGHNFLHW YLQKPGQSPQ LLIYEVSNRV    60
SGVPDRFSGS GSGTDFTLKI SRVEAEDVGV YYCQQQTQYP PTFGGGTKVE IK           112

SEQ ID NO: 420          moltype = AA  length = 125
FEATURE                 Location/Qualifiers
source                  1..125
                        mol_type = protein
                        organism = synthetic construct
SEQUENCE: 420
EVQLVESGGG LVQPGGSLRL SCAASGFTFS SYGMSWVRQA PGKGLELVAS FTGSGGAYYP    60
DSVKGRFTIS RDNAKNSLYL QMNSLRAEDT AVYYCARDLL IRFLEWSHYY GMDVWGQGTT   120
VTVSS                                                               125

SEQ ID NO: 421          moltype = AA  length = 112
FEATURE                 Location/Qualifiers
source                  1..112
                        mol_type = protein
                        organism = synthetic construct
SEQUENCE: 421
DIVMTQSPLS LPVTPGEPAS ISCRSSQSLL HSSGHNFLHW YLQKPGQSPQ LLIYEVSNRV    60
SGVPDRFSGS GSGTDFTLKI SRVEAEDVGV YYCQQQTQYP GTFGGGTKVE IK           112

SEQ ID NO: 422          moltype = AA  length = 112
FEATURE                 Location/Qualifiers
source                  1..112
                        mol_type = protein
                        organism = synthetic construct
SEQUENCE: 422
DIVMTQSPLS LPVTPGEPAS ISCRSSQSLL HSSGHNFLHW YLQKPGQSPQ LLIYEVSNRV    60
SGVPDRFSGS GSGTDFTLKI SRVEAEDVGV YYCMQQTQYP GTFGGGTKVE IK           112

SEQ ID NO: 423          moltype =     length =
SEQUENCE: 423
000

SEQ ID NO: 424          moltype =     length =
SEQUENCE: 424
000

SEQ ID NO: 425          moltype =     length =
SEQUENCE: 425
000

SEQ ID NO: 426          moltype =     length =
SEQUENCE: 426
000

SEQ ID NO: 427          moltype =     length =
SEQUENCE: 427
000

SEQ ID NO: 428          moltype =     length =
SEQUENCE: 428
000

SEQ ID NO: 429          moltype =     length =
SEQUENCE: 429
000

SEQ ID NO: 430          moltype =     length =
SEQUENCE: 430
000

SEQ ID NO: 431          moltype =     length =
SEQUENCE: 431
000

SEQ ID NO: 432          moltype =     length =
SEQUENCE: 432
000

SEQ ID NO: 433          moltype =     length =
SEQUENCE: 433
000
```

| | | |
|---|---|---|
| SEQ ID NO: 434 SEQUENCE: 434 | moltype = 000 | length = |
| SEQ ID NO: 435 SEQUENCE: 435 | moltype = 000 | length = |
| SEQ ID NO: 436 SEQUENCE: 436 | moltype = 000 | length = |
| SEQ ID NO: 437 SEQUENCE: 437 | moltype = 000 | length = |
| SEQ ID NO: 438 SEQUENCE: 438 | moltype = 000 | length = |
| SEQ ID NO: 439 SEQUENCE: 439 | moltype = 000 | length = |
| SEQ ID NO: 440 SEQUENCE: 440 | moltype = 000 | length = |
| SEQ ID NO: 441 SEQUENCE: 441 | moltype = 000 | length = |
| SEQ ID NO: 442 SEQUENCE: 442 | moltype = 000 | length = |
| SEQ ID NO: 443 SEQUENCE: 443 | moltype = 000 | length = |
| SEQ ID NO: 444 SEQUENCE: 444 | moltype = 000 | length = |
| SEQ ID NO: 445 SEQUENCE: 445 | moltype = 000 | length = |
| SEQ ID NO: 446 SEQUENCE: 446 | moltype = 000 | length = |
| SEQ ID NO: 447 SEQUENCE: 447 | moltype = 000 | length = |
| SEQ ID NO: 448 SEQUENCE: 448 | moltype = 000 | length = |
| SEQ ID NO: 449 SEQUENCE: 449 | moltype = 000 | length = |
| SEQ ID NO: 450 SEQUENCE: 450 | moltype = 000 | length = |
| SEQ ID NO: 451 SEQUENCE: 451 | moltype = 000 | length = |
| SEQ ID NO: 452 SEQUENCE: 452 | moltype = 000 | length = |
| SEQ ID NO: 453 SEQUENCE: 453 | moltype = 000 | length = |

| | | |
|---|---|---|
| SEQ ID NO: 454<br>SEQUENCE: 454<br>000 | moltype = | length = |
| SEQ ID NO: 455<br>SEQUENCE: 455<br>000 | moltype = | length = |
| SEQ ID NO: 456<br>SEQUENCE: 456<br>000 | moltype = | length = |
| SEQ ID NO: 457<br>SEQUENCE: 457<br>000 | moltype = | length = |
| SEQ ID NO: 458<br>SEQUENCE: 458<br>000 | moltype = | length = |
| SEQ ID NO: 459<br>SEQUENCE: 459<br>000 | moltype = | length = |
| SEQ ID NO: 460<br>SEQUENCE: 460<br>000 | moltype = | length = |
| SEQ ID NO: 461<br>SEQUENCE: 461<br>000 | moltype = | length = |
| SEQ ID NO: 462<br>SEQUENCE: 462<br>000 | moltype = | length = |
| SEQ ID NO: 463<br>SEQUENCE: 463<br>000 | moltype = | length = |
| SEQ ID NO: 464<br>SEQUENCE: 464<br>000 | moltype = | length = |
| SEQ ID NO: 465<br>SEQUENCE: 465<br>000 | moltype = | length = |
| SEQ ID NO: 466<br>SEQUENCE: 466<br>000 | moltype = | length = |
| SEQ ID NO: 467<br>SEQUENCE: 467<br>000 | moltype = | length = |
| SEQ ID NO: 468<br>SEQUENCE: 468<br>000 | moltype = | length = |
| SEQ ID NO: 469<br>SEQUENCE: 469<br>000 | moltype = | length = |
| SEQ ID NO: 470<br>SEQUENCE: 470<br>000 | moltype = | length = |
| SEQ ID NO: 471<br>SEQUENCE: 471<br>000 | moltype = | length = |
| SEQ ID NO: 472<br>SEQUENCE: 472<br>000 | moltype = | length = |
| SEQ ID NO: 473<br>SEQUENCE: 473 | moltype = | length = |

-continued

000

SEQ ID NO: 474            moltype =     length =
SEQUENCE: 474
000

SEQ ID NO: 475            moltype =     length =
SEQUENCE: 475
000

SEQ ID NO: 476            moltype =     length =
SEQUENCE: 476
000

SEQ ID NO: 477            moltype =     length =
SEQUENCE: 477
000

SEQ ID NO: 478            moltype =     length =
SEQUENCE: 478
000

SEQ ID NO: 479            moltype =     length =
SEQUENCE: 479
000

SEQ ID NO: 480            moltype =     length =
SEQUENCE: 480
000

SEQ ID NO: 481            moltype =     length =
SEQUENCE: 481
000

SEQ ID NO: 482            moltype =     length =
SEQUENCE: 482
000

SEQ ID NO: 483            moltype =     length =
SEQUENCE: 483
000

SEQ ID NO: 484            moltype =     length =
SEQUENCE: 484
000

SEQ ID NO: 485            moltype =     length =
SEQUENCE: 485
000

SEQ ID NO: 486            moltype =     length =
SEQUENCE: 486
000

SEQ ID NO: 487            moltype =     length =
SEQUENCE: 487
000

SEQ ID NO: 488            moltype =     length =
SEQUENCE: 488
000

SEQ ID NO: 489            moltype =     length =
SEQUENCE: 489
000

SEQ ID NO: 490            moltype =     length =
SEQUENCE: 490
000

SEQ ID NO: 491            moltype =     length =
SEQUENCE: 491
000

SEQ ID NO: 492            moltype =     length =
SEQUENCE: 492
000

SEQ ID NO: 493            moltype =     length =

```
SEQUENCE: 493
000

SEQ ID NO: 494          moltype =     length =
SEQUENCE: 494
000

SEQ ID NO: 495          moltype =     length =
SEQUENCE: 495
000

SEQ ID NO: 496          moltype =     length =
SEQUENCE: 496
000

SEQ ID NO: 497          moltype =     length =
SEQUENCE: 497
000

SEQ ID NO: 498          moltype =     length =
SEQUENCE: 498
000

SEQ ID NO: 499          moltype =     length =
SEQUENCE: 499
000

SEQ ID NO: 500          moltype =     length =
SEQUENCE: 500
000

SEQ ID NO: 501          moltype = AA  length = 452
FEATURE                 Location/Qualifiers
source                  1..452
                        mol_type = protein
                        organism = synthetic construct
SEQUENCE: 501
EVQLVESGGG LVQPGGSLRL SCAASGFTFT SYGMSWVRQA PGKGLELVAS ITGSGGETYY    60
PDSVKGRFTI SRDNAKNSLY LQMNSLRAED TAVYYCARDL LVRFLEWSHY YGMDVWGQGT   120
TVTVSSASTK GPSVFPLAPC SRSTSESTAA LGCLVKDYFP EPVTVSWNSG ALTSGVHTFP   180
AVLQSSGLYS LSSVVTVPSS SLGTKTYTCN VDHKPSNTKV DKRVESKYGP PCPPCPAPEF   240
LGGPSVFLFP PKPKDTLMIS RTPEVTCVVV DVSQEDPEVQ FNWYVDGVEV HNAKTKPREE   300
QFNSTYRVVS VLTVLHQDWL NGKEYKCKVS NKGLPSSIEK TISKAKGQPR EPQVYTLPPS   360
QEEMTKNQVS LTCLVKGFYP SDIAVEWESN GQPENNYKTT PPVLDSDGSF FLYSRLTVDK   420
SRWQEGNVFS CSVMHEALHN HYTQKSLSLS LG                                 452

SEQ ID NO: 502          moltype = AA  length = 219
FEATURE                 Location/Qualifiers
source                  1..219
                        mol_type = protein
                        organism = synthetic construct
SEQUENCE: 502
DIVMTQSPLS LPVTPGEPAS ISCRSSQSLL HSSGHNFLHW YLQKPGQSPQ LLIYETSNRA    60
PGIPDRFSGS GSGTDFTLKI SRVEAEDVGV YYCMQATQFP RPFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 503          moltype = AA  length = 451
FEATURE                 Location/Qualifiers
source                  1..451
                        mol_type = protein
                        organism = synthetic construct
SEQUENCE: 503
EVQLVESGGG LVQPGGSLRL SCAASGFTFS SYGMSWVRQA PGKGLELVAS FTGSGGTYYP    60
DSVKGRFTIS RDNAKNSLYL QMNSLRAEDT AVYYCARDLL IRFLEWSHYY GMDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                  451

SEQ ID NO: 504          moltype = AA  length = 219
FEATURE                 Location/Qualifiers
source                  1..219
                        mol_type = protein
                        organism = synthetic construct
SEQUENCE: 504
DIVMTQSPLS LPVTPGEPAS ISCRSSQSLL HSSGHNFLHW YLQKPGQSPQ LLIYEVSNRV    60
```

```
SGVPDRFSGS GSGTDFTLKI SRVEAEDVGV YYCMQQTQYP PTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                          219

SEQ ID NO: 505           moltype = AA   length = 452
FEATURE                  Location/Qualifiers
source                   1..452
                         mol_type = protein
                         organism = synthetic construct
SEQUENCE: 505
EVQLVESGGG LVQPGGSLRL SCAASGFTFT SYGMSWVRQA PGKGLELVAS ITGSGGETYY    60
PDSVKGRFTI SRDNAKNSLY LQMNSLRAED TAVYYCARDL LVRFLEWSHY YGMDVWGQGT    120
TVTVSSASTK GPSVFPLAPC SRSTSESTAA LGCLVKDYFP EPVTVSWNSG ALTSGVHTFP    180
AVLQSSGLYS LSSVVTVPSS SLGTKTYTCN VDHKPSNTKV DKRVESKYGP CPPCPAPEF     240
LGGPSVFLFP PKPKDTLMIS RTPEVTCVVV DVSQEDPEVQ FNWYVDGVEV HNAKTKPREE    300
QFNSTYRVVS VLTVLHQDWL NGKEYKCKVS NKGLPSSIEK TISKAKGQPR EPQVYTLPPS    360
QEEMTKNQVS LTCLVKGFYP SDIAVEWESN GQPENNYKTT PPVLDSDGSF FLYSRLTVDK    420
SRWQEGNVFS CSVMHEALHN HYTQKSLSLS LG                                 452

SEQ ID NO: 506           moltype = AA   length = 219
FEATURE                  Location/Qualifiers
source                   1..219
                         mol_type = protein
                         organism = synthetic construct
SEQUENCE: 506
DIVMTQSPLS LPVTPGEPAS ISCRSSQSLL HSSGHNFLHW YLQKPGQSPQ LLIYETSNRA    60
PGIPDRFSGS GSGTDFTLKI SRVEAEDVGV YYCQQATQFP RPFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                          219

SEQ ID NO: 507           moltype = AA   length = 451
FEATURE                  Location/Qualifiers
source                   1..451
                         mol_type = protein
                         organism = synthetic construct
SEQUENCE: 507
EVQLVESGGG LVQPGGSLRL SCAASGFTFS SYGMSWVRQA PGKGLELVAS FTGSGGTYYP    60
DSVKGRFTIS RDNAKNSLYL QMNSLRAEDT AVYYCARDLL IRFLEWSHYY GMDVWGQGTT    120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFL    240
GGPSVFLFPP KPKDTLMISR TPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
RWQEGNVFSC SVMHEALHNH YTQKSLSLSL G                                  451

SEQ ID NO: 508           moltype = AA   length = 219
FEATURE                  Location/Qualifiers
source                   1..219
                         mol_type = protein
                         organism = synthetic construct
SEQUENCE: 508
DIVMTQSPLS LPVTPGEPAS ISCRSSQSLL HSSGHNFLHW YLQKPGQSPQ LLIYEVSNRV    60
SGVPDRFSGS GSGTDFTLKI SRVEAEDVGV YYCQQQTQYP PTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                          219

SEQ ID NO: 509           moltype = AA   length = 451
FEATURE                  Location/Qualifiers
source                   1..451
                         mol_type = protein
                         organism = synthetic construct
SEQUENCE: 509
EVQLVESGGG LVQPGGSLRL SCAASGFTFS SYGMSWVRQA PGKGLELVAS FTGSGGAYYP    60
DSVKGRFTIS RDNAKNSLYL QMNSLRAEDT AVYYCARDLL IRFLEWSHYY GMDVWGQTT     120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFL    240
GGPSVFLFPP KPKDTLMISR TPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
RWQEGNVFSC SVMHEALHNH YTQKSLSLSL G                                  451

SEQ ID NO: 510           moltype = AA   length = 219
FEATURE                  Location/Qualifiers
source                   1..219
                         mol_type = protein
                         organism = synthetic construct
SEQUENCE: 510
DIVMTQSPLS LPVTPGEPAS ISCRSSQSLL HSSGHNFLHW YLQKPGQSPQ LLIYEVSNRV    60
SGVPDRFSGS GSGTDFTLKI SRVEAEDVGV YYCQQQTQYP GTFGGGTKVE IKRTVAAPSV    120
```

```
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 511           moltype = AA  length = 219
FEATURE                  Location/Qualifiers
source                   1..219
                         mol_type = protein
                         organism = synthetic construct
SEQUENCE: 511
DIVMTQSPLS LPVTPGEPAS ISCRSSQSLL HSSGHNFLHW YLQKPGQSPQ LLIYEVSNRV    60
SGVPDRFSGS GSGTDFTLKI SRVEAEDVGV YYCMQQTQYP GTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 512           moltype = AA  length = 16
FEATURE                  Location/Qualifiers
source                   1..16
                         mol_type = protein
                         organism = synthetic construct
VARIANT                  2
                         note = I or F
VARIANT                  8
                         note = E, T, or A
VARIANT                  9
                         note = Y or T
VARIANT                  11
                         note = P or Y
VARIANT                  12
                         note = D or P
VARIANT                  13
                         note = S or D
VARIANT                  14
                         note = V or S
VARIANT                  15
                         note = K or V
VARIANT                  16
                         note = G or K
SEQUENCE: 512
SXTGSGGXXY XXXXXX                                                    16

SEQ ID NO: 513           moltype = AA  length = 17
FEATURE                  Location/Qualifiers
source                   1..17
                         mol_type = protein
                         organism = synthetic construct
VARIANT                  4
                         note = V or I
SEQUENCE: 513
DLLXRFLEWS HYYGMDV                                                   17

SEQ ID NO: 514           moltype = AA  length = 7
FEATURE                  Location/Qualifiers
source                   1..7
                         mol_type = protein
                         organism = synthetic construct
VARIANT                  2
                         note = T or V
VARIANT                  6
                         note = A or V
VARIANT                  7
                         note = P or S
SEQUENCE: 514
EXSNRXX                                                              7

SEQ ID NO: 515           moltype = AA  length = 9
FEATURE                  Location/Qualifiers
source                   1..9
                         mol_type = protein
                         organism = synthetic construct
VARIANT                  1
                         note = Q or M
VARIANT                  3
                         note = Q or A
VARIANT                  6
                         note = Y or F
VARIANT                  8
                         note = P, R or G
VARIANT                  9
                         note = P or T
```

```
SEQUENCE: 515
XQXTQXPXX                                                                        9

SEQ ID NO: 516         moltype = AA  length = 17
FEATURE                Location/Qualifiers
source                 1..17
                       mol_type = protein
                       organism = synthetic construct
SEQUENCE: 516
SINSNGGSTY YPDSVKG                                                              17

SEQ ID NO: 517         moltype = AA  length = 17
FEATURE                Location/Qualifiers
source                 1..17
                       mol_type = protein
                       organism = synthetic construct
SEQUENCE: 517
SITGDAGRTY YPDSVKG                                                              17

SEQ ID NO: 518         moltype = AA  length = 17
FEATURE                Location/Qualifiers
source                 1..17
                       mol_type = protein
                       organism = synthetic construct
SEQUENCE: 518
DTLVRFLEWS HYYGMDV                                                              17

SEQ ID NO: 519         moltype = AA  length = 17
FEATURE                Location/Qualifiers
source                 1..17
                       mol_type = protein
                       organism = synthetic construct
SEQUENCE: 519
DLLVKFLSWS HYYGMDV                                                              17

SEQ ID NO: 520         moltype = AA  length = 16
FEATURE                Location/Qualifiers
source                 1..16
                       mol_type = protein
                       organism = synthetic construct
SEQUENCE: 520
SIGGTGATYY PDSVKG                                                               16

SEQ ID NO: 521         moltype = AA  length = 17
FEATURE                Location/Qualifiers
source                 1..17
                       mol_type = protein
                       organism = synthetic construct
SEQUENCE: 521
DLLVRFLEWG HYYGMDV                                                              17

SEQ ID NO: 522         moltype = AA  length = 16
FEATURE                Location/Qualifiers
source                 1..16
                       mol_type = protein
                       organism = synthetic construct
SEQUENCE: 522
RSSQSLLHSS GYNFLH                                                               16

SEQ ID NO: 523         moltype = AA  length = 7
FEATURE                Location/Qualifiers
source                 1..7
                       mol_type = protein
                       organism = synthetic construct
SEQUENCE: 523
AASSRAP                                                                          7

SEQ ID NO: 524         moltype = AA  length = 8
FEATURE                Location/Qualifiers
source                 1..8
                       mol_type = protein
                       organism = synthetic construct
SEQUENCE: 524
MHGGQGPT                                                                         8

SEQ ID NO: 525         moltype = AA  length = 17
FEATURE                Location/Qualifiers
source                 1..17
                       mol_type = protein
```

-continued

```
                            organism = synthetic construct
SEQUENCE: 525
DLLVRFLEWA GYYGMDV                                                            17

SEQ ID NO: 526              moltype = AA   length = 17
FEATURE                     Location/Qualifiers
source                      1..17
                            mol_type = protein
                            organism = synthetic construct
SEQUENCE: 526
DQLVRFLEWS HYYGMDV                                                            17

SEQ ID NO: 527              moltype = AA   length = 7
FEATURE                     Location/Qualifiers
source                      1..7
                            mol_type = protein
                            organism = synthetic construct
SEQUENCE: 527
AGSNRPS                                                                        7

SEQ ID NO: 528              moltype = AA   length = 17
FEATURE                     Location/Qualifiers
source                      1..17
                            mol_type = protein
                            organism = synthetic construct
SEQUENCE: 528
DLLVGFLQWS HYYGMDV                                                            17

SEQ ID NO: 529              moltype = AA   length = 5
FEATURE                     Location/Qualifiers
source                      1..5
                            mol_type = protein
                            organism = synthetic construct
SEQUENCE: 529
NYDIH                                                                          5

SEQ ID NO: 530              moltype = AA   length = 17
FEATURE                     Location/Qualifiers
source                      1..17
                            mol_type = protein
                            organism = synthetic construct
SEQUENCE: 530
GISAYHGNAI YAQKFQG                                                            17

SEQ ID NO: 531              moltype = AA   length = 14
FEATURE                     Location/Qualifiers
source                      1..14
                            mol_type = protein
                            organism = synthetic construct
SEQUENCE: 531
DRVRRDYYNF GMDV                                                               14

SEQ ID NO: 532              moltype = AA   length = 11
FEATURE                     Location/Qualifiers
source                      1..11
                            mol_type = protein
                            organism = synthetic construct
SEQUENCE: 532
RASEDITSYL A                                                                  11

SEQ ID NO: 533              moltype = AA   length = 7
FEATURE                     Location/Qualifiers
source                      1..7
                            mol_type = protein
                            organism = synthetic construct
SEQUENCE: 533
DVSSLQS                                                                        7

SEQ ID NO: 534              moltype = AA   length = 9
FEATURE                     Location/Qualifiers
source                      1..9
                            mol_type = protein
                            organism = synthetic construct
SEQUENCE: 534
LQHNAYPYG                                                                      9

SEQ ID NO: 535              moltype = AA   length = 5
FEATURE                     Location/Qualifiers
source                      1..5
```

```
                                -continued
                        mol_type = protein
                        organism = synthetic construct
SEQUENCE: 535
SNDIH                                                              5

SEQ ID NO: 536          moltype = AA  length = 17
FEATURE                 Location/Qualifiers
source                  1..17
                        mol_type = protein
                        organism = synthetic construct
SEQUENCE: 536
GIFPIFGTTI YAQKFQG                                                17

SEQ ID NO: 537          moltype = AA  length = 9
FEATURE                 Location/Qualifiers
source                  1..9
                        mol_type = protein
                        organism = synthetic construct
SEQUENCE: 537
EGLGYDFDY                                                          9

SEQ ID NO: 538          moltype = AA  length = 11
FEATURE                 Location/Qualifiers
source                  1..11
                        mol_type = protein
                        organism = synthetic construct
SEQUENCE: 538
RASQNIGNWL A                                                      11

SEQ ID NO: 539          moltype = AA  length = 7
FEATURE                 Location/Qualifiers
source                  1..7
                        mol_type = protein
                        organism = synthetic construct
SEQUENCE: 539
SASALQS                                                            7

SEQ ID NO: 540          moltype = AA  length = 10
FEATURE                 Location/Qualifiers
source                  1..10
                        mol_type = protein
                        organism = synthetic construct
SEQUENCE: 540
QQSYGAPMYS                                                        10

SEQ ID NO: 541          moltype = AA  length = 5
FEATURE                 Location/Qualifiers
source                  1..5
                        mol_type = protein
                        organism = synthetic construct
SEQUENCE: 541
IYAIH                                                              5

SEQ ID NO: 542          moltype = AA  length = 17
FEATURE                 Location/Qualifiers
source                  1..17
                        mol_type = protein
                        organism = synthetic construct
SEQUENCE: 542
GTIPVFGTAI YAQKFQG                                                17

SEQ ID NO: 543          moltype = AA  length = 18
FEATURE                 Location/Qualifiers
source                  1..18
                        mol_type = protein
                        organism = synthetic construct
SEQUENCE: 543
LTGIAAAGTH PARGGMDV                                               18

SEQ ID NO: 544          moltype = AA  length = 11
FEATURE                 Location/Qualifiers
source                  1..11
                        mol_type = protein
                        organism = synthetic construct
SEQUENCE: 544
RASPSISSYL A                                                      11

SEQ ID NO: 545          moltype = AA  length = 7
FEATURE                 Location/Qualifiers
```

```
source                          1..7
                                mol_type = protein
                                organism = synthetic construct
SEQUENCE: 545
AASRLQS                                                                          7

SEQ ID NO: 546                  moltype = AA   length = 9
FEATURE                         Location/Qualifiers
source                          1..9
                                mol_type = protein
                                organism = synthetic construct
SEQUENCE: 546
QEYLSFPLT                                                                        9

SEQ ID NO: 547                  moltype = AA   length = 5
FEATURE                         Location/Qualifiers
source                          1..5
                                mol_type = protein
                                organism = synthetic construct
SEQUENCE: 547
ELSIH                                                                            5

SEQ ID NO: 548                  moltype = AA   length = 17
FEATURE                         Location/Qualifiers
source                          1..17
                                mol_type = protein
                                organism = synthetic construct
SEQUENCE: 548
GIIPSFGTAI YAQKFQG                                                              17

SEQ ID NO: 549                  moltype = AA   length = 12
FEATURE                         Location/Qualifiers
source                          1..12
                                mol_type = protein
                                organism = synthetic construct
SEQUENCE: 549
SYSGFDLLPL DK                                                                   12

SEQ ID NO: 550                  moltype = AA   length = 11
FEATURE                         Location/Qualifiers
source                          1..11
                                mol_type = protein
                                organism = synthetic construct
SEQUENCE: 550
RASQHISTWL A                                                                    11

SEQ ID NO: 551                  moltype = AA   length = 7
FEATURE                         Location/Qualifiers
source                          1..7
                                mol_type = protein
                                organism = synthetic construct
SEQUENCE: 551
YASSLQG                                                                          7

SEQ ID NO: 552                  moltype = AA   length = 9
FEATURE                         Location/Qualifiers
source                          1..9
                                mol_type = protein
                                organism = synthetic construct
SEQUENCE: 552
LQTYTYPRT                                                                        9

SEQ ID NO: 553                  moltype = AA   length = 5
FEATURE                         Location/Qualifiers
source                          1..5
                                mol_type = protein
                                organism = synthetic construct
SEQUENCE: 553
SYTIH                                                                            5

SEQ ID NO: 554                  moltype = AA   length = 17
FEATURE                         Location/Qualifiers
source                          1..17
                                mol_type = protein
                                organism = synthetic construct
SEQUENCE: 554
GMNPSSGHTI YAQKFQG                                                              17

SEQ ID NO: 555                  moltype = AA   length = 15
```

```
FEATURE                 Location/Qualifiers
source                  1..15
                        mol_type = protein
                        organism = synthetic construct
SEQUENCE: 555
GLDYGEGYYY YGMDV                                                             15

SEQ ID NO: 556          moltype = AA   length = 11
FEATURE                 Location/Qualifiers
source                  1..11
                        mol_type = protein
                        organism = synthetic construct
SEQUENCE: 556
RASQGISESL A                                                                 11

SEQ ID NO: 557          moltype = AA   length = 7
FEATURE                 Location/Qualifiers
source                  1..7
                        mol_type = protein
                        organism = synthetic construct
SEQUENCE: 557
SASSLES                                                                       7

SEQ ID NO: 558          moltype = AA   length = 10
FEATURE                 Location/Qualifiers
source                  1..10
                        mol_type = protein
                        organism = synthetic construct
SEQUENCE: 558
QQGYSSPPYT                                                                   10

SEQ ID NO: 559          moltype = AA   length = 5
FEATURE                 Location/Qualifiers
source                  1..5
                        mol_type = protein
                        organism = synthetic construct
SEQUENCE: 559
NYNIH                                                                         5

SEQ ID NO: 560          moltype = AA   length = 17
FEATURE                 Location/Qualifiers
source                  1..17
                        mol_type = protein
                        organism = synthetic construct
SEQUENCE: 560
GINPRTGGTI YAQKFQG                                                           17

SEQ ID NO: 561          moltype = AA   length = 15
FEATURE                 Location/Qualifiers
source                  1..15
                        mol_type = protein
                        organism = synthetic construct
SEQUENCE: 561
DIYTGVAVAG SGMDY                                                             15

SEQ ID NO: 562          moltype = AA   length = 11
FEATURE                 Location/Qualifiers
source                  1..11
                        mol_type = protein
                        organism = synthetic construct
SEQUENCE: 562
RASQGISTHL A                                                                 11

SEQ ID NO: 563          moltype = AA   length = 7
FEATURE                 Location/Qualifiers
source                  1..7
                        mol_type = protein
                        organism = synthetic construct
SEQUENCE: 563
GASNLES                                                                       7

SEQ ID NO: 564          moltype = AA   length = 9
FEATURE                 Location/Qualifiers
source                  1..9
                        mol_type = protein
                        organism = synthetic construct
SEQUENCE: 564
QQANSFPWT                                                                     9
```

```
SEQ ID NO: 565           moltype = AA  length = 5
FEATURE                  Location/Qualifiers
source                   1..5
                         mol_type = protein
                         organism = synthetic construct
SEQUENCE: 565
RPAIH                                                                    5

SEQ ID NO: 566           moltype = AA  length = 17
FEATURE                  Location/Qualifiers
source                   1..17
                         mol_type = protein
                         organism = synthetic construct
SEQUENCE: 566
GINPNAATTI YAQKFQG                                                      17

SEQ ID NO: 567           moltype = AA  length = 14
FEATURE                  Location/Qualifiers
source                   1..14
                         mol_type = protein
                         organism = synthetic construct
SEQUENCE: 567
GRLLREWELR PYDT                                                         14

SEQ ID NO: 568           moltype = AA  length = 11
FEATURE                  Location/Qualifiers
source                   1..11
                         mol_type = protein
                         organism = synthetic construct
SEQUENCE: 568
RASQSIGKSL A                                                            11

SEQ ID NO: 569           moltype = AA  length = 7
FEATURE                  Location/Qualifiers
source                   1..7
                         mol_type = protein
                         organism = synthetic construct
SEQUENCE: 569
SASNLRS                                                                  7

SEQ ID NO: 570           moltype = AA  length = 10
FEATURE                  Location/Qualifiers
source                   1..10
                         mol_type = protein
                         organism = synthetic construct
SEQUENCE: 570
QQYRDVPPIT                                                              10

SEQ ID NO: 571           moltype = AA  length = 5
FEATURE                  Location/Qualifiers
source                   1..5
                         mol_type = protein
                         organism = synthetic construct
SEQUENCE: 571
SHDIH                                                                    5

SEQ ID NO: 572           moltype = AA  length = 17
FEATURE                  Location/Qualifiers
source                   1..17
                         mol_type = protein
                         organism = synthetic construct
SEQUENCE: 572
GINPSDASTI YAQKFQG                                                      17

SEQ ID NO: 573           moltype = AA  length = 16
FEATURE                  Location/Qualifiers
source                   1..16
                         mol_type = protein
                         organism = synthetic construct
SEQUENCE: 573
DLRGYSYGAE TWHFQH                                                       16

SEQ ID NO: 574           moltype = AA  length = 11
FEATURE                  Location/Qualifiers
source                   1..11
                         mol_type = protein
                         organism = synthetic construct
SEQUENCE: 574
RASQYISNYL A                                                            11
```

```
SEQ ID NO: 575          moltype = AA   length = 7
FEATURE                 Location/Qualifiers
source                  1..7
                        mol_type = protein
                        organism = synthetic construct
SEQUENCE: 575
ETSRLES                                                                    7

SEQ ID NO: 576          moltype = AA   length = 9
FEATURE                 Location/Qualifiers
source                  1..9
                        mol_type = protein
                        organism = synthetic construct
SEQUENCE: 576
QQTSSTPLT                                                                  9

SEQ ID NO: 577          moltype = AA   length = 5
FEATURE                 Location/Qualifiers
source                  1..5
                        mol_type = protein
                        organism = synthetic construct
SEQUENCE: 577
GYNIH                                                                      5

SEQ ID NO: 578          moltype = AA   length = 17
FEATURE                 Location/Qualifiers
source                  1..17
                        mol_type = protein
                        organism = synthetic construct
SEQUENCE: 578
GMNPKSGDTI YAQKFQG                                                        17

SEQ ID NO: 579          moltype = AA   length = 16
FEATURE                 Location/Qualifiers
source                  1..16
                        mol_type = protein
                        organism = synthetic construct
SEQUENCE: 579
DPGPYGSPLY YYGMDV                                                         16

SEQ ID NO: 580          moltype = AA   length = 11
FEATURE                 Location/Qualifiers
source                  1..11
                        mol_type = protein
                        organism = synthetic construct
SEQUENCE: 580
RASQIITTHL A                                                              11

SEQ ID NO: 581          moltype = AA   length = 7
FEATURE                 Location/Qualifiers
source                  1..7
                        mol_type = protein
                        organism = synthetic construct
SEQUENCE: 581
DASYLER                                                                    7

SEQ ID NO: 582          moltype = AA   length = 10
FEATURE                 Location/Qualifiers
source                  1..10
                        mol_type = protein
                        organism = synthetic construct
SEQUENCE: 582
QQYRTSSSLT                                                                10

SEQ ID NO: 583          moltype = AA   length = 5
FEATURE                 Location/Qualifiers
source                  1..5
                        mol_type = protein
                        organism = synthetic construct
SEQUENCE: 583
KDHIH                                                                      5

SEQ ID NO: 584          moltype = AA   length = 17
FEATURE                 Location/Qualifiers
source                  1..17
                        mol_type = protein
                        organism = synthetic construct
SEQUENCE: 584
```

```
GITPSSGDTI YAQKFQG                                                                    17

SEQ ID NO: 585          moltype = AA  length = 16
FEATURE                 Location/Qualifiers
source                  1..16
                        mol_type = protein
                        organism = synthetic construct
SEQUENCE: 585
DHMVRGLPNY YYGMDL                                                                     16

SEQ ID NO: 586          moltype = AA  length = 11
FEATURE                 Location/Qualifiers
source                  1..11
                        mol_type = protein
                        organism = synthetic construct
SEQUENCE: 586
RASRDIANYL A                                                                          11

SEQ ID NO: 587          moltype = AA  length = 7
FEATURE                 Location/Qualifiers
source                  1..7
                        mol_type = protein
                        organism = synthetic construct
SEQUENCE: 587
AASILQN                                                                                7

SEQ ID NO: 588          moltype = AA  length = 9
FEATURE                 Location/Qualifiers
source                  1..9
                        mol_type = protein
                        organism = synthetic construct
SEQUENCE: 588
QQAYTTPPT                                                                              9

SEQ ID NO: 589          moltype = AA  length = 5
FEATURE                 Location/Qualifiers
source                  1..5
                        mol_type = protein
                        organism = synthetic construct
SEQUENCE: 589
TFHIH                                                                                  5

SEQ ID NO: 590          moltype = AA  length = 17
FEATURE                 Location/Qualifiers
source                  1..17
                        mol_type = protein
                        organism = synthetic construct
SEQUENCE: 590
GISAYSGSTI YAQKFQG                                                                    17

SEQ ID NO: 591          moltype = AA  length = 10
FEATURE                 Location/Qualifiers
source                  1..10
                        mol_type = protein
                        organism = synthetic construct
SEQUENCE: 591
ARYVDDAFDI                                                                            10

SEQ ID NO: 592          moltype = AA  length = 11
FEATURE                 Location/Qualifiers
source                  1..11
                        mol_type = protein
                        organism = synthetic construct
SEQUENCE: 592
RASEDISNFL A                                                                          11

SEQ ID NO: 593          moltype = AA  length = 7
FEATURE                 Location/Qualifiers
source                  1..7
                        mol_type = protein
                        organism = synthetic construct
SEQUENCE: 593
AASDLLS                                                                                7

SEQ ID NO: 594          moltype = AA  length = 8
FEATURE                 Location/Qualifiers
source                  1..8
                        mol_type = protein
                        organism = synthetic construct
```

| | | |
|---|---|---|
| SEQUENCE: 594<br>QKYISAPS | | 8 |
| SEQ ID NO: 595<br>FEATURE<br>source | moltype = AA  length = 7<br>Location/Qualifiers<br>1..7<br>mol_type = protein<br>organism = synthetic construct | |
| SEQUENCE: 595<br>TSGMVVN | | 7 |
| SEQ ID NO: 596<br>FEATURE<br>source | moltype = AA  length = 17<br>Location/Qualifiers<br>1..17<br>mol_type = protein<br>organism = synthetic construct | |
| SEQUENCE: 596<br>MIDWDADNIV YNSALKS | | 17 |
| SEQ ID NO: 597<br>FEATURE<br>source | moltype = AA  length = 12<br>Location/Qualifiers<br>1..12<br>mol_type = protein<br>organism = synthetic construct | |
| SEQUENCE: 597<br>DTGSGWFDAF DI | | 12 |
| SEQ ID NO: 598<br>FEATURE<br>source | moltype = AA  length = 17<br>Location/Qualifiers<br>1..17<br>mol_type = protein<br>organism = synthetic construct | |
| SEQUENCE: 598<br>KSSQSVLYSS TNQNFLA | | 17 |
| SEQ ID NO: 599<br>FEATURE<br>source | moltype = AA  length = 7<br>Location/Qualifiers<br>1..7<br>mol_type = protein<br>organism = synthetic construct | |
| SEQUENCE: 599<br>QASTLQN | | 7 |
| SEQ ID NO: 600<br>FEATURE<br>source | moltype = AA  length = 9<br>Location/Qualifiers<br>1..9<br>mol_type = protein<br>organism = synthetic construct | |
| SEQUENCE: 600<br>QQYLTTPYT | | 9 |
| SEQ ID NO: 601<br>FEATURE<br>source | moltype = AA  length = 7<br>Location/Qualifiers<br>1..7<br>mol_type = protein<br>organism = synthetic construct | |
| SEQUENCE: 601<br>SGGSYVN | | 7 |
| SEQ ID NO: 602<br>FEATURE<br>source | moltype = AA  length = 16<br>Location/Qualifiers<br>1..16<br>mol_type = protein<br>organism = synthetic construct | |
| SEQUENCE: 602<br>MTDWDADNIV YNSALK | | 16 |
| SEQ ID NO: 603<br>FEATURE<br>source | moltype = AA  length = 16<br>Location/Qualifiers<br>1..16<br>mol_type = protein<br>organism = synthetic construct | |
| SEQUENCE: 603<br>RQNVDSYGYW GDAFDI | | 16 |
| SEQ ID NO: 604<br>FEATURE<br>source | moltype = AA  length = 17<br>Location/Qualifiers<br>1..17<br>mol_type = protein | |

-continued

```
                              organism = synthetic construct
SEQUENCE: 604
KSSQSVLYSA DNKNYLA                                                          17

SEQ ID NO: 605                moltype = AA   length = 7
FEATURE                       Location/Qualifiers
source                        1..7
                              mol_type = protein
                              organism = synthetic construct
SEQUENCE: 605
DASSLEN                                                                      7

SEQ ID NO: 606                moltype = AA   length = 9
FEATURE                       Location/Qualifiers
source                        1..9
                              mol_type = protein
                              organism = synthetic construct
SEQUENCE: 606
QQGHLFPYS                                                                    9

SEQ ID NO: 607                moltype = AA   length = 5
FEATURE                       Location/Qualifiers
source                        1..5
                              mol_type = protein
                              organism = synthetic construct
SEQUENCE: 607
KYDMS                                                                        5

SEQ ID NO: 608                moltype = AA   length = 17
FEATURE                       Location/Qualifiers
source                        1..17
                              mol_type = protein
                              organism = synthetic construct
SEQUENCE: 608
SISSSGGTRY YPDSVKG                                                          17

SEQ ID NO: 609                moltype = AA   length = 13
FEATURE                       Location/Qualifiers
source                        1..13
                              mol_type = protein
                              organism = synthetic construct
SEQUENCE: 609
DLWVASPGYG MDV                                                              13

SEQ ID NO: 610                moltype = AA   length = 16
FEATURE                       Location/Qualifiers
source                        1..16
                              mol_type = protein
                              organism = synthetic construct
SEQUENCE: 610
RSSQSLLHSS GHNYLH                                                           16

SEQ ID NO: 611                moltype = AA   length = 7
FEATURE                       Location/Qualifiers
source                        1..7
                              mol_type = protein
                              organism = synthetic construct
SEQUENCE: 611
LGSIRAP                                                                      7

SEQ ID NO: 612                moltype = AA   length = 9
FEATURE                       Location/Qualifiers
source                        1..9
                              mol_type = protein
                              organism = synthetic construct
SEQUENCE: 612
MQALLNPPT                                                                    9

SEQ ID NO: 613                moltype = AA   length = 5
FEATURE                       Location/Qualifiers
source                        1..5
                              mol_type = protein
                              organism = synthetic construct
SEQUENCE: 613
SSPYS                                                                        5

SEQ ID NO: 614                moltype = AA   length = 18
FEATURE                       Location/Qualifiers
source                        1..18
```

```
                              mol_type = protein
                              organism = synthetic construct
SEQUENCE: 614
IGYVDLAGST DYNPSLKS                                                    18

SEQ ID NO: 615                moltype = AA  length = 11
FEATURE                       Location/Qualifiers
source                        1..11
                              mol_type = protein
                              organism = synthetic construct
SEQUENCE: 615
RASQSIGINL A                                                           11

SEQ ID NO: 616                moltype = AA  length = 7
FEATURE                       Location/Qualifiers
source                        1..7
                              mol_type = protein
                              organism = synthetic construct
SEQUENCE: 616
GVSNRAT                                                                 7

SEQ ID NO: 617                moltype = AA  length = 9
FEATURE                       Location/Qualifiers
source                        1..9
                              mol_type = protein
                              organism = synthetic construct
SEQUENCE: 617
QQYGTARLT                                                               9

SEQ ID NO: 618                moltype = AA  length = 5
FEATURE                       Location/Qualifiers
source                        1..5
                              mol_type = protein
                              organism = synthetic construct
SEQUENCE: 618
DYWMN                                                                   5

SEQ ID NO: 619                moltype = AA  length = 18
FEATURE                       Location/Qualifiers
source                        1..18
                              mol_type = protein
                              organism = synthetic construct
SEQUENCE: 619
NIYPGYSDAT YNRKFKGQ                                                    18

SEQ ID NO: 620                moltype = AA  length = 13
FEATURE                       Location/Qualifiers
source                        1..13
                              mol_type = protein
                              organism = synthetic construct
SEQUENCE: 620
GRDGYNYFAA FDI                                                         13

SEQ ID NO: 621                moltype = AA  length = 12
FEATURE                       Location/Qualifiers
source                        1..12
                              mol_type = protein
                              organism = synthetic construct
SEQUENCE: 621
RASQSVASSY LA                                                          12

SEQ ID NO: 622                moltype = AA  length = 7
FEATURE                       Location/Qualifiers
source                        1..7
                              mol_type = protein
                              organism = synthetic construct
SEQUENCE: 622
DTSSRAA                                                                 7

SEQ ID NO: 623                moltype = AA  length = 9
FEATURE                       Location/Qualifiers
source                        1..9
                              mol_type = protein
                              organism = synthetic construct
SEQUENCE: 623
HQYGSSLTT                                                               9

SEQ ID NO: 624                moltype = AA  length = 5
FEATURE                       Location/Qualifiers
```

```
source                1..5
                      mol_type = protein
                      organism = synthetic construct
SEQUENCE: 624
NYAMD                                                            5

SEQ ID NO: 625        moltype = AA  length = 17
FEATURE               Location/Qualifiers
source                1..17
                      mol_type = protein
                      organism = synthetic construct
SEQUENCE: 625
YISSDASTTY YADSVKG                                              17

SEQ ID NO: 626        moltype = AA  length = 11
FEATURE               Location/Qualifiers
source                1..11
                      mol_type = protein
                      organism = synthetic construct
SEQUENCE: 626
DGGYNPGIFD Y                                                    11

SEQ ID NO: 627        moltype = AA  length = 11
FEATURE               Location/Qualifiers
source                1..11
                      mol_type = protein
                      organism = synthetic construct
SEQUENCE: 627
QASQSIGRWL N                                                    11

SEQ ID NO: 628        moltype = AA  length = 7
FEATURE               Location/Qualifiers
source                1..7
                      mol_type = protein
                      organism = synthetic construct
SEQUENCE: 628
DASILQT                                                          7

SEQ ID NO: 629        moltype = AA  length = 10
FEATURE               Location/Qualifiers
source                1..10
                      mol_type = protein
                      organism = synthetic construct
SEQUENCE: 629
QQSFTTPPLT                                                      10

SEQ ID NO: 630        moltype = AA  length = 5
FEATURE               Location/Qualifiers
source                1..5
                      mol_type = protein
                      organism = synthetic construct
SEQUENCE: 630
SYPMD                                                            5

SEQ ID NO: 631        moltype = AA  length = 17
FEATURE               Location/Qualifiers
source                1..17
                      mol_type = protein
                      organism = synthetic construct
SEQUENCE: 631
YISGRGDVTY YADSVKG                                              17

SEQ ID NO: 632        moltype = AA  length = 17
FEATURE               Location/Qualifiers
source                1..17
                      mol_type = protein
                      organism = synthetic construct
SEQUENCE: 632
VQSPSELLWF GELLPVD                                              17

SEQ ID NO: 633        moltype = AA  length = 11
FEATURE               Location/Qualifiers
source                1..11
                      mol_type = protein
                      organism = synthetic construct
SEQUENCE: 633
QASQVIKTWL N                                                    11

SEQ ID NO: 634        moltype = AA  length = 7
```

```
FEATURE                     Location/Qualifiers
source                      1..7
                            mol_type = protein
                            organism = synthetic construct
SEQUENCE: 634
DASNLQR                                                                         7

SEQ ID NO: 635              moltype = AA  length = 9
FEATURE                     Location/Qualifiers
source                      1..9
                            mol_type = protein
                            organism = synthetic construct
SEQUENCE: 635
QQSASTPIT                                                                       9

SEQ ID NO: 636              moltype = AA  length = 5
FEATURE                     Location/Qualifiers
source                      1..5
                            mol_type = protein
                            organism = synthetic construct
SEQUENCE: 636
SYSMD                                                                           5

SEQ ID NO: 637              moltype = AA  length = 17
FEATURE                     Location/Qualifiers
source                      1..17
                            mol_type = protein
                            organism = synthetic construct
SEQUENCE: 637
YITGSGDTTY YADSVKG                                                             17

SEQ ID NO: 638              moltype = AA  length = 15
FEATURE                     Location/Qualifiers
source                      1..15
                            mol_type = protein
                            organism = synthetic construct
SEQUENCE: 638
GFGWISGWAE DYFDY                                                               15

SEQ ID NO: 639              moltype = AA  length = 7
FEATURE                     Location/Qualifiers
source                      1..7
                            mol_type = protein
                            organism = synthetic construct
SEQUENCE: 639
GASRLEG                                                                         7

SEQ ID NO: 640              moltype = AA  length = 9
FEATURE                     Location/Qualifiers
source                      1..9
                            mol_type = protein
                            organism = synthetic construct
SEQUENCE: 640
QQHSTDQRT                                                                       9

SEQ ID NO: 641              moltype = AA  length = 5
FEATURE                     Location/Qualifiers
source                      1..5
                            mol_type = protein
                            organism = synthetic construct
SEQUENCE: 641
RSAIH                                                                           5

SEQ ID NO: 642              moltype = AA  length = 17
FEATURE                     Location/Qualifiers
source                      1..17
                            mol_type = protein
                            organism = synthetic construct
SEQUENCE: 642
GINPSGEATI YAQKFQG                                                             17

SEQ ID NO: 643              moltype = AA  length = 19
FEATURE                     Location/Qualifiers
source                      1..19
                            mol_type = protein
                            organism = synthetic construct
SEQUENCE: 643
DSSPQWLVTA GVYFYGMDV                                                           19
```

```
SEQ ID NO: 644          moltype = AA   length = 11
FEATURE                 Location/Qualifiers
source                  1..11
                        mol_type = protein
                        organism = synthetic construct
SEQUENCE: 644
RASQSISNWL A                                                              11

SEQ ID NO: 645          moltype = AA   length = 7
FEATURE                 Location/Qualifiers
source                  1..7
                        mol_type = protein
                        organism = synthetic construct
SEQUENCE: 645
HASTLQS                                                                    7

SEQ ID NO: 646          moltype = AA   length = 9
FEATURE                 Location/Qualifiers
source                  1..9
                        mol_type = protein
                        organism = synthetic construct
SEQUENCE: 646
QQYSSTPWT                                                                  9

SEQ ID NO: 647          moltype = AA   length = 8
FEATURE                 Location/Qualifiers
source                  1..8
                        mol_type = protein
                        organism = synthetic construct
SEQUENCE: 647
QHGGQGPT                                                                   8

SEQ ID NO: 648          moltype = AA   length = 7
FEATURE                 Location/Qualifiers
source                  1..7
                        mol_type = protein
                        organism = synthetic construct
SEQUENCE: 648
GSAFSSY                                                                    7

SEQ ID NO: 649          moltype = AA   length = 6
FEATURE                 Location/Qualifiers
source                  1..6
                        mol_type = protein
                        organism = synthetic construct
SEQUENCE: 649
NSNGGS                                                                     6

SEQ ID NO: 650          moltype = AA   length = 7
FEATURE                 Location/Qualifiers
source                  1..7
                        mol_type = protein
                        organism = synthetic construct
SEQUENCE: 650
GYTFSSY                                                                    7

SEQ ID NO: 651          moltype = AA   length = 6
FEATURE                 Location/Qualifiers
source                  1..6
                        mol_type = protein
                        organism = synthetic construct
SEQUENCE: 651
TGDAGR                                                                     6

SEQ ID NO: 652          moltype = AA   length = 15
FEATURE                 Location/Qualifiers
source                  1..15
                        mol_type = protein
                        organism = synthetic construct
SEQUENCE: 652
TLVRFLEWSH YYGMD                                                          15

SEQ ID NO: 653          moltype = AA   length = 15
FEATURE                 Location/Qualifiers
source                  1..15
                        mol_type = protein
                        organism = synthetic construct
SEQUENCE: 653
LLVKFLSWSH YYGMD                                                          15
```

```
SEQ ID NO: 654          moltype = AA  length = 5
FEATURE                 Location/Qualifiers
source                  1..5
                        mol_type = protein
                        organism = synthetic construct
SEQUENCE: 654
GGTGA                                                                    5

SEQ ID NO: 655          moltype = AA  length = 15
FEATURE                 Location/Qualifiers
source                  1..15
                        mol_type = protein
                        organism = synthetic construct
SEQUENCE: 655
LLVRFLEWGH YYGMD                                                        15

SEQ ID NO: 656          moltype = AA  length = 12
FEATURE                 Location/Qualifiers
source                  1..12
                        mol_type = protein
                        organism = synthetic construct
SEQUENCE: 656
SQSLLHSSGY NF                                                           12

SEQ ID NO: 657          moltype = AA  length = 5
FEATURE                 Location/Qualifiers
source                  1..5
                        mol_type = protein
                        organism = synthetic construct
SEQUENCE: 657
GGQGP                                                                    5

SEQ ID NO: 658          moltype = AA  length = 15
FEATURE                 Location/Qualifiers
source                  1..15
                        mol_type = protein
                        organism = synthetic construct
SEQUENCE: 658
LLVRFLEWAG YYGMD                                                        15

SEQ ID NO: 659          moltype = AA  length = 15
FEATURE                 Location/Qualifiers
source                  1..15
                        mol_type = protein
                        organism = synthetic construct
SEQUENCE: 659
QLVRFLEWSH YYGMD                                                        15

SEQ ID NO: 660          moltype = AA  length = 6
FEATURE                 Location/Qualifiers
source                  1..6
                        mol_type = protein
                        organism = synthetic construct
SEQUENCE: 660
ATQLPH                                                                   6

SEQ ID NO: 661          moltype = AA  length = 15
FEATURE                 Location/Qualifiers
source                  1..15
                        mol_type = protein
                        organism = synthetic construct
SEQUENCE: 661
LLVGFLQWSH YYGMD                                                        15

SEQ ID NO: 662          moltype = AA  length = 7
FEATURE                 Location/Qualifiers
source                  1..7
                        mol_type = protein
                        organism = synthetic construct
SEQUENCE: 662
EYTFTNY                                                                  7

SEQ ID NO: 663          moltype = AA  length = 6
FEATURE                 Location/Qualifiers
source                  1..6
                        mol_type = protein
                        organism = synthetic construct
SEQUENCE: 663
```

```
SAYHGN                                                                            6

SEQ ID NO: 664          moltype = AA  length = 12
FEATURE                 Location/Qualifiers
source                  1..12
                        mol_type = protein
                        organism = synthetic construct
SEQUENCE: 664
RVRRDYYNFG MD                                                                    12

SEQ ID NO: 665          moltype = AA  length = 7
FEATURE                 Location/Qualifiers
source                  1..7
                        mol_type = protein
                        organism = synthetic construct
SEQUENCE: 665
SEDITSY                                                                           7

SEQ ID NO: 666          moltype = AA  length = 6
FEATURE                 Location/Qualifiers
source                  1..6
                        mol_type = protein
                        organism = synthetic construct
SEQUENCE: 666
HNAYPY                                                                            6

SEQ ID NO: 667          moltype = AA  length = 7
FEATURE                 Location/Qualifiers
source                  1..7
                        mol_type = protein
                        organism = synthetic construct
SEQUENCE: 667
GYTFTSN                                                                           7

SEQ ID NO: 668          moltype = AA  length = 6
FEATURE                 Location/Qualifiers
source                  1..6
                        mol_type = protein
                        organism = synthetic construct
SEQUENCE: 668
FPIFGT                                                                            6

SEQ ID NO: 669          moltype = AA  length = 7
FEATURE                 Location/Qualifiers
source                  1..7
                        mol_type = protein
                        organism = synthetic construct
SEQUENCE: 669
GLGYDFD                                                                           7

SEQ ID NO: 670          moltype = AA  length = 7
FEATURE                 Location/Qualifiers
source                  1..7
                        mol_type = protein
                        organism = synthetic construct
SEQUENCE: 670
SQNIGNW                                                                           7

SEQ ID NO: 671          moltype = AA  length = 7
FEATURE                 Location/Qualifiers
source                  1..7
                        mol_type = protein
                        organism = synthetic construct
SEQUENCE: 671
SYGAPMY                                                                           7

SEQ ID NO: 672          moltype = AA  length = 7
FEATURE                 Location/Qualifiers
source                  1..7
                        mol_type = protein
                        organism = synthetic construct
SEQUENCE: 672
GGTFGIY                                                                           7

SEQ ID NO: 673          moltype = AA  length = 6
FEATURE                 Location/Qualifiers
source                  1..6
                        mol_type = protein
                        organism = synthetic construct
```

```
SEQUENCE: 673
IPVFGT                                                                     6

SEQ ID NO: 674          moltype = AA  length = 16
FEATURE                 Location/Qualifiers
source                  1..16
                        mol_type = protein
                        organism = synthetic construct
SEQUENCE: 674
TGIAAAGTHP ARGGMD                                                         16

SEQ ID NO: 675          moltype = AA  length = 7
FEATURE                 Location/Qualifiers
source                  1..7
                        mol_type = protein
                        organism = synthetic construct
SEQUENCE: 675
SPSISSY                                                                    7

SEQ ID NO: 676          moltype = AA  length = 6
FEATURE                 Location/Qualifiers
source                  1..6
                        mol_type = protein
                        organism = synthetic construct
SEQUENCE: 676
YLSFPL                                                                     6

SEQ ID NO: 677          moltype = AA  length = 7
FEATURE                 Location/Qualifiers
source                  1..7
                        mol_type = protein
                        organism = synthetic construct
SEQUENCE: 677
GYLLTEL                                                                    7

SEQ ID NO: 678          moltype = AA  length = 6
FEATURE                 Location/Qualifiers
source                  1..6
                        mol_type = protein
                        organism = synthetic construct
SEQUENCE: 678
IPSFGT                                                                     6

SEQ ID NO: 679          moltype = AA  length = 10
FEATURE                 Location/Qualifiers
source                  1..10
                        mol_type = protein
                        organism = synthetic construct
SEQUENCE: 679
YSGFDLLPLD                                                                10

SEQ ID NO: 680          moltype = AA  length = 7
FEATURE                 Location/Qualifiers
source                  1..7
                        mol_type = protein
                        organism = synthetic construct
SEQUENCE: 680
SQHISTW                                                                    7

SEQ ID NO: 681          moltype = AA  length = 6
FEATURE                 Location/Qualifiers
source                  1..6
                        mol_type = protein
                        organism = synthetic construct
SEQUENCE: 681
TYTYPR                                                                     6

SEQ ID NO: 682          moltype = AA  length = 7
FEATURE                 Location/Qualifiers
source                  1..7
                        mol_type = protein
                        organism = synthetic construct
SEQUENCE: 682
GGTFRSY                                                                    7

SEQ ID NO: 683          moltype = AA  length = 6
FEATURE                 Location/Qualifiers
source                  1..6
                        mol_type = protein
```

```
                        -continued

SEQUENCE: 683
NPSSGH                                                                       6

SEQ ID NO: 684          moltype = AA  length = 13
FEATURE                 Location/Qualifiers
source                  1..13
                        mol_type = protein
                        organism = synthetic construct
SEQUENCE: 684
LDYGEGYYYY GMD                                                              13

SEQ ID NO: 685          moltype = AA  length = 7
FEATURE                 Location/Qualifiers
source                  1..7
                        mol_type = protein
                        organism = synthetic construct
SEQUENCE: 685
GYSSPPY                                                                      7

SEQ ID NO: 686          moltype = AA  length = 7
FEATURE                 Location/Qualifiers
source                  1..7
                        mol_type = protein
                        organism = synthetic construct
SEQUENCE: 686
GYAFTNY                                                                      7

SEQ ID NO: 687          moltype = AA  length = 6
FEATURE                 Location/Qualifiers
source                  1..6
                        mol_type = protein
                        organism = synthetic construct
SEQUENCE: 687
NPRTGG                                                                       6

SEQ ID NO: 688          moltype = AA  length = 13
FEATURE                 Location/Qualifiers
source                  1..13
                        mol_type = protein
                        organism = synthetic construct
SEQUENCE: 688
IYTGVAVAGS GMD                                                              13

SEQ ID NO: 689          moltype = AA  length = 7
FEATURE                 Location/Qualifiers
source                  1..7
                        mol_type = protein
                        organism = synthetic construct
SEQUENCE: 689
SQGISTH                                                                      7

SEQ ID NO: 690          moltype = AA  length = 6
FEATURE                 Location/Qualifiers
source                  1..6
                        mol_type = protein
                        organism = synthetic construct
SEQUENCE: 690
ANSFPW                                                                       6

SEQ ID NO: 691          moltype = AA  length = 7
FEATURE                 Location/Qualifiers
source                  1..7
                        mol_type = protein
                        organism = synthetic construct
SEQUENCE: 691
GFTFSRP                                                                      7

SEQ ID NO: 692          moltype = AA  length = 6
FEATURE                 Location/Qualifiers
source                  1..6
                        mol_type = protein
                        organism = synthetic construct
SEQUENCE: 692
NPNAAT                                                                       6

SEQ ID NO: 693          moltype = AA  length = 12
FEATURE                 Location/Qualifiers
source                  1..12
```

```
                        mol_type = protein
                        organism = synthetic construct
SEQUENCE: 693
RLLREWELRP YD                                                           12

SEQ ID NO: 694          moltype = AA  length = 7
FEATURE                 Location/Qualifiers
source                  1..7
                        mol_type = protein
                        organism = synthetic construct
SEQUENCE: 694
SQSIGKS                                                                  7

SEQ ID NO: 695          moltype = AA  length = 7
FEATURE                 Location/Qualifiers
source                  1..7
                        mol_type = protein
                        organism = synthetic construct
SEQUENCE: 695
YRDVPPI                                                                  7

SEQ ID NO: 696          moltype = AA  length = 7
FEATURE                 Location/Qualifiers
source                  1..7
                        mol_type = protein
                        organism = synthetic construct
SEQUENCE: 696
GGTFSSH                                                                  7

SEQ ID NO: 697          moltype = AA  length = 6
FEATURE                 Location/Qualifiers
source                  1..6
                        mol_type = protein
                        organism = synthetic construct
SEQUENCE: 697
NPSDAS                                                                   6

SEQ ID NO: 698          moltype = AA  length = 14
FEATURE                 Location/Qualifiers
source                  1..14
                        mol_type = protein
                        organism = synthetic construct
SEQUENCE: 698
LRGYSYGAET WHFQ                                                         14

SEQ ID NO: 699          moltype = AA  length = 7
FEATURE                 Location/Qualifiers
source                  1..7
                        mol_type = protein
                        organism = synthetic construct
SEQUENCE: 699
SQYISNY                                                                  7

SEQ ID NO: 700          moltype = AA  length = 6
FEATURE                 Location/Qualifiers
source                  1..6
                        mol_type = protein
                        organism = synthetic construct
SEQUENCE: 700
TSSTPL                                                                   6

SEQ ID NO: 701          moltype = AA  length = 7
FEATURE                 Location/Qualifiers
source                  1..7
                        mol_type = protein
                        organism = synthetic construct
SEQUENCE: 701
GYTSTGY                                                                  7

SEQ ID NO: 702          moltype = AA  length = 6
FEATURE                 Location/Qualifiers
source                  1..6
                        mol_type = protein
                        organism = synthetic construct
SEQUENCE: 702
NPKSGD                                                                   6

SEQ ID NO: 703          moltype = AA  length = 14
FEATURE                 Location/Qualifiers
```

```
source                   1..14
                         mol_type = protein
                         organism = synthetic construct
SEQUENCE: 703
PGPYGSPLYY YGMD                                                         14

SEQ ID NO: 704           moltype = AA   length = 7
FEATURE                  Location/Qualifiers
source                   1..7
                         mol_type = protein
                         organism = synthetic construct
SEQUENCE: 704
SQIITTH                                                                  7

SEQ ID NO: 705           moltype = AA   length = 7
FEATURE                  Location/Qualifiers
source                   1..7
                         mol_type = protein
                         organism = synthetic construct
SEQUENCE: 705
YRTSSSL                                                                  7

SEQ ID NO: 706           moltype = AA   length = 6
FEATURE                  Location/Qualifiers
source                   1..6
                         mol_type = protein
                         organism = synthetic construct
SEQUENCE: 706
GYTFTK                                                                   6

SEQ ID NO: 707           moltype = AA   length = 6
FEATURE                  Location/Qualifiers
source                   1..6
                         mol_type = protein
                         organism = synthetic construct
SEQUENCE: 707
TPSSGD                                                                   6

SEQ ID NO: 708           moltype = AA   length = 14
FEATURE                  Location/Qualifiers
source                   1..14
                         mol_type = protein
                         organism = synthetic construct
SEQUENCE: 708
HMVRGLPNYY YGMD                                                         14

SEQ ID NO: 709           moltype = AA   length = 7
FEATURE                  Location/Qualifiers
source                   1..7
                         mol_type = protein
                         organism = synthetic construct
SEQUENCE: 709
SRDIANY                                                                  7

SEQ ID NO: 710           moltype = AA   length = 6
FEATURE                  Location/Qualifiers
source                   1..6
                         mol_type = protein
                         organism = synthetic construct
SEQUENCE: 710
AYTTPP                                                                   6

SEQ ID NO: 711           moltype = AA   length = 7
FEATURE                  Location/Qualifiers
source                   1..7
                         mol_type = protein
                         organism = synthetic construct
SEQUENCE: 711
GGTFSTF                                                                  7

SEQ ID NO: 712           moltype = AA   length = 6
FEATURE                  Location/Qualifiers
source                   1..6
                         mol_type = protein
                         organism = synthetic construct
SEQUENCE: 712
SAYSGS                                                                   6

SEQ ID NO: 713           moltype = AA   length = 8
```

```
FEATURE                 Location/Qualifiers
source                  1..8
                        mol_type = protein
                        organism = synthetic construct
SEQUENCE: 713
RYVDDAFD                                                                          8

SEQ ID NO: 714          moltype = AA   length = 7
FEATURE                 Location/Qualifiers
source                  1..7
                        mol_type = protein
                        organism = synthetic construct
SEQUENCE: 714
SEDISNF                                                                           7

SEQ ID NO: 715          moltype = AA   length = 5
FEATURE                 Location/Qualifiers
source                  1..5
                        mol_type = protein
                        organism = synthetic construct
SEQUENCE: 715
YISAP                                                                             5

SEQ ID NO: 716          moltype = AA   length = 9
FEATURE                 Location/Qualifiers
source                  1..9
                        mol_type = protein
                        organism = synthetic construct
SEQUENCE: 716
GFSFSTSGM                                                                         9

SEQ ID NO: 717          moltype = AA   length = 6
FEATURE                 Location/Qualifiers
source                  1..6
                        mol_type = protein
                        organism = synthetic construct
SEQUENCE: 717
DWDADN                                                                            6

SEQ ID NO: 718          moltype = AA   length = 10
FEATURE                 Location/Qualifiers
source                  1..10
                        mol_type = protein
                        organism = synthetic construct
SEQUENCE: 718
TGSGWFDAFD                                                                       10

SEQ ID NO: 719          moltype = AA   length = 13
FEATURE                 Location/Qualifiers
source                  1..13
                        mol_type = protein
                        organism = synthetic construct
SEQUENCE: 719
SQSVLYSSTN QNF                                                                   13

SEQ ID NO: 720          moltype = AA   length = 6
FEATURE                 Location/Qualifiers
source                  1..6
                        mol_type = protein
                        organism = synthetic construct
SEQUENCE: 720
YLTTPY                                                                            6

SEQ ID NO: 721          moltype = AA   length = 9
FEATURE                 Location/Qualifiers
source                  1..9
                        mol_type = protein
                        organism = synthetic construct
SEQUENCE: 721
GGSLSSGGS                                                                         9

SEQ ID NO: 722          moltype = AA   length = 13
FEATURE                 Location/Qualifiers
source                  1..13
                        mol_type = protein
                        organism = synthetic construct
SEQUENCE: 722
QNVDSYGYWG DAF                                                                   13
```

```
SEQ ID NO: 723          moltype = AA  length = 13
FEATURE                 Location/Qualifiers
source                  1..13
                        mol_type = protein
                        organism = synthetic construct
SEQUENCE: 723
SQSVLYSADN KNY                                                              13

SEQ ID NO: 724          moltype = AA  length = 6
FEATURE                 Location/Qualifiers
source                  1..6
                        mol_type = protein
                        organism = synthetic construct
SEQUENCE: 724
GHLFPY                                                                       6

SEQ ID NO: 725          moltype = AA  length = 7
FEATURE                 Location/Qualifiers
source                  1..7
                        mol_type = protein
                        organism = synthetic construct
SEQUENCE: 725
GFTFSKY                                                                      7

SEQ ID NO: 726          moltype = AA  length = 6
FEATURE                 Location/Qualifiers
source                  1..6
                        mol_type = protein
                        organism = synthetic construct
SEQUENCE: 726
SSSGGT                                                                       6

SEQ ID NO: 727          moltype = AA  length = 11
FEATURE                 Location/Qualifiers
source                  1..11
                        mol_type = protein
                        organism = synthetic construct
SEQUENCE: 727
LWVASPGYGM D                                                                11

SEQ ID NO: 728          moltype = AA  length = 12
FEATURE                 Location/Qualifiers
source                  1..12
                        mol_type = protein
                        organism = synthetic construct
SEQUENCE: 728
SQSLLHSSGH NY                                                               12

SEQ ID NO: 729          moltype = AA  length = 6
FEATURE                 Location/Qualifiers
source                  1..6
                        mol_type = protein
                        organism = synthetic construct
SEQUENCE: 729
ALLNPP                                                                       6

SEQ ID NO: 730          moltype = AA  length = 7
FEATURE                 Location/Qualifiers
source                  1..7
                        mol_type = protein
                        organism = synthetic construct
SEQUENCE: 730
GGSISSS                                                                      7

SEQ ID NO: 731          moltype = AA  length = 7
FEATURE                 Location/Qualifiers
source                  1..7
                        mol_type = protein
                        organism = synthetic construct
SEQUENCE: 731
YVDLAGS                                                                      7

SEQ ID NO: 732          moltype = AA  length = 16
FEATURE                 Location/Qualifiers
source                  1..16
                        mol_type = protein
                        organism = synthetic construct
SEQUENCE: 732
LSSRSSEWLL DQYTMD                                                           16
```

```
SEQ ID NO: 733              moltype = AA   length = 7
FEATURE                     Location/Qualifiers
source                      1..7
                            mol_type = protein
                            organism = synthetic construct
SEQUENCE: 733
SQSIGIN                                                              7

SEQ ID NO: 734              moltype = AA   length = 6
FEATURE                     Location/Qualifiers
source                      1..6
                            mol_type = protein
                            organism = synthetic construct
SEQUENCE: 734
YGTARL                                                               6

SEQ ID NO: 735              moltype = AA   length = 7
FEATURE                     Location/Qualifiers
source                      1..7
                            mol_type = protein
                            organism = synthetic construct
SEQUENCE: 735
GNRISDY                                                              7

SEQ ID NO: 736              moltype = AA   length = 7
FEATURE                     Location/Qualifiers
source                      1..7
                            mol_type = protein
                            organism = synthetic construct
SEQUENCE: 736
YPGYSDA                                                              7

SEQ ID NO: 737              moltype = AA   length = 11
FEATURE                     Location/Qualifiers
source                      1..11
                            mol_type = protein
                            organism = synthetic construct
SEQUENCE: 737
RDGYNYFAAF D                                                        11

SEQ ID NO: 738              moltype = AA   length = 6
FEATURE                     Location/Qualifiers
source                      1..6
                            mol_type = protein
                            organism = synthetic construct
SEQUENCE: 738
YGSSLT                                                               6

SEQ ID NO: 739              moltype = AA   length = 9
FEATURE                     Location/Qualifiers
source                      1..9
                            mol_type = protein
                            organism = synthetic construct
SEQUENCE: 739
GGYNPGIFD                                                            9

SEQ ID NO: 740              moltype = AA   length = 7
FEATURE                     Location/Qualifiers
source                      1..7
                            mol_type = protein
                            organism = synthetic construct
SEQUENCE: 740
SFTFSNY                                                              7

SEQ ID NO: 741              moltype = AA   length = 6
FEATURE                     Location/Qualifiers
source                      1..6
                            mol_type = protein
                            organism = synthetic construct
SEQUENCE: 741
SSDAST                                                               6

SEQ ID NO: 742              moltype = AA   length = 7
FEATURE                     Location/Qualifiers
source                      1..7
                            mol_type = protein
                            organism = synthetic construct
SEQUENCE: 742
```

```
SQSIGRW                                                                            7

SEQ ID NO: 743          moltype = AA  length = 7
FEATURE                 Location/Qualifiers
source                  1..7
                        mol_type = protein
                        organism = synthetic construct
SEQUENCE: 743
SFTTPPL                                                                            7

SEQ ID NO: 744          moltype = AA  length = 7
FEATURE                 Location/Qualifiers
source                  1..7
                        mol_type = protein
                        organism = synthetic construct
SEQUENCE: 744
GFTFGSY                                                                            7

SEQ ID NO: 745          moltype = AA  length = 6
FEATURE                 Location/Qualifiers
source                  1..6
                        mol_type = protein
                        organism = synthetic construct
SEQUENCE: 745
SGRGDV                                                                             6

SEQ ID NO: 746          moltype = AA  length = 16
FEATURE                 Location/Qualifiers
source                  1..16
                        mol_type = protein
                        organism = synthetic construct
SEQUENCE: 746
QSPSELLWFG ELLPVD                                                                 16

SEQ ID NO: 747          moltype = AA  length = 7
FEATURE                 Location/Qualifiers
source                  1..7
                        mol_type = protein
                        organism = synthetic construct
SEQUENCE: 747
SQVIKTW                                                                            7

SEQ ID NO: 748          moltype = AA  length = 6
FEATURE                 Location/Qualifiers
source                  1..6
                        mol_type = protein
                        organism = synthetic construct
SEQUENCE: 748
SASTPI                                                                             6

SEQ ID NO: 749          moltype = AA  length = 7
FEATURE                 Location/Qualifiers
source                  1..7
                        mol_type = protein
                        organism = synthetic construct
SEQUENCE: 749
GFTLSSY                                                                            7

SEQ ID NO: 750          moltype = AA  length = 6
FEATURE                 Location/Qualifiers
source                  1..6
                        mol_type = protein
                        organism = synthetic construct
SEQUENCE: 750
TGSGDT                                                                             6

SEQ ID NO: 751          moltype = AA  length = 13
FEATURE                 Location/Qualifiers
source                  1..13
                        mol_type = protein
                        organism = synthetic construct
SEQUENCE: 751
FGWISGWAED YFD                                                                    13

SEQ ID NO: 752          moltype = AA  length = 7
FEATURE                 Location/Qualifiers
source                  1..7
                        mol_type = protein
                        organism = synthetic construct
```

```
SEQUENCE: 752
SQSVYSY                                                                              7

SEQ ID NO: 753         moltype = AA  length = 6
FEATURE                Location/Qualifiers
source                 1..6
                       mol_type = protein
                       organism = synthetic construct
SEQUENCE: 753
HSTDQR                                                                               6

SEQ ID NO: 754         moltype = AA  length = 7
FEATURE                Location/Qualifiers
source                 1..7
                       mol_type = protein
                       organism = synthetic construct
SEQUENCE: 754
GFNYPRS                                                                              7

SEQ ID NO: 755         moltype = AA  length = 6
FEATURE                Location/Qualifiers
source                 1..6
                       mol_type = protein
                       organism = synthetic construct
SEQUENCE: 755
NPSGEA                                                                               6

SEQ ID NO: 756         moltype = AA  length = 17
FEATURE                Location/Qualifiers
source                 1..17
                       mol_type = protein
                       organism = synthetic construct
SEQUENCE: 756
SSPQWLVTAG VYFYGMD                                                                  17

SEQ ID NO: 757         moltype = AA  length = 7
FEATURE                Location/Qualifiers
source                 1..7
                       mol_type = protein
                       organism = synthetic construct
SEQUENCE: 757
SQSISNW                                                                              7

SEQ ID NO: 758         moltype = AA  length = 6
FEATURE                Location/Qualifiers
source                 1..6
                       mol_type = protein
                       organism = synthetic construct
SEQUENCE: 758
YSSTPW                                                                               6

SEQ ID NO: 759         moltype = AA  length = 8
FEATURE                Location/Qualifiers
source                 1..8
                       mol_type = protein
                       organism = synthetic construct
SEQUENCE: 759
GSAFSSYG                                                                             8

SEQ ID NO: 760         moltype = AA  length = 8
FEATURE                Location/Qualifiers
source                 1..8
                       mol_type = protein
                       organism = synthetic construct
SEQUENCE: 760
INSNGGST                                                                             8

SEQ ID NO: 761         moltype = AA  length = 8
FEATURE                Location/Qualifiers
source                 1..8
                       mol_type = protein
                       organism = synthetic construct
SEQUENCE: 761
GYTFSSYG                                                                             8

SEQ ID NO: 762         moltype = AA  length = 8
FEATURE                Location/Qualifiers
source                 1..8
                       mol_type = protein
```

```
                             -continued organism = synthetic construct
SEQUENCE: 762
ITGDAGRT                                                             8

SEQ ID NO: 763        moltype = AA   length = 19
FEATURE               Location/Qualifiers
source                1..19
                      mol_type = protein
                      organism = synthetic construct
SEQUENCE: 763
ARDTLVRFLE WSHYYGMDV                                                19

SEQ ID NO: 764        moltype = AA   length = 19
FEATURE               Location/Qualifiers
source                1..19
                      mol_type = protein
                      organism = synthetic construct
SEQUENCE: 764
ARDLLVKFLS WSHYYGMDV                                                19

SEQ ID NO: 765        moltype = AA   length = 7
FEATURE               Location/Qualifiers
source                1..7
                      mol_type = protein
                      organism = synthetic construct
SEQUENCE: 765
IGGTGAT                                                              7

SEQ ID NO: 766        moltype = AA   length = 19
FEATURE               Location/Qualifiers
source                1..19
                      mol_type = protein
                      organism = synthetic construct
SEQUENCE: 766
ARDLLVRFLE WGHYYGMDV                                                19

SEQ ID NO: 767        moltype = AA   length = 11
FEATURE               Location/Qualifiers
source                1..11
                      mol_type = protein
                      organism = synthetic construct
SEQUENCE: 767
QSLLHSSGYN F                                                        11

SEQ ID NO: 768        moltype = AA   length = 19
FEATURE               Location/Qualifiers
source                1..19
                      mol_type = protein
                      organism = synthetic construct
SEQUENCE: 768
ARDLLVRFLE WAGYYGMDV                                                19

SEQ ID NO: 769        moltype = AA   length = 19
FEATURE               Location/Qualifiers
source                1..19
                      mol_type = protein
                      organism = synthetic construct
SEQUENCE: 769
ARDQLVRFLE WSHYYGMDV                                                19

SEQ ID NO: 770        moltype = AA   length = 9
FEATURE               Location/Qualifiers
source                1..9
                      mol_type = protein
                      organism = synthetic construct
SEQUENCE: 770
AHATQLPHT                                                            9

SEQ ID NO: 771        moltype = AA   length = 19
FEATURE               Location/Qualifiers
source                1..19
                      mol_type = protein
                      organism = synthetic construct
SEQUENCE: 771
ARDLLVGFLQ WSHYYGMDV                                                19

SEQ ID NO: 772        moltype = AA   length = 8
FEATURE               Location/Qualifiers
source                1..8
```

```
                           mol_type = protein
                           organism = synthetic construct
SEQUENCE: 772
EYTFTNYD                                                                        8

SEQ ID NO: 773             moltype = AA   length = 8
FEATURE                    Location/Qualifiers
source                     1..8
                           mol_type = protein
                           organism = synthetic construct
SEQUENCE: 773
ISAYHGNA                                                                        8

SEQ ID NO: 774             moltype = AA   length = 16
FEATURE                    Location/Qualifiers
source                     1..16
                           mol_type = protein
                           organism = synthetic construct
SEQUENCE: 774
ARDRVRRDYY NFGMDV                                                              16

SEQ ID NO: 775             moltype = AA   length = 6
FEATURE                    Location/Qualifiers
source                     1..6
                           mol_type = protein
                           organism = synthetic construct
SEQUENCE: 775
EDITSY                                                                          6

SEQ ID NO: 776             moltype = AA   length = 8
FEATURE                    Location/Qualifiers
source                     1..8
                           mol_type = protein
                           organism = synthetic construct
SEQUENCE: 776
GYTFTSND                                                                        8

SEQ ID NO: 777             moltype = AA   length = 8
FEATURE                    Location/Qualifiers
source                     1..8
                           mol_type = protein
                           organism = synthetic construct
SEQUENCE: 777
IFPIFGTT                                                                        8

SEQ ID NO: 778             moltype = AA   length = 11
FEATURE                    Location/Qualifiers
source                     1..11
                           mol_type = protein
                           organism = synthetic construct
SEQUENCE: 778
AREGLGYDFD Y                                                                   11

SEQ ID NO: 779             moltype = AA   length = 6
FEATURE                    Location/Qualifiers
source                     1..6
                           mol_type = protein
                           organism = synthetic construct
SEQUENCE: 779
QNIGNW                                                                          6

SEQ ID NO: 780             moltype = AA   length = 8
FEATURE                    Location/Qualifiers
source                     1..8
                           mol_type = protein
                           organism = synthetic construct
SEQUENCE: 780
GGTFGIYA                                                                        8

SEQ ID NO: 781             moltype = AA   length = 8
FEATURE                    Location/Qualifiers
source                     1..8
                           mol_type = protein
                           organism = synthetic construct
SEQUENCE: 781
TIPVFGTA                                                                        8

SEQ ID NO: 782             moltype = AA   length = 20
FEATURE                    Location/Qualifiers
```

```
source                  1..20
                        mol_type = protein
                        organism = synthetic construct
SEQUENCE: 782
ASLTGIAAAG THPARGGMDV                                                   20

SEQ ID NO: 783          moltype = AA  length = 6
FEATURE                 Location/Qualifiers
source                  1..6
                        mol_type = protein
                        organism = synthetic construct
SEQUENCE: 783
PSISSY                                                                   6

SEQ ID NO: 784          moltype = AA  length = 8
FEATURE                 Location/Qualifiers
source                  1..8
                        mol_type = protein
                        organism = synthetic construct
SEQUENCE: 784
GYLLTELS                                                                 8

SEQ ID NO: 785          moltype = AA  length = 8
FEATURE                 Location/Qualifiers
source                  1..8
                        mol_type = protein
                        organism = synthetic construct
SEQUENCE: 785
IIPSFGTA                                                                 8

SEQ ID NO: 786          moltype = AA  length = 14
FEATURE                 Location/Qualifiers
source                  1..14
                        mol_type = protein
                        organism = synthetic construct
SEQUENCE: 786
AISYSGFDLL PLDK                                                         14

SEQ ID NO: 787          moltype = AA  length = 6
FEATURE                 Location/Qualifiers
source                  1..6
                        mol_type = protein
                        organism = synthetic construct
SEQUENCE: 787
QHISTW                                                                   6

SEQ ID NO: 788          moltype = AA  length = 8
FEATURE                 Location/Qualifiers
source                  1..8
                        mol_type = protein
                        organism = synthetic construct
SEQUENCE: 788
GGTFRSYT                                                                 8

SEQ ID NO: 789          moltype = AA  length = 8
FEATURE                 Location/Qualifiers
source                  1..8
                        mol_type = protein
                        organism = synthetic construct
SEQUENCE: 789
MNPSSGHT                                                                 8

SEQ ID NO: 790          moltype = AA  length = 17
FEATURE                 Location/Qualifiers
source                  1..17
                        mol_type = protein
                        organism = synthetic construct
SEQUENCE: 790
ARGLDYGEGY YYYGMDV                                                      17

SEQ ID NO: 791          moltype = AA  length = 6
FEATURE                 Location/Qualifiers
source                  1..6
                        mol_type = protein
                        organism = synthetic construct
SEQUENCE: 791
QGISES                                                                   6

SEQ ID NO: 792          moltype = AA  length = 8
```

```
FEATURE              Location/Qualifiers
source               1..8
                     mol_type = protein
                     organism = synthetic construct
SEQUENCE: 792
GYAFTNYN                                                                    8

SEQ ID NO: 793       moltype = AA  length = 8
FEATURE              Location/Qualifiers
source               1..8
                     mol_type = protein
                     organism = synthetic construct
SEQUENCE: 793
INPRTGGT                                                                    8

SEQ ID NO: 794       moltype = AA  length = 17
FEATURE              Location/Qualifiers
source               1..17
                     mol_type = protein
                     organism = synthetic construct
SEQUENCE: 794
AKDIYTGVAV AGSGMDY                                                         17

SEQ ID NO: 795       moltype = AA  length = 6
FEATURE              Location/Qualifiers
source               1..6
                     mol_type = protein
                     organism = synthetic construct
SEQUENCE: 795
QGISTH                                                                      6

SEQ ID NO: 796       moltype = AA  length = 8
FEATURE              Location/Qualifiers
source               1..8
                     mol_type = protein
                     organism = synthetic construct
SEQUENCE: 796
GFTFSRPA                                                                    8

SEQ ID NO: 797       moltype = AA  length = 8
FEATURE              Location/Qualifiers
source               1..8
                     mol_type = protein
                     organism = synthetic construct
SEQUENCE: 797
INPNAATT                                                                    8

SEQ ID NO: 798       moltype = AA  length = 16
FEATURE              Location/Qualifiers
source               1..16
                     mol_type = protein
                     organism = synthetic construct
SEQUENCE: 798
ARGRLLREWE LRPYDT                                                          16

SEQ ID NO: 799       moltype = AA  length = 6
FEATURE              Location/Qualifiers
source               1..6
                     mol_type = protein
                     organism = synthetic construct
SEQUENCE: 799
QSIGKS                                                                      6

SEQ ID NO: 800       moltype = AA  length = 8
FEATURE              Location/Qualifiers
source               1..8
                     mol_type = protein
                     organism = synthetic construct
SEQUENCE: 800
GGTFSSHD                                                                    8

SEQ ID NO: 801       moltype = AA  length = 8
FEATURE              Location/Qualifiers
source               1..8
                     mol_type = protein
                     organism = synthetic construct
SEQUENCE: 801
INPSDAST                                                                    8
```

```
SEQ ID NO: 802         moltype = AA   length = 18
FEATURE                Location/Qualifiers
source                 1..18
                       mol_type = protein
                       organism = synthetic construct
SEQUENCE: 802
ARDLRGYSYG AETWHFQH                                                  18

SEQ ID NO: 803         moltype = AA   length = 6
FEATURE                Location/Qualifiers
source                 1..6
                       mol_type = protein
                       organism = synthetic construct
SEQUENCE: 803
QYISNY                                                                6

SEQ ID NO: 804         moltype = AA   length = 8
FEATURE                Location/Qualifiers
source                 1..8
                       mol_type = protein
                       organism = synthetic construct
SEQUENCE: 804
GYTSTGYN                                                              8

SEQ ID NO: 805         moltype = AA   length = 8
FEATURE                Location/Qualifiers
source                 1..8
                       mol_type = protein
                       organism = synthetic construct
SEQUENCE: 805
MNPKSGDT                                                              8

SEQ ID NO: 806         moltype = AA   length = 18
FEATURE                Location/Qualifiers
source                 1..18
                       mol_type = protein
                       organism = synthetic construct
SEQUENCE: 806
ARDPGPYGSP LYYYGMDV                                                  18

SEQ ID NO: 807         moltype = AA   length = 6
FEATURE                Location/Qualifiers
source                 1..6
                       mol_type = protein
                       organism = synthetic construct
SEQUENCE: 807
QIITTH                                                                6

SEQ ID NO: 808         moltype = AA   length = 8
FEATURE                Location/Qualifiers
source                 1..8
                       mol_type = protein
                       organism = synthetic construct
SEQUENCE: 808
GYTFTKDH                                                              8

SEQ ID NO: 809         moltype = AA   length = 8
FEATURE                Location/Qualifiers
source                 1..8
                       mol_type = protein
                       organism = synthetic construct
SEQUENCE: 809
ITPSSGDT                                                              8

SEQ ID NO: 810         moltype = AA   length = 18
FEATURE                Location/Qualifiers
source                 1..18
                       mol_type = protein
                       organism = synthetic construct
SEQUENCE: 810
ARDHMVRGLP NYYYGMDL                                                  18

SEQ ID NO: 811         moltype = AA   length = 6
FEATURE                Location/Qualifiers
source                 1..6
                       mol_type = protein
                       organism = synthetic construct
SEQUENCE: 811
RDIANY                                                                6
```

```
SEQ ID NO: 812          moltype = AA  length = 8
FEATURE                 Location/Qualifiers
source                  1..8
                        mol_type = protein
                        organism = synthetic construct
SEQUENCE: 812
GGTFSTFH                                                                  8

SEQ ID NO: 813          moltype = AA  length = 8
FEATURE                 Location/Qualifiers
source                  1..8
                        mol_type = protein
                        organism = synthetic construct
SEQUENCE: 813
ISAYSGST                                                                  8

SEQ ID NO: 814          moltype = AA  length = 12
FEATURE                 Location/Qualifiers
source                  1..12
                        mol_type = protein
                        organism = synthetic construct
SEQUENCE: 814
ARARYVDDAF DI                                                            12

SEQ ID NO: 815          moltype = AA  length = 6
FEATURE                 Location/Qualifiers
source                  1..6
                        mol_type = protein
                        organism = synthetic construct
SEQUENCE: 815
EDISNF                                                                    6

SEQ ID NO: 816          moltype = AA  length = 10
FEATURE                 Location/Qualifiers
source                  1..10
                        mol_type = protein
                        organism = synthetic construct
SEQUENCE: 816
GFSFSTSGMV                                                               10

SEQ ID NO: 817          moltype = AA  length = 8
FEATURE                 Location/Qualifiers
source                  1..8
                        mol_type = protein
                        organism = synthetic construct
SEQUENCE: 817
IDWDADNI                                                                  8

SEQ ID NO: 818          moltype = AA  length = 14
FEATURE                 Location/Qualifiers
source                  1..14
                        mol_type = protein
                        organism = synthetic construct
SEQUENCE: 818
AKDTGSGWFD AFDI                                                          14

SEQ ID NO: 819          moltype = AA  length = 12
FEATURE                 Location/Qualifiers
source                  1..12
                        mol_type = protein
                        organism = synthetic construct
SEQUENCE: 819
QSVLYSSTNQ NF                                                            12

SEQ ID NO: 820          moltype = AA  length = 10
FEATURE                 Location/Qualifiers
source                  1..10
                        mol_type = protein
                        organism = synthetic construct
SEQUENCE: 820
GGSLSSGGSY                                                               10

SEQ ID NO: 821          moltype = AA  length = 8
FEATURE                 Location/Qualifiers
source                  1..8
                        mol_type = protein
                        organism = synthetic construct
SEQUENCE: 821
```

TDWDADNI 8

SEQ ID NO: 822    moltype = AA  length = 18
FEATURE           Location/Qualifiers
source            1..18
                  mol_type = protein
                  organism = synthetic construct
SEQUENCE: 822
AHRQNVDSYG YWGDAFDI 18

SEQ ID NO: 823    moltype = AA  length = 12
FEATURE           Location/Qualifiers
source            1..12
                  mol_type = protein
                  organism = synthetic construct
SEQUENCE: 823
QSVLYSADNK NY 12

SEQ ID NO: 824    moltype = AA  length = 8
FEATURE           Location/Qualifiers
source            1..8
                  mol_type = protein
                  organism = synthetic construct
SEQUENCE: 824
GFTFSKYD 8

SEQ ID NO: 825    moltype = AA  length = 8
FEATURE           Location/Qualifiers
source            1..8
                  mol_type = protein
                  organism = synthetic construct
SEQUENCE: 825
ISSSGGTR 8

SEQ ID NO: 826    moltype = AA  length = 15
FEATURE           Location/Qualifiers
source            1..15
                  mol_type = protein
                  organism = synthetic construct
SEQUENCE: 826
AKDLWVASPG YGMDV 15

SEQ ID NO: 827    moltype = AA  length = 11
FEATURE           Location/Qualifiers
source            1..11
                  mol_type = protein
                  organism = synthetic construct
SEQUENCE: 827
QSLLHSSGHN Y 11

SEQ ID NO: 828    moltype = AA  length = 10
FEATURE           Location/Qualifiers
source            1..10
                  mol_type = protein
                  organism = synthetic construct
SEQUENCE: 828
GGSISSSPYS 10

SEQ ID NO: 829    moltype = AA  length = 7
FEATURE           Location/Qualifiers
source            1..7
                  mol_type = protein
                  organism = synthetic construct
SEQUENCE: 829
VDLAGST 7

SEQ ID NO: 830    moltype = AA  length = 20
FEATURE           Location/Qualifiers
source            1..20
                  mol_type = protein
                  organism = synthetic construct
SEQUENCE: 830
ARALSSRSSE WLLDQYTMDV 20

SEQ ID NO: 831    moltype = AA  length = 6
FEATURE           Location/Qualifiers
source            1..6
                  mol_type = protein
                  organism = synthetic construct

```
SEQUENCE: 831
QSIGIN                                                                       6

SEQ ID NO: 832         moltype = AA  length = 8
FEATURE                Location/Qualifiers
source                 1..8
                       mol_type = protein
                       organism = synthetic construct
SEQUENCE: 832
GNRISDYW                                                                     8

SEQ ID NO: 833         moltype = AA  length = 8
FEATURE                Location/Qualifiers
source                 1..8
                       mol_type = protein
                       organism = synthetic construct
SEQUENCE: 833
IYPGYSDA                                                                     8

SEQ ID NO: 834         moltype = AA  length = 15
FEATURE                Location/Qualifiers
source                 1..15
                       mol_type = protein
                       organism = synthetic construct
SEQUENCE: 834
ARGRDGYNYF AAFDI                                                            15

SEQ ID NO: 835         moltype = AA  length = 7
FEATURE                Location/Qualifiers
source                 1..7
                       mol_type = protein
                       organism = synthetic construct
SEQUENCE: 835
QSVASSY                                                                      7

SEQ ID NO: 836         moltype = AA  length = 8
FEATURE                Location/Qualifiers
source                 1..8
                       mol_type = protein
                       organism = synthetic construct
SEQUENCE: 836
SFTFSNYA                                                                     8

SEQ ID NO: 837         moltype = AA  length = 8
FEATURE                Location/Qualifiers
source                 1..8
                       mol_type = protein
                       organism = synthetic construct
SEQUENCE: 837
ISSDASTT                                                                     8

SEQ ID NO: 838         moltype = AA  length = 13
FEATURE                Location/Qualifiers
source                 1..13
                       mol_type = protein
                       organism = synthetic construct
SEQUENCE: 838
ARDGGYNPGI FDY                                                              13

SEQ ID NO: 839         moltype = AA  length = 6
FEATURE                Location/Qualifiers
source                 1..6
                       mol_type = protein
                       organism = synthetic construct
SEQUENCE: 839
QSIGRW                                                                       6

SEQ ID NO: 840         moltype = AA  length = 8
FEATURE                Location/Qualifiers
source                 1..8
                       mol_type = protein
                       organism = synthetic construct
SEQUENCE: 840
GFTFGSYP                                                                     8

SEQ ID NO: 841         moltype = AA  length = 8
FEATURE                Location/Qualifiers
source                 1..8
                       mol_type = protein
```

```
                             organism = synthetic construct
SEQUENCE: 841
ISGRGDVT                                                                    8

SEQ ID NO: 842           moltype = AA   length = 20
FEATURE                  Location/Qualifiers
source                   1..20
                         mol_type = protein
                         organism = synthetic construct
SEQUENCE: 842
AKVQSPSELL WFGELLPVDY                                                      20

SEQ ID NO: 843           moltype = AA   length = 6
FEATURE                  Location/Qualifiers
source                   1..6
                         mol_type = protein
                         organism = synthetic construct
SEQUENCE: 843
QVIKTW                                                                      6

SEQ ID NO: 844           moltype = AA   length = 8
FEATURE                  Location/Qualifiers
source                   1..8
                         mol_type = protein
                         organism = synthetic construct
SEQUENCE: 844
GFTLSSYS                                                                    8

SEQ ID NO: 845           moltype = AA   length = 8
FEATURE                  Location/Qualifiers
source                   1..8
                         mol_type = protein
                         organism = synthetic construct
SEQUENCE: 845
ITGSGDTT                                                                    8

SEQ ID NO: 846           moltype = AA   length = 17
FEATURE                  Location/Qualifiers
source                   1..17
                         mol_type = protein
                         organism = synthetic construct
SEQUENCE: 846
ARGFGWISGW AEDYFDY                                                         17

SEQ ID NO: 847           moltype = AA   length = 6
FEATURE                  Location/Qualifiers
source                   1..6
                         mol_type = protein
                         organism = synthetic construct
SEQUENCE: 847
QSVYSY                                                                      6

SEQ ID NO: 848           moltype = AA   length = 8
FEATURE                  Location/Qualifiers
source                   1..8
                         mol_type = protein
                         organism = synthetic construct
SEQUENCE: 848
GFNYPRSA                                                                    8

SEQ ID NO: 849           moltype = AA   length = 8
FEATURE                  Location/Qualifiers
source                   1..8
                         mol_type = protein
                         organism = synthetic construct
SEQUENCE: 849
INPSGEAT                                                                    8

SEQ ID NO: 850           moltype = AA   length = 21
FEATURE                  Location/Qualifiers
source                   1..21
                         mol_type = protein
                         organism = synthetic construct
SEQUENCE: 850
ARDSSPQWLV TAGVYFYGMD V                                                    21

SEQ ID NO: 851           moltype = AA   length = 6
FEATURE                  Location/Qualifiers
source                   1..6
```

```
                        mol_type =  protein
                        organism =  synthetic construct
SEQUENCE: 851
QSISNW                                                                    6

SEQ ID NO: 852          moltype = AA   length = 126
FEATURE                 Location/Qualifiers
source                  1..126
                        mol_type =  protein
                        organism =  synthetic construct
SEQUENCE: 852
EVQLVESGGG LVQPGGSLRL SCAASGSAFS SYGMSWVRQA PGKGLELVAS INSNGGSTYY         60
PDSVKGRFTI SRDNAKNSLY LQMNSLRAED TAVYYCARDL LVRFLEWSHY YGMDVWGQGT        120
TVTVSS                                                                  126

SEQ ID NO: 853          moltype = AA   length = 126
FEATURE                 Location/Qualifiers
source                  1..126
                        mol_type =  protein
                        organism =  synthetic construct
SEQUENCE: 853
EVQLVESGGG LVQPGGSLRL SCAASGYTFS SYGMSWVRQA PGKGLELVAS ITGDAGRTYY         60
PDSVKGRFTI SRDNAKNSLY LQMNSLRAED TAVYYCARDT LVRFLEWSHY YGMDVWGQGT        120
TVTVSS                                                                  126

SEQ ID NO: 854          moltype = AA   length = 126
FEATURE                 Location/Qualifiers
source                  1..126
                        mol_type =  protein
                        organism =  synthetic construct
SEQUENCE: 854
EVQLVESGGG LVQPGGSLRL SCAASGSAFS SYGMSWVRQA PGKGLELVAS INSNGGSTYY         60
PDSVKGRFTI SRDNAKNSLY LQMNSLRAED TAVYYCARDL LVKFLSWSHY YGMDVWGQGT        120
TVTVSS                                                                  126

SEQ ID NO: 855          moltype = AA   length = 126
FEATURE                 Location/Qualifiers
source                  1..126
                        mol_type =  protein
                        organism =  synthetic construct
SEQUENCE: 855
EVQLVESGGG LVQPGGSLRL SCAASGSAFS SYGMSWVRQA PGKGLELVAS INSNGGSTYY         60
PDSVKGRFTI SRDNAKNSLY LQMNSLRAED TAVYYCARDL LVRFLEWAGY YGMDVWGQGT        120
TVTVSS                                                                  126

SEQ ID NO: 856          moltype = AA   length = 126
FEATURE                 Location/Qualifiers
source                  1..126
                        mol_type =  protein
                        organism =  synthetic construct
SEQUENCE: 856
EVQLVESGGG LVQPGGSLRL SCAASGSAFS SYGMSWVRQA PGKGLELVAS INSNGGSTYY         60
PDSVKGRFTI SRDNAKNSLY LQMNSLRAED TAVYYCARDQ LVRFLEWSHY YGMDVWGQGT        120
TVTVSS                                                                  126

SEQ ID NO: 857          moltype = AA   length = 112
FEATURE                 Location/Qualifiers
source                  1..112
                        mol_type =  protein
                        organism =  synthetic construct
SEQUENCE: 857
DIVMTQSPLS LPVTPGEPAS ISCRSSQSLL HSSGHNFLHW YLQKPGQSPQ LLIYAGSNRP         60
SGVPDRFSGS GSGTDFTLKI SRVEAEDVGV YYCAHATQLP HTFGGGTKVE IK                112

SEQ ID NO: 858          moltype = AA   length = 125
FEATURE                 Location/Qualifiers
source                  1..125
                        mol_type =  protein
                        organism =  synthetic construct
SEQUENCE: 858
EVQLVESGGG LVQPGGSLRL SCAASGSAFS SYGMSWVRQA PGKGLELVAS INSGGSTYYP         60
DSVKGRFTIS RDNAKNSLYL QMNSLRAEDT AVYYCARDLL VGFLQWSHYY GMDVWGQGTT        120
VTVSS                                                                   125

SEQ ID NO: 859          moltype = AA   length = 123
FEATURE                 Location/Qualifiers
source                  1..123
                        mol_type =  protein
                        organism =  synthetic construct
```

```
SEQUENCE: 859
QVQLVQSGAE VKKPGASVKV SCKVSEYTFT NYDIHWVRQA PGKGLEWMGG ISAYHGNAIY    60
AQKFQGRVTM TEDTSTDTAY MELSSLKSED TAVYYCARDR VRRDYYNFGM DVWGQGTTVT   120
VSS                                                                123

SEQ ID NO: 860         moltype = AA  length = 107
FEATURE                Location/Qualifiers
source                 1..107
                       mol_type = protein
                       organism = synthetic construct
SEQUENCE: 860
DIQMTQSPSS VSASVGDRVT ITCRASEDIT SYLAWYQQKP GKAPKLLIYD VSSLQSGVPS    60
RFSGSGSGTD FTLTISSLQP EDFANYYCLQ HNAYPYGFGG GTKVEIK                 107

SEQ ID NO: 861         moltype = AA  length = 118
FEATURE                Location/Qualifiers
source                 1..118
                       mol_type = protein
                       organism = synthetic construct
SEQUENCE: 861
QVQLVQSGAE VKKPGASVKV SCKVSGYTFT SNDIHWVRQA PGKGLEWMGG IFPIFGTTIY    60
AQKFQGRVTM TEDTSTDTAY MELSSLKSED TAVYYCAREG LGYDFDYWGQ GTLVTVSS     118

SEQ ID NO: 862         moltype = AA  length = 108
FEATURE                Location/Qualifiers
source                 1..108
                       mol_type = protein
                       organism = synthetic construct
SEQUENCE: 862
DIQMTQSPSS VSASVGDRVT ITCRASQNIG NWLAWYQQKP GKAPKLLIYS ASALQSGVPS    60
RFSGSGSGTD FTLTISSLQP EDFANYYCQQ SYGAPMYSFG GGTKVEIK                108

SEQ ID NO: 863         moltype = AA  length = 121
FEATURE                Location/Qualifiers
source                 1..121
                       mol_type = protein
                       organism = synthetic construct
SEQUENCE: 863
QVQLVQSGAE VKKPGASVKV SCKVSGYLLT ELSIHWVRQA PGKGLEWMGG IIPSFGTAIY    60
AQKFQGRVTM TEDTSTDTAY MELSSLKSED TAVYYCAISY SGFDLLPLDK WGQGTLVTVS   120
S                                                                  121

SEQ ID NO: 864         moltype = AA  length = 107
FEATURE                Location/Qualifiers
source                 1..107
                       mol_type = protein
                       organism = synthetic construct
SEQUENCE: 864
DIQMTQSPSS VSASVGDRVT ITCRASQHIS TWLAWYQQKP GKAPKLLIYY ASSLQGGVPS    60
RFSGSGSGTD FTLTISSLQP EDFANYYCLQ TYTYPRTFGG GTKVEIK                 107

SEQ ID NO: 865         moltype = AA  length = 124
FEATURE                Location/Qualifiers
source                 1..124
                       mol_type = protein
                       organism = synthetic construct
SEQUENCE: 865
QVQLVQSGAE VKKPGASVKV SCKVSGGTFR SYTIHWVRQA PGKGLEWMGG MNPSSGHTIY    60
AQKFQGRVTM TEDTSTDTAY MELSSLKSED TAVYYCARGL DYGEGYYYYG MDWGQGTTV    120
TVSS                                                               124

SEQ ID NO: 866         moltype = AA  length = 108
FEATURE                Location/Qualifiers
source                 1..108
                       mol_type = protein
                       organism = synthetic construct
SEQUENCE: 866
DIQMTQSPSS VSASVGDRVT ITCRASQGIS ESLAWYQQKP GKAPKLLIYS ASSLESGVPS    60
RFSGSGSGTD FTLTISSLQP EDFANYYCQQ GYSSPPYTFG GGTKVEIK                108

SEQ ID NO: 867         moltype = AA  length = 124
FEATURE                Location/Qualifiers
source                 1..124
                       mol_type = protein
                       organism = synthetic construct
SEQUENCE: 867
QVQLVQSGAE VKKPGASVKV SCKVSGYAFT NYNIHWVRQA PGKGLEWMGG INPRTGGTIY    60
AQKFQGRVTM TEDTSTDTAY MELSSLKSED TAVYYCAKDI YTGVAVAGSG MDWGQGTLV    120
TVSS                                                               124
```

```
SEQ ID NO: 868          moltype = AA  length = 107
FEATURE                 Location/Qualifiers
source                  1..107
                        mol_type = protein
                        organism = synthetic construct
SEQUENCE: 868
DIQMTQSPSS VSASVGDRVT ITCRASQGIS THLAWYQQKP GKAPKLLIYG ASNLESGVPS  60
RFSGSGSGTD FTLTISSLQP EDFANYYCQQ ANSFPWTFGG GTKVEIK              107

SEQ ID NO: 869          moltype = AA  length = 123
FEATURE                 Location/Qualifiers
source                  1..123
                        mol_type = protein
                        organism = synthetic construct
SEQUENCE: 869
QVQLVQSGAE VKKPGASVKV SCKVSGFTFS RPAIHWVRQA PGKGLEWMGG INPNAATTIY  60
AQKFQGRVTM TEDTSTDTAY MELSSLKSED TAVYYCARGR LLREWELRPY DTWGQGTLVT 120
VSS                                                              123

SEQ ID NO: 870          moltype = AA  length = 108
FEATURE                 Location/Qualifiers
source                  1..108
                        mol_type = protein
                        organism = synthetic construct
SEQUENCE: 870
DIQMTQSPSS VSASVGDRVT ITCRASQSIG KSLAWYQQKP GKAPKLLIYS ASNLRSGVPS  60
RFSGSGSGTD FTLTISSLQP EDFANYYCQQ YRDVPPITFG GGTKVEIK             108

SEQ ID NO: 871          moltype = AA  length = 125
FEATURE                 Location/Qualifiers
source                  1..125
                        mol_type = protein
                        organism = synthetic construct
SEQUENCE: 871
QVQLVQSGAE VKKPGASVKV SCKVSGGTFS SHDIHWVRQA PGKGLEWMGG INPSDASTIY  60
AQKFQGRVTM TEDTSTDTAY MELSSLKSED TAVYYCARDL RGYSYGAETW HFQHWGQGTL 120
VTVSS                                                            125

SEQ ID NO: 872          moltype = AA  length = 107
FEATURE                 Location/Qualifiers
source                  1..107
                        mol_type = protein
                        organism = synthetic construct
SEQUENCE: 872
DIQMTQSPSS VSASVGDRVT ITCRASQYIS NYLAWYQQKP GKAPKLLIYE TSRLESGVPS  60
RFSGSGSGTD FTLTISSLQP EDFANYYCQQ TSSTPLTFGG GTKVEIK              107

SEQ ID NO: 873          moltype = AA  length = 125
FEATURE                 Location/Qualifiers
source                  1..125
                        mol_type = protein
                        organism = synthetic construct
SEQUENCE: 873
QVQLVQSGAE VKKPGASVKV SCKVSGYTST GYNIHWVRQA PGKGLEWMGG MNPSGDTIY   60
AQKFQGRVTM TEDTSTDTAY MELSSLKSED TAVYYCARDP GPYGSPLYYY GMDVWGQGTT 120
VTVSS                                                            125

SEQ ID NO: 874          moltype = AA  length = 108
FEATURE                 Location/Qualifiers
source                  1..108
                        mol_type = protein
                        organism = synthetic construct
SEQUENCE: 874
DIQMTQSPSS VSASVGDRVT ITCRASQIIT THLAWYQQKP GKAPKLLIYD ASYLERGVPS  60
RFSGSGSGTD FTLTISSLQP EDFANYYCQQ YRTSSSLTFG GGTKVEIK             108

SEQ ID NO: 875          moltype = AA  length = 125
FEATURE                 Location/Qualifiers
source                  1..125
                        mol_type = protein
                        organism = synthetic construct
SEQUENCE: 875
QVQLVQSGAE VKKPGASVKV SCKVSGYTFT KDHIHWVRQA PGKGLEWMGG ITPSSGDTIY  60
AQKFQGRVTM TEDTSTDTAY MELSSLKSED TAVYYCARDH MVRGLPNYYY GMDLWGQGTT 120
VTVSS                                                            125

SEQ ID NO: 876          moltype = AA  length = 107
FEATURE                 Location/Qualifiers
```

```
source                  1..107
                        mol_type = protein
                        organism = synthetic construct
SEQUENCE: 876
DIQMTQSPSS VSASVGDRVT ITCRASRDIA NYLAWYQQKP GKAPKLLIYA ASILQNGVPS    60
RFSGSGSGTD FTLTISSLQP EDFANYYCQQ AYTTPPTFGG GTKVEIK                  107

SEQ ID NO: 877          moltype = AA   length = 119
FEATURE                 Location/Qualifiers
source                  1..119
                        mol_type = protein
                        organism = synthetic construct
SEQUENCE: 877
QVQLVQSGAE VKKPGASVKV SCKVSGGTFS TPHIHWVRQA PGKGLEWMGG ISAYSGSTIY    60
AQKFQGRVTM TEDTSTDTAY MELSSLKSED TAVYYCARAR YVDDAFDIWG QGTMVTVSS     119

SEQ ID NO: 878          moltype = AA   length = 106
FEATURE                 Location/Qualifiers
source                  1..106
                        mol_type = protein
                        organism = synthetic construct
SEQUENCE: 878
DIQMTQSPSS VSASVGDRVT ITCRASEDIS NFLAWYQQKP GKAPKLLIYA ASDLLSGVPS    60
RFSGSGSGTD FTLTISSLQP EDFANYYCQK YISAPSFGGG TKVEIK                   106

SEQ ID NO: 879          moltype = AA   length = 127
FEATURE                 Location/Qualifiers
source                  1..127
                        mol_type = protein
                        organism = synthetic construct
SEQUENCE: 879
QVTLRESGPA LVKPTQTLTL TCTVSGGSLS SGGSYVNWIR QPPGKALEWL AMTDWDADNI    60
VYNSALKSRL TISKDTSKNQ VVLTMTNMDP VDTATYYCAH RQNVDSYGYW GDAFDIWGQG    120
TMVTVSS                                                              127

SEQ ID NO: 880          moltype = AA   length = 113
FEATURE                 Location/Qualifiers
source                  1..113
                        mol_type = protein
                        organism = synthetic construct
SEQUENCE: 880
DIVMTQSPDS LAVSLGERAT INCKSSQSVL YSADNKNYLA WYQQKPGQPP KLLIYDASSL    60
ENGVPDRFSG SGSGTDFTLT ISSLQAEDVA VYYCQQGHLF PYSFGGGTKV EIK           113

SEQ ID NO: 881          moltype = AA   length = 128
FEATURE                 Location/Qualifiers
source                  1..128
                        mol_type = protein
                        organism = synthetic construct
SEQUENCE: 881
QVQLQESGPG LVKPSQTLSL TCTVSGGSIS SSPYSWSWIR QPPGKGLEWI GYVDLAGSTD    60
YNPSLKSRVT MSVDTSKNQF SLKVNSVTAA DTAVYYCARA LSSRSSEWLL DQYTMDVWGQ    120
GTTVTVSS                                                             128

SEQ ID NO: 882          moltype = AA   length = 107
FEATURE                 Location/Qualifiers
source                  1..107
                        mol_type = protein
                        organism = synthetic construct
SEQUENCE: 882
EIVMTQSPAT LSLSPGERAT LSCRASQSIG INLAWYQQKP GQAPRLLIYG VSNRATGIPA    60
RFSGSGSGTD FTLTISSLEP EDFAVYYCQQ YGTARLTFGG GTKVEIK                  107

SEQ ID NO: 883          moltype = AA   length = 122
FEATURE                 Location/Qualifiers
source                  1..122
                        mol_type = protein
                        organism = synthetic construct
SEQUENCE: 883
EVQLVQSGAE VKKPGESLKI SCKGSGNRIS DYWMNWVRQV PGKGLEWMGN IYPGYSDATY    60
NRKFKGQVTI SADKSISTAY LQWSSLKASD TAIYYCARGR DGYNYFAAFD IWGQGTMVTV    120
SS                                                                   122

SEQ ID NO: 884          moltype = AA   length = 108
FEATURE                 Location/Qualifiers
source                  1..108
                        mol_type = protein
                        organism = synthetic construct
SEQUENCE: 884
```

```
EIVLTQSPAT LSLSPGERAT LSCRASQSVA SSYLAWYQQK PGQAPRLLIY DTSSRAAGIP    60
ARFSGSGSGT DFTLTISSLE PEDFAVYYCH QYGSSLTTFG GGTKVEIK               108

SEQ ID NO: 885             moltype = AA  length = 120
FEATURE                    Location/Qualifiers
source                     1..120
                           mol_type = protein
                           organism = synthetic construct
SEQUENCE: 885
EVQLVESGGG LVQPGGSLRL SCTASSFTFS NYAMDWVRQA PGKGLEWVSY ISSDASTTYY    60
ADSVKGRFTI SRDNAKNTLY LQMNSLRAED TAVYYCARDG GYNPGIFDYW GQGTLVTVSS   120

SEQ ID NO: 886             moltype = AA  length = 108
FEATURE                    Location/Qualifiers
source                     1..108
                           mol_type = protein
                           organism = synthetic construct
SEQUENCE: 886
DIQMTQSPSS LSASVGDRVT ITCQASQSIG RWLNWYQQKP GKAPKLLIYD ASILQTGVPS    60
RFSGSGSGTD FTFTISSLQP EDIATYYCQQ SFTTPPLTFG GGTKVEIK               108

SEQ ID NO: 887             moltype = AA  length = 124
FEATURE                    Location/Qualifiers
source                     1..124
                           mol_type = protein
                           organism = synthetic construct
SEQUENCE: 887
EVQLVESGGG LVQPGGSLRL SCTASGFTLS SYSMDWVRQA PGKGLEWVSY ITGSGDTTYY    60
ADSVKGRFTI SRDNAKNTLY LQMNSLRAED TAVYYCARGF GWISGWAEDY FDYWGQGTLV   120
TVSS                                                               124

SEQ ID NO: 888             moltype = AA  length = 107
FEATURE                    Location/Qualifiers
source                     1..107
                           mol_type = protein
                           organism = synthetic construct
SEQUENCE: 888
DIQMTQSPSS LSASVGDRVT ITCQASQSVY SYLNWYQQKP GKAPKLLIYG ASRLEGGVPS    60
RFSGSGSGTD FTFTISSLQP EDIATYYCQQ HSTDQRTFGG GTKVEIK                107

SEQ ID NO: 889             moltype = AA  length = 128
FEATURE                    Location/Qualifiers
source                     1..128
                           mol_type = protein
                           organism = synthetic construct
SEQUENCE: 889
QVQLVQSGAE VKKPGASVKV SCKVSGFNYP RSAIHWVRQA PGKGLEWMGG INPSGEATIY    60
AQKFQGRVTM TEDTSTDTAY MELSSLKSED TAVYYCARDS SPQWLVTAGV YFYGMDVWGQ   120
GTTVTVSS                                                           128

SEQ ID NO: 890             moltype = AA  length = 107
FEATURE                    Location/Qualifiers
source                     1..107
                           mol_type = protein
                           organism = synthetic construct
SEQUENCE: 890
DIQMTQSPSS VSASVGDRVT ITCRASQSIS NWLAWYQQKP GKAPKLLIYH ASTLQSGVPS    60
RFSGSGSGTD FTLTISSLQP EDFANYYCQQ YSSTPWTFGG GTKVEIK                107

SEQ ID NO: 891             moltype = AA  length = 452
FEATURE                    Location/Qualifiers
source                     1..452
                           mol_type = protein
                           organism = synthetic construct
SEQUENCE: 891
EVQLVESGGG LVQPGGSLRL SCAASGSAFS SYGMSWVRQA PGKGLELVAS INSNGGSTYY    60
PDSVKGRFTI SRDNAKNSLY LQMNSLRAED TAVYYCARDL LVRFLEWSHY YGMDVWGQGT   120
TVTVSSASTK GPSVFPLAPC SRSTSESTAA LGCLVKDYFP EPVTVSWNSG ALTSGVHTFP   180
AVLQSSGLYS LSSVVTVPSS SLGTKTYTCN VDHKPSNTKV DKRVESKYGP PCPPCPAPEF   240
LGGPSVFLFP PKPKDTLMIS RTPEVTCVVV DVSQEDPEVQ FNWYVDGVEV HNAKTKPREE   300
QFNSTYRVVS VLTVLHQDWL NGKEYKCKVS NKGLPSSIEK TISKAKGQPR EPQVYTLPPS   360
QEEMTKNQVS LTCLVKGFYP SDIAVEWESN GQPENNYKTT PPVLDSDGSF FLYSRLTVDK   420
SRWQEGNVFS CSVMHEALHN HYTQKSLSLS LG                                 452

SEQ ID NO: 892             moltype = AA  length = 452
FEATURE                    Location/Qualifiers
source                     1..452
                           mol_type = protein
                           organism = synthetic construct
```

SEQUENCE: 892
EVQLVESGGG LVQPGGSLRL SCAASGYTFS SYGMSWVRQA PGKGLELVAS ITGDAGRTYY   60
PDSVKGRFTI SRDNAKNSLY LQMNSLRAED TAVYYCARDT LVRFLEWSHY YGMDVWGQGT  120
TVTVSSASTK GPSVFPLAPC SRSTSESTAA LGCLVKDYFP EPVTVSWNSG ALTSGVHTFP  180
AVLQSSGLYS LSSVVTVPSS SLGTKTYTCN VDHKPSNTKV DKRVESKYGP PCPPCPAPEF  240
LGGPSVFLFP PKPKDTLMIS RTPEVTCVVV DVSQEDPEVQ FNWYVDGVEV HNAKTKPREE  300
QFNSTYRVVS VLTVLHQDWL NGKEYKCKVS NKGLPSSIEK TISKAKGQPR EPQVYTLPPS  360
QEEMTKNQVS LTCLVKGFYP SDIAVEWESN GQPENNYKTT PPVLDSDGSF FLYSRLTVDK  420
SRWQEGNVFS CSVMHEALHN HYTQKSLSLS LG                                452

SEQ ID NO: 893         moltype = AA  length = 452
FEATURE                Location/Qualifiers
source                 1..452
                       mol_type = protein
                       organism = synthetic construct
SEQUENCE: 893
EVQLVESGGG LVQPGGSLRL SCAASGSAFS SYGMSWVRQA PGKGLELVAS INSNGGSTYY   60
PDSVKGRFTI SRDNAKNSLY LQMNSLRAED TAVYYCARDL LVKFLSWSHY YGMDVWGQGT  120
TVTVSSASTK GPSVFPLAPC SRSTSESTAA LGCLVKDYFP EPVTVSWNSG ALTSGVHTFP  180
AVLQSSGLYS LSSVVTVPSS SLGTKTYTCN VDHKPSNTKV DKRVESKYGP PCPPCPAPEF  240
LGGPSVFLFP PKPKDTLMIS RTPEVTCVVV DVSQEDPEVQ FNWYVDGVEV HNAKTKPREE  300
QFNSTYRVVS VLTVLHQDWL NGKEYKCKVS NKGLPSSIEK TISKAKGQPR EPQVYTLPPS  360
QEEMTKNQVS LTCLVKGFYP SDIAVEWESN GQPENNYKTT PPVLDSDGSF FLYSRLTVDK  420
SRWQEGNVFS CSVMHEALHN HYTQKSLSLS LG                                452

SEQ ID NO: 894         moltype = AA  length = 451
FEATURE                Location/Qualifiers
source                 1..451
                       mol_type = protein
                       organism = synthetic construct
SEQUENCE: 894
EVQLVESGGG LVQPGGSLRL SCAASGSAFS SYGMSWVRQA PGKGLELVAS IGGTGATYYP   60
DSVKGRFTIS RDNAKNSLYL QMNSLRAEDT AVYYCARDLL VRFLEWGHYY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                 451

SEQ ID NO: 895         moltype = AA  length = 218
FEATURE                Location/Qualifiers
source                 1..218
                       mol_type = protein
                       organism = synthetic construct
SEQUENCE: 895
DIVMTQSPLS LPVTPGEPAS ISCRSSQSLL HSSGYNFLHW YLQKPGQSPQ LLIYAASSRA   60
PGIPDRFSGS GSGTDFTLKI SRVEAEDVGV YYCMHGGQGP TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 896         moltype = AA  length = 452
FEATURE                Location/Qualifiers
source                 1..452
                       mol_type = protein
                       organism = synthetic construct
SEQUENCE: 896
EVQLVESGGG LVQPGGSLRL SCAASGSAFS SYGMSWVRQA PGKGLELVAS INSNGGSTYY   60
PDSVKGRFTI SRDNAKNSLY LQMNSLRAED TAVYYCARDL LVRFLEWAGY YGMDVWGQGT  120
TVTVSSASTK GPSVFPLAPC SRSTSESTAA LGCLVKDYFP EPVTVSWNSG ALTSGVHTFP  180
AVLQSSGLYS LSSVVTVPSS SLGTKTYTCN VDHKPSNTKV DKRVESKYGP PCPPCPAPEF  240
LGGPSVFLFP PKPKDTLMIS RTPEVTCVVV DVSQEDPEVQ FNWYVDGVEV HNAKTKPREE  300
QFNSTYRVVS VLTVLHQDWL NGKEYKCKVS NKGLPSSIEK TISKAKGQPR EPQVYTLPPS  360
QEEMTKNQVS LTCLVKGFYP SDIAVEWESN GQPENNYKTT PPVLDSDGSF FLYSRLTVDK  420
SRWQEGNVFS CSVMHEALHN HYTQKSLSLS LG                                452

SEQ ID NO: 897         moltype = AA  length = 452
FEATURE                Location/Qualifiers
source                 1..452
                       mol_type = protein
                       organism = synthetic construct
SEQUENCE: 897
EVQLVESGGG LVQPGGSLRL SCAASGSAFS SYGMSWVRQA PGKGLELVAS INSNGGSTYY   60
PDSVKGRFTI SRDNAKNSLY LQMNSLRAED TAVYYCARDQ LVRFLEWSHY YGMDVWGQGT  120
TVTVSSASTK GPSVFPLAPC SRSTSESTAA LGCLVKDYFP EPVTVSWNSG ALTSGVHTFP  180
AVLQSSGLYS LSSVVTVPSS SLGTKTYTCN VDHKPSNTKV DKRVESKYGP PCPPCPAPEF  240
LGGPSVFLFP PKPKDTLMIS RTPEVTCVVV DVSQEDPEVQ FNWYVDGVEV HNAKTKPREE  300
QFNSTYRVVS VLTVLHQDWL NGKEYKCKVS NKGLPSSIEK TISKAKGQPR EPQVYTLPPS  360
QEEMTKNQVS LTCLVKGFYP SDIAVEWESN GQPENNYKTT PPVLDSDGSF FLYSRLTVDK  420

```
SRWQEGNVFS CSVMHEALHN HYTQKSLSLS LG                                      452

SEQ ID NO: 898              moltype = AA  length = 219
FEATURE                     Location/Qualifiers
source                      1..219
                            mol_type = protein
                            organism = synthetic construct
SEQUENCE: 898
DIVMTQSPLS LPVTPGEPAS ISCRSSQSLL HSSGHNFLHW YLQKPGQSPQ LLIYAGSNRP        60
SGVPDRFSGS GSGTDFTLKI SRVEAEDVGV YYCAHATQLP HTFGGGTKVE IKRTVAAPSV        120
FIFPPSDEQL KSGTASVVCL LNNFYPREAK VQWKVDNALQ SGNSQESVTE QDSKDSTYSL        180
SSTLTLSKAD YEKHKVYACE VTHQGLSSPV TKSFNRGEC                               219

SEQ ID NO: 899              moltype = AA  length = 452
FEATURE                     Location/Qualifiers
source                      1..452
                            mol_type = protein
                            organism = synthetic construct
SEQUENCE: 899
EVQLVESGGG LVQPGGSLRL SCAASGSAFS SYGMSWVRQA PGKGLELVAS INSNGGSTYY        60
PDSVKGRFTI SRDNAKNSLY LQMNSLRAED TAVYYCARDL LVGFLQWSHY YGMDVWGQGT        120
TVTVSSASTK GPSVFPLAPC SRSTSESTAA LGCLVKDYFP EPVTVSWNSG ALTSGVHTFP        180
AVLQSSGLYS LSSVVTVPSS SLGTKTYTCN VDHKPSNTKV DKRVESKYGP PCPPCPAPEF        240
LGGPSVFLFP PKPKDTLMIS RTPEVTCVVV DVSQEDPEVQ FNWYVDGVEV HNAKTKPREE        300
QFNSTYRVVS VLTVLHQDWL NGKEYKCKVS NKGLPSSIEK TISKAKGQPR EPQVYTLPPS        360
QEEMTKNQVS LTCLVKGFYP SDIAVEWESN GQPENNYKTT PPVLDSDGSF FLYSRLTVDK        420
SRWQEGNVFS CSVMHEALHN HYTQKSLSLS LG                                      452

SEQ ID NO: 900              moltype = AA  length = 449
FEATURE                     Location/Qualifiers
source                      1..449
                            mol_type = protein
                            organism = synthetic construct
SEQUENCE: 900
QVQLVQSGAE VKKPGASVKV SCKVSEYTFT NYDIHWVRQA PGKGLEWMGG ISAYHGNAIY        60
AQKFQGRVTM TEDTSTDTAY MELSSLKSED TAVYYCARDR VRRDYYNFGM DVWGQGTTVT        120
VSSASTKGPS VFPLAPCSRS TSESTAALGC LVKDYFPEPV TVSWNSGALT SGVHTFPAVL        180
QSSGLYSLSS VVTVPSSSLG TKTYTCNVDH KPSNTKVDKR VESKYGPPCP APEFLGGPSV        240
FLFPPKPKDT LMISRTPEVT CVVVDVSQED PEVQFNWYVD GVEVHNAKTK PREEQFNSTY        300
(error in alignment - see original; reproducing visible lines)
STYRVVSVLT VLHQDWLNGK EYKCKVSNKG LPSSIEKTIS KAKGQPREPQ VYTLPPSQEE        360
MTKNQVSLTC LVKGFYPSDI AVEWESNGQP ENNYKTTPPV LDSDGSFFLY SRLTVDKSRW        420
QEGNVFSCSV MHEALHNHYT QKSLSLSLG                                         449

SEQ ID NO: 901              moltype = AA  length = 214
FEATURE                     Location/Qualifiers
source                      1..214
                            mol_type = protein
                            organism = synthetic construct
SEQUENCE: 901
DIQMTQSPSS VSASVGDRVT ITCRASEDIT SYLAWYQQKP GKAPKLLIYD VSSLQSGVPS        60
RFSGSGSGTD FTLTISSLQP EDFANYYCLQ HNAYPYGFGG GTKVEIKRTV AAPSVFIFPP        120
SDEQLKSGTA SVVCLLNNFY PREAKVQWKV DNALQSGNSQ ESVTEQDSKD STYSLSSTLT        180
LSKADYEKHK VYACEVTHQG LSSPVTKSFN RGEC                                    214

SEQ ID NO: 902              moltype = AA  length = 444
FEATURE                     Location/Qualifiers
source                      1..444
                            mol_type = protein
                            organism = synthetic construct
SEQUENCE: 902
QVQLVQSGAE VKKPGASVKV SCKVSGYTFT SNDIHWVRQA PGKGLEWMGG IFPIFGTTIY        60
AQKFQGRVTM TEDTSTDTAY MELSSLKSED TAVYYCAREG LGYDFDYWGQ GTLVTVSSAS        120
TKGPSVFPLA PCSRSTSEST AALGCLVKDY FPEPVTVSWN SGALTSGVHT FPAVLQSSGL        180
YSLSSVVTVP SSSLGTKTYT CNVDHKPSNT KVDKRVESKY GPPCPPCPAP EFLGGPSVFL        240
FPPKPKDTLM ISRTPEVTCV VVDVSQEDPE VQFNWYVDGV EVHNAKTKPR EEQFNSTYRV        300
VSVLTVLHQD WLNGKEYKCK VSNKGLPSSI EKTISKAKGQ PREPQVYTLP PSQEEMTKNQ        360
VSLTCLVKGF YPSDIAVEWE SNGQPENNYK TTPPVLDSDG SFFLYSRLTV DKSRWQEGNV        420
FSCSVMHEAL HNHYTQKSLS LSLG                                              444

SEQ ID NO: 903              moltype = AA  length = 215
FEATURE                     Location/Qualifiers
source                      1..215
                            mol_type = protein
                            organism = synthetic construct
SEQUENCE: 903
DIQMTQSPSS VSASVGDRVT ITCRASQNIG NWLAWYQQKP GKAPKLLIYS ASALQSGVPS        60
RFSGSGSGTD FTLTISSLQP EDFANYYCQQ SYGAPMYSFG GGTKVEIKRT VAAPSVFIFP        120
PSDEQLKSGT ASVVCLLNNF YPREAKVQWK VDNALQSGNS QESVTEQDSK DSTYSLSSTL        180
TLSKADYEKH KVYACEVTHQ GLSSPVTKSF NRGEC                                   215
```

```
SEQ ID NO: 904          moltype = AA  length = 453
FEATURE                 Location/Qualifiers
source                  1..453
                        mol_type = protein
                        organism = synthetic construct
SEQUENCE: 904
QVQLVQSGAE VKKPGASVKV SCKVSGGTFG IYAIHWVRQA PGKGLEWMGG TIPVFGTAIY    60
AQKFQGRVTM TEDTSTDTAY MELSSLKSED TAVYYCASLT GIAAAGTHPA RGGMDVWGQG   120
TTVTVSSAST KGPSVFPLAP CSRSTSESTA ALGCLVKDYF PEPVTVSWNS GALTSGVHTF   180
PAVLQSSGLY SLSSVVTVPS SSLGTKTYTC NVDHKPSNTK VDKRVESKYG PPCPPCPAPE   240
FLGGPSVFLF PPKPKDTLMI SRTPEVTCVV VDVSQEDPEV QFNWYVDGVE VHNAKTKPRE   300
EQFNSTYRVV SVLTVLHQDW LNGKEYKCKV SNKGLPSSIE KTISKAKGQP REPQVYTLPP   360
SQEEMTKNQV SLTCLVKGFY PSDIAVEWES NGQPENNYKT TPPVLDSDGS FFLYSRLTVD   420
KSRWQEGNVF SCSVMHEALH NHYTQKSLSL SLG                                453

SEQ ID NO: 905          moltype = AA  length = 214
FEATURE                 Location/Qualifiers
source                  1..214
                        mol_type = protein
                        organism = synthetic construct
SEQUENCE: 905
DIQMTQSPSS VSASVGDRVT ITCRASPSIS SYLAWYQQKP GKAPKLLIYA ASRLQSGVPS    60
RFSGSGSGTD FTLTISSLQP EDFANYYCQE YLSFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 906          moltype = AA  length = 447
FEATURE                 Location/Qualifiers
source                  1..447
                        mol_type = protein
                        organism = synthetic construct
SEQUENCE: 906
QVQLVQSGAE VKKPGASVKV SCKVSGYLLT ELSIHWVRQA PGKGLEWMGG IIPSFGTAIY    60
AQKFQGRVTM TEDTSTDTAY MELSSLKSED TAVYYCAISY SGFDLLPLDK WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLG                                      447

SEQ ID NO: 907          moltype = AA  length = 214
FEATURE                 Location/Qualifiers
source                  1..214
                        mol_type = protein
                        organism = synthetic construct
SEQUENCE: 907
DIQMTQSPSS VSASVGDRVT ITCRASQHIS TWLAWYQQKP GKAPKLLIYY ASSLQGGVPS    60
RFSGSGSGTD FTLTISSLQP EDFANYYCLQ TYTYPRTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 908          moltype = AA  length = 450
FEATURE                 Location/Qualifiers
source                  1..450
                        mol_type = protein
                        organism = synthetic construct
SEQUENCE: 908
QVQLVQSGAE VKKPGASVKV SCKVSGGTFR SYTIHWVRQA PGKGLEWMGG MNPSSGHTIY    60
AQKFQGRVTM TEDTSTDTAY MELSSLKSED TAVYYCARGL DYGEGYYYYG MDVWGQGTTV   120
TVSSASTKGP SVFPLAPCSR STSESTAALG CLVKDYFPEP VTVSWNSGAL TSGVHTFPAV   180
LQSSGLYSLS SVVTVPSSSL GTKTYTCNVD HKPSNTKVDK RVESKYGPPC PPCPAPEFLG   240
GPSVFLFPPK PKDTLMISRT PEVTCVVVDV SQEDPEVQFN WYVDGVEVHN AKTKPREEQF   300
NSTYRVVSVL TVLHQDWLNG KEYKCKVSNK GLPSSIEKTI SKAKGQPREP QVYTLPPSQE   360
EMTKNQVSLT CLVKGFYPSD IAVEWESNGQ PENNYKTTPP VLDSDGSFFL YSRLTVDKSR   420
WQEGNVFSCS VMHEALHNHY TQKSLSLSLG                                    450

SEQ ID NO: 909          moltype = AA  length = 215
FEATURE                 Location/Qualifiers
source                  1..215
                        mol_type = protein
                        organism = synthetic construct
SEQUENCE: 909
DIQMTQSPSS VSASVGDRVT ITCRASQGIS ESLAWYQQKP GKAPKLLIYS ASSLESGVPS    60
RFSGSGSGTD FTLTISSLQP EDFANYYCQQ GYSSPPYTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215
```

```
SEQ ID NO: 910            moltype = AA  length = 450
FEATURE                   Location/Qualifiers
source                    1..450
                          mol_type = protein
                          organism = synthetic construct
SEQUENCE: 910
QVQLVQSGAE VKKPGASVKV SCKVSGYAFT NYNIHWVRQA PGKGLEWMGG INPRTGGTIY    60
AQKFQGRVTM TEDTSTDTAY MELSSLKSED TAVYYCAKDI YTGVAVAGSG MDYWGQGTLV   120
TVSSASTKGP SVFPLAPCSR STSESTAALG CLVKDYFPEP VTVSWNSGAL TSGVHTFPAV   180
LQSSGLYSLS SVVTVPSSSL GTKTYTCNVD HKPSNTKVDK RVESKYGPPC PPCPAPEFLG   240
GPSVFLFPPK PKDTLMISRT PEVTCVVVDV SQEDPEVQFN WYVDGVEVHN AKTKPREEQF   300
NSTYRVVSVL TVLHQDWLNG KEYKCKVSNK GLPSSIEKTI SKAKGQPREP QVYTLPPSQE   360
EMTKNQVSLT CLVKGFYPSD IAVEWESNGQ PENNYKTTPP VLDSDGSFFL YSRLTVDKSR   420
WQEGNVFSCS VMHEALHNHY TQKSLSLSLG                                    450

SEQ ID NO: 911            moltype = AA  length = 214
FEATURE                   Location/Qualifiers
source                    1..214
                          mol_type = protein
                          organism = synthetic construct
SEQUENCE: 911
DIQMTQSPSS VSASVGDRVT ITCRASQGIS THLAWYQQKP GKAPKLLIYG ASNLESGVPS    60
RFSGSGSGTD FTLTISSLQP EDFANYYCQQ ANSFPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 912            moltype = AA  length = 449
FEATURE                   Location/Qualifiers
source                    1..449
                          mol_type = protein
                          organism = synthetic construct
SEQUENCE: 912
QVQLVQSGAE VKKPGASVKV SCKVSGFTFS RPAIHWVRQA PGKGLEWMGG INPNAATTIY    60
AQKFQGRVTM TEDTSTDTAY MELSSLKSED TAVYYCARGR LLREWELRPY DTWGQGTLVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPCP PCPAPEFLGG   240
PSVFLFPPKP KDTLMISRTP EVTCVVVDVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLG                                     449

SEQ ID NO: 913            moltype = AA  length = 215
FEATURE                   Location/Qualifiers
source                    1..215
                          mol_type = protein
                          organism = synthetic construct
SEQUENCE: 913
DIQMTQSPSS VSASVGDRVT ITCRASQSIG KSLAWYQQKP GKAPKLLIYS ASNLRSGVPS    60
RFSGSGSGTD FTLTISSLQP EDFANYYCQQ YRDVPPITFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 914            moltype = AA  length = 451
FEATURE                   Location/Qualifiers
source                    1..451
                          mol_type = protein
                          organism = synthetic construct
SEQUENCE: 914
QVQLVQSGAE VKKPGASVKV SCKVSGGTFS SHDIHWVRQA PGKGLEWMGG INPSDASTIY    60
AQKFQGRVTM TEDTSTDTAY MELSSLKSED TAVYYCARDL RGYSYGAETW HFQHWGQGTL   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                  451

SEQ ID NO: 915            moltype = AA  length = 214
FEATURE                   Location/Qualifiers
source                    1..214
                          mol_type = protein
                          organism = synthetic construct
SEQUENCE: 915
DIQMTQSPSS VSASVGDRVT ITCRASQYIS NYLAWYQQKP GKAPKLLIYE TSRLESGVPS    60
RFSGSGSGTD FTLTISSLQP EDFANYYCQQ TSSTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 916            moltype = AA  length = 451
```

```
FEATURE                 Location/Qualifiers
source                  1..451
                        mol_type = protein
                        organism = synthetic construct
SEQUENCE: 916
QVQLVQSGAE VKKPGASVKV SCKVSGYTST GYNIHWVRQA PGKGLEWMGG MNPKSGDTIY    60
AQKFQGRVTM TEDTSTDTAY MELSSLKSED TAVYYCARDP GPYGSPLYYY GMDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 917          moltype = AA  length = 215
FEATURE                 Location/Qualifiers
source                  1..215
                        mol_type = protein
                        organism = synthetic construct
SEQUENCE: 917
DIQMTQSPSS VSASVGDRVT ITCRASQIIT THLAWYQQKP GKAPKLLIYD ASYLERGVPS    60
RFSGSGSGTD FTLTISSLQP EDFANYYCQQ YRTSSSLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 918          moltype = AA  length = 451
FEATURE                 Location/Qualifiers
source                  1..451
                        mol_type = protein
                        organism = synthetic construct
SEQUENCE: 918
QVQLVQSGAE VKKPGASVKV SCKVSGYTFT KDHIHWVRQA PGKGLEWMGG ITPSSGDTIY    60
AQKFQGRVTM TEDTSTDTAY MELSSLKSED TAVYYCARDH MVRGLPNYYY GMDLWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 919          moltype = AA  length = 214
FEATURE                 Location/Qualifiers
source                  1..214
                        mol_type = protein
                        organism = synthetic construct
SEQUENCE: 919
DIQMTQSPSS VSASVGDRVT ITCRASRDIA NYLAWYQQKP GKAPKLLIYA ASILQNGVPS    60
RFSGSGSGTD FTLTISSLQP EDFANYYCQQ AYTTPPTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 920          moltype = AA  length = 445
FEATURE                 Location/Qualifiers
source                  1..445
                        mol_type = protein
                        organism = synthetic construct
SEQUENCE: 920
QVQLVQSGAE VKKPGASVKV SCKVSGGTFS TFHIHWVRQA PGKGLEWMGG ISAYSGSTIY    60
AQKFQGRVTM TEDTSTDTAY MELSSLKSED TAVYYCARAR YVDDAFDIWG QGTMVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFLGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                       445

SEQ ID NO: 921          moltype = AA  length = 213
FEATURE                 Location/Qualifiers
source                  1..213
                        mol_type = protein
                        organism = synthetic construct
SEQUENCE: 921
DIQMTQSPSS VSASVGDRVT ITCRASEDIS NFLAWYQQKP GKAPKLLIYA ASDLLSGVPS    60
RFSGSGSGTD FTLTISSLQP EDFANYYCQK YISAPSFGGG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                               213

SEQ ID NO: 922          moltype = AA  length = 449
FEATURE                 Location/Qualifiers
```

```
source                        1..449
                              mol_type = protein
                              organism = synthetic construct
SEQUENCE: 922
QVTLRESGPA LVKPTQTLTL TCTVSGFSFS TSGMVVNWIR QPPGKALEWL AMIDWDADNI    60
VYNSALKSRL TISKDTSKNQ VVLTMTNMDP VDTATYYCAK DTGSGWFDAF DIWGQGTMVT   120
VSSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPEFLGG   240
PSVFLFPPKP KDTLMISRTP EVTCVVVDVS QEDPEVQFNW YVDGVEVHNA KTKPREEQFN   300
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLG                                    449

SEQ ID NO: 923                moltype = AA    length = 220
FEATURE                       Location/Qualifiers
source                        1..220
                              mol_type = protein
                              organism = synthetic construct
SEQUENCE: 923
DIVMTQSPDS LAVSLGERAT INCKSSQSVL YSSTNQNFLA WYQQKPGQPP KLLIYQASTL    60
QNGVPDRFSG SGSGTDFTLT ISSLQAEDVA VYYCQQYLTT PYTFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 924                moltype = AA    length = 453
FEATURE                       Location/Qualifiers
source                        1..453
                              mol_type = protein
                              organism = synthetic construct
SEQUENCE: 924
QVTLRESGPA LVKPTQTLTL TCTVSGGSLS SGGSYVNWIR QPPGKALEWL AMTDWDADNI    60
VYNSALKSRL TISKDTSKNQ VVLTMTNMDP VDTATYYCAH RQNVDSYGYW GDAFDIWGQG   120
TMVTVSSAST KGPSVFPLAP CSRSTSESTA ALGCLVKDYF PEPVTVSWNS GALTSGVHTF   180
PAVLQSSGLY SLSSVVTVPS SSLGTKTYTC NVDHKPSNTK VDKRVESKYG PPCPPCPAPE   240
FLGGPSVFLF PPKPKDTLMI SRTPEVTCVV VDVSQEDPEV QFNWYVDGVE VHNAKTKPRE   300
EQFNSTYRVV SVLTVLHQDW LNGKEYKCKV SNKGLPSSIE KTISKAKGQP REPQVYTLPP   360
SQEEMTKNQV SLTCLVKGFY PSDIAVEWES NGQPENNYKT TPPVLDSDGS FFLYSRLTVD   420
KSRWQEGNVF SCSVMHEALH NHYTQKSLSL SLG                                453

SEQ ID NO: 925                moltype = AA    length = 219
FEATURE                       Location/Qualifiers
source                        1..219
                              mol_type = protein
                              organism = synthetic construct
SEQUENCE: 925
DIVMTQSPDS LAVSLGERAT INCKSSQSVL YSADNKNYLA WYQQKPGQPP KLLIYDASSL    60
ENGVPDRFSG SGSGTDFTLT ISSLQAEDVA VYYCQQYDDL PYSFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGE                          219

SEQ ID NO: 926                moltype = AA    length = 448
FEATURE                       Location/Qualifiers
source                        1..448
                              mol_type = protein
                              organism = synthetic construct
SEQUENCE: 926
EVQLVESGGG LVQPGGSLRL SCAASGFTFS KYDMSWVRQA PGKGLELVAS ISSSGGTRYY    60
PDSVKGRFTI SRDNAKNSLY LQMNSLRAED TAVYYCAKDL WVASPGYGMD VWGQGTTVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLG                                      448

SEQ ID NO: 927                moltype = AA    length = 219
FEATURE                       Location/Qualifiers
source                        1..219
                              mol_type = protein
                              organism = synthetic construct
SEQUENCE: 927
DIVMTQSPLS LPVTPGEPAS ISCRSSQSLL HSSGHNYLHW YLQKPGQSPQ LLIYLGSIRA    60
PGVPDRFSGS GSGTDFTLKI SRVEAEDVGV YYCMQALLNP PTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 928                moltype = AA    length = 454
FEATURE                       Location/Qualifiers
source                        1..454
```

```
                       mol_type = protein
                       organism = synthetic construct
SEQUENCE: 928
QVQLQESGPG LVKPSQTLSL TCTVSGGSIS SSPYSWSWIR QPPGKGLEWI GYVDLAGSTD   60
YNPSLKSRVT MSVDTSKNQF SLKVNSVTAA DTAVYYCARA LSSRSSEWLL DQYTMDVWGQ  120
GTTVTVSSAS TKGPSVFPLA PCSRSTSEST AALGCLVKDY FPEPVTVSWN SGALTSGVHT  180
FPPAVLQSSGL YSLSSVVTVP SSSLGTKTYT CNVDHKPSNT KVDKRVESKY GPPCPPCPAP  240
EFLGGPSVFL FPPKPKDTLM ISRTPEVTCV VVDVSQEDPE VQFNWYVDGV EVHNAKTKPR  300
EEQFNSTYRV VSVLTVLHQD WLNGKEYKCK VSNKGLPSSI EKTISKAKGQ PREPQVYTLP  360
PSQEEMTKNQ VSLTCLVKGF YPSDIAVEWE SNGQPENNYK TTPPVLDSDG SFFLYSRLTV  420
DKSRWQEGNV FSCSVMHEAL HNHYTQKSLS LSLG                             454

SEQ ID NO: 929         moltype = AA   length = 214
FEATURE                Location/Qualifiers
source                 1..214
                       mol_type = protein
                       organism = synthetic construct
SEQUENCE: 929
EIVMTQSPAT LSLSPGERAT LSCRASQSIG INLAWYQQKP GQAPRLLIYG VSNRATGIPA   60
RFSGSGSGTD FTLTISSLEP EDFAVYYCQQ YGTARLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 930         moltype = AA   length = 448
FEATURE                Location/Qualifiers
source                 1..448
                       mol_type = protein
                       organism = synthetic construct
SEQUENCE: 930
EVQLVQSGAE VKKPGESLKI SCKGSGNRIS DYWMNWVRQV PGKGLEWMGN IYPGYSDATY   60
NRKFKGQVTI SADKSISTAY LQWSSLKASD TAIYYCARGR DGYNYFAAFD IWGQGTMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLG                                    448

SEQ ID NO: 931         moltype = AA   length = 215
FEATURE                Location/Qualifiers
source                 1..215
                       mol_type = protein
                       organism = synthetic construct
SEQUENCE: 931
EIVLTQSPAT LSLSPGERAT LSCRASQSVA SSYLAWYQQK PGQAPRLLIY DTSSRAAGIP   60
ARFSGSGSGT DFTLTISSLE PEDFAVYYCH QYGSSLTTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 932         moltype = AA   length = 446
FEATURE                Location/Qualifiers
source                 1..446
                       mol_type = protein
                       organism = synthetic construct
SEQUENCE: 932
EVQLVESGGG LVQPGGSLRL SCTASSFTFS NYAMDWVRQA PGKGLEWVSY ISSDASTTYY   60
ADSVKGRFTI SRDNAKNTLY LQMNSLRAED TAVYYCARDG GYNPGIFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 933         moltype = AA   length = 215
FEATURE                Location/Qualifiers
source                 1..215
                       mol_type = protein
                       organism = synthetic construct
SEQUENCE: 933
DIQMTQSPSS LSASVGDRVT ITCQASQSIG RWLNWYQQKP GKAPKLLIYD ASILQTGVPS   60
RFSGSGSGTD FTFTISSLQP EDIATYYCQQ SFTTPPLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 934         moltype = AA   length = 453
FEATURE                Location/Qualifiers
source                 1..453
                       mol_type = protein
```

```
                        organism = synthetic construct
SEQUENCE: 934
EVQLVESGGG LVQPGGSLRL SCTASGFTFG SYPMDWVRQA PGKGLEWVSY ISGRGDVTYY    60
ADSVKGRFTI SRDNAKNTLY LQMNSLRAED TAVYYCAKVQ SPSELLWFGE LLPVDYWGQG   120
TLVTVSSAST KGPSVFPLAP CSRSTSESTA ALGCLVKDYF PEPVTVSWNS GALTSGVHTF   180
PAVLQSSGLY SLSSVVTVPS SSLGTKTYTC NVDHKPSNTK VDKRVESKYG PPCPPCPAPE   240
FLGGPSVFLF PPKPKDTLMI SRTPEVTCVV VDVSQEDPEV QFNWYVDGVE VHNAKTKPRE   300
EQFNSTYRVV SVLTVLHQDW LNGKEYKCKV SNKGLPSSIE KTISKAKGQP REPQVYTLPP   360
SQEEMTKNQV SLTCLVKGFY PSDIAVEWES NGQPENNYKT TPPVLDSDGS FFLYSRLTVD   420
KSRWQEGNVF SCSVMHEALH NHYTQKSLSL SLG                                453

SEQ ID NO: 935          moltype = AA  length = 214
FEATURE                 Location/Qualifiers
source                  1..214
                        mol_type = protein
                        organism = synthetic construct
SEQUENCE: 935
DIQMTQSPSS LSASVGDRVT ITCQASQVIK TWLNWYQQKP GKAPKLLIYD ASNLQRGVPS    60
RFSGSGSGTD FTFTISSLQP EDIATYYCQQ SASTPITFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 936          moltype = AA  length = 450
FEATURE                 Location/Qualifiers
source                  1..450
                        mol_type = protein
                        organism = synthetic construct
SEQUENCE: 936
EVQLVESGGG LVQPGGSLRL SCTASGFTLS SYSMDWVRQA PGKGLEWVSY ITGSGDTTYY    60
ADSVKGRFTI SRDNAKNTLY LQMNSLRAED TAVYYCARGF GWISGWAEDY FDYWGQGTLV   120
TVSSASTKGP SVFPLAPCSR STSESTAALG CLVKDYFPEP VTVSWNSGAL TSGVHTFPAV   180
LQSSGLYSLS SVVTVPSSSL GTKTYTCNVD HKPSNTKVDK RVESKYGPPC PPCPAPEFLG   240
GPSVFLFPPK PKDTLMISRT PEVTCVVVDV SQEDPEVQFN WYVDGVEVHN AKTKPREEQF   300
NSTYRVVSVL TVLHQDWLNG KEYKCKVSNK GLPSSIEKTI SKAKGQPREP QVYTLPPSQE   360
EMTKNQVSLT CLVKGFYPSD IAVEWESNGQ PENNYKTTPP VLDSDGSFFL YSRLTVDKSR   420
WQEGNVFSCS VMHEALHNHY TQKSLSLSLG                                    450

SEQ ID NO: 937          moltype = AA  length = 214
FEATURE                 Location/Qualifiers
source                  1..214
                        mol_type = protein
                        organism = synthetic construct
SEQUENCE: 937
DIQMTQSPSS LSASVGDRVT ITCQASQSVY SYLNWYQQKP GKAPKLLIYG ASRLEGGVPS    60
RFSGSGSGTD FTFTISSLQP EDIATYYCQQ HSTDQRTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 938          moltype = AA  length = 454
FEATURE                 Location/Qualifiers
source                  1..454
                        mol_type = protein
                        organism = synthetic construct
SEQUENCE: 938
QVQLVQSGAE VKKPGASVKV SCKVSGFNYP RSAIHWVRQA PGKGLEWMGG INPSGEATIY    60
AQKFQGRVTM TEDTSTDTAY MELSSLKSED TAVYYCARDS SPQWLVTAGV YFYGMDVWGQ   120
GTTVTVSSAS TKGPSVFPLA PCSRSTSEST AALGCLVKDY FPEPVTVSWN SGALTSGVHT   180
FPAVLQSSGL YSLSSVVTVP SSLGTKTYT CNVDHKPSNT KVDKRVESKY GPPCPPCPAP   240
EFLGGPSVFL FPPKPKDTLM ISRTPEVTCV VVDVSQEDPE VQFNWYVDGV EVHNAKTKPR   300
EEQFNSTYRV VSVLTVLHQD WLNGKEYKCK VSNKGLPSSI EKTISKAKGQ PREPQVYTLP   360
PSQEEMTKNQ VSLTCLVKGF YPSDIAVEWE SNGQPENNYK TTPPVLDSDG SFFLYSRLTV   420
DKSRWQEGNV FSCSVMHEAL HNHYTQKSLS LSLG                               454

SEQ ID NO: 939          moltype = AA  length = 214
FEATURE                 Location/Qualifiers
source                  1..214
                        mol_type = protein
                        organism = synthetic construct
SEQUENCE: 939
DIQMTQSPSS VSASVGDRVT ITCRASQSIS NWLAWYQQKP GKAPKLLIYH ASTLQSGVPS    60
RFSGSGSGTD FTLTISSLQP EDFANYYCQQ YSSTPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 940          moltype = AA  length = 218
FEATURE                 Location/Qualifiers
source                  1..218
                        mol_type = protein
                        organism = synthetic construct
```

```
SEQUENCE: 940
DIVMTQSPLS LPVTPGEPAS ISCRSSQSLL HSSGYNFLHW YLQKPGQSPQ LLIYAASSRA      60
PGIPDRFSGS GSGTDFTLKI SRVEAEDVGV YYCQHGGQGP TFGGGTKVEI KRTVAAPSVF     120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 941              moltype = AA   length = 6
FEATURE                     Location/Qualifiers
source                      1..6
                            mol_type = protein
                            organism = synthetic construct
SEQUENCE: 941
HHHHHH                                                                 6

SEQ ID NO: 942              moltype = AA   length = 6
FEATURE                     Location/Qualifiers
source                      1..6
                            mol_type = protein
                            organism = synthetic construct
SEQUENCE: 942
HHHHHN                                                                 6

SEQ ID NO: 943              moltype = AA   length = 4
FEATURE                     Location/Qualifiers
source                      1..4
                            mol_type = protein
                            organism = synthetic construct
SEQUENCE: 943
RSRR                                                                   4

SEQ ID NO: 944              moltype = AA   length = 17
FEATURE                     Location/Qualifiers
source                      1..17
                            mol_type = protein
                            organism = synthetic construct
SEQUENCE: 944
DLLVEFLKWS HYYGMDV                                                    17

SEQ ID NO: 945              moltype = AA   length = 17
FEATURE                     Location/Qualifiers
source                      1..17
                            mol_type = protein
                            organism = synthetic construct
SEQUENCE: 945
DLLVTFLRWS HYYGMDV                                                    17

SEQ ID NO: 946              moltype = AA   length = 17
FEATURE                     Location/Qualifiers
source                      1..17
                            mol_type = protein
                            organism = synthetic construct
SEQUENCE: 946
DLLIRFLEWG HYYGMDV                                                    17

SEQ ID NO: 947              moltype = AA   length = 17
FEATURE                     Location/Qualifiers
source                      1..17
                            mol_type = protein
                            organism = synthetic construct
SEQUENCE: 947
SITGSKGETY YPDSVKG                                                    17

SEQ ID NO: 948              moltype = AA   length = 16
FEATURE                     Location/Qualifiers
source                      1..16
                            mol_type = protein
                            organism = synthetic construct
SEQUENCE: 948
SFTGSGAAYY PDSVKG                                                     16

SEQ ID NO: 949              moltype = AA   length = 7
FEATURE                     Location/Qualifiers
source                      1..7
                            mol_type = protein
                            organism = synthetic construct
SEQUENCE: 949
ESSNRVS                                                                7

SEQ ID NO: 950              moltype = AA   length = 17
```

```
FEATURE                 Location/Qualifiers
source                  1..17
                        mol_type = protein
                        organism = synthetic construct
SEQUENCE: 950
DNLIRFLEWS HYYGMDV                                                              17

SEQ ID NO: 951          moltype = AA   length = 7
FEATURE                 Location/Qualifiers
source                  1..7
                        mol_type = protein
                        organism = synthetic construct
SEQUENCE: 951
EVSNRES                                                                          7

SEQ ID NO: 952          moltype = AA   length = 15
FEATURE                 Location/Qualifiers
source                  1..15
                        mol_type = protein
                        organism = synthetic construct
SEQUENCE: 952
LLVEFLKWSH YYGMD                                                                15

SEQ ID NO: 953          moltype = AA   length = 6
FEATURE                 Location/Qualifiers
source                  1..6
                        mol_type = protein
                        organism = synthetic construct
SEQUENCE: 953
PTFGGG                                                                           6

SEQ ID NO: 954          moltype = AA   length = 15
FEATURE                 Location/Qualifiers
source                  1..15
                        mol_type = protein
                        organism = synthetic construct
SEQUENCE: 954
LLVTFLRWSH YYGMD                                                                15

SEQ ID NO: 955          moltype = AA   length = 6
FEATURE                 Location/Qualifiers
source                  1..6
                        mol_type = protein
                        organism = synthetic construct
SEQUENCE: 955
TGSKGE                                                                           6

SEQ ID NO: 956          moltype = AA   length = 5
FEATURE                 Location/Qualifiers
source                  1..5
                        mol_type = protein
                        organism = synthetic construct
SEQUENCE: 956
TGSGA                                                                            5

SEQ ID NO: 957          moltype = AA   length = 19
FEATURE                 Location/Qualifiers
source                  1..19
                        mol_type = protein
                        organism = synthetic construct
SEQUENCE: 957
ARDLLVEFLK WSHYYGMDV                                                            19

SEQ ID NO: 958          moltype = AA   length = 19
FEATURE                 Location/Qualifiers
source                  1..19
                        mol_type = protein
                        organism = synthetic construct
SEQUENCE: 958
ARDLLVTFLR WSHYYGMDV                                                            19

SEQ ID NO: 959          moltype = AA   length = 19
FEATURE                 Location/Qualifiers
source                  1..19
                        mol_type = protein
                        organism = synthetic construct
SEQUENCE: 959
ARDLLIRFLE WGHYYGMDV                                                            19
```

-continued

| | | |
|---|---|---|
| SEQ ID NO: 960<br>FEATURE<br>source | moltype = AA length = 8<br>Location/Qualifiers<br>1..8<br>mol_type = protein<br>organism = synthetic construct | |
| SEQUENCE: 960<br>ITGSKGET | | 8 |
| SEQ ID NO: 961<br>FEATURE<br>source | moltype = AA length = 18<br>Location/Qualifiers<br>1..18<br>mol_type = protein<br>organism = synthetic construct | |
| SEQUENCE: 961<br>RDLLVRFLEW SHYYGMDV | | 18 |
| SEQ ID NO: 962<br>FEATURE<br>source | moltype = AA length = 7<br>Location/Qualifiers<br>1..7<br>mol_type = protein<br>organism = synthetic construct | |
| SEQUENCE: 962<br>FTGSGAA | | 7 |
| SEQ ID NO: 963<br>FEATURE<br>source | moltype = AA length = 19<br>Location/Qualifiers<br>1..19<br>mol_type = protein<br>organism = synthetic construct | |
| SEQUENCE: 963<br>ARDNLIRFLE WSHYYGMDV | | 19 |
| SEQ ID NO: 964<br>FEATURE<br>source | moltype = AA length = 126<br>Location/Qualifiers<br>1..126<br>mol_type = protein<br>organism = synthetic construct | |
| SEQUENCE: 964<br>EVQLVESGGG LVQPGGSLRL SCAASGSAFS SYGMSWVRQA PGKGLELVAS INSNGGSTYY<br>PDSVKGRFTI SRDNAKNSLY LQMNSLRAED TAVYYCARDL LVTFLRWSHY YGMDVWGQGT<br>TVTVSS | | 60<br>120<br>126 |
| SEQ ID NO: 965<br>FEATURE<br>source | moltype = AA length = 125<br>Location/Qualifiers<br>1..125<br>mol_type = protein<br>organism = synthetic construct | |
| SEQUENCE: 965<br>EVQLVESGGG LVQPGGSLRL SCAASGSAFS SYGMSWVRQA PGKGLELVAS IGGTGATYYP<br>DSVKGRFTIS RDNAKNSLYL QMNSLRAEDT AVYYCARDLL VRFLEWSHYY GMDVWGQGTT<br>VTVSS | | 60<br>120<br>125 |
| SEQ ID NO: 966<br>FEATURE<br>source | moltype = AA length = 125<br>Location/Qualifiers<br>1..125<br>mol_type = protein<br>organism = synthetic construct | |
| SEQUENCE: 966<br>EVQLVESGGG LVQPGGSLRL SCAASGFTFS SYGMSWVRQA PGKGLELVAS FTGSGGTYYP<br>DSVKGRFTIS RDNAKNSLYL QMNSLRAEDT AVYYCARDLL IRFLEWGHYY GMDVWGQGTT<br>VTVSS | | 60<br>120<br>125 |
| SEQ ID NO: 967<br>FEATURE<br>source | moltype = AA length = 126<br>Location/Qualifiers<br>1..126<br>mol_type = protein<br>organism = synthetic construct | |
| SEQUENCE: 967<br>EVQLVESGGG LVQPGGSLRL SCAASGFTFT SYGMSWVRQA PGKGLELVAS ITGSKGETYY<br>PDSVKGRFTI SRDNAKNSLY LQMNSLRAED TAVYYCARDL LVRFLEWSHY YGMDVWGQGT<br>TVTVSS | | 60<br>120<br>126 |
| SEQ ID NO: 968<br>FEATURE<br>source | moltype = AA length = 125<br>Location/Qualifiers<br>1..125<br>mol_type = protein<br>organism = synthetic construct | |
| SEQUENCE: 968<br>EVQLVESGGG LVQPGGSLRL SCAASGFTFS SYGMSWVRQA PGKGLELVAS FTGSGAAYYP | | 60 |

```
DSVKGRFTIS RDNAKNSLYL QMNSLRAEDT AVYYCARDLL IRFLEWSHYY GMDVWGQGTT   120
VTVSS                                                              125

SEQ ID NO: 969          moltype = AA  length = 112
FEATURE                 Location/Qualifiers
source                  1..112
                        mol_type = protein
                        organism = synthetic construct
SEQUENCE: 969
DIVMTQSPLS LPVTPGEPAS ISCRSSQSLL HSSGHNFLHW YLQKPGQSPQ LLIYESSNRV    60
SGVPDRFSGS GSGTDFTLKI SRVEAEDVGV YYCQQQTQYP PTFGGGTKVE IK           112

SEQ ID NO: 970          moltype = AA  length = 125
FEATURE                 Location/Qualifiers
source                  1..125
                        mol_type = protein
                        organism = synthetic construct
SEQUENCE: 970
EVQLVESGGG LVQPGGSLRL SCAASGFTFS SYGMSWVRQA PGKGLELVAS FTGSGGTYYP    60
DSVKGRFTIS RDNAKNSLYL QMNSLRAEDT AVYYCARDNL IRFLEWSHYY GMDVWGQGTT   120
VTVSS                                                              125

SEQ ID NO: 971          moltype = AA  length = 112
FEATURE                 Location/Qualifiers
source                  1..112
                        mol_type = protein
                        organism = synthetic construct
SEQUENCE: 971
DIVMTQSPLS LPVTPGEPAS ISCRSSQSLL HSSGHNFLHW YLQKPGQSPQ LLIYEVSNRE    60
SGVPDRFSGS GSGTDFTLKI SRVEAEDVGV YYCQQQTQYP PTFGGGTKVE IK           112

SEQ ID NO: 972          moltype = AA  length = 452
FEATURE                 Location/Qualifiers
source                  1..452
                        mol_type = protein
                        organism = synthetic construct
SEQUENCE: 972
EVQLVESGGG LVQPGGSLRL SCAASGSAFS SYGMSWVRQA PGKGLELVAS INSNGGSTYY    60
PDSVKGRFTI SRDNAKNSLY LQMNSLRAED TAVYYCARDL LVEFLKWSHY YGMDVWGQGT   120
TVTVSSASTK GPSVFPLAPC SRSTSESTAA LGCLVKDYFP EPVTVSWNSG ALTSGVHTFP   180
AVLQSSGLYS LSSVVTVPSS SLGTKTYTCN VDHKPSNTKV DKRVESKYGP PCPPCPAPEF   240
LGGPSVFLFP PKPKDTLMIS RTPEVTCVVV DVSQEDPEVQ FNWYVDGVEV HNAKTKPREE   300
QFNSTYRVVS VLTVLHQDWL NGKEYKCKVS NKGLPSSIEK TISKAKGQPR EPQVYTLPPS   360
QEEMTKNQVS LTCLVKGFYP SDIAVEWESN GQPENNYKTT PPVLDSDGSF FLYSRLTVDK   420
SRWQEGNVFS CSVMHEALHN HYTQKSLSLS LG                                 452

SEQ ID NO: 973          moltype = AA  length = 452
FEATURE                 Location/Qualifiers
source                  1..452
                        mol_type = protein
                        organism = synthetic construct
SEQUENCE: 973
EVQLVESGGG LVQPGGSLRL SCAASGSAFS SYGMSWVRQA PGKGLELVAS INSNGGSTYY    60
PDSVKGRFTI SRDNAKNSLY LQMNSLRAED TAVYYCARDL LVTFLRWSHY YGMDVWGQGT   120
TVTVSSASTK GPSVFPLAPC SRSTSESTAA LGCLVKDYFP EPVTVSWNSG ALTSGVHTFP   180
AVLQSSGLYS LSSVVTVPSS SLGTKTYTCN VDHKPSNTKV DKRVESKYGP PCPPCPAPEF   240
LGGPSVFLFP PKPKDTLMIS RTPEVTCVVV DVSQEDPEVQ FNWYVDGVEV HNAKTKPREE   300
QFNSTYRVVS VLTVLHQDWL NGKEYKCKVS NKGLPSSIEK TISKAKGQPR EPQVYTLPPS   360
QEEMTKNQVS LTCLVKGFYP SDIAVEWESN GQPENNYKTT PPVLDSDGSF FLYSRLTVDK   420
SRWQEGNVFS CSVMHEALHN HYTQKSLSLS LG                                 452

SEQ ID NO: 974          moltype = AA  length = 451
FEATURE                 Location/Qualifiers
source                  1..451
                        mol_type = protein
                        organism = synthetic construct
SEQUENCE: 974
EVQLVESGGG LVQPGGSLRL SCAASGSAFS SYGMSWVRQA PGKGLELVAS IGGTGATYYP    60
DSVKGRFTIS RDNAKNSLYL QMNSLRAEDT AVYYCARDLL VRFLEWSHYY GMDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                  451

SEQ ID NO: 975          moltype = AA  length = 451
FEATURE                 Location/Qualifiers
source                  1..451
```

```
                           mol_type = protein
                           organism = synthetic construct
SEQUENCE: 975
EVQLVESGGG LVQPGGSLRL SCAASGFTFS SYGMSWVRQA PGKGLELVAS FTGSGGTYYP    60
DSVKGRFTIS RDNAKNSLYL QMNSLRAEDT AVYYCARDLL IRFLEWGHYY GMDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 976         moltype = AA  length = 452
FEATURE                Location/Qualifiers
source                 1..452
                       mol_type = protein
                       organism = synthetic construct
SEQUENCE: 976
EVQLVESGGG LVQPGGSLRL SCAASGFTFT SYGMSWVRQA PGKGLELVAS ITGSKGETYY    60
PDSVKGRFTI SRDNAKNSLY LQMNSLRAED TAVYYCARDL LVRFLEWSHY YGMDVWGQGT   120
TVTVSSASTK GPSVFPLAPC SRSTSESTAA LGCLVKDYFP EPVTVSWNSG ALTSGVHTFP   180
AVLQSSGLYS LSSVVTVPSS SLGTKTYTCN VDHKPSNTKV DKRVESKYGP PCPPCPAPEF   240
LGGPSVFLFP PKPKDTLMIS RTPEVTCVVV DVSQEDPEVQ FNWYVDGVEV HNAKTKPREE   300
QFNSTYRVVS VLTVLHQDWL NGKEYKCKVS NKGLPSSIEK TISKAKGQPR EPQVYTLPPS   360
QEEMTKNQVS LTCLVKGFYP SDIAVEWESN GQPENNYKTT PPVLDSDGSF FLYSRLTVDK   420
SRWQEGNVFS CSVMHEALHN HYTQKSLSLS LG                                452

SEQ ID NO: 977         moltype = AA  length = 451
FEATURE                Location/Qualifiers
source                 1..451
                       mol_type = protein
                       organism = synthetic construct
SEQUENCE: 977
EVQLVESGGG LVQPGGSLRL SCAASGFTFS SYGMSWVRQA PGKGLELVAS FTGSGAAYYP    60
DSVKGRFTIS RDNAKNSLYL QMNSLRAEDT AVYYCARDLL IRFLEWSHYY GMDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 978         moltype = AA  length = 219
FEATURE                Location/Qualifiers
source                 1..219
                       mol_type = protein
                       organism = synthetic construct
SEQUENCE: 978
DIVMTQSPLS LPVTPGEPAS ISCRSSQSLL HSSGHNFLHW YLQKPGQSPQ LLIYESSNRV    60
SGVPDRFSGS GSGTDFTLKI SRVEAEDVGV YYCQQQTQYP PTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219

SEQ ID NO: 979         moltype = AA  length = 451
FEATURE                Location/Qualifiers
source                 1..451
                       mol_type = protein
                       organism = synthetic construct
SEQUENCE: 979
EVQLVESGGG LVQPGGSLRL SCAASGFTFS SYGMSWVRQA PGKGLELVAS FTGSGGTYYP    60
DSVKGRFTIS RDNAKNSLYL QMNSLRAEDT AVYYCARDNL IRFLEWSHYY GMDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 980         moltype = AA  length = 219
FEATURE                Location/Qualifiers
source                 1..219
                       mol_type = protein
                       organism = synthetic construct
SEQUENCE: 980
DIVMTQSPLS LPVTPGEPAS ISCRSSQSLL HSSGHNFLHW YLQKPGQSPQ LLIYEVSNRE    60
SGVPDRFSGS GSGTDFTLKI SRVEAEDVGV YYCQQQTQYP PTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219
```

```
SEQ ID NO: 981        moltype = AA   length = 125
FEATURE               Location/Qualifiers
source                1..125
                      mol_type = protein
                      organism = synthetic construct
SEQUENCE: 981
EVQLVESGGG LVQPGGSLRL SCAASGSAFS SYGMSWVRQA PGKGLELVAS INSNGGSTYY    60
PDSVKGRFTI SRDNAKNSLY LQMNSLRAED TAVYYCARDL LVEFLKWSHY YGMDVWGQGT   120
TVTVS                                                              125
```

The invention claimed is:

1. An antibody or antigen-binding fragment thereof that specifically binds to pro/latent myostatin, wherein the antibody or antigen-binding fragment comprises six complementarity determining regions (CDRs), an H-CDR1, an H-CDR2, an H-CDR3, an L-CDR1, an L-CDR2, and an L-CDR3, wherein:
   a) the H-CDR1 comprises the amino acid sequence of SEQ ID NO: 201, the H-CDR2 comprises the amino acid sequence of SEQ ID NO: 219, the H-CDR3 comprises the amino acid sequence of SEQ ID NO: 220, the L-CDR1 comprises the amino acid sequence of SEQ ID NO: 216, the L-CDR2 comprises the amino acid sequence of SEQ ID NO: 222, and the L-CDR3 comprises the amino acid sequence of SEQ ID NO: 223, wherein the CDR sequences are numbered according to Kabat numbering system;
   b) the H-CDR1 comprises the amino acid sequence of SEQ ID NO: 234, the H-CDR2 comprises the amino acid sequence of SEQ ID NO: 235, the H-CDR3 comprises the amino acid sequence of SEQ ID NO: 236, the L-CDR1 comprises the amino acid sequence of SEQ ID NO: 237, the L-CDR2 comprises the amino acid sequence EVS, and the L-CDR3 comprises the amino acid sequence of SEQ ID NO: 239, wherein the CDR sequences are numbered according to Chothia numbering system; or
   c) the H-CDR1 comprises the amino acid sequence of SEQ ID NO: 3, the H-CDR2 comprises the amino acid sequence of SEQ ID NO: 256, the H-CDR3 comprises the amino acid sequence of SEQ ID NO: 257, the L-CDR1 comprises the amino acid sequence of SEQ ID NO: 258, the L-CDR2 comprises the amino acid sequence EVS, and the L-CDR3 comprises the amino acid sequence of SEQ ID NO: 260, wherein the CDR sequences are numbered according to IMGT numbering system.

2. The antibody or antigen-binding fragment thereof of claim 1, comprising a heavy chain variable domain that is at least 90% identical to the amino acid sequence of SEQ ID NO: 402, a light chain variable domain that is at least 90% identical to the amino acid sequence of SEQ ID NO: 412, or a combination thereof.

3. The antibody or antigen-binding fragment thereof of claim 1, comprising a heavy chain variable domain comprising the amino acid sequence of SEQ ID NO: 402 and a light chain variable domain comprising the amino acid sequence of SEQ ID NO: 412.

4. The antibody or antigen-binding fragment thereof of claim 1, wherein the antibody is a human antibody of the IgG1 subtype or of the IgG4 subtype.

5. The antibody or antigen-binding fragment thereof of claim 1, wherein the antibody is a human antibody of the IgG4 subtype.

6. The antibody or antigen-binding fragment thereof of claim 5, wherein the antibody comprises an S228P mutation.

7. The antibody or antigen-binding fragment thereof of claim 1, comprising a heavy chain that is at least 90% identical to the amino acid sequence of SEQ ID NO: 503, a light chain that is at least 90% identical to the amino acid sequence of SEQ ID NO: 504, or a combination thereof.

8. The antibody or antigen-binding fragment thereof of claim 1, comprising a heavy chain comprising the amino acid sequence of SEQ ID NO: 503 and a light chain comprising the amino acid sequence of SEQ ID NO: 504.

9. A pharmaceutical composition comprising the antibody or antigen-binding fragment thereof of claim 1 and a pharmaceutically acceptable excipient.

10. The pharmaceutical composition of claim 9, wherein the composition is formulated for subcutaneous administration.

11. The pharmaceutical composition of claim 9, wherein the composition is formulated for intravenous administration.

* * * * *